(12) United States Patent
Schwabe et al.

(10) Patent No.: US 10,676,525 B2
(45) Date of Patent: Jun. 9, 2020

(54) ANTI-TREM2 ANTIBODIES AND METHODS OF USE THEREOF

(71) Applicant: ALECTOR LLC, South San Francisco, CA (US)

(72) Inventors: Tina Schwabe, San Francisco, CA (US); Eric Brown, Colma, CA (US); Philip Kong, San Francisco, CA (US); Ilaria Tassi, San Francisco, CA (US); Seung-Joo Lee, Benicia, CA (US); Arnon Rosenthal, Woodside, CA (US); Robert Pejchal, Norwich, VT (US); Nels P. Nielson, Hopkinton, NH (US)

(73) Assignee: ALECTOR LLC, South San Francisco, CA (US)

( * ) Notice: Subject to any disclaimer, the term of this patent is extended or adjusted under 35 U.S.C. 154(b) by 0 days.

(21) Appl. No.: 16/054,680

(22) Filed: Aug. 3, 2018

(65) Prior Publication Data

US 2019/0040130 A1 Feb. 7, 2019

Related U.S. Application Data

(60) Provisional application No. 62/636,095, filed on Feb. 27, 2018, provisional application No. 62/541,019, filed on Aug. 3, 2017.

(51) Int. Cl.
*C07K 16/28* (2006.01)
*A61P 25/28* (2006.01)
*A61K 39/00* (2006.01)

(52) U.S. Cl.
CPC ......... *C07K 16/2803* (2013.01); *A61P 25/28* (2018.01); *A61K 2039/505* (2013.01); *C07K 2317/24* (2013.01); *C07K 2317/51* (2013.01); *C07K 2317/52* (2013.01); *C07K 2317/56* (2013.01); *C07K 2317/71* (2013.01); *C07K 2317/75* (2013.01); *C07K 2317/76* (2013.01); *C07K 2317/90* (2013.01); *C07K 2317/92* (2013.01)

(58) Field of Classification Search
CPC ............ C07K 16/2803; C07K 2317/24; C07K 2317/51; C07K 2317/52; C07K 2317/56; C07K 2317/71; C07K 2317/75; C07K 2317/76; C07K 2317/90; C07K 2317/92; A61P 25/28; A61K 2039/505
See application file for complete search history.

(56) References Cited

U.S. PATENT DOCUMENTS

| | | | |
|---|---|---|---|
| 4,657,760 A | 4/1987 | Kung et al. | |
| 4,816,567 A | 3/1989 | Cabilly et al. | |
| 5,206,344 A | 4/1993 | Katre et al. | |
| 5,225,212 A | 7/1993 | Martin et al. | |
| 5,229,275 A | 7/1993 | Goroff | |
| 5,545,806 A | 8/1996 | Lonberg et al. | |
| 5,545,807 A | 8/1996 | Surani et al. | |
| 5,565,332 A | 10/1996 | Hoogenboom et al. | |
| 5,567,610 A | 10/1996 | Borrebaeck et al. | |
| 5,569,825 A | 10/1996 | Lonberg et al. | |
| 5,571,894 A | 11/1996 | Weis et al. | |
| 5,573,905 A | 11/1996 | Lerner et al. | |
| 5,587,458 A | 12/1996 | King et al. | |
| 5,591,669 A | 1/1997 | Krimpenfort et al. | |
| 5,625,126 A | 4/1997 | Lonberg et al. | |
| 5,633,425 A | 5/1997 | Lonberg et al. | |
| 5,641,870 A | 6/1997 | Rinderknecht et al. | |
| 5,648,237 A | 7/1997 | Carter | |
| 5,661,016 A | 8/1997 | Lonberg et al. | |
| 5,731,168 A | 3/1998 | Carter et al. | |
| 5,739,277 A | 4/1998 | Presta et al. | |
| 5,789,199 A | 8/1998 | Joly et al. | |
| 5,840,523 A | 11/1998 | Simmons et al. | |
| 5,869,046 A | 2/1999 | Presta et al. | |
| 5,959,177 A | 9/1999 | Hein et al. | |
| 6,040,498 A | 3/2000 | Stomp et al. | |
| 6,075,181 A | 6/2000 | Kucherlapati et al. | |
| 6,150,584 A | 11/2000 | Kucherlapati et al. | |
| 6,417,429 B1 | 7/2002 | Hein et al. | |
| 6,420,548 B1 | 7/2002 | Vézina et al. | |
| 6,982,321 B2 | 1/2006 | Winter | |
| 7,087,409 B2 | 8/2006 | Barbas, III et al. | |
| 7,125,978 B1 | 10/2006 | Vezina et al. | |
| 7,556,926 B2 | 7/2009 | Tojo et al. | |

(Continued)

FOREIGN PATENT DOCUMENTS

| | | |
|---|---|---|
| EP | 0404097 B1 | 9/1996 |
| WO | WO-1987/04462 A1 | 7/1987 |

(Continued)

OTHER PUBLICATIONS

Alegre, M.-L. et al. (Jun. 1, 1994). "A Non-Activating "Humanized" Anti-cd3 Monoclonal Antibody Retains Immunosuppressive Properties in Vivo," *Transplantation* 57(11):1537-1543.

(Continued)

*Primary Examiner* — Kimberly Ballard
(74) *Attorney, Agent, or Firm* — Morrison & Foerster LLP

(57) ABSTRACT

The present disclosure is generally directed to compositions that include antibodies, e.g., monoclonal, antibodies, antibody fragments, etc., that specifically bind a TREM2 protein, e.g., a mammalian TREM2 or human TREM2, and use of such compositions in preventing, reducing risk, or treating an individual in need thereof.

60 Claims, 18 Drawing Sheets
Specification includes a Sequence Listing.

(56) References Cited

U.S. PATENT DOCUMENTS

| | | | | |
|---|---|---|---|---|
| 8,093,360 | B2* | 1/2012 | Casey | C07K 16/1278 424/133.1 |
| 8,231,878 | B2 | 7/2012 | Colonna et al. | |
| 8,614,299 | B2 | 12/2013 | Baurin et al. | |
| 8,981,061 | B2 | 3/2015 | Colonna et al. | |
| 9,587,036 | B2* | 3/2017 | Kufer | C07K 16/2809 |
| 9,978,966 | B2* | 5/2018 | Lee | H01L 27/3267 |
| 2003/0165875 | A1 | 9/2003 | Colonna et al. | |
| 2004/0175744 | A1 | 9/2004 | Hu et al. | |
| 2005/0155089 | A1 | 7/2005 | La et al. | |
| 2005/0260670 | A1 | 11/2005 | Colonna et al. | |
| 2006/0263774 | A1 | 11/2006 | Clark et al. | |
| 2007/0148167 | A1 | 6/2007 | Strohl | |
| 2009/0081199 | A1 | 3/2009 | Colonna et al. | |
| 2009/0181855 | A1 | 7/2009 | Vasquez et al. | |
| 2010/0056386 | A1 | 3/2010 | Vasquez et al. | |
| 2010/0280227 | A1 | 11/2010 | Ambrose et al. | |
| 2013/0150559 | A1 | 6/2013 | Colonna et al. | |
| 2016/0251434 | A1 | 9/2016 | Colonna et al. | |
| 2017/0240631 | A1 | 8/2017 | Monroe et al. | |
| 2019/0010230 | A1 | 1/2019 | Monroe et al. | |
| 2019/0315858 | A1 | 10/2019 | Monroe et al. | |
| 2019/0330335 | A1 | 10/2019 | Schwabe et al. | |

FOREIGN PATENT DOCUMENTS

| | | |
|---|---|---|
| WO | WO-1991/10741 A1 | 7/1991 |
| WO | WO-1993/08829 A1 | 5/1993 |
| WO | WO-1993/11161 A1 | 6/1993 |
| WO | WO-1993/16185 A2 | 8/1993 |
| WO | WO-1994/04690 A1 | 3/1994 |
| WO | WO-1996/27011 A1 | 9/1996 |
| WO | WO-1996/33735 A1 | 10/1996 |
| WO | WO-1996/34096 A1 | 10/1996 |
| WO | WO-1997/11971 A1 | 4/1997 |
| WO | WO-1997/17852 A1 | 5/1997 |
| WO | WO-1998/24893 A2 | 6/1998 |
| WO | WO-1999/58572 A1 | 11/1999 |
| WO | WO-2001/27160 A1 | 4/2001 |
| WO | WO-2004/042072 A2 | 5/2004 |
| WO | WO-2007/106585 A1 | 9/2007 |
| WO | WO-2008/045443 A2 | 4/2008 |
| WO | WO-2008/079246 A2 | 7/2008 |
| WO | WO-2009/036379 A2 | 3/2009 |
| WO | WO-2010/056386 A1 | 5/2010 |
| WO | WO-2010/105256 A1 | 9/2010 |
| WO | WO-2012/009568 A2 | 1/2012 |
| WO | WO-2016/023019 A2 | 2/2016 |
| WO | WO-2016/049641 A1 | 3/2016 |
| WO | WO-2016/064895 A1 | 4/2016 |
| WO | WO-2017/058866 A1 | 4/2017 |
| WO | WO-2017/062672 A2 | 4/2017 |

OTHER PUBLICATIONS

Almagro, J.C. et al. (2008). "Humanization of Antibodies," *Frontiers in Bio-Science* 13:1619-1633.

Al-Shawi, R.et al. (2008). "Neurotoxic and Neurotrophic Roles of proNGF and the Receptor Sortilin in the Adult and Ageing Nervous System," *European Journal of Neuroscience* 27:2103-2114.

Angal, S. et al. (1993). "A Single Amino Acid Substitution Abolishes the Heterogeneity of Chimeric Mouse/Human (IgG4) Antibody," *Molecular Immunology* 30(1):105-108.

Armour, K.L. et al. (1999). "Recombinant Human IgG Molecules Lacking Fcγ Receptor I Binding and Monocyte Triggering Activities," *Eur. J. Immunol.* 29:2613-2624.

Armour, K.L. et al. (2003). "Differential Binding to Human FcγIIa and FcγIIb Receptors by Human IgG Wildtype and Mutant Antibodies," *Molecular Immunology* 40:585-593.

Armour, K.L. et al. (Jun. 25-28, 2000). "Mutant IgG Lacking FcγRIII Binding and ADCC Activities," *The Haematology Journal,* poster Session 1, Presented at the *5th Annual Meeting of the European Haematology Association*, Birmingham, UK, 1(Suppl. 1):27, 2 pages.

Arnett, M.G. et al. (Dec. 5, 2007; e-published on Oct. 26, 2007). "proNGF, Sortilin, and p75$^{NTR}$: Potential Mediators of Injury-Induced Apoptosis in the Mouse Dorsal Root Ganglion," *Brain Res.* 1183:32-42.

Asquith, D.L. et al. (2009). "Animal Models of Rheumatoid Arthritis," *Eur. J. Immunol.* 39:2040-2044.

Author Unkown. (Jan. 1, 2016). "Anti-TREM2 Monoclonal Antibody Clone 78," Millipore Sigma NF-MABN755, located at www.emdmillipore.com/US/en/product/Anti-TREM-2-Antibody-clone-78.MM_NF-MABN755#overview>, pp. 1-3 (Datasheet).

Author Unkown. (2006). "Anti-TREM2, Clone 78, Cat. # MABN755, Lot 3013362," Certificate of Analysis, located at www.merckmillipore.com/SG/en/product/Anti-TREM2-Antibody-clone-78,MM_NF-MABN755>, 2 pages.

Baca, M. et al. (1997). "Antibody Humanization Using Monovalent Phage Display," *The Journal of Biological Chemistry* 272(16):10678-10684.

Barbas III, C.F. et al. (Apr. 1994). "In Vitro Evolution of a Neutralizing Human Antibody to Human Immunodeficiency Virus Type 1 to Enhance Affinity and Broaden Strain Cross-Reactivity," *Proc Nat. Acad. Sci. USA* 91:3809-3813.

Bartholomaeus, P. et al. (2014). "Cell Contact-Dependent Priming and Fc Interaction with CD32+ Immune Cells Contribute to the TGN1412-Triggered Cytokine Response," *The Journal of Immunology* 192:2091-2098.

Basso, D.M. et al. (May 2006). "Basso Mouse Scale for Locomotion Detects Differences in Recovery after Spinal Cord Injury in Five Common Mouse Strains," *J. Neurotrauma* 23(5):635-659.

Bates, M.K. et al. (Feb. 2006). "Genetic Immunization for Antibody Generation in Research Animals by Intravenous Delivery of Plasmid DNA," *Biotechniques* 40(2):199-207.

Beattie, M.S. et al. (Oct. 24, 2002). "ProNGF Induces p75-Mediated Death of Oligodendrocytes following Spinal Cord Injury," *Neuron* 36(3):375-386.

Boerner, P. et al. (1991). "Production of Antigen-Specific Human Monoclonal Antibodies From In Vitro-Primed Human Splenocytes," *Journal of Immunology* 147(1):86-95.

Bolt, S. et al. (1993). "The Generation of a Humanized, Non-Mitogenic Cd3 Monoclonal Antibody Which Retains In Vitro Immunosuppressive Properties," *European Journal Immunol.* 23:403-411.

Borroni, B. et al. (Apr. 2014; e-pub. Oct. 16, 2013). "Heterozygous TREM2 Mutations in Frontotemporal Dementia," *Neurobiol Aging.* 35(4):934.e7-934.e10.

Bouchon et al. (2001). "A DAP12-Mediated Pathway Regulates Expression of CC Chemokine Receptor 7 and Maturation of Human Dendritic Cells," *J. Exp. Med.* 194(8):1111-1122.

Brennan, M. et al. (Jul. 5, 1985). "Preparation of Bispecific Antibodies by Chemical Recombination of Monoclonal Immunoglobulin G$_1$ Fragments," *Science* 229:81-83.

Bross, P.F. et al. (Jun. 2001). "Approval Summary: Gemtuzumab Ozogamicin in Relapsed Acute Myeloid Leukemia," *Clinical Cancer Research* 7(6):1490-1496.

Bruggemann, M. et al. (1993). "Designer Mice: The Production of Human Antibody Repertoires in Transgenic Animals," *Year in Immunol.* 7:33-40.

Cady, J. et al. (Apr. 2014). "TREM2 Variant p.R47H as a Risk Factor for Sporadic Amyotrophic Lateral Sclerosis," *JAMA Neurol.* 71(4):449-453.

Cantoni, C. et al. (Mar. 2015). "TREM2 Regulates Microglial Cell Activation in Response to Demyelination In Vivo," *Acta Neuropathol,* 129(3):429-447, thirty three pages.

Cao, X. et al. (Sep. 2011). "Macrophage Polarization in the Maculae of Age-Related Macular Degeneration: A Pilot Study," *Pathology International* 61(9):528-535, fourteen pages.

Capel, P.J.A. et al. (1994). "Heterogeneity of Human IgG Fc Receptors," *Immunomethods* 4:25-34.

Carter, P. et al. (Feb. 1992). "High Level *Escherichia coli* Expression and Production of a Bivalent Humanized Antibody Fragment," *Bio/technology* 10:163-167.

(56) References Cited

OTHER PUBLICATIONS

Carter, P. et al. (May 1992). "Humanization of an Anti-p185$^{HER2}$ Antibody for Human Cancer Therapy," *Proc. Natl. Acad. Sci. USA* 89:4285-4289.

Chang et al. (2002). "Retinal Degeneration Mutants in the Mouse," *Vision Research* 42:517-525.

Chen, Y. et al. (Oct. 1996). "An Experimental Model of Closed Head Injury in Mice: Pathophysiology, Histopathology, and Cognitive Deficits," *J. Neurotrauma* 13(10):557-568.

Chothia, C. et al. (1987). "Canonical Structures for the Hypervariable Regions of Immunoglobulins," *J. Mol. Biol*, 196(4):901-917.

Chu, S.Y. et al. (2008, e-pub. Aug. 8, 2008). "Inhibition of B cell Receptor-Mediated Activation of Primary Human B Cells by Coengagement of CD19 and FcγRIIb with Fc-Engineered Antibodies," *Molecular Immunology* 45(15):3926-3933.

Clackson, T. et al. (Aug. 15, 1991). "Making Antibody Fragments Using Phage Display Libraries," *Nature* 352(6336):624-628.

Cole, M.S. et al. (Aug. 27, 1999). "HuM291, A Humanized Anti-Cd3 Antibody is Immunosuppressive to T Cells While Exhibiting Reduced Mitogenicity in Vitro," *Transplantation* 68(4):563-571.

Colonna, M. (Jun. 1, 2003). "TREMS in the Immune System and Beyond," *The Journal of Immunology* 3(6):445-453.

Correale, C. et al. (Feb. 2013). "Bacterial Sensor Triggering Receptor Expressed on Myeloid Cells-2 Regulates the Mucosal Inflammatory Response," *Gastroenterology* 144(2):346-356.

Cruts, M. et al. (2008). "Loss of Progranulin Function in Frontotemporal Lobar Degeneration," *Trends Genetics* 24(4):186-194.

Cunningham, B.C. et al. (Jun. 2, 1989). "High-Resolution Epitope Mapping of Hgh-Receptor Interactions by Alanine-Scanning Mutagenesis," *Science* 244(4908):1081-1085.

Cuyvers, E. et al. (Oct. 9, 2013). "Investigating the Role of Rare Heterozygous TREM2 Variants in Alzheimer's Disease and Frontotemporal Dementia," *Neurobiol Aging* 35(3):726:e11-e19.

Daëron, M. (1997). "FC Receptor Biology," *Annu. Rev. Immunol.* 15:203-234.

Dall' Acqua, W.F. et al. (Aug. 18, 2006). "Properties of Human IgG1s Engineered for Enhanced Binding to the Neonatal Fc Receptor (FeRn)," *The Journal of Biological Chemistry* 281(33):23514-23524.

Damani, M.R. et al. (2011). "Age-Related Alterations in the Dynamic Behavior of Microglia," *Aging Cell* 10:263-176.

Daneman, R. et al. (Oct. 29, 2010). "The Mouse Blood-Brain Barrier Transcriptome: A New Resource for Understanding the Development and Function of Brain Endothelial Cells," *PLoS One* 5(10):e13741, sixteen pages.

Davidson, E. et al. (Sep. 2014). "A High-Throughput Shotgun Mutagenesis Approach to Mapping B-Cell Antibody Epitopes," *Immunology* 143(1):13-20.

Davis, P.M. et al. (2007). "Abatacept Binds to the Fc Receptor Cd64 But Does Not Mediate Complement-Dependent Cytotoxicity or Antibody-Dependent Cellular Cytotoxicity," *The Journal of Rheumatology* 34(11):2204-2210.

De Haas, M. et al. (Oct. 1995). "Fc Gamma Receptors of Phagocytes," *J. Lab. Clin. Med.* 126(4):330-341.

Ducry, L. et al. (Jan. 2010; e-pub. Sep. 21, 2009). "Antibody-Drug Conjugates: Linking Cytotoxic Payloads to Monoclonal Antibodies," *Bioconjug. Chem.* 21(1):5-13.

Edwards, B.E. et al. (2003). "The Remarkable Flexibility of the Human Antibody Repertoire; Isolation of Over One Thousand Different Antibodies to a Single Protein, BLyS," *J. Mol. Biol.* 334(1):103-118.

El-Danaf, R.N. et al. (Feb. 11, 2015). "Characteristic Patterns of Dendritic Remodeling in Early-Stage Glaucoma: Evidence from Genetically Identified Retinal Ganglion Cell Types," *The Journal of Neuroscience* 35(6):2329-2343.

Estep, P. et al. (Mar.- Apr. 2013). "High Throughput Solution-Based Measurement of Antibody-Antigen Affinity and Epitope Binning," *mAbs.* 5(2):270-278.

Fahnestock, M. et al. (2001). "The Precursor Pro-Nerve Growth Factor Is the Predominant Form of Nerve Growth Factor in Brain and Is Increased in Alzheimer's Disease," *Molecular and Cellular Neuroscience* 18:210-220.

Fan, Y.-J. (2008). "Differential effects of Pro-BDNF on Sensory Neurons after Sciatic Nerve Transection in Neonatal Rats," *European Journal of Neuroscience* 27(9):2380-2390.

Feldhaus, M.J. et al. (Jul. 2004, e-pub. May 31, 2004). "Yeast Display of Antibody Fragments: A Discovery and Characterization Platform," *J. Immunological Methods* 290(1-2):69-80.

Fellouse, F.A. et al. (Aug. 24, 2004). "Synthetic Antibodies from a Four-Amino-Acid Code: A Dominant Role for Tyrosine in Antigen Recognition," *PNAS* 101(34):12467-12472.

Fishwild, D.M. et al. (Jul. 1996). "High-Avidity Human IgGk Monoclonal Antibodies from a Novel Strain of Minilocus Transgenic Mice," *Nature Biotechnology* 14(7):845-851.

Gabathuler, R. (2010; e-pub. Aug. 5, 2009). "Approaches to Transport Therapeutic Drugs across the Blood-Brain Barrier to Treat Brain Diseases," *Neurobiology of Disease* 37(1):48-57.

Garber, K. (Nov. 2014). "Bispecific Antibodies Rise Again," *Nature Reviews Drug Discovery* 13(11):799-801.

Gattis, J.L. et al. (May 12, 2006). "The Structure of the Extracellular Domain of Triggering Receptor Expressed on Myeloid Cells Like Transcript-1 and Evidence for a Naturally Occurring Soluble Fragment," *The Journal of Biological Chemistry* 281(19):13396-13403.

Gawish, R. et al. (Apr. 2015; e.pub Dec. 4, 2014). "Triggering Receptor Expressed on Myeloid cells-2 Fine-Tunes Inflammatory Responses in Murine Gram-Negative Sepsis," *The FASEB Journal* 29(4):1247-1257.

Gerngross, T.U. (Nov. 2004). "Advances in the Production of Human Therapeutic Proteins in Yeasts and Filamentous Fungi," *Nature Biotechnology* 22(11):1409-1414.

Gibot, S. et al. (May 2006). "Modulation of the Triggering Receptor Expressed on the Myeloid Cell Type 1 Pathway in Murine Septic Shock," *Infection and Immunity* 74(5):2823-2830.

Gonçalves, L.A. et al. (Nov. 26, 2013). "TREM2 Governs Kupffer Cell Activation and Explains belr1 Genetic Resistance to Malaria liver Stage Infection," *PNAS* 110(48):19531-19536.

Gordon, M.N. et al. (May-Jun. 2001). "Correlation Between Cognitive Deficits and Aβ Deposits in Transgenic APP+PS1 Mice," *Nuerobiol. Aging* 22(3):377-385.

Graham, F.L. et al. (1977). "Characteristics of a Human Cell Line Transformed by DNA from Human Adenovirus Type 5," *Journal of General Virology* 36:59-72.

Gravestein, L.A. et al. (1994). "Novel mAbs Reveal Potent Co-Stimulatory Activity of Murine CD27," *International Immunology* 7(4):551-557.

Gravestein, L.A. et al. (Aug. 1, 1996). "CD27 Cooperates with the Pre-T Cell Receptor in the Regulation of Murine T Cell Development," *J. Exp. Med.* 184(2):675-685.

Griffith, A.D. et al. (Feb. 1993). "Human Anti-Self Antibodies with High Specificity from Phage Display Libraries," *EMBO J.* 12(2):725-734.

Gruber, M. et al. (1994). "Efficient Tumor Cell Lysis Mediated by a Bispecific Single Chain Antibody Expressed in *Escherichia coli*," *The Journal of Immunology* 152(11):5368-5374.

Guerreiro, R. et al. (Jan. 10, 2013). "TREM2 Variants in Alzheimer's Disease," *The New England Journal of Medicine* 368(2):117-127.

Guerreiro, R.J. et al. (Jan. 2013). "Using Exome Sequencing to Reveal Mutations in TREM2 Presenting as a Frontotemporal Dementia-like Syndrome Without Bone Involvement," *JAMA Neural.* 70(1):78-84, fifteen pages.

Guerreiro, R.J. et al. (Oct. 2012). "TOMM40 Association with Alzheimer Disease: Tales of APOE and Linkage Disequilibrium," *Arch Neural.* 69(10):1243-1244.

Gupta, N. et al. (2003). "Activated Microglia in Human Retinitis Pigmentosa, Late-Onset Retinal Degeneration, and Age-Related Macular Degeneration," *Experimental Eye Research* 76(4):463-471.

Hamann, P.R. et al. (2002, e-pub. Dec. 19, 2001). "Gemtuzumab Ozogamicin, A Potent and Selective Anti-CD33 Antibody-

(56) References Cited

OTHER PUBLICATIONS

Calicheamicin Conjugate for Treatment of Acute Myeloid Leukemia," *Bioconjugate Chemistry* 13(1):47-58.
Hamerman, J.A. et al. (Aug. 15, 2006). "Cutting Edge: Inhibition of TLR and FcR Responses in Macrophages by Triggering Receptor Expressed on Myeloid Cells (TREM)-2 and DAP12," *The Journal of Immunology* 177(4):2051-2055.
Hamerman, J.A. et al. (Jun. 2005; e-pub. May 15, 2005). "Enhanced Toll-Like Receptor Responses in the Absence of Signaling Adaptor DAP12," *Nat Immunol.* 6(6):579-586, twenty pages.
Hamers-Casterman, C. et al. (Jun. 3, 1993). "Naturally Occurring Antibodies Devoid of Light Chains," *Nature* 363(6428):446-448.
Han, S. et al. (Apr. 2010; e-pub. Apr. 5, 2010). "Rescuing Vasculature With Intravenous Angiopoietin-1 and avβ3 Integrin Peptide is Protective After Spinal Cord Injury," *Brain* 133(4):1026-1042.
Harrington, A.W. et al. (Apr. 20, 2004). "Secreted proNGF is a Pathophysiological Death-Inducing Ligand After Adult CNS Injury," *Proc. Natl. Acad. Sci USA* 101(16):6226-6230.
Harris, W.J. (Nov. 1, 1995). "Therapeutic Monoclonals—Production of Humanized Monoclonal Antibodies for In Vivo Imaging and Therapy," *Biochem. Soc. Transactions* 23(4):1035-1038.
Hawkins, R.E. et al. (1992). "Selection of Phage Antibodies by Binding Affinity: Mimicking Affinity Maturation," *Journal of Molecular Biology* 226(3):889-896.
Hazen, M. et al. (Jan.-Feb. 2014). "An Improved and Robust DNA Immunization Method to Develop Antibodies Against Extracellular Loops of Multi-Transmembrane Proteins," *MAbs* 6(1):95-107.
Hezareh, M. et al. (Dec. 2001). "Effector Function Activities of a Panel of Mutants of a Broadly Neutralizing Antibody against Human Immunodeficiency Virus Type 1," *Journal of Virology* vol. 75(24):12161-12168.
Hickman, S.E. et al. (Aug. 13, 2008). "Microglial Dysfunction and Defective β-Amyloid Clearance Pathways in Aging Alzheimer's Disease Mice," *J Neurosci.* 28(33):8354-8360.
Holliger, P. et al. (Jul. 1993). ""Diabodies": Small Bivalent and Bispecific Antibody Fragments," *Proceedings of the National Academy of Sciences* 90(14):6444-6448.
Hongo, J.S. et al. (1995). "Development and Characterization of Murine Monoclonal Antibodies to the Latency-Associated Peptide of Transforming Growth Factor β$_1$," *Hybridoma* 14(3):253-260.
Hoogenboom, H.R. et al. (1992). "By-Passing Immunisation. Human Antibodies from Synthetic Repertoires of Germline Hh Gene Segments Rearranged in Vitro," *Journal of Molecular Biology* 227(2):381-388.
Hsieh, C.L. et al. (May 2009; e-pub. Mar. 19, 2009). "A Role for TREM2 Ligands in the Phagocytosis of Apoptotic Neuronal Cells by Microglia," *Journal of Neurochemistry* 109(4):1144-1156, twenty one pages.
Humphrey, M.B. et al. (2006). "TREM2, a DAP12-Associated Receptor, Regulates Osteoclast Differentiation and Function," *J Bone Miner Res.* 21(2):237-245.
Hurle, M.R. et al. (Aug. 1994)."Protein Engineering Techniques for Antibody Humanization," *Current Opinion in Biotechnology* 5(4):428-433.
Hutchins, J.T. et al. (Dec. 1995). "Improved Biodistribution, Tumor Targeting, and Reduced Immunogenicity in Mice with a γ4 Variant of Campath-IH," *Proc. Natl. Acad. Sci.* 92(26):11980-11984.
Hutton, M. et al. (Jun. 18, 1998). "Association of Missense and 5'-Splice-Site Mutations in Tau with the Inherited Dementia FTDP-17," *Nature* 393(6689):702-705.
Idusogie, E.E. et al. (Feb. 15, 2001). "Engineered Antibodies With Increased Activity to Recruit Complement," *J. Immunol.* 166(4):2571-2575.
Ito, H. et al. (Jan. 2012; e-pub. Dec. 12, 2011). "TREM-2, Triggering Receptor Expressed on Myeloid cell-2, Negatively Regulates TLR responses in Dendritic Cells," *Eur. J. Immunol.* 42(1):176-185.
Jackson, J.R. et al. (Apr. 1, 1995). "In Vitro Antibody Maturation. Improvement of a High Affinity, Neutralizing Antibody against IL-1β," *The Journal of Immunology* 157(7):3310-3319.
Jakobovits, A. et al. (Mar. 18, 1993) "Germ-line Transmission and Expression of a Human-derived Yeast Artificial Chromosome," *Nature* 362(6417):255-258.
Jakobovits, A. et al. (Mar. 1993). "Analysis of Homozygous Mutant Chimeric Mice: Deletion of the Immunoglobulin Heavy-chain Joining Region Blocks B-Cell Development and Antibody Production," *Proceedings of the National Academy of Sciences* 90(6):2551-2555.
Jansen, P. et al. (Nov. 2007; e-pub. Oct. 14, 2007). "Roles for the Pro-Neurotrophin Receptor Sortilin in Neuronal Development, Aging and Brain Injury," *Nature Neuroscience* 10(11):1449-1457.
Jay, T.R. et al. (Mar. 9, 2015: e-pub Mar. 2, 2015), "TREM2 Deficiency Eliminates TREM2+ Inflammatory Macrophages and Ameliorates Pathology in Alzheimer's Disease Mouse Models," *J Exp Med* 212(3):287-295.
Johnson, L.A. et al. (Sep. 2011). "Apolipoprotein E4 Exaggerates Diabetic Dyslipidemia and Atherosclerosis in Mice Lacking the LDL Receptor," *Diabetes* 60(9):2285-2294.
Johnson, K.S. et al. (Aug. 1993). "Human Antibody Engineering: Current Opinion in Structural Biology," *Curr. Opin Struct. Biol.* 3(4):564-571.
Jones, P.T. et al. (May 29, 1986). "Replacing the Complementarity-Determining Regions in a Human Antibody with Those from a Mouse," *Nature* 321(6069):522-525.
Jonsson, T. et al. (Jan. 10, 2013). "Variant of TREM2 Associated with the Risk of Alzheimer's Disease," *The New England Journal of Medicine* 368(2):107-116.
Kelker, M.S. et al. (Dec. 10, 2004). "Crystal Structure of Mouse Triggering Receptor Expressed on Myeloid Cells 1 (TREM-1) at 1.76 Å," *Journal of Molecular Biology* 344(5):1175-1181.
Kelker, M.S. et al. (Sep. 24, 2004). "Crystal Structure of Human Triggering Receptor Expressed on Myeloid Cells 1 (TREM-1) at 1.47 Å," *Journal of Molecular Biology* 342(4):1237-1248.
Kjolby et al. (2010). "Sort1, Encoded by the CardiovascularRisk Locus 1p13.3, Is a Regulator of Hepatic Lipoprotein Export," *Cell Metabolism* 12(3):213-223.
Kleinberg, G. et al. (Jul. 2, 2014). "TREM2 Mutations Implicated in Neurodegeneration Impair Cell Surface Transport and Phagocytosis," *Sci Transl Med.* 6(243):243ra86, pp. 1-12.
Koga, T. T et al.(Apr. 15, 2004). "Costimulatory Signals Mediated by the ITAM Motif Cooperate with RANKL for Bone Homeostasis," *Nature* 428(6984):758-763.
Köhler, G. et al. (Aug. 7, 1975). "Continuous Cultures of Fused Cells Secreting Antibody of Predefined Specificity," *Nature* 256(5517):495-497.
Kostelny, S.A. et al. (Mar. 1, 1992). "Formation of a Bispecific Antibody by the Use of Leucine Zippers," *The Journal of Immunology* 148(5):1547-1553.
Kozbor, D. et al. (Dec. 1984). "A Human Hybrid Myeloma for Production of Human Monoclonal Antibodies," *The Journal of Immunology* 133(6):3001-3005.
Kuroda, R. et al. (2007; e-pub. Nov. 27, 2006). "A Novel Compound Heterozygous Mutation in the DAP12 Gene in a Patient with Nasu-Hakola Disease," *J Neurol Sci.* 252(1):88-91.
Labrijn, A.F. et al. (Oct. 2014; e-pub. Sep. 25, 2014). "Controlled Fab-arm exchange for the generation of stable bispecific IgG1," *Nature Protocols* 9(10):2450-2463.
Laird, A.S. et al. (Oct. 13, 2010). "Progranulin is Neurotrophic in Vivo and Protects against a Mutant TDP-43 Induced Axonopathy," *PLOS ONE* 5(10):e13368, seven pages.
Langer, R. (Sep. 28, 1990). "New Methods of Drug Delivery," *Science* 249(4976):1527-1533.
Lartigue, J.D. (Jul. 5, 2012). "Antibody-Drug Conjugates: Guided Missiles Deployed Against Cancerous Cells," OncLive located at www.onclive.com/printer?url=/publications/oncology-live/2012/june-2012/antibody-drug-conjugates-guided-missiles-deployed-against-cancerous-cells>, last visited on Nov. 27, 2018, four pages.
Lavail, M.M. (Jun. 30, 2011). "Retinal Degeneration Rat Model Resource—Availability of P23H and S334ter Mutant Rhodopsin Transgenic Rats and RCS Inbred and RCS Congenic Strains of Rats," University of California, San Francisco, 12 pages.
Lazar, G.A. et al. (Mar. 14, 2006). "Engineered Antibody Fc variants with Enhanced Effector Function," *PNAS* 103(11):4005-4010.

(56) References Cited

OTHER PUBLICATIONS

Lazar, G.A. et al. (Mar. 2007; e-pub. Oct. 31, 2006). "A Molecular Immunology Approach to Antibody Humanization and Functional Optimization," *Molecular Immunol* 44(8):1986-1998.
Lee, C.V. et al. (2004). "Bivalent Antibody Phage Display Mimics Natural Immunoglobulin," *Journal of Immunological Methods* 284(1-2):119-132.
Lee, C.V. et al. (2004). "High-affinity Human Antibodies from Phage-displayed Synthetic Fab Libraries with a Single Framework Scaffold," *Journal of Molecular Biology* 340(5):1073-1093.
Li, F. et al. (Aug. 19, 2011). "Inhibitory Fcγ Receptor Engagement Drives Adjuvant and Anti-Tumor Activities Tumor Activities of Agonistic CD40 Antibodies," *Science* 333(6045):1030-1034.
Li, H. et al. (Feb. 2006). "Optimization of Humanized IgGs in Glycoengineered *Pichia pastoris*," *Nature Biotechnology* 24(2):210-215.
Li, J. et al. (Mar. 7, 2006). "Human Antibodies for Immunotherapy Development Generated via a Human B Cell Hybridoma Technology," *PNAS* 103(10):3557-3562.
Lightle, S. et al. (Mar. 24, 2010; e-published on Jan. 29, 2010). "Mutations Within a Human IgG2 Antibody Form Distinct and Homogeneous Disulfide Isomers but do not Affect Fc Gamma Receptor or C1q Binding," *Protein Science* 19(4):753-762.
Lipovsek, D. et al. (Jul. 2004, e-pub. May 31, 2004). "In-Vitro Protein Evolution by Ribosome Display and mRNA Display," *J. Immunological Methods* 290(1-2):51-67.
Lloyd, C. et al. (Mar. 2009; e-pub. Oct. 29, 2008). "Modelling the Human Immune Response: Performance of a $10^{11}$ Human Antibody Repertoire Against a Broad Panel of Therapeutically Relevant Antigens," *Protein Engineering, Design & Selection* 22(3):159-168.
Lonberg, N. et al. (1995). "Human Antibodies from Transgenic Mice," *International Reviews of Immunology*. 13(1):65-93.
Lonberg, N. et al. (Apr. 28, 1994). "Antigen-Specific Human Antibodies from Mice Comprising Four Distinct Genetic Modifications," *Nature* 368(6474):856-859.
Low, D. et al. (2013). "Animal Models of Ulcerative Colitis and their Application in Drug Research," *Drug Design, Development and Therapy* 7:1341-1357.
Luigi Poliani, P. et al. (2015). "TREM2 Sustains Microglial Expansion During Aging and Response to Demyelination," *J Clin Invest*. 125(5):2161-2170.
Ma, J. et al. (Apr. 2015; e-pub. Jul. 23, 2014). "TYROBP in Alzheimer's Disease," *Mol. Neurobiol*. 51(2):820-826.
Malm, T.M. et al. (Jan. 2015; e-pub. Nov. 18, 2014). "The Evolving Biology of Microglia in Alzheimer's Disease," *Neurotherapeutics* 12(1):81-93.
Marks, J.D. et al. (1991). "By-passing immunization: Human antibodies from V-gene libraries displayed on phage," *Journal of Molecular Biology* 222(3): 581-597.
Marks, J.D. et al. (Jul. 1992)."By-Passing Immunization: Building High Affinity Human Antibodies by Chain Shuffling," *Bio/Technology* 10(7):779-782.
Martens, L.H. et al. (Nov. 2012; e-pub. Oct. 8, 2012). "Progranulin Deficiency Promotes Neuroinflammation and Neuron Loss Following Toxin-Induced Injury," *The Journal of Clinical Investigation* 122(11):3955-3959.
Mather, J.P. (Aug. 1980). "Establishment and Characterization of Two Distinct Mouse Testicular Epithelial Cell Lines," *Biology of Reproduction* 23(1):243-252.
Mather, J.P. et al. (1982). "Culture of Testicular Cells in Hormone-Supplemented Serum-Free Medium," *Annals of the New York Academy of Sciences, Testicular Cell Culture* 383:44-68.
Mccafferty, J. et al. (Dec. 6, 1990). "Phage Antibodies: Filamentous Phage Displaying Antibody Variable Domains," *Nature* 348(6301):552-554.
McEarchern, J.A. et al. (Feb. 1, 2007). "Engineered Anti-CD70 Antibody with Multiple Effector Functions Exhibits in Vitro and in Vivo Antitumor Activities," *Blood* 109(3):1185-1192.
Melchior, B. et al. (Jul. 12, 2010). "Dual Induction of TREM2 and Tolerance-Related Transcript, Tmem176b, in amyloid transgenic Mice: Implications for Vaccine-Based therapies for Alzheimer's Disease," *ASN Neuro* 2(3) e0037:157-170.
Milstein, C. et al. (Oct. 6, 1983). "Hybrid Hybridomas and Their Use in Immunohistochemistry," *Nature* 305(5934):537-540.
Mizoguchi, A. (2012). "Animal Models of Inflammatory Bowel Disease," *Progress in Molecular Biology and Translational Science* 105:263-320, fifty eight pages.
Morimoto, K. et al. (1992). "Single-Step Purification of F(ab')$_2$ Fragments of Mouse Monoclonal Antibodies (Immunoglobulins G1) by Hydrophobic Interaction High Performance Liquid Chromatography Using TSKgel Phenyl-5PW," *Journal of Biochemical and Biophysical Methods* 24(1-2):107-117.
Morrison, S.L. (Apr. 28, 1994). "Success in Specification," *Nature* 368(6474):812-813.
Morrison, S.L. et al. (Nov. 1984). "Chimeric Human Antibody Molecules: Mouse Antigen-binding Domains with Human Constant Region Domains," *Proc. Nat'l Acad. Sci* 81(21):6851-6855.
Munson, P.J. et al. (Sep. 1, 1980). "Ligand: A Versatile Computerized Approach for Characterization of Ligand-binding Systems," *Analytical Biochemistry* 107:220-239.
N.N., "Datasheet: anti-TREM-2 monoclonal antibody clone 78," Online catalogue Merck, Jan. 1, 2016 (Jan. 1, 2016), pp. 1-3, located at https://www.merckmillipore.com/DE/en/product/Anti-TREM-2-Antibody%2C-clone-78,MMNF-MABN755, three pages.
Naidoo, J. et al. (Dec. 9, 2014; e-pub. Sep. 11, 2014). "Immune Modulation for Cancer Therapy," *British Journal of Cancer* 111(12):2214-2219.
Nair, D.T. et al. (Mar. 1, 2002). "Epitome Recognition by Diverse Antibodies Suggests Conformational Convergence in an Antibody Response," *J Immunol*. 168(5):2371-2382.
Naito, K. et al. (2000). "Calicheamicin-Conjugated Humanized Anti-CD33 Monoclonal Antibody (gemtuzumab zogamicin, CMA-676) Shows Cytocidal effect on CD33-Positive Leukemia Cell Lines, But is Inactive on P-glycoprotein-Expressing sublines," *Leukemia* 14(8):1436-1443.
Nakamura, K. et al. (2007)."Intracellular Sortilin Expression Pattern Regulates proNGF-Induced Naturally Occurring Cell Death during Development," *Cell Death and Differentiation* 14(8):1552-1554.
Neary, D. et al. (Dec. 1998). "Frontotemporal Lobar Degeneration: A Consensus on Clinical Diagnostic Criteria," *Neurology* 51(6):1546-1554.
Neuberger, M. (Jul. 1996). "Generating High-Avidity Human Mabs in Mice," *Nature Biotechnology* 14(7):826, one page.
Neumann, H. et al. (Jan. 10, 2013; e-pub. Nov. 14, 2012). "Variant TREM2 as Risk Factor for Alzheimer's Disease," *The New England Journal of Medicine* 368(2):182-184.
Neumann, H. et al. (Mar. 2007; e-pub. Jan. 18, 2007). "Essential Role of the Microglial Triggering Receptor Expressed on Myeloid Cells-2 (TREM2) for Central Nervous Tissue Immune Homeostasis," *Journal of Neuroimmunology* 184(1-2):92-99.
Neumann, M. et al. (Oct. 2007). "TDP-43 Proteinopathy in Frontotemporal Lobar Degeneration and Amyotrophic Lateral Sclerosis," *Arch Neurol*. 64(10):1388-1394.
Novack, D.V. et al. (2008, e-pub. Oct. 15, 2007). "The Osteoclast: Friend or Foe?," *Annu. Rev. Pathol. Mech. Dis*. 3:457-484.
Nykjaer, A. et al. (2005, e-pub. Jan. 26, 2005). "p75$^{NTR}$—Live or Let Die," *Current Opinion in Neurobiology* 15(1):49-57.
Nykjaer, A. et al. (Feb. 26, 2004). "Sortilin is Essential for proNGF Induced Neuronal Cell Death," *Nature* 427(6977):843-848.
Oganesyan, V. et al. (Jun. 2008). "Structural characterization of a Human Fc Fragment Engineered for Lack of Effector Functions," *Acta Crystallography* 64(6):700-704.
Otero, K. et al. (2012; e-published on Feb. 6, 2012). "TREM2 and β-Catenin Regulate Bone Homeostasis by Controlling the Rate of Osteoclastogenesis,"*J Immunol* 188(6):2612-2621.
Otero, K. et al. (Jul. 2009; e-pub. Jun. 7, 2009). "Macrophage Colony-Stimulating Factor Induces the Proliferation and Survival of Macrophages via a Pathway Involving DAP12 and β-Catenin," *Nat Immunol*. 10(7):734-743.
Paloneva, J. et al. (Aug. 18, 2003). "DAP12/TREM2 Deficiency Results in Impaired Osteoclast Differentiation and Osteoporotic Features," *The Journal of Experimental Medicine* 198(4):669-675.

(56) References Cited

OTHER PUBLICATIONS

Paloneva, J. et al. (Sep. 2002; e-pub. Jun. 21, 2002). "Mutations in Two Genes Encoding Different Subunits of a Receptor Signaling Complex Result in an Identical Disease Phenotype," *American Journal of Human Genetics* 71(3):656-662.
Park, M. et al. (Jan. 2015). "Triggering Receptor Expressed on Myeloid Cells 2 (TREM2) Promotes Adipogenesis and Diet-Induced Obesity," *Diabetes* 64(1):117-127.
Peng, Q. et al. (May 18, 2010). "TREM2- and DAP12-Dependent Activation of PI3K Requires DAP10 and Is Inhibited by SHIP1," *Science Signaling* 3(122):ra38, pp. 1-15.
Pennesi, M.E. et al. (Aug. 2012). "Animal Models of Age Related Macular Degeneration," *Molecular Aspects of Medicine* 33(4):487-509, forty pages.
Peters, S.J. et al. (Jul. 13, 2012). "Engineering an Improved IgG4 Molecule with Reduced Disulfide Bond Heterogeneity and Increased Fab Domain Thermal Stability," *The Journal of Biological Chemistry* 287(29):24525-24533.
Piccio, L. et al. (May 2007). "Blockade of TREM-2 Exacerbates Experimental Autoimmune Encephalomyelitis," *European Journal of Immunology* 37(5):1290-1301.
Plückthun, A. (Dec. 1992). "Mono- and Bivalent Antibody Fragments Produced in *Escherichia coli*: Engineering, Folding and Antigen Binding," *Immunological Reviews* 130:151-188.
Poliani, P.L. et al. (May 2015). "TREM2 Sustains Microglial Expansion During Aging and Response to Demyelination," *J. Clin. Invest.* 125(5):2161-2170.
Presta, L.G. (1992). "Antibody Engineering," *Current Opinion in Structural Biology* 2:593-596.
Presta, L.G. et al. (Sep. 1, 1993). "Humanization of an Antibody Directed Against IgE," *The Journal of Immunology* 151(5):2623-2632.
Provenzano, M.J. (2008). "p75NTR and Sortilin Increase After Facial Nerve Injury," *Laryngoscope* 118(1):87-93.
Radaev, S. et al. (Dec. 2003). "Crystal Structure of the Human Myeloid Cell Activating Receptor TREM-1," *Structure* 11(12):1527-1535.
Rajagopalan, P. et al. (Oct. 17, 2013). "TREM2 Risk Variant and Loss of Brain Tissue," *N Engl J Med* 369(16):1565-1567.
Ratnavalli, E. et al. (Jun. 2002). "The Prevalence of Frontotemporal Dementia," *Neurology* 58(1 of 2):1615-1621.
Ravetch, J.V. et al. (1991). "Fc Receptors," *Annual Review Immunology* 9:457-492.
Rayaprolu, S. et al. (Jun. 21, 2013). "TREM2 in neurodegeneration: evidence for association of the p.R47H variant with frontotemporal dementia and Parkinson's disease," *Mol Neurodegener.* 8:19, pp. 1-5.
Reddy, M.P. et al. (2000). "Elimination of Fc Receptor-Dependent Effector Functions of a Modified IgG4 Monoclonal Antibody to Human CD4," *The Journal of Immunology* 164(4):1925-1933.
Ricart, A.D. (Oct. 15, 2011). "Antibody-Drug Conjugates of Calicheamicin Derivative: Gemtuzumab Ozogamicin and Inotuzumab Ozogamicin," *Clin Cancer Res* 17(20):6417-6427.
Riechmann, L. et al. (Mar. 24, 1988). "Reshaping Human Antibodies for Therapy," *Nature* 332(6162):323-327.
Rizo, J. et al. (1992). "Constrained Peptides: Models of Bioactive Peptides and Protein Substructures," *Ann Rev Biochem.* 61:387-418.
Roberts, R.W. et al. (Nov. 1997). "RNA-Peptide Fusions for the in vitro Selection of Peptides and Proteins," *Proc Natl Acad Sci* 94(23):12297-12302.
Rosok, M.J. et al. (Sep. 13, 1996). "Combinatorial Library Strategy for the Rapid Humanization of Anticarcinoma BR96 Fab," *The Journal of Biological Chemistry* 271(37):22611-22618.
Sazinsky, S.L. et al. (Dec. 23, 2008). "Aglycosylated Immunoglobulin G1 Variants Productively Engage Activating Fc Receptors," *PNAS* 105(51):20167-20172.
Schabbauer, G. et al. (Jul. 2010). "Myeloid PTEN Promotes Inflammation but Impairs Bactericidal Activities During Murine Pneumococcal Pneumonia," *The Journal of Immunology* 185(1):468-476.

Schaffitzel, C. et al. (Dec. 10, 1999). "Ribosome Display: An In Vitro Method for Selection and Evolution of Antibodies From Libraries," *J. Immunolical Methods* 231(1-2):119-135.
Schier, R. et al. (1996). "Identification of Functional and Structural Amino-Acid Residues by Parsimonious Mutagenesis," *Gene* 169(2):147-155.
Schleinitz, N. et al. (Jul. 16, 2009). "Pattern of DAP12 Expression in Leukocytes from Both Healthy and Systemic Lupus Erythematosus Patients," *PLoS ONE* 4(7):e6264, pp. 1-7.
Schymick, J.C. et al. (Jul. 2007). "Progranulin Mutations and Amyotrophic Lateral Sclerosis or Amyotrophic Lateral Sclerosis—Frontotemporal Dementia Phenotypes," *Journal of Neurology, Neurosurgery and Psychiatry* 78(7):754-756.
Seno, H. et al. (Jan. 6, 2009). "Efficient Colonic Mucosal Wound Repair Requires Trem2 Signaling," *PNAS* 106(1):256-261.
Shalaby, M.F. et al. (Jan. 1992). "Development of Humanized Bispecitic Antibodies Reactive with Cytotoxic Lymphocytes and Tumor Cells Overexpressing the HER2 Protooncogene," *The Journal of Experimental Medicine* 175(1):217-225.
Sharif, O. et al. (2008; e-pub. Sep. 7, 2008). "From Expression to Signaling: Roles of TREM-1 and TREM-2 in Innate Immunity and Bacterial Infection," *Immunobiology* 213(9-10):701-713.
Sharif, O. et al. (Jun. 12, 2014). "The Triggering Receptor Expressed on Myeloid Cells 2 Inhibits Complement Component 1 q Effector Mechanisms and Exerts Detrimental Effects during Pneumococcal Pneumonia," *PLoS Pathogen* 10(6):e1004167, sixteen pages.
Sheriff, S. et al. (Sep. 1996). "Redefining the Minimal Antigen-binding Fragment," *Nature Structural & Molecular Biology* 3(9):733-736.
Shields, R.L. et al. (Mar. 2, 2001). "High Resolution Mapping of the Binding Site on Human IgG1 for FcγRI, FcγRII, FcγRIII, and FcRn and Design of IgG1 Variants with Improved Binding to the FcγR," *The Journal of Biological Chemistry* 276(9):6591-6604.
Sidhu, S.S. et al. (Apr. 2004). "Phage-displayed Antibody Libraries of Synthetic Heavy Chain Complementarity Determining Regions," *Journal of Molecular Biology* 338(2):299-310.
Sieber, M.W. et al. (Jan. 3, 2013). "Attenuated Inflammatory Response in Triggering Receptor Expressed on Myeloid Cells 2 (TREM2) Knock-Out Mice following Stroke," *PLoS ONE* 8(1):e52982, ten pages.
Siegel, R.W. et al. (Mar. 2004). "High Efficiency Recovery and Epitope-Specific Sorting of an scFv Yeast Display Library," *Journal of Immunological Methods* 286(1-2):141-153.
Sims, M.J. et al. (Aug. 15, 1993). "A Humanized CD18 Antibody Can Block Function Without Cell Destruction," *The Journal of Immunology* 151(4):2296-2308.
Skerra, A. (1993). "Bacterial Expression of Immunoglobulin Fragments," *Current Opinion in Immunology* 5:256-262.
Sollid, L.M. et al. (Sep. 2008). "Animal Models of Inflammatory Bowel Disease at the Dawn of the New Genetics Era," *PLoS Med* 5(9)(e198):1338-1342.
Stefano, L. et al. (Jul. 2009; e-pub. Apr. 29, 2009). "The Surface-Exposed Chaperone. Hsp60, is an Agonist of the Microglial TREM2 Receptor," *Journal of Neurochemistry* 110(1):284-294.
Streit, W.J. et al. (2004). "Dystrophic Microglia in the Aging Human Brain," *GLIA* 45:208-212.
Streit, W.J. et al. (2009; e-pub. Jun. 10, 2009). "Dystrophic (Senescent) Rather than Activated Microglial Cells are Associated with Tau Pathology and Likely Precede Neurodegeneration in Alzheimer's Disease," *Acta Neuropathol* 118:475-485.
Strohl, W.R. (2009; e-published on Nov. 4, 2009). "Optimization of Fc-mediated Effector Functions of Monoclonal Antibodies," *Current Opinion in Biotechnology* 20(6):685-691.
Sudduth, T. L. et al. (Jun. 5, 2013). "Intracranial Injection of Gammagard, a Human IVIg, Modulates the Inflammatory Response of the Brain and Lowers Aβ in APP/PS1 Mice Along a Different Time Course than Anti-Aβ Antibodies," *J. Neurosc* 33(23):9684-9692.
Sun, M. et al. (May 2013). "TREM-2 Promotes Host Resistance Against *Pseudomonas aeruginosa* Infection by Suppressing Corneal Inflammation via a PI3K/Akt Signaling Pathway," *Investigative Ophthalmology & Visual Science* 54(5):3451-3462.

(56) References Cited

OTHER PUBLICATIONS

Suresh, M.R. et al. (1986). "Bispecific Monoclonal Antibodies from Hybrid Hybridomas," *Methods in Enzymology* 121:210-228.
Takahashi, K. et al. (Apr. 10, 2007). "TREM2-Transduced Myeloid Precursors Mediate Nervous Tissue Debris Clearance and Facilitate Recovery in an Animal Model of Multiple Sclerosis," *Plos Med* 4(4):e124, pp. 0675-0689.
Takahashi, K. et al. (Feb. 21, 2005). "Clearance of Apoptotic Neurons Without Inflammation by Microglial Triggering Receptor Expressed on Myeloid Cells-2," *Journal of Experimental Medicine* 201(4):647-657.
Takai, T. et al. (Feb. 11, 1994). "FcR γ Chain Deletion Results in Pleiotrophic Effector Cell Defects," *Cell* 76(3):519-529.
Takaki, R. et al. (Dec. 2006). "DAP12: An Adapter Protein with Dual Functionality," *Immunological Reviews* 214:118-129.
Tanaka, Y. et al. (2013). "Exacerbated Inflammatory Responses Related to Activated Microglia After Traumatic Brain Injury in Progranulin-Deficient Mice," *Neuroscience* 231:49-60.
Teng, H.K. et al. (Jun. 1, 2005). "ProBDNF Induces Neuronal Apoptosis via Activation of a Receptor Complex of $p75^{NTR}$ and Sortilin," *The Journal of Neuroscience* 25(22):5455-5463.
Thornton, P. et al. (Oct. 2017; e-pub. Aug. 30, 2017). "TREM2 Shedding by Cleavage at the H157-S158 Bond is Accelerated for the Alzheimer's Disease-Associated H157Y Variant," *EMBO Molecular Medicine* 9(10):1366-1378.
Traunecker, A. et al. (1991). "Bispecific Single Chain Molecules (Janusins) Target Cytotoxic Lymphocytes on HIV Infected Cells," *The EMBO Journal* 10(12):3655-3659.
Tsenter, J. et al. (Apr. 2008). "Dynamic Changes in the Recovery After Traumatic Brain Injury in Mice: Effect of Injury Severity on T2-Weighted MRI Abnormalities, and Motor and Cognitive Functions," *J. Neurotrauma* 25(4):324-333.
Turnbull, I.R. et al. (Feb. 2007; e-pub. Jan. 15, 2007). "Activating and Inhibitory Functions of DAP12," *Nature Reviews Immunology* 7(2):155-161.
Turnbull, I.R. et al. (Sep. 15, 2006). "Cutting Edge: TREM-2 Attenuates Macrophage Activation," *The Journal of Immunology* 177(6):3520-3524.
Tutt, A. et al. (Jul. 1, 1991). "Trispecific F(ab')$_3$ Derivatives that Use Cooperative Signaling Via the TCR/CD3 Complex and CD2 to Activate and Redirect Resting Cytotoxic T Cells1," *The Journal of Immunology* 147(1):60-69.
Ulland, T.K. et al. (Aug. 10, 2017). "TREM2 Maintains Microglial Metabolic Fitness in Alzheimer's Disease," *Cell* 170(4):649-663.
Ulland, T.K. et al. (Dec. 2015). "Regulation of Microglial Survival and Proliferation in Health and Diseases," *Semin Immunol.* 27(6):410-415, twelve pages.
Urlaub, G. et al. (Jul. 1980). "Isolation of Chinese Hamster Cell Mutants Deficient in Dihydrofolate Reductase Activity," *Proc. Natl. Acad. Sci.* 77(7):4216-4220.
Van Dijk, M.A et al. (2001)."Human Antibodies as Next Generation Therapeutics," *Current Opinion in Chemical Biology* 5:368-374.
Vaswani, S.K. et al. (Aug. 1998). "Humanized Antibodies as Potential Therapeutic Drugs," *Annals of Allergy, Asthma & Immunology* 81(2):105-119.
Verhoeyen, M. et al. (1988). "Reshaping Human Antibodies: Grafting an Antilysozyme Activity," *Science* 239:1534-1536.
Vetrano, S. et al. (2008). "Unique Role of Junctional Adhesion Molecule-A in Maintaining Mucosal Homeostasis in Inflammatory Bowel Disease," *Gastroenterology* 135(1):173-184.
Vincent K.J. et al. (Dec. 2012). "Current Strategies in Antibody Engineering: Fc Engineering and pH-Dependent Antigen Binding, Bispecific Antibodies and Antibody Drug Conjugates," *Biotechnol J.* 7(12):1444-1450.
Volosin, M. et al. (Jul. 19, 2006). "Interaction of Survival and Death Signaling in Basal Forebrain Neurons: Roles of Neurotrophins and Proneurotrophins," *The Journal of Neuroscience* 26(29):7756-7766.
Volosin, M. et al. (Sep. 24, 2008). "Induction of Proneurotrophins and Activation of P75ntr-Mediated Apoptosis Via Neurotrophin Receptor-Interacting Factor in Hippocampal Neurons After Seizures," *The Journal of Neuroscience* 28(39):9870-9879, twenty five pages.
Wang, Y. et al. (Mar. 12, 2015; e-published on Feb. 26, 2015). "TREM2 Lipid Sensing Sustains the Microglial Response in an Alzheimer's Disease Model," *Cell* 160(6):1061-1071.
Wark, K.L. et al. (Aug. 7, 2006; e-pub. May 22, 2006). "Latest Technologies for the Enhancement of Antibody Affinity," *Advanced Drug Delivery Reviews* 58(5-6):657-670.
Waterhouse, P. et al. (1993). "Combinatorial Infection and In Vivo Recombination: A Strategy for Making Large Phage Antibody Repertoires," *Nucleic Acids Research* 21(9):2265-2266.
Wei, Y. et al. (2007). "Enhanced Protein Expressions of Sortilin and $p75^{NTR}$ in Retina of Rat Following Elevated Intraocular Pressure-Induced Retinal Ischemia," *Neuroscience Letters* 429(2-3):169-174.
White, A.L. et al. (Jan. 12, 2015). "Conformation of the Human Immunoglobulin G2 Hinge Imparts Superagonistic Properties to Immunostimulatory Anticancer Antibodies," *Cancer Cell* 27(1):138-148.
White, A.L. et al. (May 2013; e-pub. Mar. 31, 2013). "FcγRIIB Controls the Potency of Agonistic Anti-TNFR mAbs," *Cancer Immunol. Immunother.* 62(5):941-948.
Whittaker, G.C. et al. (Jan. 29, 2010; e-pub. Nov. 30, 2009). "The Linker for Activation of B Cells (LAB)/Non-T Cell Activation Linker (NTAL) Regulates Triggering Receptor Expressed on Myeloid Cells (TREM)-2 Signaling and Macrophage Inflammatory Responses Independently of the Linker for Activation of T Cells," *The Journal of Biological Chemistry* 285(5):2976-2985.
Wilcock, D.M. et al. (Dec. 8, 2004). "Passive Immunotherapy Against Aβ in Aged APP-Transgenic Mice Reverses Cognitive Deficits and Depletes Parenchymal Amyloid Deposits in Spite of Increased Vascular Amyloid and Microhemorrhage," *J. Neuroinflammation* 1(1): 24, 11 pages.
Wilcock, D.M. et al. (Feb. 2004). "Microglial activation facilitates Aβ plaque removal following intracranial anti-Aβ antibody administration," *Neurobiology of Disease* 15(1):11-20.
Wilcock, D.M. et al. (May 1, 2003). "Intracranially Administered Anti-Aβ Antibodies Reduce β-Amyloid Deposition by Mechanisms Both Independent of and Associated with Microglial Activation," *J Neurosci* 23(9):3745-3751.
Wilkinson, I.C. et al. (2013). "Monovalent IgG4 Molecules: Immunoglobulin Fc Mutations that Result in a Monomeric Structure," *mAbs* 5(3):406-417.
Wilson, N.S. et al. (Jan. 18, 2011). "An Fcγ Receptor-Dependent Mechanism Drives Antibody-Mediated Target-Receptor Signaling in Cancer Cells," *Cancer Cell* 19(1):101-113.
Xu, D. et al. (2000). "In Vitro Characterization of Five Humanized OKT3 Effector Function Variant Antibodies," *Cellular Immunology* 200(1):16-26.
Xu, J. et al. (Jul. 2000). "Diversity in the CDR3 Region of $V_H$ Is Sufficient for Most Antibody Specificities," *Immunity* 13(1):37-45.
Xu, Y. et al. (Oct. 2013). "Addressing Polyspecificity of Antibodies Selected from an in Vitro Yeast presentation system: a FACS-based, High-throughput Selection and Analytical Tool," *Protein Engineering, Design & Selection* 26(10):663-670.
Yano, H. et al. (Nov. 25, 2009)."Proneurotrophin-3 Is a Neuronal Apoptotic Ligand: Evidence for Retrograde-Directed Cell Killing," *The Journal of Neuroscience* 29(47):14790-14802.
Yelton, D.E. et al. (1995). "Affinity maturation of the BR96 anti-carcinoma antibody by codon-based mutagenesis," *The Journal of Immunology* 155(4):1994-2004.
Yin, F. et al. (Jan. 18, 2010; e-pub. Dec. 21, 2009). "Exaggerated Inflammation, Impaired Host Defense, and Neuropathology in Progranulin-Deficient Mice," *J. Exp. Med.* 207(1):117-128.
Zapata, G. et al. (1995). "Engineering Linear F(ab')$_2$ Fragments for Efficient Production in *Escherichia coli* and Enhanced Antiproliferative Activity," *Protein Engineering Designs and Selections* 8(10):1057-1062.
Zhang, B. et al. (Apr. 25, 2013). "Integrated Systems Approach Identifies Genetic Nodes and Networks in Late-Onset Alzheimer's Disease," *Cell* 153(3):707-720.

(56) References Cited

OTHER PUBLICATIONS

Zhao, Y. (2013). "TREM-2 (B-3): sc-373828," Santa Cruz Biotechnology, Inc., Located at datasheets.scbt.com/sc-373828.pdf>, one page.
Zhao, Y. et al. (Apr. 17, 2013). "Regulation of TREM2 Expression by an NF-κB-Sensitive miRNA-34a," *Neuroreport* 24(16):318-323, twelve pages.
Zheng, H. et al. (Feb. 15, 2017; e-pub. Jan. 11, 2017). "TREM2 Promotes Microglial Survival by Activating Wnt/β-Catenin Pathway," *J Neurosci.* 37(7):1772-1784.
Zhu, Y. et al. (Sep. 15, 2014, e-pub. Jul. 31, 2014). "CSF1/CSF1 R Blockade Reprograms Tumor-Infiltrating Macrophages and Improves Response to T Cell Checkpoint Immunotherapy in Pancreatic Cancer Models," *Cancer Research* 74(18):5057-5069.
European Search Report (Partial) dated Mar. 6, 2018 for EP Application No. 15830235.6 filed on Aug. 8, 2015, six pages.
European Search Report and Search Opinion dated Jun. 18, 2018 for EP Application No. 15830235.6 filed on Aug. 8, 2015, fourteen pages.
International Preliminary Report on Patentability dated Apr. 19, 2018 for PCT Application No. PCT/US2016/055828 filed on Oct. 6, 2016, twelve pages.
International Preliminary Report on Patentability dated Feb. 23, 2017 for PCT Patent Application No. PCT/US2015/044396, filed on Aug. 8, 2015, nine pages.
International Search Report and Written Opinion dated Dec. 10, 2018 for PCT Application No. PCT/US2018/045068, filed on Aug. 2, 2018, twenty four pages.
International Search Report and Written Opinion dated Jun. 3, 2016 for PCT Patent Application No. PCT/US2015/044396, filed on Aug. 8, 2015, thirteen pages.
International Search Report dated Mar. 31, 2017 for PCT Application No. PCT/US2016/055828 filed on Oct. 6, 2016, nine pages.
Invitation to Pay Additional Fees and, where Applicable Protest Fee dated Feb. 8, 2017 for PCT Patent Application No. PCT/US2016/055828, filed on Oct. 6, 2016, twelve pages.
Invitation to Pay Additional Fees and, where Applicable Protest Fee dated Mar. 28, 2016 for PCT Patent Application No. PCT/US2015/044396, filed on Aug. 8, 2015, three pages.
Invitation to Pay Additional Fees and, where Applicable Protest Fee dated Oct. 10, 2018 for PCT Patent Application No. PCT/US2018/045068, filed on Aug. 2, 2018, fifteen pages.
Singaporean Search Report and Written Opinion dated Apr. 5, 2018, for SG Application No. 11201700901S filed on Feb. 6, 2017, thirteen pages.
Singaporean Search Report and Written Opinion dated Jan. 7, 2019, for SG Application No. 11201802114S filed on Mar. 14, 2018, fourteen pages.
Written Opinion of the International Searching Authority dated Mar. 31, 2017 for PCT Application No. PCT/US2016/055828 filed on Oct. 6, 2016, ten pages.
U.S. Appl. No. 15/766,363, filed Apr. 5, 2018 by Shwabe et al. (Copy not submitted herewith pursuant to the waiver of 37 C.F.R. § 1.98(a)(2)(iii) issued by the Office on Sep. 21, 2004).

* cited by examiner

SEQUENCE LISTING

<160> NUMBER OF SEQ ID NOS: 218

<210> SEQ ID NO 1
<211> LENGTH: 230
<212> TYPE: PRT
<213> ORGANISM: Homo sapiens

<400> SEQUENCE: 1

Met Glu Pro Leu Arg Leu Leu Ile Leu Leu Phe Val Thr Glu Leu Ser
1               5                   10                  15

Gly Ala His Asn Thr Thr Val Phe Gln Gly Val Ala Gly Gln Ser Leu
            20                  25                  30

Gln Val Ser Cys Pro Tyr Asp Ser Met Lys His Trp Gly Arg Arg Lys
        35                  40                  45

Ala Trp Cys Arg Gln Leu Gly Glu Lys Gly Pro Cys Gln Arg Val Val
50                  55                  60

Ser Thr His Asn Leu Trp Leu Leu Ser Phe Leu Arg Arg Trp Asn Gly
65                  70                  75                  80

Ser Thr Ala Ile Thr Asp Asp Thr Leu Gly Gly Thr Leu Thr Ile Thr
                85                  90                  95

Leu Arg Asn Leu Gln Pro His Asp Ala Gly Leu Tyr Gln Cys Gln Ser
                100                 105                 110

Leu His Gly Ser Glu Ala Asp Thr Leu Arg Lys Val Leu Val Glu Val
            115                 120                 125

Leu Ala Asp Pro Leu Asp His Arg Asp Ala Gly Asp Leu Trp Phe Pro
130                 135                 140

Gly Glu Ser Glu Ser Phe Glu Asp Ala His Val Glu His Ser Ile Ser
145                 150                 155                 160

Arg Ser Leu Leu Glu Gly Glu Ile Pro Phe Pro Pro Thr Ser Ile Leu
                165                 170                 175

Leu Leu Leu Ala Cys Ile Phe Leu Ile Lys Ile Leu Ala Ala Ser Ala
                180                 185                 190

Leu Trp Ala Ala Ala Trp His Gly Gln Lys Pro Gly Thr His Pro Pro
        195                 200                 205

Ser Glu Leu Asp Cys Gly His Asp Pro Gly Tyr Gln Leu Gln Thr Leu
210                 215                 220

Pro Gly Leu Arg Asp Thr
225                 230

<210> SEQ ID NO 2
<211> LENGTH: 227
<212> TYPE: PRT
<213> ORGANISM: Mus musculus

<400> SEQUENCE: 2

Met Gly Pro Leu His Gln Phe Leu Leu Leu Ile Thr Ala Leu Ser
1               5                   10                  15

Gln Ala Leu Asn Thr Thr Val Leu Gln Gly Met Ala Gly Gln Ser Leu
                20                  25                  30

Arg Val Ser Cys Thr Tyr Asp Ala Leu Lys His Trp Gly Arg Arg Lys
            35                  40                  45

Ala Trp Cys Arg Gln Leu Gly Glu Glu Gly Pro Cys Gln Arg Val Val
50                  55                  60

Ser Thr His Gly Val Trp Leu Leu Ala Phe Leu Lys Lys Arg Asn Gly
65                  70                  75                  80

Ser Thr Val Ile Ala Asp Asp Thr Leu Ala Gly Thr Val Thr Ile Thr
                85                  90                  95

Leu Lys Asn Leu Gln Ala Gly Asp Ala Gly Leu Tyr Gln Cys Gln Ser
                100                 105                 110

Leu Arg Gly Arg Glu Ala Glu Val Leu Gln Lys Val Leu Val Glu Val
            115                 120                 125

Leu Glu Asp Pro Leu Asp Asp Gln Asp Ala Gly Asp Leu Trp Val Pro
130                 135                 140

Glu Glu Ser Ser Ser Phe Glu Gly Ala Gln Val Glu His Ser Thr Ser
145                 150                 155                 160

Arg Asn Gln Glu Thr Ser Phe Pro Pro Thr Ser Ile Leu Leu Leu Leu
                165                 170                 175

Ala Cys Val Leu Leu Ser Lys Phe Leu Ala Ala Ser Ile Leu Trp Ala
                180                 185                 190

Val Ala Arg Gly Arg Gln Lys Pro Gly Thr Pro Val Val Arg Gly Leu
        195                 200                 205

Asp Cys Gly Gln Asp Ala Gly His Gln Leu Gln Ile Leu Thr Gly Pro
    210                 215                 220

Gly Gly Thr
225

<210> SEQ ID NO 3
<211> LENGTH: 228
<212> TYPE: PRT
<213> ORGANISM: Rattus norvegicus

<400> SEQUENCE: 3

Met Glu Pro Leu His Val Phe Val Leu Leu Val Thr Glu Leu Ser
1               5                   10                  15

Gln Ala Leu Asn Thr Thr Val Leu Gln Gly Val Ala Gly Gln Ser Leu
            20                  25                  30

Arg Val Ser Cys Thr Tyr Asp Ala Leu Arg His Trp Gly Arg Arg Lys
        35                  40                  45

Ala Trp Cys Arg Gln Leu Ala Glu Gly Pro Cys Gln Arg Val Val
    50                  55                  60

Ser Thr His Gly Val Trp Leu Leu Ala Phe Leu Arg Lys Gln Asn Gly
65                  70                  75                  80

Ser Thr Val Ile Thr Asp Asp Thr Leu Ala Gly Thr Val Thr Ile Thr
                    85                  90                  95

Leu Arg Asn Leu Gln Ala Gly Asp Ala Gly Leu Tyr Gln Cys Gln Ser
            100                 105                 110

Leu Arg Gly Arg Glu Ala Glu Val Leu Gln Lys Val Val Val Glu Val
        115                 120                 125

Leu Glu Asp Pro Leu Asp Asp Gln Asp Ala Gly Asp Leu Trp Val Pro
    130                 135                 140

Glu Glu Ser Glu Ser Phe Glu Gly Ala Gln Val Glu His Ser Thr Ser
145                 150                 155                 160

Ser Gln Val Ser Ser Cys Gly Ser Pro Leu Thr Tyr His Leu Pro Pro
                    165                 170                 175

Lys Glu Pro Ile Arg Lys Asp Leu Leu Pro Thr His Phe His Ser Ser
            180                 185                 190

Pro Pro Gly Leu Cys Pro Pro Glu Gln Ala Ser Tyr Ser Gln His Pro
        195                 200                 205

Leu Gly Cys Gly Gln Gly Gln Ala Glu Ala Gly Asp Thr Cys Gly Gln
    210                 215                 220

Trp Ala Arg Leu
225

<210> SEQ ID NO 4
<211> LENGTH: 260
<212> TYPE: PRT
<213> ORGANISM: Macaca mulatta

<400> SEQUENCE: 4

Met Pro Asp Pro Leu Phe Ser Ala Val Gln Gly Lys Asp Lys Ile Leu
1               5                   10                  15

His Lys Ala Leu Cys Ile Cys Pro Trp Pro Gly Lys Gly Gly Met Glu
            20                  25                  30

Pro Leu Arg Leu Leu Ile Leu Leu Phe Ala Thr Glu Leu Ser Gly Ala
        35                  40                  45

```
His Asn Thr Thr Val Phe Gln Gly Val Glu Gly Gln Ser Leu Gln Val
    50                  55                  60

Ser Cys Pro Tyr Asp Ser Met Lys His Trp Gly Arg Arg Lys Ala Trp
65                  70                  75                  80

Cys Arg Gln Leu Gly Glu Lys Gly Pro Cys Gln Arg Val Val Ser Thr
                85                  90                  95

His Asn Leu Trp Leu Leu Ser Phe Leu Arg Arg Asn Gly Ser Thr
                100                 105                 110

Ala Ile Thr Asp Asp Thr Leu Gly Gly Thr Leu Thr Ile Thr Leu Arg
            115                 120                 125

Asn Leu Gln Pro His Asp Ala Gly Phe Tyr Gln Cys Gln Ser Leu His
    130                 135                 140

Gly Ser Glu Ala Asp Thr Leu Arg Lys Val Leu Val Glu Val Leu Ala
145                 150                 155                 160

Asp Pro Leu Asp His Arg Asp Ala Gly Asp Leu Trp Val Pro Gly Glu
                165                 170                 175

Ser Glu Ser Phe Glu Asp Ala His Val Glu His Ser Ile Ser Arg Ser
                180                 185                 190

Leu Leu Glu Gly Glu Ile Pro Phe Pro Pro Thr Ser Val Leu Leu Leu
            195                 200                 205

Leu Ala Cys Ile Phe Leu Ile Lys Ile Leu Ala Ala Ser Ala Leu Trp
    210                 215                 220

Ala Ala Ala Trp His Gly Gln Lys Pro Gly Thr His Pro Pro Ser Glu
225                 230                 235                 240

Pro Asp Cys Gly His Asp Pro Gly His Gln Leu Gln Thr Leu Pro Gly
                245                 250                 255

Leu Arg Asp Thr
            260

<210> SEQ ID NO 5
<211> LENGTH: 230
<212> TYPE: PRT
<213> ORGANISM: Macaca fascicularis

<400> SEQUENCE: 5

Met Glu Pro Leu Arg Leu Leu Ile Leu Leu Phe Ala Thr Glu Leu Ser
1               5                   10                  15

Gly Ala His Asn Thr Thr Val Phe Gln Gly Val Glu Gly Gln Ser Leu
                20                  25                  30

Gln Val Ser Cys Pro Tyr Asp Ser Met Lys His Trp Gly Arg Arg Lys
            35                  40                  45

Ala Trp Cys Arg Gln Leu Gly Glu Lys Gly Pro Cys Gln Arg Val Val
    50                  55                  60

Ser Thr His Asn Leu Trp Leu Leu Ser Phe Leu Arg Arg Asn Gly
65                  70                  75                  80

Ser Thr Ala Ile Thr Asp Asp Thr Leu Gly Gly Thr Leu Thr Ile Thr
                85                  90                  95

Leu Arg Asn Leu Gln Pro His Asp Ala Gly Phe Tyr Gln Cys Gln Ser
                100                 105                 110

Leu His Gly Ser Glu Ala Asp Thr Leu Arg Lys Val Leu Val Glu Val
            115                 120                 125

Leu Ala Asp Pro Leu Asp His Arg Asp Ala Gly Asp Leu Trp Val Pro
    130                 135                 140

Gly Glu Ser Glu Ser Phe Glu Asp Ala His Val Glu His Ser Ile Ser
```

```
                    145                 150                 155                 160
Arg Ser Leu Leu Glu Gly Glu Ile Pro Phe Pro Pro Thr Ser Val Leu
                165                 170                 175

Leu Leu Leu Ala Cys Ile Phe Leu Ile Lys Ile Leu Ala Ala Ser Ala
                180                 185                 190

Leu Trp Ala Ala Ala Trp His Gly Gln Lys Pro Gly Thr His Pro Pro
            195                 200                 205

Ser Glu Pro Asp Cys Gly His Asp Pro Gly His Gln Leu Gln Thr Leu
210                 215                 220

Pro Gly Leu Arg Asp Thr
225                 230

<210> SEQ ID NO 6
<211> LENGTH: 230
<212> TYPE: PRT
<213> ORGANISM: Equus caballus

<400> SEQUENCE: 6

Met Glu Pro Leu Pro Leu Leu Ile Leu Leu Ser Val Ala Glu Leu Ser
1               5                   10                  15

Arg Gly His Asn Thr Thr Val Phe Gln Gly Thr Ala Gly Arg Ser Leu
                20                  25                  30

Lys Val Ser Cys Pro Tyr Asn Ser Leu Met His Trp Gly Arg Arg Lys
            35                  40                  45

Ala Trp Cys Arg Gln Leu Gly Glu Asp Gly Pro Cys Gln Gln Val Val
        50                  55                  60

Ser Thr His Ser Leu Trp Leu Ser Phe Leu Lys Arg Arg Asn Gly
65                  70                  75                  80

Ser Thr Val Ile Thr Asp Asp Ala Leu Gly Gly Ile Leu Thr Ile Thr
                85                  90                  95

Leu Arg Asn Leu Gln Ala His Asp Ala Gly Phe Tyr Gln Cys Gln Ser
                100                 105                 110

Leu His Gly Gly Glu Ala Asp Thr Leu Arg Lys Val Leu Val Glu Val
            115                 120                 125

Leu Ala Asp Pro Leu Asp His Gln Glu Pro Gly Asp Leu Trp Ile Pro
        130                 135                 140

Lys Glu Ser Glu Ser Phe Glu Asp Ala Gln Val Glu His Ser Ile Ser
145                 150                 155                 160

Arg Ser Leu Val Glu Glu Ile Pro Ser Leu Pro Thr Ser Ile Leu
                165                 170                 175

Leu Leu Leu Ala Cys Ile Phe Leu Ser Lys Leu Leu Ala Ala Ser Ala
                180                 185                 190

Ile Trp Ala Ala Ala Trp His Gly Gln Lys Gln Glu Thr Pro Pro Ala
            195                 200                 205

Ser Glu Pro Asp Arg Gly His Asp Pro Gly Tyr Gln Leu His Thr Leu
210                 215                 220

Thr Gly Glu Arg Asp Thr
225                 230

<210> SEQ ID NO 7
<211> LENGTH: 233
<212> TYPE: PRT
<213> ORGANISM: Sus scrofa

<400> SEQUENCE: 7

Met Glu Thr Leu Gly Leu Leu Leu Leu Leu Trp Val Ala Glu Leu Ser
```

```
  1               5                  10                 15
Arg Ala His Asn Thr Ser Val Phe Gln Gly Thr Ala Gly Gln Ser Leu
                  20                 25                 30

Arg Val Ser Cys Ser Tyr Asn Ser Leu Lys His Trp Gly Arg Arg Lys
                35                 40                 45

Ala Trp Cys Arg Gln Leu Ser Glu Glu Gly Leu Cys Gln His Val Val
         50                 55                 60

Ser Thr His Pro Thr Trp Leu Leu Ser Phe Leu Lys Arg Arg Asn Gly
65                  70                 75                 80

Ser Thr Ala Ile Thr Asp Asp Ala Leu Gly Gly Thr Leu Thr Ile Thr
                  85                 90                 95

Leu Arg Asn Leu Gln Ala His Asp Ala Gly Leu Tyr Gln Cys Gln Ser
                100                105                110

Leu His Gly Ser Glu Ala Asp Thr Leu Lys Lys Val Leu Val Glu Val
                115                120                125

Leu Ala Asp Pro Leu Glu Ser Gln Ser Lys Ser Phe Gln Asp Val Gln
130                135                140

Met Glu His Ser Ile Ser Arg Asn Leu Ser Glu Glu Ser Leu Phe Pro
145                150                155                160

Pro Thr Ser Thr Leu Phe Leu Leu Ala Cys Val Phe Leu Ser Lys Leu
                  165                170                175

Leu Val Ala Ser Ala Leu Trp Ala Ala Ala Trp His Gly His Lys Gln
                180                185                190

Arg Thr Ser Pro Ala Gly Gly Leu Asp Cys Gly Arg Asp Pro Gly Asp
                195                200                205

Gln Asp Gln Thr Leu Thr Asp Glu Leu Gly Glu Ser Ser Asp Gln Asp
                210                215                220

Gln Thr Leu Thr Glu Leu Arg Asp Thr
225                230

<210> SEQ ID NO 8
<211> LENGTH: 230
<212> TYPE: PRT
<213> ORGANISM: Canis familiaris

<400> SEQUENCE: 8

Met Glu Pro Leu Trp Leu Leu Ile Leu Leu Ala Val Thr Glu Leu Ser
1               5                  10                 15

Gly Ala His Asn Thr Thr Val Phe Gln Gly Met Ala Gly Arg Ser Leu
                  20                 25                 30

Gln Val Ser Cys Pro Tyr Asn Ser Leu Lys His Trp Gly Arg Arg Lys
                35                 40                 45

Ala Trp Cys Arg Gln Val Asp Lys Glu Gly Pro Cys Gln Arg Val Val
         50                 55                 60

Ser Thr His Arg Ser Trp Leu Leu Ser Phe Leu Lys Arg Trp Asn Gly
65                  70                 75                 80

Ser Thr Ala Ile Val Asp Asp Ala Leu Gly Gly Thr Leu Thr Ile Thr
                  85                 90                 95

Leu Arg Asn Leu Gln Ala His Asp Ala Gly Leu Tyr Gln Cys Gln Ser
                100                105                110

Leu Tyr Gly Asp Glu Ala Asp Thr Leu Arg Lys Val Leu Val Glu Val
                115                120                125

Leu Ala Asp Pro Leu Asp His Leu Asp Pro Gly Asp Leu Trp Ile Pro
130                135                140
```

-continued

```
Glu Glu Ser Lys Gly Phe Glu Asp Ala His Val Glu Pro Ser Val Ser
145                 150                 155                 160

Arg Ser Leu Ser Glu Glu Ile Pro Phe Pro Pro Thr Ser Ile Leu
            165                 170                 175

Phe Leu Leu Ala Cys Ile Phe Leu Ser Lys Phe Leu Ala Ala Ser Ala
                180                 185                 190

Leu Trp Ala Ala Ala Trp Arg Gly Gln Lys Leu Gly Thr Pro Gln Ala
            195                 200                 205

Ser Glu Leu Asp Cys Ser Cys Asp Pro Gly Tyr Gln Leu Gln Thr Leu
            210                 215                 220

Thr Glu Pro Arg Asp Met
225                 230
```

<210> SEQ ID NO 9
<211> LENGTH: 26
<212> TYPE: PRT
<213> ORGANISM: Artificial Sequence
<220> FEATURE:
<223> OTHER INFORMATION: Synthetic Construct

<400> SEQUENCE: 9

```
Gln Val Gln Leu Val Gln Ser Gly Ala Glu Val Lys Lys Pro Gly Ser
1               5                   10                  15

Ser Val Lys Val Ser Cys Lys Ala Ser Gly
            20                  25
```

<210> SEQ ID NO 10
<211> LENGTH: 26
<212> TYPE: PRT
<213> ORGANISM: Artificial Sequence
<220> FEATURE:
<223> OTHER INFORMATION: Synthetic Construct

<400> SEQUENCE: 10

```
Glu Val Gln Leu Val Gln Ser Gly Ala Glu Val Lys Lys Pro Gly Ser
1               5                   10                  15

Ser Val Lys Val Ser Cys Lys Ala Ser Gly
            20                  25
```

<210> SEQ ID NO 11
<211> LENGTH: 26
<212> TYPE: PRT
<213> ORGANISM: Artificial Sequence
<220> FEATURE:
<223> OTHER INFORMATION: Synthetic Construct

<400> SEQUENCE: 11

```
Gln Val Gln Leu Val Gln Ser Gly Ala Glu Val Lys Lys Pro Gly Ala
1               5                   10                  15

Ser Val Lys Val Ser Cys Lys Ala Ser Gly
            20                  25
```

<210> SEQ ID NO 12
<211> LENGTH: 14
<212> TYPE: PRT
<213> ORGANISM: Artificial Sequence
<220> FEATURE:
<223> OTHER INFORMATION: Synthetic Construct

<400> SEQUENCE: 12

```
Trp Val Arg Gln Ala Pro Gly Gln Gly Leu Glu Trp Met Gly
1               5                   10
```

```
<210> SEQ ID NO 13
<211> LENGTH: 14
<212> TYPE: PRT
<213> ORGANISM: Artificial Sequence
<220> FEATURE:
<223> OTHER INFORMATION: Synthetic Construct

<400> SEQUENCE: 13

Trp Val Arg Gln Ala Pro Gly Gln Arg Leu Glu Trp Ile Gly
1               5                   10

<210> SEQ ID NO 14
<211> LENGTH: 30
<212> TYPE: PRT
<213> ORGANISM: Artificial Sequence
<220> FEATURE:
<223> OTHER INFORMATION: Synthetic Construct

<400> SEQUENCE: 14

Arg Val Thr Ile Thr Ala Asp Glu Ser Thr Ser Thr Ala Tyr Met Glu
1               5                   10                  15

Leu Ser Ser Leu Arg Ser Glu Asp Thr Ala Val Tyr Tyr Cys
            20                  25                  30

<210> SEQ ID NO 15
<211> LENGTH: 30
<212> TYPE: PRT
<213> ORGANISM: Artificial Sequence
<220> FEATURE:
<223> OTHER INFORMATION: Synthetic Construct

<400> SEQUENCE: 15

Arg Val Thr Ile Thr Ala Asp Thr Ser Ala Ser Thr Ala Tyr Met Glu
1               5                   10                  15

Leu Ser Ser Leu Arg Ser Glu Asp Thr Ala Val Tyr Tyr Cys
            20                  25                  30

<210> SEQ ID NO 16
<211> LENGTH: 11
<212> TYPE: PRT
<213> ORGANISM: Artificial Sequence
<220> FEATURE:
<223> OTHER INFORMATION: Synthetic Construct

<400> SEQUENCE: 16

Trp Gly Gln Gly Thr Leu Val Thr Val Ser Ser
1               5                   10

<210> SEQ ID NO 17
<211> LENGTH: 23
<212> TYPE: PRT
<213> ORGANISM: Artificial Sequence
<220> FEATURE:
<223> OTHER INFORMATION: Synthetic Construct

<400> SEQUENCE: 17

Asp Val Val Met Thr Gln Thr Pro Leu Ser Leu Ser Val Thr Pro Gly
1               5                   10                  15

Gln Pro Ala Ser Ile Ser Cys
            20

<210> SEQ ID NO 18
<211> LENGTH: 23
<212> TYPE: PRT
<213> ORGANISM: Artificial Sequence
```

```
<220> FEATURE:
<223> OTHER INFORMATION: Synthetic Construct

<400> SEQUENCE: 18

Gly Val Val Met Thr Gln Thr Pro Leu Ser Leu Ser Val Thr Pro Gly
1               5                   10                  15

Gln Pro Ala Ser Ile Ser Cys
            20

<210> SEQ ID NO 19
<211> LENGTH: 23
<212> TYPE: PRT
<213> ORGANISM: Artificial Sequence
<220> FEATURE:
<223> OTHER INFORMATION: Synthetic Construct

<400> SEQUENCE: 19

Gly Val Val Met Ala Gln Thr Pro Leu Ser Leu Ser Val Thr Pro Gly
1               5                   10                  15

Gln Pro Ala Ser Ile Ser Cys
            20

<210> SEQ ID NO 20
<211> LENGTH: 23
<212> TYPE: PRT
<213> ORGANISM: Artificial Sequence
<220> FEATURE:
<223> OTHER INFORMATION: Synthetic Construct

<400> SEQUENCE: 20

Asp Val Val Met Thr Gln Ser Pro Asp Ser Leu Ala Val Ser Leu Gly
1               5                   10                  15

Glu Arg Ala Thr Ile Asn Cys
            20

<210> SEQ ID NO 21
<211> LENGTH: 15
<212> TYPE: PRT
<213> ORGANISM: Artificial Sequence
<220> FEATURE:
<223> OTHER INFORMATION: Synthetic Construct

<400> SEQUENCE: 21

Trp Tyr Leu Gln Lys Pro Gly Gln Ser Pro Gln Leu Leu Ile Tyr
1               5                   10                  15

<210> SEQ ID NO 22
<211> LENGTH: 15
<212> TYPE: PRT
<213> ORGANISM: Artificial Sequence
<220> FEATURE:
<223> OTHER INFORMATION: Synthetic Construct

<400> SEQUENCE: 22

Trp Tyr Gln Gln Lys Pro Gly Gln Ser Pro Lys Leu Leu Ile Tyr
1               5                   10                  15

<210> SEQ ID NO 23
<211> LENGTH: 32
<212> TYPE: PRT
<213> ORGANISM: Artificial Sequence
<220> FEATURE:
<223> OTHER INFORMATION: Synthetic Construct

<400> SEQUENCE: 23
```

Gly Val Pro Asp Arg Phe Ser Gly Ser Gly Ser Gly Thr Asp Phe Thr
1               5                   10                  15

Leu Lys Ile Ser Arg Val Glu Ala Glu Asp Val Gly Val Tyr Tyr Cys
            20                  25                  30

<210> SEQ ID NO 24
<211> LENGTH: 32
<212> TYPE: PRT
<213> ORGANISM: Artificial Sequence
<220> FEATURE:
<223> OTHER INFORMATION: Synthetic Construct

<400> SEQUENCE: 24

Gly Val Pro Asp Arg Phe Ser Gly Ser Gly Ser Gly Thr Asp Phe Thr
1               5                   10                  15

Leu Thr Ile Ser Ser Leu Gln Ala Glu Asp Val Ala Val Tyr Tyr Cys
            20                  25                  30

<210> SEQ ID NO 25
<211> LENGTH: 10
<212> TYPE: PRT
<213> ORGANISM: Artificial Sequence
<220> FEATURE:
<223> OTHER INFORMATION: Synthetic Construct

<400> SEQUENCE: 25

Phe Gly Gln Gly Thr Lys Leu Glu Ile Lys
1               5                   10

<210> SEQ ID NO 26
<211> LENGTH: 10
<212> TYPE: PRT
<213> ORGANISM: Artificial Sequence
<220> FEATURE:
<223> OTHER INFORMATION: Synthetic Construct

<400> SEQUENCE: 26

Phe Gly Gly Gly Thr Lys Val Glu Ile Lys
1               5                   10

<210> SEQ ID NO 27
<211> LENGTH: 123
<212> TYPE: PRT
<213> ORGANISM: Artificial Sequence
<220> FEATURE:
<223> OTHER INFORMATION: Synthetic Construct

<400> SEQUENCE: 27

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Ser Ser
            20                  25                  30

Trp Met Asn Trp Val Arg Gln Ala Pro Gly Gln Gly Leu Glu Trp Met
        35                  40                  45

Gly Arg Ile Tyr Pro Gly Asp Gly Asp Thr Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Leu Arg Asn Gln Pro Gly Glu Ser Tyr Ala Met Asp Tyr
            100                 105                 110

Trp Gly Gln Gly Thr Leu Val Thr Val Ser Ser
            115                 120

<210> SEQ ID NO 28
<211> LENGTH: 123
<212> TYPE: PRT
<213> ORGANISM: Artificial Sequence
<220> FEATURE:
<223> OTHER INFORMATION: Synthetic Construct

<400> SEQUENCE: 28

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Ser Ser
                20                  25                  30

Trp Met Asn Trp Val Arg Gln Ala Pro Gly Gln Gly Leu Glu Trp Met
            35                  40                  45

Gly Arg Ile Tyr Pro Gly Gly Gly Asp Thr Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Leu Arg Asn Gln Pro Gly Glu Ser Tyr Ala Met Asp Tyr
            100                 105                 110

Trp Gly Gln Gly Thr Leu Val Thr Val Ser Ser
            115                 120

<210> SEQ ID NO 29
<211> LENGTH: 123
<212> TYPE: PRT
<213> ORGANISM: Artificial Sequence
<220> FEATURE:
<223> OTHER INFORMATION: Synthetic Construct

<400> SEQUENCE: 29

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Ser Ser
                20                  25                  30

Trp Met Asn Trp Val Arg Gln Ala Pro Gly Gln Gly Leu Glu Trp Met
            35                  40                  45

Gly Arg Ile Tyr Pro Gly Glu Gly Asp Thr Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Leu Arg Asn Gln Pro Gly Glu Ser Tyr Ala Met Asp Tyr
            100                 105                 110

Trp Gly Gln Gly Thr Leu Val Thr Val Ser Ser
            115                 120

<210> SEQ ID NO 30
<211> LENGTH: 123
<212> TYPE: PRT
<213> ORGANISM: Artificial Sequence
<220> FEATURE:
<223> OTHER INFORMATION: Synthetic Construct

<400> SEQUENCE: 30

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Ser Ser
            20                  25                  30

Trp Met Asn Trp Val Arg Gln Ala Pro Gly Gln Gly Leu Glu Trp Met
        35                  40                  45

Gly Arg Ile Tyr Pro Gly Gln Gly Asp Thr Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Leu Arg Asn Gln Pro Gly Glu Ser Tyr Ala Met Asp Tyr
            100                 105                 110

Trp Gly Gln Gly Thr Leu Val Thr Val Ser Ser
        115                 120

<210> SEQ ID NO 31
<211> LENGTH: 123
<212> TYPE: PRT
<213> ORGANISM: Artificial Sequence
<220> FEATURE:
<223> OTHER INFORMATION: Synthetic Construct

<400> SEQUENCE: 31

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Leu Ser
            20                  25                  30

Trp Met Asn Trp Val Arg Gln Ala Pro Gly Gln Gly Leu Glu Trp Met
        35                  40                  45

Gly Arg Ile Tyr Pro Gly Asp Gly Asp Thr Asn Tyr Ala Gln Lys Phe
    50                  55                  60

Arg Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Leu Arg Asn Gln Pro Gly Glu Ser Tyr Ala Met Asp Tyr
            100                 105                 110

Trp Gly Gln Gly Thr Leu Val Thr Val Ser Ser
        115                 120

<210> SEQ ID NO 32
<211> LENGTH: 123
<212> TYPE: PRT
<213> ORGANISM: Artificial Sequence
<220> FEATURE:
<223> OTHER INFORMATION: Synthetic Construct

<400> SEQUENCE: 32

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Leu Ser
            20                  25                  30

Trp Met Asn Trp Val Arg Gln Ala Pro Gly Gln Gly Leu Glu Trp Met
        35                  40                  45

Gly Arg Ile Tyr Pro Gly Asp Gly Asp Thr Asn Tyr Ala Arg Lys Phe
            50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Leu Leu Arg Asn Gln Pro Gly Ser Ser Tyr Ala Met Asp Tyr
            100                 105                 110

Trp Gly Gln Gly Thr Leu Val Thr Val Ser Ser
            115                 120

<210> SEQ ID NO 33
<211> LENGTH: 123
<212> TYPE: PRT
<213> ORGANISM: Artificial Sequence
<220> FEATURE:
<223> OTHER INFORMATION: Synthetic Construct

<400> SEQUENCE: 33

Gln Val Gln Leu Val Gln Ser Gly Ala Glu Val Lys Lys Pro Gly Ser
 1               5                  10                  15

Ser Val Lys Val Ser Cys Lys Ala Ser Gly Tyr Ala Phe Ser Arg Ser
            20                  25                  30

Trp Met Asn Trp Val Arg Gln Ala Pro Gly Gln Gly Leu Glu Trp Met
        35                  40                  45

Gly Arg Ile Tyr Pro Gly Asp Gly Asp Thr Asn Tyr Ala Gln Lys Phe
    50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Leu Leu Arg Asn Gln Pro Gly Ala Ser Tyr Ala Met Asp Tyr
            100                 105                 110

Trp Gly Gln Gly Thr Leu Val Thr Val Ser Ser
            115                 120

<210> SEQ ID NO 34
<211> LENGTH: 123
<212> TYPE: PRT
<213> ORGANISM: Artificial Sequence
<220> FEATURE:
<223> OTHER INFORMATION: Synthetic Construct

<400> SEQUENCE: 34

Gln Val Gln Leu Val Gln Ser Gly Ala Glu Val Lys Lys Pro Gly Ser
 1               5                  10                  15

Ser Val Lys Val Ser Cys Lys Ala Ser Gly Tyr Ala Phe Ser Ser Asp
            20                  25                  30

Trp Met Asn Trp Val Arg Gln Ala Pro Gly Gln Gly Leu Glu Trp Met
        35                  40                  45

Gly Arg Ile Tyr Pro Gly Asp Gly Asp Thr Asn Tyr Ala Gln Lys Phe
    50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Leu Leu Arg Asn Gln Pro Gly Glu Ser Tyr Ala Met Asp Tyr
            100                 105                 110

```
Trp Gly Gln Gly Thr Leu Val Thr Val Ser Ser
        115                 120
```

<210> SEQ ID NO 35
<211> LENGTH: 123
<212> TYPE: PRT
<213> ORGANISM: Artificial Sequence
<220> FEATURE:
<223> OTHER INFORMATION: Synthetic Construct

<400> SEQUENCE: 35

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Ser Asp
            20                  25                  30

Trp Met Asn Trp Val Arg Gln Ala Pro Gly Gln Gly Leu Glu Trp Met
        35                  40                  45

Gly Arg Ile Tyr Pro Gly Asp Gly Asp Thr Asn Tyr Ala Arg Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Leu Arg Asn Gln Pro Gly Glu Ser Tyr Ala Met Asp Tyr
            100                 105                 110

Trp Gly Gln Gly Thr Leu Val Thr Val Ser Ser
        115                 120
```

<210> SEQ ID NO 36
<211> LENGTH: 123
<212> TYPE: PRT
<213> ORGANISM: Artificial Sequence
<220> FEATURE:
<223> OTHER INFORMATION: Synthetic Construct

<400> SEQUENCE: 36

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Ser His
            20                  25                  30

Trp Met Asn Trp Val Arg Gln Ala Pro Gly Gln Gly Leu Glu Trp Met
        35                  40                  45

Gly Arg Ile Tyr Pro Gly Asp Gly Asp Thr Asn Tyr Ala His Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Leu Arg Asn Gln Pro Gly Glu Ser Tyr Ala Met Asp Tyr
            100                 105                 110

Trp Gly Gln Gly Thr Leu Val Thr Val Ser Ser
        115                 120
```

<210> SEQ ID NO 37
<211> LENGTH: 123
<212> TYPE: PRT
<213> ORGANISM: Artificial Sequence
<220> FEATURE:
<223> OTHER INFORMATION: Synthetic Construct

<400> SEQUENCE: 37

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Ser His
            20                  25                  30

Trp Met Asn Trp Val Arg Gln Ala Pro Gly Gln Gly Leu Glu Trp Met
        35                  40                  45

Gly Arg Ile Tyr Pro Gly Asp Gly Asp Thr Asn Tyr Ala Gln Lys Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Leu Arg Asn Gln Pro Gly Glu Ser Tyr Ala Met Asp Tyr
            100                 105                 110

Trp Gly Gln Gly Thr Leu Val Thr Val Ser Ser
        115                 120

<210> SEQ ID NO 38
<211> LENGTH: 123
<212> TYPE: PRT
<213> ORGANISM: Artificial Sequence
<220> FEATURE:
<223> OTHER INFORMATION: Synthetic Construct

<400> SEQUENCE: 38

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Ser His
            20                  25                  30

Trp Met Asn Trp Val Arg Gln Ala Pro Gly Gln Gly Leu Glu Trp Met
        35                  40                  45

Gly Arg Ile Tyr Pro Gly Asp Gly Asp Thr Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Leu Arg Asn Gln Pro Gly Glu Ser Tyr Ala Met Asp Tyr
            100                 105                 110

Trp Gly Gln Gly Thr Leu Val Thr Val Ser Ser
        115                 120

<210> SEQ ID NO 39
<211> LENGTH: 123
<212> TYPE: PRT
<213> ORGANISM: Artificial Sequence
<220> FEATURE:
<223> OTHER INFORMATION: Synthetic Construct

<400> SEQUENCE: 39

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Ser His
            20                  25                  30

Trp Met Asn Trp Val Arg Gln Ala Pro Gly Gln Gly Leu Glu Trp Met
        35                  40                  45

Gly Arg Ile Tyr Pro Gly Asp Gly Asp Thr Asn Tyr Ala Gln Lys Phe
            50                  55                  60

Arg Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Leu Leu Arg Asn Gln Pro Gly Ala Ser Tyr Ala Met Asp Tyr
                100                 105                 110

Trp Gly Gln Gly Thr Leu Val Thr Val Ser Ser
            115                 120

<210> SEQ ID NO 40
<211> LENGTH: 123
<212> TYPE: PRT
<213> ORGANISM: Artificial Sequence
<220> FEATURE:
<223> OTHER INFORMATION: Synthetic Construct

<400> SEQUENCE: 40

Gln Val Gln Leu Val Gln Ser Gly Ala Glu Val Lys Lys Pro Gly Ser
 1               5                  10                  15

Ser Val Lys Val Ser Cys Lys Ala Ser Gly Tyr Ala Phe Ser Ser His
                 20                  25                  30

Trp Met Asn Trp Val Arg Gln Ala Pro Gly Gln Gly Leu Glu Trp Met
             35                  40                  45

Gly Arg Ile Tyr Pro Gly Asp Gly Asp Thr Asn Tyr Ala Gln Lys Arg
            50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Leu Leu Arg Asn Gln Pro Gly Glu Ser Tyr Ala Met Asp Tyr
                100                 105                 110

Trp Gly Gln Gly Thr Leu Val Thr Val Ser Ser
            115                 120

<210> SEQ ID NO 41
<211> LENGTH: 123
<212> TYPE: PRT
<213> ORGANISM: Artificial Sequence
<220> FEATURE:
<223> OTHER INFORMATION: Synthetic Construct

<400> SEQUENCE: 41

Gln Val Gln Leu Val Gln Ser Gly Ala Glu Val Lys Lys Pro Gly Ser
 1               5                  10                  15

Ser Val Lys Val Ser Cys Lys Ala Ser Gly Tyr Ala Phe Ser Ser His
                 20                  25                  30

Trp Met Asn Trp Val Arg Gln Ala Pro Gly Gln Gly Leu Glu Trp Met
             35                  40                  45

Gly Arg Ile Tyr Pro Gly Asp Gly Asp Thr Asn Tyr Ala Gln Lys Trp
            50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Leu Leu Arg Asn Gln Pro Gly Ser Ser Tyr Ala Met Asp Tyr

```
            100                 105                 110
Trp Gly Gln Gly Thr Leu Val Thr Val Ser Ser
        115                 120

<210> SEQ ID NO 42
<211> LENGTH: 123
<212> TYPE: PRT
<213> ORGANISM: Artificial Sequence
<220> FEATURE:
<223> OTHER INFORMATION: Synthetic Construct

<400> SEQUENCE: 42

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Ser His
            20                  25                  30

Trp Met Asn Trp Val Arg Gln Ala Pro Gly Gln Gly Leu Glu Trp Met
        35                  40                  45

Gly Arg Ile Tyr Pro Gly Asp Gly Asp Thr Asn Tyr Ala Arg Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Leu Arg Asn Gln Pro Gly Glu Ser Tyr Ala Met Asp Tyr
            100                 105                 110

Trp Gly Gln Gly Thr Leu Val Thr Val Ser Ser
        115                 120

<210> SEQ ID NO 43
<211> LENGTH: 123
<212> TYPE: PRT
<213> ORGANISM: Artificial Sequence
<220> FEATURE:
<223> OTHER INFORMATION: Synthetic Construct

<400> SEQUENCE: 43

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Ser His
            20                  25                  30

Trp Met Asn Trp Val Arg Gln Ala Pro Gly Gln Gly Leu Glu Trp Met
        35                  40                  45

Gly Arg Ile Tyr Pro Gly Asp Gly Asp Thr Asn Tyr Ala Trp Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Leu Arg Asn Gln Pro Gly Glu Ser Tyr Ala Met Asp Tyr
            100                 105                 110

Trp Gly Gln Gly Thr Leu Val Thr Val Ser Ser
        115                 120

<210> SEQ ID NO 44
<211> LENGTH: 123
<212> TYPE: PRT
<213> ORGANISM: Artificial Sequence
<220> FEATURE:
```

<223> OTHER INFORMATION: Synthetic Construct

<400> SEQUENCE: 44

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Ser His
            20                  25                  30

Trp Met Asn Trp Val Arg Gln Ala Pro Gly Gln Gly Leu Glu Trp Met
        35                  40                  45

Gly Arg Ile Tyr Pro Gly Asp Gly Asp Thr Asn Tyr Ala Tyr Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Leu Arg Asn Gln Pro Gly Glu Ser Tyr Ala Met Asp Tyr
            100                 105                 110

Trp Gly Gln Gly Thr Leu Val Thr Val Ser Ser
        115                 120

<210> SEQ ID NO 45
<211> LENGTH: 123
<212> TYPE: PRT
<213> ORGANISM: Artificial Sequence
<220> FEATURE:
<223> OTHER INFORMATION: Synthetic Construct

<400> SEQUENCE: 45

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Ser His
            20                  25                  30

Trp Met Asn Trp Val Arg Gln Ala Pro Gly Gln Gly Leu Glu Trp Met
        35                  40                  45

Gly Arg Ile Tyr Pro Gly Asp Gly Gln Thr Asn Tyr Ala Gln Lys Arg
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Leu Arg Asn Gln Pro Gly Glu Ser Tyr Ala Met Asp Tyr
            100                 105                 110

Trp Gly Gln Gly Thr Leu Val Thr Val Ser Ser
        115                 120

<210> SEQ ID NO 46
<211> LENGTH: 123
<212> TYPE: PRT
<213> ORGANISM: Artificial Sequence
<220> FEATURE:
<223> OTHER INFORMATION: Synthetic Construct

<400> SEQUENCE: 46

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Ser His
            20                  25                  30

Trp Met Asn Trp Val Arg Gln Ala Pro Gly Gln Gly Leu Glu Trp Met

```
                35                  40                  45

Gly Arg Ile Tyr Pro Gly Gly Asp Thr Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Leu Arg Asn Gln Pro Gly Glu Ser Tyr Ala Met Asp Tyr
                100                 105                 110

Trp Gly Gln Gly Thr Leu Val Thr Val Ser Ser
            115                 120

<210> SEQ ID NO 47
<211> LENGTH: 123
<212> TYPE: PRT
<213> ORGANISM: Artificial Sequence
<220> FEATURE:
<223> OTHER INFORMATION: Synthetic Construct

<400> SEQUENCE: 47

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Ser His
                20                  25                  30

Trp Met Asn Trp Val Arg Gln Ala Pro Gly Gln Gly Leu Glu Trp Met
            35                  40                  45

Gly Arg Ile Tyr Pro Gly Gly Asp Thr Asn Tyr Ala Gln Lys Phe
        50                  55                  60

Arg Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Leu Arg Asn Gln Pro Gly Glu Ser Tyr Ala Met Asp Tyr
                100                 105                 110

Trp Gly Gln Gly Thr Leu Val Thr Val Ser Ser
            115                 120

<210> SEQ ID NO 48
<211> LENGTH: 123
<212> TYPE: PRT
<213> ORGANISM: Artificial Sequence
<220> FEATURE:
<223> OTHER INFORMATION: Synthetic Construct

<400> SEQUENCE: 48

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Ser His
                20                  25                  30

Trp Met Asn Trp Val Arg Gln Ala Pro Gly Gln Gly Leu Glu Trp Met
            35                  40                  45

Gly Arg Ile Tyr Pro Gly Gly Asp Thr Asn Tyr Ala Gln Lys Arg
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95
```

Ala Arg Leu Leu Arg Asn Gln Pro Gly Glu Ser Tyr Ala Met Asp Tyr
            100                 105                 110

Trp Gly Gln Gly Thr Leu Val Thr Val Ser Ser
            115                 120

<210> SEQ ID NO 49
<211> LENGTH: 123
<212> TYPE: PRT
<213> ORGANISM: Artificial Sequence
<220> FEATURE:
<223> OTHER INFORMATION: Synthetic Construct

<400> SEQUENCE: 49

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Ser His
            20                  25                  30

Trp Met Asn Trp Val Arg Gln Ala Pro Gly Gln Gly Leu Glu Trp Met
        35                  40                  45

Gly Arg Ile Tyr Pro Gly Gln Gly Asp Thr Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Leu Arg Asn Gln Pro Gly Glu Ser Tyr Ala Met Asp Tyr
            100                 105                 110

Trp Gly Gln Gly Thr Leu Val Thr Val Ser Ser
            115                 120

<210> SEQ ID NO 50
<211> LENGTH: 123
<212> TYPE: PRT
<213> ORGANISM: Artificial Sequence
<220> FEATURE:
<223> OTHER INFORMATION: Synthetic Construct

<400> SEQUENCE: 50

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Ser His
            20                  25                  30

Trp Met Asn Trp Val Arg Gln Ala Pro Gly Gln Gly Leu Glu Trp Met
        35                  40                  45

Gly Arg Ile Tyr Pro Gly Val Gly Asp Thr Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Leu Arg Asn Gln Pro Gly Glu Ser Tyr Ala Met Asp Tyr
            100                 105                 110

Trp Gly Gln Gly Thr Leu Val Thr Val Ser Ser
            115                 120

<210> SEQ ID NO 51
<211> LENGTH: 123
<212> TYPE: PRT
<213> ORGANISM: Artificial Sequence
<220> FEATURE:
<223> OTHER INFORMATION: Synthetic Construct

<400> SEQUENCE: 51

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Ser Gln
            20                  25                  30

Trp Met Asn Trp Val Arg Gln Ala Pro Gly Gln Gly Leu Glu Trp Met
        35                  40                  45

Gly Arg Ile Tyr Pro Gly Asp Gly Asp Thr Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Leu Arg Asn Gln Pro Gly Glu Ser Tyr Ala Met Asp Tyr
            100                 105                 110

Trp Gly Gln Gly Thr Leu Val Thr Val Ser Ser
        115                 120

<210> SEQ ID NO 52
<211> LENGTH: 123
<212> TYPE: PRT
<213> ORGANISM: Artificial Sequence
<220> FEATURE:
<223> OTHER INFORMATION: Synthetic Construct

<400> SEQUENCE: 52

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Ser Gln
            20                  25                  30

Trp Met Asn Trp Val Arg Gln Ala Pro Gly Gln Gly Leu Glu Trp Met
        35                  40                  45

Gly Arg Ile Tyr Pro Gly Asp Gly Asp Thr Asn Tyr Ala Trp Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Leu Arg Asn Gln Pro Gly Glu Ser Tyr Ala Met Asp Tyr
            100                 105                 110

Trp Gly Gln Gly Thr Leu Val Thr Val Ser Ser
        115                 120

<210> SEQ ID NO 53
<211> LENGTH: 123
<212> TYPE: PRT
<213> ORGANISM: Artificial Sequence
<220> FEATURE:
<223> OTHER INFORMATION: Synthetic Construct

<400> SEQUENCE: 53

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Ser Gln
            20                  25                  30

```
Trp Met Asn Trp Val Arg Gln Ala Pro Gly Gln Gly Leu Glu Trp Met
            35                  40                  45

Gly Arg Ile Tyr Pro Gly Gly Asp Thr Asn Tyr Ala Arg Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Leu Arg Asn Gln Pro Gly Glu Ser Tyr Ala Met Asp Tyr
                100                 105                 110

Trp Gly Gln Gly Thr Leu Val Thr Val Ser Ser
            115                 120
```

<210> SEQ ID NO 54
<211> LENGTH: 123
<212> TYPE: PRT
<213> ORGANISM: Artificial Sequence
<220> FEATURE:
<223> OTHER INFORMATION: Synthetic Construct

<400> SEQUENCE: 54

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Ser Glu
                20                  25                  30

Trp Met Asn Trp Val Arg Gln Ala Pro Gly Gln Gly Leu Glu Trp Met
            35                  40                  45

Gly Arg Ile Tyr Pro Gly Asp Gly Thr Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Leu Arg Asn Gln Pro Gly Glu Ser Tyr Ala Met Asp Tyr
                100                 105                 110

Trp Gly Gln Gly Thr Leu Val Thr Val Ser Ser
            115                 120
```

<210> SEQ ID NO 55
<211> LENGTH: 123
<212> TYPE: PRT
<213> ORGANISM: Artificial Sequence
<220> FEATURE:
<223> OTHER INFORMATION: Synthetic Construct

<400> SEQUENCE: 55

```
Glu Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Ser Ser
                20                  25                  30

Trp Met Asn Trp Val Arg Gln Ala Pro Gly Gln Gly Leu Glu Trp Met
            35                  40                  45

Gly Arg Ile Tyr Pro Gly Asp Gly Asp Thr Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95
```

Ala Arg Leu Leu Arg Asn Gln Pro Gly Glu Ser Tyr Ala Met Asp Tyr
            100                 105                 110

Trp Gly Gln Gly Thr Leu Val Thr Val Ser Ser
        115                 120

<210> SEQ ID NO 56
<211> LENGTH: 123
<212> TYPE: PRT
<213> ORGANISM: Artificial Sequence
<220> FEATURE:
<223> OTHER INFORMATION: Synthetic Construct

<400> SEQUENCE: 56

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Ser Ser Ser
            20                  25                  30

Trp Met Asn Trp Val Arg Gln Ala Pro Gly Gln Arg Leu Glu Trp Ile
        35                  40                  45

Gly Arg Ile Tyr Pro Gly Asp Gly Asp Thr Asn Tyr Ala Gln Lys Phe
    50                  55                  60

Gln Gly Arg Val Thr Ile Thr Ala Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Leu Arg Asn Gln Pro Gly Glu Ser Tyr Ala Met Asp Tyr
            100                 105                 110

Trp Gly Gln Gly Thr Leu Val Thr Val Ser Ser
        115                 120

<210> SEQ ID NO 57
<211> LENGTH: 123
<212> TYPE: PRT
<213> ORGANISM: Artificial Sequence
<220> FEATURE:
<223> OTHER INFORMATION: Synthetic Construct

<400> SEQUENCE: 57

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Trp Ser Ser
            20                  25                  30

Trp Met Asn Trp Val Arg Gln Ala Pro Gly Gln Arg Leu Glu Trp Ile
        35                  40                  45

Gly Arg Ile Tyr Pro Gly Asp Gly Asp Thr Asn Tyr Ala Gln Lys Phe
    50                  55                  60

Gln Gly Arg Val Thr Ile Thr Ala Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Leu Arg Asn Gln Pro Gly Glu Ser Tyr Ala His Asp Tyr
            100                 105                 110

Trp Gly Gln Gly Thr Leu Val Thr Val Ser Ser
        115                 120

<210> SEQ ID NO 58
<211> LENGTH: 123
<212> TYPE: PRT

<213> ORGANISM: Artificial Sequence
<220> FEATURE:
<223> OTHER INFORMATION: Synthetic Construct

<400> SEQUENCE: 58

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Ser Ser Ser
            20                  25                  30

Trp Met Asn Trp Val Arg Gln Ala Pro Gly Gln Arg Leu Glu Trp Ile
        35                  40                  45

Gly Arg Ile Tyr Pro Gly Asp Gly Asp Thr Asn Tyr Ala Arg Lys Phe
    50                  55                  60

Gln Gly Arg Val Thr Ile Thr Ala Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Leu Arg Asn Gln Pro Gly Ala Ser Tyr Ala Met Asp Tyr
            100                 105                 110

Trp Gly Gln Gly Thr Leu Val Thr Val Ser Ser
        115                 120

<210> SEQ ID NO 59
<211> LENGTH: 123
<212> TYPE: PRT
<213> ORGANISM: Artificial Sequence
<220> FEATURE:
<223> OTHER INFORMATION: Synthetic Construct

<400> SEQUENCE: 59

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Ser Ser Gln
            20                  25                  30

Trp Met Asn Trp Val Arg Gln Ala Pro Gly Gln Arg Leu Glu Trp Ile
        35                  40                  45

Gly Arg Ile Tyr Pro Gly Gly Asp Thr Asn Tyr Ala Gly Lys Phe
    50                  55                  60

Gln Gly Arg Val Thr Ile Thr Ala Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Leu Arg Asn Gln Pro Gly Glu Ser Tyr Ala Met Asp Tyr
            100                 105                 110

Trp Gly Gln Gly Thr Leu Val Thr Val Ser Ser
        115                 120

<210> SEQ ID NO 60
<211> LENGTH: 123
<212> TYPE: PRT
<213> ORGANISM: Artificial Sequence
<220> FEATURE:
<223> OTHER INFORMATION: Synthetic Construct

<400> SEQUENCE: 60

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Ser His
            20                  25                  30

```
Trp Met Asn Trp Val Arg Gln Ala Pro Gly Gln Gly Leu Glu Trp Met
            35                  40                  45

Gly Arg Ile Tyr Pro Gly Gly Asp Thr Asn Tyr Ala Gln Lys Phe
 50                  55                  60

Arg Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                85                  90                  95

Ala Arg Leu Leu Arg Asn Gln Pro Gly Ala Ser Tyr Ala Met Asp Tyr
                100                 105                 110

Trp Gly Gln Gly Thr Leu Val Thr Val Ser Ser
            115                 120

<210> SEQ ID NO 61
<211> LENGTH: 123
<212> TYPE: PRT
<213> ORGANISM: Artificial Sequence
<220> FEATURE:
<223> OTHER INFORMATION: Synthetic Construct

<400> SEQUENCE: 61

Gln Val Gln Leu Val Gln Ser Gly Ala Glu Val Lys Lys Pro Gly Ser
 1               5                  10                  15

Ser Val Lys Val Ser Cys Lys Ala Ser Gly Tyr Ala Phe Ser Ser His
                20                  25                  30

Trp Met Asn Trp Val Arg Gln Ala Pro Gly Gln Gly Leu Glu Trp Met
            35                  40                  45

Gly Arg Ile Tyr Pro Gly Glu Gly Asp Thr Asn Tyr Ala Gln Lys Phe
 50                  55                  60

Arg Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                85                  90                  95

Ala Arg Leu Leu Arg Asn Gln Pro Gly Ala Ser Tyr Ala Met Asp Tyr
                100                 105                 110

Trp Gly Gln Gly Thr Leu Val Thr Val Ser Ser
            115                 120

<210> SEQ ID NO 62
<211> LENGTH: 123
<212> TYPE: PRT
<213> ORGANISM: Artificial Sequence
<220> FEATURE:
<223> OTHER INFORMATION: Synthetic Construct

<400> SEQUENCE: 62

Gln Val Gln Leu Val Gln Ser Gly Ala Glu Val Lys Lys Pro Gly Ser
 1               5                  10                  15

Ser Val Lys Val Ser Cys Lys Ala Ser Gly Tyr Ala Phe Ser Ser His
                20                  25                  30

Trp Met Asn Trp Val Arg Gln Ala Pro Gly Gln Gly Leu Glu Trp Met
            35                  40                  45

Gly Arg Ile Tyr Pro Gly Gly Gly Asp Thr Asn Tyr Ala Arg Lys Phe
 50                  55                  60

Arg Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
```

```
                    85                  90                  95
Ala Arg Leu Leu Arg Asn Gln Pro Gly Ala Ser Tyr Ala Met Asp Tyr
                100                 105                 110

Trp Gly Gln Gly Thr Leu Val Thr Val Ser Ser
        115                 120

<210> SEQ ID NO 63
<211> LENGTH: 123
<212> TYPE: PRT
<213> ORGANISM: Artificial Sequence
<220> FEATURE:
<223> OTHER INFORMATION: Synthetic Construct

<400> SEQUENCE: 63

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Ser Asp
                20                  25                  30

Trp Met Asn Trp Val Arg Gln Ala Pro Gly Gln Gly Leu Glu Trp Met
            35                  40                  45

Gly Arg Ile Tyr Pro Gly Glu Gly Asp Thr Asn Tyr Ala Arg Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Leu Arg Asn Lys Pro Gly Glu Ser Tyr Ala Met Asp Tyr
                100                 105                 110

Trp Gly Gln Gly Thr Leu Val Thr Val Ser Ser
        115                 120

<210> SEQ ID NO 64
<211> LENGTH: 123
<212> TYPE: PRT
<213> ORGANISM: Artificial Sequence
<220> FEATURE:
<223> OTHER INFORMATION: Synthetic Construct

<400> SEQUENCE: 64

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Ser Asp
                20                  25                  30

Trp Met Asn Trp Val Arg Gln Ala Pro Gly Gln Gly Leu Glu Trp Met
            35                  40                  45

Gly Arg Ile Tyr Pro Gly Glu Gly Asp Thr Asn Tyr Ala Arg Lys Phe
    50                  55                  60

His Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Leu Arg Asn Lys Pro Gly Glu Ser Tyr Ala Met Asp Tyr
                100                 105                 110

Trp Gly Gln Gly Thr Leu Val Thr Val Ser Ser
        115                 120

<210> SEQ ID NO 65
<211> LENGTH: 123
```

<212> TYPE: PRT
<213> ORGANISM: Artificial Sequence
<220> FEATURE:
<223> OTHER INFORMATION: Synthetic Construct

<400> SEQUENCE: 65

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Ser Asp
            20                  25                  30

Trp Met Asn Trp Val Arg Gln Ala Pro Gly Gln Gly Leu Glu Trp Met
        35                  40                  45

Gly Arg Ile Tyr Pro Gly Glu Gly Asp Thr Asn Tyr Ala Arg Lys Phe
    50                  55                  60

His Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Leu Arg Asn Lys Pro Gly Glu Ser Tyr Ala Met Asp Tyr
            100                 105                 110

Trp Gly Gln Gly Thr Leu Val Thr Val Ser Ser
        115                 120

<210> SEQ ID NO 66
<211> LENGTH: 123
<212> TYPE: PRT
<213> ORGANISM: Artificial Sequence
<220> FEATURE:
<223> OTHER INFORMATION: Synthetic Construct

<400> SEQUENCE: 66

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Ser His
            20                  25                  30

Trp Met Asn Trp Val Arg Gln Ala Pro Gly Gln Gly Leu Glu Trp Met
        35                  40                  45

Gly Arg Ile Tyr Pro Gly Glu Gly Asp Thr Asn Tyr Ala Gln Lys Phe
    50                  55                  60

His Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Leu Arg Asn Gln Pro Gly Glu Ser Tyr Ala Met Asp Tyr
            100                 105                 110

Trp Gly Gln Gly Thr Leu Val Thr Val Ser Ser
        115                 120

<210> SEQ ID NO 67
<211> LENGTH: 123
<212> TYPE: PRT
<213> ORGANISM: Artificial Sequence
<220> FEATURE:
<223> OTHER INFORMATION: Synthetic Construct

<400> SEQUENCE: 67

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Ser His

```
                    20                  25                  30

Trp Met Asn Trp Val Arg Gln Ala Pro Gly Gln Gly Leu Glu Trp Met
            35                  40                  45

Gly Arg Ile Tyr Pro Gly Glu Gly Asp Thr Asn Tyr Ala Gln Lys Phe
        50                  55                  60

His Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Leu Arg Asn Gln Pro Gly Glu Ser Tyr Ala Met Asp Tyr
            100                 105                 110

Trp Gly Gln Gly Thr Leu Val Thr Val Ser Ser
        115                 120

<210> SEQ ID NO 68
<211> LENGTH: 123
<212> TYPE: PRT
<213> ORGANISM: Artificial Sequence
<220> FEATURE:
<223> OTHER INFORMATION: Synthetic Construct

<400> SEQUENCE: 68

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Ser His
            20                  25                  30

Trp Met Asn Trp Val Arg Gln Ala Pro Gly Gln Gly Leu Glu Trp Met
            35                  40                  45

Gly Arg Ile Tyr Pro Gly Glu Gly Asp Thr Asn Tyr Ala Gln Lys Phe
        50                  55                  60

His Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Leu Arg Asn Lys Pro Gly Glu Ser Tyr Ala Met Asp Tyr
            100                 105                 110

Trp Gly Gln Gly Thr Leu Val Thr Val Ser Ser
        115                 120

<210> SEQ ID NO 69
<211> LENGTH: 123
<212> TYPE: PRT
<213> ORGANISM: Artificial Sequence
<220> FEATURE:
<223> OTHER INFORMATION: Synthetic Construct

<400> SEQUENCE: 69

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Ser His
            20                  25                  30

Trp Met Asn Trp Val Arg Gln Ala Pro Gly Gln Gly Leu Glu Trp Met
            35                  40                  45

Gly Arg Ile Tyr Pro Gly Glu Gly Asp Thr Asn Tyr Ala Gln Lys Phe
        50                  55                  60

His Gly Arg Val Thr Ile Thr Ala Asp Glu Ser Thr Ser Thr Ala Tyr
65                  70                  75                  80
```

```
Met Glu Leu Ser Ser Leu Arg Ser Glu Asp Thr Ala Val Tyr Tyr Cys
                85                  90                  95

Ala Arg Leu Leu Arg Asn Lys Pro Gly Glu Ser Tyr Ala Met Asp Tyr
            100                 105                 110

Trp Gly Gln Gly Thr Leu Val Thr Val Ser Ser
        115                 120

<210> SEQ ID NO 70
<211> LENGTH: 123
<212> TYPE: PRT
<213> ORGANISM: Artificial Sequence
<220> FEATURE:
<223> OTHER INFORMATION: Synthetic Construct

<400> SEQUENCE: 70

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Ser Gln
            20                  25                  30

Trp Met Asn Trp Val Arg Gln Ala Pro Gly Gln Gly Leu Glu Trp Met
        35                  40                  45

Gly Arg Ile Tyr Pro Gly Glu Gly Asp Thr Asn Tyr Ala Arg Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Leu Arg Asn Gln Pro Gly Glu Ser Tyr Ala Met Asp Tyr
            100                 105                 110

Trp Gly Gln Gly Thr Leu Val Thr Val Ser Ser
        115                 120

<210> SEQ ID NO 71
<211> LENGTH: 123
<212> TYPE: PRT
<213> ORGANISM: Artificial Sequence
<220> FEATURE:
<223> OTHER INFORMATION: Synthetic Construct

<400> SEQUENCE: 71

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Ser Ser Gln
            20                  25                  30

Trp Met Asn Trp Val Arg Gln Ala Pro Gly Gln Arg Leu Glu Trp Ile
        35                  40                  45

Gly Arg Ile Tyr Pro Gly Glu Gly Asp Thr Asn Tyr Ala Gly Lys Phe
    50                  55                  60

Gln Gly Arg Val Thr Ile Thr Ala Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Leu Arg Asn Gln Pro Gly Glu Ser Tyr Ala Met Asp Tyr
            100                 105                 110

Trp Gly Gln Gly Thr Leu Val Thr Val Ser Ser
        115                 120

<210> SEQ ID NO 72
```

```
<211> LENGTH: 123
<212> TYPE: PRT
<213> ORGANISM: Artificial Sequence
<220> FEATURE:
<223> OTHER INFORMATION: Synthetic Construct

<400> SEQUENCE: 72

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Ser Ser
            20                  25                  30

Trp Met Asn Trp Val Arg Gln Ala Pro Gly Gln Gly Leu Glu Trp Met
        35                  40                  45

Gly Arg Ile Tyr Pro Gly Asp Gly Asp Thr Asn Tyr Ala Gln Lys Phe
    50                  55                  60

Gln Gly Arg Ala Thr Ile Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Leu Arg Asn Gln Pro Gly Glu Ser Tyr Ala Met Asp Tyr
            100                 105                 110

Trp Gly Gln Gly Thr Leu Val Thr Val Ser Ser
        115                 120

<210> SEQ ID NO 73
<211> LENGTH: 123
<212> TYPE: PRT
<213> ORGANISM: Artificial Sequence
<220> FEATURE:
<223> OTHER INFORMATION: Synthetic Construct

<400> SEQUENCE: 73

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Ser Ser Ser
            20                  25                  30

Trp Met Asn Trp Val Arg Gln Ala Pro Gly Gln Gly Leu Glu Trp Met
        35                  40                  45

Gly Arg Ile Tyr Pro Gly Asp Gly Asp Thr Asn Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Leu Leu Arg Asn Gln Pro Gly Glu Ser Tyr Ala Met Asp Tyr
            100                 105                 110

Trp Gly Gln Gly Thr Leu Val Thr Val Ser Ser
        115                 120

<210> SEQ ID NO 74
<211> LENGTH: 123
<212> TYPE: PRT
<213> ORGANISM: Artificial Sequence
<220> FEATURE:
<223> OTHER INFORMATION: Synthetic Construct

<400> SEQUENCE: 74

Gln Val Gln Leu Val Gln Ser Gly Ala Glu Val Lys Lys Pro Gly Ala
1               5                   10                  15
```

Ser Val Lys Val Ser Cys Lys Ala Ser Gly Tyr Ala Phe Ser Ser Ser
            20                  25                  30

Trp Met Asn Trp Val Arg Gln Ala Pro Gly Gln Gly Leu Glu Trp Ile
        35                  40                  45

Gly Arg Ile Tyr Pro Gly Asp Gly Asp Thr Asn Tyr Ala Gln Lys Phe
    50                  55                  60

Gln Gly Arg Val Thr Met Thr Ala Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Leu Leu Arg Asn Gln Pro Gly Glu Ser Tyr Ala Met Asp Tyr
            100                 105                 110

Trp Gly Gln Gly Thr Leu Val Thr Val Ser Ser
        115                 120

<210> SEQ ID NO 75
<211> LENGTH: 123
<212> TYPE: PRT
<213> ORGANISM: Artificial Sequence
<220> FEATURE:
<223> OTHER INFORMATION: Synthetic Construct

<400> SEQUENCE: 75

Gln Val Gln Leu Val Gln Ser Gly Ala Glu Val Lys Lys Pro Gly Ala
1               5                   10                  15

Ser Leu Lys Ile Ser Cys Lys Ala Ser Gly Tyr Ala Phe Ser Ser Ser
            20                  25                  30

Trp Met Asn Trp Val Arg Gln Ala Pro Gly Gln Gly Leu Glu Trp Ile
        35                  40                  45

Gly Arg Ile Tyr Pro Gly Asp Gly Asp Thr Asn Tyr Ala Gln Lys Phe
    50                  55                  60

Gln Gly Arg Ala Thr Leu Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Leu Arg Asn Gln Pro Gly Glu Ser Tyr Ala Met Asp Tyr
            100                 105                 110

Trp Gly Gln Gly Ala Leu Val Thr Val Ser Ser
        115                 120

<210> SEQ ID NO 76
<211> LENGTH: 123
<212> TYPE: PRT
<213> ORGANISM: Artificial Sequence
<220> FEATURE:
<223> OTHER INFORMATION: Synthetic Construct

<400> SEQUENCE: 76

Gln Val Gln Leu Val Gln Ser Gly Ala Glu Val Val Lys Pro Gly Ala
1               5                   10                  15

Ser Leu Lys Ile Ser Cys Lys Ala Ser Gly Tyr Ala Phe Ser Ser Ser
            20                  25                  30

Trp Met Asn Trp Val Arg Gln Ala Pro Gly Gln Gly Leu Glu Trp Ile
        35                  40                  45

Gly Arg Ile Tyr Pro Gly Asp Gly Asp Thr Asn Tyr Asn Gln Lys Phe
    50                  55                  60

Gln Gly Arg Ala Thr Leu Thr Ala Asp Thr Ser Thr Ser Thr Ala Tyr
65                  70                  75                  80

```
Met Glu Leu Ser Ser Leu Arg Ser Glu Asp Thr Ala Val Tyr Phe Cys
                85                  90                  95

Ala Arg Leu Leu Arg Asn Gln Pro Gly Glu Ser Tyr Ala Met Asp Tyr
            100                 105                 110

Trp Gly Gln Gly Ala Leu Val Thr Val Ser Ser
        115                 120

<210> SEQ ID NO 77
<211> LENGTH: 123
<212> TYPE: PRT
<213> ORGANISM: Artificial Sequence
<220> FEATURE:
<223> OTHER INFORMATION: Synthetic Construct

<400> SEQUENCE: 77

Gln Val Gln Leu Val Gln Ser Gly Ala Glu Val Lys Lys Pro Gly Ala
1               5                   10                  15

Ser Leu Lys Ile Ser Cys Lys Ala Ser Gly Tyr Ala Phe Ser Ser Ser
            20                  25                  30

Trp Met Asn Trp Val Arg Gln Ala Pro Gly Gln Gly Leu Glu Trp Ile
        35                  40                  45

Gly Arg Ile Tyr Pro Gly Asp Gly Asp Thr Asn Tyr Asn Gly Glu Phe
    50                  55                  60

Arg Val Arg Ala Thr Leu Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Leu Arg Asn Gln Pro Gly Glu Ser Tyr Ala Met Asp Tyr
            100                 105                 110

Trp Gly Gln Gly Ala Leu Val Thr Val Ser Ser
        115                 120

<210> SEQ ID NO 78
<211> LENGTH: 123
<212> TYPE: PRT
<213> ORGANISM: Artificial Sequence
<220> FEATURE:
<223> OTHER INFORMATION: Synthetic Construct

<400> SEQUENCE: 78

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Ser Ser Ser
            20                  25                  30

Trp Met Asn Trp Val Arg Gln Ala Pro Gly Gln Gly Leu Glu Trp Ile
        35                  40                  45

Gly Arg Ile Tyr Pro Gly Asp Gly Asp Thr Asn Tyr Asn Gly Glu Phe
    50                  55                  60

Arg Val Arg Ala Thr Leu Thr Ala Asp Thr Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Arg Leu Leu Arg Asn Gln Pro Gly Glu Ser Tyr Ala Met Asp Tyr
            100                 105                 110

Trp Gly Gln Gly Thr Leu Val Thr Val Ser Ser
        115                 120
```

```
<210> SEQ ID NO 79
<211> LENGTH: 123
<212> TYPE: PRT
<213> ORGANISM: Artificial Sequence
<220> FEATURE:
<223> OTHER INFORMATION: Synthetic Construct

<400> SEQUENCE: 79
```

| Gln | Val | Gln | Leu | Val | Gln | Ser | Gly | Ala | Glu | Val | Lys | Lys | Pro | Gly | Ala |
|---|---|---|---|---|---|---|---|---|---|---|---|---|---|---|---|
| 1 | | | | 5 | | | | | 10 | | | | | 15 | |

| Ser | Val | Lys | Val | Ser | Cys | Lys | Ala | Ser | Gly | Tyr | Ala | Phe | Ser | Ser | Ser |
|---|---|---|---|---|---|---|---|---|---|---|---|---|---|---|---|
| | | | 20 | | | | | 25 | | | | | 30 | | |

| Trp | Met | Asn | Trp | Val | Arg | Gln | Ala | Pro | Gly | Gln | Gly | Leu | Glu | Trp | Ile |
|---|---|---|---|---|---|---|---|---|---|---|---|---|---|---|---|
| | | 35 | | | | | 40 | | | | | 45 | | | |

| Gly | Arg | Ile | Tyr | Pro | Gly | Asp | Gly | Asp | Thr | Asn | Tyr | Ala | Gln | Lys | Phe |
|---|---|---|---|---|---|---|---|---|---|---|---|---|---|---|---|
| | 50 | | | | | 55 | | | | | 60 | | | | |

| Gln | Gly | Arg | Ala | Thr | Leu | Thr | Ala | Asp | Thr | Ser | Ser | Thr | Ala | Tyr |
|---|---|---|---|---|---|---|---|---|---|---|---|---|---|---|
| 65 | | | | | 70 | | | | | 75 | | | | 80 |

| Met | Glu | Leu | Ser | Ser | Leu | Arg | Ser | Glu | Asp | Thr | Ala | Val | Tyr | Phe | Cys |
|---|---|---|---|---|---|---|---|---|---|---|---|---|---|---|---|
| | | | | 85 | | | | | 90 | | | | | 95 | |

| Ala | Arg | Leu | Leu | Arg | Asn | Gln | Pro | Gly | Glu | Ser | Tyr | Ala | Met | Asp | Tyr |
|---|---|---|---|---|---|---|---|---|---|---|---|---|---|---|---|
| | | | 100 | | | | | 105 | | | | | 110 | | |

| Trp | Gly | Gln | Gly | Thr | Leu | Val | Thr | Val | Ser | Ser |
|---|---|---|---|---|---|---|---|---|---|---|
| | | 115 | | | | | 120 | | | |

```
<210> SEQ ID NO 80
<211> LENGTH: 123
<212> TYPE: PRT
<213> ORGANISM: Artificial Sequence
<220> FEATURE:
<223> OTHER INFORMATION: Synthetic Construct

<400> SEQUENCE: 80
```

| Gln | Val | Gln | Leu | Val | Gln | Ser | Gly | Ala | Glu | Val | Lys | Lys | Pro | Gly | Ala |
|---|---|---|---|---|---|---|---|---|---|---|---|---|---|---|---|
| 1 | | | | 5 | | | | | 10 | | | | | 15 | |

| Ser | Val | Lys | Val | Ser | Cys | Lys | Ala | Ser | Gly | Tyr | Ala | Phe | Ser | Ser | Ser |
|---|---|---|---|---|---|---|---|---|---|---|---|---|---|---|---|
| | | | 20 | | | | | 25 | | | | | 30 | | |

| Trp | Met | Asn | Trp | Val | Arg | Gln | Ala | Pro | Gly | Gln | Gly | Leu | Glu | Trp | Ile |
|---|---|---|---|---|---|---|---|---|---|---|---|---|---|---|---|
| | | 35 | | | | | 40 | | | | | 45 | | | |

| Gly | Arg | Ile | Tyr | Pro | Gly | Asp | Gly | Asp | Thr | Asn | Tyr | Ala | Gln | Lys | Phe |
|---|---|---|---|---|---|---|---|---|---|---|---|---|---|---|---|
| | 50 | | | | | 55 | | | | | 60 | | | | |

| Gln | Gly | Arg | Ala | Thr | Met | Thr | Ala | Asp | Thr | Ser | Thr | Ser | Thr | Ala | Tyr |
|---|---|---|---|---|---|---|---|---|---|---|---|---|---|---|---|
| 65 | | | | | 70 | | | | | 75 | | | | | 80 |

| Met | Glu | Leu | Ser | Ser | Leu | Arg | Ser | Glu | Asp | Thr | Ala | Val | Tyr | Tyr | Cys |
|---|---|---|---|---|---|---|---|---|---|---|---|---|---|---|---|
| | | | | 85 | | | | | 90 | | | | | 95 | |

| Ala | Arg | Leu | Leu | Arg | Asn | Gln | Pro | Gly | Glu | Ser | Tyr | Ala | Met | Asp | Tyr |
|---|---|---|---|---|---|---|---|---|---|---|---|---|---|---|---|
| | | | 100 | | | | | 105 | | | | | 110 | | |

| Trp | Gly | Gln | Gly | Thr | Leu | Val | Thr | Val | Ser | Ser |
|---|---|---|---|---|---|---|---|---|---|---|
| | | 115 | | | | | 120 | | | |

```
<210> SEQ ID NO 81
<211> LENGTH: 123
<212> TYPE: PRT
<213> ORGANISM: Artificial Sequence
<220> FEATURE:
<223> OTHER INFORMATION: Synthetic Construct

<400> SEQUENCE: 81
```

| Gln | Val | Gln | Leu | Val | Gln | Ser | Gly | Ala | Glu | Val | Lys | Lys | Pro | Gly | Ala |
|---|---|---|---|---|---|---|---|---|---|---|---|---|---|---|---|
| 1 | | | | 5 | | | | | 10 | | | | | 15 | |

```
Ser Val Lys Val Ser Cys Lys Ala Ser Gly Tyr Ala Phe Ser Ser Ser
            20                  25                  30

Trp Met Asn Trp Val Arg Gln Ala Pro Gly Gln Gly Leu Glu Trp Met
        35                  40                  45

Gly Arg Ile Tyr Pro Gly Asp Gly Asp Thr Asn Tyr Ala Gln Lys Phe
    50                  55                  60

Gln Gly Arg Val Thr Met Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Leu Arg Asn Gln Pro Gly Glu Ser Tyr Ala Met Asp Tyr
            100                 105                 110

Trp Gly Gln Gly Thr Leu Val Thr Val Ser Ser
            115                 120
```

<210> SEQ ID NO 82
<211> LENGTH: 123
<212> TYPE: PRT
<213> ORGANISM: Artificial Sequence
<220> FEATURE:
<223> OTHER INFORMATION: Synthetic Construct

<400> SEQUENCE: 82

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Ser Ser
            20                  25                  30

Trp Met Asn Trp Val Arg Gln Ala Pro Gly Gln Gly Leu Glu Trp Ile
        35                  40                  45

Gly Arg Ile Tyr Pro Gly Asp Gly Asp Thr Asn Tyr Asn Gly Glu Phe
    50                  55                  60

Arg Val Arg Ala Thr Leu Thr Ala Asp Thr Ser Thr Thr Thr Ala Tyr
65                  70                  75                  80

Met Glu Leu Ser Ser Leu Arg Ser Glu Asp Thr Ala Val Tyr Phe Cys
                85                  90                  95

Ala Arg Leu Leu Arg Asn Gln Pro Gly Glu Ser Tyr Ala Met Asp Tyr
            100                 105                 110

Trp Gly Gln Gly Thr Leu Val Thr Val Ser Ser
            115                 120
```

<210> SEQ ID NO 83
<211> LENGTH: 123
<212> TYPE: PRT
<213> ORGANISM: Artificial Sequence
<220> FEATURE:
<223> OTHER INFORMATION: Synthetic Construct

<400> SEQUENCE: 83

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Ser Ser
            20                  25                  30

Trp Met Asn Trp Val Arg Gln Ala Pro Gly Gln Gly Leu Glu Trp Ile
        35                  40                  45

Gly Arg Ile Tyr Pro Gly Asp Gly Asp Thr Asn Tyr Ala Gln Lys Phe
    50                  55                  60

Gln Gly Arg Ala Thr Leu Thr Ala Asp Thr Ser Thr Thr Thr Ala Tyr
```

```
                65                  70                  75                  80
Met Glu Leu Ser Ser Leu Arg Ser Glu Asp Thr Ala Val Tyr Phe Cys
                    85                  90                  95

Ala Arg Leu Leu Arg Asn Gln Pro Gly Glu Ser Tyr Ala Met Asp Tyr
                100                 105                 110

Trp Gly Gln Gly Thr Leu Val Thr Val Ser Ser
            115                 120
```

<210> SEQ ID NO 84
<211> LENGTH: 123
<212> TYPE: PRT
<213> ORGANISM: Artificial Sequence
<220> FEATURE:
<223> OTHER INFORMATION: Synthetic Construct

<400> SEQUENCE: 84

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Ser Ser
                20                  25                  30

Trp Met Asn Trp Val Arg Gln Ala Pro Gly Gln Gly Leu Glu Trp Ile
            35                  40                  45

Gly Arg Ile Tyr Pro Gly Asp Gly Asp Thr Asn Tyr Ala Gln Lys Phe
        50                  55                  60

Gln Gly Arg Ala Thr Ile Thr Ala Asp Thr Ser Thr Ser Thr Ala Tyr
65                  70                  75                  80

Met Glu Leu Ser Ser Leu Arg Ser Glu Asp Thr Ala Val Tyr Phe Cys
                    85                  90                  95

Ala Arg Leu Leu Arg Asn Gln Pro Gly Glu Ser Tyr Ala Met Asp Tyr
                100                 105                 110

Trp Gly Gln Gly Thr Leu Val Thr Val Ser Ser
            115                 120
```

<210> SEQ ID NO 85
<211> LENGTH: 123
<212> TYPE: PRT
<213> ORGANISM: Artificial Sequence
<220> FEATURE:
<223> OTHER INFORMATION: Synthetic Construct

<400> SEQUENCE: 85

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Tyr Ala Phe Ser Ser Ser
                20                  25                  30

Trp Met Asn Trp Val Arg Gln Ala Pro Gly Lys Gly Leu Glu Trp Ile
            35                  40                  45

Gly Arg Ile Tyr Pro Gly Asp Gly Asp Thr Asn Tyr Ala Gln Lys Phe
        50                  55                  60

Gln Gly Arg Ala Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                    85                  90                  95

Ala Arg Leu Leu Arg Asn Gln Pro Gly Glu Ser Tyr Ala Met Asp Tyr
                100                 105                 110

Trp Gly Gln Gly Thr Leu Val Thr Val Ser Ser
            115                 120
```

```
<210> SEQ ID NO 86
<211> LENGTH: 123
<212> TYPE: PRT
<213> ORGANISM: Artificial Sequence
<220> FEATURE:
<223> OTHER INFORMATION: Synthetic Construct

<400> SEQUENCE: 86

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Ser Ser Ser
            20                  25                  30

Trp Met Asn Trp Val Arg Gln Ala Pro Gly Gln Arg Leu Glu Trp Met
        35                  40                  45

Gly Arg Ile Tyr Pro Gly Asp Gly Asp Thr Asn Tyr Ala Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Leu Arg Asn Gln Pro Gly Glu Ser Tyr Ala Met Asp Tyr
            100                 105                 110

Trp Gly Gln Gly Thr Leu Val Thr Val Ser Ser
        115                 120

<210> SEQ ID NO 87
<211> LENGTH: 123
<212> TYPE: PRT
<213> ORGANISM: Artificial Sequence
<220> FEATURE:
<223> OTHER INFORMATION: Synthetic Construct

<400> SEQUENCE: 87

Gln Val Gln Leu Val Gln Ser Gly Ala Glu Val Lys Lys Pro Gly Ala
1               5                   10                  15

Ser Leu Lys Val Ser Cys Lys Ala Ser Gly Tyr Ala Phe Ser Ser Ser
            20                  25                  30

Trp Met Asn Trp Val Arg Gln Ala Pro Gly Gln Arg Leu Glu Trp Ile
        35                  40                  45

Gly Arg Ile Tyr Pro Gly Asp Gly Asp Thr Asn Tyr Asn Gly Glu Phe
    50                  55                  60

Arg Val Arg Ala Thr Leu Thr Ala Asp Thr Ser Ala Ser Thr Ala Tyr
65                  70                  75                  80

Met Glu Leu Ser Ser Leu Arg Ser Glu Asp Thr Ala Val Tyr Phe Cys
                85                  90                  95

Ala Arg Leu Leu Arg Asn Gln Pro Gly Glu Ser Tyr Ala Met Asp Tyr
            100                 105                 110

Trp Gly Gln Gly Thr Leu Val Thr Val Ser Ser
        115                 120

<210> SEQ ID NO 88
<211> LENGTH: 123
<212> TYPE: PRT
<213> ORGANISM: Artificial Sequence
<220> FEATURE:
<223> OTHER INFORMATION: Synthetic Construct

<400> SEQUENCE: 88

Gln Val Gln Leu Val Gln Ser Gly Ala Glu Val Lys Lys Pro Gly Ala
```

```
1               5                   10                  15
Ser Leu Lys Val Ser Cys Lys Ala Ser Gly Tyr Ala Phe Ser Ser Ser
            20                  25                  30

Trp Met Asn Trp Val Arg Gln Ala Pro Gly Gln Arg Leu Glu Trp Ile
            35                  40                  45

Gly Arg Ile Tyr Pro Gly Asp Gly Asp Thr Asn Tyr Ala Gln Lys Phe
    50                  55                  60

Gln Gly Arg Ala Thr Leu Thr Ala Asp Thr Ser Ala Ser Thr Ala Tyr
65                  70                  75                  80

Met Glu Leu Ser Ser Leu Arg Ser Glu Asp Thr Ala Val Tyr Phe Cys
            85                  90                  95

Ala Arg Leu Leu Arg Asn Gln Pro Gly Glu Ser Tyr Ala Met Asp Tyr
            100                 105                 110

Trp Gly Gln Gly Thr Leu Val Thr Val Ser Ser
            115                 120
```

<210> SEQ ID NO 89
<211> LENGTH: 123
<212> TYPE: PRT
<213> ORGANISM: Artificial Sequence
<220> FEATURE:
<223> OTHER INFORMATION: Synthetic Construct

<400> SEQUENCE: 89

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Ser Ser Ser
            20                  25                  30

Trp Met Asn Trp Val Arg Gln Ala Pro Gly Gln Gly Leu Glu Trp Met
            35                  40                  45

Gly Arg Ile Tyr Pro Gly Asp Gly Asp Thr Asn Tyr Asn Gly Glu Phe
    50                  55                  60

Arg Val Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
            85                  90                  95

Ala Arg Leu Leu Arg Asn Gln Pro Gly Glu Ser Tyr Ala Met Asp Tyr
            100                 105                 110

Trp Gly Gln Gly Thr Leu Val Thr Val Ser Ser
            115                 120
```

<210> SEQ ID NO 90
<211> LENGTH: 123
<212> TYPE: PRT
<213> ORGANISM: Artificial Sequence
<220> FEATURE:
<223> OTHER INFORMATION: Synthetic Construct

<400> SEQUENCE: 90

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Ser Ser Ser
            20                  25                  30

Trp Met Asn Trp Val Arg Gln Ala Pro Gly Gln Arg Leu Glu Trp Ile
            35                  40                  45

Gly Arg Ile Tyr Pro Gly Asp Gly Asp Thr Asn Tyr Ala Gln Lys Phe
    50                  55                  60
```

```
Gln Gly Arg Ala Thr Ile Thr Ala Asp Thr Ser Ala Ser Thr Ala Tyr
65                  70                  75                  80

Met Glu Leu Ser Ser Leu Arg Ser Glu Asp Thr Ala Val Tyr Phe Cys
                85                  90                  95

Ala Arg Leu Leu Arg Asn Gln Pro Gly Glu Ser Tyr Ala Met Asp Tyr
            100                 105                 110

Trp Gly Gln Gly Thr Leu Val Thr Val Ser Ser
            115                 120

<210> SEQ ID NO 91
<211> LENGTH: 123
<212> TYPE: PRT
<213> ORGANISM: Artificial Sequence
<220> FEATURE:
<223> OTHER INFORMATION: Synthetic Construct

<400> SEQUENCE: 91

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Ser His
            20                  25                  30

Trp Met Asn Trp Val Arg Gln Ala Pro Gly Gln Gly Leu Glu Trp Met
        35                  40                  45

Gly Arg Ile Tyr Pro Gly Glu Gly Gln Thr Asn Tyr Ala Gln Lys Arg
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Leu Arg Asn Gln Pro Gly Glu Ser Tyr Ala Met Asp Tyr
            100                 105                 110

Trp Gly Gln Gly Thr Leu Val Thr Val Ser Ser
            115                 120

<210> SEQ ID NO 92
<211> LENGTH: 112
<212> TYPE: PRT
<213> ORGANISM: Artificial Sequence
<220> FEATURE:
<223> OTHER INFORMATION: Synthetic Construct

<400> SEQUENCE: 92

Asp Val Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Val His Ser
            20                  25                  30

Asn Gly Tyr Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr Arg Val Pro Tyr Thr Phe Gly Gln Gly Thr Lys Leu Glu Ile Lys
            100                 105                 110

<210> SEQ ID NO 93
```

```
<211> LENGTH: 112
<212> TYPE: PRT
<213> ORGANISM: Artificial Sequence
<220> FEATURE:
<223> OTHER INFORMATION: Synthetic Construct

<400> SEQUENCE: 93

Asp Val Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Val His Ser
            20                  25                  30

Asn Arg Tyr Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr Arg Val Pro Tyr Thr Phe Gly Gln Gly Thr Lys Leu Glu Ile Lys
            100                 105                 110

<210> SEQ ID NO 94
<211> LENGTH: 112
<212> TYPE: PRT
<213> ORGANISM: Artificial Sequence
<220> FEATURE:
<223> OTHER INFORMATION: Synthetic Construct

<400> SEQUENCE: 94

Asp Val Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Val His Ser
            20                  25                  30

Asn Trp Tyr Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr Arg Val Pro Tyr Thr Phe Gly Gln Gly Thr Lys Leu Glu Ile Lys
            100                 105                 110

<210> SEQ ID NO 95
<211> LENGTH: 112
<212> TYPE: PRT
<213> ORGANISM: Artificial Sequence
<220> FEATURE:
<223> OTHER INFORMATION: Synthetic Construct

<400> SEQUENCE: 95

Gly Val Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Ile His Ser
            20                  25                  30

Asn Gly Tyr Thr Tyr Leu His Trp Tyr Leu Gln Lys Pro Gly Gln Ser
        35                  40                  45
```

```
Pro Gln Leu Leu Ile Tyr Lys Val Ser Asn Arg Arg Ser Gly Val Pro
        50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ser Gln Ser
                 85                  90                  95

Thr Arg Val Pro Tyr Thr Phe Gly Gln Gly Thr Lys Leu Glu Ile Lys
            100                 105                 110
```

<210> SEQ ID NO 96
<211> LENGTH: 112
<212> TYPE: PRT
<213> ORGANISM: Artificial Sequence
<220> FEATURE:
<223> OTHER INFORMATION: Synthetic Construct

<400> SEQUENCE: 96

```
Gly Val Val Met Thr Gln Thr Pro Leu Ser Leu Ser Val Thr Pro Gly
 1               5                  10                  15

Gln Pro Ala Ser Ile Ser Cys Arg Thr Ser Gln Ser Leu Val His Ser
            20                  25                  30

Asn Gly Tyr Thr Tyr Leu His Trp Tyr Leu Gln Lys Pro Gly Gln Ser
        35                  40                  45

Pro Gln Leu Leu Ile Tyr Lys Val Ser Asn Arg Val Ser Gly Val Pro
    50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ser Gln Ser
                 85                  90                  95

Thr Arg Val Pro Tyr Thr Phe Gly Gln Gly Thr Lys Leu Glu Ile Lys
            100                 105                 110
```

<210> SEQ ID NO 97
<211> LENGTH: 112
<212> TYPE: PRT
<213> ORGANISM: Artificial Sequence
<220> FEATURE:
<223> OTHER INFORMATION: Synthetic Construct

<400> SEQUENCE: 97

```
Gly Val Val Met Thr Gln Thr Pro Leu Ser Leu Ser Val Thr Pro Gly
 1               5                  10                  15

Gln Pro Ala Ser Ile Ser Cys Arg Ser Ser Gln Ser Leu Val His Ser
            20                  25                  30

Asn Gly Tyr Thr Tyr Leu His Trp Tyr Leu Gln Lys Pro Gly Gln Ser
        35                  40                  45

Pro Gln Leu Leu Ile Tyr Lys Val Ser Asn Arg Ser Gly Val Pro
    50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ser Gln Ser
                 85                  90                  95

Thr Arg Val Pro Tyr Thr Phe Gly Gln Gly Thr Lys Leu Glu Ile Lys
            100                 105                 110
```

<210> SEQ ID NO 98
<211> LENGTH: 112
<212> TYPE: PRT
<213> ORGANISM: Artificial Sequence

```
<220> FEATURE:
<223> OTHER INFORMATION: Synthetic Construct

<400> SEQUENCE: 98

Asp Val Val Met Thr Gln Thr Pro Leu Ser Leu Ser Val Thr Pro Gly
1               5                   10                  15

Gln Pro Ala Ser Ile Ser Cys Arg Ser Ser Arg Ser Leu Val His Ser
            20                  25                  30

Asn Gly Tyr Thr Tyr Leu His Trp Tyr Leu Gln Lys Pro Gly Gln Ser
        35                  40                  45

Pro Gln Leu Leu Ile Tyr Lys Val Ser Asn Arg Val Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr Arg Val Pro Tyr Thr Phe Gly Gln Gly Thr Lys Leu Glu Ile Lys
            100                 105                 110

<210> SEQ ID NO 99
<211> LENGTH: 112
<212> TYPE: PRT
<213> ORGANISM: Artificial Sequence
<220> FEATURE:
<223> OTHER INFORMATION: Synthetic Construct

<400> SEQUENCE: 99

Gly Val Val Met Thr Gln Thr Pro Leu Ser Leu Ser Val Thr Pro Gly
1               5                   10                  15

Gln Pro Ala Ser Ile Ser Cys Arg Ser Ser Arg Ser Leu Val His Ser
            20                  25                  30

Asn Gly Tyr Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr Arg Val Pro Tyr Thr Phe Gly Gln Gly Thr Lys Leu Glu Ile Lys
            100                 105                 110

<210> SEQ ID NO 100
<211> LENGTH: 112
<212> TYPE: PRT
<213> ORGANISM: Artificial Sequence
<220> FEATURE:
<223> OTHER INFORMATION: Synthetic Construct

<400> SEQUENCE: 100

Gly Val Val Met Thr Gln Thr Pro Leu Ser Leu Ser Val Thr Pro Gly
1               5                   10                  15

Gln Pro Ala Ser Ile Ser Cys Arg Ser Ser Ser Ser Leu Val His Ser
            20                  25                  30

Asn Gly Tyr Thr Tyr Leu His Trp Tyr Leu Gln Lys Pro Gly Gln Ser
        35                  40                  45

Pro Gln Leu Leu Ile Tyr Lys Val Ser Asn Arg Lys Ser Gly Val Pro
    50                  55                  60
```

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr Arg Val Pro Tyr Thr Phe Gly Gln Gly Thr Lys Leu Glu Ile Lys
            100                 105                 110

<210> SEQ ID NO 101
<211> LENGTH: 112
<212> TYPE: PRT
<213> ORGANISM: Artificial Sequence
<220> FEATURE:
<223> OTHER INFORMATION: Synthetic Construct

<400> SEQUENCE: 101

Gly Val Val Met Thr Gln Thr Pro Leu Ser Leu Ser Val Thr Pro Gly
1               5                   10                  15

Gln Pro Ala Ser Ile Ser Cys Arg Ser Ser Arg Ser Leu Val His Ser
            20                  25                  30

Asn Gly Tyr Thr Tyr Leu His Trp Tyr Leu Gln Lys Pro Gly Gln Ser
        35                  40                  45

Pro Gln Leu Leu Ile Tyr Lys Val Ser Asn Arg Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr Arg Val Pro Tyr Thr Phe Gly Gln Gly Thr Lys Leu Glu Ile Lys
            100                 105                 110

<210> SEQ ID NO 102
<211> LENGTH: 112
<212> TYPE: PRT
<213> ORGANISM: Artificial Sequence
<220> FEATURE:
<223> OTHER INFORMATION: Synthetic Construct

<400> SEQUENCE: 102

Gly Val Val Met Thr Gln Thr Pro Leu Ser Leu Ser Val Thr Pro Gly
1               5                   10                  15

Gln Pro Ala Ser Ile Ser Cys Arg Ser Ser Arg Ser Leu Val His Ser
            20                  25                  30

Asn Gly Tyr Thr Tyr Leu His Trp Tyr Leu Gln Lys Pro Gly Gln Ser
        35                  40                  45

Pro Gln Leu Leu Ile Tyr Lys Val Ser Asn Arg Val Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr Arg Val Pro Tyr Thr Phe Gly Gln Gly Thr Lys Leu Glu Ile Lys
            100                 105                 110

<210> SEQ ID NO 103
<211> LENGTH: 112
<212> TYPE: PRT
<213> ORGANISM: Artificial Sequence
<220> FEATURE:
<223> OTHER INFORMATION: Synthetic Construct

<400> SEQUENCE: 103

Gly Val Val Met Ala Gln Thr Pro Leu Ser Leu Ser Val Thr Pro Gly
1               5                   10                  15

Gln Pro Ala Ser Ile Ser Cys Arg Thr Ser Gln Ser Leu Val His Ser
            20                  25                  30

Asn Gly Tyr Thr Tyr Leu His Trp Tyr Leu Gln Lys Pro Gly Gln Ser
        35                  40                  45

Pro Gln Leu Leu Ile Tyr Lys Val Ser Asn Arg Val Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr Arg Val Pro Tyr Thr Phe Gly Gln Gly Thr Lys Leu Glu Ile Lys
            100                 105                 110

<210> SEQ ID NO 104
<211> LENGTH: 112
<212> TYPE: PRT
<213> ORGANISM: Artificial Sequence
<220> FEATURE:
<223> OTHER INFORMATION: Synthetic Construct

<400> SEQUENCE: 104

Asp Val Val Met Thr Gln Ser Pro Asp Ser Leu Ala Val Ser Leu Gly
1               5                   10                  15

Glu Arg Ala Thr Ile Asn Cys Arg Ser Ser Gln Ser Leu Val His Ser
            20                  25                  30

Asn Gly Tyr Thr Tyr Leu His Trp Tyr Gln Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Thr Ile
65                  70                  75                  80

Ser Ser Leu Gln Ala Glu Asp Val Ala Val Tyr Tyr Cys Ser Gln Ser
                85                  90                  95

Thr Arg Val Pro Tyr Thr Phe Gly Gly Gly Thr Lys Val Glu Ile Lys
            100                 105                 110

<210> SEQ ID NO 105
<211> LENGTH: 112
<212> TYPE: PRT
<213> ORGANISM: Artificial Sequence
<220> FEATURE:
<223> OTHER INFORMATION: Synthetic Construct

<400> SEQUENCE: 105

Gly Val Val Met Thr Gln Thr Pro Leu Ser Leu Ser Val Thr Pro Gly
1               5                   10                  15

Gln Pro Ala Ser Ile Ser Cys Arg Ser Ser Arg Ser Leu Val His Ser
            20                  25                  30

Asn Arg Tyr Thr Tyr Leu His Trp Tyr Leu Gln Lys Pro Gly Gln Ser
        35                  40                  45

Pro Gln Leu Leu Ile Tyr Lys Val Ser Asn Arg Arg Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
            85                  90                  95

Thr Arg Val Pro Tyr Thr Phe Gly Gln Gly Thr Lys Leu Glu Ile Lys
        100                 105                 110

<210> SEQ ID NO 106
<211> LENGTH: 112
<212> TYPE: PRT
<213> ORGANISM: Artificial Sequence
<220> FEATURE:
<223> OTHER INFORMATION: Synthetic Construct

<400> SEQUENCE: 106

Gly Val Val Met Thr Gln Thr Pro Leu Ser Leu Ser Val Thr Pro Gly
1               5                   10                  15

Gln Pro Ala Ser Ile Ser Cys Arg Ser Ser Arg Ser Leu Val His Ser
            20                  25                  30

Asn Gln Tyr Thr Tyr Leu His Trp Tyr Leu Gln Lys Pro Gly Gln Ser
        35                  40                  45

Pro Gln Leu Leu Ile Tyr Lys Val Ser Asn Arg Arg Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
            85                  90                  95

Thr Arg Val Pro Tyr Thr Phe Gly Gln Gly Thr Lys Leu Glu Ile Lys
        100                 105                 110

<210> SEQ ID NO 107
<211> LENGTH: 112
<212> TYPE: PRT
<213> ORGANISM: Artificial Sequence
<220> FEATURE:
<223> OTHER INFORMATION: Synthetic Construct

<400> SEQUENCE: 107

Gly Val Val Met Thr Gln Thr Pro Leu Ser Leu Ser Val Thr Pro Gly
1               5                   10                  15

Gln Pro Ala Ser Ile Ser Cys Arg Thr Ser Arg Ser Leu Val His Ser
            20                  25                  30

Asn Arg Tyr Thr Tyr Leu His Trp Tyr Leu Gln Lys Pro Gly Gln Ser
        35                  40                  45

Pro Gln Leu Leu Ile Tyr Lys Val Ser Asn Arg Arg Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
            85                  90                  95

Thr Arg Val Pro Tyr Thr Phe Gly Gln Gly Thr Lys Leu Glu Ile Lys
        100                 105                 110

<210> SEQ ID NO 108
<211> LENGTH: 112
<212> TYPE: PRT
<213> ORGANISM: Artificial Sequence
<220> FEATURE:
<223> OTHER INFORMATION: Synthetic Construct

<400> SEQUENCE: 108

Asp Val Val Met Thr Gln Thr Pro Leu Ser Leu Ser Val Thr Pro Gly

```
1               5                   10                  15
Gln Pro Ala Ser Ile Ser Cys Arg Thr Ser Gln Ser Leu Val His Ser
            20                  25                  30

Asn Ala Tyr Thr Tyr Leu His Trp Tyr Leu Gln Lys Pro Gly Gln Ser
            35                  40                  45

Pro Gln Leu Leu Ile Tyr Lys Val Ser Asn Arg Val Ser Gly Val Pro
            50                  55                  60

Asp Arg Phe Ser Gly Ser Gly Ser Gly Thr Asp Phe Thr Leu Lys Ile
65                      70                  75                  80

Ser Arg Val Glu Ala Glu Asp Val Gly Val Tyr Tyr Cys Ser Gln Ser
                85                  90                  95

Thr Arg Val Pro Tyr Thr Phe Gly Gln Gly Thr Lys Leu Glu Ile Lys
            100                 105                 110

<210> SEQ ID NO 109
<211> LENGTH: 112
<212> TYPE: PRT
<213> ORGANISM: Artificial Sequence
<220> FEATURE:
<223> OTHER INFORMATION: Synthetic Construct

<400> SEQUENCE: 109

Asp Val Val Met Thr Gln Thr Pro Leu Ser Leu Ser Val Thr Pro Gly
1               5                   10                  15

Gln Pro Ala Ser Ile Ser Cys Arg Thr Ser Gln Ser Leu Val His Ser
            20                  25                  30

Asn Gln Tyr Thr Tyr Leu His Trp Tyr Leu Gln Lys Pro Gly Gln Ser
            35                  40                  45

Pro Gln Leu Leu Ile Tyr Lys Val Ser Asn Arg Val Ser Gly Val Pro
            50                  55                  60

Asp Arg Phe Ser Gly Ser Gly Ser Gly Thr Asp Phe Thr Leu Lys Ile
65                      70                  75                  80

Ser Arg Val Glu Ala Glu Asp Val Gly Val Tyr Tyr Cys Ser Gln Ser
                85                  90                  95

Thr Arg Val Pro Tyr Thr Phe Gly Gln Gly Thr Lys Leu Glu Ile Lys
            100                 105                 110

<210> SEQ ID NO 110
<211> LENGTH: 112
<212> TYPE: PRT
<213> ORGANISM: Artificial Sequence
<220> FEATURE:
<223> OTHER INFORMATION: Synthetic Construct

<400> SEQUENCE: 110

Gly Val Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Val His Ser
            20                  25                  30

Asn Gln Tyr Thr Tyr Leu His Trp Tyr Leu Gln Lys Pro Gly Gln Ser
            35                  40                  45

Pro Gln Leu Leu Ile Tyr Lys Val Ser Asn Arg Arg Ser Gly Val Pro
            50                  55                  60

Asp Arg Phe Ser Gly Ser Gly Ser Gly Thr Asp Phe Thr Leu Lys Ile
65                      70                  75                  80

Ser Arg Val Glu Ala Glu Asp Val Gly Val Tyr Tyr Cys Ser Gln Ser
                85                  90                  95
```

Thr Arg Val Pro Tyr Thr Phe Gly Gln Gly Thr Lys Leu Glu Ile Lys
            100                 105                 110

<210> SEQ ID NO 111
<211> LENGTH: 112
<212> TYPE: PRT
<213> ORGANISM: Artificial Sequence
<220> FEATURE:
<223> OTHER INFORMATION: Synthetic Construct

<400> SEQUENCE: 111

Asp Val Val Met Thr Gln Ser Pro Asp Ser Leu Ala Val Ser Leu Gly
1               5                   10                  15

Glu Arg Ala Thr Ile Asn Cys Arg Ser Ser Gln Ser Leu Val His Ser
            20                  25                  30

Asn Gln Tyr Thr Tyr Leu His Trp Tyr Gln Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Thr Ile
65                  70                  75                  80

Ser Ser Leu Gln Ala Glu Asp Val Ala Val Tyr Tyr Cys Ser Gln Ser
                85                  90                  95

Thr Arg Val Pro Tyr Thr Phe Gly Gly Gly Thr Lys Val Glu Ile Lys
            100                 105                 110

<210> SEQ ID NO 112
<211> LENGTH: 112
<212> TYPE: PRT
<213> ORGANISM: Artificial Sequence
<220> FEATURE:
<223> OTHER INFORMATION: Synthetic Construct

<400> SEQUENCE: 112

Asp Val Val Met Thr Gln Ser Pro Asp Ser Leu Ala Val Ser Leu Gly
1               5                   10                  15

Glu Arg Ala Thr Ile Asn Cys Arg Ser Ser Gln Ser Leu Val His Ser
            20                  25                  30

Asn Arg Tyr Thr Tyr Leu His Trp Tyr Gln Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr Arg Val Pro Tyr Thr Phe Gly Gln Gly Thr Lys Leu Glu Ile Lys
            100                 105                 110

<210> SEQ ID NO 113
<211> LENGTH: 112
<212> TYPE: PRT
<213> ORGANISM: Artificial Sequence
<220> FEATURE:
<223> OTHER INFORMATION: Synthetic Construct

<400> SEQUENCE: 113

Gly Val Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Val His Ser 20                  25                  30

Asn Arg Tyr Thr Tyr Leu His Trp Tyr Leu Gln Lys Pro Gly Gln Ser
                35                  40                  45

Pro Gln Leu Leu Ile Tyr Lys Val Ser Asn Arg Arg Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr Arg Val Pro Tyr Thr Phe Gly Gln Gly Thr Lys Leu Glu Ile Lys
            100                 105                 110

<210> SEQ ID NO 114
<211> LENGTH: 112
<212> TYPE: PRT
<213> ORGANISM: Artificial Sequence
<220> FEATURE:
<223> OTHER INFORMATION: Synthetic Construct

<400> SEQUENCE: 114

Asp Ile Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Val His Ser
                20                  25                  30

Asn Gly Tyr Thr Tyr Leu His Trp Tyr Leu Gln Lys Pro Gly Gln Ser
                35                  40                  45

Pro Gln Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr Arg Val Pro Tyr Thr Phe Gly Gln Gly Thr Lys Leu Glu Ile Lys
            100                 105                 110

<210> SEQ ID NO 115
<211> LENGTH: 112
<212> TYPE: PRT
<213> ORGANISM: Artificial Sequence
<220> FEATURE:
<223> OTHER INFORMATION: Synthetic Construct

<400> SEQUENCE: 115

Asp Val Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Val His Ser
                20                  25                  30

Asn Gly Tyr Thr Tyr Leu His Trp Tyr Leu Gln Lys Pro Gly Gln Ser
                35                  40                  45

Pro Gln Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr Arg Val Pro Tyr Thr Phe Gly Gln Gly Thr Lys Leu Glu Ile Lys
            100                 105                 110

<210> SEQ ID NO 116
<211> LENGTH: 112
<212> TYPE: PRT
<213> ORGANISM: Artificial Sequence
<220> FEATURE:
<223> OTHER INFORMATION: Synthetic Construct

<400> SEQUENCE: 116

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Gly Tyr Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr Arg Val Pro Tyr Thr Phe Gly Gly Gly Thr Lys Val Glu Ile Lys
            100                 105                 110

<210> SEQ ID NO 117
<211> LENGTH: 112
<212> TYPE: PRT
<213> ORGANISM: Artificial Sequence
<220> FEATURE:
<223> OTHER INFORMATION: Synthetic Construct

<400> SEQUENCE: 117

Asp Val Gln Met Thr Gln Ser Pro Ser Ser Leu Ser Ala Ser Val Gly
1               5                   10                  15

Asp Arg Val Thr Ile Thr Cys Arg Ser Ser Gln Ser Leu Val His Ser
            20                  25                  30

Asn Gly Tyr Thr Tyr Leu His Trp Tyr Gln Gln Lys Pro Gly Lys Ser
        35                  40                  45

Pro Lys Leu Leu Ile Tyr Lys Val Ser Asn Arg Phe Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Tyr Cys Ser Gln Ser
                85                  90                  95

Thr Arg Val Pro Tyr Thr Phe Gly Gly Gly Thr Lys Val Glu Ile Lys
            100                 105                 110

<210> SEQ ID NO 118
<211> LENGTH: 112
<212> TYPE: PRT
<213> ORGANISM: Artificial Sequence
<220> FEATURE:
<223> OTHER INFORMATION: Synthetic Construct

<400> SEQUENCE: 118

Gly Val Val Met Thr Gln Thr Pro Leu Ser Leu Ser Val Thr Pro Gly
1               5                   10                  15

Gln Pro Ala Ser Ile Ser Cys Arg Thr Ser Gln Ser Leu Val His Ser
            20                  25                  30

Asn Gln Tyr Thr Tyr Leu His Trp Tyr Leu Gln Lys Pro Gly Gln Ser

```
                35                  40                  45
Pro Gln Leu Leu Ile Tyr Lys Val Ser Asn Arg Val Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr Arg Val Pro Tyr Thr Phe Gly Gln Gly Thr Lys Leu Glu Ile Lys
                100                 105                 110

<210> SEQ ID NO 119
<211> LENGTH: 123
<212> TYPE: PRT
<213> ORGANISM: Artificial Sequence
<220> FEATURE:
<223> OTHER INFORMATION: Synthetic Construct

<400> SEQUENCE: 119

Gln Val Gln Leu Gln Gln Ser Gly Pro Glu Leu Val Lys Pro Gly Ala
1               5                   10                  15

Ser Leu Lys Ile Ser Cys Lys Ala Ser Gly Tyr Ala Phe Ser Ser Ser
            20                  25                  30

Trp Met Asn Trp Val Lys Gln Arg Pro Gly Lys Gly Leu Glu Trp Ile
        35                  40                  45

Gly Arg Ile Tyr Pro Gly Asp Gly Asp Thr Asn Tyr Asn Gly Glu Phe
    50                  55                  60

Arg Val Arg Ala Thr Leu Thr Ala Asp Thr Ser Ser Thr Thr Ala Tyr
65                  70                  75                  80

Met Gln Leu Ser Ser Leu Thr Ser Glu Asp Ser Ala Val Tyr Phe Cys
                85                  90                  95

Ala Arg Leu Leu Arg Asn Gln Pro Gly Glu Ser Tyr Ala Met Asp Tyr
                100                 105                 110

Trp Gly Gln Gly Ala Ser Val Thr Val Ser Ser
            115                 120

<210> SEQ ID NO 120
<211> LENGTH: 112
<212> TYPE: PRT
<213> ORGANISM: Artificial Sequence
<220> FEATURE:
<223> OTHER INFORMATION: Synthetic Construct

<400> SEQUENCE: 120

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Tyr Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Asp Asp Leu Gly Val Tyr Phe Cys Ser Gln Ser
                85                  90                  95

Thr Arg Val Pro Tyr Thr Phe Gly Gly Gly Thr Lys Leu Glu Ile Lys
                100                 105                 110
```

```
<210> SEQ ID NO 121
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 4
<223> OTHER INFORMATION: Xaa = Ser or Trp
<220> FEATURE:
<221> NAME/KEY: VARIANT
<222> LOCATION: 5
<223> OTHER INFORMATION: Xaa = Ser, Leu, or Arg
<220> FEATURE:
<221> NAME/KEY: VARIANT
<222> LOCATION: 6
<223> OTHER INFORMATION: Xaa = Ser, Asp, His, Gln, or Glu

<400> SEQUENCE: 121

Tyr Ala Phe Xaa Xaa Xaa Trp Met Asn
1               5

<210> SEQ ID NO 122
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 6
<223> OTHER INFORMATION: Xaa = Asp, Gly, Glu, Gln, or Val
<220> FEATURE:
<221> NAME/KEY: VARIANT
<222> LOCATION: 8
<223> OTHER INFORMATION: Xaa = Asp or Gln
<220> FEATURE:
<221> NAME/KEY: VARIANT
<222> LOCATION: 13
<223> OTHER INFORMATION: Xaa = Gln, Arg, His, Trp, Tyr, or Gly
<220> FEATURE:
<221> NAME/KEY: VARIANT
<222> LOCATION: 15
<223> OTHER INFORMATION: Xaa = Phe, Arg, or Trp
<220> FEATURE:
<221> NAME/KEY: VARIANT
<222> LOCATION: 16
<223> OTHER INFORMATION: Xaa = Gln, Arg, Lys, or His

<400> SEQUENCE: 122

Arg Ile Tyr Pro Gly Xaa Gly Xaa Thr Asn Tyr Ala Xaa Lys Xaa Xaa
1               5                   10                  15
Gly

<210> SEQ ID NO 123
<211> LENGTH: 16
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 7
<223> OTHER INFORMATION: Xaa = Gln or Lys
<220> FEATURE:
<221> NAME/KEY: VARIANT
<222> LOCATION: 10
<223> OTHER INFORMATION: Xaa = Glu, Ser, or Ala
<220> FEATURE:
<221> NAME/KEY: VARIANT
<222> LOCATION: 14
<223> OTHER INFORMATION: Xaa = Met or His
```

```
<400> SEQUENCE: 123

Ala Arg Leu Leu Arg Asn Xaa Pro Gly Xaa Ser Tyr Ala Xaa Asp Tyr
1               5                   10                  15

<210> SEQ ID NO 124
<211> LENGTH: 9
<212> TYPE: PRT
<213> ORGANISM: Artificial Sequence
<220> FEATURE:
<223> OTHER INFORMATION: Synthetic Construct

<400> SEQUENCE: 124

Tyr Ala Phe Ser Ser Ser Trp Met Asn
1               5

<210> SEQ ID NO 125
<211> LENGTH: 17
<212> TYPE: PRT
<213> ORGANISM: Artificial Sequence
<220> FEATURE:
<223> OTHER INFORMATION: Synthetic Construct

<400> SEQUENCE: 125

Arg Ile Tyr Pro Gly Asp Gly Asp Thr Asn Tyr Ala Gln Lys Phe Gln
1               5                   10                  15

Gly

<210> SEQ ID NO 126
<211> LENGTH: 16
<212> TYPE: PRT
<213> ORGANISM: Artificial Sequence
<220> FEATURE:
<223> OTHER INFORMATION: Synthetic Construct

<400> SEQUENCE: 126

Ala Arg Leu Leu Arg Asn Gln Pro Gly Glu Ser Tyr Ala Met Asp Tyr
1               5                   10                  15

<210> SEQ ID NO 127
<211> LENGTH: 16
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 2
<223> OTHER INFORMATION: Xaa = Ser or Thr
<220> FEATURE:
<221> NAME/KEY: VARIANT
<222> LOCATION: 4
<223> OTHER INFORMATION: Xaa = Gln, Arg, or Ser
<220> FEATURE:
<221> NAME/KEY: VARIANT
<222> LOCATION: 7
<223> OTHER INFORMATION: Xaa = Val or Ile
<220> FEATURE:
<221> NAME/KEY: VARIANT
<222> LOCATION: 11
<223> OTHER INFORMATION: Xaa = Gly, Arg, Trp, Gln, or Ala

<400> SEQUENCE: 127

Arg Xaa Ser Xaa Ser Leu Xaa His Ser Asn Xaa Tyr Thr Tyr Leu His
1               5                   10                  15

<210> SEQ ID NO 128
<211> LENGTH: 7
```

```
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 6
<223> OTHER INFORMATION: Xaa = Phe, Arg, Val, or Lys

<400> SEQUENCE: 128

Lys Val Ser Asn Arg Xaa Ser
1               5

<210> SEQ ID NO 129
<211> LENGTH: 9
<212> TYPE: PRT
<213> ORGANISM: Artificial Sequence
<220> FEATURE:
<223> OTHER INFORMATION: Synthetic Construct

<400> SEQUENCE: 129

Ser Gln Ser Thr Arg Val Pro Tyr Thr
1               5

<210> SEQ ID NO 130
<211> LENGTH: 16
<212> TYPE: PRT
<213> ORGANISM: Artificial Sequence
<220> FEATURE:
<223> OTHER INFORMATION: Synthetic Construct

<400> SEQUENCE: 130

Arg Ser Ser Gln Ser Leu Val His Ser Asn Gly Tyr Thr Tyr Leu His
1               5                   10                  15

<210> SEQ ID NO 131
<211> LENGTH: 7
<212> TYPE: PRT
<213> ORGANISM: Artificial Sequence
<220> FEATURE:
<223> OTHER INFORMATION: Synthetic Construct

<400> SEQUENCE: 131

Lys Val Ser Asn Arg Phe Ser
1               5

<210> SEQ ID NO 132
<211> LENGTH: 9
<212> TYPE: PRT
<213> ORGANISM: Artificial Sequence
<220> FEATURE:
<223> OTHER INFORMATION: Synthetic Construct

<400> SEQUENCE: 132

Tyr Ala Phe Ser Ser Gln Trp Met Asn
1               5

<210> SEQ ID NO 133
<211> LENGTH: 17
<212> TYPE: PRT
<213> ORGANISM: Artificial Sequence
<220> FEATURE:
<223> OTHER INFORMATION: Synthetic Construct

<400> SEQUENCE: 133

Arg Ile Tyr Pro Gly Gly Gly Asp Thr Asn Tyr Ala Arg Lys Phe Gln
1               5                   10                  15
```

Gly

<210> SEQ ID NO 134
<211> LENGTH: 7
<212> TYPE: PRT
<213> ORGANISM: Artificial Sequence
<220> FEATURE:
<223> OTHER INFORMATION: Synthetic Construct

<400> SEQUENCE: 134

Lys Val Ser Asn Arg Arg Ser
1               5

<210> SEQ ID NO 135
<211> LENGTH: 17
<212> TYPE: PRT
<213> ORGANISM: Artificial Sequence
<220> FEATURE:
<223> OTHER INFORMATION: Synthetic Construct

<400> SEQUENCE: 135

Arg Ile Tyr Pro Gly Gly Gly Asp Thr Asn Tyr Ala Gly Lys Phe Gln
1               5                   10                  15

Gly

<210> SEQ ID NO 136
<211> LENGTH: 9
<212> TYPE: PRT
<213> ORGANISM: Artificial Sequence
<220> FEATURE:
<223> OTHER INFORMATION: Synthetic Construct

<400> SEQUENCE: 136

Tyr Ala Phe Ser Ser Asp Trp Met Asn
1               5

<210> SEQ ID NO 137
<211> LENGTH: 17
<212> TYPE: PRT
<213> ORGANISM: Artificial Sequence
<220> FEATURE:
<223> OTHER INFORMATION: Synthetic Construct

<400> SEQUENCE: 137

Arg Ile Tyr Pro Gly Glu Gly Asp Thr Asn Tyr Ala Arg Lys Phe His
1               5                   10                  15

Gly

<210> SEQ ID NO 138
<211> LENGTH: 16
<212> TYPE: PRT
<213> ORGANISM: Artificial Sequence
<220> FEATURE:
<223> OTHER INFORMATION: Synthetic Construct

<400> SEQUENCE: 138

Ala Arg Leu Leu Arg Asn Lys Pro Gly Glu Ser Tyr Ala Met Asp Tyr
1               5                   10                  15

<210> SEQ ID NO 139
<211> LENGTH: 16
<212> TYPE: PRT
<213> ORGANISM: Artificial Sequence
<220> FEATURE:
<223> OTHER INFORMATION: Synthetic Construct

```
<400> SEQUENCE: 139

Arg Thr Ser Gln Ser Leu Val His Ser Asn Ala Tyr Thr Tyr Leu His
1               5                   10                  15

<210> SEQ ID NO 140
<211> LENGTH: 7
<212> TYPE: PRT
<213> ORGANISM: Artificial Sequence
<220> FEATURE:
<223> OTHER INFORMATION: Synthetic Construct

<400> SEQUENCE: 140

Lys Val Ser Asn Arg Val Ser
1               5

<210> SEQ ID NO 141
<211> LENGTH: 17
<212> TYPE: PRT
<213> ORGANISM: Artificial Sequence
<220> FEATURE:
<223> OTHER INFORMATION: Synthetic Construct

<400> SEQUENCE: 141

Arg Ile Tyr Pro Gly Glu Gly Asp Thr Asn Tyr Ala Arg Lys Phe Gln
1               5                   10                  15

Gly

<210> SEQ ID NO 142
<211> LENGTH: 16
<212> TYPE: PRT
<213> ORGANISM: Artificial Sequence
<220> FEATURE:
<223> OTHER INFORMATION: Synthetic Construct

<400> SEQUENCE: 142

Arg Ser Ser Gln Ser Leu Val His Ser Asn Gln Tyr Thr Tyr Leu His
1               5                   10                  15

<210> SEQ ID NO 143
<211> LENGTH: 17
<212> TYPE: PRT
<213> ORGANISM: Artificial Sequence
<220> FEATURE:
<223> OTHER INFORMATION: Synthetic Construct

<400> SEQUENCE: 143

Arg Ile Tyr Pro Gly Glu Gly Asp Thr Asn Tyr Ala Gly Lys Phe Gln
1               5                   10                  15

Gly

<210> SEQ ID NO 144
<211> LENGTH: 16
<212> TYPE: PRT
<213> ORGANISM: Artificial Sequence
<220> FEATURE:
<223> OTHER INFORMATION: Synthetic Construct

<400> SEQUENCE: 144

Arg Ser Ser Gln Ser Leu Val His Ser Asn Arg Tyr Thr Tyr Leu His
1               5                   10                  15

<210> SEQ ID NO 145
<211> LENGTH: 110
<212> TYPE: PRT
<213> ORGANISM: Homo sapiens
```

<400> SEQUENCE: 145

| | | | | | | | | | | | | | | | |
|---|---|---|---|---|---|---|---|---|---|---|---|---|---|---|---|
| Ala | Ser | Thr | Lys | Gly | Pro | Ser | Val | Phe | Pro | Leu | Ala | Pro | Cys | Ser | Arg |
| 1 | | | | 5 | | | | | 10 | | | | | 15 | |
| Ser | Thr | Ser | Glu | Ser | Thr | Ala | Ala | Leu | Gly | Cys | Leu | Val | Lys | Asp | Tyr |
| | | | 20 | | | | | 25 | | | | | 30 | | |
| Phe | Pro | Glu | Pro | Val | Thr | Val | Ser | Trp | Asn | Ser | Gly | Ala | Leu | Thr | Ser |
| | | 35 | | | | | 40 | | | | | 45 | | | |
| Gly | Val | His | Thr | Phe | Pro | Ala | Val | Leu | Gln | Ser | Ser | Gly | Leu | Tyr | Ser |
| | 50 | | | | | 55 | | | | | 60 | | | | |
| Leu | Ser | Ser | Val | Val | Thr | Val | Pro | Ser | Ser | Asn | Phe | Gly | Thr | Gln | Thr |
| 65 | | | | | 70 | | | | | 75 | | | | | 80 |
| Tyr | Thr | Cys | Asn | Val | Asp | His | Lys | Pro | Ser | Asn | Thr | Lys | Val | Asp | Lys |
| | | | | 85 | | | | | 90 | | | | | 95 | |
| Thr | Val | Glu | Arg | Lys | Cys | Cys | Val | Glu | Cys | Pro | Pro | Cys | Pro | | |
| | | | 100 | | | | | 105 | | | | | 110 | | |

<210> SEQ ID NO 146
<211> LENGTH: 330
<212> TYPE: PRT
<213> ORGANISM: Homo sapiens

<400> SEQUENCE: 146

| | | | | | | | | | | | | | | | |
|---|---|---|---|---|---|---|---|---|---|---|---|---|---|---|---|
| Ala | Ser | Thr | Lys | Gly | Pro | Ser | Val | Phe | Pro | Leu | Ala | Pro | Ser | Ser | Lys |
| 1 | | | | 5 | | | | | 10 | | | | | 15 | |
| Ser | Thr | Ser | Gly | Gly | Thr | Ala | Ala | Leu | Gly | Cys | Leu | Val | Lys | Asp | Tyr |
| | | | 20 | | | | | 25 | | | | | 30 | | |
| Phe | Pro | Glu | Pro | Val | Thr | Val | Ser | Trp | Asn | Ser | Gly | Ala | Leu | Thr | Ser |
| | | 35 | | | | | 40 | | | | | 45 | | | |
| Gly | Val | His | Thr | Phe | Pro | Ala | Val | Leu | Gln | Ser | Ser | Gly | Leu | Tyr | Ser |
| | 50 | | | | | 55 | | | | | 60 | | | | |
| Leu | Ser | Ser | Val | Val | Thr | Val | Pro | Ser | Ser | Ser | Leu | Gly | Thr | Gln | Thr |
| 65 | | | | | 70 | | | | | 75 | | | | | 80 |
| Tyr | Ile | Cys | Asn | Val | Asn | His | Lys | Pro | Ser | Asn | Thr | Lys | Val | Asp | Lys |
| | | | | 85 | | | | | 90 | | | | | 95 | |
| Lys | Val | Glu | Pro | Lys | Ser | Cys | Asp | Lys | Thr | His | Thr | Cys | Pro | Pro | Cys |
| | | | 100 | | | | | 105 | | | | | 110 | | |
| Pro | Ala | Pro | Glu | Leu | Leu | Gly | Gly | Pro | Ser | Val | Phe | Leu | Phe | Pro | Pro |
| | | 115 | | | | | 120 | | | | | 125 | | | |
| Lys | Pro | Lys | Asp | Thr | Leu | Met | Ile | Ser | Arg | Thr | Pro | Glu | Val | Thr | Cys |
| 130 | | | | | 135 | | | | | 140 | | | | | |
| Val | Val | Val | Asp | Val | Ser | His | Glu | Asp | Pro | Glu | Val | Lys | Phe | Asn | Trp |
| 145 | | | | | 150 | | | | | 155 | | | | | 160 |
| Tyr | Val | Asp | Gly | Val | Glu | Val | His | Asn | Ala | Lys | Thr | Lys | Pro | Arg | Glu |
| | | | | 165 | | | | | 170 | | | | | 175 | |
| Glu | Gln | Tyr | Asn | Ser | Thr | Tyr | Arg | Val | Val | Ser | Val | Leu | Thr | Val | Leu |
| | | | 180 | | | | | 185 | | | | | 190 | | |
| His | Gln | Asp | Trp | Leu | Asn | Gly | Lys | Glu | Tyr | Lys | Cys | Lys | Val | Ser | Asn |
| | | | 195 | | | | | 200 | | | | | 205 | | |
| Lys | Ala | Leu | Pro | Ala | Pro | Ile | Glu | Lys | Thr | Ile | Ser | Lys | Ala | Lys | Gly |
| | 210 | | | | | 215 | | | | | 220 | | | | |
| Gln | Pro | Arg | Glu | Pro | Gln | Val | Tyr | Thr | Leu | Pro | Pro | Ser | Arg | Asp | Glu |
| 225 | | | | | 230 | | | | | 235 | | | | | 240 |
| Leu | Thr | Lys | Asn | Gln | Val | Ser | Leu | Thr | Cys | Leu | Val | Lys | Gly | Phe | Tyr |
| | | | | 245 | | | | | 250 | | | | | 255 | |

```
Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 147
<211> LENGTH: 330
<212> TYPE: PRT
<213> ORGANISM: Artificial Sequence
<220> FEATURE:
<223> OTHER INFORMATION: Synthetic Construct

<400> SEQUENCE: 147

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
            130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285
```

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 148
<211> LENGTH: 330
<212> TYPE: PRT
<213> ORGANISM: Artificial Sequence
<220> FEATURE:
<223> OTHER INFORMATION: Synthetic Construct

<400> SEQUENCE: 148

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Ser Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

```
Gln Lys Ser Leu Ser Leu Ser Pro Gly Lys
            325                 330

<210> SEQ ID NO 149
<211> LENGTH: 330
<212> TYPE: PRT
<213> ORGANISM: Artificial Sequence
<220> FEATURE:
<223> OTHER INFORMATION: Synthetic Construct

<400> SEQUENCE: 149

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Ser Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Gly Ala Leu His Asn His Tyr Thr
305                 310                 315                 320

Gln Lys Ser Leu Ser Leu Ser Pro Gly Lys
            325                 330

<210> SEQ ID NO 150
```

<211> LENGTH: 330
<212> TYPE: PRT
<213> ORGANISM: Artificial Sequence
<220> FEATURE:
<223> OTHER INFORMATION: Synthetic Construct

<400> SEQUENCE: 150

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Ala Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Gly Ala Leu His Asn His Tyr Thr
305                 310                 315                 320

Gln Lys Ser Leu Ser Leu Ser Pro Gly Lys
                325                 330

<210> SEQ ID NO 151
<211> LENGTH: 330
<212> TYPE: PRT
<213> ORGANISM: Artificial Sequence
<220> FEATURE:
<223> OTHER INFORMATION: Synthetic Construct

<400> SEQUENCE: 151

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Ser Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Gly Ala Leu His Asn His Tyr Thr
305                 310                 315                 320

Gln Lys Ser Leu Ser Leu Ser Pro Gly Lys
                325                 330

<210> SEQ ID NO 152
<211> LENGTH: 330
<212> TYPE: PRT
<213> ORGANISM: Artificial Sequence
<220> FEATURE:
<223> OTHER INFORMATION: Synthetic Construct

<400> SEQUENCE: 152

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr

```
                   20                  25                  30

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
         50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
            130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ser Ser Ile Glu Lys Thr Ile Ser Lys Ala Lys Gly
            210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Gly Ala Leu His Asn His Tyr Thr
305                 310                 315                 320

Gln Lys Ser Leu Ser Leu Ser Pro Gly Lys
                325                 330

<210> SEQ ID NO 153
<211> LENGTH: 330
<212> TYPE: PRT
<213> ORGANISM: Artificial Sequence
<220> FEATURE:
<223> OTHER INFORMATION: Synthetic Construct

<400> SEQUENCE: 153

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
```

```
                  50                  55                  60
Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Ala Val Ser Asn
        195                 200                 205

Lys Ala Leu Pro Ala Ser Ile Glu Lys Thr Ile Ser Lys Ala Lys Gly
            210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
            290                 295                 300

Val Phe Ser Cys Ser Val Met His Gly Ala Leu His Asn His Tyr Thr
305                 310                 315                 320

Gln Lys Ser Leu Ser Leu Ser Pro Gly Lys
                325                 330
```

```
<210> SEQ ID NO 154
<211> LENGTH: 326
<212> TYPE: PRT
<213> ORGANISM: Homo sapiens

<400> SEQUENCE: 154

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95
```

```
Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
            165                 170                 175

Ser Thr Phe Arg Val Val Ser Val Leu Thr Val Val His Gln Asp Trp
        180                 185                 190

Leu Asn Gly Lys Glu Tyr Lys Cys Lys Val Ser Asn Lys Gly Leu Pro
    195                 200                 205

Ala Pro Ile Glu Lys Thr Ile Ser Lys Thr Lys Gly Gln Pro Arg Glu
210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
            245                 250                 255

Ala Val Glu Trp Glu Ser Asn Gly Gln Pro Glu Asn Asn Tyr Lys Thr
        260                 265                 270

Thr Pro Pro Met Leu Asp Ser Asp Gly Ser Phe Phe Leu Tyr Ser Lys
    275                 280                 285

Leu Thr Val Asp Lys Ser Arg Trp Gln Gln Gly Asn Val Phe Ser Cys
290                 295                 300

Ser Val Met His Glu Ala Leu His Asn His Tyr Thr Gln Lys Ser Leu
305                 310                 315                 320

Ser Leu Ser Pro Gly Lys
            325

<210> SEQ ID NO 155
<211> LENGTH: 326
<212> TYPE: PRT
<213> ORGANISM: Artificial Sequence
<220> FEATURE:
<223> OTHER INFORMATION: Synthetic Construct

<400> SEQUENCE: 155

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
            85                  90                  95

Thr Val Glu Arg Lys Cys Cys Val Glu Cys Pro Pro Cys Pro Ala Pro
        100                 105                 110

Pro Val Ala Gly Pro Ser Val Phe Leu Phe Pro Pro Lys Pro Lys Asp
    115                 120                 125
```

```
Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Gly Ala Leu His Asn His Tyr Thr Gln Lys Ser Leu
305                 310                 315                 320

Ser Leu Ser Pro Gly Lys
                325

<210> SEQ ID NO 156
<211> LENGTH: 326
<212> TYPE: PRT
<213> ORGANISM: Artificial Sequence
<220> FEATURE:
<223> OTHER INFORMATION: Synthetic Construct

<400> SEQUENCE: 156

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160
```

```
                                -continued

Val Glu Val His Asn Ala Lys Thr Lys Pro Arg Glu Glu Gln Phe Asn
            165                 170                 175

Ser Thr Phe Arg Val Val Ser Val Leu Thr Val Val His Gln Asp Trp
        180                 185                 190

Leu Asn Gly Lys Glu Tyr Lys Cys Lys Val Ser Asn Lys Gly Leu Pro
    195                 200                 205

Ser Ser Ile Glu Lys Thr Ile Ser Lys Thr Lys Gly Gln Pro Arg Glu
210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Gly Ala Leu His Asn His Tyr Thr Gln Lys Ser Leu
305                 310                 315                 320

Ser Leu Ser Pro Gly Lys
                325

<210> SEQ ID NO 157
<211> LENGTH: 9
<212> TYPE: PRT
<213> ORGANISM: Artificial Sequence
<220> FEATURE:
<223> OTHER INFORMATION: Synthetic Construct

<400> SEQUENCE: 157

Tyr Ala Phe Ser Leu Ser Trp Met Asn
1               5

<210> SEQ ID NO 158
<211> LENGTH: 9
<212> TYPE: PRT
<213> ORGANISM: Artificial Sequence
<220> FEATURE:
<223> OTHER INFORMATION: Synthetic Construct

<400> SEQUENCE: 158

Tyr Ala Phe Ser Arg Ser Trp Met Asn
1               5

<210> SEQ ID NO 159
<211> LENGTH: 9
<212> TYPE: PRT
<213> ORGANISM: Artificial Sequence
<220> FEATURE:
<223> OTHER INFORMATION: Synthetic Construct

<400> SEQUENCE: 159

Tyr Ala Phe Ser Ser His Trp Met Asn
1               5

<210> SEQ ID NO 160
<211> LENGTH: 9
<212> TYPE: PRT
<213> ORGANISM: Artificial Sequence
<220> FEATURE:
<223> OTHER INFORMATION: Synthetic Construct
```

<400> SEQUENCE: 160

Tyr Ala Phe Ser Ser Glu Trp Met Asn
1               5

<210> SEQ ID NO 161
<211> LENGTH: 9
<212> TYPE: PRT
<213> ORGANISM: Artificial Sequence
<220> FEATURE:
<223> OTHER INFORMATION: Synthetic Construct

<400> SEQUENCE: 161

Tyr Ala Phe Trp Ser Ser Trp Met Asn
1               5

<210> SEQ ID NO 162
<211> LENGTH: 17
<212> TYPE: PRT
<213> ORGANISM: Artificial Sequence
<220> FEATURE:
<223> OTHER INFORMATION: Synthetic Construct

<400> SEQUENCE: 162

Arg Ile Tyr Pro Gly Gly Gly Asp Thr Asn Tyr Ala Gln Lys Phe Gln
1               5                   10                  15

Gly

<210> SEQ ID NO 163
<211> LENGTH: 17
<212> TYPE: PRT
<213> ORGANISM: Artificial Sequence
<220> FEATURE:
<223> OTHER INFORMATION: Synthetic Construct

<400> SEQUENCE: 163

Arg Ile Tyr Pro Gly Glu Gly Asp Thr Asn Tyr Ala Gln Lys Phe Gln
1               5                   10                  15

Gly

<210> SEQ ID NO 164
<211> LENGTH: 17
<212> TYPE: PRT
<213> ORGANISM: Artificial Sequence
<220> FEATURE:
<223> OTHER INFORMATION: Synthetic Construct

<400> SEQUENCE: 164

Arg Ile Tyr Pro Gly Gln Gly Asp Thr Asn Tyr Ala Gln Lys Phe Gln
1               5                   10                  15

Gly

<210> SEQ ID NO 165
<211> LENGTH: 17
<212> TYPE: PRT
<213> ORGANISM: Artificial Sequence
<220> FEATURE:
<223> OTHER INFORMATION: Synthetic Construct

<400> SEQUENCE: 165

Arg Ile Tyr Pro Gly Asp Gly Asp Thr Asn Tyr Ala Gln Lys Phe Arg
1               5                   10                  15

Gly

```
<210> SEQ ID NO 166
<211> LENGTH: 17
<212> TYPE: PRT
<213> ORGANISM: Artificial Sequence
<220> FEATURE:
<223> OTHER INFORMATION: Synthetic Construct

<400> SEQUENCE: 166

Arg Ile Tyr Pro Gly Asp Gly Asp Thr Asn Tyr Ala Arg Lys Phe Gln
1               5                   10                  15

Gly

<210> SEQ ID NO 167
<211> LENGTH: 17
<212> TYPE: PRT
<213> ORGANISM: Artificial Sequence
<220> FEATURE:
<223> OTHER INFORMATION: Synthetic Construct

<400> SEQUENCE: 167

Arg Ile Tyr Pro Gly Asp Gly Asp Thr Asn Tyr Ala His Lys Phe Gln
1               5                   10                  15

Gly

<210> SEQ ID NO 168
<211> LENGTH: 17
<212> TYPE: PRT
<213> ORGANISM: Artificial Sequence
<220> FEATURE:
<223> OTHER INFORMATION: Synthetic Construct

<400> SEQUENCE: 168

Arg Ile Tyr Pro Gly Asp Gly Asp Thr Asn Tyr Ala Gln Lys Phe Lys
1               5                   10                  15

Gly

<210> SEQ ID NO 169
<211> LENGTH: 17
<212> TYPE: PRT
<213> ORGANISM: Artificial Sequence
<220> FEATURE:
<223> OTHER INFORMATION: Synthetic Construct

<400> SEQUENCE: 169

Arg Ile Tyr Pro Gly Asp Gly Asp Thr Asn Tyr Ala Gln Lys Arg Gln
1               5                   10                  15

Gly

<210> SEQ ID NO 170
<211> LENGTH: 17
<212> TYPE: PRT
<213> ORGANISM: Artificial Sequence
<220> FEATURE:
<223> OTHER INFORMATION: Synthetic Construct

<400> SEQUENCE: 170

Arg Ile Tyr Pro Gly Asp Gly Asp Thr Asn Tyr Ala Gln Lys Trp Gln
1               5                   10                  15

Gly

<210> SEQ ID NO 171
<211> LENGTH: 17
<212> TYPE: PRT
```

<213> ORGANISM: Artificial Sequence
<220> FEATURE:
<223> OTHER INFORMATION: Synthetic Construct

<400> SEQUENCE: 171

Arg Ile Tyr Pro Gly Asp Gly Asp Thr Asn Tyr Ala Trp Lys Phe Gln
1               5                   10                  15
Gly

<210> SEQ ID NO 172
<211> LENGTH: 17
<212> TYPE: PRT
<213> ORGANISM: Artificial Sequence
<220> FEATURE:
<223> OTHER INFORMATION: Synthetic Construct

<400> SEQUENCE: 172

Arg Ile Tyr Pro Gly Asp Gly Asp Thr Asn Tyr Ala Tyr Lys Phe Gln
1               5                   10                  15
Gly

<210> SEQ ID NO 173
<211> LENGTH: 17
<212> TYPE: PRT
<213> ORGANISM: Artificial Sequence
<220> FEATURE:
<223> OTHER INFORMATION: Synthetic Construct

<400> SEQUENCE: 173

Arg Ile Tyr Pro Gly Asp Gly Gln Thr Asn Tyr Ala Gln Lys Arg Gln
1               5                   10                  15
Gly

<210> SEQ ID NO 174
<211> LENGTH: 17
<212> TYPE: PRT
<213> ORGANISM: Artificial Sequence
<220> FEATURE:
<223> OTHER INFORMATION: Synthetic Construct

<400> SEQUENCE: 174

Arg Ile Tyr Pro Gly Gly Gly Asp Thr Asn Tyr Ala Gln Lys Phe Arg
1               5                   10                  15
Gly

<210> SEQ ID NO 175
<211> LENGTH: 17
<212> TYPE: PRT
<213> ORGANISM: Artificial Sequence
<220> FEATURE:
<223> OTHER INFORMATION: Synthetic Construct

<400> SEQUENCE: 175

Arg Ile Tyr Pro Gly Gly Gly Asp Thr Asn Tyr Ala Gln Lys Arg Gln
1               5                   10                  15
Gly

<210> SEQ ID NO 176
<211> LENGTH: 17
<212> TYPE: PRT
<213> ORGANISM: Artificial Sequence
<220> FEATURE:
<223> OTHER INFORMATION: Synthetic Construct

```
<400> SEQUENCE: 176

Arg Ile Tyr Pro Gly Val Gly Asp Thr Asn Tyr Ala Gln Lys Phe Gln
1               5                   10                  15

Gly

<210> SEQ ID NO 177
<211> LENGTH: 17
<212> TYPE: PRT
<213> ORGANISM: Artificial Sequence
<220> FEATURE:
<223> OTHER INFORMATION: Synthetic Construct

<400> SEQUENCE: 177

Arg Ile Tyr Pro Gly Glu Gly Asp Thr Asn Tyr Ala Gln Lys Phe Arg
1               5                   10                  15

Gly

<210> SEQ ID NO 178
<211> LENGTH: 17
<212> TYPE: PRT
<213> ORGANISM: Artificial Sequence
<220> FEATURE:
<223> OTHER INFORMATION: Synthetic Construct

<400> SEQUENCE: 178

Arg Ile Tyr Pro Gly Gly Gly Asp Thr Asn Tyr Ala Arg Lys Phe Arg
1               5                   10                  15

Gly

<210> SEQ ID NO 179
<211> LENGTH: 17
<212> TYPE: PRT
<213> ORGANISM: Artificial Sequence
<220> FEATURE:
<223> OTHER INFORMATION: Synthetic Construct

<400> SEQUENCE: 179

Arg Ile Tyr Pro Gly Glu Gly Asp Thr Asn Tyr Ala Gln Lys Phe His
1               5                   10                  15

Gly

<210> SEQ ID NO 180
<211> LENGTH: 17
<212> TYPE: PRT
<213> ORGANISM: Artificial Sequence
<220> FEATURE:
<223> OTHER INFORMATION: Synthetic Construct

<400> SEQUENCE: 180

Arg Ile Tyr Pro Gly Glu Gly Gln Thr Asn Tyr Ala Gln Lys Arg Gln
1               5                   10                  15

Gly

<210> SEQ ID NO 181
<211> LENGTH: 16
<212> TYPE: PRT
<213> ORGANISM: Artificial Sequence
<220> FEATURE:
<223> OTHER INFORMATION: Synthetic Construct

<400> SEQUENCE: 181

Ala Arg Leu Leu Arg Asn Gln Pro Gly Ser Ser Tyr Ala Met Asp Tyr
1               5                   10                  15
```

```
<210> SEQ ID NO 182
<211> LENGTH: 16
<212> TYPE: PRT
<213> ORGANISM: Artificial Sequence
<220> FEATURE:
<223> OTHER INFORMATION: Synthetic Construct

<400> SEQUENCE: 182

Ala Arg Leu Leu Arg Asn Gln Pro Gly Ala Ser Tyr Ala Met Asp Tyr
1               5                   10                  15

<210> SEQ ID NO 183
<211> LENGTH: 16
<212> TYPE: PRT
<213> ORGANISM: Artificial Sequence
<220> FEATURE:
<223> OTHER INFORMATION: Synthetic Construct

<400> SEQUENCE: 183

Ala Arg Leu Leu Arg Asn Gln Pro Gly Glu Ser Tyr Ala His Asp Tyr
1               5                   10                  15

<210> SEQ ID NO 184
<211> LENGTH: 16
<212> TYPE: PRT
<213> ORGANISM: Artificial Sequence
<220> FEATURE:
<223> OTHER INFORMATION: Synthetic Construct

<400> SEQUENCE: 184

Arg Ser Ser Gln Ser Leu Val His Ser Asn Trp Tyr Thr Tyr Leu His
1               5                   10                  15

<210> SEQ ID NO 185
<211> LENGTH: 16
<212> TYPE: PRT
<213> ORGANISM: Artificial Sequence
<220> FEATURE:
<223> OTHER INFORMATION: Synthetic Construct

<400> SEQUENCE: 185

Arg Ser Ser Gln Ser Leu Ile His Ser Asn Gly Tyr Thr Tyr Leu His
1               5                   10                  15

<210> SEQ ID NO 186
<211> LENGTH: 16
<212> TYPE: PRT
<213> ORGANISM: Artificial Sequence
<220> FEATURE:
<223> OTHER INFORMATION: Synthetic Construct

<400> SEQUENCE: 186

Arg Thr Ser Gln Ser Leu Val His Ser Asn Gly Tyr Thr Tyr Leu His
1               5                   10                  15

<210> SEQ ID NO 187
<211> LENGTH: 16
<212> TYPE: PRT
<213> ORGANISM: Artificial Sequence
<220> FEATURE:
<223> OTHER INFORMATION: Synthetic Construct

<400> SEQUENCE: 187

Arg Ser Ser Arg Ser Leu Val His Ser Asn Gly Tyr Thr Tyr Leu His
1               5                   10                  15
```

```
<210> SEQ ID NO 188
<211> LENGTH: 16
<212> TYPE: PRT
<213> ORGANISM: Artificial Sequence
<220> FEATURE:
<223> OTHER INFORMATION: Synthetic Construct

<400> SEQUENCE: 188

Arg Ser Ser Ser Ser Leu Val His Ser Asn Gly Tyr Thr Tyr Leu His
1               5                   10                  15

<210> SEQ ID NO 189
<211> LENGTH: 16
<212> TYPE: PRT
<213> ORGANISM: Artificial Sequence
<220> FEATURE:
<223> OTHER INFORMATION: Synthetic Construct

<400> SEQUENCE: 189

Arg Ser Ser Arg Ser Leu Val His Ser Asn Arg Tyr Thr Tyr Leu His
1               5                   10                  15

<210> SEQ ID NO 190
<211> LENGTH: 16
<212> TYPE: PRT
<213> ORGANISM: Artificial Sequence
<220> FEATURE:
<223> OTHER INFORMATION: Synthetic Construct

<400> SEQUENCE: 190

Arg Ser Ser Arg Ser Leu Val His Ser Asn Gln Tyr Thr Tyr Leu His
1               5                   10                  15

<210> SEQ ID NO 191
<211> LENGTH: 16
<212> TYPE: PRT
<213> ORGANISM: Artificial Sequence
<220> FEATURE:
<223> OTHER INFORMATION: Synthetic Construct

<400> SEQUENCE: 191

Arg Thr Ser Arg Ser Leu Val His Ser Asn Arg Tyr Thr Tyr Leu His
1               5                   10                  15

<210> SEQ ID NO 192
<211> LENGTH: 16
<212> TYPE: PRT
<213> ORGANISM: Artificial Sequence
<220> FEATURE:
<223> OTHER INFORMATION: Synthetic Construct

<400> SEQUENCE: 192

Arg Thr Ser Gln Ser Leu Val His Ser Asn Gln Tyr Thr Tyr Leu His
1               5                   10                  15

<210> SEQ ID NO 193
<211> LENGTH: 7
<212> TYPE: PRT
<213> ORGANISM: Artificial Sequence
<220> FEATURE:
<223> OTHER INFORMATION: Synthetic Construct

<400> SEQUENCE: 193

Lys Val Ser Asn Arg Lys Ser
1               5
```

```
<210> SEQ ID NO 194
<211> LENGTH: 5
<212> TYPE: PRT
<213> ORGANISM: Artificial Sequence
<220> FEATURE:
<223> OTHER INFORMATION: Synthetic Construct

<400> SEQUENCE: 194

Ser Gln Trp Met Asn
1               5

<210> SEQ ID NO 195
<211> LENGTH: 14
<212> TYPE: PRT
<213> ORGANISM: Artificial Sequence
<220> FEATURE:
<223> OTHER INFORMATION: Synthetic Construct

<400> SEQUENCE: 195

Leu Leu Arg Asn Gln Pro Gly Glu Ser Tyr Ala Met Asp Tyr
1               5                   10

<210> SEQ ID NO 196
<211> LENGTH: 5
<212> TYPE: PRT
<213> ORGANISM: Artificial Sequence
<220> FEATURE:
<223> OTHER INFORMATION: Synthetic Construct

<400> SEQUENCE: 196

Ser Asp Trp Met Asn
1               5

<210> SEQ ID NO 197
<211> LENGTH: 14
<212> TYPE: PRT
<213> ORGANISM: Artificial Sequence
<220> FEATURE:
<223> OTHER INFORMATION: Synthetic Construct

<400> SEQUENCE: 197

Leu Leu Arg Asn Lys Pro Gly Glu Ser Tyr Ala Met Asp Tyr
1               5                   10

<210> SEQ ID NO 198
<211> LENGTH: 453
<212> TYPE: PRT
<213> ORGANISM: Artificial Sequence
<220> FEATURE:
<223> OTHER INFORMATION: Synthetic Construct

<400> SEQUENCE: 198

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Ser Ser Gln
                20                  25                  30

Trp Met Asn Trp Val Arg Gln Ala Pro Gly Gln Arg Leu Glu Trp Ile
            35                  40                  45

Gly Arg Ile Tyr Pro Gly Gly Gly Asp Thr Asn Tyr Ala Gly Lys Phe
        50                  55                  60

Gln Gly Arg Val Thr Ile Thr Ala Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95
```

```
Ala Arg Leu Leu Arg Asn Gln Pro Gly Glu Ser Tyr Ala Met Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450

<210> SEQ ID NO 199
<211> LENGTH: 452
<212> TYPE: PRT
<213> ORGANISM: Artificial Sequence
<220> FEATURE:
<223> OTHER INFORMATION: Synthetic Construct

<400> SEQUENCE: 199
```

```
Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Ala Phe Ser Ser Gln
             20                  25                  30

Trp Met Asn Trp Val Arg Gln Ala Pro Gly Gln Arg Leu Glu Trp Ile
         35                  40                  45

Gly Arg Ile Tyr Pro Gly Gly Asp Thr Asn Tyr Ala Gly Lys Phe
     50                  55                  60

Gln Gly Arg Val Thr Ile Thr Ala Asp Thr Ser Ala Ser Thr Ala Tyr
 65                  70                  75                  80

Met Glu Leu Ser Ser Leu Arg Ser Glu Asp Thr Ala Val Tyr Tyr Cys
             85                  90                  95

Ala Arg Leu Leu Arg Asn Gln Pro Gly Glu Ser Tyr Ala Met Asp Tyr
            100                 105                 110

Trp Gly Gln Gly Thr Leu Val Thr Val Ser Ser Ala Ser Thr Lys Gly
            115                 120                 125

Pro Ser Val Phe Pro Leu Ala Pro Ser Ser Lys Ser Thr Ser Gly Gly
            130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
            195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
    275                 280                 285

Glu Val His Asn Ala Lys Thr Lys Pro Arg Glu Glu Gln Tyr Asn Ser
            290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
            355                 360                 365

Val Ser Leu Thr Cys Leu Val Lys Gly Phe Tyr Pro Ser Asp Ile Ala
            370                 375                 380

Val Glu Trp Glu Ser Asn Gly Gln Pro Glu Asn Tyr Lys Thr Thr
385                 390                 395                 400

Pro Pro Val Leu Asp Ser Asp Gly Ser Phe Phe Leu Tyr Ser Lys Leu
            405                 410                 415

Thr Val Asp Lys Ser Arg Trp Gln Gln Gly Asn Val Phe Ser Cys Ser
```

```
                420             425             430
Val Met His Glu Ala Leu His Asn His Tyr Thr Gln Lys Ser Leu Ser
        435                 440                 445

Leu Ser Pro Gly
    450

<210> SEQ ID NO 200
<211> LENGTH: 453
<212> TYPE: PRT
<213> ORGANISM: Artificial Sequence
<220> FEATURE:
<223> OTHER INFORMATION: Synthetic Construct

<400> SEQUENCE: 200

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Ser Ser Gln
            20                  25                  30

Trp Met Asn Trp Val Arg Gln Ala Pro Gly Gln Arg Leu Glu Trp Ile
        35                  40                  45

Gly Arg Ile Tyr Pro Gly Gly Gly Asp Thr Asn Tyr Ala Gly Lys Phe
    50                  55                  60

Gln Gly Arg Val Thr Ile Thr Ala Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Leu Arg Asn Gln Pro Gly Glu Ser Tyr Ala Met Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
```

```
                        325                 330                 335
Ser Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
            355                 360                 365

Val Ser Leu Thr Cys Leu Val Lys Gly Phe Tyr Pro Ser Asp Ile Ala
            370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
            405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
            435                 440                 445

Leu Ser Pro Gly Lys
            450

<210> SEQ ID NO 201
<211> LENGTH: 452
<212> TYPE: PRT
<213> ORGANISM: Artificial Sequence
<220> FEATURE:
<223> OTHER INFORMATION: Synthetic Construct

<400> SEQUENCE: 201

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Ser Ser Gln
            20                  25                  30

Trp Met Asn Trp Val Arg Gln Ala Pro Gly Gln Arg Leu Glu Trp Ile
            35                  40                  45

Gly Arg Ile Tyr Pro Gly Gly Asp Thr Asn Tyr Ala Gly Lys Phe
        50                  55                  60

Gln Gly Arg Val Thr Ile Thr Ala Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Leu Arg Asn Gln Pro Gly Glu Ser Tyr Ala Met Asp Tyr
            100                 105                 110

Trp Gly Gln Gly Thr Leu Val Thr Val Ser Ser Ala Ser Thr Lys Gly
            115                 120                 125

Pro Ser Val Phe Pro Leu Ala Pro Ser Ser Lys Ser Thr Ser Gly Gly
            130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
            195                 200                 205

Asn His Lys Pro Ser Asn Thr Lys Val Asp Lys Lys Val Glu Pro Lys
        210                 215                 220

Ser Cys Asp Lys Thr His Thr Cys Pro Pro Cys Pro Ala Pro Glu Leu
```

```
                  225                 230                 235                 240

Leu Gly Gly Pro Ser Val Phe Leu Phe Pro Lys Pro Lys Asp Thr
                    245                 250                 255

Leu Met Ile Ser Arg Thr Pro Glu Val Thr Cys Val Val Asp Val
                    260                 265                 270

Ser His Glu Asp Pro Glu Val Lys Phe Asn Trp Tyr Val Asp Gly Val
                    275                 280                 285

Glu Val His Asn Ala Lys Thr Lys Pro Arg Glu Glu Gln Tyr Asn Ser
                290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                    325                 330                 335

Ser Ile Glu Lys Thr Ile Ser Lys Ala Lys Gly Gln Pro Arg Glu Pro
                    340                 345                 350

Gln Val Tyr Thr Leu Pro Pro Ser Arg Asp Glu Leu Thr Lys Asn Gln
                    355                 360                 365

Val Ser Leu Thr Cys Leu Val Lys Gly Phe Tyr Pro Ser Asp Ile Ala
                370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                    405                 410                 415

Thr Val Asp Lys Ser Arg Trp Gln Gln Gly Asn Val Phe Ser Cys Ser
                    420                 425                 430

Val Met His Gly Ala Leu His Asn His Tyr Thr Gln Lys Ser Leu Ser
                435                 440                 445

Leu Ser Pro Gly
    450

<210> SEQ ID NO 202
<211> LENGTH: 453
<212> TYPE: PRT
<213> ORGANISM: Artificial Sequence
<220> FEATURE:
<223> OTHER INFORMATION: Synthetic Construct

<400> SEQUENCE: 202

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Ser Asp
                20                  25                  30

Trp Met Asn Trp Val Arg Gln Ala Pro Gly Gln Gly Leu Glu Trp Met
                35                  40                  45

Gly Arg Ile Tyr Pro Gly Glu Gly Asp Thr Asn Tyr Ala Arg Lys Phe
    50                  55                  60

His Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Leu Arg Asn Lys Pro Gly Glu Ser Tyr Ala Met Asp Tyr
                100                 105                 110

Trp Gly Gln Gly Thr Leu Val Thr Val Ser Ser Ala Ser Thr Lys Gly
                115                 120                 125

Pro Ser Val Phe Pro Leu Ala Pro Ser Ser Lys Ser Thr Ser Gly Gly
```

```
            130                 135                 140
Thr Ala Ala Leu Gly Cys Leu Val Lys Asp Tyr Phe Pro Glu Pro Val
145                 150                 155                 160
Thr Val Ser Trp Asn Ser Gly Ala Leu Thr Ser Gly Val His Thr Phe
                165                 170                 175
Pro Ala Val Leu Gln Ser Ser Gly Leu Tyr Ser Leu Ser Ser Val Val
            180                 185                 190
Thr Val Pro Ser Ser Ser Leu Gly Thr Gln Thr Tyr Ile Cys Asn Val
        195                 200                 205
Asn His Lys Pro Ser Asn Thr Lys Val Asp Lys Val Glu Pro Lys
    210                 215                 220
Ser Cys Asp Lys Thr His Thr Cys Pro Pro Cys Pro Ala Pro Glu Leu
225                 230                 235                 240
Leu Gly Gly Pro Ser Val Phe Leu Phe Pro Pro Lys Pro Lys Asp Thr
                245                 250                 255
Leu Met Ile Ser Arg Thr Pro Glu Val Thr Cys Val Val Val Asp Val
            260                 265                 270
Ser His Glu Asp Pro Glu Val Lys Phe Asn Trp Tyr Val Asp Gly Val
        275                 280                 285
Glu Val His Asn Ala Lys Thr Lys Pro Arg Glu Glu Gln Tyr Asn Ser
    290                 295                 300
Thr Tyr Arg Val Val Ser Val Leu Thr Val Leu His Gln Asp Trp Leu
305                 310                 315                 320
Asn Gly Lys Glu Tyr Lys Cys Lys Val Ser Asn Lys Ala Leu Pro Ala
                325                 330                 335
Pro Ile Glu Lys Thr Ile Ser Lys Ala Lys Gly Gln Pro Arg Glu Pro
            340                 345                 350
Gln Val Tyr Thr Leu Pro Pro Ser Arg Asp Glu Leu Thr Lys Asn Gln
        355                 360                 365
Val Ser Leu Thr Cys Leu Val Lys Gly Phe Tyr Pro Ser Asp Ile Ala
    370                 375                 380
Val Glu Trp Glu Ser Asn Gly Gln Pro Glu Asn Asn Tyr Lys Thr Thr
385                 390                 395                 400
Pro Pro Val Leu Asp Ser Asp Gly Ser Phe Phe Leu Tyr Ser Lys Leu
                405                 410                 415
Thr Val Asp Lys Ser Arg Trp Gln Gln Gly Asn Val Phe Ser Cys Ser
            420                 425                 430
Val Met His Glu Ala Leu His Asn His Tyr Thr Gln Lys Ser Leu Ser
        435                 440                 445
Leu Ser Pro Gly Lys
    450

<210> SEQ ID NO 203
<211> LENGTH: 452
<212> TYPE: PRT
<213> ORGANISM: Artificial Sequence
<220> FEATURE:
<223> OTHER INFORMATION: Synthetic Construct

<400> SEQUENCE: 203

Gln Val Gln Leu Val Gln Ser Gly Ala Glu Val Lys Lys Pro Gly Ser
1               5                   10                  15
Ser Val Lys Val Ser Cys Lys Ala Ser Gly Tyr Ala Phe Ser Ser Asp
                20                  25                  30
Trp Met Asn Trp Val Arg Gln Ala Pro Gly Gln Gly Leu Glu Trp Met
```

```
                35                  40                  45
Gly Arg Ile Tyr Pro Gly Glu Gly Asp Thr Asn Tyr Ala Arg Lys Phe
 50                  55                  60
His Gly Arg Val Thr Ile Thr Ala Asp Glu Ser Thr Ser Thr Ala Tyr
 65                  70                  75                  80
Met Glu Leu Ser Ser Leu Arg Ser Glu Asp Thr Ala Val Tyr Tyr Cys
                 85                  90                  95
Ala Arg Leu Leu Arg Asn Lys Pro Gly Glu Ser Tyr Ala Met Asp Tyr
                100                 105                 110
Trp Gly Gln Gly Thr Leu Val Thr Val Ser Ser Ala Ser Thr Lys Gly
                115                 120                 125
Pro Ser Val Phe Pro Leu Ala Pro Ser Ser Lys Ser Thr Ser Gly Gly
                130                 135                 140
Thr Ala Ala Leu Gly Cys Leu Val Lys Asp Tyr Phe Pro Glu Pro Val
145                 150                 155                 160
Thr Val Ser Trp Asn Ser Gly Ala Leu Thr Ser Gly Val His Thr Phe
                165                 170                 175
Pro Ala Val Leu Gln Ser Ser Gly Leu Tyr Ser Leu Ser Ser Val Val
                180                 185                 190
Thr Val Pro Ser Ser Ser Leu Gly Thr Gln Thr Tyr Ile Cys Asn Val
                195                 200                 205
Asn His Lys Pro Ser Asn Thr Lys Val Asp Lys Lys Val Glu Pro Lys
210                 215                 220
Ser Cys Asp Lys Thr His Thr Cys Pro Pro Cys Pro Ala Pro Glu Leu
225                 230                 235                 240
Leu Gly Gly Pro Ser Val Phe Leu Phe Pro Pro Lys Pro Lys Asp Thr
                245                 250                 255
Leu Met Ile Ser Arg Thr Pro Glu Val Thr Cys Val Val Val Asp Val
                260                 265                 270
Ser His Glu Asp Pro Glu Val Lys Phe Asn Trp Tyr Val Asp Gly Val
                275                 280                 285
Glu Val His Asn Ala Lys Thr Lys Pro Arg Glu Glu Gln Tyr Asn Ser
                290                 295                 300
Thr Tyr Arg Val Val Ser Val Leu Thr Val Leu His Gln Asp Trp Leu
305                 310                 315                 320
Asn Gly Lys Glu Tyr Lys Cys Lys Val Ser Asn Lys Ala Leu Pro Ala
                325                 330                 335
Pro Ile Glu Lys Thr Ile Ser Lys Ala Lys Gly Gln Pro Arg Glu Pro
                340                 345                 350
Gln Val Tyr Thr Leu Pro Pro Ser Arg Asp Glu Leu Thr Lys Asn Gln
                355                 360                 365
Val Ser Leu Thr Cys Leu Val Lys Gly Phe Tyr Pro Ser Asp Ile Ala
                370                 375                 380
Val Glu Trp Glu Ser Asn Gly Gln Pro Glu Asn Asn Tyr Lys Thr Thr
385                 390                 395                 400
Pro Pro Val Leu Asp Ser Asp Gly Ser Phe Phe Leu Tyr Ser Lys Leu
                405                 410                 415
Thr Val Asp Lys Ser Arg Trp Gln Gln Gly Asn Val Phe Ser Cys Ser
                420                 425                 430
Val Met His Glu Ala Leu His Asn His Tyr Thr Gln Lys Ser Leu Ser
                435                 440                 445
Leu Ser Pro Gly
                450
```

<210> SEQ ID NO 204
<211> LENGTH: 453
<212> TYPE: PRT
<213> ORGANISM: Artificial Sequence
<220> FEATURE:
<223> OTHER INFORMATION: Synthetic Construct

<400> SEQUENCE: 204

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Ser Asp
            20                  25                  30

Trp Met Asn Trp Val Arg Gln Ala Pro Gly Gln Gly Leu Glu Trp Met
        35                  40                  45

Gly Arg Ile Tyr Pro Gly Glu Gly Asp Thr Asn Tyr Ala Arg Lys Phe
    50                  55                  60

His Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Leu Arg Asn Lys Pro Gly Glu Ser Tyr Ala Met Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Ser Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365
```

```
Val Ser Leu Thr Cys Leu Val Lys Gly Phe Tyr Pro Ser Asp Ile Ala
        370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Gly Ala Leu His Asn His Tyr Thr Gln Lys Ser Leu Ser
        435                 440                 445

Leu Ser Pro Gly Lys
        450

<210> SEQ ID NO 205
<211> LENGTH: 452
<212> TYPE: PRT
<213> ORGANISM: Artificial Sequence
<220> FEATURE:
<223> OTHER INFORMATION: Synthetic Construct

<400> SEQUENCE: 205

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Ser Asp
            20                  25                  30

Trp Met Asn Trp Val Arg Gln Ala Pro Gly Gln Gly Leu Glu Trp Met
        35                  40                  45

Gly Arg Ile Tyr Pro Gly Glu Gly Asp Thr Asn Tyr Ala Arg Lys Phe
    50                  55                  60

His Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Leu Arg Asn Lys Pro Gly Glu Ser Tyr Ala Met Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270
```

```
Ser His Glu Asp Pro Glu Val Lys Phe Asn Trp Tyr Val Asp Gly Val
            275                 280                 285

Glu Val His Asn Ala Lys Thr Lys Pro Arg Glu Glu Gln Tyr Asn Ser
        290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Ser Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Gly Ala Leu His Asn His Tyr Thr Gln Lys Ser Leu Ser
        435                 440                 445

Leu Ser Pro Gly
        450

<210> SEQ ID NO 206
<211> LENGTH: 453
<212> TYPE: PRT
<213> ORGANISM: Artificial Sequence
<220> FEATURE:
<223> OTHER INFORMATION: Synthetic Construct

<400> SEQUENCE: 206

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Ser Gln
            20                  25                  30

Trp Met Asn Trp Val Arg Gln Ala Pro Gly Gln Gly Leu Glu Trp Met
        35                  40                  45

Gly Arg Ile Tyr Pro Gly Glu Gly Asp Thr Asn Tyr Ala Arg Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Leu Arg Asn Gln Pro Gly Glu Ser Tyr Ala Met Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175
```

Pro Ala Val Leu Gln Ser Ser Gly Leu Tyr Ser Leu Ser Val Val
            180                 185                 190

Thr Val Pro Ser Ser Leu Gly Thr Gln Thr Tyr Ile Cys Asn Val
        195                 200                 205

Asn His Lys Pro Ser Asn Thr Lys Val Asp Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450

<210> SEQ ID NO 207
<211> LENGTH: 452
<212> TYPE: PRT
<213> ORGANISM: Artificial Sequence
<220> FEATURE:
<223> OTHER INFORMATION: Synthetic Construct

<400> SEQUENCE: 207

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Ser Gln
            20                  25                  30

Trp Met Asn Trp Val Arg Gln Ala Pro Gly Gln Gly Leu Glu Trp Met
        35                  40                  45

Gly Arg Ile Tyr Pro Gly Glu Gly Asp Thr Asn Tyr Ala Arg Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Leu Arg Asn Gln Pro Gly Glu Ser Tyr Ala Met Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly
    450

<210> SEQ ID NO 208
<211> LENGTH: 453
<212> TYPE: PRT
<213> ORGANISM: Artificial Sequence
<220> FEATURE:

<223> OTHER INFORMATION: Synthetic Construct

<400> SEQUENCE: 208

```
Gln Val Gln Leu Val Gln Ser Gly Ala Glu Val Lys Lys Pro Gly Ser
1               5                   10                  15
Ser Val Lys Val Ser Cys Lys Ala Ser Gly Tyr Ala Phe Ser Ser His
            20                  25                  30
Trp Met Asn Trp Val Arg Gln Ala Pro Gly Gln Gly Leu Glu Trp Met
        35                  40                  45
Gly Arg Ile Tyr Pro Gly Gly Asp Thr Asn Tyr Ala Gln Lys Phe
    50                  55                  60
Arg Gly Arg Val Thr Ile Thr Ala Asp Glu Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Leu Leu Arg Asn Gln Pro Gly Ala Ser Tyr Ala Met Asp Tyr
            100                 105                 110
Trp Gly Gln Gly Thr Leu Val Thr Val Ser Ser Ala Ser Thr Lys Gly
        115                 120                 125
Pro Ser Val Phe Pro Leu Ala Pro Ser Ser Lys Ser Thr Ser Gly Gly
    130                 135                 140
Thr Ala Ala Leu Gly Cys Leu Val Lys Asp Tyr Phe Pro Glu Pro Val
145                 150                 155                 160
Thr Val Ser Trp Asn Ser Gly Ala Leu Thr Ser Gly Val His Thr Phe
                165                 170                 175
Pro Ala Val Leu Gln Ser Ser Gly Leu Tyr Ser Leu Ser Ser Val Val
            180                 185                 190
Thr Val Pro Ser Ser Ser Leu Gly Thr Gln Thr Tyr Ile Cys Asn Val
        195                 200                 205
Asn His Lys Pro Ser Asn Thr Lys Val Asp Lys Lys Val Glu Pro Lys
    210                 215                 220
Ser Cys Asp Lys Thr His Thr Cys Pro Pro Cys Pro Ala Pro Glu Leu
225                 230                 235                 240
Leu Gly Gly Pro Ser Val Phe Leu Phe Pro Pro Lys Pro Lys Asp Thr
                245                 250                 255
Leu Met Ile Ser Arg Thr Pro Glu Val Thr Cys Val Val Val Asp Val
            260                 265                 270
Ser His Glu Asp Pro Glu Val Lys Phe Asn Trp Tyr Val Asp Gly Val
        275                 280                 285
Glu Val His Asn Ala Lys Thr Lys Pro Arg Glu Glu Gln Tyr Asn Ser
    290                 295                 300
Thr Tyr Arg Val Val Ser Val Leu Thr Val Leu His Gln Asp Trp Leu
305                 310                 315                 320
Asn Gly Lys Glu Tyr Lys Cys Lys Val Ser Asn Lys Ala Leu Pro Ala
                325                 330                 335
Pro Ile Glu Lys Thr Ile Ser Lys Ala Lys Gly Gln Pro Arg Glu Pro
            340                 345                 350
Gln Val Tyr Thr Leu Pro Pro Ser Arg Asp Glu Leu Thr Lys Asn Gln
        355                 360                 365
Val Ser Leu Thr Cys Leu Val Lys Gly Phe Tyr Pro Ser Asp Ile Ala
    370                 375                 380
Val Glu Trp Glu Ser Asn Gly Gln Pro Glu Asn Asn Tyr Lys Thr Thr
385                 390                 395                 400
```

```
Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450

<210> SEQ ID NO 209
<211> LENGTH: 452
<212> TYPE: PRT
<213> ORGANISM: Artificial Sequence
<220> FEATURE:
<223> OTHER INFORMATION: Synthetic Construct

<400> SEQUENCE: 209

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Ser His
            20                  25                  30

Trp Met Asn Trp Val Arg Gln Ala Pro Gly Gln Gly Leu Glu Trp Met
        35                  40                  45

Gly Arg Ile Tyr Pro Gly Gly Asp Thr Asn Tyr Ala Gln Lys Phe
    50                  55                  60

Arg Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Leu Arg Asn Gln Pro Gly Ala Ser Tyr Ala Met Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300
```

```
Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
            325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
            355                 360                 365

Val Ser Leu Thr Cys Leu Val Lys Gly Phe Tyr Pro Ser Asp Ile Ala
        370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
                420                 425                 430

Val Met His Glu Ala Leu His Asn His Tyr Thr Gln Lys Ser Leu Ser
                435                 440                 445

Leu Ser Pro Gly
    450

<210> SEQ ID NO 210
<211> LENGTH: 453
<212> TYPE: PRT
<213> ORGANISM: Artificial Sequence
<220> FEATURE:
<223> OTHER INFORMATION: Synthetic Construct

<400> SEQUENCE: 210

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Ser His
            20                  25                  30

Trp Met Asn Trp Val Arg Gln Ala Pro Gly Gln Gly Leu Glu Trp Met
        35                  40                  45

Gly Arg Ile Tyr Pro Gly Gly Gly Asp Thr Asn Tyr Ala Arg Lys Phe
    50                  55                  60

Arg Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Leu Arg Asn Gln Pro Gly Ala Ser Tyr Ala Met Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205
```

```
Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450

<210> SEQ ID NO 211
<211> LENGTH: 452
<212> TYPE: PRT
<213> ORGANISM: Artificial Sequence
<220> FEATURE:
<223> OTHER INFORMATION: Synthetic Construct

<400> SEQUENCE: 211

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Ser His
                20                  25                  30

Trp Met Asn Trp Val Arg Gln Ala Pro Gly Gln Gly Leu Glu Trp Met
            35                  40                  45

Gly Arg Ile Tyr Pro Gly Gly Asp Thr Asn Tyr Ala Arg Lys Phe
    50                  55                  60

Arg Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Leu Arg Asn Gln Pro Gly Ala Ser Tyr Ala Met Asp Tyr
            100                 105                 110
```

```
Trp Gly Gln Gly Thr Leu Val Thr Val Ser Ser Ala Ser Thr Lys Gly
            115                 120                 125

Pro Ser Val Phe Pro Leu Ala Pro Ser Ser Lys Ser Thr Ser Gly Gly
        130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly
        450

<210> SEQ ID NO 212
<211> LENGTH: 453
<212> TYPE: PRT
<213> ORGANISM: Artificial Sequence
<220> FEATURE:
<223> OTHER INFORMATION: Synthetic Construct

<400> SEQUENCE: 212

Gln Val Gln Leu Val Gln Ser Gly Ala Glu Val Lys Lys Pro Gly Ser
1               5                   10                  15
```

-continued

Ser Val Lys Val Ser Cys Lys Ala Ser Gly Tyr Ala Phe Ser Ser His
            20                  25                  30

Trp Met Asn Trp Val Arg Gln Ala Pro Gly Gln Gly Leu Glu Trp Met
        35                  40                  45

Gly Arg Ile Tyr Pro Gly Glu Gly Asp Thr Asn Tyr Ala Gln Lys Phe
    50                  55                  60

Arg Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Leu Arg Asn Gln Pro Gly Ala Ser Tyr Ala Met Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser 435                 440                 445

Leu Ser Pro Gly Lys
        450

<210> SEQ ID NO 213
<211> LENGTH: 452
<212> TYPE: PRT
<213> ORGANISM: Artificial Sequence
<220> FEATURE:
<223> OTHER INFORMATION: Synthetic Construct

<400> SEQUENCE: 213

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Ser His
            20                  25                  30

Trp Met Asn Trp Val Arg Gln Ala Pro Gly Gln Gly Leu Glu Trp Met
        35                  40                  45

Gly Arg Ile Tyr Pro Gly Glu Gly Asp Thr Asn Tyr Ala Gln Lys Phe
    50                  55                  60

Arg Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Leu Arg Asn Gln Pro Gly Ala Ser Tyr Ala Met Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro

-continued

```
                340                 345                 350
Gln Val Tyr Thr Leu Pro Pro Ser Arg Asp Glu Leu Thr Lys Asn Gln
            355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
            405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
            435                 440                 445

Leu Ser Pro Gly
    450
```

<210> SEQ ID NO 214
<211> LENGTH: 219
<212> TYPE: PRT
<213> ORGANISM: Artificial Sequence
<220> FEATURE:
<223> OTHER INFORMATION: Synthetic Construct

<400> SEQUENCE: 214

```
Asp Val Val Met Thr Gln Ser Pro Asp Ser Leu Ala Val Ser Leu Gly
1               5                   10                  15

Glu Arg Ala Thr Ile Asn Cys Arg Ser Ser Gln Ser Leu Val His Ser
            20                  25                  30

Asn Arg Tyr Thr Tyr Leu His Trp Tyr Gln Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr Arg Val Pro Tyr Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 215
<211> LENGTH: 219
<212> TYPE: PRT

<213> ORGANISM: Artificial Sequence
<220> FEATURE:
<223> OTHER INFORMATION: Synthetic Construct

<400> SEQUENCE: 215

```
Asp Val Val Met Thr Gln Thr Pro Leu Ser Leu Ser Val Thr Pro Gly
1               5                   10                  15

Gln Pro Ala Ser Ile Ser Cys Arg Thr Ser Gln Ser Leu Val His Ser
            20                  25                  30

Asn Ala Tyr Thr Tyr Leu His Trp Tyr Leu Gln Lys Pro Gly Gln Ser
        35                  40                  45

Pro Gln Leu Leu Ile Tyr Lys Val Ser Asn Arg Val Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr Arg Val Pro Tyr Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 216
<211> LENGTH: 219
<212> TYPE: PRT
<213> ORGANISM: Artificial Sequence
<220> FEATURE:
<223> OTHER INFORMATION: Synthetic Construct

<400> SEQUENCE: 216

```
Gly Val Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Val His Ser
            20                  25                  30

Asn Gln Tyr Thr Tyr Leu His Trp Tyr Leu Gln Lys Pro Gly Gln Ser
        35                  40                  45

Pro Gln Leu Leu Ile Tyr Lys Val Ser Asn Arg Arg Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr Arg Val Pro Tyr Thr Phe Gly Gln Gly Thr Lys Leu Glu Ile Lys
            100                 105                 110
```

```
Arg Thr Val Ala Ala Pro Ser Val Phe Ile Phe Pro Ser Asp Glu
            115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 217
<211> LENGTH: 219
<212> TYPE: PRT
<213> ORGANISM: Artificial Sequence
<220> FEATURE:
<223> OTHER INFORMATION: Synthetic Construct

<400> SEQUENCE: 217

Gly Val Val Met Thr Gln Thr Pro Leu Ser Leu Ser Val Thr Pro Gly
1               5                   10                  15

Gln Pro Ala Ser Ile Ser Cys Arg Ser Ser Arg Ser Leu Val His Ser
            20                  25                  30

Asn Gln Tyr Thr Tyr Leu His Trp Tyr Leu Gln Lys Pro Gly Gln Ser
        35                  40                  45

Pro Gln Leu Leu Ile Tyr Lys Val Ser Asn Arg Arg Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr Arg Val Pro Tyr Thr Phe Gly Gln Gly Thr Lys Leu Glu Ile Lys
            100                 105                 110

Arg Thr Val Ala Ala Pro Ser Val Phe Ile Phe Pro Ser Asp Glu
            115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 218
<211> LENGTH: 219
<212> TYPE: PRT
<213> ORGANISM: Artificial Sequence
<220> FEATURE:
```

<223> OTHER INFORMATION: Synthetic Construct

<400> SEQUENCE: 218

```
Gly Val Val Met Thr Gln Thr Pro Leu Ser Leu Ser Val Thr Pro Gly
1               5                   10                  15

Gln Pro Ala Ser Ile Ser Cys Arg Thr Ser Arg Ser Leu Val His Ser
            20                  25                  30

Asn Arg Tyr Thr Tyr Leu His Trp Tyr Leu Gln Lys Pro Gly Gln Ser
        35                  40                  45

Pro Gln Leu Leu Ile Tyr Lys Val Ser Asn Arg Arg Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr Arg Val Pro Tyr Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

ANTI-TREM2 ANTIBODIES AND METHODS OF USE THEREOF

CROSS-REFERENCE TO RELATED APPLICATIONS

This application claims the benefit of U.S. Provisional Application No. 62/541,019, filed Aug. 3, 2017 and 62/636,095 filed Feb. 27, 2018, which are hereby incorporated by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 735022001800SEQLIST.TXT, date recorded: Aug. 2, 2018, size: 238 KB).

FIELD OF THE PRESENT DISCLOSURE

The present disclosure relates to anti-TREM2 antibodies and therapeutic uses of such antibodies.

BACKGROUND OF THE PRESENT DISCLOSURE

Triggering receptor expressed on myeloid cells-2 (TREM2) is an immunoglobulin-like receptor that is expressed, for example, on myeloid lineage cells.

TREM2 activity has been implicated in diseases, disorders, and conditions, such as frontotemporal dementia (FTD), Alzheimer's disease, Parkinson's disease, stroke/ischemic brain injury, multiple sclerosis, and Nasu-Hakola disease (Neumann, H et al., (2007) J Neuroimmunol 184: 92-99; Takahashi, K et al., (2005) J Exp Med 201: 647-657; Takahashi, K et al., (2007) PLoS Med 4: e124; and Hsieh, C L et al., (2009) J Neurochem 109: 1144-1156; Malm, T M et al, *Neurotherapeutics*. 2014 Nov. 18; Paloneva, J et al., (2002) Am J Hum Genet 71: 656-662; and Paloneva, J et al., (2003) J Exp Med 198: 669-675; Guerreiro, R J et al., (2013) JAMA Neurol 70: 78-84; Guerreiro, R J et al., (2012) Arch Neurol: 1-7; Guerreiro, R et al., (2013) N Engl J Med 368: 117-127; Jonsson, T et al., (2013) N Engl J Med 368: 107-116; and Neumann, H et al., (2013) N Engl J Med 368: 182-184; and Wang Y, Cell. 2015; 160(6):1061-71).

Accordingly, there is a need for therapeutic anti-TREM2 antibodies to treat diseases, disorders, and conditions associated with decreased TREM2 activity.

All references cited herein, including patent applications and publications, are hereby incorporated by reference in their entirety.

SUMMARY OF THE PRESENT DISCLOSURE

The present disclosure is generally directed to compositions that include antibodies, e.g., monoclonal, chimeric, humanized antibodies, antibody fragments, etc., that specifically bind a TREM2 protein, e.g., a mammalian TREM2 (e.g., any non-human mammal) or human TREM2, and to methods of using such compositions.

Certain aspects of the present disclosure are based, at least in part, on the identification of anti-TREM2 antibodies with improved affinity and functional characteristics. Surprisingly, the functional characteristics of the anti-TREM2 antibodies were not predictable from the increase in affinity. In some embodiments, anti-TREM2 antibodies of the present disclosure bind both human and cynomolgus monkey TREM2 with an affinity that is at least about 1-fold higher than an anti-TREM2 antibody selected from anti-TREM2 antibody comprising a heavy chain variable region comprising the amino acid sequence of SEQ ID NO: 27 and a light chain variable region comprising the amino acid sequence of SEQ ID NO: 56 (e.g., antibody AL2p-h50); an anti-TREM2 antibody comprising a heavy chain variable region comprising the amino acid sequence of SEQ ID NO: 91 and a light chain variable region comprising the amino acid sequence of SEQ ID NO: 103 (e.g., antibody AL2p-h77); and an anti-TREM2 antibody comprising a heavy chain variable region comprising the amino acid sequence of SEQ ID NO: 119 and a light chain variable region comprising the amino acid sequence of SEQ ID NO: 120 (e.g., antibody AL2). In some embodiments, anti-TREM2 antibodies of the present disclosure bind to primary human immune cells with an affinity that is at least about 10 times higher than that of an anti-TREM2 antibody selected from an anti-TREM2 antibody comprising a heavy chain variable region comprising the amino acid sequence of SEQ ID NO: 27 and a light chain variable region comprising the amino acid sequence of SEQ ID NO: 56; an anti-TREM2 antibody comprising a heavy chain variable region comprising the amino acid sequence of SEQ ID NO: 91 and a light chain variable region comprising the amino acid sequence of SEQ ID NO: 103; and an anti-TREM2 antibody comprising a heavy chain variable region comprising the amino acid sequence of SEQ ID NO: 119 and a light chain variable region comprising the amino acid sequence of SEQ ID NO: 120. In some embodiments, anti-TREM2 antibodies of the present disclosure cluster and activate TREM2 signaling in an amount that is at least about 1-fold greater than that of an anti-TREM2 antibody selected from an anti-TREM2 antibody comprising a heavy chain variable region comprising the amino acid sequence of SEQ ID NO: 27 and a light chain variable region comprising the amino acid sequence of SEQ ID NO: 56; an anti-TREM2 antibody comprising a heavy chain variable region comprising the amino acid sequence of SEQ ID NO: 91 and a light chain variable region comprising the amino acid sequence of SEQ ID NO: 103; and an anti-TREM2 antibody comprising a heavy chain variable region comprising the amino acid sequence of SEQ ID NO: 119 and a light chain variable region comprising the amino acid sequence of SEQ ID NO: 120. In some embodiments, anti-TREM2 antibodies of the present disclosure increase immune cell survival in vitro that to an extent that is greater than an anti-TREM2 antibody selected from an anti-TREM2 antibody comprising a heavy chain variable region comprising the amino acid sequence of SEQ ID NO: 27 and a light chain variable region comprising the amino acid sequence of SEQ ID NO: 56; an anti-TREM2 antibody comprising a heavy chain variable region comprising the amino acid sequence of SEQ ID NO: 91 and a light chain variable region comprising the amino acid sequence of SEQ ID NO: 103; and an anti-TREM2 antibody comprising a heavy chain variable region comprising the amino acid sequence of SEQ ID NO: 119 and a light chain variable region comprising the amino acid sequence of SEQ ID NO: 120. In some embodiments, anti-TREM2 antibodies of the present disclosure may also have improved in vivo half-lives. In some embodiments, anti-TREM2 antibodies of the present disclosure may also decreases plasma levels of soluble TREM2 in vivo. In some embodiments, anti-TREM2 antibodies of the present disclosure may also decrease soluble TREM2. In some embodiments, the soluble TREM2 is decreased about any of 10, 20, 30, 40, 50 or 60%.

Accordingly, certain aspects of the present disclosure relate to relate to an antibody that binds to a TREM2 protein, wherein the antibody comprises a heavy chain variable region and a light chain variable region, wherein the heavy chain variable region comprises: an HVR-H1 comprising the sequence according to Formula I: YAFX$_1$X$_2$X$_3$WMN, wherein X$_1$ is S or W, X$_2$ is S, L, or R, and X$_3$ is S, D, H, Q, or E (SEQ ID NO: 121); an HVR-H2 comprising the sequence according to Formula II: RIYPGX$_1$GX$_2$TNYAX$_3$KX$_4$X$_5$G, wherein X$_1$ is D, G, E, Q, or V, X$_2$ is D or Q, X$_3$ is Q, R, H, W, Y, or G, X$_4$ is F, R, or W, and X$_5$ is Q, R, K, or H (SEQ ID NO: 122); and an HVR-H3 comprising the sequence according to Formula III: ARLLRNX$_1$PGX$_2$SYAX$_3$DY, wherein X$_1$ is Q or K, X$_2$ is E, S, or A, and X$_3$ is M or H (SEQ ID NO: 123), and wherein the antibody is not an antibody comprising a heavy chain variable region comprising an HVR-H1 comprising the sequence of YAFSSSWMN (SEQ ID NO: 124), an HVR-H2 comprising the sequence of RIYPGDGDTNYAQKFQG (SEQ ID NO: 125), and an HVR-H3 comprising the sequence of ARLLRNQPGESYAMDY (SEQ ID NO: 126). Other aspects of the present disclosure relate to an antibody that binds to a TREM2 protein, wherein the antibody comprises a heavy chain variable region and a light chain variable region, wherein the light chain variable region comprises: an HVR-L1 comprising the sequence according to Formula IV: RX$_1$SX$_2$SLX$_3$HSNX$_4$YTYLH, wherein X$_1$ is S or T, X$_2$ is Q, R, or S, X$_3$ is V or I, and X$_4$ is G, R, W, Q, or A (SEQ ID NO: 127); an HVR-L2 comprising the sequence according to Formula V: KVSNRX$_1$S, wherein X$_1$ is F, R, V, or K (SEQ ID NO: 128); and an HVR-L3 comprising the sequence according to Formula V: SQSTRVPYT (SEQ ID NO: 129), and wherein the antibody is not an antibody comprising a light chain variable region comprising an HVR-L1 comprising the sequence of RSSQSLVHSNGYTYLH (SEQ ID NO: 130), an HVR-L2 comprising the sequence of KVSNRFS (SEQ ID NO: 131), and an HVR-L3 comprising the sequence of SQSTRVPYT (SEQ ID NO: 129). Other aspects of the present disclosure relate to an antibody that binds to a TREM2 protein, wherein the antibody comprises a heavy chain variable region and a light chain variable region, wherein the heavy chain variable region comprises: an HVR-H1 comprising the sequence according to Formula I: YAFX$_1$X$_2$X$_3$WMN, wherein X$_1$ is S or W, X$_2$ is S, L, or R, and X$_3$ is S, D, H, Q, or E (SEQ ID NO: 121); an HVR-H2 comprising the sequence according to Formula II: RIYPGX$_1$GX$_2$TNYAX$_3$KX$_4$X$_5$G, wherein X$_1$ is D, G, E, Q, or V, X$_2$ is D or Q, X$_3$ is Q, R, H, W, Y, or G, X$_4$ is F, R, or W, and X$_5$ is Q, R, K, or H (SEQ ID NO: 122); and an HVR-H3 comprising the sequence according to Formula III: ARLLRNX$_1$PGX$_2$SYAX$_3$DY, wherein X$_1$ is Q or K, X$_2$ is E, S, or A, and X$_3$ is M or H (SEQ ID NO: 123), and the light chain variable region comprises: an HVR-L1 comprising the sequence according to Formula IV: RX$_1$SX$_2$SLX$_3$HSNX$_4$YTYLH, wherein X$_1$ is S or T, X$_2$ is Q, R, or S, X$_3$ is V or I, and X$_4$ is G, R, W, Q, or A (SEQ ID NO: 127); an HVR-L2 comprising the sequence according to Formula V: KVSNRX$_1$S, wherein X$_1$ is F, R, V, or K (SEQ ID NO: 128); and an HVR-L3 comprising the sequence: SQSTRVPYT (SEQ ID NO: 129), and wherein the antibody is not an antibody comprising a heavy chain variable region comprising an HVR-H1 comprising the sequence of YAFSSSWMN (SEQ ID NO: 124), an HVR-H2 comprising the sequence of RIYPGDGDTNYAQKFQG (SEQ ID NO: 125), and an HVR-H3 comprising the sequence of ARLLRNQPGESYAMDY (SEQ ID NO: 126), and comprising a light chain variable region comprising an HVR-L1 comprising the sequence of RSSQSLVHSNGYTYLH (SEQ ID NO: 130), an HVR-L2 comprising the sequence of KVSNRFS (SEQ ID NO: 131), and an HVR-L3 comprising the sequence of SQSTRVPYT (SEQ ID NO: 129).

Other aspects of the present disclosure relate to an antibody that binds to a TREM2 protein, wherein the antibody comprises a heavy chain variable region and a light chain variable region, wherein the heavy chain variable region comprises: an HVR-H1 comprising a sequence selected from the group consisting of SEQ ID Nos: 132 and 136; an HVR-H2 comprising a sequence selected from the group consisting of SEQ ID Nos: 133, 135, 137, and 141; and an HVR-H3 comprising a sequence selected from the group consisting of SEQ ID Nos: 126 and 138; and/or the light the light chain variable region comprises: an HVR-L1 comprising a sequence selected from the group consisting of 130, 139, 142, and 144; an HVR-L2 comprising a sequence selected from the group consisting of SEQ ID Nos: 131, 134, and 140; and an HVR-L3 comprising the sequence of SEQ ID NO: 129. Other aspects of the present disclosure relate to an antibody that binds to a TREM2 protein, wherein the antibody comprises a heavy chain variable region and a light chain variable region, wherein the heavy chain variable region comprises: an HVR-H1 comprising the sequence of SEQ ID No: 132; an HVR-H2 comprising a sequence selected from the group consisting of SEQ ID Nos: 133, 135, and 141; and an HVR-H3 comprising the sequence of SEQ ID No: 126; and/or the light the light chain variable region comprises: an HVR-L1 comprising a sequence selected from the group consisting of 130, 142, and 144; an HVR-L2 comprising a sequence selected from the group consisting of SEQ ID Nos: 131 and 134; and an HVR-L3 comprising the sequence of SEQ ID NO: 129.

Other aspects of the present disclosure relate to an antibody that binds to a TREM2 protein, wherein the antibody comprises a heavy chain variable region and a light chain variable region, wherein the heavy chain variable region comprises the HVR-H1, HVR-H2, and HVR-H3 of antibody AL2p-2, AL2p-3, AL2p-4, AL2p-7, AL2p-8, AL2p-9, AL2p-10, AL2p-11, AL2p-12, AL2p-13, AL2p-14, AL2p-15, AL2p-16, AL2p-17, AL2p-18, AL2p-19, AL2p-20, AL2p-21, AL2p-22, AL2p-23, AL2p-24, AL2p-25, AL2p-26, AL2p-27, AL2p-28, AL2p-29, AL2p-30, AL2p-31, AL2p-32, AL2p-35, AL2p-36, AL2p-37, AL2p-38, AL2p-39, AL2p-40, AL2p-41, AL2p-42, AL2p-43, AL2p-44, AL2p-45, AL2p-46, AL2p-47, AL2p-48, AL2p-49, AL2p-50, AL2p-51, AL2p-52, AL2p-53, AL2p-54, AL2p-55, AL2p-56, AL2p-57, AL2p-58, AL2p-59, AL2p-60, AL2p-61, or AL2p-62 (as shown in Tables 2A to 2C). Other aspects of the present disclosure relate to an antibody that binds to a TREM2 protein, wherein the antibody comprises a heavy chain variable region and a light chain variable region, wherein the light chain variable region comprises the HVR-L1, HVR-L2, and HVR-L3 of antibody AL2p-5, AL2p-6, AL2p-7, AL2p-8, AL2p-9, AL2p-10, AL2p-11, AL2p-12, AL2p-13, AL2p-14, AL2p-15, AL2p-16, AL2p-17, AL2p-18, AL2p-19, AL2p-20, AL2p-21, AL2p-22, AL2p-23, AL2p-24, AL2p-25, AL2p-26, AL2p-27, AL2p-28, AL2p-29, AL2p-30, AL2p-31, AL2p-32, AL2p-33, AL2p-38, AL2p-39, AL2p-40, AL2p-41, AL2p-42, AL2p-43, AL2p-44, AL2p-45, AL2p-46, AL2p-47, AL2p-48, AL2p-49, AL2p-50, AL2p-51, AL2p-52, AL2p-53, AL2p-54, AL2p-55, AL2p-56, AL2p-57, AL2p-58, AL2p-59, AL2p-60, AL2p-61, or AL2p-62 (as shown in Tables 3A to 3C). Other aspects of the present disclosure relate to an antibody that binds to a TREM2 protein, wherein the antibody comprises a heavy chain variable region and a light chain variable region, wherein the heavy chain variable region comprises the HVR-H1, HVR-H2, and HVR-H3 of antibody AL2p-2, AL2p-3, AL2p-4, AL2p-7, AL2p-8, AL2p-9, AL2p-10, AL2p-11, AL2p-12, AL2p-13, AL2p-14, AL2p-15, AL2p-16, AL2p-17, AL2p-18, AL2p-19, AL2p-20, AL2p-21, AL2p-22, AL2p-23, AL2p-24, AL2p-25, AL2p-26, AL2p-27, AL2p-28, AL2p-29, AL2p-30, AL2p-31, AL2p-32, AL2p-35, AL2p-36, AL2p-37, AL2p-38, AL2p-39, AL2p-40, AL2p-41, AL2p-42, AL2p-43, AL2p-44, AL2p-45, AL2p-46, AL2p-47, AL2p-48, AL2p-49, AL2p-50, AL2p-51, AL2p-52, AL2p-53, AL2p-54, AL2p-55, AL2p-56, AL2p-57, AL2p-58, AL2p-59, AL2p-60, AL2p-61, or AL2p-62 (as shown in Tables 2A to 2C); and the light chain variable region comprises the HVR-L1, HVR-L2, and HVR-L3 of antibody AL2p-5, AL2p-6, AL2p-7, AL2p-8, AL2p-9, AL2p-10, AL2p-11, AL2p-12, AL2p-13, AL2p-14, AL2p-15, AL2p-16, AL2p-17, AL2p-18, AL2p-19, AL2p-20, AL2p-21, AL2p-22, AL2p-23, AL2p-24, AL2p-25, AL2p-26, AL2p-27, AL2p-28, AL2p-29, AL2p-30, AL2p-31, AL2p-32, AL2p-33, AL2p-38, AL2p-39, AL2p-40, AL2p-41, AL2p-42, AL2p-43, AL2p-44, AL2p-45, AL2p-46, AL2p-47, AL2p-48, AL2p-49, AL2p-50, AL2p-51, AL2p-52, AL2p-53, AL2p-54, AL2p-55, AL2p-56, AL2p-57, AL2p-58, AL2p-59, AL2p-60, AL2p-61, or AL2p-62 (as shown in Tables 3A to 3C). Other aspects of the present disclosure relate to an antibody that binds to a TREM2 protein, wherein the antibody comprises a heavy chain variable region comprising an HVR-H1, HVR-H2, and HVR-H3 and a light chain variable region comprising an HVR-L1, HVR-L2, and HVR-L3, wherein the antibody comprises the HVR-H1, HVR-H2, HVR-H3, HVR-L1, HVR-L2, and HVR-L3 of antibody AL2p-2, AL2p-3, AL2p-4, AL2p-5, AL2p-6, AL2p-7, AL2p-8, AL2p-9, AL2p-10, AL2p-11, AL2p-12, AL2p-13, AL2p-14, AL2p-15, AL2p-16, AL2p-17, AL2p-18, AL2p-19, AL2p-20, AL2p-21, AL2p-22, AL2p-23, AL2p-24, AL2p-25, AL2p-26, AL2p-27, AL2p-28, AL2p-29, AL2p-30, AL2p-31, AL2p-32, AL2p-33, AL2p-35, AL2p-36, AL2p-37, AL2p-38, AL2p-39, AL2p-40, AL2p-41, AL2p-42, AL2p-43, AL2p-44, AL2p-45, AL2p-46, AL2p-47, AL2p-48, AL2p-49, AL2p-50, AL2p-51, AL2p-52, AL2p-53, AL2p-54, AL2p-55, AL2p-56, AL2p-57, AL2p-58, AL2p-59, AL2p-60, AL2p-61, or AL2p-62 (as shown in Tables 2A to 2C and 3A to 3C).

In some embodiments that may be combined with any of the preceding embodiments, the heavy chain variable region comprises one, two, three or four frame work regions selected from VH FR1, VH FR2, VH FR3, and VH FR4, wherein: the VH FR1 comprises a sequence selected from the group consisting of SEQ ID NOs: 9-11, the VH FR2 comprises a sequence selected from the group consisting of SEQ ID NOs: 12 and 13, the VH FR3 comprises a sequence selected from the group consisting of SEQ ID NOs: 14 and 15, and the VH FR4 comprises the sequence of SEQ ID NO: 16; and/or the light chain variable region comprises one, two, three or four frame work regions selected from VL FR1, VL FR2, VL FR3, and VL FR4, wherein: the VL FR1 comprises a sequence selected from the group consisting of SEQ ID NOs: 17-20, the VL FR2 comprises a sequence selected from the group consisting of SEQ ID NOs: 21 and 22, the VL FR3 comprises a sequence selected from the group consisting of SEQ ID NOs: 23 and 24, and the VL FR4 comprises a sequence selected from the group consisting of SEQ ID NOs: 25 and 26. In some embodiments that may be combined with any of the preceding embodiments, the antibody comprises a heavy chain variable region comprising an amino acid sequence selected from the group consisting of SEQ ID NOs: 27-71 and 91; and/or a light chain variable region comprising an amino acid sequence selected from the group consisting of SEQ ID NOs: 92-113 and 118. In some embodiments that may be combined with any of the preceding embodiments, the antibody comprises the heavy chain variable region of antibody AL2p-h50, AL2p-2, AL2p-3, AL2p-4, AL2p-5, AL2p-6, AL2p-7, AL2p-8, AL2p-9, AL2p-10, AL2p-11, AL2p-12, AL2p-13, AL2p-14, AL2p-15, AL2p-16, AL2p-17, AL2p-18, AL2p-19, AL2p-20, AL2p-21, AL2p-22, AL2p-23, AL2p-24, AL2p-25, AL2p-26, AL2p-27, AL2p-28, AL2p-29, AL2p-30, AL2p-31, AL2p-32, AL2p-33, AL2p-h77, AL2p-35, AL2p-36, AL2p-37, AL2p-38, AL2p-39, AL2p-40, AL2p-41, AL2p-42, AL2p-43, AL2p-44, AL2p-45, AL2p-46, AL2p-47, AL2p-48, AL2p-49, AL2p-50, AL2p-51, AL2p-52, AL2p-53, AL2p-54, AL2p-55, AL2p-56, AL2p-57, AL2p-58, AL2p-59, AL2p-60, AL2p-61, or AL2p-62 (as shown in Table 6A); and/or the antibody comprises the light chain variable region of antibody AL2p-h50, AL2p-2, AL2p-3, AL2p-4, AL2p-5, AL2p-6, AL2p-7, AL2p-8, AL2p-9, AL2p-10, AL2p-11, AL2p-12, AL2p-13, AL2p-14, AL2p-15, AL2p-16, AL2p-17, AL2p-18, AL2p-19, AL2p-20, AL2p-21, AL2p-22, AL2p-23, AL2p-24, AL2p-25, AL2p-26, AL2p-27, AL2p-28, AL2p-29, AL2p-30, AL2p-31, AL2p-32, AL2p-33, AL2p-h77, AL2p-35, AL2p-36, AL2p-37, AL2p-38, AL2p-39, AL2p-40, AL2p-41, AL2p-42, AL2p-43, AL2p-44, AL2p-45, AL2p-46, AL2p-47, AL2p-48, AL2p-49, AL2p-50, AL2p-51, AL2p-52, AL2p-53, AL2p-54, AL2p-55, AL2p-56, AL2p-57, AL2p-58, AL2p-59, AL2p-60, AL2p-61, or AL2p-62 (as shown in Table 7A). In some embodiments that may be combined with any of the preceding embodiments: (a) the HVR-H1 comprises the amino acid sequence YAFSSQWMN (SEQ ID NO: 132), the HVR-H2 comprises the amino acid sequence RIYPGGGDTNYARKFQG (SEQ ID NO: 133), the HVR-H3 comprises the amino acid sequence ARLLRNQPGESYAMDY (SEQ ID NO: 126), the HVR-L1 comprises the amino acid sequence RSSQSLVHSNGYTYLH (SEQ ID NO: 130), the HVR-L2 comprises the amino acid sequence KVSNRRS (SEQ ID NO: 134), and the HVR-L3 comprises the amino acid sequence SQSTRVPYT (SEQ ID NO: 129); (b) the HVR-H1 comprises the amino acid sequence YAFSSQWMN (SEQ ID NO: 132), the HVR-H2 comprises the amino acid sequence RIYPGGGDTNYAGKFQG (SEQ ID NO: 135), the HVR-H3 comprises the amino acid sequence ARLLRNQPGESYAMDY (SEQ ID NO: 126), the HVR-L1 comprises the amino acid sequence RSSQSLVHSNGYTYLH (SEQ ID NO: 130), the HVR-L2 comprises the amino acid sequence KVSNRFS (SEQ ID NO: 131), and the HVR-L3 comprises the amino acid sequence SQSTRVPYT (SEQ ID NO: 129); (c) the HVR-H1 comprises the amino acid sequence YAFSSDWMN (SEQ ID NO: 136), the HVR-H2 comprises the amino acid sequence RIYPGEGDTNYARKFHG (SEQ ID NO: 137), the HVR-H3 comprises the amino acid sequence ARLLRNKPGESYAMDY (SEQ ID NO: 138), the HVR-L1 comprises the amino acid sequence RTSQSLVHSNAYTYLH (SEQ ID NO: 139), the HVR-L2 comprises the amino acid sequence KVSNRVS (SEQ ID NO: 140), and the HVR-L3 comprises the amino acid sequence SQSTRVPYT (SEQ ID NO: 129); (d) the HVR-H1 comprises the amino acid sequence YAFSSQWMN (SEQ ID NO: 132), the HVR-H2 comprises the amino acid sequence RIYPGEGDTNYARKFQG (SEQ ID NO: 141), the HVR-H3 comprises the amino acid sequence ARLLRNQPGESYAMDY (SEQ ID NO: 126), the HVR-L1 comprises the amino acid sequence RSSQSLVHSNQYTYLH (SEQ ID NO: 142), the HVR-L2 comprises the amino acid sequence KVSNRRS (SEQ ID NO: 134), and the HVR-L3 comprises the amino acid sequence SQSTRVPYT (SEQ ID NO: 129); (e) the HVR-H1 comprises the amino acid sequence YAFSSQWMN (SEQ ID NO: 132), the HVR-H2 comprises the amino acid sequence RIYPGEGDT-NYAGKFQG (SEQ ID NO: 143), the HVR-H3 comprises the amino acid sequence ARLLRNQPGESYAMDY (SEQ ID NO: 126), the HVR-L1 comprises the amino acid sequence RSSQSLVHSNQYTYLH (SEQ ID NO: 142), the HVR-L2 comprises the amino acid sequence KVSNRFS (SEQ ID NO: 131), and the HVR-L3 comprises the amino acid sequence SQSTRVPYT (SEQ ID NO: 129); (f) the HVR-H1 comprises the amino acid sequence YAF-SSQWMN (SEQ ID NO: 132), the HVR-H2 comprises the amino acid sequence RIYPGGGDTNYAGKFQG (SEQ ID NO: 135), the HVR-H3 comprises the amino acid sequence ARLLRNQPGESYAMDY (SEQ ID NO: 126), the HVR-L1 comprises the amino acid sequence RSSQSLVHSNRY-TYLH (SEQ ID NO: 144), the HVR-L2 comprises the amino acid sequence KVSNRFS (SEQ ID NO: 131), and the HVR-L3 comprises the amino acid sequence SQSTRVPYT (SEQ ID NO: 129); or (g) the HVR-H1 comprises the amino acid sequence YAFSSQWMN (SEQ ID NO: 132), the HVR-H2 comprises the amino acid sequence RIYPGGGDT-NYARKFQG (SEQ ID NO: 133), the HVR-H3 comprises the amino acid sequence ARLLRNQPGESYAMDY (SEQ ID NO: 126), the HVR-L1 comprises the amino acid sequence RSSQSLVHSNRYTYLH (SEQ ID NO: 144), the HVR-L2 comprises the amino acid sequence KVSNRRS (SEQ ID NO: 134), and the HVR-L3 comprises the amino acid sequence SQSTRVPYT (SEQ ID NO: 129). In some embodiments that may be combined with any of the preceding embodiments, the HVR-H1 comprises the amino acid sequence YAFSSQWMN (SEQ ID NO: 132), the HVR-H2 comprises the amino acid sequence RIYPGGGDT-NYARKFQG (SEQ ID NO: 133), the HVR-H3 comprises the amino acid sequence ARLLRNQPGESYAMDY (SEQ ID NO: 126), the HVR-L1 comprises the amino acid sequence RSSQSLVHSNGYTYLH (SEQ ID NO: 130), the HVR-L2 comprises the amino acid sequence KVSNRRS (SEQ ID NO: 134), and the HVR-L3 comprises the amino acid sequence SQSTRVPYT (SEQ ID NO: 129). In some embodiments that may be combined with any of the preceding embodiments, the HVR-H1 comprises the amino acid sequence YAFSSQWMN (SEQ ID NO: 132), the HVR-H2 comprises the amino acid sequence RIYPGGGDT-NYAGKFQG (SEQ ID NO: 135), the HVR-H3 comprises the amino acid sequence ARLLRNQPGESYAMDY (SEQ ID NO: 126), the HVR-L1 comprises the amino acid sequence RSSQSLVHSNGYTYLH (SEQ ID NO: 130), the HVR-L2 comprises the amino acid sequence KVSNRFS (SEQ ID NO: 131), and the HVR-L3 comprises the amino acid sequence SQSTRVPYT (SEQ ID NO: 129). In some embodiments that may be combined with any of the preceding embodiments, the HVR-H1 comprises the amino acid sequence YAFSSDWMN (SEQ ID NO: 136), the HVR-H2 comprises the amino acid sequence RIYPGEGDT-NYARKFHG (SEQ ID NO: 137), the HVR-H3 comprises the amino acid sequence ARLLRNKPGESYAMDY (SEQ ID NO: 138), the HVR-L1 comprises the amino acid sequence RTSQSLVHSNAYTYLH (SEQ ID NO: 139), the HVR-L2 comprises the amino acid sequence KVSNRVS (SEQ ID NO: 140), and the HVR-L3 comprises the amino acid sequence SQSTRVPYT (SEQ ID NO: 129). In some embodiments that may be combined with any of the preceding embodiments, the HVR-H1 comprises the amino acid sequence YAFSSQWMN (SEQ ID NO: 132), the HVR-H2 comprises the amino acid sequence RIYPGEGDT-NYARKFQG (SEQ ID NO: 141), the HVR-H3 comprises the amino acid sequence ARLLRNQPGESYAMDY (SEQ ID NO: 126), the HVR-L1 comprises the amino acid sequence RSSQSLVHSNQYTYLH (SEQ ID NO: 142), the HVR-L2 comprises the amino acid sequence KVSNRRS (SEQ ID NO: 134), and the HVR-L3 comprises the amino acid sequence SQSTRVPYT (SEQ ID NO: 129). In some embodiments that may be combined with any of the preceding embodiments, the HVR-H1 comprises the amino acid sequence YAFSSQWMN (SEQ ID NO: 132), the HVR-H2 comprises the amino acid sequence RIYPGEGDT-NYAGKFQG (SEQ ID NO: 143), the HVR-H3 comprises the amino acid sequence ARLLRNQPGESYAMDY (SEQ ID NO: 126), the HVR-L1 comprises the amino acid sequence RSSQSLVHSNQYTYLH (SEQ ID NO: 142), the HVR-L2 comprises the amino acid sequence KVSNRFS (SEQ ID NO: 131), and the HVR-L3 comprises the amino acid sequence SQSTRVPYT (SEQ ID NO: 129). In some embodiments that may be combined with any of the preceding embodiments, the HVR-H1 comprises the amino acid sequence YAFSSQWMN (SEQ ID NO: 132), the HVR-H2 comprises the amino acid sequence RIYPGGGDT-NYAGKFQG (SEQ ID NO: 135), the HVR-H3 comprises the amino acid sequence ARLLRNQPGESYAMDY (SEQ ID NO: 126), the HVR-L1 comprises the amino acid sequence RSSQSLVHSNRYTYLH (SEQ ID NO: 144), the HVR-L2 comprises the amino acid sequence KVSNRFS (SEQ ID NO: 131), and the HVR-L3 comprises the amino acid sequence SQSTRVPYT (SEQ ID NO: 129). In some embodiments that may be combined with any of the preceding embodiments, the HVR-H1 comprises the amino acid sequence YAFSSQWMN (SEQ ID NO: 132), the HVR-H2 comprises the amino acid sequence RIYPGGGDT-NYARKFQG (SEQ ID NO: 133), the HVR-H3 comprises the amino acid sequence ARLLRNQPGESYAMDY (SEQ ID NO: 126), the HVR-L1 comprises the amino acid sequence RSSQSLVHSNRYTYLH (SEQ ID NO: 144), the HVR-L2 comprises the amino acid sequence KVSNRRS (SEQ ID NO: 134), and the HVR-L3 comprises the amino acid sequence SQSTRVPYT (SEQ ID NO: 129). In some embodiments, the HVR-H1 comprises the amino acid sequence YAFSSQWMN (SEQ ID NO: 132), the HVR-H2 comprises the amino acid sequence RIYPGGGDTNYAG-KFQG (SEQ ID NO: 135), the HVR-H3 comprises the amino acid sequence ARLLRNQPGESYAMDY (SEQ ID NO: 126), the HVR-L1 comprises the amino acid sequence RSSQSLVHSNRYTYLH (SEQ ID NO: 144), the HVR-L2 comprises the amino acid sequence KVSNRFS (SEQ ID NO: 131), and the HVR-L3 comprises the amino acid sequence SQSTRVPYT (SEQ ID NO: 129).

Other aspects of the present disclosure relate to an antibody that binds to a TREM2 protein, wherein the antibody comprises a heavy chain variable region and a light chain variable region, wherein the heavy chain variable region comprises Kabat CDRs; and/or the light chain variable region comprises Kabat CDRs. In some embodiments, the heavy chain variable region comprises a CDR-H1 comprising the sequence of SQWMN (SEQ ID NO: 194), a CDR-H2 comprising the sequence of RIYPGGGDTNYAGKFQG (SEQ ID NO: 135); and a CDR-H3 comprising the sequence of LLRNQPGESYAMDY (SEQ ID NO: 195). In some embodiments, the light chain variable region comprises a CDR-L1 comprising the sequence of RSSQSLVHSNGY-TYLH (SEQ ID NO: 130), a CDR-L2 comprising the sequence of KVSNRFS (SEQ ID NO: 131); and a CDR-L3 comprising the sequence of SQSTRVPYT (SEQ ID NO:

129). In some embodiments, the heavy chain variable region comprises a CDR-H1 comprising the sequence of SQWMN (SEQ ID NO: 194), a CDR-H2 comprising the sequence of RIYPGGGDTNYAGKFQG (SEQ ID NO: 135); and a CDR-H3 comprising the sequence of LLRNQPGE-SYAMDY (SEQ ID NO: 195); and the light chain variable region comprises a CDR-L1 comprising the sequence of RSSQSLVHSNGYTYLH (SEQ ID NO: 130), a CDR-L2 comprising the sequence of KVSNRFS (SEQ ID NO: 131); and a CDR-L3 comprising the sequence of SQSTRVPYT (SEQ ID NO: 129).

Other aspects of the present disclosure relate to an antibody that binds to a TREM2 protein, wherein the antibody comprises a heavy chain variable region and a light chain variable region, wherein the heavy chain variable region comprises Kabat CDRs; and/or the light chain variable region comprises Kabat CDRs. In some embodiments, the heavy chain variable region comprises a CDR-H1 comprising the sequence of SDWMN (SEQ ID NO: 196), a CDR-H2 comprising the sequence of RIYPGEGDTNYARKFHG (SEQ ID NO: 137); and a CDR-H3 comprising the sequence of LLRNKPGESYAMDY (SEQ ID NO: 197). In some embodiments, the light chain variable region comprises a CDR-L1 comprising the sequence of RTSQSLVHSNAY-TYLH (SEQ ID NO: 139), a CDR-L2 comprising the sequence of KVSNRVS (SEQ ID NO: 140); and a CDR-L3 comprising the sequence of SQSTRVPYT (SEQ ID NO: 129). In some embodiments, the heavy chain variable region comprises a CDR-H1 comprising the sequence of SDWMN (SEQ ID NO: 196), a CDR-H2 comprising the sequence of RIYPGEGDTNYARKFHG (SEQ ID NO: 137); and a CDR-H3 comprising the sequence of LLRNKPGESYAMDY (SEQ ID NO: 197); and the light chain variable region comprises a CDR-L1 comprising the sequence of RTSQS-LVHSNAYTYLH (SEQ ID NO: 139), a CDR-L2 comprising the sequence of KVSNRVS (SEQ ID NO: 140); and a CDR-L3 comprising the sequence of SQSTRVPYT (SEQ ID NO: 129).

Other aspects of the present disclosure relate to an antibody that binds to a TREM2 protein, wherein the antibody comprises a heavy chain variable region and a light chain variable region, wherein the heavy chain variable region comprises Kabat CDRs; and/or the light chain variable region comprises Kabat CDRs. In some embodiments, the heavy chain variable region comprises a CDR-H1 comprising the sequence of SQWMN (SEQ ID NO: 194), a CDR-H2 comprising the sequence of RIYPGGGDTNYAGKFQG (SEQ ID NO: 135); and a CDR-H3 comprising the sequence of LLRNQPGESYAMDY (SEQ ID NO: 195). In some embodiments, the light chain variable region comprises a CDR-L1 comprising the sequence of RSSQSLVHSNRY-TYLH (SEQ ID NO: 144), a CDR-L2 comprising the sequence of KVSNRFS (SEQ ID NO: 131); and a CDR-L3 comprising the sequence of SQSTRVPYT (SEQ ID NO: 129). In some embodiments, the heavy chain variable region comprises a CDR-H1 comprising the sequence of SQWMN (SEQ ID NO: 194), a CDR-H2 comprising the sequence of RIYPGGGDTNYAGKFQG (SEQ ID NO: 135); and a Kabat CDR-H3 comprising the sequence of LLRNQPGE-SYAMDY (SEQ ID NO: 195); and the light chain variable region comprises a CDR-L1 comprising the sequence of RSSQSLVHSNRYTYLH (SEQ ID NO: 144), a CDR-L2 comprising the sequence of KVSNRFS (SEQ ID NO: 131); and a CDR-L3 comprising the sequence of SQSTRVPYT (SEQ ID NO: 129).

Other aspects of the present disclosure relate to an antibody that binds to a TREM2 protein, wherein the antibody comprises a heavy chain variable region and a light chain variable region, wherein the heavy chain variable region comprises Kabat CDRs; and/or the light chain variable region comprises Kabat CDRs. In some embodiments, the heavy chain variable region comprises a CDR-H1 comprising the sequence of SQWMN (SEQ ID NO: 194), a CDR-H2 comprising the sequence of RIYPGGGDTNYARKFQG (SEQ ID NO: 133); and a CDR-H3 comprising the sequence of LLRNQPGESYAMDY (SEQ ID NO: 195). In some embodiments, the light chain variable region comprises a CDR-L1 comprising the sequence of RSSQSLVHSNRY-TYLH (SEQ ID NO: 144), a CDR-L2 comprising the sequence of KVSNRRS (SEQ ID NO: 134); and a CDR-L3 comprising the sequence of SQSTRVPYT (SEQ ID NO: 129). In some embodiments, the heavy chain variable region comprises a CDR-H1 comprising the sequence of SQWMN (SEQ ID NO: 194), a CDR-H2 comprising the sequence of RIYPGGGDTNYARKFQG (SEQ ID NO: 133); and a CDR-H3 comprising the sequence of LLRNQPGESYAMDY (SEQ ID NO: 195); and the light chain variable region comprises a CDR-L1 comprising the sequence of RSSQS-LVHSNRYTYLH (SEQ ID NO: 144), a CDR-L2 comprising the sequence of KVSNRRS (SEQ ID NO: 134); and a CDR-L3 comprising the sequence of SQSTRVPYT (SEQ ID NO: 129).

Other aspects of the present disclosure relate to an antibody that binds to a TREM2 protein, wherein the antibody comprises a heavy chain variable region and a light chain variable region, wherein the heavy chain variable region comprises Kabat CDRs; and/or the light chain variable region comprises Kabat CDRs. In some embodiments, the heavy chain variable region comprises a CDR-H1 comprising the sequence of SQWMN (SEQ ID NO: 194), a CDR-H2 comprising the sequence of RIYPGEGDTNYARKFQG (SEQ ID NO: 141); and a CDR-H3 comprising the sequence of LLRNQPGESYAMDY (SEQ ID NO: 195). In some embodiments, the light chain variable region comprises a CDR-L1 comprising the sequence of RSSQSLVHSNQY-TYLH (SEQ ID NO: 142), a CDR-L2 comprising the sequence of KVSNRRS (SEQ ID NO: 134); and a CDR-L3 comprising the sequence of SQSTRVPYT (SEQ ID NO: 129). In some embodiments, the heavy chain variable region comprises a CDR-H1 comprising the sequence of SQWMN (SEQ ID NO: 194), a CDR-H2 comprising the sequence of RIYPGEGDTNYARKFQG (SEQ ID NO: 141); and a CDR-H3 comprising the sequence of LLRNQPGESYAMDY (SEQ ID NO: 195); and the light chain variable region comprises a CDR-L1 comprising the sequence of RSSQS-LVHSNQYTYLH (SEQ ID NO: 142), a CDR-L2 comprising the sequence of KVSNRRS (SEQ ID NO: 134); and a CDR-L3 comprising the sequence of SQSTRVPYT (SEQ ID NO: 129).

Other aspects of the present disclosure relate to an antibody that binds to a TREM2 protein, wherein the antibody comprises a heavy chain variable region comprising an amino acid sequence selected from the group consisting of SEQ ID NOs: 27-71 and 91; and/or a light chain variable region comprising an amino acid sequence selected from the group consisting of SEQ ID NOs: 92-113 and 118. In some embodiments, the antibody comprises the heavy chain variable region of antibody AL2p-h50, AL2p-2, AL2p-3, AL2p-4, AL2p-5, AL2p-6, AL2p-7, AL2p-8, AL2p-9, AL2p-10, AL2p-11, AL2p-12, AL2p-13, AL2p-14, AL2p-15, AL2p-16, AL2p-17, AL2p-18, AL2p-19, AL2p-20, AL2p-21, AL2p-22, AL2p-23, AL2p-24, AL2p-25, AL2p-26, AL2p-27, AL2p-28, AL2p-29, AL2p-30, AL2p-31, AL2p-32, AL2p-33, AL2p-h77, AL2p-35, AL2p-36, AL2p-37, AL2p-

38, AL2p-39, AL2p-40, AL2p-41, AL2p-42, AL2p-43, AL2p-44, AL2p-45, AL2p-46, AL2p-47, AL2p-48, AL2p-49, AL2p-50, AL2p-51, AL2p-52, AL2p-53, AL2p-54, AL2p-55, AL2p-56, AL2p-57, AL2p-58, AL2p-59, AL2p-60, AL2p-61, or AL2p-62 (as shown in Table 6A); and/or the antibody comprises the light chain variable region of antibody AL2p-h50, AL2p-2, AL2p-3, AL2p-4, AL2p-5, AL2p-6, AL2p-7, AL2p-8, AL2p-9, AL2p-10, AL2p-11, AL2p-12, AL2p-13, AL2p-14, AL2p-15, AL2p-16, AL2p-17, AL2p-18, AL2p-19, AL2p-20, AL2p-21, AL2p-22, AL2p-23, AL2p-24, AL2p-25, AL2p-26, AL2p-27, AL2p-28, AL2p-29, AL2p-30, AL2p-31, AL2p-32, AL2p-33, AL2p-h77, AL2p-35, AL2p-36, AL2p-37, AL2p-38, AL2p-39, AL2p-40, AL2p-41, AL2p-42, AL2p-43, AL2p-44, AL2p-45, AL2p-46, AL2p-47, AL2p-48, AL2p-49, AL2p-50, AL2p-51, AL2p-52, AL2p-53, AL2p-54, AL2p-55, AL2p-56, AL2p-57, AL2p-58, AL2p-59, AL2p-60, AL2p-61, or AL2p-62 (as shown in Table 7A). In some embodiments: (a) the heavy chain variable region comprises the amino acid sequence of SEQ ID NO: 53, and/or the light chain variable region comprises the amino acid sequence of SEQ ID NO: 97; (b) the heavy chain variable region comprises the amino acid sequence of SEQ ID NO: 59; and/or the light chain variable region comprises the amino acid sequence of SEQ ID NO: 104; (c) the heavy chain variable region comprises the amino acid sequence of SEQ ID NO: 64; and/or the light chain variable region comprises the amino acid sequence of SEQ ID NO: 108; (d) the heavy chain variable region comprises the amino acid sequence of SEQ ID NO: 70; and/or the light chain variable region comprises the amino acid sequence of SEQ ID NO: 110; (e) the heavy chain variable region comprises the amino acid sequence of SEQ ID NO: 71; and/or the light chain variable region comprises the amino acid sequence of SEQ ID NO: 111; (f) the heavy chain variable region comprises the amino acid sequence of SEQ ID NO: 59; and/or the light chain variable region comprises the amino acid sequence of SEQ ID NO: 112; or (g) the heavy chain variable region comprises the amino acid sequence of SEQ ID NO: 53; and/or the light chain variable region comprises the amino acid sequence of SEQ ID NO: 113. In some embodiments, the antibody comprises an Fc region comprising an amino acid sequence selected from the group consisting of SEQ ID Nos: 146-156. In some embodiments, the antibody comprises an Fc region comprising the amino acid sequence of SEQ ID NO: 146. In some embodiments, the antibody comprises an Fc region comprising the amino acid sequence of SEQ ID NO: 147. In some embodiments, the antibody comprises an Fc region comprising the amino acid sequence of SEQ ID NO: 148. In some embodiments, the antibody comprises an Fc region comprising the amino acid sequence of SEQ ID NO: 149. In some embodiments, the antibody comprises an Fc region comprising the amino acid sequence of SEQ ID NO: 150. In some embodiments, the antibody comprises an Fc region comprising the amino acid sequence of SEQ ID NO: 151. In some embodiments, the antibody comprises an Fc region comprising the amino acid sequence of SEQ ID NO: 152. In some embodiments, the antibody comprises an Fc region comprising the amino acid sequence of SEQ ID NO: 153. In some embodiments, the antibody comprises an Fc region comprising the amino acid sequence of SEQ ID NO: 154. In some embodiments, the antibody comprises an Fc region comprising the amino acid sequence of SEQ ID NO: 155. In some embodiments, the antibody comprises an Fc region comprising the amino acid sequence of SEQ ID NO: 156. In some embodiments, the antibody comprises a heavy chain comprising an amino acid sequence selected from the group consisting of SEQ ID NOs: 198-213; and/or a light chain comprising an amino acid sequence selected from the group consisting of SEQ ID NOs: 214-218. In some embodiments, the antibody comprises a heavy chain comprising an amino acid sequence selected from the group consisting of SEQ ID NOs: 198 and 199; and a light chain comprising the amino acid sequence of SEQ ID NO: 214. In some embodiments, the antibody comprises a heavy chain comprising an amino acid sequence selected from the group consisting of SEQ ID NOs: 200 and 201; and a light chain comprising the amino acid sequence of SEQ ID NO: 214. In some embodiments, the antibody comprises a heavy chain comprising an amino acid sequence selected from the group consisting of SEQ ID NOs: 202 and 203; and a light chain comprising the amino acid sequence of SEQ ID NO: 215. In some embodiments, the antibody comprises a heavy chain comprising an amino acid sequence selected from the group consisting of SEQ ID NOs: 204 and 205; and a light chain comprising the amino acid sequence of SEQ ID NO: 215. In some embodiments, the antibody comprises a heavy chain comprising an amino acid sequence selected from the group consisting of SEQ ID NOs: 206 and 207; and a light chain comprising the amino acid sequence of SEQ ID NO: 216. In some embodiments, the antibody comprises a heavy chain comprising an amino acid sequence selected from the group consisting of SEQ ID NOs: 208 and 209; and a light chain comprising the amino acid sequence of SEQ ID NO: 218. In some embodiments, the antibody comprises a heavy chain comprising an amino acid sequence selected from the group consisting of SEQ ID NOs: 210 and 211; and a light chain comprising the amino acid sequence of SEQ ID NO: 218. In some embodiments, the antibody comprises a heavy chain comprising an amino acid sequence selected from the group consisting of SEQ ID NOs: 212 and 213; and a light chain comprising the amino acid sequence of SEQ ID NO: 217.

In some embodiments, the heavy chain variable region comprises the amino acid sequence of SEQ ID NO: 53, and/or the light chain variable region comprises the amino acid sequence of SEQ ID NO: 97. In some embodiments, the heavy chain variable region comprises the amino acid sequence of SEQ ID NO: 59; and/or the light chain variable region comprises the amino acid sequence of SEQ ID NO: 104. In some embodiments, the heavy chain variable region comprises the amino acid sequence of SEQ ID NO: 64; and/or the light chain variable region comprises the amino acid sequence of SEQ ID NO: 108. In some embodiments, the heavy chain variable region comprises the amino acid sequence of SEQ ID NO: 70; and/or the light chain variable region comprises the amino acid sequence of SEQ ID NO: 110. In some embodiments, the heavy chain variable region comprises the amino acid sequence of SEQ ID NO: 71; and/or the light chain variable region comprises the amino acid sequence of SEQ ID NO: 11. In some embodiments, the heavy chain variable region comprises the amino acid sequence of SEQ ID NO: 59; and/or the light chain variable region comprises the amino acid sequence of SEQ ID NO: 112. In some embodiments, the heavy chain variable region comprises the amino acid sequence of SEQ ID NO: 53; and/or the light chain variable region comprises the amino acid sequence of SEQ ID NO: 113.

Other aspects of the present disclosure relate to an antibody that binds to a TREM2 protein, wherein the antibody comprises a heavy chain variable region comprising an amino acid sequence selected from the group consisting of SEQ ID NOs: 27, 56 and 72-90; and/or a light chain variable region comprising an amino acid sequence selected from the group consisting of SEQ ID NOs: 92, 104, and 114-117. In some embodiments, the antibody comprises the heavy chain variable region of antibody AL2p-h19, AL2p-h21, AL2p-h22, AL2p-h23, AL2p-h24, AL2p-h25, AL2p-h26, AL2p-h27, AL2p-h28, AL2p-h29, AL2p-h30, AL2p-h31, AL2p-h32, AL2p-h33, AL2p-h34, AL2p-h35, AL2p-h36, AL2p-h42, AL2p-h43, AL2p-h44, AL2p-h47, AL2p-h59, AL2p-h76, or AL2p-h90 (as shown in Table 6A); and/or the antibody comprises the light chain variable region of antibody AL2p-h19, AL2p-h21, AL2p-h22, AL2p-h23, AL2p-h24, AL2p-h25, AL2p-h26, AL2p-h27, AL2p-h28, AL2p-h29, AL2p-h30, AL2p-h31, AL2p-h32, AL2p-h33, AL2p-h34, AL2p-h35, AL2p-h36, AL2p-h42, AL2p-h43, AL2p-h44, AL2p-h47, AL2p-h59, AL2p-h76, or AL2p-h90 (as shown in Table 7A).

Other aspects of the present disclosure relate to an antibody that binds to a TREM2 protein, wherein the antibody comprises a heavy chain comprising an amino acid sequence selected from the group consisting of SEQ ID NOs: 198-213; and/or a light chain comprising an amino acid sequence selected from the group consisting of SEQ ID NOs: 214-218. In some embodiments, the antibody comprises a heavy chain comprising an amino acid sequence selected from the group consisting of SEQ ID NOs: 198 and 199; and a light chain comprising the amino acid sequence of SEQ ID NO: 214. In some embodiments, the antibody comprises a heavy chain comprising an amino acid sequence selected from the group consisting of SEQ ID NOs: 200 and 201; and a light chain comprising the amino acid sequence of SEQ ID NO: 214. In some embodiments, the antibody comprises a heavy chain comprising an amino acid sequence selected from the group consisting of SEQ ID NOs: 202 and 203; and a light chain comprising the amino acid sequence of SEQ ID NO: 215. In some embodiments, the antibody comprises a heavy chain comprising an amino acid sequence selected from the group consisting of SEQ ID NOs: 204 and 205; and a light chain comprising the amino acid sequence of SEQ ID NO: 215. In some embodiments, the antibody comprises a heavy chain comprising an amino acid sequence selected from the group consisting of SEQ ID NOs: 206 and 207; and a light chain comprising the amino acid sequence of SEQ ID NO: 216. In some embodiments, the antibody comprises a heavy chain comprising an amino acid sequence selected from the group consisting of SEQ ID NOs: 208 and 209; and a light chain comprising the amino acid sequence of SEQ ID NO: 218. In some embodiments, the antibody comprises a heavy chain comprising an amino acid sequence selected from the group consisting of SEQ ID NOs: 210 and 211; and a light chain comprising the amino acid sequence of SEQ ID NO: 218. In some embodiments, the antibody comprises a heavy chain comprising an amino acid sequence selected from the group consisting of SEQ ID NOs: 212 and 213; and a light chain comprising the amino acid sequence of SEQ ID NO: 217.

In some embodiments that may be combined with any of the preceding embodiments, the antibody is of the IgG class, the IgM class, or the IgA class. In some embodiments that may be combined with any of the preceding embodiments, the antibody is of the IgG class and has an IgG1, IgG2, IgG3, or IgG4 isotype. In some embodiments that may be combined with any of the preceding embodiments, the antibody comprises one or more amino acid substitutions in the Fc region at a residue position selected from the group consisting of: C127S, L234A, L234F, L235A, L235E, S267E, K322A, L328F, A330S, P331S, E345R, E430G, S440Y, and any combination thereof, wherein the numbering of the residues is according to EU or Kabat numbering. In some embodiments that may be combined with any of the preceding embodiments: (a) the Fc region comprises an amino acid substitution at positions E430G, L243A, L235A, and P331S, wherein the numbering of the residue position is according to EU numbering; (b) the Fc region comprises an amino acid substitution at positions E430G and P331S, wherein the numbering of the residue position is according to EU numbering; (c) the Fc region comprises an amino acid substitution at positions E430G and K322A, wherein the numbering of the residue position is according to EU numbering; (d) the Fc region comprises an amino acid substitution at positions E430G, A330S, and P331S, wherein the numbering of the residue position is according to EU numbering; (e) the Fc region comprises an amino acid substitution at positions E430G, K322A, A330S, and P331S, wherein the numbering of the residue position is according to EU numbering; (f) the Fc region comprises an amino acid substitution at positions E430G, K322A, and A330S, wherein the numbering of the residue position is according to EU numbering; (g) the Fc region comprises an amino acid substitution at positions E430G, K322A, and P331S, wherein the numbering of the residue position is according to EU numbering; (h) the Fc region comprises an amino acid substitution at positions S267E and L328F, wherein the numbering of the residue position is according to EU numbering; (i) the Fc region comprises an amino acid substitution at position C127S, wherein the numbering of the residue position is according to EU numbering; (j) the Fc region comprises an amino acid substitution at positions E345R, E430G and S440Y, wherein the numbering of the residue position is according to EU numbering; or (k) the Fc region comprises an amino acid sequence selected from the group consisting of SEQ ID NOs: 146-156. In some embodiments, the Fc region comprises an amino acid substitution at positions E430G and P331S, wherein the numbering of the residue position is according to EU numbering. In some embodiments, the Fc region comprises an amino acid substitution at positions E430G and K322A, wherein the numbering of the residue position is according to EU numbering. In some embodiments, the Fc region comprises an amino acid substitution at positions E430G, A330S, and P331S, wherein the numbering of the residue position is according to EU numbering. In some embodiments, the Fc region comprises the amino acid sequence of SEQ ID NO: 146. In some embodiments, the Fc region comprises the amino acid sequence of SEQ ID NO: 147. In some embodiments, the Fc region comprises the amino acid sequence of SEQ ID NO: 148. In some embodiments, the Fc region comprises the amino acid sequence of SEQ ID NO: 149. In some embodiments, the Fc region comprises the amino acid sequence of SEQ ID NO: 150. In some embodiments, the Fc region comprises the amino acid sequence of SEQ ID NO: 151. In some embodiments, the Fc region comprises the amino acid sequence of SEQ ID NO: 152. In some embodiments, the Fc region comprises the amino acid sequence of SEQ ID NO: 153. In some embodiments, the Fc region comprises the amino acid sequence of SEQ ID NO: 154. In some embodiments, the Fc region comprises the amino acid sequence of SEQ ID NO: 155. In some embodiments, the Fc region comprises the amino acid sequence of SEQ ID NO: 156.

In some embodiments that may be combined with any of the preceding embodiments, the TREM2 protein is human protein. In some embodiments that may be combined with any of the preceding embodiments, the TREM2 protein is a wild-type protein. In some embodiments that may be combined with any of the preceding embodiments, the TREM2 protein is a naturally occurring variant. In some embodiments that may be combined with any of the preceding embodiments, the antibody is an antibody fragment that binds to one or more human proteins selected from the group consisting of human TREM2, a naturally occurring variant of human TREM2, and a disease variant of human TREM2, and optionally wherein the antibody fragment is cross-linked to a second antibody fragment that binds to one or more human proteins selected from the group consisting of human TREM2, a naturally occurring variant of human TREM2, and a disease variant of human TREM2. In some embodiments that may be combined with any of the preceding embodiments, the fragment is an Fab, Fab', Fab'-SH, F(ab')2, Fv or scFv fragment. In some embodiments that may be combined with any of the preceding embodiments, the antibody is a monoclonal antibody. In some embodiments that may be combined with any of the preceding embodiments, the antibody is a humanized antibody.

In some embodiments that may be combined with any of the preceding embodiments, the antibody is a bispecific antibody recognizing a first antigen and a second antigen, wherein the first antigen is human TREM2 or a naturally occurring variant thereof, and the second antigen is: (a) an antigen facilitating transport across the blood-brain-barrier; (b) an antigen facilitating transport across the blood-brain-barrier selected from the group consisting of transferrin receptor (TR), insulin receptor (HIR), insulin-like growth factor receptor (IGFR), low-density lipoprotein receptor related proteins 1 and 2 (LPR-1 and 2), diphtheria toxin receptor, CRM197, a llama single domain antibody, TMEM 30(A), a protein transduction domain, TAT, Syn-B, penetratin, a poly-arginine peptide, an angiopeptide, and ANG1005; (c) a disease-causing agent selected from the group consisting of disease-causing peptides or proteins or, disease-causing nucleic acids, wherein the disease-causing nucleic acids are antisense GGCCCC (G2C4) repeat-expansion RNA, the disease-causing proteins are selected from the group consisting of amyloid beta, oligomeric amyloid beta, amyloid beta plaques, amyloid precursor protein or fragments thereof, Tau, IAPP, alpha-synuclein, TDP-43, FUS protein, C9orf72 (chromosome 9 open reading frame 72) c9RAN protein, prion protein, PrPSc, huntingtin, calcitonin, superoxide dismutase, ataxin, ataxin 1, ataxin 2, ataxin 3, ataxin 7, ataxin 8, ataxin 10, Lewy body, atrial natriuretic factor, islet amyloid polypeptide, insulin, apolipoprotein AI, serum amyloid A, medin, prolactin, transthyretin, lysozyme, beta 2 microglobulin, gelsolin, keratoepithelin, cystatin, immunoglobulin light chain AL, S-IBM protein, Repeat-associated non-ATG (RAN) translation products, DiPeptide repeat (DPR) peptides, glycine-alanine (GA) repeat peptides, glycine-proline (GP) repeat peptides, glycine-arginine (GR) repeat peptides, proline-alanine (PA) repeat peptides, ubiquitin, and proline-arginine (PR) repeat peptides; (d) ligands and/or proteins expressed on immune cells, wherein the ligands and/or proteins selected from the group consisting of CD40, OX40, ICOS, CD28, CD137/4-1BB, CD27, GITR, PD-L1, CTLA-4, PD-L2, PD-1, B7-H3, B7-H4, HVEM, BTLA, KIR, GAL9, TIM3, A2AR, LAG-3, and phosphatidylserine; and (e) a protein, lipid, polysaccharide, or glycolipid expressed on one or more tumor cells. In some embodiments that may be combined with any of the preceding embodiments, the antibody binds specifically to both human TREM2 and cynomolgus monkey TREM2. In some embodiments that may be combined with any of the preceding embodiments, the antibody has a dissociation constant ($K_D$) for human TREM2 and/or cynomolgus monkey TREM2 that is at least 1-fold lower than an anti-TREM2 antibody comprising a heavy chain variable region comprising the amino acid sequence of SEQ ID NO: 27 and a light chain variable region comprising the amino acid sequence of SEQ ID NO: 56; or at least 1-fold lower than an anti-TREM2 antibody comprising a heavy chain variable region comprising the amino acid sequence of SEQ ID NO: 91 and a light chain variable region comprising the amino acid sequence of SEQ ID NO: 103. In some embodiments that may be combined with any of the preceding embodiments, the antibody has a dissociation constant ($K_D$) for human TREM2 that ranges from about 9 μM to about 100 pM, or less than 100 pM, wherein the $K_D$ is determined at a temperature of approximately 25° C. In some embodiments that may be combined with any of the preceding embodiments, the antibody has a dissociation constant ($K_D$) for cynomolgus monkey TREM2 that ranges from about 50 nM to about 100 pM, or less than 100 pM, wherein the $K_D$ is determined at a temperature of approximately 25° C. In some embodiments that may be combined with any of the preceding embodiments, the antibody binds to primary human immune cells with an affinity that is at least 10 times higher than that of an anti-TREM2 antibody comprising a heavy chain variable region comprising the amino acid sequence of SEQ ID NO: 27 and a light chain variable region comprising the amino acid sequence of SEQ ID NO: 56; or at least 10 times higher than an anti-TREM2 antibody comprising a heavy chain variable region comprising the amino acid sequence of SEQ ID NO: 91 and a light chain variable region comprising the amino acid sequence of SEQ ID NO: 103. In some embodiments that may be combined with any of the preceding embodiments, the antibody clusters and activates TREM2 signaling in an amount that is at least 1-fold greater than that of an anti-TREM2 antibody comprising a heavy chain variable region comprising the amino acid sequence of SEQ ID NO: 27 and a light chain variable region comprising the amino acid sequence of SEQ ID NO: 56; or at least 1-fold greater than an anti-TREM2 antibody comprising a heavy chain variable region comprising the amino acid sequence of SEQ ID NO: 91 and a light chain variable region comprising the amino acid sequence of SEQ ID NO: 103. In some embodiments that may be combined with any of the preceding embodiments, the antibody increases immune cell survival in vitro that to an extent that is greater than an anti-TREM2 antibody comprising a heavy chain variable region comprising the amino acid sequence of SEQ ID NO: 27 and a light chain variable region comprising the amino acid sequence of SEQ ID NO: 56; or that is greater than an anti-TREM2 antibody comprising a heavy chain variable region comprising the amino acid sequence of SEQ ID NO: 91 and a light chain variable region comprising the amino acid sequence of SEQ ID NO: 103. In some embodiments that may be combined with any of the preceding embodiments, the antibody has an in vivo half-life that is lower than a human control IgG1 antibody. In some embodiments that may be combined with any of the preceding embodiments, the antibody decreases plasma levels of soluble TREM2 in vivo by an amount that is at least 25% greater than that of a human control IgG1 antibody. In some embodiments that may be combined with any of the preceding embodiments, the antibody decreases plasma levels of soluble TREM2 in vivo by blocking cleavage, by inhibiting one or more metalloproteases, and/or by inducing internalization. In some embodiments, soluble TREM2 is decreased by about any of 10, 20, 30, 40, or 50%. In some embodiments that may be combined with any of the preceding embodiments, the antibody competes with one or more antibodies selected from the group consisting of AL2p-h50, AL2p-2, AL2p-3, AL2p-4, AL2p-5, AL2p-6, AL2p-7, AL2p-8, AL2p-9, AL2p-10, AL2p-11, AL2p-12, AL2p-13, AL2p-14, AL2p-15, AL2p-16, AL2p-17, AL2p-18, AL2p-19, AL2p-20, AL2p-21, AL2p-22, AL2p-23, AL2p-24, AL2p-25, AL2p-26, AL2p-27, AL2p-28, AL2p-29, AL2p-30, AL2p-31, AL2p-32, AL2p-33, AL2p-h77, AL2p-35, AL2p-36, AL2p-37, AL2p-38, AL2p-39, AL2p-40, AL2p-41, AL2p-42, AL2p-43, AL2p-44, AL2p-45, AL2p-46, AL2p-47, AL2p-48, AL2p-49, AL2p-50, AL2p-51, AL2p-52, AL2p-53, AL2p-54, AL2p-55, AL2p-56, AL2p-57, AL2p-58, AL2p-59, AL2p-60, AL2p-61, AL2p-62, AL2p-h19, AL2p-h21, AL2p-h22, AL2p-h23, AL2p-h24, AL2p-h25, AL2p-h26, AL2p-h27, AL2p-h28, AL2p-h29, AL2p-h30, AL2p-h31, AL2p-h32, AL2p-h33, AL2p-h34, AL2p-h35, AL2p-h36, AL2p-h42, AL2p-h43, AL2p-h44, AL2p-h47, AL2p-h59, AL2p-h76, AL2p-h90, and any combination thereof for binding to TREM2. In some embodiments that may be combined with any of the preceding embodiments, the antibody binds essentially the same TREM2 epitope as an antibody selected from the group consisting of: AL2p-h50, AL2p-2, AL2p-3, AL2p-4, AL2p-5, AL2p-6, AL2p-7, AL2p-8, AL2p-9, AL2p-10, AL2p-11, AL2p-12, AL2p-13, AL2p-14, AL2p-15, AL2p-16, AL2p-17, AL2p-18, AL2p-19, AL2p-20, AL2p-21, AL2p-22, AL2p-23, AL2p-24, AL2p-25, AL2p-26, AL2p-27, AL2p-28, AL2p-29, AL2p-30, AL2p-31, AL2p-32, AL2p-33, AL2p-h77, AL2p-35, AL2p-36, AL2p-37, AL2p-38, AL2p-39, AL2p-40, AL2p-41, AL2p-42, AL2p-43, AL2p-44, AL2p-45, AL2p-46, AL2p-47, AL2p-48, AL2p-49, AL2p-50, AL2p-51, AL2p-52, AL2p-53, AL2p-54, AL2p-55, AL2p-56, AL2p-57, AL2p-58, AL2p-59, AL2p-60, AL2p-61, AL2p-62, AL2p-h19, AL2p-h21, AL2p-h22, AL2p-h23, AL2p-h24, AL2p-h25, AL2p-h26, AL2p-h27, AL2p-h28, AL2p-h29, AL2p-h30, AL2p-h31, AL2p-h32, AL2p-h33, AL2p-h34, AL2p-h35, AL2p-h36, AL2p-h42, AL2p-h43, AL2p-h44, AL2p-h47, AL2p-h59, AL2p-h76, and AL2p-h90. In some embodiments that may be combined with any of the preceding embodiments, the antibody binds to one or more amino acids within amino acid residues 149-157 of SEQ ID NO: 1. In some embodiments that may be combined with any of the preceding embodiments, the antibody binds to one or more amino acid residues selected from the group consisting of E151, D152, and E156 of SEQ ID NO: 1.

Other aspects of the present disclosure relate to an isolated nucleic acid comprising a nucleic acid sequence encoding the antibody of any one of the preceding embodiments. Other aspects of the present disclosure relate to a vector comprising the nucleic acid of any one of the preceding embodiments. Other aspects of the present disclosure relate to an isolated host cell comprising the vector of any one of the preceding embodiments. Other aspects of the present disclosure relate to a method of producing an antibody that binds to TREM2, comprising culturing the cell of any one of the preceding embodiments so that the antibody is produced. In some embodiments, the method further comprises recovering the antibody produced by the cell. Other aspects of the present disclosure relate to an isolated antibody that binds to TREM2 produced by the method of any one of the preceding embodiments. Other aspects of the present disclosure relate to a pharmaceutical composition comprising the antibody of any one of the preceding embodiments and a pharmaceutically acceptable carrier.

Other aspects of the present disclosure relate to a method of preventing, reducing risk, or treating an individual having a disease, disorder, or injury selected from the group consisting of dementia, frontotemporal dementia, Alzheimer's disease, Nasu-Hakola disease, cognitive deficit, memory loss, spinal cord injury, traumatic brain injury, multiple sclerosis, chronic colitis, ulcerative colitis, and cancer, comprising administering to an individual in need thereof a therapeutically effective amount of the antibody of the preceding embodiments. In some embodiments, the disease, disorder, or injury is Alzheimer's disease.

Other aspects of the present disclosure relate to an antibody comprising an Fc region, wherein the antibody comprises an amino acid substitution at position E430G and one or more amino acid substitutions in the Fc region at a residue position selected from the group consisting of: L234F, L235A, L235E, S267E, K322A, L328F, A330S, P331S, and any combination thereof, wherein the numbering of the residues is according to EU or Kabat numbering. In some embodiments: (a) the Fc region comprises an amino acid substitution at positions E430G, L243A, L235A, and P331S, wherein the numbering of the residue position is according to EU numbering; (b) the Fc region comprises an amino acid substitution at positions E430G and P331S, wherein the numbering of the residue position is according to EU numbering; (c) the Fc region comprises an amino acid substitution at positions E430G and K322A, wherein the numbering of the residue position is according to EU numbering; (d) the Fc region comprises an amino acid substitution at positions E430G, A330S, and P331S, wherein the numbering of the residue position is according to EU numbering; (e) the Fc region comprises an amino acid substitution at positions E430G, K322A, A330S, and P331S, wherein the numbering of the residue position is according to EU numbering; (f) the Fc region comprises an amino acid substitution at positions E430G, K322A, and A330S, wherein the numbering of the residue position is according to EU numbering; (g) the Fc region comprises an amino acid substitution at positions E430G, K322A, and P331S, wherein the numbering of the residue position is according to EU numbering; of (h) the Fc region comprises an amino acid sequence selected from the group consisting of SEQ ID NOs: 146-156. In some embodiments, the Fc region comprises an amino acid substitution at positions E430G, L243A, L235A, and P331S, wherein the numbering of the residue position is according to EU numbering. In some embodiments, the Fc region comprises an amino acid substitution at positions E430G and P331S, wherein the numbering of the residue position is according to EU numbering. In some embodiments, the Fc region comprises an amino acid substitution at positions E430G and K322A, wherein the numbering of the residue position is according to EU numbering. In some embodiments, the Fc region comprises an amino acid substitution at positions E430G, A330S, and P331S, wherein the numbering of the residue position is according to EU numbering. In some embodiments, the Fc region comprises an amino acid substitution at positions E430G, K322A, A330S, and P331S, wherein the numbering of the residue position is according to EU numbering. In some embodiments, the Fc region comprises an amino acid substitution at positions E430G, K322A, and A330S, wherein the numbering of the residue position is according to EU numbering. In some embodiments, the Fc region comprises an amino acid substitution at positions E430G, K322A, and P331S, wherein the numbering of the residue position is according to EU numbering. In some embodiments, the Fc region increases clustering without activating complement as compared to a corresponding antibody comprising an Fc region that does not comprise the amino acid substitutions. In some embodiments, the antibody induces one or more activities of a target specifically bound by the antibody. In some embodiments, the antibody binds to TREM2.

It is to be understood that one, some, or all of the properties of the various embodiments described herein may be combined to form other embodiments of the present invention. These and other aspects of the invention will become apparent to one of skill in the art. These and other embodiments of the invention are further described by the detailed description that follows.

DETAILED DESCRIPTION OF THE PRESENT DISCLOSURE

General Techniques

Figure 1A:
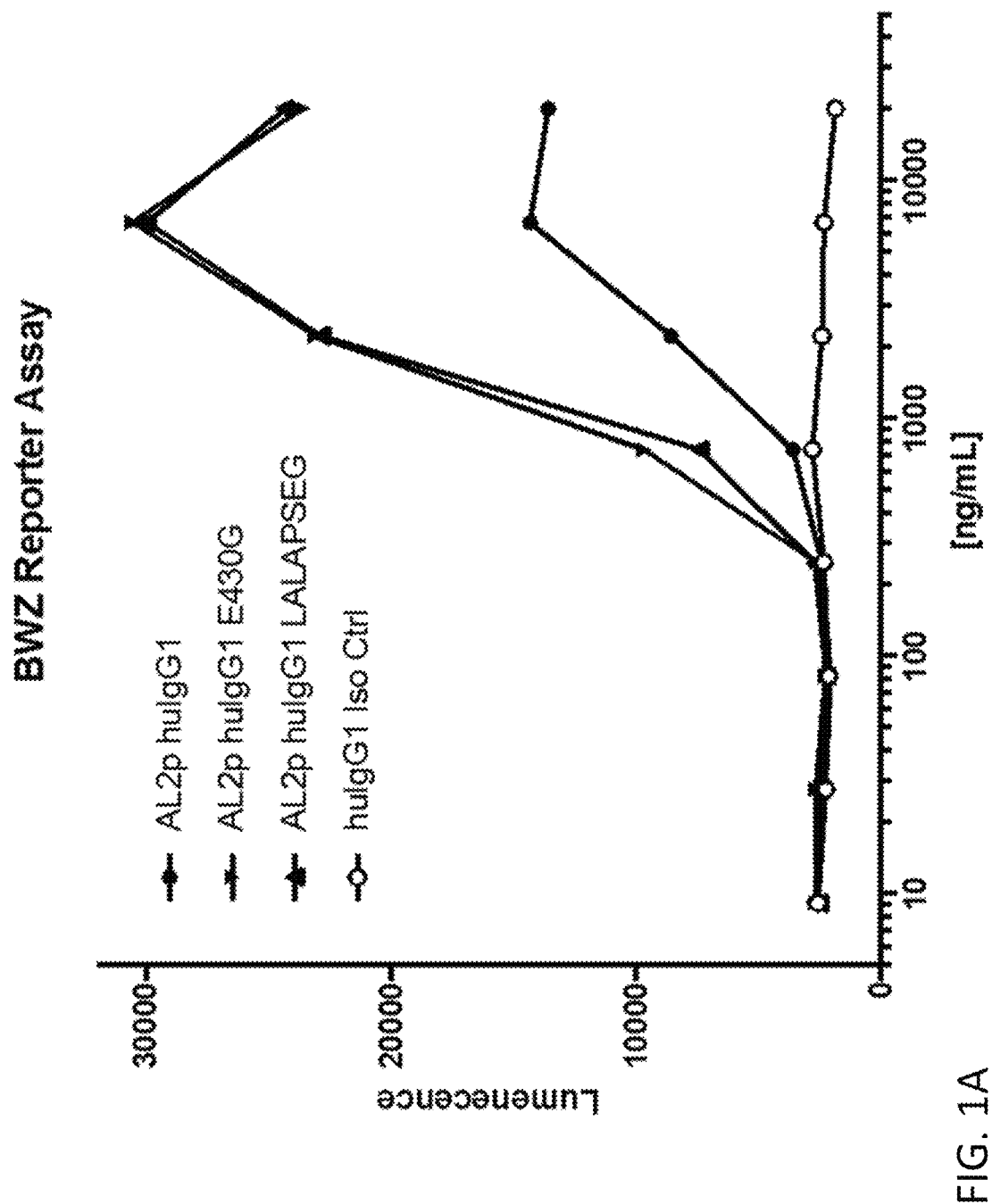
FIG. 1A shows increased agonistic activity of Fc variant anti-TREM2 antibodies. Luciferase activity after 6 h culture with Fc variants of an anti-TREM2 antibody.

The techniques and procedures described or referenced herein are generally well understood and commonly employed using conventional methodology by those skilled in the art, such as, for example, the widely utilized methodologies described in Sambrook et al., *Molecular Cloning: A Laboratory Manual* 3d edition (2001) Cold Spring Harbor Laboratory Press, Cold Spring Harbor, N.Y.; *Current Protocols in Molecular Biology* (F. M. Ausubel, et al. eds., (2003)); the series *Methods in Enzymology* (Academic Press, Inc.): *PCR 2: A Practical Approach* (M. J. MacPherson, B. D. Hames and G. R. Taylor eds. (1995)), Harlow and Lane, eds. (1988) *Antibodies, A Laboratory Manual*, and *Animal Cell Culture* (R. I. Freshney, ed. (1987)); *Oligonucleotide Synthesis* (M. J. Gait, ed., 1984); *Methods in Molecular Biology*, Humana Press; *Cell Biology: A Laboratory Notebook* (J. E. Cellis, ed., 1998) Academic Press; *Animal Cell Culture* (R. I. Freshney), ed., 1987); *Introduction to Cell and Tissue Culture* (J. P. Mather and P. E. Roberts, 1998) Plenum Press; *Cell and Tissue Culture: Laboratory Procedures* (A. Doyle, J. B. Griffiths, and D. G. Newell, eds., 1993-8) J. Wiley and Sons; *Handbook of Experimental Immunology* (D. M. Weir and C. C. Blackwell, eds.); *Gene Transfer Vectors for Mammalian Cells* (J. M. Miller and M. P. Calos, eds., 1987); *PCR: The Polymerase Chain Reaction*, (Mullis et al., eds., 1994); *Current Protocols in Immunology* (J. E. Coligan et al., eds., 1991); *Short Protocols in Molecular Biology* (Wiley and Sons, 1999); *Immunobiology* (C. A. Janeway and P. Travers, 1997); *Antibodies* (P. Finch, 1997); *Antibodies: A Practical Approach* (D. Catty, ed., IRL Press, 1988-1989); Monoclonal *Antibodies: A Practical Approach* (P. Shepherd and C. Dean, eds., Oxford University Press, 2000); *Using Antibodies: A Laboratory Manual* (E. Harlow and D. Lane (Cold Spring Harbor Laboratory Press, 1999); *The Antibodies* (M. Zanetti and J. D. Capra, eds., Harwood Academic Publishers, 1995); and *Cancer: Principles and Practice of Oncology* (V. T. DeVita et al., eds., J. B. Lippincott Company, 1993).

Definitions

As used herein, the term "preventing" includes providing prophylaxis with respect to occurrence or recurrence of a particular disease, disorder, or condition in an individual. An individual may be predisposed to, susceptible to a particular disease, disorder, or condition, or at risk of developing such a disease, disorder, or condition, but has not yet been diagnosed with the disease, disorder, or condition.

As used herein, an individual "at risk" of developing a particular disease, disorder, or condition may or may not have detectable disease or symptoms of disease, and may or may not have displayed detectable disease or symptoms of disease prior to the treatment methods described herein. "At risk" denotes that an individual has one or more risk factors, which are measurable parameters that correlate with development of a particular disease, disorder, or condition, as known in the art. An individual having one or more of these risk factors has a higher probability of developing a particular disease, disorder, or condition than an individual without one or more of these risk factors.

As used herein, the term "treatment" refers to clinical intervention designed to alter the natural course of the individual being treated during the course of clinical pathology. Desirable effects of treatment include decreasing the rate of progression, ameliorating or palliating the pathological state, and remission or improved prognosis of a particular disease, disorder, or condition. An individual is successfully "treated", for example, if one or more symptoms associated with a particular disease, disorder, or condition are mitigated or eliminated.

An "effective amount" refers to at least an amount effective, at dosages and for periods of time necessary, to achieve the desired therapeutic or prophylactic result. An effective amount can be provided in one or more administrations. An effective amount herein may vary according to factors such as the disease state, age, sex, and weight of the individual, and the ability of the treatment to elicit a desired response in the individual. An effective amount is also one in which any toxic or detrimental effects of the treatment are outweighed by the therapeutically beneficial effects. For prophylactic use, beneficial or desired results include results such as eliminating or reducing the risk, lessening the severity, or delaying the onset of the disease, including biochemical, histological and/or behavioral symptoms of the disease, its complications and intermediate pathological phenotypes presenting during development of the disease. For therapeutic use, beneficial or desired results include clinical results such as decreasing one or more symptoms resulting from the disease, increasing the quality of life of those suffering from the disease, decreasing the dose of other medications required to treat the disease, enhancing effect of another medication such as via targeting, delaying the progression of the disease, and/or prolonging survival. An effective amount of drug, compound, or pharmaceutical composition is an amount sufficient to accomplish prophylactic or therapeutic treatment either directly or indirectly. As is understood in the clinical context, an effective amount of a drug, compound, or pharmaceutical composition may or may not be achieved in conjunction with another drug, compound, or pharmaceutical composition. Thus, an "effective amount" may be considered in the context of administering one or more therapeutic agents, and a single agent may be considered to be given in an effective amount if, in conjunction with one or more other agents, a desirable result may be or is achieved.

An "individual" for purposes of treatment, prevention, or reduction of risk refers to any animal classified as a mammal, including humans, domestic and farm animals, and zoo, sport, or pet animals, such as dogs, horses, rabbits, cattle, pigs, hamsters, gerbils, mice, ferrets, rats, cats, and the like. In some embodiments, the individual is human.

As used herein, administration "in conjunction" with another compound or composition includes simultaneous administration and/or administration at different times. Administration in conjunction also encompasses administration as a co-formulation or administration as separate compositions, including at different dosing frequencies or intervals, and using the same route of administration or different routes of administration.

The term "immunoglobulin" (Ig) is used interchangeably with "antibody" herein. The term "antibody" herein is used in the broadest sense and specifically covers monoclonal antibodies, polyclonal antibodies, multispecific antibodies (e.g., bispecific antibodies) formed from at least two intact antibodies, and antibody fragments so long as they exhibit the desired biological activity.

The basic 4-chain antibody unit is a heterotetrameric glycoprotein composed of two identical light (L) chains and two identical heavy (H) chains. The pairing of a $V_H$ and $V_L$ together forms a single antigen-binding site. For the structure and properties of the different classes of antibodies, see, e.g., *Basic and Clinical Immunology*, 8th Ed., Daniel P. Stites, Abba I. Terr and Tristram G. Parslow (eds.), Appleton & Lange, Norwalk, Conn., 1994, page 71 and Chapter 6.

The L chain from any vertebrate species can be assigned to one of two clearly distinct types, called kappa ("κ") and lambda ("λ"), based on the amino acid sequences of their constant domains. Depending on the amino acid sequence of the constant domain of their heavy chains (CH), immunoglobulins can be assigned to different classes or isotypes. There are five classes of immunoglobulins: IgA, IgD, IgE, IgG, and IgM, having heavy chains designated alpha ("α"), delta ("δ"), epsilon ("ε"), gamma ("γ") and mu ("μ"), respectively. The γ and α classes are further divided into subclasses (isotypes) on the basis of relatively minor differences in the CH sequence and function, e.g., humans express the following subclasses: IgG1, IgG2, IgG3, IgG4, IgA1, and IgA2. The subunit structures and three dimensional configurations of different classes of immunoglobulins are well known and described generally in, for example, Abbas et al., Cellular and Molecular Immunology, $4^{th}$ ed. (W.B. Saunders Co., 2000).

"Native antibodies" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intra-chain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light chain and heavy chain variable domains.

An "isolated" antibody, such as an isolated anti-TREM2 antibody of the present disclosure, is one that has been identified, separated and/or recovered from a component of its production environment (e.g., naturally or recombinantly). Preferably, the isolated polypeptide is free of association with all other contaminant components from its production environment. Contaminant components from its production environment, such as those resulting from recombinant transfected cells, are materials that would typically interfere with research, diagnostic or therapeutic uses for the antibody, and may include enzymes, hormones, and other proteinaceous or non-proteinaceous solutes. In preferred embodiments, the polypeptide will be purified: (1) to greater than 95% by weight of antibody as determined by, for example, the Lowry method, and in some embodiments, to greater than 99% by weight; (2) to a degree sufficient to obtain at least 15 residues of N-terminal or internal amino acid sequence by use of a spinning cup sequenator, or (3) to homogeneity by SDS-PAGE under non-reducing or reducing conditions using Coomassie blue or, preferably, silver stain. Isolated antibody includes the antibody in situ within recombinant T-cells since at least one component of the antibody's natural environment will not be present. Ordinarily, however, an isolated polypeptide or antibody will be prepared by at least one purification step.

The "variable region" or "variable domain" of an antibody, such as an anti-TREM2 antibody of the present disclosure, refers to the amino-terminal domains of the heavy or light chain of the antibody. The variable domains of the heavy chain and light chain may be referred to as "$V_H$" and "$V_L$", respectively. These domains are generally the most variable parts of the antibody (relative to other antibodies of the same class) and contain the antigen binding sites.

The term "variable" refers to the fact that certain segments of the variable domains differ extensively in sequence among antibodies, such as anti-TREM2 antibodies of the present disclosure. The V domain mediates antigen binding and defines the specificity of a particular antibody for its particular antigen. However, the variability is not evenly distributed across the entire span of the variable domains. Instead, it is concentrated in three segments called hypervariable regions (HVRs) both in the light-chain and the heavy chain variable domains. The more highly conserved portions of variable domains are called the framework regions (FR). The variable domains of native heavy and light chains each comprise four FR regions, largely adopting a beta-sheet configuration, connected by three HVRs, which form loops connecting, and in some cases forming part of, the beta-sheet structure. The HVRs in each chain are held together in close proximity by the FR regions and, with the HVRs from the other chain, contribute to the formation of the antigen-binding site of antibodies (see Kabat et al., *Sequences of Immunological Interest*, Fifth Edition, National Institute of Health, Bethesda, Md. (1991)). The constant domains are not involved directly in the binding of antibody to an antigen, but exhibit various effector functions, such as participation of the antibody in antibody-dependent-cellular toxicity.

The term "monoclonal antibody" as used herein refers to an antibody, such as a monoclonal anti-TREM2 antibody of the present disclosure, obtained from a population of substantially homogeneous antibodies, i.e., the individual antibodies comprising the population are identical except for possible naturally occurring mutations and/or post-translation modifications (e.g., isomerizations, amidations, etc.) that may be present in minor amounts. Monoclonal antibodies are highly specific, being directed against a single antigenic site. In contrast to polyclonal antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including, for example, the hybridoma method (e.g., Kohler and Milstein, *Nature,* 256: 495-97 (1975); Hongo et al., *Hybridoma,* 14 (3):253-260 (1995), Harlow et al., *Antibodies*: A Laboratory Manual, (Cold Spring Harbor Laboratory Press, 2d ed. 1988); Hammerling et al., in: *Monoclonal Antibodies and T-Cell Hybridomas* 563-681 (Elsevier, N.Y., 1981)), recombinant DNA methods (see, e.g., U.S. Pat. No. 4,816,567), phage-display technologies (see, e.g., Clackson et al., Nature, 352:624-628 (1991); Marks et al., *J. Mol. Biol.* 222:581-597 (1992); Sidhu et al., *J. Mol. Biol.* 338(2): 299-310 (2004); Lee et al., *J. Mol. Biol.* 340(5):1073-1093 (2004); Fellouse, *Proc. Nat'l Acad. Sci. USA* 101(34):12467-472 (2004); and Lee et al., *J. Immunol. Methods* 284(1-2): 119-132 (2004), yeast presentation technologies (see, e.g., WO2009/036379A2; WO2010105256; WO2012009568, and Xu et al., *Protein Eng. Des. Sel.,* 26(10): 663-70 (2013), and technologies for producing human or human-like antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits et al., *Proc. Nat'l Acad Sci. USA* 90:2551 (1993); Jakobovits et al., *Nature* 362:255-258 (1993); Bruggemann et al., Year in Immunol. 7:33 (1993); U.S. Pat. Nos. 5,545,807; 5,545,806; 5,569,825; 5,625,126; 5,633,425; and 5,661,016; Marks et al., Bio/Technology 10:779-783 (1992); Lonberg et al., *Nature* 368:856-859 (1994); Morrison, *Nature* 368:812-813 (1994); Fishwild et al., *Nature Biotechnol.* 14:845-851 (1996); Neuberger, *Nature Biotechnol.* 14:826 (1996); and Lonberg and Huszar, *Intern. Rev. Immunol.* 13:65-93 (1995).

The terms "full-length antibody," "intact antibody" or "whole antibody" are used interchangeably to refer to an antibody, such as an anti-TREM2 antibody of the present disclosure, in its substantially intact form, as opposed to an antibody fragment. Specifically whole antibodies include those with heavy and light chains including an Fc region. The constant domains may be native sequence constant domains (e.g., human native sequence constant domains) or amino acid sequence variants thereof. In some cases, the intact antibody may have one or more effector functions.

An "antibody fragment" comprises a portion of an intact antibody, preferably the antigen binding and/or the variable region of the intact antibody. Examples of antibody fragments include Fab, Fab', F(ab')$_2$ and Fv fragments; diabodies; linear antibodies (see U.S. Pat. No. 5,641,870, Example 2; Zapata et al., *Protein Eng.* 8(10):1057-1062 (1995)); single-chain antibody molecules and multispecific antibodies formed from antibody fragments.

Papain digestion of antibodies, such as anti-TREM2 antibodies of the present disclosure, produces two identical antigen-binding fragments, called "Fab" fragments, and a residual "Fc" fragment, a designation reflecting the ability to crystallize readily. The Fab fragment consists of an entire L chain along with the variable region domain of the H chain ($V_H$), and the first constant domain of one heavy chain ($C_H1$). Each Fab fragment is monovalent with respect to antigen binding, i.e., it has a single antigen-binding site. Pepsin treatment of an antibody yields a single large F(ab')$_2$ fragment which roughly corresponds to two disulfide linked Fab fragments having different antigen-binding activity and is still capable of cross-linking antigen. Fab' fragments differ from Fab fragments by having a few additional residues at the carboxy terminus of the $C_H1$ domain including one or more cysteines from the antibody hinge region. Fab'-SH is the designation herein for Fab' in which the cysteine residue (s) of the constant domains bear a free thiol group. F(ab')$_2$ antibody fragments originally were produced as pairs of Fab' fragments which have hinge cysteines between them. Other chemical couplings of antibody fragments are also known.

The Fc fragment comprises the carboxy-terminal portions of both H chains held together by disulfides. The effector functions of antibodies are determined by sequences in the Fc region, the region which is also recognized by Fc receptors (FcR) found on certain types of cells.

"Fv" is the minimum antibody fragment which contains a complete antigen-recognition and -binding site. This fragment consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three HVRs specific for an antigen) has the ability to recognize and bind antigen, although at a lower affinity than the entire binding site.

"Single-chain Fv" also abbreviated as "sFv" or "scFv" are antibody fragments that comprise the VH and VL antibody domains connected into a single polypeptide chain. Preferably, the sFv polypeptide further comprises a polypeptide linker between the $V_H$ and $V_L$ domains, which enables the sFv to form the desired structure for antigen binding. For a review of the sFv, see Plückthun in *The Pharmacology of Monoclonal Antibodies*, vol. 113, Rosenburg and Moore eds., Springer-VerLAG-3, New York, pp. 269-315 (1994).

"Functional fragments" of antibodies, such as anti-TREM2 antibodies of the present disclosure, comprise a portion of an intact antibody, generally including the antigen binding or variable region of the intact antibody or the F region of an antibody which retains or has modified FcR binding capability. Examples of antibody fragments include linear antibody, single-chain antibody molecules and multispecific antibodies formed from antibody fragments.

The term "diabodies" refers to small antibody fragments prepared by constructing sFv fragments (see preceding paragraph) with short linkers (about 5-10) residues) between the $V_H$ and $V_L$ domains such that inter-chain but not intra-chain pairing of the V domains is achieved, thereby resulting in a bivalent fragment, i.e., a fragment having two antigen-binding sites. Bispecific diabodies are heterodimers of two "crossover" sFv fragments in which the $V_H$ and $V_L$ domains of the two antibodies are present on different polypeptide chains. Diabodies are described in greater detail in, for example, EP 404,097; WO 93/11161; Hollinger et al., *Proc. Nat'l Acad Sci. USA* 90:6444-48 (1993).

As used herein, a "chimeric antibody" refers to an antibody (immunoglobulin), such as a chimeric anti-TREM2 antibody of the present disclosure, in which a portion of the heavy and/or light chain is identical with or homologous to corresponding sequences in antibodies derived from a particular species or belonging to a particular antibody class or subclass, while the remainder of the chain(s) is(are) identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., *Proc. Nat'l Acad. Sci. USA*, 81:6851-55 (1984)). Chimeric antibodies of interest herein include PRIMATIZED® antibodies wherein the antigen-binding region of the antibody is derived from an antibody produced by, e.g., immunizing macaque monkeys with an antigen of interest. As used herein, "humanized antibody" is used a subset of "chimeric antibodies."

"Humanized" forms of non-human (e.g., murine) antibodies, such as humanized forms of anti-TREM2 antibodies of the present disclosure, are chimeric antibodies that contain minimal sequence derived from non-human immunoglobulin. In one embodiment, a humanized antibody is a human immunoglobulin (recipient antibody) in which residues from an HVR of the recipient are replaced by residues from an HVR of a non-human species (donor antibody) such as mouse, rat, rabbit or non-human primate having the desired specificity, affinity, and/or capacity. In some instances, FR residues of the human immunoglobulin are replaced by corresponding non-human residues. Furthermore, humanized antibodies may comprise residues that are not found in the recipient antibody or in the donor antibody. These modifications may be made to further refine antibody performance, such as binding affinity. In general, a humanized antibody will comprise substantially all of at least one, and typically two, variable domains, in which all or substantially all of the hypervariable loops correspond to those of a non-human immunoglobulin sequence, and all or substantially all of the FR regions are those of a human immunoglobulin sequence, although the FR regions may include one or more individual FR residue substitutions that improve antibody performance, such as binding affinity, isomerization, immunogenicity, and the like. The number of these amino acid substitutions in the FR is typically no more than 6 in the H chain, and in the L chain, no more than 3. The humanized antibody optionally will also comprise at least a portion of an immunoglobulin constant region (Fc), typically that of a human immunoglobulin. For further details, see, e.g., Jones et al., *Nature* 321:522-525 (1986); Riechmann et al., *Nature* 332:323-329 (1988); and Presta, *Curr. Op. Struct. Biol.* 2:593-596 (1992). See also, for example, Vaswani and Hamilton, *Ann. Allergy, Asthma & Immunol.* 1:105-115 (1998); Harris, *Biochem. Soc. Transactions* 23:1035-1038 (1995); Hurle and Gross, *Curr. Op. Biotech.* 5:428-433 (1994); and U.S. Pat. Nos. 6,982,321 and 7,087,409.

A "human antibody" is one that possesses an amino-acid sequence corresponding to that of an antibody, such as an anti-TREM2 antibody of the present disclosure, produced by a human and/or has been made using any of the techniques for making human antibodies as disclosed herein. This definition of a human antibody specifically excludes a humanized antibody comprising non-human antigen-binding residues. Human antibodies can be produced using various techniques known in the art, including phage-display libraries. Hoogenboom and Winter, *J. Mol. Biol.*, 227: 381 (1991); Marks et al., *J. Mol. Biol.*, 222:581 (1991). Also available for the preparation of human monoclonal antibodies are methods described in Cole et al., Monoclonal *Antibodies* and Cancer Therapy, Alan R. Liss, p. 77 (1985); Boerner et al., *J. Immunol.*, 147(1):86-95 (1991). See also van Dijk and van de Winkel, *Curr. Opin. Pharmacol.* 5:368-74 (2001). Human antibodies can be prepared by administering the antigen to a transgenic animal that has been modified to produce such antibodies in response to antigenic challenge, but whose endogenous loci have been disabled, e.g., immunized xenomice (see, e.g., U.S. Pat. Nos. 6,075,181 and 6,150,584 regarding XENOMOUSE™ technology). See also, for example, Li et al., *Proc. Nat'l Acad Sci. USA*, 103:3557-3562 (2006) regarding human antibodies generated via a human B-cell hybridoma technology. Alternatively, human antibodies can also be prepared by employing yeast libraries and methods as disclosed in, for example, WO2009/036379A2; WO2010105256; WO2012009568; and Xu et al., *Protein Eng. Des. Sel.,* 26(10): 663-70 (2013).

The term "hypervariable region," "HVR," or "HV," when used herein refers to the regions of an antibody-variable domain, such as that of an anti-TREM2 antibody of the present disclosure, that are hypervariable in sequence and/or form structurally defined loops. Generally, antibodies comprise six HVRs; three in the VH (H1, H2, H3), and three in the VL (L1, L2, L3). In native antibodies, H3 and L3 display the most diversity of the six HVRs, and H3 in particular is believed to play a unique role in conferring fine specificity to antibodies. See, e.g., Xu et al., *Immunity* 13:37-45 (2000); Johnson and Wu in *Methods in Molecular Biology* 248:1-25 (Lo, ed., Human Press, Totowa, N.J., 2003)). Indeed, naturally occurring camelid antibodies consisting of a heavy chain only are functional and stable in the absence of light chain. See, e.g., Hamers-Casterman et al., *Nature* 363:446-448 (1993) and Sheriff et al., *Nature Struct. Biol.* 3:733-736 (1996).

A number of HVR delineations are in use and are encompassed herein. In some embodiments, the HVRs may be Kabat complementarity-determining regions (CDRs) based on sequence variability and are the most commonly used (Kabat et al., supra). In some embodiments, the HVRs may be Chothia CDRs. Chothia refers to the location of the structural loops (Chothia and Lesk *J. Mol. Biol.* 196: 901-917 (1987)). In some embodiments, the HVRs may be AbM HVRs. The AbM HVRs represent a compromise between the Kabat CDRs and Chothia structural loops, and are used by Oxford Molecular's AbM antibody-modeling software. In some embodiments, the HVRs may be "contact" HVRs. The "contact" HVRs are based on an analysis of the available complex crystal structures. The residues from each of these HVRs are noted below.

| Loop | Kabat | AbM | Chothia | Contact |
| --- | --- | --- | --- | --- |
| L1 | L24-L34 | L24-L34 | L26-L32 | L30-L36 |
| L2 | L50-L56 | L50-L56 | L50-L52 | L46-L55 |
| L3 | L89-L97 | L89-L97 | L91-L96 | L89-L96 |
| H1 | H31-H35B | H26-H35B | H26-H32 | |
| | H30-H35B (Kabat numbering) | | | |
| H1 | H31-H35 | H26-H35 | H26-H32 | |
| | H30-H35 (Chothia numbering) | | | |
| H2 | H50-H65 | H50-H58 | H53-H55 | H47-H58 |
| H3 | H95-H102 | H95-H102 | H96-H101 | H93-H101 |

HVRs may comprise "extended HVRs" as follows: 24-36 or 24-34 (L1), 46-56 or 50-56 (L2), and 89-97 or 89-96 (L3) in the VL, and 26-35 (H1), 50-65 or 49-65 (a preferred embodiment) (H2), and 93-102, 94-102, or 95-102 (H3) in the VH. The variable-domain residues are numbered according to Kabat et al., supra, for each of these extended-HVR definitions.

"Framework" or "FR" residues are those variable-domain residues other than the HVR residues as herein defined.

The phrase "variable-domain residue-numbering as in Kabat" or "amino-acid-position numbering as in Kabat," and variations thereof, refers to the numbering system used for heavy-chain variable domains or light-chain variable domains of the compilation of antibodies in Kabat et al., supra. Using this numbering system, the actual linear amino acid sequence may contain fewer or additional amino acids corresponding to a shortening of, or insertion into, a FR or HVR of the variable domain. For example, a heavy-chain variable domain may include a single amino acid insert (residue 52a according to Kabat) after residue 52 of H2 and inserted residues (e.g., residues 82a, 82b, and 82c, etc. according to Kabat) after heavy-chain FR residue 82. The Kabat numbering of residues may be determined for a given antibody by alignment at regions of homology of the sequence of the antibody with a "standard" Kabat numbered sequence.

The Kabat numbering system is generally used when referring to a residue in the variable domain (approximately residues 1-107 of the light chain and residues 1-113 of the heavy chain) (e.g., Kabat et al., Sequences of Immunological Interest. 5th Ed. Public Health Service, National Institutes of Health, Bethesda, Md. (1991)). The "EU or, Kabat numbering system" or "EU index" is generally used when referring to a residue in an immunoglobulin heavy chain constant region (e.g., the EU index reported in Kabat et al., supra). The "EU index as in Kabat" refers to the residue numbering of the human IgG1 EU antibody. References to residue numbers in the variable domain of antibodies means residue numbering by the Kabat numbering system. References to residue numbers in the constant domain of antibodies means residue numbering by the EU or, Kabat numbering system (e.g., see United States Patent Publication No. 2010-280227).

An "acceptor human framework" as used herein is a framework comprising the amino acid sequence of a VL or VH framework derived from a human immunoglobulin framework or a human consensus framework. An acceptor human framework "derived from" a human immunoglobulin framework or a human consensus framework may comprise the same amino acid sequence thereof, or it may contain pre-existing amino acid sequence changes. In some embodiments, the number of pre-existing amino acid changes are 10 or less, 9 or less, 8 or less, 7 or less, 6 or less, 5 or less, 4 or less, 3 or less, or 2 or less. Where pre-existing amino acid changes are present in a VH, preferable those changes occur at only three, two, or one of positions 71H, 73H and 78H; for instance, the amino acid residues at those positions may by 71A, 73T and/or 78A. In one embodiment, the VL acceptor human framework is identical in sequence to the VL human immunoglobulin framework sequence or human consensus framework sequence.

A "human consensus framework" is a framework that represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest,* 5th Ed. Public Health Service, National Institutes of Health, Bethesda, Md. (1991). Examples include for the VL, the subgroup may be subgroup kappa I, kappa II, kappa III or kappa IV as in Kabat et al., supra. Additionally, for the VH, the subgroup may be subgroup I, subgroup II, or subgroup III as in Kabat et al., supra.

An "amino-acid modification" at a specified position, e.g., of an anti-TREM2 antibody of the present disclosure, refers to the substitution or deletion of the specified residue, or the insertion of at least one amino acid residue adjacent the specified residue. Insertion "adjacent" to a specified residue means insertion within one to two residues thereof. The insertion may be N-terminal or C-terminal to the specified residue. The preferred amino acid modification herein is a substitution.

An "affinity-matured" antibody, such as an affinity matured anti-TREM2 antibody of the present disclosure, is one with one or more alterations in one or more HVRs thereof that result in an improvement in the affinity of the antibody for antigen, compared to a parent antibody that does not possess those alteration(s). In one embodiment, an affinity-matured antibody has nanomolar or even picomolar affinities for the target antigen. Affinity-matured antibodies are produced by procedures known in the art. For example, Marks et al., *Bio/Technology* 10:779-783 (1992) describes affinity maturation by VH- and VL-domain shuffling. Random mutagenesis of HVR and/or framework residues is described by, for example: Barbas et al. *Proc Nat. Acad. Sci. USA* 91:3809-3813 (1994); Schier et al. Gene 169:147-155 (1995); Yelton et al. *J. Immunol.* 155:1994-2004 (1995); Jackson et al., *J. Immunol.* 154(7):3310-9 (1995); and Hawkins et al, *J. Mol. Biol.* 226:889-896 (1992).

As use herein, the term "specifically recognizes" or "specifically binds" refers to measurable and reproducible interactions such as attraction or binding between a target and an antibody, such as between an anti-TREM2 antibody and TREM2 that is determinative of the presence of the target in the presence of a heterogeneous population of molecules including biological molecules. For example, an antibody, such as an anti-TREM2 antibody of the present disclosure, that specifically or preferentially binds to a target or an epitope is an antibody that binds this target or epitope with greater affinity, avidity, more readily, and/or with greater duration than it binds to other targets or other epitopes of the target. It is also understood by reading this definition that, for example, an antibody (or a moiety) that specifically or preferentially binds to a first target may or may not specifically or preferentially bind to a second target. As such, "specific binding" or "preferential binding" does not necessarily require (although it can include) exclusive binding. An antibody that specifically binds to a target may have an association constant of at least about $10^3$ $M^{-1}$ or $10^4$ $M^{-1}$, sometimes about $10^5$ $M^{-1}$ or $10^6$ $M^{-1}$, in other instances about $10^6$ $M^{-1}$ or $10^7$ $M^{-1}$, about $10$ $M^{-1}$ to $10^9$ $M^{-1}$, or about $10^{10}$ $M^{-1}$ to $10^{11}$ $M^{-1}$ or higher. A variety of immunoassay formats can be used to select antibodies specifically immunoreactive with a particular protein. For example, solid-phase ELISA immunoassays are routinely used to select monoclonal antibodies specifically immunoreactive with a protein. See, e.g., Harlow and Lane (1988) Antibodies, A Laboratory Manual, Cold Spring Harbor Publications, New York, for a description of immunoassay formats and conditions that can be used to determine specific immunoreactivity.

As used herein, an "interaction" between a TREM2 protein and a second protein encompasses, without limitation, protein-protein interaction, a physical interaction, a chemical interaction, binding, covalent binding, and ionic binding. As used herein, an antibody "inhibits interaction" between two proteins when the antibody disrupts, reduces, or completely eliminates an interaction between the two proteins. An antibody of the present disclosure, or fragment thereof, "inhibits interaction" between two proteins when the antibody or fragment thereof binds to one of the two proteins.

An "agonist" antibody or an "activating" antibody is an antibody that induces (e.g., increases) one or more activities or functions of the antigen after the antibody binds the antigen.

An "antagonist" antibody or a "blocking" antibody is an antibody that reduces or eliminates (e.g., decreases) antigen binding to one or more ligand after the antibody binds the antigen, and/or that reduces or eliminates (e.g., decreases) one or more activities or functions of the antigen after the antibody binds the antigen. In some embodiments, antagonist antibodies, or blocking antibodies substantially or completely inhibit antigen binding to one or more ligand and/or one or more activities or functions of the antigen.

Antibody "effector functions" refer to those biological activities attributable to the Fc region (a native sequence Fc region or amino acid sequence variant Fc region) of an antibody, and vary with the antibody isotype.

The term "Fc region" herein is used to define a C-terminal region of an immunoglobulin heavy chain, including native-sequence Fc regions and variant Fc regions. Although the boundaries of the Fc region of an immunoglobulin heavy chain might vary, the human IgG heavy-chain Fc region is usually defined to stretch from an amino acid residue at position Cys226, or from Pro230, to the carboxyl-terminus thereof. The C-terminal lysine (residue 447 according to the EU or, Kabat numbering system) of the Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue. Suitable native-sequence Fc regions for use in the antibodies of the present disclosure include human IgG1, IgG2, IgG3 and IgG4.

A "native sequence Fc region" comprises an amino acid sequence identical to the amino acid sequence of an Fc region found in nature. Native sequence human Fc regions include a native sequence human IgG1 Fc region (non-A and A allotypes); native sequence human IgG2 Fc region; native sequence human IgG3 Fc region; and native sequence human IgG4 Fc region as well as naturally occurring variants thereof.

A "variant Fc region" comprises an amino acid sequence which differs from that of a native sequence Fc region by virtue of at least one amino acid modification, preferably one or more amino acid substitution(s). Preferably, the variant Fc region has at least one amino acid substitution compared to a native sequence Fc region or to the Fc region of a parent polypeptide, e.g. from about one to about ten amino acid substitutions, and preferably from about one to about five amino acid substitutions in a native sequence Fc region or in the Fc region of the parent polypeptide. The variant Fc region herein will preferably possess at least about 80% homology with a native sequence Fc region and/or with an Fc region of a parent polypeptide, and most preferably at least about 90% homology therewith, more preferably at least about 95% homology therewith.

"Fc receptor" or "FcR" describes a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors, FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif ("ITAM") in its cytoplasmic domain. Inhibiting receptor FcγRIIB contains an immunoreceptor tyrosine-based inhibition motif ("ITIM") in its cytoplasmic domain. (see, e.g., M. Daeron, *Annu. Rev.*

*Immunol.* 15:203-234 (1997)). FcRs are reviewed in Ravetch and Kinet, *Annu. Rev. Immunol.* 9:457-92 (1991); Capel et al., *Immunomethods* 4:25-34 (1994); and de Haas et al., *J. Lab. Clin. Med.* 126: 330-41 (1995). Other FcRs, including those to be identified in the future, are encompassed by the term "FcR" herein. FcRs can also increase the serum half-life of antibodies.

Binding to FcRn in vivo and serum half-life of human FcRn high-affinity binding polypeptides can be assayed, e.g., in transgenic mice or transfected human cell lines expressing human FcRn, or in primates to which the polypeptides having a variant Fc region are administered. WO 2004/42072 (Presta) describes antibody variants with improved or diminished binding to FcRs. See also, e.g., Shields et al., *J. Biol. Chem.* 9(2):6591-6604 (2001).

As used herein, "percent (%) amino acid sequence identity" and "homology" with respect to a peptide, polypeptide or antibody sequence refers to the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or MEGALIGN™ (DNASTAR) software. Those skilled in the art can determine appropriate parameters for measuring alignment, including any algorithms known in the art needed to achieve maximal alignment over the full-length of the sequences being compared.

An "isolated" nucleic acid molecule encoding an antibody, such as an anti-TREM2 antibody of the present disclosure, is a nucleic acid molecule that is identified and separated from at least one contaminant nucleic acid molecule with which it is ordinarily associated in the environment in which it was produced. Preferably, the isolated nucleic acid is free of association with all components associated with the production environment. The isolated nucleic acid molecules encoding the polypeptides and antibodies herein is in a form other than in the form or setting in which it is found in nature. Isolated nucleic acid molecules therefore are distinguished from nucleic acid encoding the polypeptides and antibodies herein existing naturally in cells.

The term "vector," as used herein, is intended to refer to a nucleic acid molecule capable of transporting another nucleic acid to which it has been linked. One type of vector is a "plasmid," which refers to a circular double stranded DNA into which additional DNA segments may be ligated. Another type of vector is a phage vector. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors," or simply, "expression vectors." In general, expression vectors of utility in recombinant DNA techniques are often in the form of plasmids. In the present specification, "plasmid" and "vector" may be used interchangeably as the plasmid is the most commonly used form of vector.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase or by a synthetic reaction. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may comprise modification(s) made after synthesis, such as conjugation to a label. Other types of modifications include, for example, "caps," substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotides(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid or semi-solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl-, 2'-fluoro- or 2'-azido-ribose, carbocyclic sugar analogs, α-anomeric sugars, epimeric sugars such as arabinose, xyloses or lyxoses, pyranose sugars, furanose sugars, sedoheptuloses, acyclic analogs, and basic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), (O)NR2 ("amidate"), P(O)R, P(O)OR', CO, or CH2 ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

A "host cell" includes an individual cell or cell culture that can be or has been a recipient for vector(s) for incorporation of polynucleotide inserts. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) of this invention.

"Carriers" as used herein include pharmaceutically acceptable carriers, excipients, or stabilizers that are non-toxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

The term "about" as used herein refers to the usual error range for the respective value readily known to the skilled person in this technical field. Reference to "about" a value or parameter herein includes (and describes) embodiments that are directed to that value or parameter per se.

As used herein and in the appended claims, the singular forms "a," "an," and "the" include plural reference unless the context clearly indicates otherwise. For example, reference to an "antibody" is a reference to from one to many antibodies, such as molar amounts, and includes equivalents thereof known to those skilled in the art, and so forth.

It is understood that aspect and embodiments of the present disclosure described herein include "comprising," "consisting," and "consisting essentially of" aspects and embodiments.

Overview

The present disclosure relates to anti-TREM2 antibodies (e.g., monoclonal antibodies) with improved affinity and functional characteristics; methods of making and using such antibodies; pharmaceutical compositions containing such antibodies; nucleic acids encoding such antibodies; and host cells containing nucleic acids encoding such antibodies.

Accordingly, certain aspects of the present disclosure are based, at least in part, on the identification of anti-TREM2 antibodies that are capable of binding to both human and cynomolgus monkey TREM2 with high affinity (see, e.g., Examples 2 and 6); that are capable of binding to primary human immune cells with high affinity (see, e.g., Examples 1-3); that have improved capability of clustering and activating TREM2 signaling in vitro and in vivo (see, e.g., Examples 3, 7, and 11); and that have improved capability of increase immune cell survival in vitro (see, e.g., Examples 3 and 9). Advantageously, anti-TREM2 antibodies of the present disclosure were shown have improved in vivo half-lives and to be able decreases plasma levels of soluble TREM2 in vitro and in vivo (see, e.g., Examples 4, 8, and 10). In some embodiments, anti-TREM2 antibodies of the present disclosure induce, increase, or otherwise enhance one or more TREM2 activities of the present disclosure. In some embodiments, anti-TREM2 antibodies of the present disclosure have one or more of these improved affinity and functional characteristics, as compared to an anti-TREM2 antibody having the heavy chain variable region and light chain variable region of antibody AL2p-h50 or AL2p-h77. Moreover, based on the results described in Examples 2-11, the functional characteristics of affinity matured anti-TREM2 antibodies of the present disclosure, would not have been predictable from their improved affinity for TREM2.

In some embodiments, anti-TREM2 antibodies of the present disclosure have high affinity for TREM2 exhibit the following functional properties: the ability to elevate TREM2 signaling both in soluble and in plate-bound format; the ability to promote survival of primary human macrophages and primary human dendritic cells; the ability to reduce production of soluble TREM2 (sTREM2) both in vitro by primary human myeloid cells and in vivo; and have relatively low polyspecific reactivity (PSR), which is a measure of unspecific binding. As disclosed herein, affinity maturation can lead to anti-TREM2 antibody variants that have both increased binding affinity and increased PSR (i.e., relatively high unspecific binding). While certain antibodies of the present disclosure, such as AL2p-31 and AL2p-60, have higher binding affinity and better functional properties than other affinity matured antibody variants, these also exhibit high PSR and have high levels of background binding to cells (see, e.g., Example 12). Surprisingly, antibodies AL2p-58 and AL2p-47 exhibit both high binding affinity and relatively low PSR as compared to other high affinity antibody variants, such as AL2p-31 and AL2p-60, while also having the ability to elevate TREM2 signaling both in soluble and in plate-bound format, to promote survival of primary human macrophages and primary human dendritic cells; and to reduce production of soluble TREM2 (sTREM2) both in vitro by primary human myeloid cells and in vivo (see, e.g., Examples 2-12). Based on these results, it was unexpected that antibodies AL2p-58 and AL2p-47 exhibit high affinity to TREM2 and good functional properties without showing any significant PSR or background binding to cells.

Figure 8A:
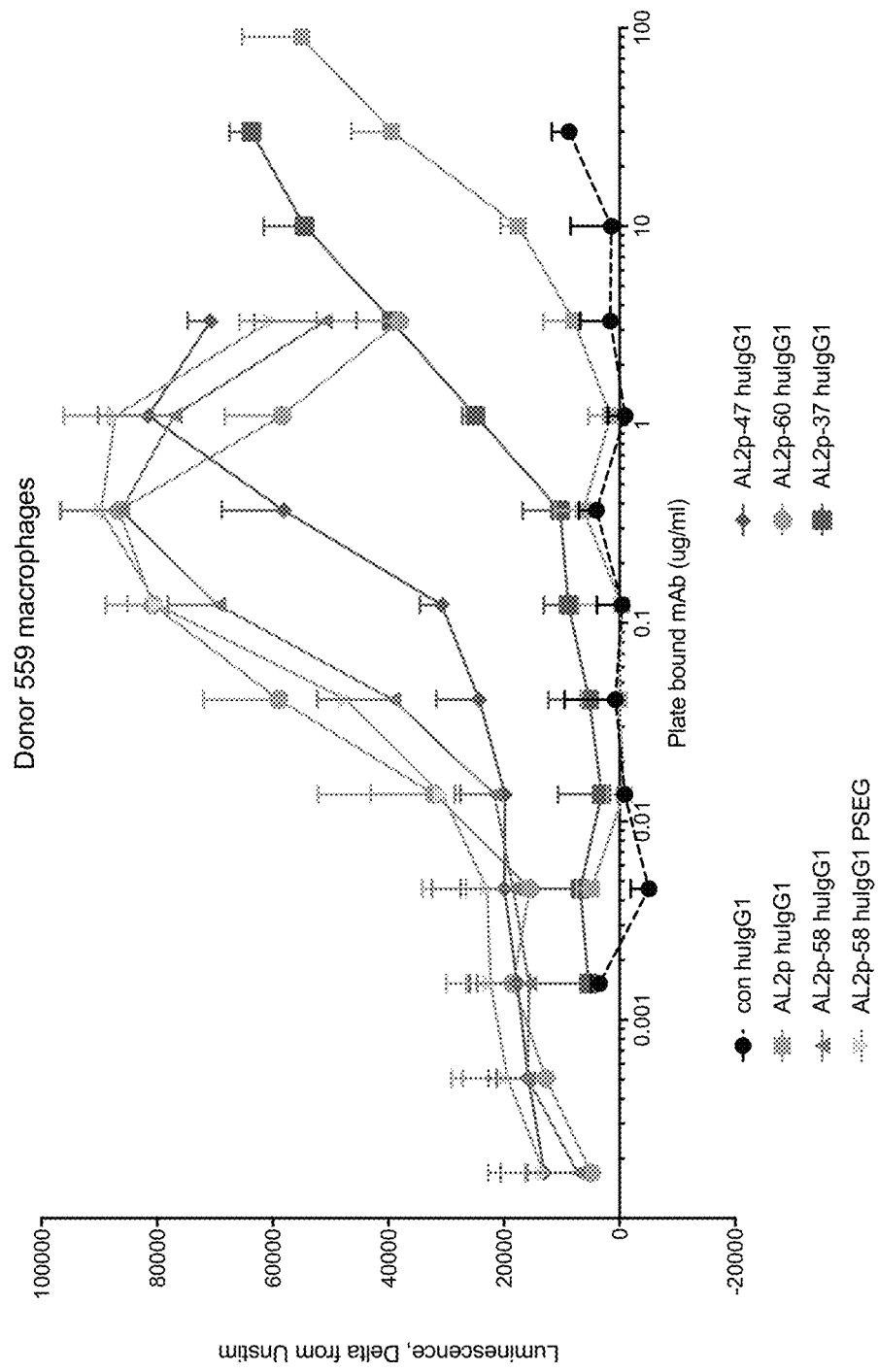
FIG. 8A and FIG. 8B depict increased viability (as increase in cellular ATP) after stimulation of primary human macrophages (FIG. 8A) or human primary dendritic cells (FIG. 8B) from one donor with plate bound TREM2 antibodies vs. control IgG for 48 hours.
Figure 8B:
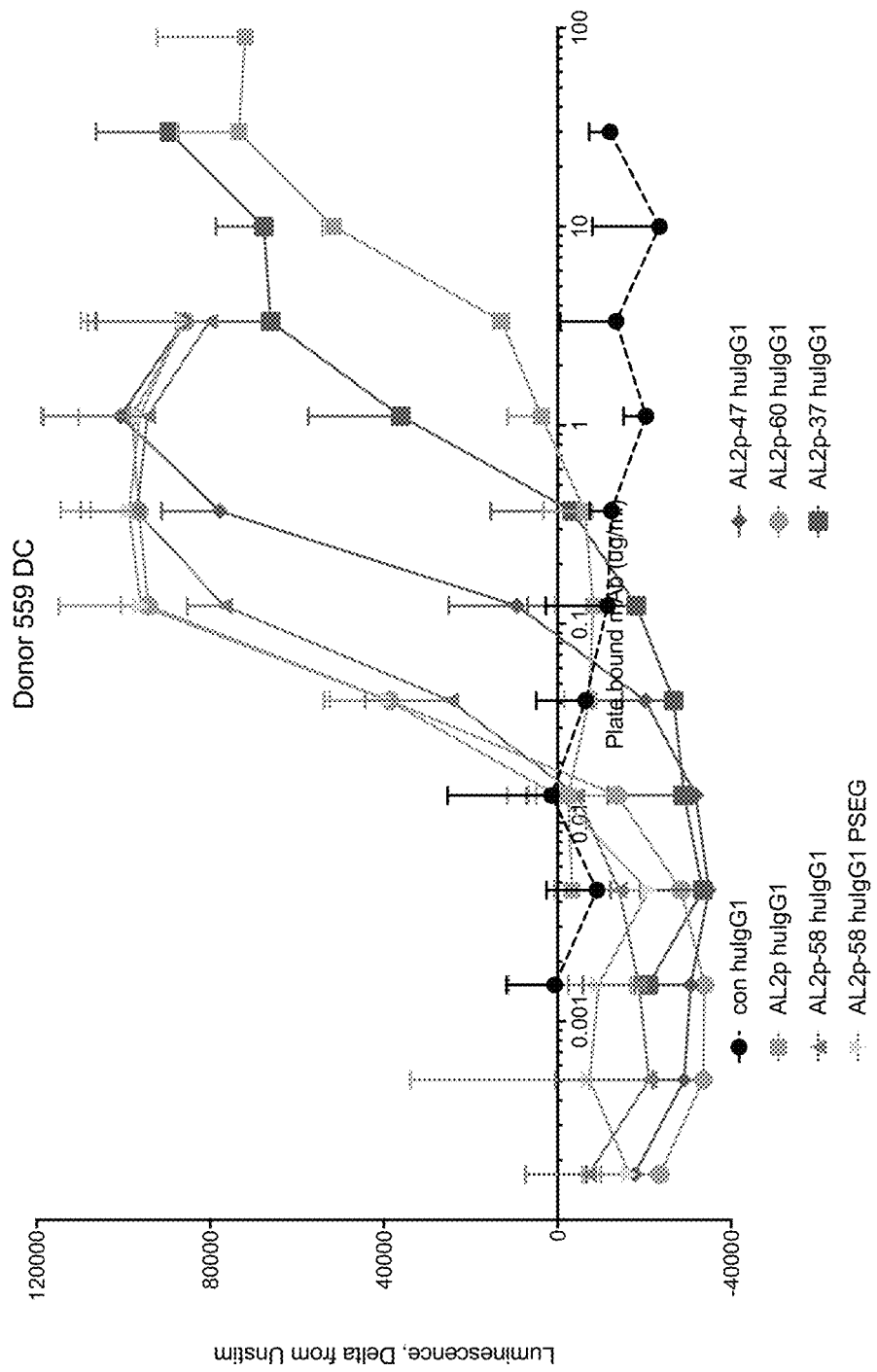
Figure 8C:
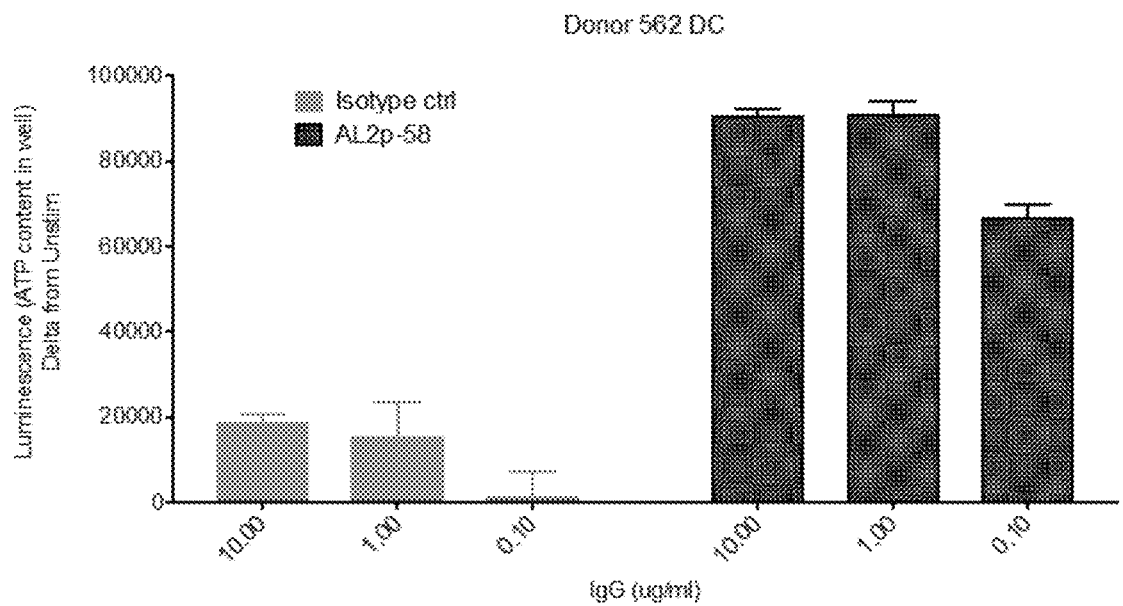
FIG. 8C, FIG. 8D, FIG. 8E, and FIG. 8F depict increased viability (as increase in cellular ATP) after stimulation of primary human dendritic cells of two donors (FIG. 8C and FIG. 8D) or human primary macrophages of two donors (FIG. 8E and FIG. 8F) with soluble AL2p-58 huIgG1 vs. control human IgG1 for 48 hours.
Figure 8D:
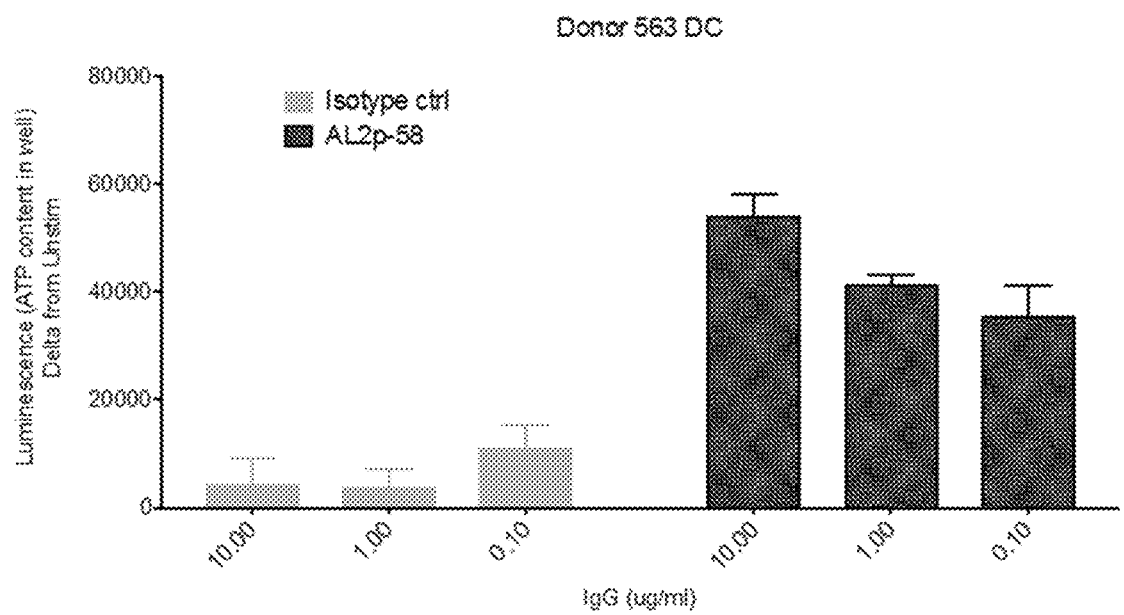
Figure 8E:
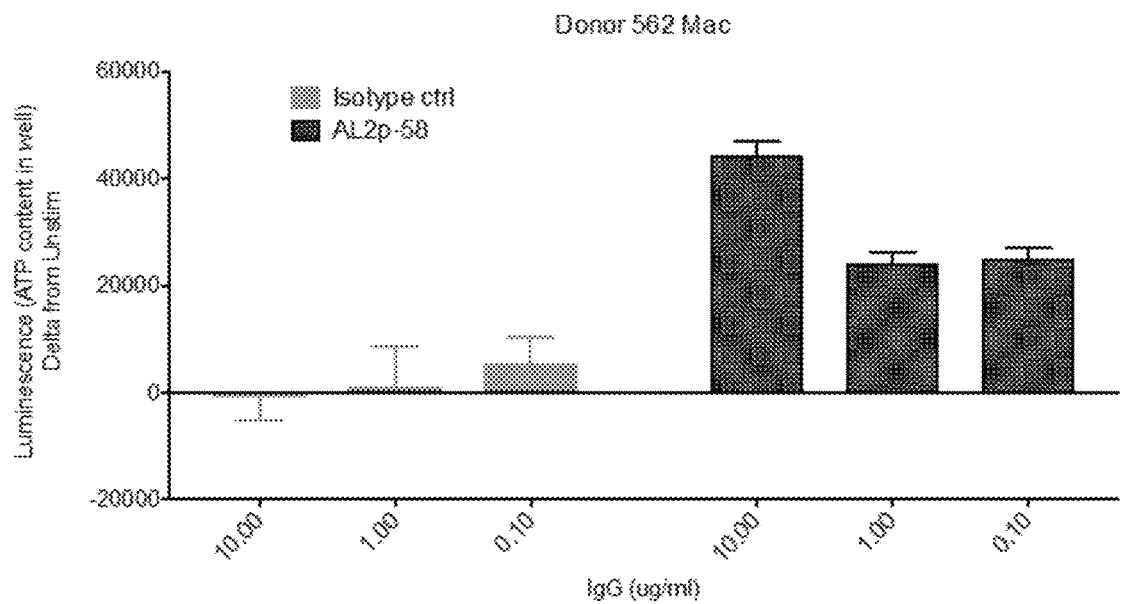
Figure 8F:
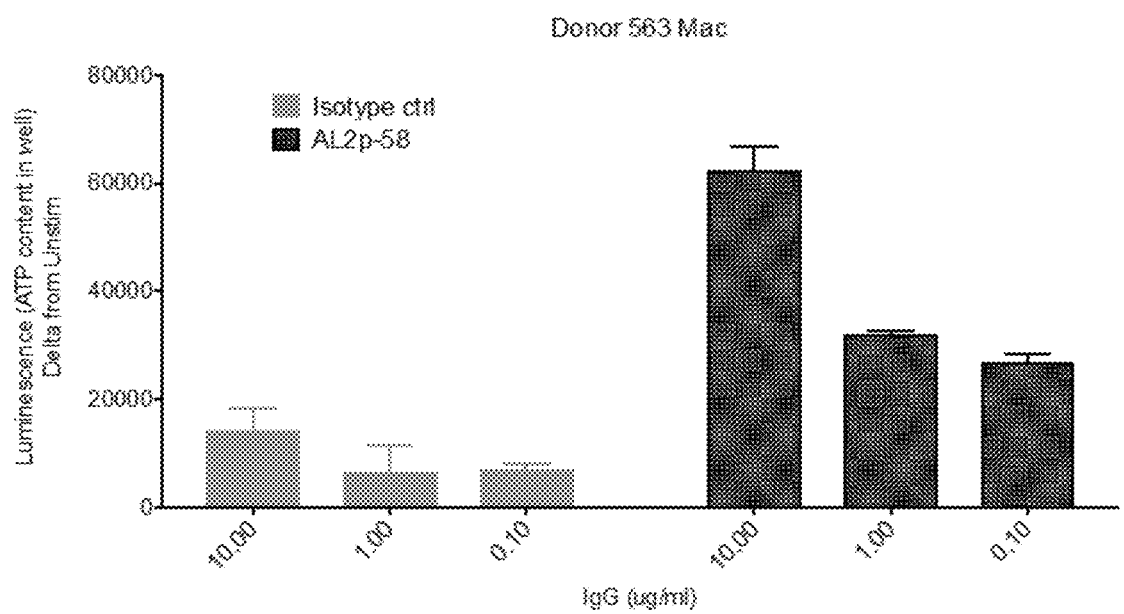

The results in Example 9 also surprisingly show that affinity matured anti-TREM2 antibodies of the present disclosure, such as AL2p-58 and AL2p-47, induce a several hundred-fold increase in cell viability of primary human macrophages and dendritic cells (see, e.g., Table 14 and FIGS. 8A and 8B). This functional property is surprising, as affinity matured anti-TREM2 antibodies, such as AL2p-58 and AL2p-47, exhibit only approximately a 10-fold improvement in affinity ($K_D$) for binding to human TREM2-Fc as compared to the parental mouse anti-TREM2 antibody AL2p (see, e.g., Tables 1 and 8), but have a several hundred-fold increase in their ability to promote cell viability. In addition, it is surprising that antibody AL2p-37, which has approximately similar binding affinity than AL2p-58 and AL2p-47, has relatively lower potency than AL2p-58 and AL2p-47 for promoting cell viability.

TREM2 Proteins

In one aspect, the present disclosure provides antibodies that bind to a TREM2 protein of the present disclosure with improved affinity and induce one or more TREM2 activities and/or enhance one or more TREM2 activities after binding to a TREM2 protein expressed in a cell.

TREM2 proteins of the present disclosure include, without limitation, a human TREM2 protein (Uniprot Accession No. Q9NZC2; SEQ ID NO: 1), and a non-human mammalian TREM2 protein, such as mouse TREM2 protein (Uniprot Accession No. Q99NH8; SEQ ID NO: 2), rat TREM2 protein (Uniprot Accession No. D3ZZ89; SEQ ID NO: 3), Rhesus monkey TREM2 protein (Uniprot Accession No. F6QVF2; SEQ ID NO: 4), cynomolgus monkey TREM2 protein (NCBI Accession No. XP_015304909.1; SEQ ID NO: 5), equine TREM2 protein (Uniprot Accession No. F7D6L0; SEQ ID NO: 6), pig TREM2 protein (Uniprot Accession No. H2EZZ3; SEQ ID NO: 7), and dog TREM2 protein (Uniprot Accession No. E2RP46; SEQ ID NO: 8).

As used herein "TREM2 protein" refers to both wild-type sequences and naturally occurring variant sequences.

Triggering receptor expressed on myeloid cells-2 (TREM2) is variously referred to as TREM-2, TREM2a, TREM2b, TREM2c, triggering receptor expressed on myeloid cells-2a, and triggering receptor expressed on monocytes-2. TREM2 is a 230 amino acid membrane protein. TREM2 is an immunoglobulin-like receptor primarily expressed on myeloid lineage cells, including without limitation, macrophages, dendritic cells, monocytes, Langerhans cells of skin, Kupffer cells, osteoclasts, and microglia. In some embodiments, TREM2 forms a receptor signaling complex with DAP12. In some embodiments, TREM2 phosphorylates and signals through DAP12 (an ITAM domain adaptor protein). In some embodiments TREM2 signaling results in the downstream activation of PI3K or other intracellular signals. On Myeloid cells, Toll-like receptor (TLR) signals are important for the activation of TREM2 activities, e.g., in the context of an infection response. TLRs also play a key role in the pathological inflammatory response, e.g., TLRs expressed in macrophages and dendritic cells.

In some embodiments, an example of a human TREM2 amino acid sequence is set forth below as SEQ ID NO: 1:

```
         10         20         30         40
 MEPLRLLILL FVTELSGAHN TTVFQGVAGQ SLQVSCPYDS 50         60         70         80
 MKHWGRRKAW CRQLGEKGPC QRVVSTHNLW LLSFLRRWNG 90        100        110        120
 STAITDDTLG GTLTITLRNL QPHDAGLYQC QSLHGSEADT 130        140        150        160
 LRKVLVEVLA DPLDHRDAGD LWFPGESESF EDAHVEHSIS 170        180        190        200
 RSLLEGEIPF PPTSILLLLA CIFLIKILAA SALWAAAWHG 210        220        230
 QKPGTHPPSE LDCGHDPGYQ LQTLPGLRDT
```

In some embodiments, the human TREM2 is a preprotein that includes a signal peptide. In some embodiments, the human TREM2 is a mature protein. In some embodiments, the mature TREM2 protein does not include a signal peptide. In some embodiments, the mature TREM2 protein is expressed on a cell. In some embodiments, TREM2 contains a signal peptide located at amino acid residues 1-18 of human TREM2 (SEQ ID NO: 1); an extracellular immunoglobulin-like variable-type (IgV) domain located at amino acid residues 29-112 of human TREM2 (SEQ ID NO: 1); additional extracellular sequences located at amino acid residues 113-174 of human TREM2 (SEQ ID NO: 1); a transmembrane domain located at amino acid residues 175-195 of human TREM2 (SEQ ID NO: 1); and an intracellular domain located at amino acid residues 196-230 of human TREM2 (SEQ ID NO: 1).

The transmembrane domain of human TREM2 contains a lysine at amino acid residue 186 that can interact with an aspartic acid in DAP12, which is a key adaptor protein that transduces signaling from TREM2, TREM1, and other related IgV family members.

Homologues of human TREM2 include, without limitation, the natural killer (NK) cell receptor NK-p44 (NCTR2), the polymeric immunoglobulin receptor (pIgR), CD300E, CD300A, CD300C, and TREML1/TLT1. In some embodiments, NCTR2 has similarity with TREM2 within the IgV domain.

Anti-TREM2 Antibodies

Certain aspects of the present disclosure relate to antibodies (e.g., monoclonal antibodies) that specifically bind to TREM2 with improved affinity. In some embodiments, antibodies of the present disclosure bind a mature TREM2 protein. In some embodiments, antibodies of the present disclosure bind a mature TREM2 protein, wherein the mature TREM2 protein is expressed on a cell. In some embodiments, antibodies of the present disclosure bind a TREM2 protein expressed on one or more human cells selected from human dendritic cells, human macrophages, human monocytes, human osteoclasts, human Langerhans cells of skin, human Kupffer cells, human microglia, and any combinations thereof.

In some embodiments, anti-TREM2 antibodies of the present disclosure bind to a TREM2 protein without competing with, inhibiting, or otherwise blocking one or more TREM2 ligands from binding to the TREM2 protein. Examples of suitable TREM2 ligands include, without limitation, TREM2 ligands expressed by E. coli cells, apoptotic cells, nucleic acids, anionic lipids, APOE, APOE2, APOE3, APOE4, anionic APOE, anionic APOE2, anionic APOE3, anionic APOE4, lipidated APOE, lipidated APOE2, lipidated APOE3, lipidated APOE4, zwitterionic lipids, negatively charged phospholipids, phosphatidylserine, sulfatides, phosphatidylcholin, sphingomyelin, membrane phospholipids, lipidated proteins, proteolipids, lipidated peptides, and lipidated amyloid beta peptide. Accordingly, in certain embodiments, the one or more TREM2 ligands comprise E. coli cells, apoptotic cells, nucleic acids, anionic lipids, zwitterionic lipids, negatively charged phospholipids, phosphatidylserine (PS), sulfatides, phosphatidylcholin, sphingomyelin (SM), phospholipids, lipidated proteins, proteolipids, lipidated peptides, and lipidated amyloid beta peptide.

In some embodiments, anti-TREM2 antibodies of the present disclosure do not inhibit the growth of one or more innate immune cells. In some embodiments, anti-TREM2 antibodies of the present disclosure bind to one or more primary immune cells with an affinity that is from five times higher to 100 times higher than an anti-TREM2 antibody selected from an anti-TREM2 antibody comprising a heavy chain variable region comprising the amino acid sequence of SEQ ID NO: 27 and comprising light chain variable region comprising the amino acid sequence of SEQ ID NO: 56; an anti-TREM2 antibody comprising a heavy chain variable region comprising the amino acid sequence of SEQ ID NO: 91 and a light chain variable region comprising the amino acid sequence of SEQ ID NO: 103; and an anti-TREM2 antibody comprising a heavy chain variable region comprising the amino acid sequence of SEQ ID NO: 119 and a light chain variable region comprising the amino acid sequence of SEQ ID NO: 120. In some embodiments, anti-TREM2 antibodies of the present disclosure bind to one or more primary immune cells with an affinity that is at least five times higher, at least six times higher, at least seven times higher, at least eight times higher, at least nine times higher, at least 10 times higher, at least 11 times higher, at least 12 times higher, at least 13 times higher, at least 14 times higher, at least 15 times higher, at least 16 times higher, at least 17 times higher, at least 18 times higher, at least 19 times higher, at least 20 times higher, at least 21 times higher, at least 22 times higher, at least 23 times higher, at least 24 times higher, at least 25 times higher, at least 26 times higher, at least 27 times higher, at least 28 times higher, at least 29 times higher, at least 30 times higher, at least 35 times higher, at least 40 times higher, at least 45 times higher, at least 50 times higher than an anti-TREM2 antibody selected from an anti-TREM2 antibody comprising a heavy chain variable region comprising the amino acid sequence of SEQ ID NO: 27 and comprising light chain variable region comprising the amino acid sequence of SEQ ID NO: 56; an anti-TREM2 antibody comprising a heavy chain variable region comprising the amino acid sequence of SEQ ID NO: 91 and a light chain variable region comprising the amino acid sequence of SEQ ID NO: 103; and an anti-TREM2 antibody comprising a heavy chain variable region comprising the amino acid sequence of SEQ ID NO: 119 and a light chain variable region comprising the amino acid sequence of SEQ ID NO: 120. In some embodiments, anti-TREM2 antibodies of the present disclosure bind to one or more primary immune cells with a mean fluorescence intensity (MFI) that ranges from 100 to 1500, or greater than 1500. In some embodiments, anti-TREM2 antibodies of the present disclosure bind to one or more primary immune cells with a mean fluorescence intensity (MFI) that is at least 100, at least 110, at least 120, at least 130, at least 140, at least 141, at least 150, at least 152, at least 155, at least 159, at least 160, at least 170, at least 180, at least 187, at least 190, at least 194, at least 195, at least 200, at least 210, at least 220, at least 224, at least 230, at least 235, at least 240, at least 250, at least 260, at least 262, at least 270, at least 280, at least 288, at least 290, at least 296, at least 300, at least 310, at least 318, at least 320, at least 322, at least 327, at least 330, at least 340, at least 350, at least 360, at least 370, at least 372, at least 380, at least 390, at least 400, at least 408, at least 410, at least 413, at least 420, at least 430, at least 440, at least 450, at least 460, at least 470, at least 480, at least 490, at least 499, at least 500, at least 510, at least 520, at least 530, at least 534, at least 540, at least 547, at least 550, at least 560, at least 570, at least 580, at least 590, at least 600, at least 610, at least 620, at least 630, at least 640, at least 650, at least 660, at least 662, at least 670, at least 680, at least 690, at least 700, at least 710, at least 720, at least 730, at least 740, at least 750, at least 760, at least 770, at least 780, at least 790, at least 800, at least 810, at least 820, at least 830, at least 840, at least 850, at least 860, at least 870, at least 880, at least 890, at least 900, at least 910, at least 920, at least 930, at least 940, at least 950, at least 960, at least 970, at least 980, at least 990, at least 1000, at least 1035, at least 1110, at least 1120, at least 1130, at least 1140, at least 1150, at least 1160, at least 1170, at least 1180, at least 1190, at least 1200, at least 1210, at least 1220, at least 1230, at least 1240, at least 1250, at least 1260, at least 1270, at least 1280, at least 1290, at least 1300, at least 1310, at least 1320, at least 1330, at least 1340, at least 1350, at least 1360, at least 1370, at least 1380, at least 1390, at least 1400, at least 1410, at least 1420, at least 1430, at least 1440, at least 1450, at least 1460, at least 1467, at least 1470, at least 1480, at least 1490, or at least 1500. In some embodiments, the MFI is determined at a temperature of approximately 25° C. In some embodiments, the $K_D$ is determined using a monovalent antibody (e.g., a Fab) or a full-length antibody in a monovalent form. Methods for the preparation and selection of antibodies that interact and/or bind with specificity to TREM2 are described herein. (e.g., see Examples 1 and 2).

In some embodiments, anti-TREM2 antibodies of the present disclosure cluster and activate TREM2 signaling in an amount that is at least 0.5-fold greater, at least 0.6-fold greater, at least 0.7-fold greater, at least 0.8-fold greater, at least 0.9-fold greater, at least 1-fold greater, at least 2-fold greater, at least 3-fold greater, at least 4-fold greater, at least 5-fold greater, at least 6-fold greater, at least 7-fold greater, at least 8-fold greater, at least 9-fold greater, or at least 10-fold greater than that of an anti-TREM2 antibody selected from an anti-TREM2 antibody comprising a heavy chain variable region comprising the amino acid sequence of SEQ ID NO: 27 and comprising light chain variable region comprising the amino acid sequence of SEQ ID NO: 56; an anti-TREM2 antibody comprising a heavy chain variable region comprising the amino acid sequence of SEQ ID NO: 91 and a light chain variable region comprising the amino acid sequence of SEQ ID NO: 103; and an anti-TREM2 antibody comprising a heavy chain variable region comprising the amino acid sequence of SEQ ID NO: 119 and a light chain variable region comprising the amino acid sequence of SEQ ID NO: 120.

In some embodiments, anti-TREM2 antibodies of the present disclosure cluster and activate TREM2 signaling in an amount that ranges from about 1-fold over control (FOC) to about 30-fold over control (FOC). In some embodiments, anti-TREM2 antibodies of the present disclosure cluster and activate TREM2 signaling in an amount that is at least 1-fold over control (FOC), at least 1.1-fold over control (FOC), at least 1.2-fold over control (FOC), at least 1.3-fold over control (FOC), at least 1.4-fold over control (FOC), at least 1.5-fold over control (FOC), at least 1.6-fold over control (FOC), at least 1.7-fold over control (FOC), at least 1.8-fold over control (FOC), at least 1.9-fold over control (FOC), at least 2-fold over control (FOC), at least 2.1-fold over control (FOC), at least 2.2-fold over control (FOC), at least 2.3-fold over control (FOC), at least 2.4-fold over control (FOC), at least 2.5-fold over control (FOC), at least 2.6-fold over control (FOC), at least 2.7-fold over control (FOC), at least 2.8-fold over control (FOC), at least 2.9-fold over control (FOC), 3-fold over control (FOC), at least 3.1-fold over control (FOC), at least 3.2-fold over control (FOC), at least 3.3-fold over control (FOC), at least 3.4-fold over control (FOC), at least 3.5-fold over control (FOC), at least 3.6-fold over control (FOC), at least 3.7-fold over control (FOC), at least 3.8-fold over control (FOC), at least 3.9-fold over control (FOC), 4-fold over control (FOC), at least 4.1-fold over control (FOC), at least 4.2-fold over control (FOC), at least 4.3-fold over control (FOC), at least 4.4-fold over control (FOC), at least 4.5-fold over control (FOC), at least 4.6-fold over control (FOC), at least 4.7-fold over control (FOC), at least 4.8-fold over control (FOC), at least 4.9-fold over control (FOC), 5-fold over control (FOC), at least 5.1-fold over control (FOC), at least 5.2-fold over control (FOC), at least 5.3-fold over control (FOC), at least 5.4-fold over control (FOC), at least 5.5-fold over control (FOC), at least 5.6-fold over control (FOC), at least 5.7-fold over control (FOC), at least 5.8-fold over control (FOC), at least 5.9-fold over control (FOC), 6-fold over control (FOC), at least 6.1-fold over control (FOC), at least 6.2-fold over control (FOC), at least 6.3-fold over control (FOC), at least 6.4-fold over control (FOC), at least 6.5-fold over control (FOC), at least 6.6-fold over control (FOC), at least 6.7-fold over control (FOC), at least 6.8-fold over control (FOC), at least 6.9-fold over control (FOC), 7-fold over control (FOC), at least 7.1-fold over control (FOC), at least 7.2-fold over control (FOC), at least 7.3-fold over control (FOC), at least 7.4-fold over control (FOC), at least 7.5-fold over control (FOC), at least 7.6-fold over control (FOC), at least 7.7-fold over control (FOC), at least 7.8-fold over control (FOC), at least 7.9-fold over control (FOC), 8-fold over control (FOC), at least 8.1-fold over control (FOC), at least 8.2-fold over control (FOC), at least 8.3-fold over control (FOC), at least 8.4-fold over control (FOC), at least 8.5-fold over control (FOC), at least 8.6-fold over control (FOC), at least 8.7-fold over control (FOC), at least 8.8-fold over control (FOC), at least 8.9-fold over control (FOC), 9-fold over control (FOC), at least 9.1-fold over control (FOC), at least 9.2-fold over control (FOC), at least 9.3-fold over control (FOC), at least 9.4-fold over control (FOC), at least 9.5-fold over control (FOC), at least 9.6-fold over control (FOC), at least 9.7-fold over control (FOC), at least 9.8-fold over control (FOC), at least 9.9-fold over control (FOC), at least 10-fold over control (FOC), at least 11-fold over control (FOC), at least 12-fold over control (FOC), at least 13-fold over control (FOC), at least 14-fold over control (FOC), at least 15-fold over control (FOC), at least 16-fold over control (FOC), at least 17-fold over control (FOC), at least 18-fold over control (FOC), at least 19-fold over control (FOC), at least 20-fold over control (FOC), at least 21-fold over control (FOC), at least 22-fold over control (FOC), at least 23-fold over control (FOC), at least 24-fold over control (FOC), at least 25-fold over control (FOC), at least 26-fold over control (FOC), at least 27-fold over control (FOC), at least 28-fold over control (FOC), at least 29-fold over control (FOC), or at least 30-fold over control (FOC). In some embodiments, clustering and activation of TREM2 signaling is determined at 37° C. using a monovalent antibody (e.g., a Fab) or a full-length antibody in a monovalent form. Methods for the measuring clustering and activation of TREM2 signaling are described herein (e.g., see Example 3).

In some embodiments, anti-TREM2 antibodies of the present disclosure increase immune cell survival in vitro that to an extent that is that is at least one and a half times higher, at least two times higher, at least three times higher, at least four times higher, at least five times higher, at least six times higher, at least seven times higher, at least eight times higher, at least nine times higher, at least 10 times higher, at least 11 times higher, at least 12 times higher, at least 13 times higher, at least 14 times higher, at least 15 times higher, at least 16 times higher, at least 17 times higher, at least 18 times higher, at least 19 times higher, at least 20 times higher, at least 21 times higher, at least 22 times higher, at least 23 times higher, at least 24 times higher, at least 25 times higher, at least 26 times higher, at least 27 times higher, at least 28 times higher, at least 29 times higher, at least 30 times higher, at least 35 times higher, at least 40 times higher, at least 45 times higher, at least 50 times higher, at least 55 times higher, at least 60 times higher, at least 65 times higher, at least 70 times higher, at least 75 times higher, at least 80 times higher, at least 85 times higher, at least 90 times higher, at least 95 times higher, or at least 100 times higher than an anti-TREM2 antibody selected from an anti-TREM2 antibody comprising a heavy chain variable region comprising the amino acid sequence of SEQ ID NO: 27 and comprising light chain variable region comprising the amino acid sequence of SEQ ID NO: 56; an anti-TREM2 antibody comprising a heavy chain variable region comprising the amino acid sequence of SEQ ID NO: 91 and a light chain variable region comprising the amino acid sequence of SEQ ID NO: 103; and an anti-TREM2 antibody comprising a heavy chain variable region comprising the amino acid sequence of SEQ ID NO: 119 and a light chain variable region comprising the amino acid sequence of SEQ ID NO: 120.

In some embodiments, the ability of anti-TREM2 antibodies of the present disclosure to increase immune cell survival in vitro is measured by determining the area under the curve (AUC) of growth curves of primary immune cells in culture that were treated with anti-TREM2 antibodies of the present disclosure. In some embodiments, anti-TREM2 antibodies of the present disclosure increase immune cell survival in vitro with an AUC that ranges from about 200000 to about 1500000. In some embodiments, anti-TREM2 antibodies of the present disclosure increase immune cell survival in vitro with an AUC that is at least 200000, at least 210000, at least 220000, at least 230000, at least 240000, at least 250000, at least 260000, at least 270000, at least 280000, at least 290000, at least 300000, at least 310000, at least 320000, at least 330000, at least 340000, at least 350000, at least 360000, at least 370000, at least 380000, at least 390000, at least 400000, at least 410000, at least 420000, at least 430000, at least 440000, at least 450000, at least 460000, at least 470000, at least 480000, at least 490000, at least 500000, at least 510000, at least 520000, at least 530000, at least 540000, at least 550000, at least 560000, at least 570000, at least 580000, at least 590000, at least 600000, at least 610000, at least 620000, at least 630000, at least 640000, at least 650000, at least 660000, at least 670000, at least 680000, at least 690000, at least 700000, at least 710000, at least 720000, at least 730000, at least 740000, at least 750000, at least 760000, at least 770000, at least 780000, at least 790000, at least 800000, at least 810000, at least 820000, at least 830000, at least 840000, at least 850000, at least 860000, at least 870000, at least 880000, at least 890000, at least 900000, at least 910000, at least 920000, at least 930000, at least 940000, at least 950000, at least 960000, at least 970000, at least 980000, at least 990000, at least 1000000, at least 1010000, at least 1020000, at least 1030000, at least 1040000, at least 1050000, at least 1060000, at least 1070000, at least 1080000, at least 1090000, at least 1100000, at least 1110000, at least 1120000, at least 1130000, at least 1140000, at least 1150000, at least 1160000, at least 1170000, at least 1180000, at least 1190000, at least 1200000, at least 1210000, at least 1220000, at least 1230000, at least 1240000, at least 1250000, at least 1260000, at least 1270000, at least 1280000, at least 1290000, at least 1300000, at least 1310000, at least 1320000, at least 1330000, at least 1340000, at least 1350000, at least 1360000, at least 1370000, at least 1380000, at least 1390000, at least 1400000, at least 1410000, at least 1420000, at least 1430000, at least 1440000, at least 1450000, at least 1460000, at least 1470000, at least 1480000, at least 1490000, or at least 1500000. In some embodiments, immune cell survival in vitro is measured at 4° C. using a monovalent antibody (e.g., a Fab) or a full-length antibody in a monovalent form. Methods for measuring immune cell survival in vitro are described herein (e.g., see Example 3).

In some embodiments, anti-TREM2 antibodies of the present disclosure have an in vivo half-life that is lower than a human control IgG1 antibody. In some embodiments, anti-TREM2 antibodies of the present disclosure have an in vivo half-life that is at least one and a half times lower, at least two times lower, at least three times lower, at least four times lower, at least five times lower, at least six times lower, at least seven times lower, at least eight times lower, at least nine times lower, at least 10 times lower, at least 11 times lower, at least 12 times lower, at least 13 times lower, at least 14 times lower, at least 15 times lower, at least 16 times lower, at least 17 times lower, at least 18 times lower, at least 19 times lower, at least 20 times lower, at least 21 times lower, at least 22 times lower, at least 23 times lower, at least 24 times lower, at least 25 times lower, at least 26 times lower, at least 27 times lower, at least 28 times lower, at least 29 times lower, at least 30 times lower, at least 35 times lower, at least 40 times lower, at least 45 times lower, at least 50 times lower, at least 55 times lower, at least 60 times lower, at least 65 times lower, at least 70 times lower, at least 75 times lower, at least 80 times lower, at least 85 times lower, at least 90 times lower, at least 95 times lower, or at least 100 times lower than an anti-TREM2 antibody selected from an anti-TREM2 antibody comprising a heavy chain variable region comprising the amino acid sequence of SEQ ID NO: 27 and comprising light chain variable region comprising the amino acid sequence of SEQ ID NO: 56; an anti-TREM2 antibody comprising a heavy chain variable region comprising the amino acid sequence of SEQ ID NO: 91 and a light chain variable region comprising the amino acid sequence of SEQ ID NO: 103; and an anti-TREM2 antibody comprising a heavy chain variable region comprising the amino acid sequence of SEQ ID NO: 119 and a light chain variable region comprising the amino acid sequence of SEQ ID NO: 120.

In some embodiments, anti-TREM2 antibodies of the present disclosure have an in vivo half-life that ranges from about 0.1 days to about 10 days. In some embodiments, anti-TREM2 antibodies of the present disclosure have an in vivo half-life that is about 0.1 days, about 0.2 days, about 0.3 days, about 0.4 days, about 0.5 days, about 0.6 days, about 0.7 days, about 0.8 days, about 0.9 days, about 1 day, about 1.1 days, about 1.2 days, about 1.3 days, about 1.4 days, about 1.5 days, about 1.6 days, about 1.7 days, about 1.8 days, about 1.9 days, about 2 days, about 2.1 days, about 2.2 days, about 2.3 days, about 2.4 days, about 2.5 days, about 2.6 days, about 2.7 days, about 2.8 days, about 2.9 days, about 3 days, about 3.1 days, about 3.2 days, about 3.3 days, about 3.4 days, about 3.5 days, about 3.6 days, about 3.7 days, about 3.8 days, about 3.9 days, about 4 days, about 4.1 days, about 4.2 days, about 4.3 days, about 4.4 days, about 4.5 days, about 4.6 days, about 4.7 days, about 4.8 days, about 4.9 days, about 5 days, about 5.1 days, about 5.2 days, about 5.3 days, about 5.4 days, about 5.5 days, about 5.6 days, about 5.7 days, about 5.8 days, about 5.9 days, about 6 days, about 6.1 days, about 6.2 days, about 6.3 days, about 6.4 days, about 6.5 days, about 6.6 days, about 6.7 days, about 6.8 days, about 6.9 days, about 7 days, about 7.1 days, about 7.2 days, about 7.3 days, about 7.4 days, about 7.5 days, about 7.6 days, about 7.7 days, about 7.8 days, about 7.9 days, about 8 days, about 8.1 days, about 8.2 days, about 8.3 days, about 8.4 days, about 8.5 days, about 8.6 days, about 8.7 days, about 8.8 days, about 8.9 days, about 9 days, about 9.1 days, about 9.2 days, about 9.3 days, about 9.4 days, about 9.5 days, about 9.6 days, about 9.7 days, about 9.8 days, about 9.9 days, or about 10 days. In some embodiments, in vivo half-life is measured using a monovalent antibody (e.g., a Fab) or a full-length antibody in a monovalent form. Methods for measuring in vivo half-life are described herein (e.g., see Example 4).

Anti-TREM2 antibodies of the present disclosure generally bind with high affinity to one or more TREM2 proteins expressed on a cell. For example, the TREM2 receptor is thought to require clustering on the cell surface in order to transduce a signal. Thus agonist antibodies may have unique features to stimulate, for example, the TREM2 receptor. For example, they may have the correct epitope specificity that is compatible with receptor activation, as well as the ability to induce or retain receptor clustering on the cell surface. In addition, anti-TREM2 antibodies of the present disclosure may display the ability to bind TREM2 without blocking simultaneous binding of one or more TREM2 ligands. The anti-TREM2 antibodies of the present disclosure may further display additive and/or synergistic functional interactions with one or more TREM2 ligands. Thus, in some embodiments, the maximal activity of TREM2 when bound to anti-TREM2 antibodies of the present disclosure in combination with one or more TREM2 ligands of the present disclosure may be greater (e.g., enhanced) than the maximal activity of TREM2 when exposed to saturating concentrations of ligand alone or to saturating concentrations of the antibody alone. In addition, the activity of TREM2 at a given concentration of TREM2 ligand may be greater (e.g., enhanced) in the presence of the antibody. Accordingly, in some embodiments, anti-TREM2 antibodies of the present disclosure have an additive effect with the one or more TREM2 ligands to enhance the one or more TREM2 activities when bound to the TREM2 protein. In some embodiments, anti-TREM2 antibodies of the present disclosure synergize with the one or more TREM2 ligands to enhance the one or more TREM2 activities. In some embodiments, anti-TREM2 antibodies of the present disclosure increase the potency of the one or more TREM2 ligands to induce the one or more TREM2 activities, as compared to the potency of the one or more TREM2 ligands to induce the one or more TREM2 activities in the absence of the antibody. In some embodiments, anti-TREM2 antibodies of the present disclosure enhance the one or more TREM2 activities in the absence of cell surface clustering of TREM2. In some embodiments, anti-TREM2 antibodies of the present disclosure enhance the one or more TREM2 activities by inducing or retaining cell surface clustering of TREM2. In some embodiments, anti-TREM2 antibodies of the present disclosure are clustered by one or more Fc-gamma receptors expressed on one or more immune cells, including without limitation, B cells and microglial cells. In some embodiments, enhancement of the one or more TREM2 activities induced by binding of one or more TREM2 ligands to the TREM2 protein is measured on primary cells, including without limitation, dendritic cells, bone marrow-derived dendritic cells, monocytes, microglia, macrophages, neutrophils, NK cells, osteoclasts, Langerhans cells of skin, and Kupffer cells, or on cell lines, and the enhancement of the one or more TREM2 activities induced by binding of one or more TREM2 ligands to the TREM2 protein is measured, for example, utilizing an in vitro cell assay.

In vivo, anti-TREM2 antibodies of the present disclosure may activate receptors by multiple potential mechanisms. In some embodiments, anti-TREM2 antibodies of the present disclosure, have, due to the correct epitope specificity, the ability to activate TREM2 in solution without having to be clustered with a secondary antibody, bound on plates, or clustered through Fcg receptors. In some embodiments, anti-TREM2 antibodies of the present disclosure have isotypes of human antibodies, such as IgG2, that have, due to their unique structure, an intrinsic ability to cluster receptors or retain receptors in a clustered configuration, thereby activating receptors such as TREM2 without binding to an Fc receptor (e.g., White et al., (2015) Cancer Cell 27, 138-148).

In some embodiments, anti-TREM2 antibodies of the present disclosure cluster receptors (e.g., TREM2) by binding to Fcg receptors on adjacent cells. Binding of the constant IgG Fc part of the antibody to Fcg receptors leads to aggregation of the antibodies, and the antibodies in turn aggregate the receptors to which they bind through their variable region (Chu et al (2008) Mol Immunol, 45:3926-3933; and Wilson et al., (2011) Cancer Cell 19, 101-113). Binding to the inhibitory Fcg receptor FcgR (FcgRIIB) that does not elicit cytokine secretion, oxidative burst, increased phagocytosis, and enhanced antibody-dependent, cell-mediated cytotoxicity (ADCC) is often a preferred way to cluster antibodies in vivo, since binding to FcgRIIB is not associated with immune adverse effects. Any suitable assay described herein may be used to determine antibody clustering.

Other mechanisms may also be used to cluster receptors (e.g., TREM2). For example, in some embodiments, antibody fragments (e.g., Fab fragments) that are cross-linked together may be used to cluster receptors (e.g., TREM2) in a manner similar to antibodies with Fc regions that bind Fcg receptors, as described above. In some embodiments, cross-linked antibody fragments (e.g., Fab fragments) may function as agonist antibodies if they induce receptor clustering on the cell surface and bind an appropriate epitope on the target (e.g., TREM2).

In some embodiments, antibodies of the present disclosure that bind a TREM2 protein may include antibodies that due to their epitope specificity bind TREM2 and activate one or more TREM2 activities. In some embodiments, such antibodies may bind to the ligand-binding site on TREM2 and mimic the action of one or more TREM2 ligands, or stimulate the target antigen to transduce signal by binding to one or more domains that are not the ligand-binding sites. In some embodiments, the antibodies do not compete with or otherwise block ligand binding to TREM2. In some embodiments, the antibodies, act additively or synergistically with one or more TREM2 ligands to activate and/or enhance one more TREM2 activities.

In some embodiments, TREM2 activities that may be induced and/or enhanced by anti-TREM2 antibodies of the present disclosure and/or one or more TREM2 ligands of the present disclosure include, without limitation, TREM2 binding to DAP12; DAP12 phosphorylation; activation of Syk kinase; modulation of one or more pro-inflammatory mediators selected from IFN-β, IL-1α, IL-1β, TNF-α, IL-6, IL-8, CRP, CD86, MCP-1/CCL2, CCL3, CCL4, CCL5, CCR2, CXCL-10, Gata3, IL-20 family members, IL-33, LIF, IFN-gamma, OSM, CNTF, CSF-1, OPN, CD11c, GM-CSF, IL-11, IL-12, IL-17, IL-18, and IL-23, where the modulation may occurs in one or more cells selected from macrophages, M1 macrophages, activated M1 macrophages, M2 macrophages, dendritic cells, monocytes, osteoclasts, Langerhans cells of skin, Kupffer cells, and microglial cells; recruitment of Syk to a DAP12/TREM2 complex; increasing activity of one or more TREM2-dependent genes, where the one or more TREM2-dependent genes comprise nuclear factor of activated T-cells (NFAT) transcription factors; increased survival of dendritic cells, macrophages, M1 macrophages, activated M1 macrophages, M2 macrophages, monocytes, osteoclasts, Langerhans cells of skin, Kupffer cells, microglia, M1 microglia, activated M1 microglia, and M2 microglia, or any combination thereof; modulated expression of one or more stimulatory molecules selected from CD83, CD86 MHC class II, CD40, and any combination thereof, where the CD40 may be expressed on dendritic cells, monocytes, macrophages, or any combination thereof, and where the dendritic cells may comprise bone marrow-derived dendritic cells; increasing memory; and reducing cognitive deficit.

As used herein, an anti-TREM2 antibody of the present disclosure enhances one or more TREM2 activities induced by binding of one or more TREM2 ligands to the TREM2 protein if it induces at least a 2-fold, at least a 3-fold, at least a 4-fold, at least a 5-fold, at least a 6-fold, at least a 7-fold, at least a 8-fold, at least a 9-fold, at least a 10-fold, at least an 11-fold, at least a 12-fold, at least a 13-fold, at least a 14-fold, at least a 15-fold, at least a 16-fold, at least a 17-fold, at least an 18-fold, at least a 19-fold, at least a 20-fold or greater increase in the one or more TREM2 activities as compared to levels of the one or more TREM2 activities induced by binding of one or more TREM2 ligands to the TREM2 protein in the absence of the anti-TREM2 antibody. In some embodiments, the increase in one more TEM2 activities may be measured by any suitable in vitro cell-based assays or suitable in vivo model described herein or known in the art, for example, by utilizing a luciferase-based reporter assay to measure TREM2-dependent gene expression, using Western blot analysis to measure increase in TREM2-induced phosphorylation of downstream signaling partners, such as Syk, or by utilizing flow cytometry, such as fluorescence-activated cell sorting (FACS) to measure changes in cell surface levels of markers of TREM2 activation. Any in vitro cell-based assays or suitable in vivo model described herein or known in the art may be used to measure interaction (e.g., binding) between TREM2 and one or more TREM2 ligands.

In some embodiments an anti-TREM2 antibody of the present disclosure enhances one or more TREM2 activities induced by binding of a TREM2 ligand to the TREM2 protein if it induces an increase that ranges from about 1-fold to about 6-fold, or more than 6-fold in ligand-induced TREM2-dependent gene transcription when used at a concentration that ranges from about 0.5 nM to about 50 nM, or greater than 50 nM, and as compared to the level of TREM2-dependent gene transcription induced by binding of the TREM2 ligand to the TREM2 protein in the absence of the anti-TREM2 antibody when the TREM2 ligand is used at its $EC_{50}$ concentration. In some embodiments the increase in ligand-induced TREM2-dependent gene transcription is at least 1-fold, at least 2-fold, at least a 3-fold, at least a 4-fold, at least a 5-fold, at least a 6-fold, at least a 7-fold, at least a 8-fold, at least a 9-fold, at least a 10-fold, at least an 11-fold, at least a 12-fold, at least a 13-fold, at least a 14-fold, at least a 15-fold, at least a 16-fold, at least a 17-fold, at least an 18-fold, at least a 19-fold, at least a 20-fold or greater when used at a concentration that ranges from about 0.5 nM to about 50 nM, or greater than 50 nM, and as compared to the level of TREM2-dependent gene transcription induced by binding of the TREM2 ligand to the TREM2 protein in the absence of the anti-TREM2 antibody when the TREM2 ligand is used at its $EC_{50}$ concentration. In some embodiments, the anti-TREM2 antibody is used at a concentration of at least 0.5 nM, at least 0.6 nM, at least 0.7 nM, at least 0.8 nM, at least 0.9 nM, at least 1 nM, at least 2 nM, at least 3 nM, at least 4 nM, at least 5 nM, at least 6 nM, at least 7 nM, at least 8 nM, at least 9 nM, at least 10 nM, at least 15 nM, at least 20 nM, at least 25 nM, at least 30 nM, at least 35 nM, at least 40 nM, at least 45 nM, at least 46 nM, at least 47 nM, at least 48 nM, at least 49 nM, or at least 50 nM. In some embodiments, the TREM2 ligand is phosphatidylserine (PS). In some embodiments, the TREM2 ligand is sphingomyelin (SM). In some embodiments, the increase in one more TEM2 activities may be measured by any suitable in vitro cell-based assays or suitable in vivo model described herein or known in the art. In some embodiments, a luciferase-based reporter assay is used to measure the fold increase of ligand-induced TREM2-dependent gene expression in the presence and absence of antibody.

As used herein, an anti-TREM2 antibody of the present disclosure does not compete with, inhibit, or otherwise block the interaction (e.g., binding) between one or more TREM2 ligands and TREM2 if it decreases ligand binding to TREM2 by less than 20% at saturating antibody concentrations utilizing any in vitro assay or cell-based culture assay described herein or known in the art. In some embodiments, anti-TREM2 antibodies of the present disclosure inhibit interaction (e.g., binding) between one or more TREM2 ligands and TREM2 by less than 20%, less than 19%, less than 18%, less than 17%, less than 16%, less than 15%, less than 14%, less than 13%, less than 12%, less than 11%, less than 10%, less than 9%, less than 8%, less than 7%, less than 6%, less than 5%, less than 4%, less than 3%, less than 2%, or less than 1% at saturating antibody concentrations utilizing any in vitro assay or cell-based culture assay described herein or known in the art.

In some embodiments, an anti-TREM2 antibody of the present disclosure induces one or more TREM2 activities. In some embodiments, the antibody induces one or more activities of TREM2 after binding to a TREM2 protein that is expressed on a cell. In some embodiments, the antibody induces one or more activities of TREM2 after binding to a soluble TREM2 protein that is not bound to the cell membrane. In certain embodiments, the TREM2 protein is expressed on a cell surface. In certain embodiments, soluble TREM2 protein (sTREM2) may be found, without limitation, in extracellular milieu, in blood serum, in cerebrospinal fluid (CSF), and in the interstitial space within tissues. In certain embodiments, soluble TREM2 protein (sTREM2) is non-cellular. In some embodiments a soluble TREM2 (sTREM2) protein of the present disclosure corresponds to amino acid residues 19-160 of SEQ ID NO:1. In some embodiments a soluble TREM2 (sTREM2) protein of the present disclosure corresponds to amino acid residues 19-159 of SEQ ID NO:1. In some embodiments a soluble TREM2 (sTREM2) protein of the present disclosure corresponds to amino acid residues 19-158 of SEQ ID NO:1. In some embodiments a soluble TREM2 (sTREM2) protein of the present disclosure corresponds to amino acid residues 19-157 of SEQ ID NO: 1. In some embodiments a soluble TREM2 (sTREM2) protein of the present disclosure corresponds to amino acid residues 19-156 of SEQ ID NO:1. In some embodiments a soluble TREM2 (sTREM2) protein of the present disclosure corresponds to amino acid residues 19-155 of SEQ ID NO: 1. In some embodiments a soluble TREM2 (sTREM2) protein of the present disclosure corresponds to amino acid residues 19-154 of SEQ ID NO:1.

In some embodiments, soluble TREM2 (sTREM2) proteins of the present disclosure may be inactive variants of cellular TREM2 receptors. In some embodiments, sTREM2 may be present in the periphery, such as in the plasma, or brains of subject.

In some embodiments, anti-TREM2 antibodies of the present disclosure decrease plasma levels of soluble TREM2 in vivo. In some embodiments, anti-TREM2 antibodies of the present disclosure decrease plasma levels of soluble TREM2 in vivo by blocking cleavage, by inhibiting one or more metalloproteases, or by inducing internalization.

In some embodiments, anti-TREM2 antibodies of the present disclosure decrease plasma levels of soluble TREM2 in vivo by an amount that ranges from about 5% greater to about 50% greater than that of a human control IgG1 antibody. In some embodiments, anti-TREM2 antibodies of the present disclosure decreases plasma levels of soluble TREM2 in vivo by an amount that is at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, at least 30%, at least 31%, at least 32%, at least 33%, at least 34%, at least 35%, at least 36%, at least 37%, at least 38%, at least 39%, at least 40%, at least 41%, at least 42%, at least 43%, at least 44%, at least 45%, at least 46%, at least 47%, at least 48%, at least 49%, or at least 50% greater than that of a human control IgG1 antibody.

In some embodiments, anti-TREM2 antibodies of the present disclosure decrease plasma levels of soluble TREM2 in vivo such that the plasma level of soluble TREM2 as a percentage of baseline six days of after antibody treatment is at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, at least 30%, at least 31%, at least 32%, at least 33%, at least 34%, at least 35%, at least 36%, at least 37%, at least 38%, at least 39%, at least 40%, at least 41%, at least 42%, at least 43%, at least 44%, at least 45%, at least 46%, at least 47%, at least 48%, at least 49%, at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, or at least 80%. In some embodiments, plasma levels of soluble TREM2 in vivo are measured using a monovalent antibody (e.g., a Fab) or a full-length antibody in a monovalent form. Methods for measuring plasma levels of soluble TREM2 in vivo are described herein (e.g., see Example 4).

Anti-TREM2 antibodies of the present disclosure can be used to prevent, reduce risk of, or treat dementia, frontotemporal dementia, Alzheimer's disease, vascular dementia, mixed dementia, Creutzfeldt-Jakob disease, normal pressure hydrocephalus, amyotrophic lateral sclerosis, Huntington's disease, tauopathy disease, Nasu-Hakola disease, stroke, acute trauma, chronic trauma, cognitive deficit, memory loss, lupus, acute and chronic colitis, rheumatoid arthritis, wound healing, Crohn's disease, inflammatory bowel disease, ulcerative colitis, obesity, malaria, essential tremor, central nervous system lupus, Behcet's disease, Parkinson's disease, dementia with Lewy bodies, multiple system atrophy, Shy-Drager syndrome, progressive supranuclear palsy, cortical basal ganglionic degeneration, acute disseminated encephalomyelitis, granulomartous disorders, sarcoidosis, diseases of aging, seizures, spinal cord injury, traumatic brain injury, age related macular degeneration, glaucoma, retinitis pigmentosa, retinal degeneration, respiratory tract infection, sepsis, eye infection, systemic infection, lupus, arthritis, multiple sclerosis, low bone density, osteoporosis, osteogenesis, osteopetrotic disease, Paget's disease of bone, solid and blood cancer, bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, acute lymphoblastic leukemia (ALL), acute myeloid leukemia (AML), chronic lymphocytic leukemia (CLL), chronic myeloid leukemia (CML), multiple myeloma, polycythemia vera, essential thrombocytosis, primary or idiopathic myelofibrosis, primary or idiopathic myelosclerosis, myeloid-derived tumors, tumors that express TREM2, thyroid cancer, infections, CNS herpes, parasitic infections, Trypanosome infection, Cruzi infection, *Pseudomonas aeruginosa* infection, *Leishmania donovani* infection, group B *Streptococcus* infection, *Campylobacter jejuni* infection, *Neisseria meningiditis* infection, type I HIV, and *Haemo-*

*philus influenza*. The methods provided herein also find use in inducing or promoting the survival, maturation, functionality, migration, or proliferation of one or more immune cells in an individual in need thereof. The methods provided herein find further use in decreasing the activity, functionality, or survival of regulatory T cells, tumor-imbedded immunosuppressor dendritic cells, tumor-imbedded immunosuppressor macrophages, myeloid-derived suppressor cells, tumor-associated macrophages, acute myeloid leukemia (AML) cells, chronic lymphocytic leukemia (CLL) cell, or chronic myeloid leukemia (CML) cell in an individual in need thereof. The methods provided herein find further use in increasing memory and/or reducing cognitive deficit.

The anti-TREM2 antibodies of the present disclosure may also be used in advanced wound care. In some embodiments, the anti-TREM2 antibodies of the present disclosure are monoclonal antibodies. Anti-TREM2 antibodies of the present disclosure may be tested for inducing one or more TREM2 activities. Useful assays may include western blots (e.g., for tyrosine-phosphorylated DAP12 or threonine/serine-phosphorylated PI3K-kinase substrates), ELISA (e.g., for secreted interleukin or cytokine secretion), FACS (e.g., for anti-TREM2 binding to TREM2), immunocytochemistry (e.g., for e.g., for tyrosine-phosphorylated DAP12 or threonine/serine-phosphorylated PI3K-kinase substrates), reporter-gene assays (e.g., for TLR activation), increased survival and/or function of dendritic cells, macrophages, monocytes, osteoclasts, Langerhans cells of skin, Kupffer cells, and/or microglia, increased phagocytosis of apoptotic neurons, damaged synapses, amyloid beta or fragments thereof, Tau, IAPP, alpha-synuclein, TDP-43, FUS protein, prion protein, PrPSc, huntingtin, calcitonin, superoxide dismutase, ataxin, Lewy body, atrial natriuretic factor, islet amyloid polypeptide, insulin, apolipoprotein AI, serum amyloid A, medin, prolactin, transthyretin, lysozyme, beta 2 microglobulin, gelsolin, keratoepithelin, cystatin, immunoglobulin light chain AL, S-IBM protein, Repeat-associated non-ATG (RAN) translation products, DiPeptide repeat (DPR) peptides, glycine-alanine (GA) repeat peptides, glycine-proline (GP) repeat peptides, glycine-arginine (GR) repeat peptides, proline-alanine (PA) repeat peptides, and proline-arginine (PR) repeat peptides, nerve tissue debris, non-nerve tissue debris, bacteria, other foreign bodies, disease-causing proteins, disease-causing peptides, disease-causing nucleic acid, or tumor cells by macrophages, dendritic cells, Langerhans cells of skin, Kupffer cells, monocytes, osteoclasts, and/or microglial cells, increased cytoskeleton reorganization, and decreased microglial pro-inflammatory responses, or other assays known in the art.

An antibody dependent on binding to FcgR receptor to activate targeted receptors may lose its agonist activity if engineered to eliminate FcgR binding (see, e.g., Wilson et al., (2011) Cancer Cell 19, 101-113; Armour at al., (2003) Immunology 40 (2003) 585-593; and White et al., (2015) Cancer Cell 27, 138-148). As such, it is thought that an anti-TREM2 antibody of the present disclosure with the correct epitope specificity can activate the target antigen, with minimal adverse effects, when the antibody has an Fc domain from a human IgG2 isotype (CH1 and hinge region) or another type of Fc domain that is capable of preferentially binding the inhibitory FcgRIIB r receptors, or a variation thereof.

Exemplary antibody Fc isotypes and modifications are provided in Table A below. In some embodiments, the antibody has an Fc isotype listed in Table A below.

TABLE A

Exemplary antibody Fc isotypes that are capable of binding Fc gamma receptor

| Fc Isotype | Mutation (EU numbering scheme) |
|---|---|
| IgG1 | N297A |
| IgG1 | D265A and N297A |
| IgG1 | D270A |
| IgG1 | L234A and L235A<br>L234A and G237A<br>L234A and L235A and G237A |
| IgG1 | P238D and/or L328E and/or S267E/L328F and/or E233 and/or G237D and/or H268D and/or P271G and/or A330R |
| IgG1 | P238D and L328E and E233D and G237D and H268D and P271G and A330R |
| IgG1 | P238D and L328E and G237D and H268D and P271G and A330R |
| IgG1 | P238D and S267E and L328F and E233D and G237D and H268D and P271G and A330R |
| IgG1 | P238D and S267E and L328F and G237D and H268D and P271G and A330R |
| IgG2 | V234A and G237A |
| IgG4 | L235A and G237A and E318A |
| IgG4 | S228P and L236E |
| IgG2/4 hybrid | IgG2 aa 118 to 260 and IgG4 aa 261 to 447 |
|  | H268Q and V309L; and A330S and P331S |
| IgG1 | C226S and C229S and E233P and L234V and L235A |
| IgG1 | L234F and L235E and P331S |
| IgG2 | C232S or C233S |
| IgG2 | A330S and P331S |
| IgG1 | S267E, and L328F<br>S267E alone |
| IgG2 | S267E and L328F |
| IgG4 | S267E and L328F |
| IgG2 | WT HC with Kappa (light chain) LC<br>HC C127S with Kappa LC<br>Kappa LC C214S<br>Kappa LC C214S and HC C233S<br>Kappa LC C214S and HC C232S<br>Any of the above listed mutations together with A330S and P331S mutations<br>F(ab')2 fragment of WT IgG1 and any of the above listed mutations |
| IgG1 | Substitute the Constant Heavy 1 (CH1) and hinge region of IgG1 With CH1 and hinge region of IGg2<br>ASTKGPSVFP LAPCSRSTSE STAALGCLVK DYFPEPVTVS WNSGALTSGV HTFPAVLQSS GLYSLSSVVT VPSSNFGTQT YTCNVDHKPS NTKVDKTVER KCCVECPPCP<br>(SEQ ID NO: 145)<br>With a Kappa LC |

TABLE A-continued

Exemplary antibody Fc isotypes that are capable of binding Fc gamma receptor

| Fc Isotype | Mutation (EU numbering scheme) |
|---|---|
| IgG1 | Any of the above listed mutations together with A330L/A330S and/or L234F and/or L235E and/or P331S |
| IgG1, IgG2, or IgG4 | Any of the above listed mutations together with M252Y and/or S254T and/or T256E |
| Mouse IgG1 | For mouse disease models |
| IgG4 | WT |
| IgG1 | Any of the above listed mutation together with E430G, E430S, E430F, E430T, E345K, E345Q, E345R, E345Y, S440Y, S440W and/or any combination thereof. |
| IgG2 | Any of the above listed mutation together with E430G, E430S, E430F, E430T, E345K, E345Q, E345R, E345Y, S440Y, S440W and/or any combination thereof. |

In addition to the isotypes described in Table A, and without wishing to be bound to theory, it is thought that antibodies with human IgG1 or IgG3 isotypes and mutants thereof (e.g. Strohl (2009) Current Opinion in Biotechnology 2009, 20:685-691) that bind the activating Fcg Receptors I, IIA, IIC, IIIA, IIIB in human and/or Fcg Receptors I, III and IV in mouse, may also act as agonist antibodies in vivo but may be associated with adverse effects related to ADCC. However, such Fcg receptors appear to be less available for antibody binding in vivo, as compared to the Inhibitory Fcg receptor FcgRIIB (see, e.g., White, et al., (2013) Cancer Immunol. Immunother. 62, 941-948; and Li et al., (2011) Science 333(6045):1030-1034.).

In some embodiments, the antibody is of the IgG class, the IgM class, or the IgA class. In some embodiments, the antibody has an IgG1, IgG2, IgG3, or IgG4 isotype.

In certain embodiments, the antibody has an IgG2 isotype. In some embodiments, the antibody contains a human IgG2 constant region. In some embodiments, the human IgG2 constant region includes an Fc region. In some embodiments, the antibody induces the one or more TREM2 activities, the DAP12 activities, or both independently of binding to an Fc receptor. In some embodiments, the antibody binds an inhibitory Fc receptor. In certain embodiments, the inhibitory Fc receptor is inhibitory Fc-gamma receptor IIB (FcγIIB). In some embodiments, the Fc region contains one or more modifications. For example, in some embodiments, the Fc region contains one or more amino acid substitutions (e.g., relative to a wild-type Fc region of the same isotype). In some embodiments, the one or more amino acid substitutions are selected from V234A (Alegre et al., (1994) Transplantation 57:1537-1543. 31; Xu et al., (2000) Cell Immunol, 200:16-26), G237A (Cole et al. (1999) Transplantation, 68:563-571), H268Q, V309L, A330S, P331S (US 2007/0148167; Armour et al. (1999) Eur J Immunol 29: 2613-2624; Armour et al. (2000) The Haematology Journal 1(Suppl. 1):27; Armour et al. (2000) The Haematology Journal 1(Suppl.1):27), C232S, and/or C233S (White et al., (2015) Cancer Cell 27, 138-148), S267E, L328F (Chu et al., (2008) Mol Immunol, 45:3926-3933), M252Y, S254T, and/or T256E, where the amino acid position is according to the EU or, Kabat numbering convention.

In some embodiments, the antibody has an IgG2 isotype with a heavy chain constant domain that contains a C127S amino acid substitution, where the amino acid position is according to the EU or, Kabat numbering convention (White et al., (2015) Cancer Cell 27, 138-148; Lightle et al., (2010) PROTEIN SCIENCE 19:753-762; and WO2008079246).

In some embodiments, the antibody has an IgG2 isotype with a Kappa light chain constant domain that contains a C214S amino acid substitution, where the amino acid position is according to the EU or, Kabat numbering convention (White et al., (2015) Cancer Cell 27, 138-148; Lightle et al., (2010) PROTEIN SCIENCE 19:753-762; and WO2008079246).

In certain embodiments, the antibody has an IgG1 isotype. In some embodiments, the antibody contains a mouse IgG1 constant region. In some embodiments, the antibody contains a human IgG1 constant region. In some embodiments, the human IgG1 constant region includes an Fc region. In some embodiments, the antibody binds an inhibitory Fc receptor. In certain embodiments, the inhibitory Fc receptor is inhibitory Fc-gamma receptor IIB (FcγIIB). In some embodiments, the Fc region contains one or more modifications. For example, in some embodiments, the Fc region contains one or more amino acid substitutions (e.g., relative to a wild-type Fc region of the same isotype). In some embodiments, the one or more amino acid substitutions are selected from N297A (Bolt S et al. (1993) Eur J Immunol 23:403-411), D265A (Shields et al. (2001) R. J. Biol. Chem. 276, 6591-6604), L234A, L235A (Hutchins et al. (1995) Proc Natl Acad Sci USA, 92:11980-11984; Alegre et al., (1994) Transplantation 57:1537-1543. 31; Xu et al., (2000) Cell Immunol, 200:16-26), G237A (Alegre et al. (1994) Transplantation 57:1537-1543. 31; Xu et al. (2000) Cell Immunol, 200:16-26), C226S, C229S, E233P, L234V, L234F, L235E (McEarchern et al., (2007) Blood, 109:1185-1192), P331S (Sazinsky et al., (2008) Proc Natl Acad Sci USA 2008, 105:20167-20172), S267E, L328F, A330L, M252Y, S254T, and/or T256E, where the amino acid position is according to the EU or, Kabat numbering convention.

In some embodiments, the antibody includes an IgG2 isotype heavy chain constant domain 1(CH1) and hinge region (White et al., (2015) Cancer Cell 27, 138-148). In certain embodiments, the IgG2 isotype CH1 and hinge region contain the amino acid sequence of ASTKGPSVF-PLAPCSRSTSESTAALGCLVKDYFPEPVTVSWNS-GALTSGVHTFPAVLQSSGLY SLSSVVTVPSSNFGTQ-TYTCNVDHKPSNTKVDKTVERKCCVECPPCP (SEQ ID NO: 145). In some embodiments, the antibody Fc region contains a S267E amino acid substitution, a L328F amino acid substitution, or both, and/or a N297A or N297Q amino acid substitution, where the amino acid position is according to the EU or, Kabat numbering convention.

In certain embodiments, the antibody has an IgG4 isotype. In some embodiments, the antibody contains a human IgG4 constant region. In some embodiments, the human IgG4 constant region includes an Fc region. In some embodiments, the antibody binds an inhibitory Fc receptor. In certain embodiments, the inhibitory Fc receptor is inhibitory Fc-gamma receptor IIB (FcγIIB). In some embodiments, the Fc region contains one or more modifications. For example, in some embodiments, the Fc region contains one or more amino acid substitutions (e.g., relative to a wild-type Fc region of the same isotype). In some embodiments, the one or more amino acid substitutions are selected from L235A, G237A, S228P, L236E (Reddy et al., (2000) *J Immunol*, 164:1925-1933), S267E, E318A, L328F, M252Y, S254T, and/or T256E, where the amino acid position is according to the EU or, Kabat numbering convention.

In certain embodiments, the antibody has a hybrid IgG2/4 isotype. In some embodiments, the antibody includes an amino acid sequence containing amino acids 118 to 260 according to EU or, Kabat numbering of human IgG2 and amino acids 261-447 according to EU or, Kabat numbering of human IgG4 (WO 1997/11971; WO 2007/106585).

In certain embodiments, the antibody contains a mouse IgG4 constant region (Bartholomaeus, et al. (2014). J. Immunol. 192, 2091-2098).

In some embodiments, the Fc region further contains one or more additional amino acid substitutions selected from A330L, L234F; L235E, or P331S according to EU or, Kabat numbering; and any combination thereof.

In certain embodiments, the antibody contains one or more amino acid substitutions in the Fc region at a residue position selected from C127S, L234A, L234F, L235A, L235E, S267E, K322A, L328F, A330S, P331S, E345R, E430G, S440Y, and any combination thereof, where the numbering of the residues is according to EU or Kabat numbering. In some embodiments, the Fc region contains an amino acid substitution at positions E430G, L243A, L235A, and P331S, where the numbering of the residue position is according to EU numbering. In some embodiments, the Fc region contains an amino acid substitution at positions E430G and P331S, where the numbering of the residue position is according to EU numbering. In some embodiments, the Fc region contains an amino acid substitution at positions E430G and K322A, where the numbering of the residue position is according to EU numbering. In some embodiments, the Fc region contains an amino acid substitution at positions E430G, A330S, and P331S, where the numbering of the residue position is according to EU numbering. In some embodiments, the Fc region contains an amino acid substitution at positions E430G, K322A, A330S, and P331S, where the numbering of the residue position is according to EU numbering. In some embodiments, the Fc region contains an amino acid substitution at positions E430G, K322A, and A330S, where the numbering of the residue position is according to EU numbering. In some embodiments, the Fc region contains an amino acid substitution at positions E430G, K322A, and P331S, where the numbering of the residue position is according to EU numbering. In some embodiments, the Fc region contains an amino acid substitution at positions S267E and L328F, where the numbering of the residue position is according to EU numbering. In some embodiments, the Fc region contains an amino acid substitution at position C127S, where the numbering of the residue position is according to EU numbering. In some embodiments, the Fc region contains an amino acid substitution at positions E345R, E430G and S440Y, where the numbering of the residue position is according to EU numbering.

Further IgG Mutations

In some embodiments, one or more of the IgG1 variants described herein may be combined with an A330L mutation (Lazar et al., (2006) Proc Natl Acad Sci USA, 103:4005-4010), or one or more of L234F, L235E, and/or P331S mutations (Sazinsky et al., (2008) Proc Natl Acad Sci USA, 105:20167-20172), where the amino acid position is according to the EU or, Kabat numbering convention, to eliminate complement activation. In some embodiments, the IgG variants described herein may be combined with one or more mutations to enhance the antibody half-life in human serum (e.g. M252Y, S254T, T256E mutations according to the EU or, Kabat numbering convention) (Dall'Acqua et al., (2006) J Biol Chem, 281:23514-23524; and Strohl e al., (2009) Current Opinion in Biotechnology, 20:685-691).

In some embodiments, an IgG4 variant of the present disclosure may be combined with an S228P mutation according to the EU or, Kabat numbering convention (Angal et al., (1993) Mol Immunol, 30:105-108) and/or with one or more mutations described in Peters et al., (2012) J Biol Chem. 13; 287(29):24525-33) to enhance antibody stabilization.

Exemplary Anti-TREM2 Antibodies

In some embodiments, an isolated anti-TREM2 antibody of the present disclosure binds to TREM2 with high affinity and enhances one or more TREM2 activities induced by binding of one or more TREM2 ligands to the TREM2 protein, as compared to the one or more TREM2 activities induced by binding of the one or more TREM2 ligands to the TREM2 protein in the absence of the isolated antibody. In some embodiments, the anti-TREM2 antibody enhances the one or more TREM2 activities without competing with or otherwise blocking binding of the one or more TREM2 ligands to the TREM2 protein. In some embodiments, the antibody is a humanized antibody, a bispecific antibody, a multivalent antibody, or a chimeric antibody. Exemplary descriptions of such antibodies are found throughout the present disclosure. In some embodiments, the antibody is a bispecific antibody recognizing a first antigen and a second antigen.

In some embodiments, anti-TREM2 antibodies of the present disclosure bind to a human TREM2, or a homolog thereof, including without limitation a mammalian (e.g., non-human mammalian) TREM2 protein, mouse TREM2 protein (Uniprot Accession No. Q99NH8), rat TREM2 protein (Uniprot Accession No. D3ZZ89), Rhesus monkey TREM2 protein (Uniprot Accession No. F6QVF2), cynomolgus monkey TREM2 protein (NCBI Accession No. XP_015304909.1), equine TREM2 protein (Uniprot Accession No. F7D6L0), pig TREM2 protein (Uniprot Accession No. H2EZZ3), and dog TREM2 protein (Uniprot Accession No. E2RP46). In some embodiments, anti-TREM2 antibodies of the present disclosure specifically bind to human TREM2. In some embodiments, anti-TREM2 antibodies of the present disclosure specifically bind to cynomolgus monkey TREM2. In some embodiments, anti-TREM2 antibodies of the present disclosure specifically bind to both human TREM2 and cynomolgus monkey TREM2. In some embodiments, anti-TREM2 antibodies of the present disclosure induce at least one TREM2 activity of the present disclosure.

Anti-TREM2 Antibody-Binding Regions

Certain aspects of the preset disclosure relate to anti-TREM2 antibodies that bind to an epitope of human TREM2 that is the same as or overlaps with the TREM2 epitope bound by an anti-TREM2 antibody comprising a heavy chain variable region comprising the amino acid sequence of SEQ ID NO: 119 and a light chain variable region comprising the amino acid sequence of SEQ ID NO: 120. In some embodiments, anti-TREM2 antibodies of the present disclosure bind essentially the same TREM2 epitope bound by an anti-TREM2 antibody comprising a heavy chain variable region comprising the amino acid sequence of SEQ ID NO: 119 and a light chain variable region comprising the amino acid sequence of SEQ ID NO: 120. In some embodiments, anti-TREM2 antibodies of the present disclosure bind to one or more amino acids within amino acid residues SFE-DAHVEH (amino acid residues 149-157 of SEQ ID NO: 1).

In some embodiments, anti-TREM2 antibodies of the present disclosure bind to one or more amino acid residues selected from E151, D152, and E156 of SEQ ID NO: 1. In some embodiments, anti-TREM2 antibodies of the present disclosure bind amino acid residues E151, D152, and E156 of SEQ ID NO: 1.

In some embodiments, anti-TREM2 antibodies of the present disclosure competitively inhibit binding of an anti-TREM2 antibody comprising a heavy chain variable region comprising the amino acid sequence of SEQ ID NO: 119 and a light chain variable region comprising the amino acid sequence of SEQ ID NO: 120. In some embodiments, anti-TREM2 antibodies of the present disclosure compete with an anti-TREM2 antibody comprising a heavy chain variable region comprising the amino acid sequence of SEQ ID NO: 119 and a light chain variable region comprising the amino acid sequence of SEQ ID NO: 120 for binding to TREM2.

In some embodiments, anti-TREM2 antibodies of the present disclosure competitively inhibit binding of at least one antibody selected from any of the antibodies listed in Tables 2A-2C, 3A-3C, 4A-4D, 5A-5D, 6, and 7. In some embodiments, anti-TREM2 antibodies of the present disclosure competitively inhibit binding of at least one antibody selected from AL2p-h50, AL2p-2, AL2p-3, AL2p-4, AL2p-5, AL2p-6, AL2p-7, AL2p-8, AL2p-9, AL2p-10, AL2p-11, AL2p-12, AL2p-13, AL2p-14, AL2p-15, AL2p-16, AL2p-17, AL2p-18, AL2p-19, AL2p-20, AL2p-21, AL2p-22, AL2p-23, AL2p-24, AL2p-25, AL2p-26, AL2p-27, AL2p-28, AL2p-29, AL2p-30, AL2p-31, AL2p-32, AL2p-33, AL2p-h77, AL2p-35, AL2p-36, AL2p-37, AL2p-38, AL2p-39, AL2p-40, AL2p-41, AL2p-42, AL2p-43, AL2p-44, AL2p-45, AL2p-46, AL2p-47, AL2p-48, AL2p-49, AL2p-50, AL2p-51, AL2p-52, AL2p-53, AL2p-54, AL2p-55, AL2p-56, AL2p-57, AL2p-58, AL2p-59, AL2p-60, AL2p-61, AL2p-62, AL2p-h19, AL2p-h21, AL2p-h22, AL2p-h23, AL2p-h24, AL2p-h25, AL2p-h26, AL2p-h27, AL2p-h28, AL2p-h29, AL2p-h30, AL2p-h31, AL2p-h32, AL2p-h33, AL2p-h34, AL2p-h35, AL2p-h36, AL2p-h42, AL2p-h43, AL2p-h44, AL2p-h47, AL2p-h59, AL2p-h76, and AL2p-h90. In some embodiments, anti-TREM2 antibodies of the present disclosure competitively inhibit binding of antibody AL2p-31. In some embodiments, anti-TREM2 antibodies of the present disclosure competitively inhibit binding of antibody AL2p-37. In some embodiments, anti-TREM2 antibodies of the present disclosure competitively inhibit binding of antibody AL2p-47. In some embodiments, anti-TREM2 antibodies of the present disclosure competitively inhibit binding of antibody AL2p-58. In some embodiments, anti-TREM2 antibodies of the present disclosure competitively inhibit binding of antibody AL2p-60. In some embodiments, anti-TREM2 antibodies of the present disclosure competitively inhibit binding of antibody AL2p-61. In some embodiments, anti-TREM2 antibodies of the present disclosure competitively inhibit binding of antibody AL2p-62.

In some embodiments, anti-TREM2 antibodies of the present disclosure bind to an epitope of human TREM2 that is the same as or overlaps with the TREM2 epitope bound by at least one antibody selected from any of the antibodies listed in Tables 2A-2C, 3A-3C, 4A-4D, 5A-5D, 6, and 7. In some embodiments, anti-TREM2 antibodies of the present disclosure bind to an epitope of human TREM2 that is the same as or overlaps with the TREM2 epitope bound by at least one antibody selected from AL2p-h50, AL2p-2, AL2p-3, AL2p-4, AL2p-5, AL2p-6, AL2p-7, AL2p-8, AL2p-9, AL2p-10, AL2p-11, AL2p-12, AL2p-13, AL2p-14, AL2p-15, AL2p-16, AL2p-17, AL2p-18, AL2p-19, AL2p-20, AL2p-21, AL2p-22, AL2p-23, AL2p-24, AL2p-25, AL2p-26, AL2p-27, AL2p-28, AL2p-29, AL2p-30, AL2p-31, AL2p-32, AL2p-33, AL2p-h77, AL2p-35, AL2p-36, AL2p-37, AL2p-38, AL2p-39, AL2p-40, AL2p-41, AL2p-42, AL2p-43, AL2p-44, AL2p-45, AL2p-46, AL2p-47, AL2p-48, AL2p-49, AL2p-50, AL2p-51, AL2p-52, AL2p-53, AL2p-54, AL2p-55, AL2p-56, AL2p-57, AL2p-58, AL2p-59, AL2p-60, AL2p-61, AL2p-62, AL2p-h19, AL2p-h21, AL2p-h22, AL2p-h23, AL2p-h24, AL2p-h25, AL2p-h26, AL2p-h27, AL2p-h28, AL2p-h29, AL2p-h30, AL2p-h31, AL2p-h32, AL2p-h33, AL2p-h34, AL2p-h35, AL2p-h36, AL2p-h42, AL2p-h43, AL2p-h44, AL2p-h47, AL2p-h59, AL2p-h76, and AL2p-h90. In some embodiments, anti-TREM2 antibodies of the present disclosure bind to an epitope of human TREM2 that is the same as or overlaps with the TREM2 epitope bound by antibody AL2p-31. In some embodiments, anti-TREM2 antibodies of the present disclosure bind to an epitope of human TREM2 that is the same as or overlaps with the TREM2 epitope bound by antibody AL2p-37. In some embodiments, anti-TREM2 antibodies of the present disclosure bind to an epitope of human TREM2 that is the same as or overlaps with the TREM2 epitope bound by antibody AL2p-47. In some embodiments, anti-TREM2 antibodies of the present disclosure bind to an epitope of human TREM2 that is the same as or overlaps with the TREM2 epitope bound by antibody AL2p-58. In some embodiments, anti-TREM2 antibodies of the present disclosure bind to an epitope of human TREM2 that is the same as or overlaps with the TREM2 epitope bound by antibody AL2p-60. In some embodiments, anti-TREM2 antibodies of the present disclosure bind to an epitope of human TREM2 that is the same as or overlaps with the TREM2 epitope bound by antibody AL2p-61. In some embodiments, anti-TREM2 antibodies of the present disclosure bind to an epitope of human TREM2 that is the same as or overlaps with the TREM2 epitope bound by antibody AL2p-62.

In some embodiments, anti-TREM2 antibodies of the present disclosure bind essentially the same TREM2 epitope bound by at least one antibody selected from any of the antibodies listed in Tables 2A-2C, 3A-3C, 4A-4D, 5A-5D, 6, and 7. In some embodiments, anti-TREM2 antibodies of the present disclosure bind essentially the same TREM2 epitope bound by at least one antibody selected from AL2p-h50, AL2p-2, AL2p-3, AL2p-4, AL2p-5, AL2p-6, AL2p-7, AL2p-8, AL2p-9, AL2p-10, AL2p-11, AL2p-12, AL2p-13, AL2p-14, AL2p-15, AL2p-16, AL2p-17, AL2p-18, AL2p-19, AL2p-20, AL2p-21, AL2p-22, AL2p-23, AL2p-24, AL2p-25, AL2p-26, AL2p-27, AL2p-28, AL2p-29, AL2p-30, AL2p-31, AL2p-32, AL2p-33, AL2p-h77, AL2p-35, AL2p-36, AL2p-37, AL2p-38, AL2p-39, AL2p-40, AL2p-41, AL2p-42, AL2p-43, AL2p-44, AL2p-45, AL2p-46, AL2p-47, AL2p-48, AL2p-49, AL2p-50, AL2p-51, AL2p-52, AL2p-53, AL2p-54, AL2p-55, AL2p-56, AL2p-57, AL2p-58, AL2p-59, AL2p-60, AL2p-61, AL2p-62, AL2p-h19, AL2p-h21, AL2p-h22, AL2p-h23, AL2p-h24, AL2p-h25, AL2p-h26, AL2p-h27, AL2p-h28, AL2p-h29, AL2p-h30, AL2p-h31, AL2p-h32, AL2p-h33, AL2p-h34, AL2p-h35, AL2p-h36, AL2p-h42, AL2p-h43, AL2p-h44, AL2p-h47, AL2p-h59, AL2p-h76, and AL2p-h90. Detailed exemplary methods for mapping an epitope to which an antibody binds are provided in Morris (1996) "Epitope Mapping Protocols," in *Methods in Molecular Biology* vol. 66 (Humana Press, Totowa, N.J.). In some embodiments, anti-TREM2 antibodies of the present disclosure bind essentially the same TREM2 epitope bound by antibody AL2p-31.

In some embodiments, anti-TREM2 antibodies of the present disclosure bind essentially the same TREM2 epitope bound by antibody AL2p-37. In some embodiments, anti-TREM2 antibodies of the present disclosure bind essentially the same TREM2 epitope bound by antibody AL2p-47. In some embodiments, anti-TREM2 antibodies of the present disclosure bind essentially the same TREM2 epitope bound by antibody AL2p-58. In some embodiments, anti-TREM2 antibodies of the present disclosure bind essentially the same TREM2 epitope bound by antibody AL2p-60. In some embodiments, anti-TREM2 antibodies of the present disclosure bind essentially the same TREM2 epitope bound by antibody AL2p-61. In some embodiments, anti-TREM2 antibodies of the present disclosure bind essentially the same TREM2 epitope bound by antibody AL2p-62.

In some embodiments, anti-TREM2 antibodies of the present disclosure compete with one or more antibodies selected from AL2p-h50, AL2p-2, AL2p-3, AL2p-4, AL2p-5, AL2p-6, AL2p-7, AL2p-8, AL2p-9, AL2p-10, AL2p-11, AL2p-12, AL2p-13, AL2p-14, AL2p-15, AL2p-16, AL2p-17, AL2p-18, AL2p-19, AL2p-20, AL2p-21, AL2p-22, AL2p-23, AL2p-24, AL2p-25, AL2p-26, AL2p-27, AL2p-28, AL2p-29, AL2p-30, AL2p-31, AL2p-32, AL2p-33, AL2p-h77, AL2p-35, AL2p-36, AL2p-37, AL2p-38, AL2p-39, AL2p-40, AL2p-41, AL2p-42, AL2p-43, AL2p-44, AL2p-45, AL2p-46, AL2p-47, AL2p-48, AL2p-49, AL2p-50, AL2p-51, AL2p-52, AL2p-53, AL2p-54, AL2p-55, AL2p-56, AL2p-57, AL2p-58, AL2p-59, AL2p-60, AL2p-61, AL2p-62, AL2p-h19, AL2p-h21, AL2p-h22, AL2p-h23, AL2p-h24, AL2p-h25, AL2p-h26, AL2p-h27, AL2p-h28, AL2p-h29, AL2p-h30, AL2p-h31, AL2p-h32, AL2p-h33, AL2p-h34, AL2p-h35, AL2p-h36, AL2p-h42, AL2p-h43, AL2p-h44, AL2p-h47, AL2p-h59, AL2p-h76, and AL2p-h90, and any combination thereof for binding to TREM2. In some embodiments, anti-TREM2 antibodies of the present disclosure compete with antibody AL2p-31 for binding to TREM2 for binding to TREM2. In some embodiments, anti-TREM2 antibodies of the present disclosure compete with antibody AL2p-37 for binding to TREM2. In some embodiments, anti-TREM2 antibodies of the present disclosure compete with antibody AL2p-47 for binding to TREM2. In some embodiments, anti-TREM2 antibodies of the present disclosure compete with antibody AL2p-58 for binding to TREM2. In some embodiments, anti-TREM2 antibodies of the present disclosure compete with antibody AL2p-60 for binding to TREM2. In some embodiments, anti-TREM2 antibodies of the present disclosure compete with antibody AL2p-61 for binding to TREM2. In some embodiments, anti-TREM2 antibodies of the present disclosure compete with antibody AL2p-62 for binding to TREM2.

In an exemplary competition assay, immobilized TREM2 or cells expressing TREM2 on the cell surface are incubated in a solution comprising a first labeled antibody that binds to TREM2 (e.g., human or non-human primate) and a second unlabeled antibody that is being tested for its ability to compete with the first antibody for binding to TREM2. The second antibody may be present in a hybridoma supernatant. As a control, immobilized TREM2 or cells expressing TREM2 is incubated in a solution comprising the first labeled antibody but not the second unlabeled antibody. After incubation under conditions permissive for binding of the first antibody to TREM2, excess unbound antibody is removed, and the amount of label associated with immobilized TREM2 or cells expressing TREM2 is measured. If the amount of label associated with immobilized TREM2 or cells expressing TREM2 is substantially reduced in the test sample relative to the control sample, then that indicates that the second antibody is competing with the first antibody for binding to TREM2. See, Harlow and Lane (1988) *Antibodies: A Laboratory Manual* ch. 14 (Cold Spring Harbor Laboratory, Cold Spring Harbor, N.Y.).

Anti-TREM2 Antibody Light Chain and Heavy Chain Variable Regions

In some embodiments, anti-TREM2 antibodies of the present disclosure comprise (a) a heavy chain variable region comprising at least one, two, or three HVRs selected from HVR-H1, HVR-H2, and HVR-H3 of any one of the antibodies listed in Tables 2A-2C, or selected from AL2p-2, AL2p-3, AL2p-4, AL2p-7, AL2p-8, AL2p-9, AL2p-10, AL2p-11, AL2p-12, AL2p-13, AL2p-14, AL2p-15, AL2p-16, AL2p-17, AL2p-18, AL2p-19, AL2p-20, AL2p-21, AL2p-22, AL2p-23, AL2p-24, AL2p-25, AL2p-26, AL2p-27, AL2p-28, AL2p-29, AL2p-30, AL2p-31, AL2p-32, AL2p-35, AL2p-36, AL2p-37, AL2p-38, AL2p-39, AL2p-40, AL2p-41, AL2p-42, AL2p-43, AL2p-44, AL2p-45, AL2p-46, AL2p-47, AL2p-48, AL2p-49, AL2p-50, AL2p-51, AL2p-52, AL2p-53, AL2p-54, AL2p-55, AL2p-56, AL2p-57, AL2p-58, AL2p-59, AL2p-60, AL2p-61, or AL2p-62, and any combination thereof; and/or (b) a light chain variable region comprising at least one, two, or three HVRs selected from HVR-H1, HVR-H2, and HVR-H3 of any one of the antibodies listed in Tables 3A-3C, or selected from AL2p-5, AL2p-6, AL2p-7, AL2p-8, AL2p-9, AL2p-10, AL2p-11, AL2p-12, AL2p-13, AL2p-14, AL2p-15, AL2p-16, AL2p-17, AL2p-18, AL2p-19, AL2p-20, AL2p-21, AL2p-22, AL2p-23, AL2p-24, AL2p-25, AL2p-26, AL2p-27, AL2p-28, AL2p-29, AL2p-30, AL2p-31, AL2p-32, AL2p-33, AL2p-38, AL2p-39, AL2p-40, AL2p-41, AL2p-42, AL2p-43, AL2p-44, AL2p-45, AL2p-46, AL2p-47, AL2p-48, AL2p-49, AL2p-50, AL2p-51, AL2p-52, AL2p-53, AL2p-54, AL2p-55, AL2p-56, AL2p-57, AL2p-58, AL2p-59, AL2p-60, AL2p-61, or AL2p-62, and any combination thereof. In some embodiments, the HVR-H1, HVR-H2, HVR-H3, HVR-L1, HVR-L2, and HVR-L3 comprise EU or Kabat HVR, Chothia HVR, or Contact HVR sequences as shown in Tables 2A-2C, 3A-3C, 6, and 7, or from an antibody selected from AL2p-2, AL2p-3, AL2p-4, AL2p-5, AL2p-6, AL2p-7, AL2p-8, AL2p-9, AL2p-10, AL2p-11, AL2p-12, AL2p-13, AL2p-14, AL2p-15, AL2p-16, AL2p-17, AL2p-18, AL2p-19, AL2p-20, AL2p-21, AL2p-22, AL2p-23, AL2p-24, AL2p-25, AL2p-26, AL2p-27, AL2p-28, AL2p-29, AL2p-30, AL2p-31, AL2p-32, AL2p-33, AL2p-35, AL2p-36, AL2p-37, AL2p-38, AL2p-39, AL2p-40, AL2p-41, AL2p-42, AL2p-43, AL2p-44, AL2p-45, AL2p-46, AL2p-47, AL2p-48, AL2p-49, AL2p-50, AL2p-51, AL2p-52, AL2p-53, AL2p-54, AL2p-55, AL2p-56, AL2p-57, AL2p-58, AL2p-59, AL2p-60, AL2p-61, or AL2p-62, and any combination thereof.

In some embodiments, anti-TREM2 antibodies of the present disclosure comprise a heavy chain variable region and a light chain variable region, wherein the heavy chain variable region comprises: an HVR-H1 comprising the sequence according to Formula I: YAFX$_1$X$_2$X$_3$WMN, wherein X$_1$ is S or W, X$_2$ is S, L, or R, and X$_3$ is S, D, H, Q, or E (SEQ ID NO: 121); an HVR-H2 comprising the sequence according to Formula II: RIYPGX$_1$GX$_2$TNYAX$_3$KX$_4$X$_5$G, wherein X$_1$ is D, G, E, Q, or V, X$_2$ is D or Q, X$_3$ is Q, R, H, W, Y, or G, X$_4$ is F, R, or W, and X$_5$ is Q, R, K, or H (SEQ ID NO: 122); and an HVR-H3 comprising the sequence according to Formula III: ARLLRNX$_1$PGX$_2$SYAX$_3$DY, wherein X$_1$ is Q or K, X$_2$ is E, S, or A, and X$_3$ is M or H (SEQ ID NO: 123), and wherein the antibody is not an antibody comprising a heavy chain variable region comprising an HVR-H1 comprising the sequence of YAFSSSWMN (SEQ ID NO: 124), an HVR-H2 comprising the sequence of RIYPGDGDTNYAQKFQG (SEQ ID NO: 125), and an HVR-H3 comprising the sequence of ARLLRNQPGESYAMDY (SEQ ID NO: 126).

In some embodiments, anti-TREM2 antibodies of the present disclosure comprise a heavy chain variable region and a light chain variable region, wherein the light chain variable region comprises: an HVR-L1 comprising the sequence according to Formula IV: $RX_1SX_2SLX_3HSNX_4YTYLH$, wherein $X_1$ is S or T, $X_2$ is Q, R, or S, $X_3$ is V or I, and $X_4$ is G, R, W, Q, or A (SEQ ID NO: 127) an HVR-L2 comprising the sequence according to Formula V: $KVSNRX_1S$, wherein $X_1$ is F, R, V, or K (SEQ ID NO: 128); and an HVR-L3 comprising the sequence according to Formula V: SQSTRVPYT (SEQ ID NO: 129), and wherein the antibody is not an antibody comprising a light chain variable region comprising an HVR-L1 comprising the sequence of RSSQSLVHSNGY-TYLH (SEQ ID NO: 130), an HVR-L2 comprising the sequence of KVSNRFS (SEQ ID NO: 131), and an HVR-L3 comprising the sequence of SQSTRVPYT (SEQ ID NO: 129).

In some embodiments, anti-TREM2 antibodies of the present disclosure comprise a heavy chain variable region and a light chain variable region, wherein the heavy chain variable region comprises: an HVR-H1 comprising the sequence according to Formula I, wherein $X_1$ is S or W, $X_2$ is S, L, or R, and $X_3$ is S, D, H, Q, or E; an HVR-H2 comprising the sequence according to Formula II, wherein $X_1$ is D, G, E, Q, or V, $X_2$ is D or Q, $X_3$ is Q, R, H, W, Y, or G, $X_4$ is F, R, or W, and $X_5$ is Q, R, K, or H; and an HVR-H3 comprising the sequence according to Formula III, wherein $X_1$ is Q or K, $X_2$ is E, S, or A, and $X_3$ is M or H, and the light chain variable region comprises: an HVR-L1 comprising the sequence according to Formula IV, wherein $X_1$ is S or T, $X_2$ is Q, R, or S, $X_3$ is V or I, and $X_4$ is G, R, W, Q, or A; an HVR-L2 comprising the sequence according to Formula V, wherein $X_1$ is F, R, V, or K; and an HVR-L3 comprising the sequence: SQSTRVPYT (SEQ ID NO: 129), and wherein the antibody is not an antibody comprising a heavy chain variable region comprising an HVR-H1 comprising the sequence of YAFSSSWMN (SEQ ID NO: 124), an HVR-H2 comprising the sequence of RIYPGDGDT-NYAQKFQG (SEQ ID NO: 125), and an HVR-H3 comprising the sequence of ARLLRNQPGESYAMDY (SEQ ID NO: 126), and comprising a light chain variable region comprising an HVR-L1 comprising the sequence of RSSQS-LVHSNGYTYLH (SEQ ID NO: 130), an HVR-L2 comprising the sequence of KVSNRFS (SEQ ID NO: 131), and an HVR-L3 comprising the sequence of SQSTRVPYT (SEQ ID NO: 129).

In some embodiments, anti-TREM2 antibodies of the present disclosure comprise a light chain variable domain and a heavy chain variable domain, wherein the heavy chain variable domain comprises one or more of: (a) an HVR-H1 comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to an HVR-H1 amino acid sequence of antibody AL2p-2, AL2p-3, AL2p-4, AL2p-7, AL2p-8, AL2p-9, AL2p-10, AL2p-11, AL2p-12, AL2p-13, AL2p-14, AL2p-15, AL2p-16, AL2p-17, AL2p-18, AL2p-19, AL2p-20, AL2p-21, AL2p-22, AL2p-23, AL2p-24, AL2p-25, AL2p-26, AL2p-27, AL2p-28, AL2p-29, AL2p-30, AL2p-31, AL2p-32, AL2p-35, AL2p-36, AL2p-37, AL2p-38, AL2p-39, AL2p-40, AL2p-41, AL2p-42, AL2p-43, AL2p-44, AL2p-45, AL2p-46, AL2p-47, AL2p-48, AL2p-49, AL2p-50, AL2p-51, AL2p-52, AL2p-53, AL2p-54, AL2p-55, AL2p-56, AL2p-57, AL2p-58, AL2p-59, AL2p-60, AL2p-61, or AL2p-62; (b) an HVR-H2 comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to an HVR-H2 amino acid sequence of antibody AL2p-2, AL2p-3, AL2p-4, AL2p-7, AL2p-8, AL2p-9, AL2p-10, AL2p-11, AL2p-12, AL2p-13, AL2p-14, AL2p-15, AL2p-16, AL2p-17, AL2p-18, AL2p-19, AL2p-20, AL2p-21, AL2p-22, AL2p-23, AL2p-24, AL2p-25, AL2p-26, AL2p-27, AL2p-28, AL2p-29, AL2p-30, AL2p-31, AL2p-32, AL2p-35, AL2p-36, AL2p-37, AL2p-38, AL2p-39, AL2p-40, AL2p-41, AL2p-42, AL2p-43, AL2p-44, AL2p-45, AL2p-46, AL2p-47, AL2p-48, AL2p-49, AL2p-50, AL2p-51, AL2p-52, AL2p-53, AL2p-54, AL2p-55, AL2p-56, AL2p-57, AL2p-58, AL2p-59, AL2p-60, AL2p-61, or AL2p-62; and (c) an HVR-H3 comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to an HVR-H3 amino acid sequence of antibody AL2p-2, AL2p-3, AL2p-4, AL2p-7, AL2p-8, AL2p-9, AL2p-10, AL2p-11, AL2p-12, AL2p-13, AL2p-14, AL2p-15, AL2p-16, AL2p-17, AL2p-18, AL2p-19, AL2p-20, AL2p-21, AL2p-22, AL2p-23, AL2p-24, AL2p-25, AL2p-26, AL2p-27, AL2p-28, AL2p-29, AL2p-30, AL2p-31, AL2p-32, AL2p-35, AL2p-36, AL2p-37, AL2p-38, AL2p-39, AL2p-40, AL2p-41, AL2p-42, AL2p-43, AL2p-44, AL2p-45, AL2p-46, AL2p-47, AL2p-48, AL2p-49, AL2p-50, AL2p-51, AL2p-52, AL2p-53, AL2p-54, AL2p-55, AL2p-56, AL2p-57, AL2p-58, AL2p-59, AL2p-60, AL2p-61, or AL2p-62; and/or wherein the light chain variable domain comprises one or more of: (a) an HVR-L1 comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to an HVR-L1 amino acid sequence of antibody AL2p-2, AL2p-3, AL2p-4, AL2p-7, AL2p-8, AL2p-9, AL2p-10, AL2p-11, AL2p-12, AL2p-13, AL2p-14, AL2p-15, AL2p-16, AL2p-17, AL2p-18, AL2p-19, AL2p-20, AL2p-21, AL2p-22, AL2p-23, AL2p-24, AL2p-25, AL2p-26, AL2p-27, AL2p-28, AL2p-29, AL2p-30, AL2p-31, AL2p-32, AL2p-35, AL2p-36, AL2p-37, AL2p-38, AL2p-39, AL2p-40, AL2p-41, AL2p-42, AL2p-43, AL2p-44, AL2p-45, AL2p-46, AL2p-47, AL2p-48, AL2p-49, AL2p-50, AL2p-51, AL2p-52, AL2p-53, AL2p-54, AL2p-55, AL2p-56, AL2p-57, AL2p-58, AL2p-59, AL2p-60, AL2p-61, or AL2p-62; (b) an HVR-L2 comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to an HVR-L1 amino acid sequence of antibody AL2p-2, AL2p-3, AL2p-4, AL2p-7, AL2p-8, AL2p-9, AL2p-10, AL2p-11, AL2p-12, AL2p-13, AL2p-14, AL2p-15, AL2p-16, AL2p-17, AL2p-18, AL2p-19, AL2p-20, AL2p-21, AL2p-22, AL2p-23, AL2p-24, AL2p-25, AL2p-26, AL2p-27, AL2p-28, AL2p-29, AL2p-30, AL2p-31, AL2p-32, AL2p-35, AL2p-36, AL2p-37, AL2p-38, AL2p-39, AL2p-40, AL2p-41, AL2p-42, AL2p-43, AL2p-44, AL2p-45, AL2p-46, AL2p-47, AL2p-48, AL2p-49, AL2p-50, AL2p-51, AL2p-52, AL2p-53, AL2p-54, AL2p-

55, AL2p-56, AL2p-57, AL2p-58, AL2p-59, AL2p-60, AL2p-61, or AL2p-62; and (c) an HVR-L3 comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to an HVR-L3 amino acid sequence of antibody AL2p-2, AL2p-3, AL2p-4, AL2p-7, AL2p-8, AL2p-9, AL2p-10, AL2p-11, AL2p-12, AL2p-13, AL2p-14, AL2p-15, AL2p-16, AL2p-17, AL2p-18, AL2p-19, AL2p-20, AL2p-21, AL2p-22, AL2p-23, AL2p-24, AL2p-25, AL2p-26, AL2p-27, AL2p-28, AL2p-29, AL2p-30, AL2p-31, AL2p-32, AL2p-35, AL2p-36, AL2p-37, AL2p-38, AL2p-39, AL2p-40, AL2p-41, AL2p-42, AL2p-43, AL2p-44, AL2p-45, AL2p-46, AL2p-47, AL2p-48, AL2p-49, AL2p-50, AL2p-51, AL2p-52, AL2p-53, AL2p-54, AL2p-55, AL2p-56, AL2p-57, AL2p-58, AL2p-59, AL2p-60, AL2p-61, or AL2p-62.

In some embodiments, anti-TREM2 antibodies of the present disclosure comprise a light chain variable domain and a heavy chain variable domain, wherein the heavy chain variable region comprises an HVR-H1 comprising the amino acid sequence YAFSSQWMN (SEQ ID NO: 132), an HVR-H2 comprising the amino acid sequence RIYPGGGDTNYARKFQG (SEQ ID NO: 133), an HVR-H3 comprising the amino acid sequence ARLLRNQPGESYAMDY (SEQ ID NO: 126), and the light chain variable region comprises an HVR-L1 comprising the amino acid sequence RSSQSLVHSNGYTYLH (SEQ ID NO: 130), an HVR-L2 comprising the amino acid sequence KVSNRRS (SEQ ID NO: 134), and an HVR-L3 comprising the amino acid sequence SQSTRVPYT (SEQ ID NO: 129). In some embodiments, anti-TREM2 antibodies of the present disclosure comprise a light chain variable domain and a heavy chain variable domain, wherein the heavy chain variable region comprises an HVR-H1 comprising the amino acid sequence YAFSSQWMN (SEQ ID NO: 132), an HVR-H2 comprising the amino acid sequence RIYPGGGDTNYAG-KFQG (SEQ ID NO: 135), an HVR-H3 comprising the amino acid sequence ARLLRNQPGESYAMDY (SEQ ID NO: 126), and the light chain variable region comprises an HVR-L1 comprising the amino acid sequence RSSQSLVHSNGYTYLH (SEQ ID NO: 130), an HVR-L2 comprising the amino acid sequence KVSNRFS (SEQ ID NO: 131), and an HVR-L3 comprising the amino acid sequence SQSTRVPYT (SEQ ID NO: 129). In some embodiments, anti-TREM2 antibodies of the present disclosure comprise a light chain variable domain and a heavy chain variable domain, wherein the heavy chain variable region comprises an HVR-H1 comprising the amino acid sequence YAFSS-DWMN (SEQ ID NO: 136), an HVR-H2 comprising the amino acid sequence RIYPGEGDTNYARKFHG (SEQ ID NO: 137), an HVR-H3 comprising the amino acid sequence ARLLRNKPGESYAMDY (SEQ ID NO: 138), and the light chain variable region comprises an HVR-L1 comprising the amino acid sequence RTSQSLVHSNAYTYLH (SEQ ID NO: 139), an HVR-L2 comprising the amino acid sequence KVSNRVS (SEQ ID NO: 140), and an HVR-L3 comprising the amino acid sequence SQSTRVPYT (SEQ ID NO: 129). In some embodiments, anti-TREM2 antibodies of the present disclosure comprise a light chain variable domain and a heavy chain variable domain, wherein the heavy chain variable region comprises an HVR-H1 comprising the amino acid sequence YAFSSQWMN (SEQ ID NO: 132), an HVR-H2 comprising the amino acid sequence RIYPGEGDTNYARKFQG (SEQ ID NO: 141), an HVR-H3 comprising the amino acid sequence ARLLRNQPGE-SYAMDY (SEQ ID NO: 126), and the light chain variable region comprises an HVR-L1 comprising the amino acid sequence RSSQSLVHSNQYTYLH (SEQ ID NO: 142), an HVR-L2 comprising the amino acid sequence KVSNRRS (SEQ ID NO: 134), and an HVR-L3 comprising the amino acid sequence SQSTRVPYT (SEQ ID NO: 129). In some embodiments, anti-TREM2 antibodies of the present disclosure comprise a light chain variable domain and a heavy chain variable domain, wherein the heavy chain variable region comprises an HVR-H1 comprising the amino acid sequence YAFSSQWMN (SEQ ID NO: 132), an HVR-H2 comprising the amino acid sequence RIYPGEGDTNYAG-KFQG (SEQ ID NO: 143), an HVR-H3 comprising the amino acid sequence ARLLRNQPGESYAMDY (SEQ ID NO: 126), and the light chain variable region comprises an HVR-L1 comprising the amino acid sequence RSSQSLVH-SNQYTYLH (SEQ ID NO: 142), an HVR-L2 comprising the amino acid sequence KVSNRFS (SEQ ID NO: 131), and an HVR-L3 comprising the amino acid sequence SQSTRVPYT (SEQ ID NO: 129). In some embodiments, anti-TREM2 antibodies of the present disclosure comprise a light chain variable domain and a heavy chain variable domain, wherein the heavy chain variable region comprises an HVR-H1 comprising the amino acid sequence YAF-SSQWMN (SEQ ID NO: 132), an HVR-H2 comprising the amino acid sequence RIYPGGGDTNYAGKFQG (SEQ ID NO: 135), an HVR-H3 comprising the amino acid sequence ARLLRNQPGESYAMDY (SEQ ID NO: 126), and the light chain variable region comprises an HVR-L1 comprising the amino acid sequence RSSQSLVHSNRYTYLH (SEQ ID NO: 144), an HVR-L2 comprising the amino acid sequence KVSNRFS (SEQ ID NO: 131), and an HVR-L3 comprising the amino acid sequence SQSTRVPYT (SEQ ID NO: 129). In some embodiments, anti-TREM2 antibodies of the present disclosure comprise a light chain variable domain and a heavy chain variable domain, wherein the heavy chain variable region comprises an HVR-H1 comprising the amino acid sequence YAFSSQWMN (SEQ ID NO: 132), an HVR-H2 comprising the amino acid sequence RIYPGGGDTNYARKFQG (SEQ ID NO: 133), an HVR-H3 comprising the amino acid sequence ARLLRNQPGE-SYAMDY (SEQ ID NO: 126), and the light chain variable region comprises an HVR-L1 comprising the amino acid sequence RSSQSLVHSNRYTYLH (SEQ ID NO: 144), an HVR-L2 comprising the amino acid sequence KVSNRRS (SEQ ID NO: 134), and an HVR-L3 comprising the amino acid sequence SQSTRVPYT (SEQ ID NO: 129). In some embodiments, anti-TREM2 antibodies of the present disclosure comprise a heavy chain variable region and a light chain variable region, wherein the heavy chain variable region comprises one, two, three or four frame work regions selected from VH FR1, VH FR2, VH FR3, and VH FR4, wherein: the VH FR1 comprises a sequence selected from the group consisting of SEQ ID NOs: 9-11, the VH FR2 comprises a sequence selected from the group consisting of SEQ ID NOs: 12 and 13, the VH FR3 comprises a sequence selected from the group consisting of SEQ ID NOs: 14 and 15, and the VH FR4 comprises the sequence of SEQ ID NO: 16; and/or the light chain variable region comprises one, two, three or four frame work regions selected from VL FR1, VL FR2, VL FR3, and VL FR4, wherein: the L FR1 comprises a sequence selected from the group consisting of SEQ ID NOs: 17-20, the VL FR2 comprises a sequence selected from the group consisting of SEQ ID NOs: 21 and 22, the VL FR3 comprises a sequence selected from the group consisting of SEQ ID NOs: 23 and 24, and the VL FR4 comprises a sequence selected from the group consisting of SEQ ID NOs: 25 and 26.

In some embodiments, anti-TREM2 antibodies of the present disclosure comprise a heavy chain variable region of any one of the antibodies listed in Table 6A, or selected from AL2p-h50, AL2p-2, AL2p-3, AL2p-4, AL2p-5, AL2p-6, AL2p-7, AL2p-8, AL2p-9, AL2p-10, AL2p-11, AL2p-12, AL2p-13, AL2p-14, AL2p-15, AL2p-16, AL2p-17, AL2p-18, AL2p-19, AL2p-20, AL2p-21, AL2p-22, AL2p-23, AL2p-24, AL2p-25, AL2p-26, AL2p-27, AL2p-28, AL2p-29, AL2p-30, AL2p-31, AL2p-32, AL2p-33, AL2p-h77, AL2p-35, AL2p-36, AL2p-37, AL2p-38, AL2p-39, AL2p-40, AL2p-41, AL2p-42, AL2p-43, AL2p-44, AL2p-45, AL2p-46, AL2p-47, AL2p-48, AL2p-49, AL2p-50, AL2p-51, AL2p-52, AL2p-53, AL2p-54, AL2p-55, AL2p-56, AL2p-57, AL2p-58, AL2p-59, AL2p-60, AL2p-61, AL2p-62, AL2p-h19, AL2p-h21, AL2p-h22, AL2p-h23, AL2p-h24, AL2p-h25, AL2p-h26, AL2p-h27, AL2p-h28, AL2p-h29, AL2p-h30, AL2p-h31, AL2p-h32, AL2p-h33, AL2p-h34, AL2p-h35, AL2p-h36, AL2p-h42, AL2p-h43, AL2p-h44, AL2p-h47, AL2p-h59, AL2p-h76, and AL2p-h90; and/or a light chain variable region of any one of the antibodies listed in Table 7A, or selected from AL2p-h50, AL2p-2, AL2p-3, AL2p-4, AL2p-5, AL2p-6, AL2p-7, AL2p-8, AL2p-9, AL2p-10, AL2p-11, AL2p-12, AL2p-13, AL2p-14, AL2p-15, AL2p-16, AL2p-17, AL2p-18, AL2p-19, AL2p-20, AL2p-21, AL2p-22, AL2p-23, AL2p-24, AL2p-25, AL2p-26, AL2p-27, AL2p-28, AL2p-29, AL2p-30, AL2p-31, AL2p-32, AL2p-33, AL2p-h77, AL2p-35, AL2p-36, AL2p-37, AL2p-38, AL2p-39, AL2p-40, AL2p-41, AL2p-42, AL2p-43, AL2p-44, AL2p-45, AL2p-46, AL2p-47, AL2p-48, AL2p-49, AL2p-50, AL2p-51, AL2p-52, AL2p-53, AL2p-54, AL2p-55, AL2p-56, AL2p-57, AL2p-58, AL2p-59, AL2p-60, AL2p-61, AL2p-62, AL2p-h19, AL2p-h21, AL2p-h22, AL2p-h23, AL2p-h24, AL2p-h25, AL2p-h26, AL2p-h27, AL2p-h28, AL2p-h29, AL2p-h30, AL2p-h31, AL2p-h32, AL2p-h33, AL2p-h34, AL2p-h35, AL2p-h36, AL2p-h42, AL2p-h43, AL2p-h44, AL2p-h47, AL2p-h59, AL2p-h76, and AL2p-h90. In some embodiments, anti-TREM2 antibodies of the present disclosure comprise a heavy chain variable region comprising an amino acid sequence selected from any of SEQ ID NOs: 27-71 and 91; and/or a light chain variable domain comprising an amino acid sequence selected from any of SEQ ID NOs: 92-113 and 118. In some embodiments, anti-TREM2 antibodies of the present disclosure comprise a heavy chain variable region comprising an amino acid sequence selected from any of SEQ ID NOs: 27, 56 and 72-90; and/or a light chain variable domain comprising an amino acid sequence selected from any of SEQ ID NOs: 92, 104, and 114-117.

In some embodiments, anti-TREM2 antibodies of the present disclosure comprise a light chain variable domain and a heavy chain variable domain, wherein the heavy chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-2 or to the amino acid sequence of SEQ ID NO: 28; and/or the light chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-2 or to the amino acid sequence of SEQ ID NO: 92. In some embodiments, anti-TREM2 antibodies of the present disclosure comprise a heavy chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-2 or to the amino acid sequence of SEQ ID NO: 28, wherein the heavy chain variable domain comprises the HVR-H1, HVR-H2, and HVR-H3 amino acid sequences of antibody AL2p-2. In some embodiments, anti-TREM2 antibodies of the present disclosure comprise a light chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-2 or to the amino acid sequence of SEQ ID NO: 92, wherein the light chain variable domain comprises the HVR-L1, HVR-L2, and HVR-L3 amino acid sequences of antibody AL2p-2. In some embodiments, the anti-TREM2 antibody comprises a heavy chain variable domain (VH) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-2 or to the amino acid sequence of SEQ ID NO: 28 and contains substitutions (e.g., conservative substitutions, insertions, or deletions relative to the reference sequence), but the anti-TREM2 antibody comprising that sequence retains the ability to bind to TREM2. In certain embodiments, a total of 1 to 10 amino acids have been substituted, inserted, and/or deleted in the heavy chain variable domain amino acid sequence of antibody AL2p-2 or the amino acid sequence of SEQ ID NO: 28. In certain embodiments, a total of 1 to 5 amino acids have been substituted, inserted and/or deleted in the heavy chain variable domain amino acid sequence of antibody AL2p-2 or the amino acid sequence of SEQ ID NO: 28. In certain embodiments, substitutions, insertions, or deletions occur in regions outside the HVRs (i.e., in the FR regions). In some embodiments, the substitutions, insertions, or deletions occur in in the FR regions. Optionally, the anti-TREM2 antibody comprises the VH sequence of antibody AL2p-2 or of SEQ ID NO: 28, including post-translational modifications of that sequence. In a particular embodiment, the VH comprises one, two or three HVRs selected from: (a) the HVR-H1 amino acid sequence of antibody AL2p-2, (b) the HVR-H2 amino acid sequence of antibody AL2p-2, and (c) the HVR-H3 amino acid sequence of antibody AL2p-2. In some embodiments, anti-TREM2 antibodies of the present disclosure comprise a light chain variable domain (VL) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-2 or to the amino acid sequence of SEQ ID NO: 92 and contains substitutions (e.g., conservative substitutions, insertions, or deletions relative to the reference sequence), but the anti-TREM2 antibody comprising that sequence retains the ability to bind to TREM2. In certain embodiments, a total of 1 to 10 amino acids have been substituted, inserted, and/or deleted in the light chain variable domain amino acid sequence of antibody AL2p-2 or the amino acid sequence of SEQ ID NO: 92. In certain embodiments, a total of 1 to 5 amino acids have been substituted, inserted and/or deleted in the light chain variable domain amino acid sequence of antibody AL2p-2 or the amino acid sequence of SEQ ID NO: 92. In certain embodiments, substitutions, insertions, or deletions occur in regions outside the HVRs (i.e., in the FR regions). In some embodiments, the substitutions, insertions, or deletions occur in in the FR regions. Optionally, the anti-TREM2 antibody comprises the VL sequence of antibody AL2p-2 or of SEQ ID NO: 92, including post-translational modifications of that sequence. In a particular embodiment, the VL comprises one, two or three HVRs selected from: (a) the HVR-L1 amino acid sequence of antibody AL2p-2, (b) the HVR-L2 amino acid sequence of antibody AL2p-2, and (c) the HVR-L3 amino acid sequence of antibody AL2p-2.

In some embodiments, anti-TREM2 antibodies of the present disclosure comprise a light chain variable domain and a heavy chain variable domain, wherein the heavy chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-3 or to the amino acid sequence of SEQ ID NO: 29; and/or the light chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-3 or to the amino acid sequence of SEQ ID NO: 92. In some embodiments, anti-TREM2 antibodies of the present disclosure comprise a heavy chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-3 or to the amino acid sequence of SEQ ID NO: 29, wherein the heavy chain variable domain comprises the HVR-H1, HVR-H2, and HVR-H3 amino acid sequences of antibody AL2p-3. In some embodiments, anti-TREM2 antibodies of the present disclosure comprise a light chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-3 or to the amino acid sequence of SEQ ID NO: 92, wherein the light chain variable domain comprises the HVR-L1, HVR-L2, and HVR-L3 amino acid sequences of antibody AL2p-3. In some embodiments, the anti-TREM2 antibody comprises a heavy chain variable domain (VH) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-3 or to the amino acid sequence of SEQ ID NO: 29 and contains substitutions (e.g., conservative substitutions, insertions, or deletions relative to the reference sequence), but the anti-TREM2 antibody comprising that sequence retains the ability to bind to TREM2. In certain embodiments, a total of 1 to 10 amino acids have been substituted, inserted, and/or deleted in the heavy chain variable domain amino acid sequence of antibody AL2p-3 or the amino acid sequence of SEQ ID NO: 29. In certain embodiments, a total of 1 to 5 amino acids have been substituted, inserted and/or deleted in the heavy chain variable domain amino acid sequence of antibody AL2p-3 or the amino acid sequence of SEQ ID NO: 29. In certain embodiments, substitutions, insertions, or deletions occur in regions outside the HVRs (i.e., in the FR regions). In some embodiments, the substitutions, insertions, or deletions occur in in the FR regions. Optionally, the anti-TREM2 antibody comprises the VH sequence of antibody AL2p-3 or of SEQ ID NO: 29, including post-translational modifications of that sequence. In a particular embodiment, the VH comprises one, two or three HVRs selected from: (a) the HVR-H1 amino acid sequence of antibody AL2p-3, (b) the HVR-H2 amino acid sequence of antibody AL2p-3, and (c) the HVR-H3 amino acid sequence of antibody AL2p-3. In some embodiments, anti-TREM2 antibodies of the present disclosure comprise a light chain variable domain (VL) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-3 or to the amino acid sequence of SEQ ID NO: 92 and contains substitutions (e.g., conservative substitutions, insertions, or deletions relative to the reference sequence), but the anti-TREM2 antibody comprising that sequence retains the ability to bind to TREM2. In certain embodiments, a total of 1 to 10 amino acids have been substituted, inserted, and/or deleted in the light chain variable domain amino acid sequence of antibody AL2p-3 or the amino acid sequence of SEQ ID NO: 92. In certain embodiments, a total of 1 to 5 amino acids have been substituted, inserted and/or deleted in the light chain variable domain amino acid sequence of antibody AL2p-3 or the amino acid sequence of SEQ ID NO: 92. In certain embodiments, substitutions, insertions, or deletions occur in regions outside the HVRs (i.e., in the FR regions). In some embodiments, the substitutions, insertions, or deletions occur in in the FR regions. Optionally, the anti-TREM2 antibody comprises the VL sequence of antibody AL2p-3 or of SEQ ID NO: 92, including post-translational modifications of that sequence. In a particular embodiment, the VL comprises one, two or three HVRs selected from: (a) the HVR-L1 amino acid sequence of antibody AL2p-3, (b) the HVR-L2 amino acid sequence of antibody AL2p-3, and (c) the HVR-L3 amino acid sequence of antibody AL2p-3.

In some embodiments, anti-TREM2 antibodies of the present disclosure comprise a light chain variable domain and a heavy chain variable domain, wherein the heavy chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-4 or to the amino acid sequence of SEQ ID NO: 30; and/or the light chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-4 or to the amino acid sequence of SEQ ID NO: 92. In some embodiments, anti-TREM2 antibodies of the present disclosure comprise a heavy chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-4 or to the amino acid sequence of SEQ ID NO: 30, wherein the heavy chain variable domain comprises the HVR-H1, HVR-H2, and HVR-H3 amino acid sequences of antibody AL2p-4. In some embodiments, anti-TREM2 antibodies of the present disclosure comprise a light chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-4 or to the amino acid sequence of SEQ ID NO: 92, wherein the light chain variable domain comprises the HVR-L1, HVR-L2, and HVR-L3 amino acid sequences of antibody AL2p-4. In some embodiments, the anti-TREM2 antibody comprises a heavy chain variable domain (VH) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-4 or to the amino acid sequence of SEQ ID NO: 30 and contains substitutions (e.g., conservative substitutions, insertions, or deletions relative to the reference sequence), but the anti-TREM2 antibody comprising that sequence retains the ability to bind to TREM2. In certain embodiments, a total of 1 to 10 amino acids have been substituted, inserted, and/or deleted in the heavy chain variable domain amino acid sequence of antibody AL2p-4 or the amino acid sequence of SEQ ID NO: 30. In certain embodiments, a total of 1 to 5 amino acids have been substituted, inserted and/or deleted in the heavy chain variable domain amino acid sequence of antibody AL2p-4 or the amino acid sequence of SEQ ID NO: 30. In certain embodiments, substitutions, insertions, or deletions occur in regions outside the HVRs (i.e., in the FR regions). In some embodiments, the substitutions, insertions, or deletions occur in in the FR regions. Optionally, the anti-TREM2 antibody comprises the VH sequence of antibody AL2p-4 or of SEQ ID NO: 30, including post-translational modifications of that sequence. In a particular embodiment, the VH comprises one, two or three HVRs selected from: (a) the HVR-H1 amino acid sequence of antibody AL2p-4, (b) the HVR-H2 amino acid sequence of antibody AL2p-4, and (c) the HVR-H3 amino acid sequence of antibody AL2p-4. In some embodiments, anti-TREM2 antibodies of the present disclosure comprise a light chain variable domain (VL) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-4 or to the amino acid sequence of SEQ ID NO: 92 and contains substitutions (e.g., conservative substitutions, insertions, or deletions relative to the reference sequence), but the anti-TREM2 antibody comprising that sequence retains the ability to bind to TREM2. In certain embodiments, a total of 1 to 10 amino acids have been substituted, inserted, and/or deleted in the light chain variable domain amino acid sequence of antibody AL2p-4 or the amino acid sequence of SEQ ID NO: 92. In certain embodiments, a total of 1 to 5 amino acids have been substituted, inserted and/or deleted in the light chain variable domain amino acid sequence of antibody AL2p-4 or the amino acid sequence of SEQ ID NO: 92. In certain embodiments, substitutions, insertions, or deletions occur in regions outside the HVRs (i.e., in the FR regions). In some embodiments, the substitutions, insertions, or deletions occur in in the FR regions. Optionally, the anti-TREM2 antibody comprises the VL sequence of antibody AL2p-4 or of SEQ ID NO: 92, including post-translational modifications of that sequence. In a particular embodiment, the VL comprises one, two or three HVRs selected from: (a) the HVR-L1 amino acid sequence of antibody AL2p-4, (b) the HVR-L2 amino acid sequence of antibody AL2p-4, and (c) the HVR-L3 amino acid sequence of antibody AL2p-4.

In some embodiments, anti-TREM2 antibodies of the present disclosure comprise a light chain variable domain and a heavy chain variable domain, wherein the heavy chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-7 or to the amino acid sequence of SEQ ID NO: 31; and/or the light chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-7 or to the amino acid sequence of SEQ ID NO: 95. In some embodiments, anti-TREM2 antibodies of the present disclosure comprise a heavy chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-7 or to the amino acid sequence of SEQ ID NO: 31, wherein the heavy chain variable domain comprises the HVR-H1, HVR-H2, and HVR-H3 amino acid sequences of antibody AL2p-7. In some embodiments, anti-TREM2 antibodies of the present disclosure comprise a light chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-7 or to the amino acid sequence of SEQ ID NO: 95, wherein the light chain variable domain comprises the HVR-L1, HVR-L2, and HVR-L3 amino acid sequences of antibody AL2p-7. In some embodiments, the anti-TREM2 antibody comprises a heavy chain variable domain (VH) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-7 or to the amino acid sequence of SEQ ID NO: 31 and contains substitutions (e.g., conservative substitutions, insertions, or deletions relative to the reference sequence), but the anti-TREM2 antibody comprising that sequence retains the ability to bind to TREM2. In certain embodiments, a total of 1 to 10 amino acids have been substituted, inserted, and/or deleted in the heavy chain variable domain amino acid sequence of antibody AL2p-7 or the amino acid sequence of SEQ ID NO: 31. In certain embodiments, a total of 1 to 5 amino acids have been substituted, inserted and/or deleted in the heavy chain variable domain amino acid sequence of antibody AL2p-7 or the amino acid sequence of SEQ ID NO: 31. In certain embodiments, substitutions, insertions, or deletions occur in regions outside the HVRs (i.e., in the FR regions). In some embodiments, the substitutions, insertions, or deletions occur in in the FR regions. Optionally, the anti-TREM2 antibody comprises the VH sequence of antibody AL2p-7 or of SEQ ID NO: 31, including post-translational modifications of that sequence. In a particular embodiment, the VH comprises one, two or three HVRs selected from: (a) the HVR-H1 amino acid sequence of antibody AL2p-7, (b) the HVR-H2 amino acid sequence of antibody AL2p-7, and (c) the HVR-H3 amino acid sequence of antibody AL2p-7. In some embodiments, anti-TREM2 antibodies of the present disclosure comprise a light chain variable domain (VL) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-7 or to the amino acid sequence of SEQ ID NO: 95 and contains substitutions (e.g., conservative substitutions, insertions, or deletions relative to the reference sequence), but the anti-TREM2 antibody comprising that sequence retains the ability to bind to TREM2. In certain embodiments, a total of 1 to 10 amino acids have been substituted, inserted, and/or deleted in the light chain variable domain amino acid sequence of antibody AL2p-7 or the amino acid sequence of SEQ ID NO: 95. In certain embodiments, a total of 1 to 5 amino acids have been substituted, inserted and/or deleted in the light chain variable domain amino acid sequence of antibody AL2p-7 or the amino acid sequence of SEQ ID NO: 95. In certain embodiments, substitutions, insertions, or deletions occur in regions outside the HVRs (i.e., in the FR regions). In some embodiments, the substitutions, insertions, or deletions occur in in the FR regions. Optionally, the anti-TREM2 antibody comprises the VL sequence of antibody AL2p-7 or of SEQ ID NO: 95, including post-translational modifications of that sequence. In a particular embodiment, the VL comprises one, two or three HVRs selected from: (a) the HVR-L1 amino acid sequence of antibody AL2p-7, (b) the HVR-L2 amino acid sequence of antibody AL2p-7, and (c) the HVR-L3 amino acid sequence of antibody AL2p-7.

In some embodiments, anti-TREM2 antibodies of the present disclosure comprise a light chain variable domain and a heavy chain variable domain, wherein the heavy chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-8 or to the amino acid sequence of SEQ ID NO: 32; and/or the light chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-8 or to the amino acid sequence of SEQ ID NO: 95. In some embodiments, anti-TREM2 antibodies of the present disclosure comprise a heavy chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-8 or to the amino acid sequence of SEQ ID NO: 32, wherein the heavy chain variable domain comprises the HVR-H1, HVR-H2, and HVR-H3 amino acid sequences of antibody AL2p-8. In some embodiments, anti-TREM2 antibodies of the present disclosure comprise a light chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-8 or to the amino acid sequence of SEQ ID NO: 95, wherein the light chain variable domain comprises the HVR-L1, HVR-L2, and HVR-L3 amino acid sequences of antibody AL2p-8. In some embodiments, the anti-TREM2 antibody comprises a heavy chain variable domain (VH) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-8 or to the amino acid sequence of SEQ ID NO: 32 and contains substitutions (e.g., conservative substitutions, insertions, or deletions relative to the reference sequence), but the anti-TREM2 antibody comprising that sequence retains the ability to bind to TREM2. In certain embodiments, a total of 1 to 10 amino acids have been substituted, inserted, and/or deleted in the heavy chain variable domain amino acid sequence of antibody AL2p-8 or the amino acid sequence of SEQ ID NO: 32. In certain embodiments, a total of 1 to 5 amino acids have been substituted, inserted and/or deleted in the heavy chain variable domain amino acid sequence of antibody AL2p-8 or the amino acid sequence of SEQ ID NO: 32. In certain embodiments, substitutions, insertions, or deletions occur in regions outside the HVRs (i.e., in the FR regions). In some embodiments, the substitutions, insertions, or deletions occur in in the FR regions. Optionally, the anti-TREM2 antibody comprises the VH sequence of antibody AL2p-8 or of SEQ ID NO: 32, including post-translational modifications of that sequence. In a particular embodiment, the VH comprises one, two or three HVRs selected from: (a) the HVR-H1 amino acid sequence of antibody AL2p-8, (b) the HVR-H2 amino acid sequence of antibody AL2p-8, and (c) the HVR-H3 amino acid sequence of antibody AL2p-8. In some embodiments, anti-TREM2 antibodies of the present disclosure comprise a light chain variable domain (VL) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-8 or to the amino acid sequence of SEQ ID NO: 95 and contains substitutions (e.g., conservative substitutions, insertions, or deletions relative to the reference sequence), but the anti-TREM2 antibody comprising that sequence retains the ability to bind to TREM2. In certain embodiments, a total of 1 to 10 amino acids have been substituted, inserted, and/or deleted in the light chain variable domain amino acid sequence of antibody AL2p-8 or the amino acid sequence of SEQ ID NO: 95. In certain embodiments, a total of 1 to 5 amino acids have been substituted, inserted and/or deleted in the light chain variable domain amino acid sequence of antibody AL2p-8 or the amino acid sequence of SEQ ID NO: 95. In certain embodiments, substitutions, insertions, or deletions occur in regions outside the HVRs (i.e., in the FR regions). In some embodiments, the substitutions, insertions, or deletions occur in in the FR regions. Optionally, the anti-TREM2 antibody comprises the VL sequence of antibody AL2p-8 or of SEQ ID NO: 95, including post-translational modifications of that sequence. In a particular embodiment, the VL comprises one, two or three HVRs selected from: (a) the HVR-L1 amino acid sequence of antibody AL2p-8, (b) the HVR-L2 amino acid sequence of antibody AL2p-8, and (c) the HVR-L3 amino acid sequence of antibody AL2p-8.

In some embodiments, anti-TREM2 antibodies of the present disclosure comprise a light chain variable domain and a heavy chain variable domain, wherein the heavy chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-9 or to the amino acid sequence of SEQ ID NO: 33; and/or the light chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-9 or to the amino acid sequence of SEQ ID NO: 96. In some embodiments, anti-TREM2 antibodies of the present disclosure comprise a heavy chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-9 or to the amino acid sequence of SEQ ID NO: 33, wherein the heavy chain variable domain comprises the HVR-H1, HVR-H2, and HVR-H3 amino acid sequences of antibody AL2p-9. In some embodiments, anti-TREM2 antibodies of the present disclosure comprise a light chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-9 or to the amino acid sequence of SEQ ID NO: 96, wherein the light chain variable domain comprises the HVR-L1, HVR-L2, and HVR-L3 amino acid sequences of antibody AL2p-9. In some embodiments, the anti-TREM2 antibody comprises a heavy chain variable domain (VH) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-9 or to the amino acid sequence of SEQ ID NO: 33 and contains substitutions (e.g., conservative substitutions, insertions, or deletions relative to the reference sequence), but the anti-TREM2 antibody comprising that sequence retains the ability to bind to TREM2. In certain embodiments, a total of 1 to 10 amino acids have been substituted, inserted, and/or deleted in the heavy chain variable domain amino acid sequence of antibody AL2p-9 or the amino acid sequence of SEQ ID NO: 33. In certain embodiments, a total of 1 to 5 amino acids have been substituted, inserted and/or deleted in the heavy chain variable domain amino acid sequence of antibody AL2p-9 or the amino acid sequence of SEQ ID NO: 33. In certain embodiments, substitutions, insertions, or deletions occur in regions outside the HVRs (i.e., in the FR regions). In some embodiments, the substitutions, insertions, or deletions occur in in the FR regions. Optionally, the anti-TREM2 antibody comprises the VH sequence of antibody AL2p-9 or of SEQ ID NO: 33, including post-translational modifications of that sequence. In a particular embodiment, the VH comprises one, two or three HVRs selected from: (a) the HVR-H1 amino acid sequence of antibody AL2p-9, (b) the HVR-H2 amino acid sequence of antibody AL2p-9, and (c) the HVR-H3 amino acid sequence of antibody AL2p-9. In some embodiments, anti-TREM2 antibodies of the present disclosure comprise a light chain variable domain (VL) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-9 or to the amino acid sequence of SEQ ID NO: 96 and contains substitutions (e.g., conservative substitutions, insertions, or deletions relative to the reference sequence), but the anti-TREM2 antibody comprising that sequence retains the ability to bind to TREM2. In certain embodiments, a total of 1 to 10 amino acids have been substituted, inserted, and/or deleted in the light chain variable domain amino acid sequence of antibody AL2p-9 or the amino acid sequence of SEQ ID NO: 96. In certain embodiments, a total of 1 to 5 amino acids have been substituted, inserted and/or deleted in the light chain variable domain amino acid sequence of antibody AL2p-9 or the amino acid sequence of SEQ ID NO: 96. In certain embodiments, substitutions, insertions, or deletions occur in regions outside the HVRs (i.e., in the FR regions). In some embodiments, the substitutions, insertions, or deletions occur in in the FR regions. Optionally, the anti-TREM2 antibody comprises the VL sequence of antibody AL2p-9 or of SEQ ID NO: 96, including post-translational modifications of that sequence. In a particular embodiment, the VL comprises one, two or three HVRs selected from: (a) the HVR-L1 amino acid sequence of antibody AL2p-9, (b) the HVR-L2 amino acid sequence of antibody AL2p-9, and (c) the HVR-L3 amino acid sequence of antibody AL2p-9.

In some embodiments, anti-TREM2 antibodies of the present disclosure comprise a light chain variable domain and a heavy chain variable domain, wherein the heavy chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-10 or to the amino acid sequence of SEQ ID NO: 34; and/or the light chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-10 or to the amino acid sequence of SEQ ID NO: 97. In some embodiments, anti-TREM2 antibodies of the present disclosure comprise a heavy chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-10 or to the amino acid sequence of SEQ ID NO: 34, wherein the heavy chain variable domain comprises the HVR-H1, HVR-H2, and HVR-H3 amino acid sequences of antibody AL2p-10. In some embodiments, anti-TREM2 antibodies of the present disclosure comprise a light chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-10 or to the amino acid sequence of SEQ ID NO: 97, wherein the light chain variable domain comprises the HVR-L1, HVR-L2, and HVR-L3 amino acid sequences of antibody AL2p-10. In some embodiments, the anti-TREM2 antibody comprises a heavy chain variable domain (VH) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-10 or to the amino acid sequence of SEQ ID NO: 34 and contains substitutions (e.g., conservative substitutions, insertions, or deletions relative to the reference sequence), but the anti-TREM2 antibody comprising that sequence retains the ability to bind to TREM2. In certain embodiments, a total of 1 to 10 amino acids have been substituted, inserted, and/or deleted in the heavy chain variable domain amino acid sequence of antibody AL2p-10 or the amino acid sequence of SEQ ID NO: 34. In certain embodiments, a total of 1 to 5 amino acids have been substituted, inserted and/or deleted in the heavy chain variable domain amino acid sequence of antibody AL2p-10 or the amino acid sequence of SEQ ID NO: 34. In certain embodiments, substitutions, insertions, or deletions occur in regions outside the HVRs (i.e., in the FR regions). In some embodiments, the substitutions, insertions, or deletions occur in in the FR regions. Optionally, the anti-TREM2 antibody comprises the VH sequence of antibody AL2p-10 or of SEQ ID NO: 34, including post-translational modifications of that sequence. In a particular embodiment, the VH comprises one, two or three HVRs selected from: (a) the HVR-H1 amino acid sequence of antibody AL2p-10, (b) the HVR-H2 amino acid sequence of antibody AL2p-10, and (c) the HVR-H3 amino acid sequence of antibody AL2p-10. In some embodiments, anti-TREM2 antibodies of the present disclosure comprise a light chain variable domain (VL) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-10 or to the amino acid sequence of SEQ ID NO: 97 and contains substitutions (e.g., conservative substitutions, insertions, or deletions relative to the reference sequence), but the anti-TREM2 antibody comprising that sequence retains the ability to bind to TREM2. In certain embodiments, a total of 1 to 10 amino acids have been substituted, inserted, and/or deleted in the light chain variable domain amino acid sequence of antibody AL2p-10 or the amino acid sequence of SEQ ID NO: 97. In certain embodiments, a total of 1 to 5 amino acids have been substituted, inserted and/or deleted in the light chain variable domain amino acid sequence of antibody AL2p-10 or the amino acid sequence of SEQ ID NO: 97. In certain embodiments, substitutions, insertions, or deletions occur in regions outside the HVRs (i.e., in the FR regions). In some embodiments, the substitutions, insertions, or deletions occur in in the FR regions. Optionally, the anti-TREM2 antibody comprises the VL sequence of antibody AL2p-10 or of SEQ ID NO: 97, including post-translational modifications of that sequence. In a particular embodiment, the VL comprises one, two or three HVRs selected from: (a) the HVR-L1 amino acid sequence of antibody AL2p-10, (b) the HVR-L2 amino acid sequence of antibody AL2p-10, and (c) the HVR-L3 amino acid sequence of antibody AL2p-10.

In some embodiments, anti-TREM2 antibodies of the present disclosure comprise a light chain variable domain and a heavy chain variable domain, wherein the heavy chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-11 or to the amino acid sequence of SEQ ID NO: 35; and/or the light chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-11 or to the amino acid sequence of SEQ ID NO: 98. In some embodiments, anti-TREM2 antibodies of the present disclosure comprise a heavy chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-11 or to the amino acid sequence of SEQ ID NO: 35, wherein the heavy chain variable domain comprises the HVR-H1, HVR-H2, and HVR-H3 amino acid sequences of antibody AL2p-11. In some embodiments, anti-TREM2 antibodies of the present disclosure comprise a light chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-11 or to the amino acid sequence of SEQ ID NO: 98, wherein the light chain variable domain comprises the HVR-L1, HVR-L2, and HVR-L3 amino acid sequences of antibody AL2p-11. In some embodiments, the anti-TREM2 antibody comprises a heavy chain variable domain (VH) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-11 or to the amino acid sequence of SEQ ID NO: 35 and contains substitutions (e.g., conservative substitutions, insertions, or deletions relative to the reference sequence), but the anti-TREM2 antibody comprising that sequence retains the ability to bind to TREM2. In certain embodiments, a total of 1 to 10 amino acids have been substituted, inserted, and/or deleted in the heavy chain variable domain amino acid sequence of antibody AL2p-11 or the amino acid sequence of SEQ ID NO: 35. In certain embodiments, a total of 1 to 5 amino acids have been substituted, inserted and/or deleted in the heavy chain variable domain amino acid sequence of antibody AL2p-11 or the amino acid sequence of SEQ ID NO: 35. In certain embodiments, substitutions, insertions, or deletions occur in regions outside the HVRs (i.e., in the FR regions). In some embodiments, the substitutions, insertions, or deletions occur in in the FR regions. Optionally, the anti-TREM2 antibody comprises the VH sequence of antibody AL2p-11 or of SEQ ID NO: 35, including post-translational modifications of that sequence. In a particular embodiment, the VH comprises one, two or three HVRs selected from: (a) the HVR-H1 amino acid sequence of antibody AL2p-11, (b) the HVR-H2 amino acid sequence of antibody AL2p-11, and (c) the HVR-H3 amino acid sequence of antibody AL2p-11. In some embodiments, anti-TREM2 antibodies of the present disclosure comprise a light chain variable domain (VL) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-11 or to the amino acid sequence of SEQ ID NO: 98 and contains substitutions (e.g., conservative substitutions, insertions, or deletions relative to the reference sequence), but the anti-TREM2 antibody comprising that sequence retains the ability to bind to TREM2. In certain embodiments, a total of 1 to 10 amino acids have been substituted, inserted, and/or deleted in the light chain variable domain amino acid sequence of antibody AL2p-11 or the amino acid sequence of SEQ ID NO: 98. In certain embodiments, a total of 1 to 5 amino acids have been substituted, inserted and/or deleted in the light chain variable domain amino acid sequence of antibody AL2p-11 or the amino acid sequence of SEQ ID NO: 98. In certain embodiments, substitutions, insertions, or deletions occur in regions outside the HVRs (i.e., in the FR regions). In some embodiments, the substitutions, insertions, or deletions occur in in the FR regions. Optionally, the anti-TREM2 antibody comprises the VL sequence of antibody AL2p-11 or of SEQ ID NO: 98, including post-translational modifications of that sequence. In a particular embodiment, the VL comprises one, two or three HVRs selected from: (a) the HVR-L1 amino acid sequence of antibody AL2p-11, (b) the HVR-L2 amino acid sequence of antibody AL2p-11, and (c) the HVR-L3 amino acid sequence of antibody AL2p-11.

In some embodiments, anti-TREM2 antibodies of the present disclosure comprise a light chain variable domain and a heavy chain variable domain, wherein the heavy chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-12 or to the amino acid sequence of SEQ ID NO: 36; and/or the light chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-12 or to the amino acid sequence of SEQ ID NO: 97. In some embodiments, anti-TREM2 antibodies of the present disclosure comprise a heavy chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-12 or to the amino acid sequence of SEQ ID NO: 36, wherein the heavy chain variable domain comprises the HVR-H1, HVR-H2, and HVR-H3 amino acid sequences of antibody AL2p-12. In some embodiments, anti-TREM2 antibodies of the present disclosure comprise a light chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-12 or to the amino acid sequence of SEQ ID NO: 97, wherein the light chain variable domain comprises the HVR-L1, HVR-L2, and HVR-L3 amino acid sequences of antibody AL2p-12. In some embodiments, the anti-TREM2 antibody comprises a heavy chain variable domain (VH) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-12 or to the amino acid sequence of SEQ ID NO: 36 and contains substitutions (e.g., conservative substitutions, insertions, or deletions relative to the reference sequence), but the anti-TREM2 antibody comprising that sequence retains the ability to bind to TREM2. In certain embodiments, a total of 1 to 10 amino acids have been substituted, inserted, and/or deleted in the heavy chain variable domain amino acid sequence of antibody AL2p-12 or the amino acid sequence of SEQ ID NO: 36. In certain embodiments, a total of 1 to 5 amino acids have been substituted, inserted and/or deleted in the heavy chain variable domain amino acid sequence of antibody AL2p-12 or the amino acid sequence of SEQ ID NO: 36. In certain embodiments, substitutions, insertions, or deletions occur in regions outside the HVRs (i.e., in the FR regions). In some embodiments, the substitutions, insertions, or deletions occur in in the FR regions. Optionally, the anti-TREM2 antibody comprises the VH sequence of antibody AL2p-12 or of SEQ ID NO: 36, including post-translational modifications of that sequence. In a particular embodiment, the VH comprises one, two or three HVRs selected from: (a) the HVR-H1 amino acid sequence of antibody AL2p-12, (b) the HVR-H2 amino acid sequence of antibody AL2p-12, and (c) the HVR-H3 amino acid sequence of antibody AL2p-12. In some embodiments, anti-TREM2 antibodies of the present disclosure comprise a light chain variable domain (VL) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-12 or to the amino acid sequence of SEQ ID NO: 97 and contains substitutions (e.g., conservative substitutions, insertions, or deletions relative to the reference sequence), but the anti-TREM2 antibody comprising that sequence retains the ability to bind to TREM2. In certain embodiments, a total of 1 to 10 amino acids have been substituted, inserted, and/or deleted in the light chain variable domain amino acid sequence of antibody AL2p-12 or the amino acid sequence of SEQ ID NO: 97. In certain embodiments, a total of 1 to 5 amino acids have been substituted, inserted and/or deleted in the light chain variable domain amino acid sequence of antibody AL2p-12 or the amino acid sequence of SEQ ID NO: 97. In certain embodiments, substitutions, insertions, or deletions occur in regions outside the HVRs (i.e., in the FR regions). In some embodiments, the substitutions, insertions, or deletions occur in in the FR regions. Optionally, the anti-TREM2 antibody comprises the VL sequence of antibody AL2p-12 or of SEQ ID NO: 97, including post-translational modifications of that sequence. In a particular embodiment, the VL comprises one, two or three HVRs selected from: (a) the HVR-L1 amino acid sequence of antibody AL2p-12, (b) the HVR-L2 amino acid sequence of antibody AL2p-12, and (c) the HVR-L3 amino acid sequence of antibody AL2p-12.

In some embodiments, anti-TREM2 antibodies of the present disclosure comprise a light chain variable domain and a heavy chain variable domain, wherein the heavy chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-13 or to the amino acid sequence of SEQ ID NO: 37; and/or the light chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-13 or to the amino acid sequence of SEQ ID NO: 95. In some embodiments, anti-TREM2 antibodies of the present disclosure comprise a heavy chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-13 or to the amino acid sequence of SEQ ID NO: 37, wherein the heavy chain variable domain comprises the HVR-H1, HVR-H2, and HVR-H3 amino acid sequences of antibody AL2p-13. In some embodiments, anti-TREM2 antibodies of the present disclosure comprise a light chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-13 or to the amino acid sequence of SEQ ID NO: 95, wherein the light chain variable domain comprises the HVR-L1, HVR-L2, and HVR-L3 amino acid sequences of antibody AL2p-13. In some embodiments, the anti-TREM2 antibody comprises a heavy chain variable domain (VH) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-13 or to the amino acid sequence of SEQ ID NO: 37 and contains substitutions (e.g., conservative substitutions, insertions, or deletions relative to the reference sequence), but the anti-TREM2 antibody comprising that sequence retains the ability to bind to TREM2. In certain embodiments, a total of 1 to 10 amino acids have been substituted, inserted, and/or deleted in the heavy chain variable domain amino acid sequence of antibody AL2p-13 or the amino acid sequence of SEQ ID NO: 37. In certain embodiments, a total of 1 to 5 amino acids have been substituted, inserted and/or deleted in the heavy chain variable domain amino acid sequence of antibody AL2p-13 or the amino acid sequence of SEQ ID NO: 37. In certain embodiments, substitutions, insertions, or deletions occur in regions outside the HVRs (i.e., in the FR regions). In some embodiments, the substitutions, insertions, or deletions occur in in the FR regions. Optionally, the anti-TREM2 antibody comprises the VH sequence of antibody AL2p-13 or of SEQ ID NO: 37, including post-translational modifications of that sequence. In a particular embodiment, the VH comprises one, two or three HVRs selected from: (a) the HVR-H1 amino acid sequence of antibody AL2p-13, (b) the HVR-H2 amino acid sequence of antibody AL2p-13, and (c) the HVR-H3 amino acid sequence of antibody AL2p-13. In some embodiments, anti-TREM2 antibodies of the present disclosure comprise a light chain variable domain (VL) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-13 or to the amino acid sequence of SEQ ID NO: 95 and contains substitutions (e.g., conservative substitutions, insertions, or deletions relative to the reference sequence), but the anti-TREM2 antibody comprising that sequence retains the ability to bind to TREM2. In certain embodiments, a total of 1 to 10 amino acids have been substituted, inserted, and/or deleted in the light chain variable domain amino acid sequence of antibody AL2p-13 or the amino acid sequence of SEQ ID NO: 95. In certain embodiments, a total of 1 to 5 amino acids have been substituted, inserted and/or deleted in the light chain variable domain amino acid sequence of antibody AL2p-13 or the amino acid sequence of SEQ ID NO: 95. In certain embodiments, substitutions, insertions, or deletions occur in regions outside the HVRs (i.e., in the FR regions). In some embodiments, the substitutions, insertions, or deletions occur in in the FR regions. Optionally, the anti-TREM2 antibody comprises the VL sequence of antibody AL2p-13 or of SEQ ID NO: 95, including post-translational modifications of that sequence. In a particular embodiment, the VL comprises one, two or three HVRs selected from: (a) the HVR-L1 amino acid sequence of antibody AL2p-13, (b) the HVR-L2 amino acid sequence of antibody AL2p-13, and (c) the HVR-L3 amino acid sequence of antibody AL2p-13.

In some embodiments, anti-TREM2 antibodies of the present disclosure comprise a light chain variable domain and a heavy chain variable domain, wherein the heavy chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-14 or to the amino acid sequence of SEQ ID NO: 38; and/or the light chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-14 or to the amino acid sequence of SEQ ID NO: 99. In some embodiments, anti-TREM2 antibodies of the present disclosure comprise a heavy chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-14 or to the amino acid sequence of SEQ ID NO: 38, wherein the heavy chain variable domain comprises the HVR-H1, HVR-H2, and HVR-H3 amino acid sequences of antibody AL2p-14. In some embodiments, anti-TREM2 antibodies of the present disclosure comprise a light chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-14 or to the amino acid sequence of SEQ ID NO: 99, wherein the light chain variable domain comprises the HVR-L1, HVR-L2, and HVR-L3 amino acid sequences of antibody AL2p-14. In some embodiments, the anti-TREM2 antibody comprises a heavy chain variable domain (VH) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-14 or to the amino acid sequence of SEQ ID NO: 38 and contains substitutions (e.g., conservative substitutions, insertions, or deletions relative to the reference sequence), but the anti-TREM2 antibody comprising that sequence retains the ability to bind to TREM2. In certain embodiments, a total of 1 to 10 amino acids have been substituted, inserted, and/or deleted in the heavy chain variable domain amino acid sequence of antibody AL2p-14 or the amino acid sequence of SEQ ID NO: 38. In certain embodiments, a total of 1 to 5 amino acids have been substituted, inserted and/or deleted in the heavy chain variable domain amino acid sequence of antibody AL2p-14 or the amino acid sequence of SEQ ID NO: 38. In certain embodiments, substitutions, insertions, or deletions occur in regions outside the HVRs (i.e., in the FR regions). In some embodiments, the substitutions, insertions, or deletions occur in in the FR regions. Optionally, the anti-TREM2 antibody comprises the VH sequence of antibody AL2p-14 or of SEQ ID NO: 38, including post-translational modifications of that sequence. In a particular embodiment, the VH comprises one, two or three HVRs selected from: (a) the HVR-H1 amino acid sequence of antibody AL2p-14, (b) the HVR-H2 amino acid sequence of antibody AL2p-14, and (c) the HVR-H3 amino acid sequence of antibody AL2p-14. In some embodiments, anti-TREM2 antibodies of the present disclosure comprise a light chain variable domain (VL) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-14 or to the amino acid sequence of SEQ ID NO: 99 and contains substitutions (e.g., conservative substitutions, insertions, or deletions relative to the reference sequence), but the anti-TREM2 antibody comprising that sequence retains the ability to bind to TREM2. In certain embodiments, a total of 1 to 10 amino acids have been substituted, inserted, and/or deleted in the light chain variable domain amino acid sequence of antibody AL2p-14 or the amino acid sequence of SEQ ID NO: 99. In certain embodiments, a total of 1 to 5 amino acids have been substituted, inserted and/or deleted in the light chain variable domain amino acid sequence of antibody AL2p-14 or the amino acid sequence of SEQ ID NO: 99. In certain embodiments, substitutions, insertions, or deletions occur in regions outside the HVRs (i.e., in the FR regions). In some embodiments, the substitutions, insertions, or deletions occur in in the FR regions. Optionally, the anti-TREM2 antibody comprises the VL sequence of antibody AL2p-14 or of SEQ ID NO: 99, including post-translational modifications of that sequence. In a particular embodiment, the VL comprises one, two or three HVRs selected from: (a) the HVR-L1 amino acid sequence of antibody AL2p-14, (b) the HVR-L2 amino acid sequence of antibody AL2p-14, and (c) the HVR-L3 amino acid sequence of antibody AL2p-14.

In some embodiments, anti-TREM2 antibodies of the present disclosure comprise a light chain variable domain and a heavy chain variable domain, wherein the heavy chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-15 or to the amino acid sequence of SEQ ID NO: 38; and/or the light chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-15 or to the amino acid sequence of SEQ ID NO: 100. In some embodiments, anti-TREM2 antibodies of the present disclosure comprise a heavy chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-15 or to the amino acid sequence of SEQ ID NO: 38, wherein the heavy chain variable domain comprises the HVR-H1, HVR-H2, and HVR-H3 amino acid sequences of antibody AL2p-15. In some embodiments, anti-TREM2 antibodies of the present disclosure comprise a light chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-15 or to the amino acid sequence of SEQ ID NO: 100, wherein the light chain variable domain comprises the HVR-L1, HVR-L2, and HVR-L3 amino acid sequences of antibody AL2p-15. In some embodiments, the anti-TREM2 antibody comprises a heavy chain variable domain (VH) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-15 or to the amino acid sequence of SEQ ID NO: 38 and contains substitutions (e.g., conservative substitutions, insertions, or deletions relative to the reference sequence), but the anti-TREM2 antibody comprising that sequence retains the ability to bind to TREM2. In certain embodiments, a total of 1 to 10 amino acids have been substituted, inserted, and/or deleted in the heavy chain variable domain amino acid sequence of antibody AL2p-15 or the amino acid sequence of SEQ ID NO: 38. In certain embodiments, a total of 1 to 5 amino acids have been substituted, inserted and/or deleted in the heavy chain variable domain amino acid sequence of antibody AL2p-15 or the amino acid sequence of SEQ ID NO: 38. In certain embodiments, substitutions, insertions, or deletions occur in regions outside the HVRs (i.e., in the FR regions). In some embodiments, the substitutions, insertions, or deletions occur in in the FR regions. Optionally, the anti-TREM2 antibody comprises the VH sequence of antibody AL2p-15 or of SEQ ID NO: 38, including post-translational modifications of that sequence. In a particular embodiment, the VH comprises one, two or three HVRs selected from: (a) the HVR-H1 amino acid sequence of antibody AL2p-15, (b) the HVR-H2 amino acid sequence of antibody AL2p-15, and (c) the HVR-H3 amino acid sequence of antibody AL2p-15. In some embodiments, anti-TREM2 antibodies of the present disclosure comprise a light chain variable domain (VL) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-15 or to the amino acid sequence of SEQ ID NO: 100 and contains substitutions (e.g., conservative substitutions, insertions, or deletions relative to the reference sequence), but the anti-TREM2 antibody comprising that sequence retains the ability to bind to TREM2. In certain embodiments, a total of 1 to 10 amino acids have been substituted, inserted, and/or deleted in the light chain variable domain amino acid sequence of antibody AL2p-15 or the amino acid sequence of SEQ ID NO: 100. In certain embodiments, a total of 1 to 5 amino acids have been substituted, inserted and/or deleted in the light chain variable domain amino acid sequence of antibody AL2p-15 or the amino acid sequence of SEQ ID NO: 100. In certain embodiments, substitutions, insertions, or deletions occur in regions outside the HVRs (i.e., in the FR regions). In some embodiments, the substitutions, insertions, or deletions occur in in the FR regions. Optionally, the anti-TREM2 antibody comprises the VL sequence of antibody AL2p-15 or of SEQ ID NO: 100, including post-translational modifications of that sequence. In a particular embodiment, the VL comprises one, two or three HVRs selected from: (a) the HVR-L1 amino acid sequence of antibody AL2p-15, (b) the HVR-L2 amino acid sequence of antibody AL2p-15, and (c) the HVR-L3 amino acid sequence of antibody AL2p-15.

In some embodiments, anti-TREM2 antibodies of the present disclosure comprise a light chain variable domain and a heavy chain variable domain, wherein the heavy chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-16 or to the amino acid sequence of SEQ ID NO: 39; and/or the light chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-16 or to the amino acid sequence of SEQ ID NO: 96. In some embodiments, anti-TREM2 antibodies of the present disclosure comprise a heavy chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-16 or to the amino acid sequence of SEQ ID NO: 39, wherein the heavy chain variable domain comprises the HVR-H1, HVR-H2, and HVR-H3 amino acid sequences of antibody AL2p-16. In some embodiments, anti-TREM2 antibodies of the present disclosure comprise a light chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-16 or to the amino acid sequence of SEQ ID NO: 96, wherein the light chain variable domain comprises the HVR-L1, HVR-L2, and HVR-L3 amino acid sequences of antibody AL2p-16. In some embodiments, the anti-TREM2 antibody comprises a heavy chain variable domain (VH) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-16 or to the amino acid sequence of SEQ ID NO: 39 and contains substitutions (e.g., conservative substitutions, insertions, or deletions relative to the reference sequence), but the anti-TREM2 antibody comprising that sequence retains the ability to bind to TREM2. In certain embodiments, a total of 1 to 10 amino acids have been substituted, inserted, and/or deleted in the heavy chain variable domain amino acid sequence of antibody AL2p-16 or the amino acid sequence of SEQ ID NO: 39. In certain embodiments, a total of 1 to 5 amino acids have been substituted, inserted and/or deleted in the heavy chain variable domain amino acid sequence of antibody AL2p-16 or the amino acid sequence of SEQ ID NO: 39. In certain embodiments, substitutions, insertions, or deletions occur in regions outside the HVRs (i.e., in the FR regions). In some embodiments, the substitutions, insertions, or deletions occur in in the FR regions. Optionally, the anti-TREM2 antibody comprises the VH sequence of antibody AL2p-16 or of SEQ ID NO: 39, including post-translational modifications of that sequence. In a particular embodiment, the VH comprises one, two or three HVRs selected from: (a) the HVR-H1 amino acid sequence of antibody AL2p-16, (b) the HVR-H2 amino acid sequence of antibody AL2p-16, and (c) the HVR-H3 amino acid sequence of antibody AL2p-16. In some embodiments, anti-TREM2 antibodies of the present disclosure comprise a light chain variable domain (VL) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-16 or to the amino acid sequence of SEQ ID NO: 96 and contains substitutions (e.g., conservative substitutions, insertions, or deletions relative to the reference sequence), but the anti-TREM2 antibody comprising that sequence retains the ability to bind to TREM2. In certain embodiments, a total of 1 to 10 amino acids have been substituted, inserted, and/or deleted in the light chain variable domain amino acid sequence of antibody AL2p-16 or the amino acid sequence of SEQ ID NO: 96. In certain embodiments, a total of 1 to 5 amino acids have been substituted, inserted and/or deleted in the light chain variable domain amino acid sequence of antibody AL2p-16 or the amino acid sequence of SEQ ID NO: 96. In certain embodiments, substitutions, insertions, or deletions occur in regions outside the HVRs (i.e., in the FR regions). In some embodiments, the substitutions, insertions, or deletions occur in in the FR regions. Optionally, the anti-TREM2 antibody comprises the VL sequence of antibody AL2p-16 or of SEQ ID NO: 96, including post-translational modifications of that sequence. In a particular embodiment, the VL comprises one, two or three HVRs selected from: (a) the HVR-L1 amino acid sequence of antibody AL2p-16, (b) the HVR-L2 amino acid sequence of antibody AL2p-16, and (c) the HVR-L3 amino acid sequence of antibody AL2p-16.

In some embodiments, anti-TREM2 antibodies of the present disclosure comprise a light chain variable domain and a heavy chain variable domain, wherein the heavy chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-17 or to the amino acid sequence of SEQ ID NO: 40; and/or the light chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-17 or to the amino acid sequence of SEQ ID NO: 98. In some embodiments, anti-TREM2 antibodies of the present disclosure comprise a heavy chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-17 or to the amino acid sequence of SEQ ID NO: 40, wherein the heavy chain variable domain comprises the HVR-H1, HVR-H2, and HVR-H3 amino acid sequences of antibody AL2p-17. In some embodiments, anti-TREM2 antibodies of the present disclosure comprise a light chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-17 or to the amino acid sequence of SEQ ID NO: 98, wherein the light chain variable domain comprises the HVR-L1, HVR-L2, and HVR-L3 amino acid sequences of antibody AL2p-17. In some embodiments, the anti-TREM2 antibody comprises a heavy chain variable domain (VH) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-17 or to the amino acid sequence of SEQ ID NO: 40 and contains substitutions (e.g., conservative substitutions, insertions, or deletions relative to the reference sequence), but the anti-TREM2 antibody comprising that sequence retains the ability to bind to TREM2. In certain embodiments, a total of 1 to 10 amino acids have been substituted, inserted, and/or deleted in the heavy chain variable domain amino acid sequence of antibody AL2p-17 or the amino acid sequence of SEQ ID NO: 40. In certain embodiments, a total of 1 to 5 amino acids have been substituted, inserted and/or deleted in the heavy chain variable domain amino acid sequence of antibody AL2p-17 or the amino acid sequence of SEQ ID NO: 40. In certain embodiments, substitutions, insertions, or deletions occur in regions outside the HVRs (i.e., in the FR regions). In some embodiments, the substitutions, insertions, or deletions occur in in the FR regions. Optionally, the anti-TREM2 antibody comprises the VH sequence of antibody AL2p-17 or of SEQ ID NO: 40, including post-translational modifications of that sequence. In a particular embodiment, the VH comprises one, two or three HVRs selected from: (a) the HVR-H1 amino acid sequence of antibody AL2p-17, (b) the HVR-H2 amino acid sequence of antibody AL2p-17, and (c) the HVR-H3 amino acid sequence of antibody AL2p-17. In some embodiments, anti-TREM2 antibodies of the present disclosure comprise a light chain variable domain (VL) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-17 or to the amino acid sequence of SEQ ID NO: 98 and contains substitutions (e.g., conservative substitutions, insertions, or deletions relative to the reference sequence), but the anti-TREM2 antibody comprising that sequence retains the ability to bind to TREM2. In certain embodiments, a total of 1 to 10 amino acids have been substituted, inserted, and/or deleted in the light chain variable domain amino acid sequence of antibody AL2p-17 or the amino acid sequence of SEQ ID NO: 98. In certain embodiments, a total of 1 to 5 amino acids have been substituted, inserted and/or deleted in the light chain variable domain amino acid sequence of antibody AL2p-17 or the amino acid sequence of SEQ ID NO: 98. In certain embodiments, substitutions, insertions, or deletions occur in regions outside the HVRs (i.e., in the FR regions). In some embodiments, the substitutions, insertions, or deletions occur in in the FR regions. Optionally, the anti-TREM2 antibody comprises the VL sequence of antibody AL2p-17 or of SEQ ID NO: 98, including post-translational modifications of that sequence. In a particular embodiment, the VL comprises one, two or three HVRs selected from: (a) the HVR-L1 amino acid sequence of antibody AL2p-17, (b) the HVR-L2 amino acid sequence of antibody AL2p-17, and (c) the HVR-L3 amino acid sequence of antibody AL2p-17.

In some embodiments, anti-TREM2 antibodies of the present disclosure comprise a light chain variable domain and a heavy chain variable domain, wherein the heavy chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-18 or to the amino acid sequence of SEQ ID NO: 41; and/or the light chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-18 or to the amino acid sequence of SEQ ID NO: 96. In some embodiments, anti-TREM2 antibodies of the present disclosure comprise a heavy chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-18 or to the amino acid sequence of SEQ ID NO: 41, wherein the heavy chain variable domain comprises the HVR-H1, HVR-H2, and HVR-H3 amino acid sequences of antibody AL2p-18. In some embodiments, anti-TREM2 antibodies of the present disclosure comprise a light chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-18 or to the amino acid sequence of SEQ ID NO: 96, wherein the light chain variable domain comprises the HVR-L1, HVR-L2, and HVR-L3 amino acid sequences of antibody AL2p-18. In some embodiments, the anti-TREM2 antibody comprises a heavy chain variable domain (VH) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-18 or to the amino acid sequence of SEQ ID NO: 41 and contains substitutions (e.g., conservative substitutions, insertions, or deletions relative to the reference sequence), but the anti-TREM2 antibody comprising that sequence retains the ability to bind to TREM2. In certain embodiments, a total of 1 to 10 amino acids have been substituted, inserted, and/or deleted in the heavy chain variable domain amino acid sequence of antibody AL2p-18 or the amino acid sequence of SEQ ID NO: 41. In certain embodiments, a total of 1 to 5 amino acids have been substituted, inserted and/or deleted in the heavy chain variable domain amino acid sequence of antibody AL2p-18 or the amino acid sequence of SEQ ID NO: 41. In certain embodiments, substitutions, insertions, or deletions occur in regions outside the HVRs (i.e., in the FR regions). In some embodiments, the substitutions, insertions, or deletions occur in in the FR regions. Optionally, the anti-TREM2 antibody comprises the VH sequence of antibody AL2p-18 or of SEQ ID NO: 41, including post-translational modifications of that sequence. In a particular embodiment, the VH comprises one, two or three HVRs selected from: (a) the HVR-H1 amino acid sequence of antibody AL2p-18, (b) the HVR-H2 amino acid sequence of antibody AL2p-18, and (c) the HVR-H3 amino acid sequence of antibody AL2p-18. In some embodiments, anti-TREM2 antibodies of the present disclosure comprise a light chain variable domain (VL) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-18 or to the amino acid sequence of SEQ ID NO: 96 and contains substitutions (e.g., conservative substitutions, insertions, or deletions relative to the reference sequence), but the anti-TREM2 antibody comprising that sequence retains the ability to bind to TREM2. In certain embodiments, a total of 1 to 10 amino acids have been substituted, inserted, and/or deleted in the light chain variable domain amino acid sequence of antibody AL2p-18 or the amino acid sequence of SEQ ID NO: 96. In certain embodiments, a total of 1 to 5 amino acids have been substituted, inserted and/or deleted in the light chain variable domain amino acid sequence of antibody AL2p-18 or the amino acid sequence of SEQ ID NO: 96. In certain embodiments, substitutions, insertions, or deletions occur in regions outside the HVRs (i.e., in the FR regions). In some embodiments, the substitutions, insertions, or deletions occur in in the FR regions. Optionally, the anti-TREM2 antibody comprises the VL sequence of antibody AL2p-18 or of SEQ ID NO: 96, including post-translational modifications of that sequence. In a particular embodiment, the VL comprises one, two or three HVRs selected from: (a) the HVR-L1 amino acid sequence of antibody AL2p-18, (b) the HVR-L2 amino acid sequence of antibody AL2p-18, and (c) the HVR-L3 amino acid sequence of antibody AL2p-18.

In some embodiments, anti-TREM2 antibodies of the present disclosure comprise a light chain variable domain and a heavy chain variable domain, wherein the heavy chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-19 or to the amino acid sequence of SEQ ID NO: 42; and/or the light chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-19 or to the amino acid sequence of SEQ ID NO: 98. In some embodiments, anti-TREM2 antibodies of the present disclosure comprise a heavy chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-19 or to the amino acid sequence of SEQ ID NO: 42, wherein the heavy chain variable domain comprises the HVR-H1, HVR-H2, and HVR-H3 amino acid sequences of antibody AL2p-19. In some embodiments, anti-TREM2 antibodies of the present disclosure comprise a light chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-19 or to the amino acid sequence of SEQ ID NO: 98, wherein the light chain variable domain comprises the HVR-L1, HVR-L2, and HVR-L3 amino acid sequences of antibody AL2p-19. In some embodiments, the anti-TREM2 antibody comprises a heavy chain variable domain (VH) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-19 or to the amino acid sequence of SEQ ID NO: 42 and contains substitutions (e.g., conservative substitutions, insertions, or deletions relative to the reference sequence), but the anti-TREM2 antibody comprising that sequence retains the ability to bind to TREM2. In certain embodiments, a total of 1 to 10 amino acids have been substituted, inserted, and/or deleted in the heavy chain variable domain amino acid sequence of antibody AL2p-19 or the amino acid sequence of SEQ ID NO: 42. In certain embodiments, a total of 1 to 5 amino acids have been substituted, inserted and/or deleted in the heavy chain variable domain amino acid sequence of antibody AL2p-19 or the amino acid sequence of SEQ ID NO: 42. In certain embodiments, substitutions, insertions, or deletions occur in regions outside the HVRs (i.e., in the FR regions). In some embodiments, the substitutions, insertions, or deletions occur in in the FR regions. Optionally, the anti-TREM2 antibody comprises the VH sequence of antibody AL2p-19 or of SEQ ID NO: 42, including post-translational modifications of that sequence. In a particular embodiment, the VH comprises one, two or three HVRs selected from: (a) the HVR-H1 amino acid sequence of antibody AL2p-19, (b) the HVR-H2 amino acid sequence of antibody AL2p-19, and (c) the HVR-H3 amino acid sequence of antibody AL2p-19. In some embodiments, anti-TREM2 antibodies of the present disclosure comprise a light chain variable domain (VL) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-19 or to the amino acid sequence of SEQ ID NO: 98 and contains substitutions (e.g., conservative substitutions, insertions, or deletions relative to the reference sequence), but the anti-TREM2 antibody comprising that sequence retains the ability to bind to TREM2. In certain embodiments, a total of 1 to 10 amino acids have been substituted, inserted, and/or deleted in the light chain variable domain amino acid sequence of antibody AL2p-19 or the amino acid sequence of SEQ ID NO: 98. In certain embodiments, a total of 1 to 5 amino acids have been substituted, inserted and/or deleted in the light chain variable domain amino acid sequence of antibody AL2p-19 or the amino acid sequence of SEQ ID NO: 98. In certain embodiments, substitutions, insertions, or deletions occur in regions outside the HVRs (i.e., in the FR regions). In some embodiments, the substitutions, insertions, or deletions occur in in the FR regions. Optionally, the anti-TREM2 antibody comprises the VL sequence of antibody AL2p-19 or of SEQ ID NO: 98, including post-translational modifications of that sequence. In a particular embodiment, the VL comprises one, two or three HVRs selected from: (a) the HVR-L1 amino acid sequence of antibody AL2p-19, (b) the HVR-L2 amino acid sequence of antibody AL2p-19, and (c) the HVR-L3 amino acid sequence of antibody AL2p-19.

In some embodiments, anti-TREM2 antibodies of the present disclosure comprise a light chain variable domain and a heavy chain variable domain, wherein the heavy chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-20 or to the amino acid sequence of SEQ ID NO: 42; and/or the light chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-20 or to the amino acid sequence of SEQ ID NO: 96. In some embodiments, anti-TREM2 antibodies of the present disclosure comprise a heavy chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-20 or to the amino acid sequence of SEQ ID NO: 42, wherein the heavy chain variable domain comprises the HVR-H1, HVR-H2, and HVR-H3 amino acid sequences of antibody AL2p-20. In some embodiments, anti-TREM2 antibodies of the present disclosure comprise a light chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-20 or to the amino acid sequence of SEQ ID NO: 96, wherein the light chain variable domain comprises the HVR-L1, HVR-L2, and HVR-L3 amino acid sequences of antibody AL2p-20. In some embodiments, the anti-TREM2 antibody comprises a heavy chain variable domain (VH) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-20 or to the amino acid sequence of SEQ ID NO: 42 and contains substitutions (e.g., conservative substitutions, insertions, or deletions relative to the reference sequence), but the anti-TREM2 antibody comprising that sequence retains the ability to bind to TREM2. In certain embodiments, a total of 1 to 10 amino acids have been substituted, inserted, and/or deleted in the heavy chain variable domain amino acid sequence of antibody AL2p-20 or the amino acid sequence of SEQ ID NO: 42. In certain embodiments, a total of 1 to 5 amino acids have been substituted, inserted and/or deleted in the heavy chain variable domain amino acid sequence of antibody AL2p-20 or the amino acid sequence of SEQ ID NO: 42. In certain embodiments, substitutions, insertions, or deletions occur in regions outside the HVRs (i.e., in the FR regions). In some embodiments, the substitutions, insertions, or deletions occur in in the FR regions. Optionally, the anti-TREM2 antibody comprises the VH sequence of antibody AL2p-20 or of SEQ ID NO: 42, including post-translational modifications of that sequence. In a particular embodiment, the VH comprises one, two or three HVRs selected from: (a) the HVR-H1 amino acid sequence of antibody AL2p-20, (b) the HVR-H2 amino acid sequence of antibody AL2p-20, and (c) the HVR-H3 amino acid sequence of antibody AL2p-20. In some embodiments, anti-TREM2 antibodies of the present disclosure comprise a light chain variable domain (VL) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-20 or to the amino acid sequence of SEQ ID NO: 96 and contains substitutions (e.g., conservative substitutions, insertions, or deletions relative to the reference sequence), but the anti-TREM2 antibody comprising that sequence retains the ability to bind to TREM2. In certain embodiments, a total of 1 to 10 amino acids have been substituted, inserted, and/or deleted in the light chain variable domain amino acid sequence of antibody AL2p-20 or the amino acid sequence of SEQ ID NO: 96. In certain embodiments, a total of 1 to 5 amino acids have been substituted, inserted and/or deleted in the light chain variable domain amino acid sequence of antibody AL2p-20 or the amino acid sequence of SEQ ID NO: 96. In certain embodiments, substitutions, insertions, or deletions occur in regions outside the HVRs (i.e., in the FR regions). In some embodiments, the substitutions, insertions, or deletions occur in in the FR regions. Optionally, the anti-TREM2 antibody comprises the VL sequence of antibody AL2p-20 or of SEQ ID NO: 96, including post-translational modifications of that sequence. In a particular embodiment, the VL comprises one, two or three HVRs selected from: (a) the HVR-L1 amino acid sequence of antibody AL2p-20, (b) the HVR-L2 amino acid sequence of antibody AL2p-20, and (c) the HVR-L3 amino acid sequence of antibody AL2p-20.

In some embodiments, anti-TREM2 antibodies of the present disclosure comprise a light chain variable domain and a heavy chain variable domain, wherein the heavy chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-21 or to the amino acid sequence of SEQ ID NO: 43; and/or the light chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-21 or to the amino acid sequence of SEQ ID NO: 100. In some embodiments, anti-TREM2 antibodies of the present disclosure comprise a heavy chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-21 or to the amino acid sequence of SEQ ID NO: 43, wherein the heavy chain variable domain comprises the HVR-H1, HVR-H2, and HVR-H3 amino acid sequences of antibody AL2p-21. In some embodiments, anti-TREM2 antibodies of the present disclosure comprise a light chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-21 or to the amino acid sequence of SEQ ID NO: 100, wherein the light chain variable domain comprises the HVR-L1, HVR-L2, and HVR-L3 amino acid sequences of antibody AL2p-21. In some embodiments, the anti-TREM2 antibody comprises a heavy chain variable domain (VH) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-21 or to the amino acid sequence of SEQ ID NO: 43 and contains substitutions (e.g., conservative substitutions, insertions, or deletions relative to the reference sequence), but the anti-TREM2 antibody comprising that sequence retains the ability to bind to TREM2. In certain embodiments, a total of 1 to 10 amino acids have been substituted, inserted, and/or deleted in the heavy chain variable domain amino acid sequence of antibody AL2p-21 or the amino acid sequence of SEQ ID NO: 43. In certain embodiments, a total of 1 to 5 amino acids have been substituted, inserted and/or deleted in the heavy chain variable domain amino acid sequence of antibody AL2p-21 or the amino acid sequence of SEQ ID NO: 43. In certain embodiments, substitutions, insertions, or deletions occur in regions outside the HVRs (i.e., in the FR regions). In some embodiments, the substitutions, insertions, or deletions occur in in the FR regions. Optionally, the anti-TREM2 antibody comprises the VH sequence of antibody AL2p-21 or of SEQ ID NO: 43, including post-translational modifications of that sequence. In a particular embodiment, the VH comprises one, two or three HVRs selected from: (a) the HVR-H1 amino acid sequence of antibody AL2p-21, (b) the HVR-H2 amino acid sequence of antibody AL2p-21, and (c) the HVR-H3 amino acid sequence of antibody AL2p-21. In some embodiments, anti-TREM2 antibodies of the present disclosure comprise a light chain variable domain (VL) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-21 or to the amino acid sequence of SEQ ID NO: 100 and contains substitutions (e.g., conservative substitutions, insertions, or deletions relative to the reference sequence), but the anti-TREM2 antibody comprising that sequence retains the ability to bind to TREM2. In certain embodiments, a total of 1 to 10 amino acids have been substituted, inserted, and/or deleted in the light chain variable domain amino acid sequence of antibody AL2p-21 or the amino acid sequence of SEQ ID NO: 100. In certain embodiments, a total of 1 to 5 amino acids have been substituted, inserted and/or deleted in the light chain variable domain amino acid sequence of antibody AL2p-21 or the amino acid sequence of SEQ ID NO: 100. In certain embodiments, substitutions, insertions, or deletions occur in regions outside the HVRs (i.e., in the FR regions). In some embodiments, the substitutions, insertions, or deletions occur in in the FR regions. Optionally, the anti-TREM2 antibody comprises the VL sequence of antibody AL2p-21 or of SEQ ID NO: 100, including post-translational modifications of that sequence. In a particular embodiment, the VL comprises one, two or three HVRs selected from: (a) the HVR-L1 amino acid sequence of antibody AL2p-21, (b) the HVR-L2 amino acid sequence of antibody AL2p-21, and (c) the HVR-L3 amino acid sequence of antibody AL2p-21.

In some embodiments, anti-TREM2 antibodies of the present disclosure comprise a light chain variable domain and a heavy chain variable domain, wherein the heavy chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-22 or to the amino acid sequence of SEQ ID NO: 44; and/or the light chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-22 or to the amino acid sequence of SEQ ID NO: 101. In some embodiments, anti-TREM2 antibodies of the present disclosure comprise a heavy chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-22 or to the amino acid sequence of SEQ ID NO: 44, wherein the heavy chain variable domain comprises the HVR-H1, HVR-H2, and HVR-H3 amino acid sequences of antibody AL2p-22. In some embodiments, anti-TREM2 antibodies of the present disclosure comprise a light chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-22 or to the amino acid sequence of SEQ ID NO: 101, wherein the light chain variable domain comprises the HVR-L1, HVR-L2, and HVR-L3 amino acid sequences of antibody AL2p-22. In some embodiments, the anti-TREM2 antibody comprises a heavy chain variable domain (VH) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-22 or to the amino acid sequence of SEQ ID NO: 44 and contains substitutions (e.g., conservative substitutions, insertions, or deletions relative to the reference sequence), but the anti-TREM2 antibody comprising that sequence retains the ability to bind to TREM2. In certain embodiments, a total of 1 to 10 amino acids have been substituted, inserted, and/or deleted in the heavy chain variable domain amino acid sequence of antibody AL2p-22 or the amino acid sequence of SEQ ID NO: 44. In certain embodiments, a total of 1 to 5 amino acids have been substituted, inserted and/or deleted in the heavy chain variable domain amino acid sequence of antibody AL2p-22 or the amino acid sequence of SEQ ID NO: 44. In certain embodiments, substitutions, insertions, or deletions occur in regions outside the HVRs (i.e., in the FR regions). In some embodiments, the substitutions, insertions, or deletions occur in in the FR regions. Optionally, the anti-TREM2 antibody comprises the VH sequence of antibody AL2p-22 or of SEQ ID NO: 44, including post-translational modifications of that sequence. In a particular embodiment, the VH comprises one, two or three HVRs selected from: (a) the HVR-H1 amino acid sequence of antibody AL2p-22, (b) the HVR-H2 amino acid sequence of antibody AL2p-22, and (c) the HVR-H3 amino acid sequence of antibody AL2p-22. In some embodiments, anti-TREM2 antibodies of the present disclosure comprise a light chain variable domain (VL) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-22 or to the amino acid sequence of SEQ ID NO: 101 and contains substitutions (e.g., conservative substitutions, insertions, or deletions relative to the reference sequence), but the anti-TREM2 antibody comprising that sequence retains the ability to bind to TREM2. In certain embodiments, a total of 1 to 10 amino acids have been substituted, inserted, and/or deleted in the light chain variable domain amino acid sequence of antibody AL2p-22 or the amino acid sequence of SEQ ID NO: 101. In certain embodiments, a total of 1 to 5 amino acids have been substituted, inserted and/or deleted in the light chain variable domain amino acid sequence of antibody AL2p-22 or the amino acid sequence of SEQ ID NO: 101. In certain embodiments, substitutions, insertions, or deletions occur in regions outside the HVRs (i.e., in the FR regions). In some embodiments, the substitutions, insertions, or deletions occur in in the FR regions. Optionally, the anti-TREM2 antibody comprises the VL sequence of antibody AL2p-22 or of SEQ ID NO: 101, including post-translational modifications of that sequence. In a particular embodiment, the VL comprises one, two or three HVRs selected from: (a) the HVR-L1 amino acid sequence of antibody AL2p-22, (b) the HVR-L2 amino acid sequence of antibody AL2p-22, and (c) the HVR-L3 amino acid sequence of antibody AL2p-22.

In some embodiments, anti-TREM2 antibodies of the present disclosure comprise a light chain variable domain and a heavy chain variable domain, wherein the heavy chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-23 or to the amino acid sequence of SEQ ID NO: 45; and/or the light chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-23 or to the amino acid sequence of SEQ ID NO: 96. In some embodiments, anti-TREM2 antibodies of the present disclosure comprise a heavy chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-23 or to the amino acid sequence of SEQ ID NO: 45, wherein the heavy chain variable domain comprises the HVR-H1, HVR-H2, and HVR-H3 amino acid sequences of antibody AL2p-23. In some embodiments, anti-TREM2 antibodies of the present disclosure comprise a light chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-23 or to the amino acid sequence of SEQ ID NO: 96, wherein the light chain variable domain comprises the HVR-L1, HVR-L2, and HVR-L3 amino acid sequences of antibody AL2p-23. In some embodiments, the anti-TREM2 antibody comprises a heavy chain variable domain (VH) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-23 or to the amino acid sequence of SEQ ID NO: 45 and contains substitutions (e.g., conservative substitutions, insertions, or deletions relative to the reference sequence), but the anti-TREM2 antibody comprising that sequence retains the ability to bind to TREM2. In certain embodiments, a total of 1 to 10 amino acids have been substituted, inserted, and/or deleted in the heavy chain variable domain amino acid sequence of antibody AL2p-23 or the amino acid sequence of SEQ ID NO: 45. In certain embodiments, a total of 1 to 5 amino acids have been substituted, inserted and/or deleted in the heavy chain variable domain amino acid sequence of antibody AL2p-23 or the amino acid sequence of SEQ ID NO: 45. In certain embodiments, substitutions, insertions, or deletions occur in regions outside the HVRs (i.e., in the FR regions). In some embodiments, the substitutions, insertions, or deletions occur in in the FR regions. Optionally, the anti-TREM2 antibody comprises the VH sequence of antibody AL2p-23 or of SEQ ID NO: 45, including post-translational modifications of that sequence. In a particular embodiment, the VH comprises one, two or three HVRs selected from: (a) the HVR-H1 amino acid sequence of antibody AL2p-23, (b) the HVR-H2 amino acid sequence of antibody AL2p-23, and (c) the HVR-H3 amino acid sequence of antibody AL2p-23. In some embodiments, anti-TREM2 antibodies of the present disclosure comprise a light chain variable domain (VL) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-23 or to the amino acid sequence of SEQ ID NO: 96 and contains substitutions (e.g., conservative substitutions, insertions, or deletions relative to the reference sequence), but the anti-TREM2 antibody comprising that sequence retains the ability to bind to TREM2. In certain embodiments, a total of 1 to 10 amino acids have been substituted, inserted, and/or deleted in the light chain variable domain amino acid sequence of antibody AL2p-23 or the amino acid sequence of SEQ ID NO: 96. In certain embodiments, a total of 1 to 5 amino acids have been substituted, inserted and/or deleted in the light chain variable domain amino acid sequence of antibody AL2p-23 or the amino acid sequence of SEQ ID NO: 96. In certain embodiments, substitutions, insertions, or deletions occur in regions outside the HVRs (i.e., in the FR regions). In some embodiments, the substitutions, insertions, or deletions occur in in the FR regions. Optionally, the anti-TREM2 antibody comprises the VL sequence of antibody AL2p-23 or of SEQ ID NO: 96, including post-translational modifications of that sequence. In a particular embodiment, the VL comprises one, two or three HVRs selected from: (a) the HVR-L1 amino acid sequence of antibody AL2p-23, (b) the HVR-L2 amino acid sequence of antibody AL2p-23, and (c) the HVR-L3 amino acid sequence of antibody AL2p-23.

In some embodiments, anti-TREM2 antibodies of the present disclosure comprise a light chain variable domain and a heavy chain variable domain, wherein the heavy chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-24 or to the amino acid sequence of SEQ ID NO: 46; and/or the light chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-24 or to the amino acid sequence of SEQ ID NO: 99. In some embodiments, anti-TREM2 antibodies of the present disclosure comprise a heavy chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-24 or to the amino acid sequence of SEQ ID NO: 46, wherein the heavy chain variable domain comprises the HVR-H1, HVR-H2, and HVR-H3 amino acid sequences of antibody AL2p-24. In some embodiments, anti-TREM2 antibodies of the present disclosure comprise a light chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-24 or to the amino acid sequence of SEQ ID NO: 99, wherein the light chain variable domain comprises the HVR-L1, HVR-L2, and HVR-L3 amino acid sequences of antibody AL2p-24. In some embodiments, the anti-TREM2 antibody comprises a heavy chain variable domain (VH) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-24 or to the amino acid sequence of SEQ ID NO: 46 and contains substitutions (e.g., conservative substitutions, insertions, or deletions relative to the reference sequence), but the anti-TREM2 antibody comprising that sequence retains the ability to bind to TREM2. In certain embodiments, a total of 1 to 10 amino acids have been substituted, inserted, and/or deleted in the heavy chain variable domain amino acid sequence of antibody AL2p-24 or the amino acid sequence of SEQ ID NO: 46. In certain embodiments, a total of 1 to 5 amino acids have been substituted, inserted and/or deleted in the heavy chain variable domain amino acid sequence of antibody AL2p-24 or the amino acid sequence of SEQ ID NO: 46. In certain embodiments, substitutions, insertions, or deletions occur in regions outside the HVRs (i.e., in the FR regions). In some embodiments, the substitutions, insertions, or deletions occur in in the FR regions. Optionally, the anti-TREM2 antibody comprises the VH sequence of antibody AL2p-24 or of SEQ ID NO: 46, including post-translational modifications of that sequence. In a particular embodiment, the VH comprises one, two or three HVRs selected from: (a) the HVR-H1 amino acid sequence of antibody AL2p-24, (b) the HVR-H2 amino acid sequence of antibody AL2p-24, and (c) the HVR-H3 amino acid sequence of antibody AL2p-24. In some embodiments, anti-TREM2 antibodies of the present disclosure comprise a light chain variable domain (VL) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-24 or to the amino acid sequence of SEQ ID NO: 99 and contains substitutions (e.g., conservative substitutions, insertions, or deletions relative to the reference sequence), but the anti-TREM2 antibody comprising that sequence retains the ability to bind to TREM2. In certain embodiments, a total of 1 to 10 amino acids have been substituted, inserted, and/or deleted in the light chain variable domain amino acid sequence of antibody AL2p-24 or the amino acid sequence of SEQ ID NO: 99. In certain embodiments, a total of 1 to 5 amino acids have been substituted, inserted and/or deleted in the light chain variable domain amino acid sequence of antibody AL2p-24 or the amino acid sequence of SEQ ID NO: 99. In certain embodiments, substitutions, insertions, or deletions occur in regions outside the HVRs (i.e., in the FR regions). In some embodiments, the substitutions, insertions, or deletions occur in in the FR regions. Optionally, the anti-TREM2 antibody comprises the VL sequence of antibody AL2p-24 or of SEQ ID NO: 99, including post-translational modifications of that sequence. In a particular embodiment, the VL comprises one, two or three HVRs selected from: (a) the HVR-L1 amino acid sequence of antibody AL2p-24, (b) the HVR-L2 amino acid sequence of antibody AL2p-24, and (c) the HVR-L3 amino acid sequence of antibody AL2p-24.

In some embodiments, anti-TREM2 antibodies of the present disclosure comprise a light chain variable domain and a heavy chain variable domain, wherein the heavy chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-25 or to the amino acid sequence of SEQ ID NO: 47; and/or the light chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-25 or to the amino acid sequence of SEQ ID NO: 96. In some embodiments, anti-TREM2 antibodies of the present disclosure comprise a heavy chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-25 or to the amino acid sequence of SEQ ID NO: 47, wherein the heavy chain variable domain comprises the HVR-H1, HVR-H2, and HVR-H3 amino acid sequences of antibody AL2p-25. In some embodiments, anti-TREM2 antibodies of the present disclosure comprise a light chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-25 or to the amino acid sequence of SEQ ID NO: 96, wherein the light chain variable domain comprises the HVR-L1, HVR-L2, and HVR-L3 amino acid sequences of antibody AL2p-25. In some embodiments, the anti-TREM2 antibody comprises a heavy chain variable domain (VH) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-25 or to the amino acid sequence of SEQ ID NO: 47 and contains substitutions (e.g., conservative substitutions, insertions, or deletions relative to the reference sequence), but the anti-TREM2 antibody comprising that sequence retains the ability to bind to TREM2. In certain embodiments, a total of 1 to 10 amino acids have been substituted, inserted, and/or deleted in the heavy chain variable domain amino acid sequence of antibody AL2p-25 or the amino acid sequence of SEQ ID NO: 47. In certain embodiments, a total of 1 to 5 amino acids have been substituted, inserted and/or deleted in the heavy chain variable domain amino acid sequence of antibody AL2p-25 or the amino acid sequence of SEQ ID NO: 47. In certain embodiments, substitutions, insertions, or deletions occur in regions outside the HVRs (i.e., in the FR regions). In some embodiments, the substitutions, insertions, or deletions occur in in the FR regions. Optionally, the anti-TREM2 antibody comprises the VH sequence of antibody AL2p-25 or of SEQ ID NO: 47, including post-translational modifications of that sequence. In a particular embodiment, the VH comprises one, two or three HVRs selected from: (a) the HVR-H1 amino acid sequence of antibody AL2p-25, (b) the HVR-H2 amino acid sequence of antibody AL2p-25, and (c) the HVR-H3 amino acid sequence of antibody AL2p-25. In some embodiments, anti-TREM2 antibodies of the present disclosure comprise a light chain variable domain (VL) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-25 or to the amino acid sequence of SEQ ID NO: 96 and contains substitutions (e.g., conservative substitutions, insertions, or deletions relative to the reference sequence), but the anti-TREM2 antibody comprising that sequence retains the ability to bind to TREM2. In certain embodiments, a total of 1 to 10 amino acids have been substituted, inserted, and/or deleted in the light chain variable domain amino acid sequence of antibody AL2p-25 or the amino acid sequence of SEQ ID NO: 96. In certain embodiments, a total of 1 to 5 amino acids have been substituted, inserted and/or deleted in the light chain variable domain amino acid sequence of antibody AL2p-25 or the amino acid sequence of SEQ ID NO: 96. In certain embodiments, substitutions, insertions, or deletions occur in regions outside the HVRs (i.e., in the FR regions). In some embodiments, the substitutions, insertions, or deletions occur in in the FR regions. Optionally, the anti-TREM2 antibody comprises the VL sequence of antibody AL2p-25 or of SEQ ID NO: 96, including post-translational modifications of that sequence. In a particular embodiment, the VL comprises one, two or three HVRs selected from: (a) the HVR-L1 amino acid sequence of antibody AL2p-25, (b) the HVR-L2 amino acid sequence of antibody AL2p-25, and (c) the HVR-L3 amino acid sequence of antibody AL2p-25.

In some embodiments, anti-TREM2 antibodies of the present disclosure comprise a light chain variable domain and a heavy chain variable domain, wherein the heavy chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-26 or to the amino acid sequence of SEQ ID NO: 48; and/or the light chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-26 or to the amino acid sequence of SEQ ID NO: 95. In some embodiments, anti-TREM2 antibodies of the present disclosure comprise a heavy chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-26 or to the amino acid sequence of SEQ ID NO: 48, wherein the heavy chain variable domain comprises the HVR-H1, HVR-H2, and HVR-H3 amino acid sequences of antibody AL2p-26. In some embodiments, anti-TREM2 antibodies of the present disclosure comprise a light chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-26 or to the amino acid sequence of SEQ ID NO: 95, wherein the light chain variable domain comprises the HVR-L1, HVR-L2, and HVR-L3 amino acid sequences of antibody AL2p-26. In some embodiments, the anti-TREM2 antibody comprises a heavy chain variable domain (VH) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-26 or to the amino acid sequence of SEQ ID NO: 48 and contains substitutions (e.g., conservative substitutions, insertions, or deletions relative to the reference sequence), but the anti-TREM2 antibody comprising that sequence retains the ability to bind to TREM2. In certain embodiments, a total of 1 to 10 amino acids have been substituted, inserted, and/or deleted in the heavy chain variable domain amino acid sequence of antibody AL2p-26 or the amino acid sequence of SEQ ID NO: 48. In certain embodiments, a total of 1 to 5 amino acids have been substituted, inserted and/or deleted in the heavy chain variable domain amino acid sequence of antibody AL2p-26 or the amino acid sequence of SEQ ID NO: 48. In certain embodiments, substitutions, insertions, or deletions occur in regions outside the HVRs (i.e., in the FR regions). In some embodiments, the substitutions, insertions, or deletions occur in in the FR regions. Optionally, the anti-TREM2 antibody comprises the VH sequence of antibody AL2p-26 or of SEQ ID NO: 48, including post-translational modifications of that sequence. In a particular embodiment, the VH comprises one, two or three HVRs selected from: (a) the HVR-H1 amino acid sequence of antibody AL2p-26, (b) the HVR-H2 amino acid sequence of antibody AL2p-26, and (c) the HVR-H3 amino acid sequence of antibody AL2p-26. In some embodiments, anti-TREM2 antibodies of the present disclosure comprise a light chain variable domain (VL) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-26 or to the amino acid sequence of SEQ ID NO: 95 and contains substitutions (e.g., conservative substitutions, insertions, or deletions relative to the reference sequence), but the anti-TREM2 antibody comprising that sequence retains the ability to bind to TREM2. In certain embodiments, a total of 1 to 10 amino acids have been substituted, inserted, and/or deleted in the light chain variable domain amino acid sequence of antibody AL2p-26 or the amino acid sequence of SEQ ID NO: 95. In certain embodiments, a total of 1 to 5 amino acids have been substituted, inserted and/or deleted in the light chain variable domain amino acid sequence of antibody AL2p-26 or the amino acid sequence of SEQ ID NO: 95. In certain embodiments, substitutions, insertions, or deletions occur in regions outside the HVRs (i.e., in the FR regions). In some embodiments, the substitutions, insertions, or deletions occur in in the FR regions. Optionally, the anti-TREM2 antibody comprises the VL sequence of antibody AL2p-26 or of SEQ ID NO: 95, including post-translational modifications of that sequence. In a particular embodiment, the VL comprises one, two or three HVRs selected from: (a) the HVR-L1 amino acid sequence of antibody AL2p-26, (b) the HVR-L2 amino acid sequence of antibody AL2p-26, and (c) the HVR-L3 amino acid sequence of antibody AL2p-26.

In some embodiments, anti-TREM2 antibodies of the present disclosure comprise a light chain variable domain and a heavy chain variable domain, wherein the heavy chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-27 or to the amino acid sequence of SEQ ID NO: 49; and/or the light chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-27 or to the amino acid sequence of SEQ ID NO: 102. In some embodiments, anti-TREM2 antibodies of the present disclosure comprise a heavy chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-27 or to the amino acid sequence of SEQ ID NO: 49, wherein the heavy chain variable domain comprises the HVR-H1, HVR-H2, and HVR-H3 amino acid sequences of antibody AL2p-27. In some embodiments, anti-TREM2 antibodies of the present disclosure comprise a light chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-27 or to the amino acid sequence of SEQ ID NO: 102, wherein the light chain variable domain comprises the HVR-L1, HVR-L2, and HVR-L3 amino acid sequences of antibody AL2p-27. In some embodiments, the anti-TREM2 antibody comprises a heavy chain variable domain (VH) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-27 or to the amino acid sequence of SEQ ID NO: 49 and contains substitutions (e.g., conservative substitutions, insertions, or deletions relative to the reference sequence), but the anti-TREM2 antibody comprising that sequence retains the ability to bind to TREM2. In certain embodiments, a total of 1 to 10 amino acids have been substituted, inserted, and/or deleted in the heavy chain variable domain amino acid sequence of antibody AL2p-27 or the amino acid sequence of SEQ ID NO: 49. In certain embodiments, a total of 1 to 5 amino acids have been substituted, inserted and/or deleted in the heavy chain variable domain amino acid sequence of antibody AL2p-27 or the amino acid sequence of SEQ ID NO: 49. In certain embodiments, substitutions, insertions, or deletions occur in regions outside the HVRs (i.e., in the FR regions). In some embodiments, the substitutions, insertions, or deletions occur in in the FR regions. Optionally, the anti-TREM2 antibody comprises the VH sequence of antibody AL2p-27 or of SEQ ID NO: 49, including post-translational modifications of that sequence. In a particular embodiment, the VH comprises one, two or three HVRs selected from: (a) the HVR-H1 amino acid sequence of antibody AL2p-27, (b) the HVR-H2 amino acid sequence of antibody AL2p-27, and (c) the HVR-H3 amino acid sequence of antibody AL2p-27. In some embodiments, anti-TREM2 antibodies of the present disclosure comprise a light chain variable domain (VL) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-27 or to the amino acid sequence of SEQ ID NO: 102 and contains substitutions (e.g., conservative substitutions, insertions, or deletions relative to the reference sequence), but the anti-TREM2 antibody comprising that sequence retains the ability to bind to TREM2. In certain embodiments, a total of 1 to 10 amino acids have been substituted, inserted, and/or deleted in the light chain variable domain amino acid sequence of antibody AL2p-27 or the amino acid sequence of SEQ ID NO: 102. In certain embodiments, a total of 1 to 5 amino acids have been substituted, inserted and/or deleted in the light chain variable domain amino acid sequence of antibody AL2p-27 or the amino acid sequence of SEQ ID NO: 102. In certain embodiments, substitutions, insertions, or deletions occur in regions outside the HVRs (i.e., in the FR regions). In some embodiments, the substitutions, insertions, or deletions occur in in the FR regions. Optionally, the anti-TREM2 antibody comprises the VL sequence of antibody AL2p-27 or of SEQ ID NO: 102, including post-translational modifications of that sequence. In a particular embodiment, the VL comprises one, two or three HVRs selected from: (a) the HVR-L1 amino acid sequence of antibody AL2p-27, (b) the HVR-L2 amino acid sequence of antibody AL2p-27, and (c) the HVR-L3 amino acid sequence of antibody AL2p-27.

In some embodiments, anti-TREM2 antibodies of the present disclosure comprise a light chain variable domain and a heavy chain variable domain, wherein the heavy chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-28 or to the amino acid sequence of SEQ ID NO: 50; and/or the light chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-28 or to the amino acid sequence of SEQ ID NO: 96. In some embodiments, anti-TREM2 antibodies of the present disclosure comprise a heavy chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-28 or to the amino acid sequence of SEQ ID NO: 50, wherein the heavy chain variable domain comprises the HVR-H1, HVR-H2, and HVR-H3 amino acid sequences of antibody AL2p-28. In some embodiments, anti-TREM2 antibodies of the present disclosure comprise a light chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-28 or to the amino acid sequence of SEQ ID NO: 96, wherein the light chain variable domain comprises the HVR-L1, HVR-L2, and HVR-L3 amino acid sequences of antibody AL2p-28. In some embodiments, the anti-TREM2 antibody comprises a heavy chain variable domain (VH) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-28 or to the amino acid sequence of SEQ ID NO: 50 and contains substitutions (e.g., conservative substitutions, insertions, or deletions relative to the reference sequence), but the anti-TREM2 antibody comprising that sequence retains the ability to bind to TREM2. In certain embodiments, a total of 1 to 10 amino acids have been substituted, inserted, and/or deleted in the heavy chain variable domain amino acid sequence of antibody AL2p-28 or the amino acid sequence of SEQ ID NO: 50. In certain embodiments, a total of 1 to 5 amino acids have been substituted, inserted and/or deleted in the heavy chain variable domain amino acid sequence of antibody AL2p-28 or the amino acid sequence of SEQ ID NO: 50. In certain embodiments, substitutions, insertions, or deletions occur in regions outside the HVRs (i.e., in the FR regions). In some embodiments, the substitutions, insertions, or deletions occur in in the FR regions. Optionally, the anti-TREM2 antibody comprises the VH sequence of antibody AL2p-28 or of SEQ ID NO: 50, including post-translational modifications of that sequence. In a particular embodiment, the VH comprises one, two or three HVRs selected from: (a) the HVR-H1 amino acid sequence of antibody AL2p-28, (b) the HVR-H2 amino acid sequence of antibody AL2p-28, and (c) the HVR-H3 amino acid sequence of antibody AL2p-28. In some embodiments, anti-TREM2 antibodies of the present disclosure comprise a light chain variable domain (VL) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-28 or to the amino acid sequence of SEQ ID NO: 96 and contains substitutions (e.g., conservative substitutions, insertions, or deletions relative to the reference sequence), but the anti-TREM2 antibody comprising that sequence retains the ability to bind to TREM2. In certain embodiments, a total of 1 to 10 amino acids have been substituted, inserted, and/or deleted in the light chain variable domain amino acid sequence of antibody AL2p-28 or the amino acid sequence of SEQ ID NO: 96. In certain embodiments, a total of 1 to 5 amino acids have been substituted, inserted and/or deleted in the light chain variable domain amino acid sequence of antibody AL2p-28 or the amino acid sequence of SEQ ID NO: 96. In certain embodiments, substitutions, insertions, or deletions occur in regions outside the HVRs (i.e., in the FR regions). In some embodiments, the substitutions, insertions, or deletions occur in in the FR regions. Optionally, the anti-TREM2 antibody comprises the VL sequence of antibody AL2p-28 or of SEQ ID NO: 96, including post-translational modifications of that sequence. In a particular embodiment, the VL comprises one, two or three HVRs selected from: (a) the HVR-L1 amino acid sequence of antibody AL2p-28, (b) the HVR-L2 amino acid sequence of antibody AL2p-28, and (c) the HVR-L3 amino acid sequence of antibody AL2p-28.

In some embodiments, anti-TREM2 antibodies of the present disclosure comprise a light chain variable domain and a heavy chain variable domain, wherein the heavy chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-29 or to the amino acid sequence of SEQ ID NO: 51; and/or the light chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-29 or to the amino acid sequence of SEQ ID NO: 99. In some embodiments, anti-TREM2 antibodies of the present disclosure comprise a heavy chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-29 or to the amino acid sequence of SEQ ID NO: 51, wherein the heavy chain variable domain comprises the HVR-H1, HVR-H2, and HVR-H3 amino acid sequences of antibody AL2p-29. In some embodiments, anti-TREM2 antibodies of the present disclosure comprise a light chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-29 or to the amino acid sequence of SEQ ID NO: 99, wherein the light chain variable domain comprises the HVR-L1, HVR-L2, and HVR-L3 amino acid sequences of antibody AL2p-29. In some embodiments, the anti-TREM2 antibody comprises a heavy chain variable domain (VH) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-29 or to the amino acid sequence of SEQ ID NO: 51 and contains substitutions (e.g., conservative substitutions, insertions, or deletions relative to the reference sequence), but the anti-TREM2 antibody comprising that sequence retains the ability to bind to TREM2. In certain embodiments, a total of 1 to 10 amino acids have been substituted, inserted, and/or deleted in the heavy chain variable domain amino acid sequence of antibody AL2p-29 or the amino acid sequence of SEQ ID NO: 51. In certain embodiments, a total of 1 to 5 amino acids have been substituted, inserted and/or deleted in the heavy chain variable domain amino acid sequence of antibody AL2p-29 or the amino acid sequence of SEQ ID NO: 51. In certain embodiments, substitutions, insertions, or deletions occur in regions outside the HVRs (i.e., in the FR regions). In some embodiments, the substitutions, insertions, or deletions occur in in the FR regions. Optionally, the anti-TREM2 antibody comprises the VH sequence of antibody AL2p-29 or of SEQ ID NO: 51, including post-translational modifications of that sequence. In a particular embodiment, the VH comprises one, two or three HVRs selected from: (a) the HVR-H1 amino acid sequence of antibody AL2p-29, (b) the HVR-H2 amino acid sequence of antibody AL2p-29, and (c) the HVR-H3 amino acid sequence of antibody AL2p-29. In some embodiments, anti-TREM2 antibodies of the present disclosure comprise a light chain variable domain (VL) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-29 or to the amino acid sequence of SEQ ID NO: 99 and contains substitutions (e.g., conservative substitutions, insertions, or deletions relative to the reference sequence), but the anti-TREM2 antibody comprising that sequence retains the ability to bind to TREM2. In certain embodiments, a total of 1 to 10 amino acids have been substituted, inserted, and/or deleted in the light chain variable domain amino acid sequence of antibody AL2p-29 or the amino acid sequence of SEQ ID NO: 99. In certain embodiments, a total of 1 to 5 amino acids have been substituted, inserted and/or deleted in the light chain variable domain amino acid sequence of antibody AL2p-29 or the amino acid sequence of SEQ ID NO: 99. In certain embodiments, substitutions, insertions, or deletions occur in regions outside the HVRs (i.e., in the FR regions). In some embodiments, the substitutions, insertions, or deletions occur in in the FR regions. Optionally, the anti-TREM2 antibody comprises the VL sequence of antibody AL2p-29 or of SEQ ID NO: 99, including post-translational modifications of that sequence. In a particular embodiment, the VL comprises one, two or three HVRs selected from: (a) the HVR-L1 amino acid sequence of antibody AL2p-29, (b) the HVR-L2 amino acid sequence of antibody AL2p-29, and (c) the HVR-L3 amino acid sequence of antibody AL2p-29.

In some embodiments, anti-TREM2 antibodies of the present disclosure comprise a light chain variable domain and a heavy chain variable domain, wherein the heavy chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-30 or to the amino acid sequence of SEQ ID NO: 52; and/or the light chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-30 or to the amino acid sequence of SEQ ID NO: 100. In some embodiments, anti-TREM2 antibodies of the present disclosure comprise a heavy chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-30 or to the amino acid sequence of SEQ ID NO: 52, wherein the heavy chain variable domain comprises the HVR-H1, HVR-H2, and HVR-H3 amino acid sequences of antibody AL2p-30. In some embodiments, anti-TREM2 antibodies of the present disclosure comprise a light chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-30 or to the amino acid sequence of SEQ ID NO: 100, wherein the light chain variable domain comprises the HVR-L1, HVR-L2, and HVR-L3 amino acid sequences of antibody AL2p-30. In some embodiments, the anti-TREM2 antibody comprises a heavy chain variable domain (VH) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-30 or to the amino acid sequence of SEQ ID NO: 52 and contains substitutions (e.g., conservative substitutions, insertions, or deletions relative to the reference sequence), but the anti-TREM2 antibody comprising that sequence retains the ability to bind to TREM2. In certain embodiments, a total of 1 to 10 amino acids have been substituted, inserted, and/or deleted in the heavy chain variable domain amino acid sequence of antibody AL2p-30 or the amino acid sequence of SEQ ID NO: 52. In certain embodiments, a total of 1 to 5 amino acids have been substituted, inserted and/or deleted in the heavy chain variable domain amino acid sequence of antibody AL2p-30 or the amino acid sequence of SEQ ID NO: 52. In certain embodiments, substitutions, insertions, or deletions occur in regions outside the HVRs (i.e., in the FR regions). In some embodiments, the substitutions, insertions, or deletions occur in in the FR regions. Optionally, the anti-TREM2 antibody comprises the VH sequence of antibody AL2p-30 or of SEQ ID NO: 52, including post-translational modifications of that sequence. In a particular embodiment, the VH comprises one, two or three HVRs selected from: (a) the HVR-H1 amino acid sequence of antibody AL2p-30, (b) the HVR-H2 amino acid sequence of antibody AL2p-30, and (c) the HVR-H3 amino acid sequence of antibody AL2p-30. In some embodiments, anti-TREM2 antibodies of the present disclosure comprise a light chain variable domain (VL) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-30 or to the amino acid sequence of SEQ ID NO: 100 and contains substitutions (e.g., conservative substitutions, insertions, or deletions relative to the reference sequence), but the anti-TREM2 antibody comprising that sequence retains the ability to bind to TREM2. In certain embodiments, a total of 1 to 10 amino acids have been substituted, inserted, and/or deleted in the light chain variable domain amino acid sequence of antibody AL2p-30 or the amino acid sequence of SEQ ID NO: 100. In certain embodiments, a total of 1 to 5 amino acids have been substituted, inserted and/or deleted in the light chain variable domain amino acid sequence of antibody AL2p-30 or the amino acid sequence of SEQ ID NO: 100. In certain embodiments, substitutions, insertions, or deletions occur in regions outside the HVRs (i.e., in the FR regions). In some embodiments, the substitutions, insertions, or deletions occur in in the FR regions. Optionally, the anti-TREM2 antibody comprises the VL sequence of antibody AL2p-30 or of SEQ ID NO: 100, including post-translational modifications of that sequence. In a particular embodiment, the VL comprises one, two or three HVRs selected from: (a) the HVR-L1 amino acid sequence of antibody AL2p-30, (b) the HVR-L2 amino acid sequence of antibody AL2p-30, and (c) the HVR-L3 amino acid sequence of antibody AL2p-30.

In some embodiments, anti-TREM2 antibodies of the present disclosure comprise a light chain variable domain and a heavy chain variable domain, wherein the heavy chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-31 or to the amino acid sequence of SEQ ID NO: 53; and/or the light chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-31 or to the amino acid sequence of SEQ ID NO: 97. In some embodiments, anti-TREM2 antibodies of the present disclosure comprise a heavy chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-31 or to the amino acid sequence of SEQ ID NO: 53, wherein the heavy chain variable domain comprises the HVR-H1, HVR-H2, and HVR-H3 amino acid sequences of antibody AL2p-31. In some embodiments, anti-TREM2 antibodies of the present disclosure comprise a light chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-31 or to the amino acid sequence of SEQ ID NO: 97, wherein the light chain variable domain comprises the HVR-L1, HVR-L2, and HVR-L3 amino acid sequences of antibody AL2p-31. In some embodiments, the anti-TREM2 antibody comprises a heavy chain variable domain (VH) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-31 or to the amino acid sequence of SEQ ID NO: 53 and contains substitutions (e.g., conservative substitutions, insertions, or deletions relative to the reference sequence), but the anti-TREM2 antibody comprising that sequence retains the ability to bind to TREM2. In certain embodiments, a total of 1 to 10 amino acids have been substituted, inserted, and/or deleted in the heavy chain variable domain amino acid sequence of antibody AL2p-31 or the amino acid sequence of SEQ ID NO: 53. In certain embodiments, a total of 1 to 5 amino acids have been substituted, inserted and/or deleted in the heavy chain variable domain amino acid sequence of antibody AL2p-31 or the amino acid sequence of SEQ ID NO: 53. In certain embodiments, substitutions, insertions, or deletions occur in regions outside the HVRs (i.e., in the FR regions). In some embodiments, the substitutions, insertions, or deletions occur in in the FR regions. Optionally, the anti-TREM2 antibody comprises the VH sequence of antibody AL2p-31 or of SEQ ID NO: 53, including post-translational modifications of that sequence. In a particular embodiment, the VH comprises one, two or three HVRs selected from: (a) the HVR-H1 amino acid sequence of antibody AL2p-31, (b) the HVR-H2 amino acid sequence of antibody AL2p-31, and (c) the HVR-H3 amino acid sequence of antibody AL2p-31. In some embodiments, anti-TREM2 antibodies of the present disclosure comprise a light chain variable domain (VL) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-31 or to the amino acid sequence of SEQ ID NO: 97 and contains substitutions (e.g., conservative substitutions, insertions, or deletions relative to the reference sequence), but the anti-TREM2 antibody comprising that sequence retains the ability to bind to TREM2. In certain embodiments, a total of 1 to 10 amino acids have been substituted, inserted, and/or deleted in the light chain variable domain amino acid sequence of antibody AL2p-31 or the amino acid sequence of SEQ ID NO: 97. In certain embodiments, a total of 1 to 5 amino acids have been substituted, inserted and/or deleted in the light chain variable domain amino acid sequence of antibody AL2p-31 or the amino acid sequence of SEQ ID NO: 97. In certain embodiments, substitutions, insertions, or deletions occur in regions outside the HVRs (i.e., in the FR regions). In some embodiments, the substitutions, insertions, or deletions occur in in the FR regions. Optionally, the anti-TREM2 antibody comprises the VL sequence of antibody AL2p-31 or of SEQ ID NO: 97, including post-translational modifications of that sequence. In a particular embodiment, the VL comprises one, two or three HVRs selected from: (a) the HVR-L1 amino acid sequence of antibody AL2p-31, (b) the HVR-L2 amino acid sequence of antibody AL2p-31, and (c) the HVR-L3 amino acid sequence of antibody AL2p-31.

In some embodiments, anti-TREM2 antibodies of the present disclosure comprise a light chain variable domain and a heavy chain variable domain, wherein the heavy chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-32 or to the amino acid sequence of SEQ ID NO: 54; and/or the light chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-32 or to the amino acid sequence of SEQ ID NO: 97. In some embodiments, anti-TREM2 antibodies of the present disclosure comprise a heavy chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-32 or to the amino acid sequence of SEQ ID NO: 54, wherein the heavy chain variable domain comprises the HVR-H1, HVR-H2, and HVR-H3 amino acid sequences of antibody AL2p-32. In some embodiments, anti-TREM2 antibodies of the present disclosure comprise a light chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-32 or to the amino acid sequence of SEQ ID NO: 97, wherein the light chain variable domain comprises the HVR-L1, HVR-L2, and HVR-L3 amino acid sequences of antibody AL2p-32. In some embodiments, the anti-TREM2 antibody comprises a heavy chain variable domain (VH) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-32 or to the amino acid sequence of SEQ ID NO: 54 and contains substitutions (e.g., conservative substitutions, insertions, or deletions relative to the reference sequence), but the anti-TREM2 antibody comprising that sequence retains the ability to bind to TREM2. In certain embodiments, a total of 1 to 10 amino acids have been substituted, inserted, and/or deleted in the heavy chain variable domain amino acid sequence of antibody AL2p-32 or the amino acid sequence of SEQ ID NO: 54. In certain embodiments, a total of 1 to 5 amino acids have been substituted, inserted and/or deleted in the heavy chain variable domain amino acid sequence of antibody AL2p-32 or the amino acid sequence of SEQ ID NO: 54. In certain embodiments, substitutions, insertions, or deletions occur in regions outside the HVRs (i.e., in the FR regions). In some embodiments, the substitutions, insertions, or deletions occur in in the FR regions. Optionally, the anti-TREM2 antibody comprises the VH sequence of antibody AL2p-32 or of SEQ ID NO: 54, including post-translational modifications of that sequence. In a particular embodiment, the VH comprises one, two or three HVRs selected from: (a) the HVR-H1 amino acid sequence of antibody AL2p-32, (b) the HVR-H2 amino acid sequence of antibody AL2p-32, and (c) the HVR-H3 amino acid sequence of antibody AL2p-32. In some embodiments, anti-TREM2 antibodies of the present disclosure comprise a light chain variable domain (VL) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-32 or to the amino acid sequence of SEQ ID NO: 97 and contains substitutions (e.g., conservative substitutions, insertions, or deletions relative to the reference sequence), but the anti-TREM2 antibody comprising that sequence retains the ability to bind to TREM2. In certain embodiments, a total of 1 to 10 amino acids have been substituted, inserted, and/or deleted in the light chain variable domain amino acid sequence of antibody AL2p-32 or the amino acid sequence of SEQ ID NO: 97. In certain embodiments, a total of 1 to 5 amino acids have been substituted, inserted and/or deleted in the light chain variable domain amino acid sequence of antibody AL2p-32 or the amino acid sequence of SEQ ID NO: 97. In certain embodiments, substitutions, insertions, or deletions occur in regions outside the HVRs (i.e., in the FR regions). In some embodiments, the substitutions, insertions, or deletions occur in in the FR regions. Optionally, the anti-TREM2 antibody comprises the VL sequence of antibody AL2p-32 or of SEQ ID NO: 97, including post-translational modifications of that sequence. In a particular embodiment, the VL comprises one, two or three HVRs selected from: (a) the HVR-L1 amino acid sequence of antibody AL2p-32, (b) the HVR-L2 amino acid sequence of antibody AL2p-32, and (c) the HVR-L3 amino acid sequence of antibody AL2p-32.

In some embodiments, anti-TREM2 antibodies of the present disclosure comprise a light chain variable domain and a heavy chain variable domain, wherein the heavy chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-33 or to the amino acid sequence of SEQ ID NO: 55; and/or the light chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-33 or to the amino acid sequence of SEQ ID NO: 103. In some embodiments, anti-TREM2 antibodies of the present disclosure comprise a heavy chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-33 or to the amino acid sequence of SEQ ID NO: 55, wherein the heavy chain variable domain comprises the HVR-H1, HVR-H2, and HVR-H3 amino acid sequences of antibody AL2p-33. In some embodiments, anti-TREM2 antibodies of the present disclosure comprise a light chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-33 or to the amino acid sequence of SEQ ID NO: 103, wherein the light chain variable domain comprises the HVR-L1, HVR-L2, and HVR-L3 amino acid sequences of antibody AL2p-33. In some embodiments, the anti-TREM2 antibody comprises a heavy chain variable domain (VH) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-33 or to the amino acid sequence of SEQ ID NO: 55 and contains substitutions (e.g., conservative substitutions, insertions, or deletions relative to the reference sequence), but the anti-TREM2 antibody comprising that sequence retains the ability to bind to TREM2. In certain embodiments, a total of 1 to 10 amino acids have been substituted, inserted, and/or deleted in the heavy chain variable domain amino acid sequence of antibody AL2p-33 or the amino acid sequence of SEQ ID NO: 55. In certain embodiments, a total of 1 to 5 amino acids have been substituted, inserted and/or deleted in the heavy chain variable domain amino acid sequence of antibody AL2p-33 or the amino acid sequence of SEQ ID NO: 55. In certain embodiments, substitutions, insertions, or deletions occur in regions outside the HVRs (i.e., in the FR regions). In some embodiments, the substitutions, insertions, or deletions occur in in the FR regions. Optionally, the anti-TREM2 antibody comprises the VH sequence of antibody AL2p-33 or of SEQ ID NO: 55, including post-translational modifications of that sequence. In a particular embodiment, the VH comprises one, two or three HVRs selected from: (a) the HVR-H1 amino acid sequence of antibody AL2p-33, (b) the HVR-H2 amino acid sequence of antibody AL2p-33, and (c) the HVR-H3 amino acid sequence of antibody AL2p-33. In some embodiments, anti-TREM2 antibodies of the present disclosure comprise a light chain variable domain (VL) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-33 or to the amino acid sequence of SEQ ID NO: 103 and contains substitutions (e.g., conservative substitutions, insertions, or deletions relative to the reference sequence), but the anti-TREM2 antibody comprising that sequence retains the ability to bind to TREM2. In certain embodiments, a total of 1 to 10 amino acids have been substituted, inserted, and/or deleted in the light chain variable domain amino acid sequence of antibody AL2p-33 or the amino acid sequence of SEQ ID NO: 103. In certain embodiments, a total of 1 to 5 amino acids have been substituted, inserted and/or deleted in the light chain variable domain amino acid sequence of antibody AL2p-33 or the amino acid sequence of SEQ ID NO: 103. In certain embodiments, substitutions, insertions, or deletions occur in regions outside the HVRs (i.e., in the FR regions). In some embodiments, the substitutions, insertions, or deletions occur in in the FR regions. Optionally, the anti-TREM2 antibody comprises the VL sequence of antibody AL2p-33 or of SEQ ID NO: 103, including post-translational modifications of that sequence. In a particular embodiment, the VL comprises one, two or three HVRs selected from: (a) the HVR-L1 amino acid sequence of antibody AL2p-33, (b) the HVR-L2 amino acid sequence of antibody AL2p-33, and (c) the HVR-L3 amino acid sequence of antibody AL2p-33.

In some embodiments, anti-TREM2 antibodies of the present disclosure comprise a light chain variable domain and a heavy chain variable domain, wherein the heavy chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-35 or to the amino acid sequence of SEQ ID NO: 57; and/or the light chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-35 or to the amino acid sequence of SEQ ID NO: 104. In some embodiments, anti-TREM2 antibodies of the present disclosure comprise a heavy chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-35 or to the amino acid sequence of SEQ ID NO: 57, wherein the heavy chain variable domain comprises the HVR-H1, HVR-H2, and HVR-H3 amino acid sequences of antibody AL2p-35. In some embodiments, anti-TREM2 antibodies of the present disclosure comprise a light chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-35 or to the amino acid sequence of SEQ ID NO: 104, wherein the light chain variable domain comprises the HVR-L1, HVR-L2, and HVR-L3 amino acid sequences of antibody AL2p-35. In some embodiments, the anti-TREM2 antibody comprises a heavy chain variable domain (VH) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-35 or to the amino acid sequence of SEQ ID NO: 57 and contains substitutions (e.g., conservative substitutions, insertions, or deletions relative to the reference sequence), but the anti-TREM2 antibody comprising that sequence retains the ability to bind to TREM2. In certain embodiments, a total of 1 to 10 amino acids have been substituted, inserted, and/or deleted in the heavy chain variable domain amino acid sequence of antibody AL2p-35 or the amino acid sequence of SEQ ID NO: 57. In certain embodiments, a total of 1 to 5 amino acids have been substituted, inserted and/or deleted in the heavy chain variable domain amino acid sequence of antibody AL2p-35 or the amino acid sequence of SEQ ID NO: 57. In certain embodiments, substitutions, insertions, or deletions occur in regions outside the HVRs (i.e., in the FR regions). In some embodiments, the substitutions, insertions, or deletions occur in in the FR regions. Optionally, the anti-TREM2 antibody comprises the VH sequence of antibody AL2p-35 or of SEQ ID NO: 57, including post-translational modifications of that sequence. In a particular embodiment, the VH comprises one, two or three HVRs selected from: (a) the HVR-H1 amino acid sequence of antibody AL2p-35, (b) the HVR-H2 amino acid sequence of antibody AL2p-35, and (c) the HVR-H3 amino acid sequence of antibody AL2p-35. In some embodiments, anti-TREM2 antibodies of the present disclosure comprise a light chain variable domain (VL) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-35 or to the amino acid sequence of SEQ ID NO: 104 and contains substitutions (e.g., conservative substitutions, insertions, or deletions relative to the reference sequence), but the anti-TREM2 antibody comprising that sequence retains the ability to bind to TREM2. In certain embodiments, a total of 1 to 10 amino acids have been substituted, inserted, and/or deleted in the light chain variable domain amino acid sequence of antibody AL2p-35 or the amino acid sequence of SEQ ID NO: 104. In certain embodiments, a total of 1 to 5 amino acids have been substituted, inserted and/or deleted in the light chain variable domain amino acid sequence of antibody AL2p-35 or the amino acid sequence of SEQ ID NO: 104. In certain embodiments, substitutions, insertions, or deletions occur in regions outside the HVRs (i.e., in the FR regions). In some embodiments, the substitutions, insertions, or deletions occur in in the FR regions. Optionally, the anti-TREM2 antibody comprises the VL sequence of antibody AL2p-35 or of SEQ ID NO: 104, including post-translational modifications of that sequence. In a particular embodiment, the VL comprises one, two or three HVRs selected from: (a) the HVR-L1 amino acid sequence of antibody AL2p-35, (b) the HVR-L2 amino acid sequence of antibody AL2p-35, and (c) the HVR-L3 amino acid sequence of antibody AL2p-35.

In some embodiments, anti-TREM2 antibodies of the present disclosure comprise a light chain variable domain and a heavy chain variable domain, wherein the heavy chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-36 or to the amino acid sequence of SEQ ID NO: 58; and/or the light chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-36 or to the amino acid sequence of SEQ ID NO: 104. In some embodiments, anti-TREM2 antibodies of the present disclosure comprise a heavy chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-36 or to the amino acid sequence of SEQ ID NO: 58, wherein the heavy chain variable domain comprises the HVR-H1, HVR-H2, and HVR-H3 amino acid sequences of antibody AL2p-36. In some embodiments, anti-TREM2 antibodies of the present disclosure comprise a light chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-36 or to the amino acid sequence of SEQ ID NO: 104, wherein the light chain variable domain comprises the HVR-L1, HVR-L2, and HVR-L3 amino acid sequences of antibody AL2p-36. In some embodiments, the anti-TREM2 antibody comprises a heavy chain variable domain (VH) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-36 or to the amino acid sequence of SEQ ID NO: 58 and contains substitutions (e.g., conservative substitutions, insertions, or deletions relative to the reference sequence), but the anti-TREM2 antibody comprising that sequence retains the ability to bind to TREM2. In certain embodiments, a total of 1 to 10 amino acids have been substituted, inserted, and/or deleted in the heavy chain variable domain amino acid sequence of antibody AL2p-36 or the amino acid sequence of SEQ ID NO: 58. In certain embodiments, a total of 1 to 5 amino acids have been substituted, inserted and/or deleted in the heavy chain variable domain amino acid sequence of antibody AL2p-36 or the amino acid sequence of SEQ ID NO: 58. In certain embodiments, substitutions, insertions, or deletions occur in regions outside the HVRs (i.e., in the FR regions). In some embodiments, the substitutions, insertions, or deletions occur in in the FR regions. Optionally, the anti-TREM2 antibody comprises the VH sequence of antibody AL2p-36 or of SEQ ID NO: 58, including post-translational modifications of that sequence. In a particular embodiment, the VH comprises one, two or three HVRs selected from: (a) the HVR-H1 amino acid sequence of antibody AL2p-36, (b) the HVR-H2 amino acid sequence of antibody AL2p-36, and (c) the HVR-H3 amino acid sequence of antibody AL2p-36. In some embodiments, anti-TREM2 antibodies of the present disclosure comprise a light chain variable domain (VL) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-36 or to the amino acid sequence of SEQ ID NO: 104 and contains substitutions (e.g., conservative substitutions, insertions, or deletions relative to the reference sequence), but the anti-TREM2 antibody comprising that sequence retains the ability to bind to TREM2. In certain embodiments, a total of 1 to 10 amino acids have been substituted, inserted, and/or deleted in the light chain variable domain amino acid sequence of antibody AL2p-36 or the amino acid sequence of SEQ ID NO: 104. In certain embodiments, a total of 1 to 5 amino acids have been substituted, inserted and/or deleted in the light chain variable domain amino acid sequence of antibody AL2p-36 or the amino acid sequence of SEQ ID NO: 104. In certain embodiments, substitutions, insertions, or deletions occur in regions outside the HVRs (i.e., in the FR regions). In some embodiments, the substitutions, insertions, or deletions occur in in the FR regions. Optionally, the anti-TREM2 antibody comprises the VL sequence of antibody AL2p-36 or of SEQ ID NO: 104, including post-translational modifications of that sequence. In a particular embodiment, the VL comprises one, two or three HVRs selected from: (a) the HVR-L1 amino acid sequence of antibody AL2p-36, (b) the HVR-L2 amino acid sequence of antibody AL2p-36, and (c) the HVR-L3 amino acid sequence of antibody AL2p-36.

In some embodiments, anti-TREM2 antibodies of the present disclosure comprise a light chain variable domain and a heavy chain variable domain, wherein the heavy chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-37 or to the amino acid sequence of SEQ ID NO: 59; and/or the light chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-37 or to the amino acid sequence of SEQ ID NO: 104. In some embodiments, anti-TREM2 antibodies of the present disclosure comprise a heavy chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-37 or to the amino acid sequence of SEQ ID NO: 59, wherein the heavy chain variable domain comprises the HVR-H1, HVR-H2, and HVR-H3 amino acid sequences of antibody AL2p-37. In some embodiments, anti-TREM2 antibodies of the present disclosure comprise a light chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-37 or to the amino acid sequence of SEQ ID NO: 104, wherein the light chain variable domain comprises the HVR-L1, HVR-L2, and HVR-L3 amino acid sequences of antibody AL2p-37. In some embodiments, the anti-TREM2 antibody comprises a heavy chain variable domain (VH) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-37 or to the amino acid sequence of SEQ ID NO: 59 and contains substitutions (e.g., conservative substitutions, insertions, or deletions relative to the reference sequence), but the anti-TREM2 antibody comprising that sequence retains the ability to bind to TREM2. In certain embodiments, a total of 1 to 10 amino acids have been substituted, inserted, and/or deleted in the heavy chain variable domain amino acid sequence of antibody AL2p-37 or the amino acid sequence of SEQ ID NO: 59. In certain embodiments, a total of 1 to 5 amino acids have been substituted, inserted and/or deleted in the heavy chain variable domain amino acid sequence of antibody AL2p-37 or the amino acid sequence of SEQ ID NO: 59. In certain embodiments, substitutions, insertions, or deletions occur in regions outside the HVRs (i.e., in the FR regions). In some embodiments, the substitutions, insertions, or deletions occur in in the FR regions. Optionally, the anti-TREM2 antibody comprises the VH sequence of antibody AL2p-37 or of SEQ ID NO: 59, including post-translational modifications of that sequence. In a particular embodiment, the VH comprises one, two or three HVRs selected from: (a) the HVR-H1 amino acid sequence of antibody AL2p-37, (b) the HVR-H2 amino acid sequence of antibody AL2p-37, and (c) the HVR-H3 amino acid sequence of antibody AL2p-37. In some embodiments, anti-TREM2 antibodies of the present disclosure comprise a light chain variable domain (VL) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-37 or to the amino acid sequence of SEQ ID NO: 104 and contains substitutions (e.g., conservative substitutions, insertions, or deletions relative to the reference sequence), but the anti-TREM2 antibody comprising that sequence retains the ability to bind to TREM2. In certain embodiments, a total of 1 to 10 amino acids have been substituted, inserted, and/or deleted in the light chain variable domain amino acid sequence of antibody AL2p-37 or the amino acid sequence of SEQ ID NO: 104. In certain embodiments, a total of 1 to 5 amino acids have been substituted, inserted and/or deleted in the light chain variable domain amino acid sequence of antibody AL2p-37 or the amino acid sequence of SEQ ID NO: 104. In certain embodiments, substitutions, insertions, or deletions occur in regions outside the HVRs (i.e., in the FR regions). In some embodiments, the substitutions, insertions, or deletions occur in in the FR regions. Optionally, the anti-TREM2 antibody comprises the VL sequence of antibody AL2p-37 or of SEQ ID NO: 104, including post-translational modifications of that sequence. In a particular embodiment, the VL comprises one, two or three HVRs selected from: (a) the HVR-L1 amino acid sequence of antibody AL2p-37, (b) the HVR-L2 amino acid sequence of antibody AL2p-37, and (c) the HVR-L3 amino acid sequence of antibody AL2p-37.

In some embodiments, anti-TREM2 antibodies of the present disclosure comprise a light chain variable domain and a heavy chain variable domain, wherein the heavy chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-38 or to the amino acid sequence of SEQ ID NO: 60; and/or the light chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-38 or to the amino acid sequence of SEQ ID NO: 105. In some embodiments, anti-TREM2 antibodies of the present disclosure comprise a heavy chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-38 or to the amino acid sequence of SEQ ID NO: 60, wherein the heavy chain variable domain comprises the HVR-H1, HVR-H2, and HVR-H3 amino acid sequences of antibody AL2p-38. In some embodiments, anti-TREM2 antibodies of the present disclosure comprise a light chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-38 or to the amino acid sequence of SEQ ID NO: 105, wherein the light chain variable domain comprises the HVR-L1, HVR-L2, and HVR-L3 amino acid sequences of antibody AL2p-38. In some embodiments, the anti-TREM2 antibody comprises a heavy chain variable domain (VH) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-38 or to the amino acid sequence of SEQ ID NO: 60 and contains substitutions (e.g., conservative substitutions, insertions, or deletions relative to the reference sequence), but the anti-TREM2 antibody comprising that sequence retains the ability to bind to TREM2. In certain embodiments, a total of 1 to 10 amino acids have been substituted, inserted, and/or deleted in the heavy chain variable domain amino acid sequence of antibody AL2p-38 or the amino acid sequence of SEQ ID NO: 60. In certain embodiments, a total of 1 to 5 amino acids have been substituted, inserted and/or deleted in the heavy chain variable domain amino acid sequence of antibody AL2p-38 or the amino acid sequence of SEQ ID NO: 60. In certain embodiments, substitutions, insertions, or deletions occur in regions outside the HVRs (i.e., in the FR regions). In some embodiments, the substitutions, insertions, or deletions occur in in the FR regions. Optionally, the anti-TREM2 antibody comprises the VH sequence of antibody AL2p-38 or of SEQ ID NO: 60, including post-translational modifications of that sequence. In a particular embodiment, the VH comprises one, two or three HVRs selected from: (a) the HVR-H1 amino acid sequence of antibody AL2p-38, (b) the HVR-H2 amino acid sequence of antibody AL2p-38, and (c) the HVR-H3 amino acid sequence of antibody AL2p-38. In some embodiments, anti-TREM2 antibodies of the present disclosure comprise a light chain variable domain (VL) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-38 or to the amino acid sequence of SEQ ID NO: 105 and contains substitutions (e.g., conservative substitutions, insertions, or deletions relative to the reference sequence), but the anti-TREM2 antibody comprising that sequence retains the ability to bind to TREM2. In certain embodiments, a total of 1 to 10 amino acids have been substituted, inserted, and/or deleted in the light chain variable domain amino acid sequence of antibody AL2p-38 or the amino acid sequence of SEQ ID NO: 105. In certain embodiments, a total of 1 to 5 amino acids have been substituted, inserted and/or deleted in the light chain variable domain amino acid sequence of antibody AL2p-38 or the amino acid sequence of SEQ ID NO: 105. In certain embodiments, substitutions, insertions, or deletions occur in regions outside the HVRs (i.e., in the FR regions). In some embodiments, the substitutions, insertions, or deletions occur in in the FR regions. Optionally, the anti-TREM2 antibody comprises the VL sequence of antibody AL2p-38 or of SEQ ID NO: 105, including post-translational modifications of that sequence. In a particular embodiment, the VL comprises one, two or three HVRs selected from: (a) the HVR-L1 amino acid sequence of antibody AL2p-38, (b) the HVR-L2 amino acid sequence of antibody AL2p-38, and (c) the HVR-L3 amino acid sequence of antibody AL2p-38.

In some embodiments, anti-TREM2 antibodies of the present disclosure comprise a light chain variable domain and a heavy chain variable domain, wherein the heavy chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-39 or to the amino acid sequence of SEQ ID NO: 60; and/or the light chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-39 or to the amino acid sequence of SEQ ID NO: 106. In some embodiments, anti-TREM2 antibodies of the present disclosure comprise a heavy chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-39 or to the amino acid sequence of SEQ ID NO: 60, wherein the heavy chain variable domain comprises the HVR-H1, HVR-H2, and HVR-H3 amino acid sequences of antibody AL2p-39. In some embodiments, anti-TREM2 antibodies of the present disclosure comprise a light chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-39 or to the amino acid sequence of SEQ ID NO: 106, wherein the light chain variable domain comprises the HVR-L1, HVR-L2, and HVR-L3 amino acid sequences of antibody AL2p-39. In some embodiments, the anti-TREM2 antibody comprises a heavy chain variable domain (VH) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-39 or to the amino acid sequence of SEQ ID NO: 60 and contains substitutions (e.g., conservative substitutions, insertions, or deletions relative to the reference sequence), but the anti-TREM2 antibody comprising that sequence retains the ability to bind to TREM2. In certain embodiments, a total of 1 to 10 amino acids have been substituted, inserted, and/or deleted in the heavy chain variable domain amino acid sequence of antibody AL2p-39 or the amino acid sequence of SEQ ID NO: 60. In certain embodiments, a total of 1 to 5 amino acids have been substituted, inserted and/or deleted in the heavy chain variable domain amino acid sequence of antibody AL2p-39 or the amino acid sequence of SEQ ID NO: 60. In certain embodiments, substitutions, insertions, or deletions occur in regions outside the HVRs (i.e., in the FR regions). In some embodiments, the substitutions, insertions, or deletions occur in in the FR regions. Optionally, the anti-TREM2 antibody comprises the VH sequence of antibody AL2p-39 or of SEQ ID NO: 60, including post-translational modifications of that sequence. In a particular embodiment, the VH comprises one, two or three HVRs selected from: (a) the HVR-H1 amino acid sequence of antibody AL2p-39, (b) the HVR-H2 amino acid sequence of antibody AL2p-39, and (c) the HVR-H3 amino acid sequence of antibody AL2p-39. In some embodiments, anti-TREM2 antibodies of the present disclosure comprise a light chain variable domain (VL) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-39 or to the amino acid sequence of SEQ ID NO: 106 and contains substitutions (e.g., conservative substitutions, insertions, or deletions relative to the reference sequence), but the anti-TREM2 antibody comprising that sequence retains the ability to bind to TREM2. In certain embodiments, a total of 1 to 10 amino acids have been substituted, inserted, and/or deleted in the light chain variable domain amino acid sequence of antibody AL2p-39 or the amino acid sequence of SEQ ID NO: 106. In certain embodiments, a total of 1 to 5 amino acids have been substituted, inserted and/or deleted in the light chain variable domain amino acid sequence of antibody AL2p-39 or the amino acid sequence of SEQ ID NO: 106. In certain embodiments, substitutions, insertions, or deletions occur in regions outside the HVRs (i.e., in the FR regions). In some embodiments, the substitutions, insertions, or deletions occur in in the FR regions. Optionally, the anti-TREM2 antibody comprises the VL sequence of antibody AL2p-39 or of SEQ ID NO: 106, including post-translational modifications of that sequence. In a particular embodiment, the VL comprises one, two or three HVRs selected from: (a) the HVR-L1 amino acid sequence of antibody AL2p-39, (b) the HVR-L2 amino acid sequence of antibody AL2p-39, and (c) the HVR-L3 amino acid sequence of antibody AL2p-39.

In some embodiments, anti-TREM2 antibodies of the present disclosure comprise a light chain variable domain and a heavy chain variable domain, wherein the heavy chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-40 or to the amino acid sequence of SEQ ID NO: 60; and/or the light chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-40 or to the amino acid sequence of SEQ ID NO: 107. In some embodiments, anti-TREM2 antibodies of the present disclosure comprise a heavy chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-40 or to the amino acid sequence of SEQ ID NO: 60, wherein the heavy chain variable domain comprises the HVR-H1, HVR-H2, and HVR-H3 amino acid sequences of antibody AL2p-40. In some embodiments, anti-TREM2 antibodies of the present disclosure comprise a light chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-40 or to the amino acid sequence of SEQ ID NO: 107, wherein the light chain variable domain comprises the HVR-L1, HVR-L2, and HVR-L3 amino acid sequences of antibody AL2p-40. In some embodiments, the anti-TREM2 antibody comprises a heavy chain variable domain (VH) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-40 or to the amino acid sequence of SEQ ID NO: 60 and contains substitutions (e.g., conservative substitutions, insertions, or deletions relative to the reference sequence), but the anti-TREM2 antibody comprising that sequence retains the ability to bind to TREM2. In certain embodiments, a total of 1 to 10 amino acids have been substituted, inserted, and/or deleted in the heavy chain variable domain amino acid sequence of antibody AL2p-40 or the amino acid sequence of SEQ ID NO: 60. In certain embodiments, a total of 1 to 5 amino acids have been substituted, inserted and/or deleted in the heavy chain variable domain amino acid sequence of antibody AL2p-40 or the amino acid sequence of SEQ ID NO: 60. In certain embodiments, substitutions, insertions, or deletions occur in regions outside the HVRs (i.e., in the FR regions). In some embodiments, the substitutions, insertions, or deletions occur in in the FR regions. Optionally, the anti-TREM2 antibody comprises the VH sequence of antibody AL2p-40 or of SEQ ID NO: 60, including post-translational modifications of that sequence. In a particular embodiment, the VH comprises one, two or three HVRs selected from: (a) the HVR-H1 amino acid sequence of antibody AL2p-40, (b) the HVR-H2 amino acid sequence of antibody AL2p-40, and (c) the HVR-H3 amino acid sequence of antibody AL2p-40. In some embodiments, anti-TREM2 antibodies of the present disclosure comprise a light chain variable domain (VL) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-40 or to the amino acid sequence of SEQ ID NO: 107 and contains substitutions (e.g., conservative substitutions, insertions, or deletions relative to the reference sequence), but the anti-TREM2 antibody comprising that sequence retains the ability to bind to TREM2. In certain embodiments, a total of 1 to 10 amino acids have been substituted, inserted, and/or deleted in the light chain variable domain amino acid sequence of antibody AL2p-40 or the amino acid sequence of SEQ ID NO: 107. In certain embodiments, a total of 1 to 5 amino acids have been substituted, inserted and/or deleted in the light chain variable domain amino acid sequence of antibody AL2p-40 or the amino acid sequence of SEQ ID NO: 107. In certain embodiments, substitutions, insertions, or deletions occur in regions outside the HVRs (i.e., in the FR regions). In some embodiments, the substitutions, insertions, or deletions occur in in the FR regions. Optionally, the anti-TREM2 antibody comprises the VL sequence of antibody AL2p-40 or of SEQ ID NO: 107, including post-translational modifications of that sequence. In a particular embodiment, the VL comprises one, two or three HVRs selected from: (a) the HVR-L1 amino acid sequence of antibody AL2p-40, (b) the HVR-L2 amino acid sequence of antibody AL2p-40, and (c) the HVR-L3 amino acid sequence of antibody AL2p-40.

In some embodiments, anti-TREM2 antibodies of the present disclosure comprise a light chain variable domain and a heavy chain variable domain, wherein the heavy chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-41 or to the amino acid sequence of SEQ ID NO: 61; and/or the light chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-41 or to the amino acid sequence of SEQ ID NO: 106. In some embodiments, anti-TREM2 antibodies of the present disclosure comprise a heavy chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-41 or to the amino acid sequence of SEQ ID NO: 61, wherein the heavy chain variable domain comprises the HVR-H1, HVR-H2, and HVR-H3 amino acid sequences of antibody AL2p-41. In some embodiments, anti-TREM2 antibodies of the present disclosure comprise a light chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-41 or to the amino acid sequence of SEQ ID NO: 106, wherein the light chain variable domain comprises the HVR-L1, HVR-L2, and HVR-L3 amino acid sequences of antibody AL2p-41. In some embodiments, the anti-TREM2 antibody comprises a heavy chain variable domain (VH) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-41 or to the amino acid sequence of SEQ ID NO: 61 and contains substitutions (e.g., conservative substitutions, insertions, or deletions relative to the reference sequence), but the anti-TREM2 antibody comprising that sequence retains the ability to bind to TREM2. In certain embodiments, a total of 1 to 10 amino acids have been substituted, inserted, and/or deleted in the heavy chain variable domain amino acid sequence of antibody AL2p-41 or the amino acid sequence of SEQ ID NO: 61. In certain embodiments, a total of 1 to 5 amino acids have been substituted, inserted and/or deleted in the heavy chain variable domain amino acid sequence of antibody AL2p-41 or the amino acid sequence of SEQ ID NO: 61. In certain embodiments, substitutions, insertions, or deletions occur in regions outside the HVRs (i.e., in the FR regions). In some embodiments, the substitutions, insertions, or deletions occur in in the FR regions. Optionally, the anti-TREM2 antibody comprises the VH sequence of antibody AL2p-41 or of SEQ ID NO: 61, including post-translational modifications of that sequence. In a particular embodiment, the VH comprises one, two or three HVRs selected from: (a) the HVR-H1 amino acid sequence of antibody AL2p-41, (b) the HVR-H2 amino acid sequence of antibody AL2p-41, and (c) the HVR-H3 amino acid sequence of antibody AL2p-41. In some embodiments, anti-TREM2 antibodies of the present disclosure comprise a light chain variable domain (VL) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-41 or to the amino acid sequence of SEQ ID NO: 106 and contains substitutions (e.g., conservative substitutions, insertions, or deletions relative to the reference sequence), but the anti-TREM2 antibody comprising that sequence retains the ability to bind to TREM2. In certain embodiments, a total of 1 to 10 amino acids have been substituted, inserted, and/or deleted in the light chain variable domain amino acid sequence of antibody AL2p-41 or the amino acid sequence of SEQ ID NO: 106. In certain embodiments, a total of 1 to 5 amino acids have been substituted, inserted and/or deleted in the light chain variable domain amino acid sequence of antibody AL2p-41 or the amino acid sequence of SEQ ID NO: 106. In certain embodiments, substitutions, insertions, or deletions occur in regions outside the HVRs (i.e., in the FR regions). In some embodiments, the substitutions, insertions, or deletions occur in in the FR regions. Optionally, the anti-TREM2 antibody comprises the VL sequence of antibody AL2p-41 or of SEQ ID NO: 106, including post-translational modifications of that sequence. In a particular embodiment, the VL comprises one, two or three HVRs selected from: (a) the HVR-L1 amino acid sequence of antibody AL2p-41, (b) the HVR-L2 amino acid sequence of antibody AL2p-41, and (c) the HVR-L3 amino acid sequence of antibody AL2p-41.

In some embodiments, anti-TREM2 antibodies of the present disclosure comprise a light chain variable domain and a heavy chain variable domain, wherein the heavy chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-42 or to the amino acid sequence of SEQ ID NO: 61; and/or the light chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-42 or to the amino acid sequence of SEQ ID NO: 107. In some embodiments, anti-TREM2 antibodies of the present disclosure comprise a heavy chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-42 or to the amino acid sequence of SEQ ID NO: 61, wherein the heavy chain variable domain comprises the HVR-H1, HVR-H2, and HVR-H3 amino acid sequences of antibody AL2p-42. In some embodiments, anti-TREM2 antibodies of the present disclosure comprise a light chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-42 or to the amino acid sequence of SEQ ID NO: 107, wherein the light chain variable domain comprises the HVR-L1, HVR-L2, and HVR-L3 amino acid sequences of antibody AL2p-42. In some embodiments, the anti-TREM2 antibody comprises a heavy chain variable domain (VH) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-42 or to the amino acid sequence of SEQ ID NO: 61 and contains substitutions (e.g., conservative substitutions, insertions, or deletions relative to the reference sequence), but the anti-TREM2 antibody comprising that sequence retains the ability to bind to TREM2. In certain embodiments, a total of 1 to 10 amino acids have been substituted, inserted, and/or deleted in the heavy chain variable domain amino acid sequence of antibody AL2p-42 or the amino acid sequence of SEQ ID NO: 61. In certain embodiments, a total of 1 to 5 amino acids have been substituted, inserted and/or deleted in the heavy chain variable domain amino acid sequence of antibody AL2p-42 or the amino acid sequence of SEQ ID NO: 61. In certain embodiments, substitutions, insertions, or deletions occur in regions outside the HVRs (i.e., in the FR regions). In some embodiments, the substitutions, insertions, or deletions occur in in the FR regions. Optionally, the anti-TREM2 antibody comprises the VH sequence of antibody AL2p-42 or of SEQ ID NO: 61, including post-translational modifications of that sequence. In a particular embodiment, the VH comprises one, two or three HVRs selected from: (a) the HVR-H1 amino acid sequence of antibody AL2p-42, (b) the HVR-H2 amino acid sequence of antibody AL2p-42, and (c) the HVR-H3 amino acid sequence of antibody AL2p-42. In some embodiments, anti-TREM2 antibodies of the present disclosure comprise a light chain variable domain (VL) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-42 or to the amino acid sequence of SEQ ID NO: 107 and contains substitutions (e.g., conservative substitutions, insertions, or deletions relative to the reference sequence), but the anti-TREM2 antibody comprising that sequence retains the ability to bind to TREM2. In certain embodiments, a total of 1 to 10 amino acids have been substituted, inserted, and/or deleted in the light chain variable domain amino acid sequence of antibody AL2p-42 or the amino acid sequence of SEQ ID NO: 107. In certain embodiments, a total of 1 to 5 amino acids have been substituted, inserted and/or deleted in the light chain variable domain amino acid sequence of antibody AL2p-42 or the amino acid sequence of SEQ ID NO: 107. In certain embodiments, substitutions, insertions, or deletions occur in regions outside the HVRs (i.e., in the FR regions). In some embodiments, the substitutions, insertions, or deletions occur in in the FR regions. Optionally, the anti-TREM2 antibody comprises the VL sequence of antibody AL2p-42 or of SEQ ID NO: 107, including post-translational modifications of that sequence. In a particular embodiment, the VL comprises one, two or three HVRs selected from: (a) the HVR-L1 amino acid sequence of antibody AL2p-42, (b) the HVR-L2 amino acid sequence of antibody AL2p-42, and (c) the HVR-L3 amino acid sequence of antibody AL2p-42.

In some embodiments, anti-TREM2 antibodies of the present disclosure comprise a light chain variable domain and a heavy chain variable domain, wherein the heavy chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-43 or to the amino acid sequence of SEQ ID NO: 62; and/or the light chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-43 or to the amino acid sequence of SEQ ID NO: 105. In some embodiments, anti-TREM2 antibodies of the present disclosure comprise a heavy chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-43 or to the amino acid sequence of SEQ ID NO: 62, wherein the heavy chain variable domain comprises the HVR-H1, HVR-H2, and HVR-H3 amino acid sequences of antibody AL2p-43. In some embodiments, anti-TREM2 antibodies of the present disclosure comprise a light chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-43 or to the amino acid sequence of SEQ ID NO: 105, wherein the light chain variable domain comprises the HVR-L1, HVR-L2, and HVR-L3 amino acid sequences of antibody AL2p-43. In some embodiments, the anti-TREM2 antibody comprises a heavy chain variable domain (VH) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-43 or to the amino acid sequence of SEQ ID NO: 62 and contains substitutions (e.g., conservative substitutions, insertions, or deletions relative to the reference sequence), but the anti-TREM2 antibody comprising that sequence retains the ability to bind to TREM2. In certain embodiments, a total of 1 to 10 amino acids have been substituted, inserted, and/or deleted in the heavy chain variable domain amino acid sequence of antibody AL2p-43 or the amino acid sequence of SEQ ID NO: 62. In certain embodiments, a total of 1 to 5 amino acids have been substituted, inserted and/or deleted in the heavy chain variable domain amino acid sequence of antibody AL2p-43 or the amino acid sequence of SEQ ID NO: 62. In certain embodiments, substitutions, insertions, or deletions occur in regions outside the HVRs (i.e., in the FR regions). In some embodiments, the substitutions, insertions, or deletions occur in in the FR regions. Optionally, the anti-TREM2 antibody comprises the VH sequence of antibody AL2p-43 or of SEQ ID NO: 62, including post-translational modifications of that sequence. In a particular embodiment, the VH comprises one, two or three HVRs selected from: (a) the HVR-H1 amino acid sequence of antibody AL2p-43, (b) the HVR-H2 amino acid sequence of antibody AL2p-43, and (c) the HVR-H3 amino acid sequence of antibody AL2p-43. In some embodiments, anti-TREM2 antibodies of the present disclosure comprise a light chain variable domain (VL) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-43 or to the amino acid sequence of SEQ ID NO: 105 and contains substitutions (e.g., conservative substitutions, insertions, or deletions relative to the reference sequence), but the anti-TREM2 antibody comprising that sequence retains the ability to bind to TREM2. In certain embodiments, a total of 1 to 10 amino acids have been substituted, inserted, and/or deleted in the light chain variable domain amino acid sequence of antibody AL2p-43 or the amino acid sequence of SEQ ID NO: 105. In certain embodiments, a total of 1 to 5 amino acids have been substituted, inserted and/or deleted in the light chain variable domain amino acid sequence of antibody AL2p-43 or the amino acid sequence of SEQ ID NO: 105. In certain embodiments, substitutions, insertions, or deletions occur in regions outside the HVRs (i.e., in the FR regions). In some embodiments, the substitutions, insertions, or deletions occur in in the FR regions. Optionally, the anti-TREM2 antibody comprises the VL sequence of antibody AL2p-43 or of SEQ ID NO: 105, including post-translational modifications of that sequence. In a particular embodiment, the VL comprises one, two or three HVRs selected from: (a) the HVR-L1 amino acid sequence of antibody AL2p-43, (b) the HVR-L2 amino acid sequence of antibody AL2p-43, and (c) the HVR-L3 amino acid sequence of antibody AL2p-43.

In some embodiments, anti-TREM2 antibodies of the present disclosure comprise a light chain variable domain and a heavy chain variable domain, wherein the heavy chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-44 or to the amino acid sequence of SEQ ID NO: 62; and/or the light chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-44 or to the amino acid sequence of SEQ ID NO: 107. In some embodiments, anti-TREM2 antibodies of the present disclosure comprise a heavy chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-44 or to the amino acid sequence of SEQ ID NO: 62, wherein the heavy chain variable domain comprises the HVR-H1, HVR-H2, and HVR-H3 amino acid sequences of antibody AL2p-44. In some embodiments, anti-TREM2 antibodies of the present disclosure comprise a light chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-44 or to the amino acid sequence of SEQ ID NO: 107, wherein the light chain variable domain comprises the HVR-L1, HVR-L2, and HVR-L3 amino acid sequences of antibody AL2p-44. In some embodiments, the anti-TREM2 antibody comprises a heavy chain variable domain (VH) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-44 or to the amino acid sequence of SEQ ID NO: 62 and contains substitutions (e.g., conservative substitutions, insertions, or deletions relative to the reference sequence), but the anti-TREM2 antibody comprising that sequence retains the ability to bind to TREM2. In certain embodiments, a total of 1 to 10 amino acids have been substituted, inserted, and/or deleted in the heavy chain variable domain amino acid sequence of antibody AL2p-44 or the amino acid sequence of SEQ ID NO: 62. In certain embodiments, a total of 1 to 5 amino acids have been substituted, inserted and/or deleted in the heavy chain variable domain amino acid sequence of antibody AL2p-44 or the amino acid sequence of SEQ ID NO: 62. In certain embodiments, substitutions, insertions, or deletions occur in regions outside the HVRs (i.e., in the FR regions). In some embodiments, the substitutions, insertions, or deletions occur in in the FR regions. Optionally, the anti-TREM2 antibody comprises the VH sequence of antibody AL2p-44 or of SEQ ID NO: 62, including post-translational modifications of that sequence. In a particular embodiment, the VH comprises one, two or three HVRs selected from: (a) the HVR-H1 amino acid sequence of antibody AL2p-44, (b) the HVR-H2 amino acid sequence of antibody AL2p-44, and (c) the HVR-H3 amino acid sequence of antibody AL2p-44. In some embodiments, anti-TREM2 antibodies of the present disclosure comprise a light chain variable domain (VL) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-44 or to the amino acid sequence of SEQ ID NO: 107 and contains substitutions (e.g., conservative substitutions, insertions, or deletions relative to the reference sequence), but the anti-TREM2 antibody comprising that sequence retains the ability to bind to TREM2. In certain embodiments, a total of 1 to 10 amino acids have been substituted, inserted, and/or deleted in the light chain variable domain amino acid sequence of antibody AL2p-44 or the amino acid sequence of SEQ ID NO: 107. In certain embodiments, a total of 1 to 5 amino acids have been substituted, inserted and/or deleted in the light chain variable domain amino acid sequence of antibody AL2p-44 or the amino acid sequence of SEQ ID NO: 107. In certain embodiments, substitutions, insertions, or deletions occur in regions outside the HVRs (i.e., in the FR regions). In some embodiments, the substitutions, insertions, or deletions occur in in the FR regions. Optionally, the anti-TREM2 antibody comprises the VL sequence of antibody AL2p-44 or of SEQ ID NO: 107, including post-translational modifications of that sequence. In a particular embodiment, the VL comprises one, two or three HVRs selected from: (a) the HVR-L1 amino acid sequence of antibody AL2p-44, (b) the HVR-L2 amino acid sequence of antibody AL2p-44, and (c) the HVR-L3 amino acid sequence of antibody AL2p-44.

In some embodiments, anti-TREM2 antibodies of the present disclosure comprise a light chain variable domain and a heavy chain variable domain, wherein the heavy chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-45 or to the amino acid sequence of SEQ ID NO: 63; and/or the light chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-45 or to the amino acid sequence of SEQ ID NO: 108. In some embodiments, anti-TREM2 antibodies of the present disclosure comprise a heavy chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-45 or to the amino acid sequence of SEQ ID NO: 63, wherein the heavy chain variable domain comprises the HVR-H1, HVR-H2, and HVR-H3 amino acid sequences of antibody AL2p-45. In some embodiments, anti-TREM2 antibodies of the present disclosure comprise a light chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-45 or to the amino acid sequence of SEQ ID NO: 108, wherein the light chain variable domain comprises the HVR-L1, HVR-L2, and HVR-L3 amino acid sequences of antibody AL2p-45. In some embodiments, the anti-TREM2 antibody comprises a heavy chain variable domain (VH) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-45 or to the amino acid sequence of SEQ ID NO: 63 and contains substitutions (e.g., conservative substitutions, insertions, or deletions relative to the reference sequence), but the anti-TREM2 antibody comprising that sequence retains the ability to bind to TREM2. In certain embodiments, a total of 1 to 10 amino acids have been substituted, inserted, and/or deleted in the heavy chain variable domain amino acid sequence of antibody AL2p-45 or the amino acid sequence of SEQ ID NO: 63. In certain embodiments, a total of 1 to 5 amino acids have been substituted, inserted and/or deleted in the heavy chain variable domain amino acid sequence of antibody AL2p-45 or the amino acid sequence of SEQ ID NO: 63. In certain embodiments, substitutions, insertions, or deletions occur in regions outside the HVRs (i.e., in the FR regions). In some embodiments, the substitutions, insertions, or deletions occur in in the FR regions. Optionally, the anti-TREM2 antibody comprises the VH sequence of antibody AL2p-45 or of SEQ ID NO: 63, including post-translational modifications of that sequence. In a particular embodiment, the VH comprises one, two or three HVRs selected from: (a) the HVR-H1 amino acid sequence of antibody AL2p-45, (b) the HVR-H2 amino acid sequence of antibody AL2p-45, and (c) the HVR-H3 amino acid sequence of antibody AL2p-45. In some embodiments, anti-TREM2 antibodies of the present disclosure comprise a light chain variable domain (VL) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-45 or to the amino acid sequence of SEQ ID NO: 108 and contains substitutions (e.g., conservative substitutions, insertions, or deletions relative to the reference sequence), but the anti-TREM2 antibody comprising that sequence retains the ability to bind to TREM2. In certain embodiments, a total of 1 to 10 amino acids have been substituted, inserted, and/or deleted in the light chain variable domain amino acid sequence of antibody AL2p-45 or the amino acid sequence of SEQ ID NO: 108. In certain embodiments, a total of 1 to 5 amino acids have been substituted, inserted and/or deleted in the light chain variable domain amino acid sequence of antibody AL2p-45 or the amino acid sequence of SEQ ID NO: 108. In certain embodiments, substitutions, insertions, or deletions occur in regions outside the HVRs (i.e., in the FR regions). In some embodiments, the substitutions, insertions, or deletions occur in in the FR regions. Optionally, the anti-TREM2 antibody comprises the VL sequence of antibody AL2p-45 or of SEQ ID NO: 108, including post-translational modifications of that sequence. In a particular embodiment, the VL comprises one, two or three HVRs selected from: (a) the HVR-L1 amino acid sequence of antibody AL2p-45, (b) the HVR-L2 amino acid sequence of antibody AL2p-45, and (c) the HVR-L3 amino acid sequence of antibody AL2p-45.

In some embodiments, anti-TREM2 antibodies of the present disclosure comprise a light chain variable domain and a heavy chain variable domain, wherein the heavy chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-46 or to the amino acid sequence of SEQ ID NO: 63; and/or the light chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-46 or to the amino acid sequence of SEQ ID NO: 109. In some embodiments, anti-TREM2 antibodies of the present disclosure comprise a heavy chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-46 or to the amino acid sequence of SEQ ID NO: 63, wherein the heavy chain variable domain comprises the HVR-H1, HVR-H2, and HVR-H3 amino acid sequences of antibody AL2p-46. In some embodiments, anti-TREM2 antibodies of the present disclosure comprise a light chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-46 or to the amino acid sequence of SEQ ID NO: 109, wherein the light chain variable domain comprises the HVR-L1, HVR-L2, and HVR-L3 amino acid sequences of antibody AL2p-46. In some embodiments, the anti-TREM2 antibody comprises a heavy chain variable domain (VH) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-46 or to the amino acid sequence of SEQ ID NO: 63 and contains substitutions (e.g., conservative substitutions, insertions, or deletions relative to the reference sequence), but the anti-TREM2 antibody comprising that sequence retains the ability to bind to TREM2. In certain embodiments, a total of 1 to 10 amino acids have been substituted, inserted, and/or deleted in the heavy chain variable domain amino acid sequence of antibody AL2p-46 or the amino acid sequence of SEQ ID NO: 63. In certain embodiments, a total of 1 to 5 amino acids have been substituted, inserted and/or deleted in the heavy chain variable domain amino acid sequence of antibody AL2p-46 or the amino acid sequence of SEQ ID NO: 63. In certain embodiments, substitutions, insertions, or deletions occur in regions outside the HVRs (i.e., in the FR regions). In some embodiments, the substitutions, insertions, or deletions occur in in the FR regions. Optionally, the anti-TREM2 antibody comprises the VH sequence of antibody AL2p-46 or of SEQ ID NO: 63, including post-translational modifications of that sequence. In a particular embodiment, the VH comprises one, two or three HVRs selected from: (a) the HVR-H1 amino acid sequence of antibody AL2p-46, (b) the HVR-H2 amino acid sequence of antibody AL2p-46, and (c) the HVR-H3 amino acid sequence of antibody AL2p-46. In some embodiments, anti-TREM2 antibodies of the present disclosure comprise a light chain variable domain (VL) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-46 or to the amino acid sequence of SEQ ID NO: 109 and contains substitutions (e.g., conservative substitutions, insertions, or deletions relative to the reference sequence), but the anti-TREM2 antibody comprising that sequence retains the ability to bind to TREM2. In certain embodiments, a total of 1 to 10 amino acids have been substituted, inserted, and/or deleted in the light chain variable domain amino acid sequence of antibody AL2p-46 or the amino acid sequence of SEQ ID NO: 109. In certain embodiments, a total of 1 to 5 amino acids have been substituted, inserted and/or deleted in the light chain variable domain amino acid sequence of antibody AL2p-46 or the amino acid sequence of SEQ ID NO: 109. In certain embodiments, substitutions, insertions, or deletions occur in regions outside the HVRs (i.e., in the FR regions). In some embodiments, the substitutions, insertions, or deletions occur in in the FR regions. Optionally, the anti-TREM2 antibody comprises the VL sequence of antibody AL2p-46 or of SEQ ID NO: 109, including post-translational modifications of that sequence. In a particular embodiment, the VL comprises one, two or three HVRs selected from: (a) the HVR-L1 amino acid sequence of antibody AL2p-46, (b) the HVR-L2 amino acid sequence of antibody AL2p-46, and (c) the HVR-L3 amino acid sequence of antibody AL2p-46.

In some embodiments, anti-TREM2 antibodies of the present disclosure comprise a light chain variable domain and a heavy chain variable domain, wherein the heavy chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-47 or to the amino acid sequence of SEQ ID NO: 64; and/or the light chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-47 or to the amino acid sequence of SEQ ID NO: 108. In some embodiments, anti-TREM2 antibodies of the present disclosure comprise a heavy chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-47 or to the amino acid sequence of SEQ ID NO: 64, wherein the heavy chain variable domain comprises the HVR-H1, HVR-H2, and HVR-H3 amino acid sequences of antibody AL2p-47. In some embodiments, anti-TREM2 antibodies of the present disclosure comprise a light chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-47 or to the amino acid sequence of SEQ ID NO: 108, wherein the light chain variable domain comprises the HVR-L1, HVR-L2, and HVR-L3 amino acid sequences of antibody AL2p-47. In some embodiments, the anti-TREM2 antibody comprises a heavy chain variable domain (VH) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-47 or to the amino acid sequence of SEQ ID NO: 64 and contains substitutions (e.g., conservative substitutions, insertions, or deletions relative to the reference sequence), but the anti-TREM2 antibody comprising that sequence retains the ability to bind to TREM2. In certain embodiments, a total of 1 to 10 amino acids have been substituted, inserted, and/or deleted in the heavy chain variable domain amino acid sequence of antibody AL2p-47 or the amino acid sequence of SEQ ID NO: 64. In certain embodiments, a total of 1 to 5 amino acids have been substituted, inserted and/or deleted in the heavy chain variable domain amino acid sequence of antibody AL2p-47 or the amino acid sequence of SEQ ID NO: 64. In certain embodiments, substitutions, insertions, or deletions occur in regions outside the HVRs (i.e., in the FR regions). In some embodiments, the substitutions, insertions, or deletions occur in in the FR regions. Optionally, the anti-TREM2 antibody comprises the VH sequence of antibody AL2p-47 or of SEQ ID NO: 64, including post-translational modifications of that sequence. In a particular embodiment, the VH comprises one, two or three HVRs selected from: (a) the HVR-H1 amino acid sequence of antibody AL2p-47, (b) the HVR-H2 amino acid sequence of antibody AL2p-47, and (c) the HVR-H3 amino acid sequence of antibody AL2p-47. In some embodiments, anti-TREM2 antibodies of the present disclosure comprise a light chain variable domain (VL) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-47 or to the amino acid sequence of SEQ ID NO: 108 and contains substitutions (e.g., conservative substitutions, insertions, or deletions relative to the reference sequence), but the anti-TREM2 antibody comprising that sequence retains the ability to bind to TREM2. In certain embodiments, a total of 1 to 10 amino acids have been substituted, inserted, and/or deleted in the light chain variable domain amino acid sequence of antibody AL2p-47 or the amino acid sequence of SEQ ID NO: 108. In certain embodiments, a total of 1 to 5 amino acids have been substituted, inserted and/or deleted in the light chain variable domain amino acid sequence of antibody AL2p-47 or the amino acid sequence of SEQ ID NO: 108. In certain embodiments, substitutions, insertions, or deletions occur in regions outside the HVRs (i.e., in the FR regions). In some embodiments, the substitutions, insertions, or deletions occur in in the FR regions. Optionally, the anti-TREM2 antibody comprises the VL sequence of antibody AL2p-47 or of SEQ ID NO: 108, including post-translational modifications of that sequence. In a particular embodiment, the VL comprises one, two or three HVRs selected from: (a) the HVR-L1 amino acid sequence of antibody AL2p-47, (b) the HVR-L2 amino acid sequence of antibody AL2p-47, and (c) the HVR-L3 amino acid sequence of antibody AL2p-47.

In some embodiments, anti-TREM2 antibodies of the present disclosure comprise a light chain variable domain and a heavy chain variable domain, wherein the heavy chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-48 or to the amino acid sequence of SEQ ID NO: 64; and/or the light chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-48 or to the amino acid sequence of SEQ ID NO: 109. In some embodiments, anti-TREM2 antibodies of the present disclosure comprise a heavy chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-48 or to the amino acid sequence of SEQ ID NO: 64, wherein the heavy chain variable domain comprises the HVR-H1, HVR-H2, and HVR-H3 amino acid sequences of antibody AL2p-48. In some embodiments, anti-TREM2 antibodies of the present disclosure comprise a light chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-48 or to the amino acid sequence of SEQ ID NO: 109, wherein the light chain variable domain comprises the HVR-L1, HVR-L2, and HVR-L3 amino acid sequences of antibody AL2p-48. In some embodiments, the anti-TREM2 antibody comprises a heavy chain variable domain (VH) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-48 or to the amino acid sequence of SEQ ID NO: 64 and contains substitutions (e.g., conservative substitutions, insertions, or deletions relative to the reference sequence), but the anti-TREM2 antibody comprising that sequence retains the ability to bind to TREM2. In certain embodiments, a total of 1 to 10 amino acids have been substituted, inserted, and/or deleted in the heavy chain variable domain amino acid sequence of antibody AL2p-48 or the amino acid sequence of SEQ ID NO: 64. In certain embodiments, a total of 1 to 5 amino acids have been substituted, inserted and/or deleted in the heavy chain variable domain amino acid sequence of antibody AL2p-48 or the amino acid sequence of SEQ ID NO: 64. In certain embodiments, substitutions, insertions, or deletions occur in regions outside the HVRs (i.e., in the FR regions). In some embodiments, the substitutions, insertions, or deletions occur in in the FR regions. Optionally, the anti-TREM2 antibody comprises the VH sequence of antibody AL2p-48 or of SEQ ID NO: 64, including post-translational modifications of that sequence. In a particular embodiment, the VH comprises one, two or three HVRs selected from: (a) the HVR-H1 amino acid sequence of antibody AL2p-48, (b) the HVR-H2 amino acid sequence of antibody AL2p-48, and (c) the HVR-H3 amino acid sequence of antibody AL2p-48. In some embodiments, anti-TREM2 antibodies of the present disclosure comprise a light chain variable domain (VL) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-48 or to the amino acid sequence of SEQ ID NO: 109 and contains substitutions (e.g., conservative substitutions, insertions, or deletions relative to the reference sequence), but the anti-TREM2 antibody comprising that sequence retains the ability to bind to TREM2. In certain embodiments, a total of 1 to 10 amino acids have been substituted, inserted, and/or deleted in the light chain variable domain amino acid sequence of antibody AL2p-48 or the amino acid sequence of SEQ ID NO: 109. In certain embodiments, a total of 1 to 5 amino acids have been substituted, inserted and/or deleted in the light chain variable domain amino acid sequence of antibody AL2p-48 or the amino acid sequence of SEQ ID NO: 109. In certain embodiments, substitutions, insertions, or deletions occur in regions outside the HVRs (i.e., in the FR regions). In some embodiments, the substitutions, insertions, or deletions occur in in the FR regions. Optionally, the anti-TREM2 antibody comprises the VL sequence of antibody AL2p-48 or of SEQ ID NO: 109, including post-translational modifications of that sequence. In a particular embodiment, the VL comprises one, two or three HVRs selected from: (a) the HVR-L1 amino acid sequence of antibody AL2p-48, (b) the HVR-L2 amino acid sequence of antibody AL2p-48, and (c) the HVR-L3 amino acid sequence of antibody AL2p-48.

In some embodiments, anti-TREM2 antibodies of the present disclosure comprise a light chain variable domain and a heavy chain variable domain, wherein the heavy chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-49 or to the amino acid sequence of SEQ ID NO: 65; and/or the light chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-49 or to the amino acid sequence of SEQ ID NO: 109. In some embodiments, anti-TREM2 antibodies of the present disclosure comprise a heavy chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-49 or to the amino acid sequence of SEQ ID NO: 65, wherein the heavy chain variable domain comprises the HVR-H1, HVR-H2, and HVR-H3 amino acid sequences of antibody AL2p-49. In some embodiments, anti-TREM2 antibodies of the present disclosure comprise a light chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-49 or to the amino acid sequence of SEQ ID NO: 109, wherein the light chain variable domain comprises the HVR-L1, HVR-L2, and HVR-L3 amino acid sequences of antibody AL2p-49. In some embodiments, the anti-TREM2 antibody comprises a heavy chain variable domain (VH) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-49 or to the amino acid sequence of SEQ ID NO: 65 and contains substitutions (e.g., conservative substitutions, insertions, or deletions relative to the reference sequence), but the anti-TREM2 antibody comprising that sequence retains the ability to bind to TREM2. In certain embodiments, a total of 1 to 10 amino acids have been substituted, inserted, and/or deleted in the heavy chain variable domain amino acid sequence of antibody AL2p-49 or the amino acid sequence of SEQ ID NO: 65. In certain embodiments, a total of 1 to 5 amino acids have been substituted, inserted and/or deleted in the heavy chain variable domain amino acid sequence of antibody AL2p-49 or the amino acid sequence of SEQ ID NO: 65. In certain embodiments, substitutions, insertions, or deletions occur in regions outside the HVRs (i.e., in the FR regions). In some embodiments, the substitutions, insertions, or deletions occur in in the FR regions. Optionally, the anti-TREM2 antibody comprises the VH sequence of antibody AL2p-49 or of SEQ ID NO: 65, including post-translational modifications of that sequence. In a particular embodiment, the VH comprises one, two or three HVRs selected from: (a) the HVR-H1 amino acid sequence of antibody AL2p-49, (b) the HVR-H2 amino acid sequence of antibody AL2p-49, and (c) the HVR-H3 amino acid sequence of antibody AL2p-49. In some embodiments, anti-TREM2 antibodies of the present disclosure comprise a light chain variable domain (VL) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-49 or to the amino acid sequence of SEQ ID NO: 109 and contains substitutions (e.g., conservative substitutions, insertions, or deletions relative to the reference sequence), but the anti-TREM2 antibody comprising that sequence retains the ability to bind to TREM2. In certain embodiments, a total of 1 to 10 amino acids have been substituted, inserted, and/or deleted in the light chain variable domain amino acid sequence of antibody AL2p-49 or the amino acid sequence of SEQ ID NO: 109. In certain embodiments, a total of 1 to 5 amino acids have been substituted, inserted and/or deleted in the light chain variable domain amino acid sequence of antibody AL2p-49 or the amino acid sequence of SEQ ID NO: 109. In certain embodiments, substitutions, insertions, or deletions occur in regions outside the HVRs (i.e., in the FR regions). In some embodiments, the substitutions, insertions, or deletions occur in in the FR regions. Optionally, the anti-TREM2 antibody comprises the VL sequence of antibody AL2p-49 or of SEQ ID NO: 109, including post-translational modifications of that sequence. In a particular embodiment, the VL comprises one, two or three HVRs selected from: (a) the HVR-L1 amino acid sequence of antibody AL2p-49, (b) the HVR-L2 amino acid sequence of antibody AL2p-49, and (c) the HVR-L3 amino acid sequence of antibody AL2p-49.

In some embodiments, anti-TREM2 antibodies of the present disclosure comprise a light chain variable domain and a heavy chain variable domain, wherein the heavy chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-50 or to the amino acid sequence of SEQ ID NO: 66; and/or the light chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-50 or to the amino acid sequence of SEQ ID NO: 108. In some embodiments, anti-TREM2 antibodies of the present disclosure comprise a heavy chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-50 or to the amino acid sequence of SEQ ID NO: 66, wherein the heavy chain variable domain comprises the HVR-H1, HVR-H2, and HVR-H3 amino acid sequences of antibody AL2p-50. In some embodiments, anti-TREM2 antibodies of the present disclosure comprise a light chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-50 or to the amino acid sequence of SEQ ID NO: 108, wherein the light chain variable domain comprises the HVR-L1, HVR-L2, and HVR-L3 amino acid sequences of antibody AL2p-50. In some embodiments, the anti-TREM2 antibody comprises a heavy chain variable domain (VH) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-50 or to the amino acid sequence of SEQ ID NO: 66 and contains substitutions (e.g., conservative substitutions, insertions, or deletions relative to the reference sequence), but the anti-TREM2 antibody comprising that sequence retains the ability to bind to TREM2. In certain embodiments, a total of 1 to 10 amino acids have been substituted, inserted, and/or deleted in the heavy chain variable domain amino acid sequence of antibody AL2p-50 or the amino acid sequence of SEQ ID NO: 66. In certain embodiments, a total of 1 to 5 amino acids have been substituted, inserted and/or deleted in the heavy chain variable domain amino acid sequence of antibody AL2p-50 or the amino acid sequence of SEQ ID NO: 66. In certain embodiments, substitutions, insertions, or deletions occur in regions outside the HVRs (i.e., in the FR regions). In some embodiments, the substitutions, insertions, or deletions occur in in the FR regions. Optionally, the anti-TREM2 antibody comprises the VH sequence of antibody AL2p-50 or of SEQ ID NO: 66, including post-translational modifications of that sequence. In a particular embodiment, the VH comprises one, two or three HVRs selected from: (a) the HVR-H1 amino acid sequence of antibody AL2p-50, (b) the HVR-H2 amino acid sequence of antibody AL2p-50, and (c) the HVR-H3 amino acid sequence of antibody AL2p-50. In some embodiments, anti-TREM2 antibodies of the present disclosure comprise a light chain variable domain (VL) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-50 or to the amino acid sequence of SEQ ID NO: 108 and contains substitutions (e.g., conservative substitutions, insertions, or deletions relative to the reference sequence), but the anti-TREM2 antibody comprising that sequence retains the ability to bind to TREM2. In certain embodiments, a total of 1 to 10 amino acids have been substituted, inserted, and/or deleted in the light chain variable domain amino acid sequence of antibody AL2p-50 or the amino acid sequence of SEQ ID NO: 108. In certain embodiments, a total of 1 to 5 amino acids have been substituted, inserted and/or deleted in the light chain variable domain amino acid sequence of antibody AL2p-50 or the amino acid sequence of SEQ ID NO: 108. In certain embodiments, substitutions, insertions, or deletions occur in regions outside the HVRs (i.e., in the FR regions). In some embodiments, the substitutions, insertions, or deletions occur in in the FR regions. Optionally, the anti-TREM2 antibody comprises the VL sequence of antibody AL2p-50 or of SEQ ID NO: 108, including post-translational modifications of that sequence. In a particular embodiment, the VL comprises one, two or three HVRs selected from: (a) the HVR-L1 amino acid sequence of antibody AL2p-50, (b) the HVR-L2 amino acid sequence of antibody AL2p-50, and (c) the HVR-L3 amino acid sequence of antibody AL2p-50.

In some embodiments, anti-TREM2 antibodies of the present disclosure comprise a light chain variable domain and a heavy chain variable domain, wherein the heavy chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-51 or to the amino acid sequence of SEQ ID NO: 66; and/or the light chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-51 or to the amino acid sequence of SEQ ID NO: 109. In some embodiments, anti-TREM2 antibodies of the present disclosure comprise a heavy chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-51 or to the amino acid sequence of SEQ ID NO: 66, wherein the heavy chain variable domain comprises the HVR-H1, HVR-H2, and HVR-H3 amino acid sequences of antibody AL2p-51. In some embodiments, anti-TREM2 antibodies of the present disclosure comprise a light chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-51 or to the amino acid sequence of SEQ ID NO: 109, wherein the light chain variable domain comprises the HVR-L1, HVR-L2, and HVR-L3 amino acid sequences of antibody AL2p-51. In some embodiments, the anti-TREM2 antibody comprises a heavy chain variable domain (VH) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-51 or to the amino acid sequence of SEQ ID NO: 66 and contains substitutions (e.g., conservative substitutions, insertions, or deletions relative to the reference sequence), but the anti-TREM2 antibody comprising that sequence retains the ability to bind to TREM2. In certain embodiments, a total of 1 to 10 amino acids have been substituted, inserted, and/or deleted in the heavy chain variable domain amino acid sequence of antibody AL2p-51 or the amino acid sequence of SEQ ID NO: 66. In certain embodiments, a total of 1 to 5 amino acids have been substituted, inserted and/or deleted in the heavy chain variable domain amino acid sequence of antibody AL2p-51 or the amino acid sequence of SEQ ID NO: 66. In certain embodiments, substitutions, insertions, or deletions occur in regions outside the HVRs (i.e., in the FR regions). In some embodiments, the substitutions, insertions, or deletions occur in in the FR regions. Optionally, the anti-TREM2 antibody comprises the VH sequence of antibody AL2p-51 or of SEQ ID NO: 66, including post-translational modifications of that sequence. In a particular embodiment, the VH comprises one, two or three HVRs selected from: (a) the HVR-H1 amino acid sequence of antibody AL2p-51, (b) the HVR-H2 amino acid sequence of antibody AL2p-51, and (c) the HVR-H3 amino acid sequence of antibody AL2p-51. In some embodiments, anti-TREM2 antibodies of the present disclosure comprise a light chain variable domain (VL) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-51 or to the amino acid sequence of SEQ ID NO: 109 and contains substitutions (e.g., conservative substitutions, insertions, or deletions relative to the reference sequence), but the anti-TREM2 antibody comprising that sequence retains the ability to bind to TREM2. In certain embodiments, a total of 1 to 10 amino acids have been substituted, inserted, and/or deleted in the light chain variable domain amino acid sequence of antibody AL2p-51 or the amino acid sequence of SEQ ID NO: 109. In certain embodiments, a total of 1 to 5 amino acids have been substituted, inserted and/or deleted in the light chain variable domain amino acid sequence of antibody AL2p-51 or the amino acid sequence of SEQ ID NO: 109. In certain embodiments, substitutions, insertions, or deletions occur in regions outside the HVRs (i.e., in the FR regions). In some embodiments, the substitutions, insertions, or deletions occur in in the FR regions. Optionally, the anti-TREM2 antibody comprises the VL sequence of antibody AL2p-51 or of SEQ ID NO: 109, including post-translational modifications of that sequence. In a particular embodiment, the VL comprises one, two or three HVRs selected from: (a) the HVR-L1 amino acid sequence of antibody AL2p-51, (b) the HVR-L2 amino acid sequence of antibody AL2p-51, and (c) the HVR-L3 amino acid sequence of antibody AL2p-51.

In some embodiments, anti-TREM2 antibodies of the present disclosure comprise a light chain variable domain and a heavy chain variable domain, wherein the heavy chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-52 or to the amino acid sequence of SEQ ID NO: 67; and/or the light chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-52 or to the amino acid sequence of SEQ ID NO: 108. In some embodiments, anti-TREM2 antibodies of the present disclosure comprise a heavy chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-52 or to the amino acid sequence of SEQ ID NO: 67, wherein the heavy chain variable domain comprises the HVR-H1, HVR-H2, and HVR-H3 amino acid sequences of antibody AL2p-52. In some embodiments, anti-TREM2 antibodies of the present disclosure comprise a light chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-52 or to the amino acid sequence of SEQ ID NO: 108, wherein the light chain variable domain comprises the HVR-L1, HVR-L2, and HVR-L3 amino acid sequences of antibody AL2p-52. In some embodiments, the anti-TREM2 antibody comprises a heavy chain variable domain (VH) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-52 or to the amino acid sequence of SEQ ID NO: 67 and contains substitutions (e.g., conservative substitutions, insertions, or deletions relative to the reference sequence), but the anti-TREM2 antibody comprising that sequence retains the ability to bind to TREM2. In certain embodiments, a total of 1 to 10 amino acids have been substituted, inserted, and/or deleted in the heavy chain variable domain amino acid sequence of antibody AL2p-52 or the amino acid sequence of SEQ ID NO: 67. In certain embodiments, a total of 1 to 5 amino acids have been substituted, inserted and/or deleted in the heavy chain variable domain amino acid sequence of antibody AL2p-52 or the amino acid sequence of SEQ ID NO: 67. In certain embodiments, substitutions, insertions, or deletions occur in regions outside the HVRs (i.e., in the FR regions). In some embodiments, the substitutions, insertions, or deletions occur in in the FR regions. Optionally, the anti-TREM2 antibody comprises the VH sequence of antibody AL2p-52 or of SEQ ID NO: 67, including post-translational modifications of that sequence. In a particular embodiment, the VH comprises one, two or three HVRs selected from: (a) the HVR-H1 amino acid sequence of antibody AL2p-52, (b) the HVR-H2 amino acid sequence of antibody AL2p-52, and (c) the HVR-H3 amino acid sequence of antibody AL2p-52. In some embodiments, anti-TREM2 antibodies of the present disclosure comprise a light chain variable domain (VL) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-52 or to the amino acid sequence of SEQ ID NO: 108 and contains substitutions (e.g., conservative substitutions, insertions, or deletions relative to the reference sequence), but the anti-TREM2 antibody comprising that sequence retains the ability to bind to TREM2. In certain embodiments, a total of 1 to 10 amino acids have been substituted, inserted, and/or deleted in the light chain variable domain amino acid sequence of antibody AL2p-52 or the amino acid sequence of SEQ ID NO: 108. In certain embodiments, a total of 1 to 5 amino acids have been substituted, inserted and/or deleted in the light chain variable domain amino acid sequence of antibody AL2p-52 or the amino acid sequence of SEQ ID NO: 108. In certain embodiments, substitutions, insertions, or deletions occur in regions outside the HVRs (i.e., in the FR regions). In some embodiments, the substitutions, insertions, or deletions occur in in the FR regions. Optionally, the anti-TREM2 antibody comprises the VL sequence of antibody AL2p-52 or of SEQ ID NO: 108, including post-translational modifications of that sequence. In a particular embodiment, the VL comprises one, two or three HVRs selected from: (a) the HVR-L1 amino acid sequence of antibody AL2p-52, (b) the HVR-L2 amino acid sequence of antibody AL2p-52, and (c) the HVR-L3 amino acid sequence of antibody AL2p-52.

In some embodiments, anti-TREM2 antibodies of the present disclosure comprise a light chain variable domain and a heavy chain variable domain, wherein the heavy chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-53 or to the amino acid sequence of SEQ ID NO: 67; and/or the light chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-53 or to the amino acid sequence of SEQ ID NO: 109. In some embodiments, anti-TREM2 antibodies of the present disclosure comprise a heavy chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-53 or to the amino acid sequence of SEQ ID NO: 67, wherein the heavy chain variable domain comprises the HVR-H1, HVR-H2, and HVR-H3 amino acid sequences of antibody AL2p-53. In some embodiments, anti-TREM2 antibodies of the present disclosure comprise a light chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-53 or to the amino acid sequence of SEQ ID NO: 109, wherein the light chain variable domain comprises the HVR-L1, HVR-L2, and HVR-L3 amino acid sequences of antibody AL2p-53. In some embodiments, the anti-TREM2 antibody comprises a heavy chain variable domain (VH) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-53 or to the amino acid sequence of SEQ ID NO: 67 and contains substitutions (e.g., conservative substitutions, insertions, or deletions relative to the reference sequence), but the anti-TREM2 antibody comprising that sequence retains the ability to bind to TREM2. In certain embodiments, a total of 1 to 10 amino acids have been substituted, inserted, and/or deleted in the heavy chain variable domain amino acid sequence of antibody AL2p-53 or the amino acid sequence of SEQ ID NO: 67. In certain embodiments, a total of 1 to 5 amino acids have been substituted, inserted and/or deleted in the heavy chain variable domain amino acid sequence of antibody AL2p-53 or the amino acid sequence of SEQ ID NO: 67. In certain embodiments, substitutions, insertions, or deletions occur in regions outside the HVRs (i.e., in the FR regions). In some embodiments, the substitutions, insertions, or deletions occur in in the FR regions. Optionally, the anti-TREM2 antibody comprises the VH sequence of antibody AL2p-53 or of SEQ ID NO: 67, including post-translational modifications of that sequence. In a particular embodiment, the VH comprises one, two or three HVRs selected from: (a) the HVR-H1 amino acid sequence of antibody AL2p-53, (b) the HVR-H2 amino acid sequence of antibody AL2p-53, and (c) the HVR-H3 amino acid sequence of antibody AL2p-53. In some embodiments, anti-TREM2 antibodies of the present disclosure comprise a light chain variable domain (VL) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-53 or to the amino acid sequence of SEQ ID NO: 109 and contains substitutions (e.g., conservative substitutions, insertions, or deletions relative to the reference sequence), but the anti-TREM2 antibody comprising that sequence retains the ability to bind to TREM2. In certain embodiments, a total of 1 to 10 amino acids have been substituted, inserted, and/or deleted in the light chain variable domain amino acid sequence of antibody AL2p-53 or the amino acid sequence of SEQ ID NO: 109. In certain embodiments, a total of 1 to 5 amino acids have been substituted, inserted and/or deleted in the light chain variable domain amino acid sequence of antibody AL2p-53 or the amino acid sequence of SEQ ID NO: 109. In certain embodiments, substitutions, insertions, or deletions occur in regions outside the HVRs (i.e., in the FR regions). In some embodiments, the substitutions, insertions, or deletions occur in in the FR regions. Optionally, the anti-TREM2 antibody comprises the VL sequence of antibody AL2p-53 or of SEQ ID NO: 109, including post-translational modifications of that sequence. In a particular embodiment, the VL comprises one, two or three HVRs selected from: (a) the HVR-L1 amino acid sequence of antibody AL2p-53, (b) the HVR-L2 amino acid sequence of antibody AL2p-53, and (c) the HVR-L3 amino acid sequence of antibody AL2p-53.

In some embodiments, anti-TREM2 antibodies of the present disclosure comprise a light chain variable domain and a heavy chain variable domain, wherein the heavy chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-54 or to the amino acid sequence of SEQ ID NO: 68; and/or the light chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-54 or to the amino acid sequence of SEQ ID NO: 109. In some embodiments, anti-TREM2 antibodies of the present disclosure comprise a heavy chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-54 or to the amino acid sequence of SEQ ID NO: 68, wherein the heavy chain variable domain comprises the HVR-H1, HVR-H2, and HVR-H3 amino acid sequences of antibody AL2p-54. In some embodiments, anti-TREM2 antibodies of the present disclosure comprise a light chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-54 or to the amino acid sequence of SEQ ID NO: 109, wherein the light chain variable domain comprises the HVR-L1, HVR-L2, and HVR-L3 amino acid sequences of antibody AL2p-54. In some embodiments, the anti-TREM2 antibody comprises a heavy chain variable domain (VH) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-54 or to the amino acid sequence of SEQ ID NO: 68 and contains substitutions (e.g., conservative substitutions, insertions, or deletions relative to the reference sequence), but the anti-TREM2 antibody comprising that sequence retains the ability to bind to TREM2. In certain embodiments, a total of 1 to 10 amino acids have been substituted, inserted, and/or deleted in the heavy chain variable domain amino acid sequence of antibody AL2p-54 or the amino acid sequence of SEQ ID NO: 68. In certain embodiments, a total of 1 to 5 amino acids have been substituted, inserted and/or deleted in the heavy chain variable domain amino acid sequence of antibody AL2p-54 or the amino acid sequence of SEQ ID NO: 68. In certain embodiments, substitutions, insertions, or deletions occur in regions outside the HVRs (i.e., in the FR regions). In some embodiments, the substitutions, insertions, or deletions occur in in the FR regions. Optionally, the anti-TREM2 antibody comprises the VH sequence of antibody AL2p-54 or of SEQ ID NO: 68, including post-translational modifications of that sequence. In a particular embodiment, the VH comprises one, two or three HVRs selected from: (a) the HVR-H1 amino acid sequence of antibody AL2p-54, (b) the HVR-H2 amino acid sequence of antibody AL2p-54, and (c) the HVR-H3 amino acid sequence of antibody AL2p-54. In some embodiments, anti-TREM2 antibodies of the present disclosure comprise a light chain variable domain (VL) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-54 or to the amino acid sequence of SEQ ID NO: 109 and contains substitutions (e.g., conservative substitutions, insertions, or deletions relative to the reference sequence), but the anti-TREM2 antibody comprising that sequence retains the ability to bind to TREM2. In certain embodiments, a total of 1 to 10 amino acids have been substituted, inserted, and/or deleted in the light chain variable domain amino acid sequence of antibody AL2p-54 or the amino acid sequence of SEQ ID NO: 109. In certain embodiments, a total of 1 to 5 amino acids have been substituted, inserted and/or deleted in the light chain variable domain amino acid sequence of antibody AL2p-54 or the amino acid sequence of SEQ ID NO: 109. In certain embodiments, substitutions, insertions, or deletions occur in regions outside the HVRs (i.e., in the FR regions). In some embodiments, the substitutions, insertions, or deletions occur in in the FR regions. Optionally, the anti-TREM2 antibody comprises the VL sequence of antibody AL2p-54 or of SEQ ID NO: 109, including post-translational modifications of that sequence. In a particular embodiment, the VL comprises one, two or three HVRs selected from: (a) the HVR-L1 amino acid sequence of antibody AL2p-54, (b) the HVR-L2 amino acid sequence of antibody AL2p-54, and (c) the HVR-L3 amino acid sequence of antibody AL2p-54.

In some embodiments, anti-TREM2 antibodies of the present disclosure comprise a light chain variable domain and a heavy chain variable domain, wherein the heavy chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-55 or to the amino acid sequence of SEQ ID NO: 69; and/or the light chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-55 or to the amino acid sequence of SEQ ID NO: 108. In some embodiments, anti-TREM2 antibodies of the present disclosure comprise a heavy chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-55 or to the amino acid sequence of SEQ ID NO: 69, wherein the heavy chain variable domain comprises the HVR-H1, HVR-H2, and HVR-H3 amino acid sequences of antibody AL2p-55. In some embodiments, anti-TREM2 antibodies of the present disclosure comprise a light chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-55 or to the amino acid sequence of SEQ ID NO: 108, wherein the light chain variable domain comprises the HVR-L1, HVR-L2, and HVR-L3 amino acid sequences of antibody AL2p-55. In some embodiments, the anti-TREM2 antibody comprises a heavy chain variable domain (VH) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-55 or to the amino acid sequence of SEQ ID NO: 69 and contains substitutions (e.g., conservative substitutions, insertions, or deletions relative to the reference sequence), but the anti-TREM2 antibody comprising that sequence retains the ability to bind to TREM2. In certain embodiments, a total of 1 to 10 amino acids have been substituted, inserted, and/or deleted in the heavy chain variable domain amino acid sequence of antibody AL2p-55 or the amino acid sequence of SEQ ID NO: 69. In certain embodiments, a total of 1 to 5 amino acids have been substituted, inserted and/or deleted in the heavy chain variable domain amino acid sequence of antibody AL2p-55 or the amino acid sequence of SEQ ID NO: 69. In certain embodiments, substitutions, insertions, or deletions occur in regions outside the HVRs (i.e., in the FR regions). In some embodiments, the substitutions, insertions, or deletions occur in in the FR regions. Optionally, the anti-TREM2 antibody comprises the VH sequence of antibody AL2p-55 or of SEQ ID NO: 69, including post-translational modifications of that sequence. In a particular embodiment, the VH comprises one, two or three HVRs selected from: (a) the HVR-H1 amino acid sequence of antibody AL2p-55, (b) the HVR-H2 amino acid sequence of antibody AL2p-55, and (c) the HVR-H3 amino acid sequence of antibody AL2p-55. In some embodiments, anti-TREM2 antibodies of the present disclosure comprise a light chain variable domain (VL) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-55 or to the amino acid sequence of SEQ ID NO: 108 and contains substitutions (e.g., conservative substitutions, insertions, or deletions relative to the reference sequence), but the anti-TREM2 antibody comprising that sequence retains the ability to bind to TREM2. In certain embodiments, a total of 1 to 10 amino acids have been substituted, inserted, and/or deleted in the light chain variable domain amino acid sequence of antibody AL2p-55 or the amino acid sequence of SEQ ID NO: 108. In certain embodiments, a total of 1 to 5 amino acids have been substituted, inserted and/or deleted in the light chain variable domain amino acid sequence of antibody AL2p-55 or the amino acid sequence of SEQ ID NO: 108. In certain embodiments, substitutions, insertions, or deletions occur in regions outside the HVRs (i.e., in the FR regions). In some embodiments, the substitutions, insertions, or deletions occur in in the FR regions. Optionally, the anti-TREM2 antibody comprises the VL sequence of antibody AL2p-55 or of SEQ ID NO: 108, including post-translational modifications of that sequence. In a particular embodiment, the VL comprises one, two or three HVRs selected from: (a) the HVR-L1 amino acid sequence of antibody AL2p-55, (b) the HVR-L2 amino acid sequence of antibody AL2p-55, and (c) the HVR-L3 amino acid sequence of antibody AL2p-55.

In some embodiments, anti-TREM2 antibodies of the present disclosure comprise a light chain variable domain and a heavy chain variable domain, wherein the heavy chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-56 or to the amino acid sequence of SEQ ID NO: 69; and/or the light chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-56 or to the amino acid sequence of SEQ ID NO: 108. In some embodiments, anti-TREM2 antibodies of the present disclosure comprise a heavy chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-56 or to the amino acid sequence of SEQ ID NO: 69, wherein the heavy chain variable domain comprises the HVR-H1, HVR-H2, and HVR-H3 amino acid sequences of antibody AL2p-56. In some embodiments, anti-TREM2 antibodies of the present disclosure comprise a light chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-56 or to the amino acid sequence of SEQ ID NO: 108, wherein the light chain variable domain comprises the HVR-L1, HVR-L2, and HVR-L3 amino acid sequences of antibody AL2p-56. In some embodiments, the anti-TREM2 antibody comprises a heavy chain variable domain (VH) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-56 or to the amino acid sequence of SEQ ID NO: 69 and contains substitutions (e.g., conservative substitutions, insertions, or deletions relative to the reference sequence), but the anti-TREM2 antibody comprising that sequence retains the ability to bind to TREM2. In certain embodiments, a total of 1 to 10 amino acids have been substituted, inserted, and/or deleted in the heavy chain variable domain amino acid sequence of antibody AL2p-56 or the amino acid sequence of SEQ ID NO: 69. In certain embodiments, a total of 1 to 5 amino acids have been substituted, inserted and/or deleted in the heavy chain variable domain amino acid sequence of antibody AL2p-56 or the amino acid sequence of SEQ ID NO: 69. In certain embodiments, substitutions, insertions, or deletions occur in regions outside the HVRs (i.e., in the FR regions). In some embodiments, the substitutions, insertions, or deletions occur in in the FR regions. Optionally, the anti-TREM2 antibody comprises the VH sequence of antibody AL2p-56 or of SEQ ID NO: 69, including post-translational modifications of that sequence. In a particular embodiment, the VH comprises one, two or three HVRs selected from: (a) the HVR-H1 amino acid sequence of antibody AL2p-56, (b) the HVR-H2 amino acid sequence of antibody AL2p-56, and (c) the HVR-H3 amino acid sequence of antibody AL2p-56. In some embodiments, anti-TREM2 antibodies of the present disclosure comprise a light chain variable domain (VL) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-56 or to the amino acid sequence of SEQ ID NO: 108 and contains substitutions (e.g., conservative substitutions, insertions, or deletions relative to the reference sequence), but the anti-TREM2 antibody comprising that sequence retains the ability to bind to TREM2. In certain embodiments, a total of 1 to 10 amino acids have been substituted, inserted, and/or deleted in the light chain variable domain amino acid sequence of antibody AL2p-56 or the amino acid sequence of SEQ ID NO: 108. In certain embodiments, a total of 1 to 5 amino acids have been substituted, inserted and/or deleted in the light chain variable domain amino acid sequence of antibody AL2p-56 or the amino acid sequence of SEQ ID NO: 108. In certain embodiments, substitutions, insertions, or deletions occur in regions outside the HVRs (i.e., in the FR regions). In some embodiments, the substitutions, insertions, or deletions occur in in the FR regions. Optionally, the anti-TREM2 antibody comprises the VL sequence of antibody AL2p-56 or SEQ ID NO: 108, including post-translational modifications of that sequence. In a particular embodiment, the VL comprises one, two or three HVRs selected from: (a) the HVR-L1 amino acid sequence of antibody AL2p-56, (b) the HVR-L2 amino acid sequence of antibody AL2p-56, and (c) the HVR-L3 amino acid sequence of antibody AL2p-56.

In some embodiments, anti-TREM2 antibodies of the present disclosure comprise a light chain variable domain and a heavy chain variable domain, wherein the heavy chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-57 or to the amino acid sequence of SEQ ID NO: 69; and/or the light chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-57 or to the amino acid sequence of SEQ ID NO: 109. In some embodiments, anti-TREM2 antibodies of the present disclosure comprise a heavy chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-57 or to the amino acid sequence of SEQ ID NO: 69, wherein the heavy chain variable domain comprises the HVR-H1, HVR-H2, and HVR-H3 amino acid sequences of antibody AL2p-57. In some embodiments, anti-TREM2 antibodies of the present disclosure comprise a light chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-57 or to the amino acid sequence of SEQ ID NO: 109, wherein the light chain variable domain comprises the HVR-L1, HVR-L2, and HVR-L3 amino acid sequences of antibody AL2p-57. In some embodiments, the anti-TREM2 antibody comprises a heavy chain variable domain (VH) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-57 or to the amino acid sequence of SEQ ID NO: 69 and contains substitutions (e.g., conservative substitutions, insertions, or deletions relative to the reference sequence), but the anti-TREM2 antibody comprising that sequence retains the ability to bind to TREM2. In certain embodiments, a total of 1 to 10 amino acids have been substituted, inserted, and/or deleted in the heavy chain variable domain amino acid sequence of antibody AL2p-57 or the amino acid sequence of SEQ ID NO: 69. In certain embodiments, a total of 1 to 5 amino acids have been substituted, inserted and/or deleted in the heavy chain variable domain amino acid sequence of antibody AL2p-57 or the amino acid sequence of SEQ ID NO: 69. In certain embodiments, substitutions, insertions, or deletions occur in regions outside the HVRs (i.e., in the FR regions). In some embodiments, the substitutions, insertions, or deletions occur in in the FR regions. Optionally, the anti-TREM2 antibody comprises the VH sequence of antibody AL2p-57 or of SEQ ID NO: 69, including posttranslational modifications of that sequence. In a particular embodiment, the VH comprises one, two or three HVRs selected from: (a) the HVR-H1 amino acid sequence of antibody AL2p-57, (b) the HVR-H2 amino acid sequence of antibody AL2p-57, and (c) the HVR-H3 amino acid sequence of antibody AL2p-57. In some embodiments, anti-TREM2 antibodies of the present disclosure comprise a light chain variable domain (VL) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-57 or to the amino acid sequence of SEQ ID NO: 109 and contains substitutions (e.g., conservative substitutions, insertions, or deletions relative to the reference sequence), but the anti-TREM2 antibody comprising that sequence retains the ability to bind to TREM2. In certain embodiments, a total of 1 to 10 amino acids have been substituted, inserted, and/or deleted in the light chain variable domain amino acid sequence of antibody AL2p-57 or the amino acid sequence of SEQ ID NO: 109. In certain embodiments, a total of 1 to 5 amino acids have been substituted, inserted and/or deleted in the light chain variable domain amino acid sequence of antibody AL2p-57 or the amino acid sequence of SEQ ID NO: 109. In certain embodiments, substitutions, insertions, or deletions occur in regions outside the HVRs (i.e., in the FR regions). In some embodiments, the substitutions, insertions, or deletions occur in in the FR regions. Optionally, the anti-TREM2 antibody comprises the VL sequence of antibody AL2p-57 or of SEQ ID NO: 109, including posttranslational modifications of that sequence. In a particular embodiment, the VL comprises one, two or three HVRs selected from: (a) the HVR-L1 amino acid sequence of antibody AL2p-57, (b) the HVR-L2 amino acid sequence of antibody AL2p-57, and (c) the HVR-L3 amino acid sequence of antibody AL2p-57.

In some embodiments, anti-TREM2 antibodies of the present disclosure comprise a light chain variable domain and a heavy chain variable domain, wherein the heavy chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-58 or to the amino acid sequence of SEQ ID NO: 59; and/or the light chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-58 or to the amino acid sequence of SEQ ID NO: 112. In some embodiments, anti-TREM2 antibodies of the present disclosure comprise a heavy chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-58 or to the amino acid sequence of SEQ ID NO: 59, wherein the heavy chain variable domain comprises the HVR-H1, HVR-H2, and HVR-H3 amino acid sequences of antibody AL2p-58. In some embodiments, anti-TREM2 antibodies of the present disclosure comprise a light chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-58 or to the amino acid sequence of SEQ ID NO: 112, wherein the light chain variable domain comprises the HVR-L1, HVR-L2, and HVR-L3 amino acid sequences of antibody AL2p-58. In some embodiments, the anti-TREM2 antibody comprises a heavy chain variable domain (VH) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-58 or to the amino acid sequence of SEQ ID NO: 59 and contains substitutions (e.g., conservative substitutions, insertions, or deletions relative to the reference sequence), but the anti-TREM2 antibody comprising that sequence retains the ability to bind to TREM2. In certain embodiments, a total of 1 to 10 amino acids have been substituted, inserted, and/or deleted in the heavy chain variable domain amino acid sequence of antibody AL2p-58 or the amino acid sequence of SEQ ID NO: 59. In certain embodiments, a total of 1 to 5 amino acids have been substituted, inserted and/or deleted in the heavy chain variable domain amino acid sequence of antibody AL2p-58 or the amino acid sequence of SEQ ID NO: 59. In certain embodiments, substitutions, insertions, or deletions occur in regions outside the HVRs (i.e., in the FR regions). In some embodiments, the substitutions, insertions, or deletions occur in in the FR regions. Optionally, the anti-TREM2 antibody comprises the VH sequence of antibody AL2p-58 or of SEQ ID NO: 59, including posttranslational modifications of that sequence. In a particular embodiment, the VH comprises one, two or three HVRs selected from: (a) the HVR-H1 amino acid sequence of antibody AL2p-58, (b) the HVR-H2 amino acid sequence of antibody AL2p-58, and (c) the HVR-H3 amino acid sequence of antibody AL2p-58. In some embodiments, anti-TREM2 antibodies of the present disclosure comprise a light chain variable domain (VL) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-58 or to the amino acid sequence of SEQ ID NO: 112 and contains substitutions (e.g., conservative substitutions, insertions, or deletions relative to the reference sequence), but the anti-TREM2 antibody comprising that sequence retains the ability to bind to TREM2. In certain embodiments, a total of 1 to 10 amino acids have been substituted, inserted, and/or deleted in the light chain variable domain amino acid sequence of antibody AL2p-58 or the amino acid sequence of SEQ ID NO: 112. In certain embodiments, a total of 1 to 5 amino acids have been substituted, inserted and/or deleted in the light chain variable domain amino acid sequence of antibody AL2p-58 or the amino acid sequence of SEQ ID NO: 112. In certain embodiments, substitutions, insertions, or deletions occur in regions outside the HVRs (i.e., in the FR regions). In some embodiments, the substitutions, insertions, or deletions occur in in the FR regions. Optionally, the anti-TREM2 antibody comprises the VL sequence of antibody AL2p-58 or of SEQ ID NO: 112, including posttranslational modifications of that sequence. In a particular embodiment, the VL comprises one, two or three HVRs selected from: (a) the HVR-L1 amino acid sequence of antibody AL2p-58, (b) the HVR-L2 amino acid sequence of antibody AL2p-58, and (c) the HVR-L3 amino acid sequence of antibody AL2p-58.

In some embodiments, anti-TREM2 antibodies of the present disclosure comprise a light chain variable domain and a heavy chain variable domain, wherein the heavy chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-59 or to the amino acid sequence of SEQ ID NO: 91; and/or the light chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-59 or to the amino acid sequence of SEQ ID NO: 118. In some embodiments, anti-TREM2 antibodies of the present disclosure comprise a heavy chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-59 or to the amino acid sequence of SEQ ID NO: 91, wherein the heavy chain variable domain comprises the HVR-H1, HVR-H2, and HVR-H3 amino acid sequences of antibody AL2p-59. In some embodiments, anti-TREM2 antibodies of the present disclosure comprise a light chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-59 or to the amino acid sequence of SEQ ID NO: 118, wherein the light chain variable domain comprises the HVR-L1, HVR-L2, and HVR-L3 amino acid sequences of antibody AL2p-59. In some embodiments, the anti-TREM2 antibody comprises a heavy chain variable domain (VH) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-59 or to the amino acid sequence of SEQ ID NO: 91 and contains substitutions (e.g., conservative substitutions, insertions, or deletions relative to the reference sequence), but the anti-TREM2 antibody comprising that sequence retains the ability to bind to TREM2. In certain embodiments, a total of 1 to 10 amino acids have been substituted, inserted, and/or deleted in the heavy chain variable domain amino acid sequence of antibody AL2p-59 or the amino acid sequence of SEQ ID NO: 91. In certain embodiments, a total of 1 to 5 amino acids have been substituted, inserted and/or deleted in the heavy chain variable domain amino acid sequence of antibody AL2p-59 or the amino acid sequence of SEQ ID NO: 91. In certain embodiments, substitutions, insertions, or deletions occur in regions outside the HVRs (i.e., in the FR regions). In some embodiments, the substitutions, insertions, or deletions occur in in the FR regions. Optionally, the anti-TREM2 antibody comprises the VH sequence of antibody AL2p-59 or of SEQ ID NO: 91, including post-translational modifications of that sequence. In a particular embodiment, the VH comprises one, two or three HVRs selected from: (a) the HVR-H1 amino acid sequence of antibody AL2p-59, (b) the HVR-H2 amino acid sequence of antibody AL2p-59, and (c) the HVR-H3 amino acid sequence of antibody AL2p-59. In some embodiments, anti-TREM2 antibodies of the present disclosure comprise a light chain variable domain (VL) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-59 or to the amino acid sequence of SEQ ID NO: 118 and contains substitutions (e.g., conservative substitutions, insertions, or deletions relative to the reference sequence), but the anti-TREM2 antibody comprising that sequence retains the ability to bind to TREM2. In certain embodiments, a total of 1 to 10 amino acids have been substituted, inserted, and/or deleted in the light chain variable domain amino acid sequence of antibody AL2p-59 or the amino acid sequence of SEQ ID NO: 118. In certain embodiments, a total of 1 to 5 amino acids have been substituted, inserted and/or deleted in the light chain variable domain amino acid sequence of antibody AL2p-59 or the amino acid sequence of SEQ ID NO: 118. In certain embodiments, substitutions, insertions, or deletions occur in regions outside the HVRs (i.e., in the FR regions). In some embodiments, the substitutions, insertions, or deletions occur in in the FR regions. Optionally, the anti-TREM2 antibody comprises the VL sequence of antibody AL2p-59 or of SEQ ID NO: 118, including post-translational modifications of that sequence. In a particular embodiment, the VL comprises one, two or three HVRs selected from: (a) the HVR-L1 amino acid sequence of antibody AL2p-59, (b) the HVR-L2 amino acid sequence of antibody AL2p-59, and (c) the HVR-L3 amino acid sequence of antibody AL2p-59.

In some embodiments, anti-TREM2 antibodies of the present disclosure comprise a light chain variable domain and a heavy chain variable domain, wherein the heavy chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-60 or to the amino acid sequence of SEQ ID NO: 53; and/or the light chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-60 or to the amino acid sequence of SEQ ID NO: 113. In some embodiments, anti-TREM2 antibodies of the present disclosure comprise a heavy chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-60 or to the amino acid sequence of SEQ ID NO: 53, wherein the heavy chain variable domain comprises the HVR-H1, HVR-H2, and HVR-H3 amino acid sequences of antibody AL2p-60. In some embodiments, anti-TREM2 antibodies of the present disclosure comprise a light chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-60 or to the amino acid sequence of SEQ ID NO: 113, wherein the light chain variable domain comprises the HVR-L1, HVR-L2, and HVR-L3 amino acid sequences of antibody AL2p-60. In some embodiments, the anti-TREM2 antibody comprises a heavy chain variable domain (VH) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-60 or to the amino acid sequence of SEQ ID NO: 53 and contains substitutions (e.g., conservative substitutions, insertions, or deletions relative to the reference sequence), but the anti-TREM2 antibody comprising that sequence retains the ability to bind to TREM2. In certain embodiments, a total of 1 to 10 amino acids have been substituted, inserted, and/or deleted in the heavy chain variable domain amino acid sequence of antibody AL2p-60 or the amino acid sequence of SEQ ID NO: 53. In certain embodiments, a total of 1 to 5 amino acids have been substituted, inserted and/or deleted in the heavy chain variable domain amino acid sequence of antibody AL2p-60 or the amino acid sequence of SEQ ID NO: 53. In certain embodiments, substitutions, insertions, or deletions occur in regions outside the HVRs (i.e., in the FR regions). In some embodiments, the substitutions, insertions, or deletions occur in in the FR regions. Optionally, the anti-TREM2 antibody comprises the VH sequence of antibody AL2p-60 or of SEQ ID NO: 53, including post-translational modifications of that sequence. In a particular embodiment, the VH comprises one, two or three HVRs selected from: (a) the HVR-H1 amino acid sequence of antibody AL2p-60, (b) the HVR-H2 amino acid sequence of antibody AL2p-60, and (c) the HVR-H3 amino acid sequence of antibody AL2p-60. In some embodiments, anti-TREM2 antibodies of the present disclosure comprise a light chain variable domain (VL) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-60 or to the amino acid sequence of SEQ ID NO: 113 and contains substitutions (e.g., conservative substitutions, insertions, or deletions relative to the reference sequence), but the anti-TREM2 antibody comprising that sequence retains the ability to bind to TREM2. In certain embodiments, a total of 1 to 10 amino acids have been substituted, inserted, and/or deleted in the light chain variable domain amino acid sequence of antibody AL2p-60 or the amino acid sequence of SEQ ID NO: 113. In certain embodiments, a total of 1 to 5 amino acids have been substituted, inserted and/or deleted in the light chain variable domain amino acid sequence of antibody AL2p-60 or the amino acid sequence of SEQ ID NO: 113. In certain embodiments, substitutions, insertions, or deletions occur in regions outside the HVRs (i.e., in the FR regions). In some embodiments, the substitutions, insertions, or deletions occur in in the FR regions. Optionally, the anti-TREM2 antibody comprises the VL sequence of antibody AL2p-60 or of SEQ ID NO: 113, including post-translational modifications of that sequence. In a particular embodiment, the VL comprises one, two or three HVRs selected from: (a) the HVR-L1 amino acid sequence of antibody AL2p-60, (b) the HVR-L2 amino acid sequence of antibody AL2p-60, and (c) the HVR-L3 amino acid sequence of antibody AL2p-60.

In some embodiments, anti-TREM2 antibodies of the present disclosure comprise a light chain variable domain and a heavy chain variable domain, wherein the heavy chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-61 or to the amino acid sequence of SEQ ID NO: 70; and/or the light chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-61 or to the amino acid sequence of SEQ ID NO: 110. In some embodiments, anti-TREM2 antibodies of the present disclosure comprise a heavy chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-61 or to the amino acid sequence of SEQ ID NO: 70, wherein the heavy chain variable domain comprises the HVR-H1, HVR-H2, and HVR-H3 amino acid sequences of antibody AL2p-61. In some embodiments, anti-TREM2 antibodies of the present disclosure comprise a light chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-61 or to the amino acid sequence of SEQ ID NO: 110, wherein the light chain variable domain comprises the HVR-L1, HVR-L2, and HVR-L3 amino acid sequences of antibody AL2p-61. In some embodiments, the anti-TREM2 antibody comprises a heavy chain variable domain (VH) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-61 or to the amino acid sequence of SEQ ID NO: 70 and contains substitutions (e.g., conservative substitutions, insertions, or deletions relative to the reference sequence), but the anti-TREM2 antibody comprising that sequence retains the ability to bind to TREM2. In certain embodiments, a total of 1 to 10 amino acids have been substituted, inserted, and/or deleted in the heavy chain variable domain amino acid sequence of antibody AL2p-61 or the amino acid sequence of SEQ ID NO: 70. In certain embodiments, a total of 1 to 5 amino acids have been substituted, inserted and/or deleted in the heavy chain variable domain amino acid sequence of antibody AL2p-61 or the amino acid sequence of SEQ ID NO: 70. In certain embodiments, substitutions, insertions, or deletions occur in regions outside the HVRs (i.e., in the FR regions). In some embodiments, the substitutions, insertions, or deletions occur in in the FR regions. Optionally, the anti-TREM2 antibody comprises the VH sequence of antibody AL2p-61 or of SEQ ID NO: 70, including post-translational modifications of that sequence. In a particular embodiment, the VH comprises one, two or three HVRs selected from: (a) the HVR-H1 amino acid sequence of antibody AL2p-61, (b) the HVR-H2 amino acid sequence of antibody AL2p-61, and (c) the HVR-H3 amino acid sequence of antibody AL2p-61. In some embodiments, anti-TREM2 antibodies of the present disclosure comprise a light chain variable domain (VL) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-61 or to the amino acid sequence of SEQ ID NO: 110 and contains substitutions (e.g., conservative substitutions, insertions, or deletions relative to the reference sequence), but the anti-TREM2 antibody comprising that sequence retains the ability to bind to TREM2. In certain embodiments, a total of 1 to 10 amino acids have been substituted, inserted, and/or deleted in the light chain variable domain amino acid sequence of antibody AL2p-61 or the amino acid sequence of SEQ ID NO: 110. In certain embodiments, a total of 1 to 5 amino acids have been substituted, inserted and/or deleted in the light chain variable domain amino acid sequence of antibody AL2p-61 or the amino acid sequence of SEQ ID NO: 110. In certain embodiments, substitutions, insertions, or deletions occur in regions outside the HVRs (i.e., in the FR regions). In some embodiments, the substitutions, insertions, or deletions occur in in the FR regions. Optionally, the anti-TREM2 antibody comprises the VL sequence of antibody AL2p-61 or of SEQ ID NO: 110, including post-translational modifications of that sequence. In a particular embodiment, the VL comprises one, two or three HVRs selected from: (a) the HVR-L1 amino acid sequence of antibody AL2p-61, (b) the HVR-L2 amino acid sequence of antibody AL2p-61, and (c) the HVR-L3 amino acid sequence of antibody AL2p-61.

In some embodiments, anti-TREM2 antibodies of the present disclosure comprise a light chain variable domain and a heavy chain variable domain, wherein the heavy chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-62 or to the amino acid sequence of SEQ ID NO: 71; and/or the light chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-62 or to the amino acid sequence of SEQ ID NO: 111. In some embodiments, anti-TREM2 antibodies of the present disclosure comprise a heavy chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-62 or to the amino acid sequence of SEQ ID NO: 71, wherein the heavy chain variable domain comprises the HVR-H1, HVR-H2, and HVR-H3 amino acid sequences of antibody AL2p-62. In some embodiments, anti-TREM2 antibodies of the present disclosure comprise a light chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-62 or to the amino acid sequence of SEQ ID NO: 111, wherein the light chain variable domain comprises the HVR-L1, HVR-L2, and HVR-L3 amino acid sequences of antibody AL2p-62. In some embodiments, the anti-TREM2 antibody comprises a heavy chain variable domain (VH) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AL2p-62 or to the amino acid sequence of SEQ ID NO: 71 and contains substitutions (e.g., conservative substitutions, insertions, or deletions relative to the reference sequence), but the anti-TREM2 antibody comprising that sequence retains the ability to bind to TREM2. In certain embodiments, a total of 1 to 10 amino acids have been substituted, inserted, and/or deleted in the heavy chain variable domain amino acid sequence of antibody AL2p-62 or the amino acid sequence of SEQ ID NO: 71. In certain embodiments, a total of 1 to 5 amino acids have been substituted, inserted and/or deleted in the heavy chain variable domain amino acid sequence of antibody AL2p-62 or the amino acid sequence of SEQ ID NO: 71. In certain embodiments, substitutions, insertions, or deletions occur in regions outside the HVRs (i.e., in the FR regions). In some embodiments, the substitutions, insertions, or deletions occur in in the FR regions. Optionally, the anti-TREM2 antibody comprises the VH sequence of antibody AL2p-62 or of SEQ ID NO: 71, including post-translational modifications of that sequence. In a particular embodiment, the VH comprises one, two or three HVRs selected from: (a) the HVR-H1 amino acid sequence of antibody AL2p-62, (b) the HVR-H2 amino acid sequence of antibody AL2p-62, and (c) the HVR-H3 amino acid sequence of antibody AL2p-62. In some embodiments, anti-TREM2 antibodies of the present disclosure comprise a light chain variable domain (VL) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AL2p-62 or to the amino acid sequence of SEQ ID NO: 111 and contains substitutions (e.g., conservative substitutions, insertions, or deletions relative to the reference sequence), but the anti-TREM2 antibody comprising that sequence retains the ability to bind to TREM2. In certain embodiments, a total of 1 to 10 amino acids have been substituted, inserted, and/or deleted in the light chain variable domain amino acid sequence of antibody AL2p-62 or the amino acid sequence of SEQ ID NO: 111. In certain embodiments, a total of 1 to 5 amino acids have been substituted, inserted and/or deleted in the light chain variable domain amino acid sequence of antibody AL2p-62 or the amino acid sequence of SEQ ID NO: 111. In certain embodiments, substitutions, insertions, or deletions occur in regions outside the HVRs (i.e., in the FR regions). In some embodiments, the substitutions, insertions, or deletions occur in in the FR regions. Optionally, the anti-TREM2 antibody comprises the VL sequence of antibody AL2p-62 or of SEQ ID NO: 111, including posttranslational modifications of that sequence. In a particular embodiment, the VL comprises one, two or three HVRs selected from: (a) the HVR-L1 amino acid sequence of antibody AL2p-62, (b) the HVR-L2 amino acid sequence of antibody AL2p-62, and (c) the HVR-L3 amino acid sequence of antibody AL2p-62.

In some embodiments, the anti-TREM2 antibody is provided, wherein the antibody comprises a VH as in any of the embodiments provided above, and a VL as in any of the embodiments provided above. In some embodiments, provided herein are anti-TREM2 antibodies, wherein the antibody comprises a VH as in any of the embodiments provided above, and a VL as in any of the embodiments provided above. In one embodiment, the antibody comprises the VH and VL sequences in SEQ ID NOs: 27-71 and 91 and SEQ ID NOs: 92-113 and 118, respectively, including posttranslational modifications of those sequences.

In some embodiments, the antibody comprises a heavy chain variable region comprising the amino acid sequence of SEQ ID NO: 53, and/or a light chain variable region comprising the amino acid sequence of SEQ ID NO: 97. In some embodiments, the antibody comprises a heavy chain variable region comprising the amino acid sequence of SEQ ID NO: 59; and/or a light chain variable region comprising the amino acid sequence of SEQ ID NO: 104. In some embodiments, the antibody comprises a heavy chain variable region comprising the amino acid sequence of SEQ ID NO: 64; and/or a light chain variable region comprising the amino acid sequence of SEQ ID NO: 108. In some embodiments, the antibody comprises a heavy chain variable region comprising the amino acid sequence of SEQ ID NO: 70; and/or a light chain variable region comprising the amino acid sequence of SEQ ID NO: 110. In some embodiments, the antibody comprises a heavy chain variable region comprising the amino acid sequence of SEQ ID NO: 71; and/or a light chain variable region comprising the amino acid sequence of SEQ ID NO: 111. In some embodiments, the antibody comprises a heavy chain variable region comprising the amino acid sequence of SEQ ID NO: 59; and/or a light chain variable region comprising the amino acid sequence of SEQ ID NO: 112. In some embodiments, the antibody comprises a heavy chain variable region comprising the amino acid sequence of SEQ ID NO: 53; and/or a light chain variable region comprising the amino acid sequence of SEQ ID NO: 113.

Any of the antibodies of the present disclosure may be produced by a cell line. In some embodiments, the cell line may be a mammalian cell line. In certain embodiments, the cell line may be a hybridoma cell line. In other embodiments, the cell line may be a yeast cell line. Any cell line known in the art suitable for antibody production may be used to produce an antibody of the present disclosure. Exemplary cell lines for antibody production are described throughout the present disclosure.

In some embodiments, the anti-TREM2 antibody is an anti-TREM2 monoclonal antibody selected from AL2p-h50, AL2p-2, AL2p-3, AL2p-4, AL2p-5, AL2p-6, AL2p-7, AL2p-8, AL2p-9, AL2p-10, AL2p-11, AL2p-12, AL2p-13, AL2p-14, AL2p-15, AL2p-16, AL2p-17, AL2p-18, AL2p-19, AL2p-20, AL2p-21, AL2p-22, AL2p-23, AL2p-24, AL2p-25, AL2p-26, AL2p-27, AL2p-28, AL2p-29, AL2p-30, AL2p-31, AL2p-32, AL2p-33, AL2p-h77, AL2p-35, AL2p-36, AL2p-37, AL2p-38, AL2p-39, AL2p-40, AL2p-41, AL2p-42, AL2p-43, AL2p-44, AL2p-45, AL2p-46, AL2p-47, AL2p-48, AL2p-49, AL2p-50, AL2p-51, AL2p-52, AL2p-53, AL2p-54, AL2p-55, AL2p-56, AL2p-57, AL2p-58, AL2p-59, AL2p-60, AL2p-61, AL2p-62, AL2p-h19, AL2p-h21, AL2p-h22, AL2p-h23, AL2p-h24, AL2p-h25, AL2p-h26, AL2p-h27, AL2p-h28, AL2p-h29, AL2p-h30, AL2p-h31, AL2p-h32, AL2p-h33, AL2p-h34, AL2p-h35, AL2p-h36, AL2p-h42, AL2p-h43, AL2p-h44, AL2p-h47, AL2p-h59, AL2p-h76, and AL2p-h90.

In some embodiments, the anti-TREM2 antibody is anti-TREM2 monoclonal antibody AL2p-31. In some embodiments, the anti-TREM2 antibody is an isolated antibody which binds essentially the same TREM2 epitope as AL2p-31. In some embodiments, the anti-TREM2 antibody is an isolated antibody comprising the HVR-H1, HVR-H2, and HVR-H3 of the heavy chain variable domain of monoclonal antibody AL2p-31. In some embodiments, the anti-TREM2 antibody is an isolated antibody comprising the HVR-L1, HVR-L2, and HVR-L3 of the light chain variable domain of monoclonal antibody AL2p-31. In some embodiments, the anti-TREM2 antibody is an isolated antibody comprising the HVR-H1, HVR-H2, and HVR-H3 of the heavy chain variable domain and the HVR-L1, HVR-L2, and HVR-L3 of the light chain variable domain of monoclonal antibody AL2p-31.

In some embodiments, the anti-TREM2 antibody is anti-TREM2 monoclonal antibody AL2p-37. In some embodiments, the anti-TREM2 antibody is an isolated antibody which binds essentially the same TREM2 epitope as AL2p-37. In some embodiments, the anti-TREM2 antibody is an isolated antibody comprising the HVR-H1, HVR-H2, and HVR-H3 of the heavy chain variable domain of monoclonal antibody AL2p-37. In some embodiments, the anti-TREM2 antibody is an isolated antibody comprising the HVR-L1, HVR-L2, and HVR-L3 of the light chain variable domain of monoclonal antibody AL2p-37. In some embodiments, the anti-TREM2 antibody is an isolated antibody comprising the HVR-H1, HVR-H2, and HVR-H3 of the heavy chain variable domain and the HVR-L1, HVR-L2, and HVR-L3 of the light chain variable domain of monoclonal antibody AL2p-37.

In some embodiments, the anti-TREM2 antibody is anti-TREM2 monoclonal antibody AL2p-47. In some embodiments, the anti-TREM2 antibody is an isolated antibody which binds essentially the same TREM2 epitope as AL2p-47. In some embodiments, the anti-TREM2 antibody is an isolated antibody comprising the HVR-H1, HVR-H2, and HVR-H3 of the heavy chain variable domain of monoclonal antibody AL2p-47. In some embodiments, the anti-TREM2 antibody is an isolated antibody comprising the HVR-L1, HVR-L2, and HVR-L3 of the light chain variable domain of monoclonal antibody AL2p-47. In some embodiments, the anti-TREM2 antibody is an isolated antibody comprising the HVR-H1, HVR-H2, and HVR-H3 of the heavy chain variable domain and the HVR-L1, HVR-L2, and HVR-L3 of the light chain variable domain of monoclonal antibody AL2p-47.

In some embodiments, the anti-TREM2 antibody is anti-TREM2 monoclonal antibody AL2p-58. In some embodiments, the anti-TREM2 antibody is an isolated antibody which binds essentially the same TREM2 epitope as AL2p-58. In some embodiments, the anti-TREM2 antibody is an isolated antibody comprising the HVR-H1, HVR-H2, and HVR-H3 of the heavy chain variable domain of monoclonal antibody AL2p-58. In some embodiments, the anti-TREM2 antibody is an isolated antibody comprising the HVR-L1, HVR-L2, and HVR-L3 of the light chain variable domain of monoclonal antibody AL2p-58. In some embodiments, the anti-TREM2 antibody is an isolated antibody comprising the HVR-H1, HVR-H2, and HVR-H3 of the heavy chain variable domain and the HVR-L1, HVR-L2, and HVR-L3 of the light chain variable domain of monoclonal antibody AL2p-58.

In some embodiments, the anti-TREM2 antibody is anti-TREM2 monoclonal antibody AL2p-60. In some embodiments, the anti-TREM2 antibody is an isolated antibody which binds essentially the same TREM2 epitope as AL2p-60. In some embodiments, the anti-TREM2 antibody is an isolated antibody comprising the HVR-H1, HVR-H2, and HVR-H3 of the heavy chain variable domain of monoclonal antibody AL2p-60. In some embodiments, the anti-TREM2 antibody is an isolated antibody comprising the HVR-L1, HVR-L2, and HVR-L3 of the light chain variable domain of monoclonal antibody AL2p-60. In some embodiments, the anti-TREM2 antibody is an isolated antibody comprising the HVR-H1, HVR-H2, and HVR-H3 of the heavy chain variable domain and the HVR-L1, HVR-L2, and HVR-L3 of the light chain variable domain of monoclonal antibody AL2p-60.

In some embodiments, the anti-TREM2 antibody is anti-TREM2 monoclonal antibody AL2p-61. In some embodiments, the anti-TREM2 antibody is an isolated antibody which binds essentially the same TREM2 epitope as AL2p-61. In some embodiments, the anti-TREM2 antibody is an isolated antibody comprising the HVR-H1, HVR-H2, and HVR-H3 of the heavy chain variable domain of monoclonal antibody AL2p-61. In some embodiments, the anti-TREM2 antibody is an isolated antibody comprising the HVR-L1, HVR-L2, and HVR-L3 of the light chain variable domain of monoclonal antibody AL2p-61. In some embodiments, the anti-TREM2 antibody is an isolated antibody comprising the HVR-H1, HVR-H2, and HVR-H3 of the heavy chain variable domain and the HVR-L1, HVR-L2, and HVR-L3 of the light chain variable domain of monoclonal antibody AL2p-61.

In some embodiments, the anti-TREM2 antibody is anti-TREM2 monoclonal antibody AL2p-62. In some embodiments, the anti-TREM2 antibody is an isolated antibody which binds essentially the same TREM2 epitope as AL2p-62. In some embodiments, the anti-TREM2 antibody is an isolated antibody comprising the HVR-H1, HVR-H2, and HVR-H3 of the heavy chain variable domain of monoclonal antibody AL2p-62. In some embodiments, the anti-TREM2 antibody is an isolated antibody comprising the HVR-L1, HVR-L2, and HVR-L3 of the light chain variable domain of monoclonal antibody AL2p-62. In some embodiments, the anti-TREM2 antibody is an isolated antibody comprising the HVR-H1, HVR-H2, and HVR-H3 of the heavy chain variable domain and the HVR-L1, HVR-L2, and HVR-L3 of the light chain variable domain of monoclonal antibody AL2p-62.

In some embodiments, anti-TREM2 antibodies of the present disclosure do not compete with one or more TREM2 ligands for binding to TREM2. In some embodiments, anti-TREM2 antibodies of the present disclosure are capable of binding TREM2 without blocking simultaneous binding of one or more TREM2 ligands to TREM2. In some embodiments anti-TREM2 antibodies of the present disclosure are capable of additive and/or synergistic functional interactions with one or more TREM2 ligands. In some embodiments, anti-TREM2 antibodies of the present disclosure increase the maximal activity of TREM2 exposed to saturating concentrations of one or more TREM2 ligands. In some embodiments, anti-TREM2 antibodies of the present disclosure increase the activity of TREM2 obtained at any concentration of one or more TREM2 ligands.

Anti-TREM2 Antibody Binding Affinity

The dissociation constants ($K_D$) of anti-TREM2 antibodies for human TREM2 and cynomolgus monkey TREM2 may be at least 1-fold lower, at least 2-fold lower, at least 3-fold lower, at least 4-fold lower, at least 5-fold lower, at least 6-fold lower, at least 7-fold lower, at least 8-fold lower, at least 9-fold lower, at least 10-fold lower, at least 11-fold lower, at least 12-fold lower, at least 13-fold lower, at least 14-fold lower, at least 15-fold lower, at least 16-fold lower, at least 17-fold lower, at least 18-fold lower, at least 19-fold lower, at least 20-fold lower or lower than an anti-TREM2 antibody selected from an anti-TREM2 antibody comprising a heavy chain variable region comprising the amino acid sequence of SEQ ID NO: 27 and comprising light chain variable region comprising the amino acid sequence of SEQ ID NO: 56; an anti-TREM2 antibody comprising a heavy chain variable region comprising the amino acid sequence of SEQ ID NO: 91 and a light chain variable region comprising the amino acid sequence of SEQ ID NO: 103; and an anti-TREM2 antibody comprising a heavy chain variable region comprising the amino acid sequence of SEQ ID NO: 119 and a light chain variable region comprising the amino acid sequence of SEQ ID NO: 120. In some embodiments, the dissociation constant ($K_D$) is determined at a temperature of approximately 25° C. In some embodiments, the $K_D$ is determined using a monovalent antibody (e.g., a Fab) or a full-length antibody in a monovalent form. Methods for the preparation and selection of antibodies that interact and/or bind with specificity to TREM2 are described herein. (e.g., see Examples 1 and 2).

In some embodiments, the dissociation constants ($K_D$) of anti-TREM2 antibodies for human TREM2 may range from about 300 nM to about 100 pM, from about 200 nM to about 100 pM, from about 100 nM to about 100 pM, from about 90 nM to about 100 pM, from about 80 nM to about 100 pM, from about 70 nM to about 100 pM, from about 60 nM to about 100 pM, from about 50 nM to about 100 pM, from about 40 nM to about 100 pM, from about 30 nM to about 100 pM, from about 20 nM to about 100 pM, from about 10 nM to about 100 pM, from about 9 nM to about 100 pM, from about 8 nM to about 100 pM, from about 7 nM to about 100 pM, from about 6 nM to about 100 pM, from about 5 nM to about 100 pM, from about 4 nM to about 100 pM, from about 3 nM to about 100 pM, from about 2 nM to about 100 pM, from about 1 nM to about 100 pM, from 900 pM to about 100 pM, from about 800 pM to about 100 pM, from 700 pM to about 100 pM, from 600 pM to about 500 pM, from 400 pM to about 100 pM, from 300 pM to about 100 pM, from 200 pM to about 100 pM, from 900 pM to about 100 pM, or less than 100 pM. In some embodiments, the dissociation constant ($K_D$) is determined at a temperature of approximately 25° C. In some embodiments, the $K_D$ is determined using a monovalent antibody (e.g., a Fab) or a full-length antibody in a monovalent form. Methods for the preparation and selection of antibodies that interact and/or bind with specificity to TREM2 are described herein. (e.g., see Examples 1 and 2).

In some embodiments, the dissociation constants ($K_D$) of anti-TREM2 antibodies for human TREM2 may range from about 300 nM to about 90 pM, from about 300 nM to about 80 pM, from about 300 nM to about 70 pM, from about 300 nM to about 60 pM, from about 300 nM to about 50 pM, from about 300 nM to about 40 pM, from about 300 nM to about 30 pM, from about 300 nM to about 20 pM, from about 300 nM to about 10 pM, from about 300 nM to about 9 pM, from about 300 nM to about 8 pM, from about 300 nM to about 7 pM, from about 300 nM to about 6 pM, from about 300 nM to about 5 pM, from about 300 nM to about 4 pM, from about 300 nM to about 3 pM, from about 300 nM to about 2 pM, from about 300 nM to about 1 pM, or less than 1 pM. The dissociation constants ($K_D$) of anti-TREM2 antibodies for human TREM2 may range from about 200 nM to about 90 pM, from about 200 nM to about 80 pM, from about 200 nM to about 70 pM, from about 200 nM to about 60 pM, from about 200 nM to about 50 pM, from about 200 nM to about 40 pM, from about 200 nM to about 30 pM, from about 200 nM to about 20 pM, from about 200 nM to about 10 pM, from about 200 nM to about 9 pM, from about 200 nM to about 8 pM, from about 200 nM to about 7 pM, from about 200 nM to about 6 pM, from about 200 nM to about 5 pM, from about 200 nM to about 4 pM, from about 200 nM to about 3 pM, from about 200 nM to about 2 pM, from about 200 nM to about 1 pM, or less than 1 pM. The dissociation constants ($K_D$) of anti-TREM2 antibodies for human TREM2 may range from about 100 nM to about 90 pM, from about 100 nM to about 80 pM, from about 100 nM to about 70 pM, from about 100 nM to about 60 pM, from about 100 nM to about 50 pM, from about 100 nM to about 40 pM, from about 100 nM to about 30 pM, from about 100 nM to about 20 pM, from about 100 nM to about 10 pM, from about 100 nM to about 9 pM, from about 100 nM to about 8 pM, from about 100 nM to about 7 pM, from about 100 nM to about 6 pM, from about 100 nM to about 5 pM, from about 100 nM to about 4 pM, from about 100 nM to about 3 pM, from about 100 nM to about 2 pM, from about 100 nM to about 1 pM, or less than 1 pM. The dissociation constants ($K_D$) of anti-TREM2 antibodies for human TREM2 may range from about 90 nM to about 90 pM, from about 90 nM to about 80 pM, from about 90 nM to about 70 pM, from about 90 nM to about 60 pM, from about 90 nM to about 50 pM, from about 90 nM to about 40 pM, from about 90 nM to about 30 pM, from about 90 nM to about 20 pM, from about 90 nM to about 10 pM, from about 90 nM to about 9 pM, from about 90 nM to about 8 pM, from about 90 nM to about 7 pM, from about 90 nM to about 6 pM, from about 90 nM to about 5 pM, from about 90 nM to about 4 pM, from about 90 nM to about 3 pM, from about 90 nM to about 2 pM, from about 90 nM to about 1 pM, or less than 1 pM. The dissociation constants ($K_D$) of anti-TREM2 antibodies for human TREM2 may range from about 80 nM to about 90 pM, from about 80 nM to about 80 pM, from about 80 nM to about 70 pM, from about 80 nM to about 60 pM, from about 80 nM to about 50 pM, from about 80 nM to about 40 pM, from about 80 nM to about 30 pM, from about 80 nM to about 20 pM, from about 80 nM to about 10 pM, from about 80 nM to about 9 pM, from about 80 nM to about 8 pM, from about 80 nM to about 7 pM, from about 80 nM to about 6 pM, from about 80 nM to about 5 pM, from about 80 nM to about 4 pM, from about 80 nM to about 3 pM, from about 80 nM to about 2 pM, from about 80 nM to about 1 pM, or less than 1 pM. The dissociation constants ($K_D$) of anti-TREM2 antibodies for human TREM2 may range from about 70 nM to about 90 pM, from about 70 nM to about 80 pM, from about 70 nM to about 70 pM, from about 70 nM to about 60 pM, from about 70 nM to about 50 pM, from about 70 nM to about 40 pM, from about 70 nM to about 30 pM, from about 70 nM to about 20 pM, from about 70 nM to about 10 pM, from about 70 nM to about 9 pM, from about 70 nM to about 8 pM, from about 70 nM to about 7 pM, from about 70 nM to about 6 pM, from about 70 nM to about 5 pM, from about 70 nM to about 4 pM, from about 70 nM to about 3 pM, from about 70 nM to about 2 pM, from about 70 nM to about 1 pM, or less than 1 pM. The dissociation constants ($K_D$) of anti-TREM2 antibodies for human TREM2 may range from about 60 nM to about 90 pM, from about 60 nM to about 80 pM, from about 60 nM to about 70 pM, from about 60 nM to about 60 pM, from about 60 nM to about 50 pM, from about 60 nM to about 40 pM, from about 60 nM to about 30 pM, from about 60 nM to about 20 pM, from about 60 nM to about 10 pM, from about 60 nM to about 9 pM, from about 60 nM to about 8 pM, from about 60 nM to about 7 pM, from about 60 nM to about 6 pM, from about 60 nM to about 5 pM, from about 60 nM to about 4 pM, from about 60 nM to about 3 pM, from about 60 nM to about 2 pM, from about 60 nM to about 1 pM, or less than 1 pM. The dissociation constants ($K_D$) of anti-TREM2 antibodies for human TREM2 may range from about 50 nM to about 90 pM, from about 50 nM to about 80 pM, from about 50 nM to about 70 pM, from about 50 nM to about 60 pM, from about 50 nM to about 50 pM, from about 50 nM to about 40 pM, from about 50 nM to about 30 pM, from about 50 nM to about 20 pM, from about 50 nM to about 10 pM, from about 50 nM to about 9 pM, from about 50 nM to about 8 pM, from about 50 nM to about 7 pM, from about 50 nM to about 6 pM, from about 50 nM to about 5 pM, from about 50 nM to about 4 pM, from about 50 nM to about 3 pM, from about 50 nM to about 2 pM, from about 50 nM to about 1 pM, or less than 1 pM. The dissociation constants ($K_D$) of anti-TREM2 antibodies for human TREM2 may range from about 40 nM to about 90 pM, from about 40 nM to about 80 pM, from about 40 nM to about 70 pM, from about 40 nM to about 60 pM, from about 40 nM to about 50 pM, from about 40 nM to about 40 pM, from about 40 nM to about 30 pM, from about 40 nM to about 20 pM, from about 40 nM to about 10 pM, from about 40 nM to about 9 pM, from about 40 nM to about 8 pM, from about 40 nM to about 7 pM, from about 40 nM to about 6 pM, from about 40 nM to about 5 pM, from about 40 nM to about 4 pM, from about 40 nM to about 3 pM, from about 40 nM to about 2 pM, from about 40 nM to about 1 pM, or less than 1 pM. The dissociation constants ($K_D$) of anti-TREM2 antibodies for human TREM2 may range from about 30 nM to about 90 pM, from about 30 nM to about 80 pM, from about 30 nM to about 70 pM, from about 30 nM to about 60 pM, from about 30 nM to about 50 pM, from about 30 nM to about 40 pM, from about 30 nM to about 30 pM, from about 30 nM to about 20 pM, from about 30 nM to about 10 pM, from about 30 nM to about 9 pM, from about 30 nM to about 8 pM, from about 30 nM to about 7 pM, from about 30 nM to about 6 pM, from about 30 nM to about 5 pM, from about 30 nM to about 4 pM, from about 30 nM to about 3 pM, from about 30 nM to about 2 pM, from about 30 nM to about 1 pM, or less than 1 pM. The dissociation constants ($K_D$) of anti-TREM2 antibodies for human TREM2 may range from about 20 nM to about 90 pM, from about 20 nM to about 80 pM, from about 20 nM to about 70 pM, from about 20 nM to about 60 pM, from about 20 nM to about 50 pM, from about 20 nM to about 40 pM, from about 20 nM to about 30 pM, from about 20 nM to about 20 pM, from about 20 nM to about 10 pM, from about 20 nM to about 9 pM, from about 20 nM to about 8 pM, from about 20 nM to about 7 pM, from about 20 nM to about 6 pM, from about 20 nM to about 5 pM, from about 20 nM to about 4 pM, from about 20 nM to about 3 pM, from about 20 nM to about 2 pM, from about 20 nM to about 1 pM, or less than 1 pM. The dissociation constants ($K_D$) of anti-TREM2 antibodies for human TREM2 may range from about 10 nM to about 90 pM, from about 10 nM to about 80 pM, from about 10 nM to about 70 pM, from about 10 nM to about 60 pM, from about 10 nM to about 50 pM, from about 10 nM to about 40 pM, from about 10 nM to about 30 pM, from about 10 nM to about 20 pM, from about 10 nM to about 10 pM, from about 10 nM to about 9 pM, from about 10 nM to about 8 pM, from about 10 nM to about 7 pM, from about 10 nM to about 6 pM, from about 10 nM to about 5 pM, from about 10 nM to about 4 pM, from about 10 nM to about 3 pM, from about 10 nM to about 2 pM, from about 10 nM to about 1 pM, or less than 1 pM. The dissociation constants ($K_D$) of anti-TREM2 antibodies for human TREM2 may range from about 5 nM to about 90 pM, from about 5 nM to about 80 pM, from about 5 nM to about 70 pM, from about 5 nM to about 60 pM, from about 5 nM to about 50 pM, from about 5 nM to about 40 pM, from about 5 nM to about 30 pM, from about 5 nM to about 20 pM, from about 5 nM to about 10 pM, from about 5 nM to about 9 pM, from about 5 nM to about 8 pM, from about 5 nM to about 7 pM, from about 5 nM to about 6 pM, from about 5 nM to about 5 pM, from about 5 nM to about 4 pM, from about 5 nM to about 3 pM, from about 5 nM to about 2 pM, from about 5 nM to about 1 pM, or less than 1 pM. The dissociation constants ($K_D$) of anti-TREM2 antibodies for human TREM2 may range from about 1 nM to about 90 pM, from about 1 nM to about 80 pM, from about 1 nM to about 70 pM, from about 1 nM to about 60 pM, from about 1 nM to about 50 pM, from about 1 nM to about 40 pM, from about 1 nM to about 30 pM, from about 1 nM to about 20 pM, from about 1 nM to about 10 pM, from about 1 nM to about 9 pM, from about 1 nM to about 8 pM, from about 1 nM to about 7 pM, from about 1 nM to about 6 pM, from about 1 nM to about 5 pM, from about 1 nM to about 4 pM, from about 1 nM to about 3 pM, from about 1 nM to about 2 pM, from about 1 nM to about 1 pM, or less than 1 pM. The dissociation constants ($K_D$) of anti-TREM2 antibodies for human TREM2 may range from about 500 pM to about 90 pM, from about 500 pM to about 80 pM, from about 500 pM to about 70 pM, from about 500 pM to about 60 pM, from about 500 pM to about 50 pM, from about 500 pM to about 40 pM, from about 500 pM to about 30 pM, from about 500 pM to about 20 pM, from about 500 pM to about 10 pM, from about 500 pM to about 9 pM, from about 500 pM to about 8 pM, from about 500 pM to about 7 pM, from about 500 pM to about 6 pM, from about 500 pM to about 5 pM, from about 500 pM to about 4 pM, from about 500 pM to about 3 pM, from about 500 pM to about 2 pM, from about 500 pM to about 1 pM, or less than 1 pM. The dissociation constants ($K_D$) of anti-TREM2 antibodies for human TREM2 may range from about 250 pM to about 90 pM, from about 250 pM to about 80 pM, from about 250 pM to about 70 pM, from about 250 pM to about 60 pM, from about 250 pM to about 50 pM, from about 250 pM to about 40 pM, from about 250 pM to about 30 pM, from about 250 pM to about 20 pM, from about 250 pM to about 10 pM, from about 250 pM to about 9 pM, from about 250 pM to about 8 pM, from about 250 pM to about 7 pM, from about 250 pM to about 6 pM, from about 250 pM to about 5 pM, from about 250 pM to about 4 pM, from about 250 pM to about 3 pM, from about 250 pM to about 2 pM, from about 250 pM to about 1 pM, or less than 1 pM. The dissociation constants ($K_D$) of anti-TREM2 antibodies for human TREM2 may range from about 100 pM to about 90 pM, from about 100 pM to about 80 pM, from about 100 pM to about 70 pM, from about 100 pM to about 60 pM, from about 100 pM to about 50 pM, from about 100 pM to about 40 pM, from about 100 pM to about 30 pM, from about 100 pM to about 20 pM, from about 100 pM to about 10 pM, from about 100 pM to about 9 pM, from about 100 pM to about 8 pM, from about 100 pM to about 7 pM, from about 100 pM to about 6 pM, from about 100 pM to about 5 pM, from about 100 pM to about 4 pM, from about 100 pM to about 3 pM, from about 100 pM to about 2 pM, from about 100 pM to about 1 pM, or less than 1 pM. In some embodiments, the dissociation constant ($K_D$) is determined at a temperature of approximately 25° C. In some embodiments, the $K_D$ is determined using a monovalent antibody (e.g., a Fab) or a full-length antibody in a monovalent form. Methods for the preparation and selection of antibodies that interact and/or bind with specificity to TREM2 are described herein. (e.g., see Examples 1 and 2).

In some embodiments, the dissociation constants ($K_D$) of anti-TREM2 antibodies for human TREM2 may be less than 260 nM, may be less than 225 nM, may be less than 200 nM, may be less than 150 nM, may be less than 135 nM, may be less than 125 nM, may be less than 100 nM, may be less than 95 nM, may be less than 90 nM, may be less than 85 nM, may be less than 80 nM, may be less than 75 nM, may be less than 70 nM, may be less than 65 nM, may be less than 60 nM, may be less than 55 nM, may be less than 50 nM, may be less than 45 nM, may be less than 40 nM, may be less than 36 nM, may be less than 35 nM, may be less than 30 nM, may be less than 29 nM, may be less than 28 nM, may be less than 27 nM, may be less than 26 nM, may be less than 25 nM, may be less than 24 nM, may be less than 23 nM, may be less than 22 nM, may be less than 21 nM, may be less than 20 nM, may be less than 19 nM, may be less than 18.5 nM, may be less than 18 nM, may be less than 15 nM, may be less than 14 nM, may be less than 13 nM, may be less than 12 nM, may be less than 11 nM, may be less than 10 nM, may be less than 9.5 nM, may be less than 9 nM, may be less than 8.5 nM, may be less than 8 nM, may be less than 7.5 nM, may be less than 7 nM, may be less than 6.5 nM, may be less than 6 nM, may be less than 5.5 nM, may be less than 5 nM, may be less than 4.5 nM, may be less than 4 nM, may be less than 3.5 nM, may be less than 3 nM, may be less than 2.5 nM, may be less than 2 nM, may be less than 1.5 nM, may be less than 1 nM, may be less than 950 pM, may be less than 900 pM, may be less than 850 pM, may be less than 830 pM, may be less than 800 pM, may be less than 750 pM, may be less than 730 pM, may be less than 700 pM, may be less than 650 pM, may be less than 630 pM, may be less than 600 pM, may be less than 550 pM, may be less than 500 pM, may be less than 450 pM, may be less than 415 pM, may be less than 400 pM, may be less than 350 pM, may be less than 300 pM, may be less than 250 pM, may be less than 200 pM, may be less than 150 pM, may be less than 100 pM, may be less than 95 pM, may be less than 90 pM, may be less than 85 pM, may be less than 80 pM, may be less than 75 pM, may be less than 70 pM, may be less than 65 pM, may be less than 60 pM, may be less than 55 pM, may be less than 50 pM, may be less than 45 pM, may be less than 40 pM, may be less than 35 pM, may be less than 30 pM, may be less than 25 pM, may be less than 20 pM, may be less than 15 pM, may be less than 10 pM, may be less than 9 pM, may be less than 8 pM, may be less than 7 pM, may be less than 6 pM, may be less than 5 pM, may be less than 4 pM, may be less than 3 pM, may be less than 2 pM, or may be less than 1 pM. In some embodiments, the dissociation constant ($K_D$) is determined at a temperature of approximately 25° C. In some embodiments, the $K_D$ is determined using a monovalent antibody (e.g., a Fab) or a full-length antibody in a monovalent form. Methods for the preparation and selection of antibodies that interact and/or bind with specificity to TREM2 are described herein. (e.g., see Examples 1 and 2).

In some embodiments, the dissociation constants ($K_D$) of anti-TREM2 antibodies for cynomolgus monkey TREM2 may range from about 10 µM to about 100 pM, from about 200 nM to about 100 pM, from about 100 nM to about 100 pM, from about 90 nM to about 100 pM, from about 80 nM to about 100 pM, from about 70 nM to about 100 pM, from about 60 nM to about 100 pM, from about 50 nM to about 100 pM, from about 40 nM to about 100 pM, from about 30 nM to about 100 pM, from about 20 nM to about 100 pM, from about 10 nM to about 100 pM, from about 9 nM to about 100 pM, from about 8 nM to about 100 pM, from about 7 nM to about 100 pM, from about 6 nM to about 100 pM, from about 5 nM to about 100 pM, from about 4 nM to about 100 pM, from about 3 nM to about 100 pM, from about 2 nM to about 100 pM, from about 1 nM to about 100 pM, from 900 pM to about 100 pM, from about 800 pM to about 100 pM, from 700 pM to about 100 pM, from 600 pM to about 500 pM, from 400 pM to about 100 pM, from 300 pM to about 100 pM, from 200 pM to about 100 pM, from 900 pM to about 100 pM, or less than 100 pM. In some embodiments, the dissociation constant ($K_D$) is determined at a temperature of approximately 25° C. In some embodiments, the $K_D$ is determined using a monovalent antibody (e.g., a Fab) or a full-length antibody in a monovalent form. Methods for the preparation and selection of antibodies that interact and/or bind with specificity to TREM2 are described herein. (e.g., see Examples 1 and 2).

In some embodiments, the dissociation constants ($K_D$) of anti-TREM2 antibodies for cynomolgus monkey TREM2 may range from about 10 μM to about 900 pM, from about 10 μM to about 800 pM, from about 10 μM to about 700 pM, from about 10 μM to about 600 pM, from about 10 μM to about 500 pM, from about 10 μM to about 400 pM, from about 10 μM to about 300 pM, from about 10 μM to about 200 pM, from about 10 μM to about 100 pM, or less than 100 pM. In some embodiments, the dissociation constants ($K_D$) of anti-TREM2 antibodies for cynomolgus monkey TREM2 may range from about 5 μM to about 900 pM, from about 5 μM to about 800 pM, from about 5 μM to about 700 pM, from about 5 μM to about 600 pM, from about 5 μM to about 500 pM, from about 5 μM to about 400 pM, from about 5 μM to about 300 pM, from about 5 μM to about 200 pM, from about 5 μM to about 100 pM, or less than 100 pM. In some embodiments, the dissociation constants ($K_D$) of anti-TREM2 antibodies for cynomolgus monkey TREM2 may range from about 1 μM to about 900 pM, from about 1 μM to about 800 pM, from about 1 μM to about 700 pM, from about 1 μM to about 600 pM, from about 1 μM to about 500 pM, from about 1 μM to about 400 pM, from about 1 μM to about 300 pM, from about 1 μM to about 200 pM, from about 1 μM to about 100 pM, or less than 100 pM. In some embodiments, the dissociation constants ($K_D$) of anti-TREM2 antibodies for cynomolgus monkey TREM2 may range from about 900 nM to about 900 pM, from about 900 nM to about 800 pM, from about 900 nM to about 700 pM, from about 900 nM to about 600 pM, from about 900 nM to about 500 pM, from about 900 nM to about 400 pM, from about 900 nM to about 300 pM, from about 900 nM to about 200 pM, from about 900 nM to about 100 pM, or less than 100 pM. In some embodiments, the dissociation constants ($K_D$) of anti-TREM2 antibodies for cynomolgus monkey TREM2 may range from about 800 nM to about 900 pM, from about 800 nM to about 800 pM, from about 800 nM to about 700 pM, from about 800 nM to about 600 pM, from about 800 nM to about 500 pM, from about 800 nM to about 400 pM, from about 800 nM to about 300 pM, from about 800 nM to about 200 pM, from about 800 nM to about 100 pM, or less than 100 pM. In some embodiments, the dissociation constants ($K_D$) of anti-TREM2 antibodies for cynomolgus monkey TREM2 may range from about 700 nM to about 900 pM, from about 700 nM to about 800 pM, from about 700 nM to about 700 pM, from about 700 nM to about 600 pM, from about 700 nM to about 500 pM, from about 700 nM to about 400 pM, from about 700 nM to about 300 pM, from about 700 nM to about 200 pM, from about 700 nM to about 100 pM, or less than 100 pM. In some embodiments, the dissociation constants ($K_D$) of anti-TREM2 antibodies for cynomolgus monkey TREM2 may range from about 600 nM to about 900 pM, from about 600 nM to about 800 pM, from about 600 nM to about 700 pM, from about 600 nM to about 600 pM, from about 600 nM to about 500 pM, from about 600 nM to about 400 pM, from about 600 nM to about 300 pM, from about 600 nM to about 200 pM, from about 600 nM to about 100 pM, or less than 100 pM. In some embodiments, the dissociation constants ($K_D$) of anti-TREM2 antibodies for cynomolgus monkey TREM2 may range from about 500 nM to about 900 pM, from about 500 nM to about 800 pM, from about 500 nM to about 700 pM, from about 500 nM to about 600 pM, from about 500 nM to about 500 pM, from about 500 nM to about 400 pM, from about 500 nM to about 300 pM, from about 500 nM to about 200 pM, from about 500 nM to about 100 pM, or less than 100 pM. In some embodiments, the dissociation constants ($K_D$) of anti-TREM2 antibodies for cynomolgus monkey TREM2 may range from about 400 nM to about 900 pM, from about 400 nM to about 800 pM, from about 400 nM to about 700 pM, from about 400 nM to about 600 pM, from about 400 nM to about 500 pM, from about 400 nM to about 400 pM, from about 400 nM to about 300 pM, from about 400 nM to about 200 pM, from about 400 nM to about 100 pM, or less than 100 pM. In some embodiments, the dissociation constants ($K_D$) of anti-TREM2 antibodies for cynomolgus monkey TREM2 may range from about 300 nM to about 900 pM, from about 300 nM to about 800 pM, from about 300 nM to about 700 pM, from about 300 nM to about 600 pM, from about 300 nM to about 500 pM, from about 300 nM to about 400 pM, from about 300 nM to about 300 pM, from about 300 nM to about 200 pM, from about 300 nM to about 100 pM, or less than 100 pM. In some embodiments, the dissociation constants ($K_D$) of anti-TREM2 antibodies for cynomolgus monkey TREM2 may range from about 200 nM to about 900 pM, from about 200 nM to about 800 pM, from about 200 nM to about 700 pM, from about 200 nM to about 600 pM, from about 200 nM to about 500 pM, from about 200 nM to about 400 pM, from about 200 nM to about 300 pM, from about 200 nM to about 200 pM, from about 200 nM to about 100 pM, or less than 100 pM. In some embodiments, the dissociation constants ($K_D$) of anti-TREM2 antibodies for cynomolgus monkey TREM2 may range from about 100 nM to about 900 pM, from about 100 nM to about 800 pM, from about 100 nM to about 700 pM, from about 100 nM to about 600 pM, from about 100 nM to about 500 pM, from about 100 nM to about 400 pM, from about 100 nM to about 300 pM, from about 100 nM to about 200 pM, from about 100 nM to about 100 pM, or less than 100 pM. In some embodiments, the dissociation constants ($K_D$) of anti-TREM2 antibodies for cynomolgus monkey TREM2 may range from about 90 nM to about 900 pM, from about 90 nM to about 800 pM, from about 90 nM to about 700 pM, from about 90 nM to about 600 pM, from about 90 nM to about 500 pM, from about 90 nM to about 400 pM, from about 90 nM to about 300 pM, from about 90 nM to about 200 pM, from about 90 nM to about 100 pM, or less than 100 pM. In some embodiments, the dissociation constants ($K_D$) of anti-TREM2 antibodies for cynomolgus monkey TREM2 may range from about 80 nM to about 900 pM, from about 80 nM to about 800 pM, from about 80 nM to about 700 pM, from about 80 nM to about 600 pM, from about 80 nM to about 500 pM, from about 80 nM to about 400 pM, from about 80 nM to about 300 pM, from about 80 nM to about 200 pM, from about 80 nM to about 100 pM, or less than 100 pM. In some embodiments, the dissociation constants ($K_D$) of anti-TREM2 antibodies for cynomolgus monkey TREM2 may range from about 70 nM to about 900 pM, from about 70 nM to about 800 pM, from about 70 nM to about 700 pM, from about 70 nM to about 600 pM, from about 70 nM to about 500 pM, from about 70 nM to about 400 pM, from about 70 nM to about 300 pM, from about 70 nM to about 200 pM, from about 70 nM to about 100 pM, or less than 100 pM. In some embodiments, the dissociation constants ($K_D$) of anti-TREM2 antibodies for cynomolgus monkey TREM2 may range from about 60 nM to about 900 pM, from about 60 nM to about 800 pM, from about 60 nM to about 700 pM, from about 60 nM to about 600 pM, from about 60 nM to about 500 pM, from about 60 nM to about 400 pM, from about 60 nM to about 300 pM, from about 60 nM to about 200 pM, from about 60 nM to about 100 pM, or less than 100 pM. In some embodiments, the dissociation constants ($K_D$) of anti-TREM2 antibodies for cynomolgus monkey TREM2 may range from about 50 nM to about 900 pM, from about 50 nM to about 800 pM, from about 50 nM to about 700 pM, from about 50 nM to about 600 pM, from about 50 nM to about 500 pM, from about 50 nM to about 400 pM, from about 50 nM to about 300 pM, from about 50 nM to about 200 pM, from about 50 nM to about 100 pM, or less than 100 pM. In some embodiments, the dissociation constants ($K_D$) of anti-TREM2 antibodies for cynomolgus monkey TREM2 may range from about 40 nM to about 900 pM, from about 40 nM to about 800 pM, from about 40 nM to about 700 pM, from about 40 nM to about 600 pM, from about 40 nM to about 500 pM, from about 40 nM to about 400 pM, from about 40 nM to about 300 pM, from about 40 nM to about 200 pM, from about 40 nM to about 100 pM, or less than 100 pM. In some embodiments, the dissociation constants ($K_D$) of anti-TREM2 antibodies for cynomolgus monkey TREM2 may range from about 30 nM to about 900 pM, from about 30 nM to about 800 pM, from about 30 nM to about 700 pM, from about 30 nM to about 600 pM, from about 30 nM to about 500 pM, from about 30 nM to about 400 pM, from about 30 nM to about 300 pM, from about 30 nM to about 200 pM, from about 30 nM to about 100 pM, or less than 100 pM, from about 20 nM to about 900 pM, from about 20 nM to about 800 pM, from about 20 nM to about 700 pM, from about 20 nM to about 600 pM, from about 20 nM to about 500 pM, from about 20 nM to about 400 pM, from about 20 nM to about 300 pM, from about 20 nM to about 200 pM, from about 20 nM to about 100 pM, or less than 100 pM. In some embodiments, the dissociation constants ($K_D$) of anti-TREM2 antibodies for cynomolgus monkey TREM2 may range from about 10 nM to about 900 pM, from about 10 nM to about 800 pM, from about 10 nM to about 700 pM, from about 10 nM to about 600 pM, from about 10 nM to about 500 pM, from about 10 nM to about 400 pM, from about 10 nM to about 300 pM, from about 10 nM to about 200 pM, from about 10 nM to about 100 pM, or less than 100 pM. In some embodiments, the dissociation constants ($K_D$) of anti-TREM2 antibodies for cynomolgus monkey TREM2 may range from about 9 nM to about 900 pM, from about 9 nM to about 800 pM, from about 9 nM to about 700 pM, from about 9 nM to about 600 pM, from about 9 nM to about 500 pM, from about 9 nM to about 400 pM, from about 9 nM to about 300 pM, from about 9 nM to about 200 pM, from about 9 nM to about 100 pM, or less than 100 pM. In some embodiments, the dissociation constants ($K_D$) of anti-TREM2 antibodies for cynomolgus monkey TREM2 may range from about 8 nM to about 900 pM, from about 8 nM to about 800 pM, from about 8 nM to about 700 pM, from about 8 nM to about 600 pM, from about 8 nM to about 500 pM, from about 8 nM to about 400 pM, from about 8 nM to about 300 pM, from about 8 nM to about 200 pM, from about 8 nM to about 100 pM, or less than 100 pM. In some embodiments, the dissociation constants ($K_D$) of anti-TREM2 antibodies for cynomolgus monkey TREM2 may range from about 7 nM to about 900 pM, from about 7 nM to about 800 pM, from about 7 nM to about 700 pM, from about 7 nM to about 600 pM, from about 7 nM to about 500 pM, from about 7 nM to about 400 pM, from about 7 nM to about 300 pM, from about 7 nM to about 200 pM, from about 7 nM to about 100 pM, or less than 100 pM. In some embodiments, the dissociation constants ($K_D$) of anti-TREM2 antibodies for cynomolgus monkey TREM2 may range from about 6 nM to about 900 pM, from about 6 nM to about 800 pM, from about 6 nM to about 700 pM, from about 6 nM to about 600 pM, from about 6 nM to about 500 pM, from about 6 nM to about 400 pM, from about 6 nM to about 300 pM, from about 6 nM to about 200 pM, from about 6 nM to about 100 pM, or less than 100 pM. In some embodiments, the dissociation constants ($K_D$) of anti-TREM2 antibodies for cynomolgus monkey TREM2 may range from about 5 nM to about 900 pM, from about 5 nM to about 800 pM, from about 5 nM to about 700 pM, from about 5 nM to about 600 pM, from about 5 nM to about 500 pM, from about 5 nM to about 400 pM, from about 5 nM to about 300 pM, from about 5 nM to about 200 pM, from about 5 nM to about 100 pM, or less than 100 pM. In some embodiments, the dissociation constants ($K_D$) of anti-TREM2 antibodies for cynomolgus monkey TREM2 may range from about 4 nM to about 900 pM, from about 4 nM to about 800 pM, from about 4 nM to about 700 pM, from about 4 nM to about 600 pM, from about 4 nM to about 500 pM, from about 4 nM to about 400 pM, from about 4 nM to about 300 pM, from about 4 nM to about 200 pM, from about 4 nM to about 100 pM, or less than 100 pM. In some embodiments, the dissociation constants ($K_D$) of anti-TREM2 antibodies for cynomolgus monkey TREM2 may range from about 3 nM to about 900 pM, from about 3 nM to about 800 pM, from about 3 nM to about 700 pM, from about 3 nM to about 600 pM, from about 3 nM to about 500 pM, from about 3 nM to about 400 pM, from about 3 nM to about 300 pM, from about 3 nM to about 200 pM, from about 3 nM to about 100 pM, or less than 100 pM. In some embodiments, the dissociation constants ($K_D$) of anti-TREM2 antibodies for cynomolgus monkey TREM2 may range from about 2 nM to about 900 pM, from about 2 nM to about 800 pM, from about 2 nM to about 700 pM, from about 2 nM to about 600 pM, from about 2 nM to about 500 pM, from about 2 nM to about 400 pM, from about 2 nM to about 300 pM, from about 2 nM to about 200 pM, from about 2 nM to about 100 pM, or less than 100 pM. In some embodiments, the dissociation constants ($K_D$) of anti-TREM2 antibodies for cynomolgus monkey TREM2 may range from about 1 nM to about 900 pM, from about 1 nM to about 800 pM, from about 1 nM to about 700 pM, from about 1 nM to about 600 pM, from about 1 nM to about 500 pM, from about 1 nM to about 400 pM, from about 1 nM to about 300 pM, from about 1 nM to about 200 pM, from about 1 nM to about 100 pM, or less than 100 pM. In some embodiments, the dissociation constant ($K_D$) is determined at a temperature of approximately 25° C. In some embodiments, the $K_D$ is determined using a monovalent antibody (e.g., a Fab) or a full-length antibody in a monovalent form. Methods for the preparation and selection of antibodies that interact and/or bind with specificity to TREM2 are described herein. (e.g., see Examples 1 and 2).

In some embodiments, the dissociation constants ($K_D$) of anti-TREM2 antibodies for cynomolgus monkey TREM2 may be less than 6 µM, may be less than 5 µM, may be less than 4.6 µM, may be less than 4 µM, may be less than 3 µM, may be less than 2 µM, may be less than 1.5 µM, may be less than 1 µM, may be less than 900 nM, may be less than 800 nM, may be less than 700 nM, may be less than 600 nM, may be less than 500 nM, may be less than 400 nM, may be less than 300 nM, may be less than 200 nM, may be less than 100 nM, may be less than 95 nM, may be less than 90 nM, may be less than 85 nM, may be less than 80 nM, may be less than 75 nM, may be less than 70 nM, may be less than 65 nM, may be less than 60 nM, may be less than 55 nM, may be less than 50 nM, may be less than 45 nM, may be less than 40 nM, may be less than 36 nM, may be less than 35 nM, may be less than 31 nM, may be less than 30 nM, may be less than 29 nM, may be less than 28 nM, may be less than 27 nM, may be less than 26 nM, may be less than 25 nM, may be less than 24 nM, may be less than 23 nM, may be less than 22 nM, may be less than 21 nM, may be less than 20 nM, may be less than 19 nM, may be less than 18.5 nM, may be less than 18 nM, may be less than, may be less than 17 nM, may be than 16.5 nM, may be less than 16 nM, may be less than 15.5 nM, may be less than 15 nM, may be less than 14.5 nM, may be less than 14 nM, may be less than 13 nM, may be less than 12 nM, may be less than 11 nM, may be less than 10 nM, may be less than 9.5 nM, may be less than 9 nM, may be less than 8.5 nM, may be less than 8 nM, may be less than 7.5 nM, may be less than 7 nM, may be less than 6.5 nM, may be less than 6 nM, may be less than 5.5 nM, may be less than 5 nM, may be less than 4.5 nM, may be less than 4 nM, may be less than 3.5 nM, may be less than 3 nM, may be less than 2.5 nM, may be less than 2 nM, may be less than 1.5 nM, may be less than 1 nM, may be less than 950 pM, may be less than 900 pM, may be less than 890 pM, may be less than 850 pM, may be less than 800 pM, may be less than 750 pM, may be less than 700 pM, may be less than 650 pM, may be less than 600 pM, may be less than 550 pM, may be less than 500 pM, may be less than 450 pM, may be less than 400 pM, may be less than 375 pM, may be less than 350 pM, may be less than 325 pM, may be less than 300 pM, may be less than 270 pM, may be less than 250 pM, may be less than 225 pM, may be less than 200 pM, may be less than 150 pM, or may be less than 100 pM. In some embodiments, the dissociation constant ($K_D$) is determined at a temperature of approximately 25° C. In some embodiments, the $K_D$ is determined using a monovalent antibody (e.g., a Fab) or a full-length antibody in a monovalent form. Methods for the preparation and selection of antibodies that interact and/or bind with specificity to TREM2 are described herein. (e.g., see Examples 1 and 2).

Dissociation constants may be determined through any analytical technique, including any biochemical or biophysical technique such as ELISA, surface plasmon resonance (SPR), bio-layer interferometry (see, e.g., Octet System by ForteBio), isothermal titration calorimetry (ITC), differential scanning calorimetry (DSC), circular dichroism (CD), stopped-flow analysis, and colorimetric or fluorescent protein melting analyses. In some embodiments, the dissociation constant ($K_D$) for TREM2 is determined at a temperature of approximately 25° C. In some embodiments, the $K_D$ is determined using a monovalent antibody (e.g., a Fab) or a full-length antibody. In some embodiments, the $K_D$ is determined using a full-length antibody in a monovalent form. Utilizing, for example, any assay described herein (see, e.g., Examples 1 and 2).

Additional anti-TREM2 antibodies, e.g., antibodies that specifically bind to a TREM2 protein of the present disclosure, may be identified, screened, and/or characterized for their physical/chemical properties and/or biological activities by various assays known in the art.

Bispecific Antibodies

Certain aspects of the present disclosure relate to bispecific antibodies that bind to a TREM2 protein of the present disclosure and a second antigen. Methods of generating bispecific antibodies are well known in the art and described herein. In some embodiments, bispecific antibodies of the present disclosure bind to one or more amino acid residues of human TREM2 (SEQ ID NO: 1), or amino acid residues on a TREM2 protein corresponding to amino acid residues of SEQ ID NO: 1. In other embodiments, bispecific antibodies of the present disclosure also bind to one or more amino acid residues of human DAP12.

In some embodiments, bispecific antibodies of the present disclosure recognize a first antigen and a second antigen. In some embodiments, the first antigen is human TREM2 or a naturally occurring variant thereof, or human DAP12 or a naturally occurring variant thereof. In some embodiments, the second antigen is a) an antigen facilitating transport across the blood-brain-barrier; (b) an antigen facilitating transport across the blood-brain-barrier selected from transferrin receptor (TR), insulin receptor (HIR), insulin-like growth factor receptor (IGFR), low-density lipoprotein receptor related proteins 1 and 2 (LPR-1 and 2), diphtheria toxin receptor, CRM197, a llama single domain antibody, TMEM 30(A), a protein transduction domain, TAT, Syn-B, penetratin, a poly-arginine peptide, an angiopep peptide, and ANG1005; (c) a disease-causing protein selected from amyloid beta, oligomeric amyloid beta, amyloid beta plaques, amyloid precursor protein or fragments thereof, Tau, IAPP, alpha-synuclein, TDP-43, FUS protein, C9orf72 (chromosome 9 open reading frame 72), c9RAN protein, prion protein, PrPSc, huntingtin, calcitonin, superoxide dismutase, ataxin, ataxin 1, ataxin 2, ataxin 3, ataxin 7, ataxin 8, ataxin 10, Lewy body, atrial natriuretic factor, islet amyloid polypeptide, insulin, apolipoprotein AI, serum amyloid A, medin, prolactin, transthyretin, lysozyme, beta 2 microglobulin, gelsolin, keratoepithelin, cystatin, immunoglobulin light chain AL, S-IBM protein, Repeat-associated non-ATG (RAN) translation products, DiPeptide repeat (DPR) peptides, glycine-alanine (GA) repeat peptides, glycine-proline (GP) repeat peptides, glycine-arginine (GR) repeat peptides, proline-alanine (PA) repeat peptides, ubiquitin, and proline-arginine (PR) repeat peptides; and (d) ligands and/or proteins expressed on immune cells, wherein the ligands and/or proteins selected from CD40, OX40, ICOS, CD28, CD137/4-1BB, CD27, GITR, PD-L1, CTLA-4, PD-L2, PD-1, B7-H3, B7-H4, HVEM, BTLA, KIR, GAL9, TIM3, A2AR, LAG-3, and phosphatidylserine; and (e) a protein, lipid, polysaccharide, or glycolipid expressed on one or more tumor cells and any combination thereof.

Antibody Fragments

Certain aspects of the present disclosure relate to antibody fragments that bind to one or more of human TREM2, a naturally occurring variant of human TREM2, and a disease variant of human TREM2. In some embodiments, the antibody fragment is an Fab, Fab', Fab'-SH, F(ab')2, Fv or scFv fragment. In some embodiments, the antibody fragment is used in combination with one or more antibodies that specifically bind a disease-causing protein selected from: a)

an antigen facilitating transport across the blood-brain-barrier; (b) an antigen facilitating transport across the blood-brain-barrier selected from transferrin receptor (TR), insulin receptor (HIR), insulin-like growth factor receptor (IGFR), low-density lipoprotein receptor related proteins 1 and 2 (LPR-1 and 2), diphtheria toxin receptor, CRM197, a llama single domain antibody, TMEM 30(A), a protein transduction domain, TAT, Syn-B, penetratin, a poly-arginine peptide, an angiopep peptide, and ANG1005; (c) a disease-causing protein selected from amyloid beta, oligomeric amyloid beta, amyloid beta plaques, amyloid precursor protein or fragments thereof, Tau, IAPP, alpha-synuclein, TDP-43, FUS protein, C9orf72 (chromosome 9 open reading frame 72), c9RAN protein, prion protein, PrPSc, huntingtin, calcitonin, superoxide dismutase, ataxin, ataxin 1, ataxin 2, ataxin 3, ataxin 7, ataxin 8, ataxin 10, Lewy body, atrial natriuretic factor, islet amyloid polypeptide, insulin, apolipoprotein AI, serum amyloid A, medin, prolactin, transthyretin, lysozyme, beta 2 microglobulin, gelsolin, keratoepithelin, cystatin, immunoglobulin light chain AL, S-IBM protein, Repeat-associated non-ATG (RAN) translation products, DiPeptide repeat (DPR) peptides, glycine-alanine (GA) repeat peptides, glycine-proline (GP) repeat peptides, glycine-arginine (GR) repeat peptides, proline-alanine (PA) repeat peptides, ubiquitin, and proline-arginine (PR) repeat peptides; and (d) ligands and/or proteins expressed on immune cells, wherein the ligands and/or proteins selected from CD40, OX40, ICOS, CD28, CD137/4-1BB, CD27, GITR, PD-L1, CTLA-4, PD-L2, PD-1, B7-H3, B7-H4, HVEM, BTLA, KIR, GAL9, TIM3, A2AR, LAG-3, and phosphatidylserine; and (e) a protein, lipid, polysaccharide, or glycolipid expressed on one or more tumor cells, and any combination thereof.

Antibody Frameworks

Any of the antibodies described herein further include a framework. In some embodiments, the framework is a human immunoglobulin framework. For example, in some embodiments, an antibody (e.g., an anti-TREM2 antibody) comprises HVRs as in any of the above embodiments and further comprises an acceptor human framework, e.g., a human immunoglobulin framework or a human consensus framework. Human immunoglobulin frameworks may be part of the human antibody, or a non-human antibody may be humanized by replacing one or more endogenous frameworks with human framework region(s). Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Natl. Acad. Sci. USA,* 89:4285 (1992); and Presta et al. *J. Immunol.,* 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

In some embodiments, an antibody comprises a heavy chain variable region comprising an HVR-H1, an HVR-H2, and an HVR-H3 of the present disclosure and one, two, three or four of the heavy chain framework regions as shown in Tables 4A to 4D. In some embodiments, an antibody comprises a light chain variable region comprising an HVR-L1, an HVR-L2, and an HVR-L3 of the present disclosure and one, two, three or four of the light chain framework regions as shown in Tables 5A to 5D. In some embodiments, an antibody comprises a heavy chain variable region comprising an HVR-H1, an HVR-H2, and an HVR-H3 of the present disclosure and one, two, three or four of the heavy chain framework regions as shown in Tables 4A to 4D and further comprises a light chain variable region comprising an HVR-L1, an HVR-L2, and an HVR-L3 of the present disclosure and one, two, three or four of the light chain framework regions as shown in Tables 5A to 5D.

Modulated Expression of Pro-Inflammatory Mediators

In some embodiments, the anti-TREM2 antibodies of the present disclosure may modulate (e.g., increase or decrease) the expression of pro-inflammatory mediators after binding to a TREM2 protein expressed in a cell.

As used herein, pro-inflammatory mediators are proteins involved either directly or indirectly (e.g., by way of pro-inflammatory signaling pathways) in a mechanism that induces, activates, promotes, or otherwise increases an inflammatory response. Any method known in the art for identifying and characterizing pro-inflammatory mediators may be used. Examples of pro-inflammatory mediators include, without limitation, cytokines such as IFN-β, IL-1α, IL-1β, TNF-α, IL-6, IL-8, CRP, CD86, MCP-1/CCL2, CCL3, CCL4, CCL5, CCR2, CXCL-10, Gata3, IL-20 family members, IL-33, LIF, IFN-gamma, OSM, CNTF, CSF-1, OPN, CD11c, GM-CSF, IL-11, IL-12, IL-17, IL-18, and IL-23.

In some embodiments, the anti-TREM2 antibodies of the present disclosure may modulate functional expression and/or secretion of pro-inflammatory mediators, such as FN-β, IL-1α, IL-1β, CD86, TNF-α, IL-6, IL-8, CRP, MCP-1/CCL2, CCL3, CCL4, CCL5, CCR2, CXCL-10, Gata3, IL-20 family members, IL-33, LIF, IFN-gamma, OSM, CNTF, CSF1, OPN, CD11c, GM-CSF, IL-11, IL-12, IL-17, IL-18, and IL-23. In certain embodiments, modulated expression of the pro-inflammatory mediators occurs in macrophages, dendritic cells, monocytes, osteoclasts, Langerhans cells of skin, Kupffer cells, and/or microglial cells. Modulated expression may include, without limitation, modulated gene expression, modulated transcriptional expression, or modulated protein expression. Any method known in the art for determining gene, transcript (e.g., mRNA), and/or protein expression may be used. For example, Northern blot analysis may be used to determine pro-inflammatory mediator gene expression levels, RT-PCR may be used to determine the level of pro-inflammatory mediator transcription, and Western blot analysis may be used to determine pro-inflammatory mediator protein levels.

In certain embodiments, pro-inflammatory mediators include inflammatory cytokines. Accordingly, in certain embodiments, the anti-TREM2 antibodies of the present disclosure may modulate secretion of one or more inflammatory cytokines. Examples of inflammatory cytokines whose secretion may be reduced by the anti-TREM2 antibodies of the present disclosure include, without limitation, FN-β, IL-1α, IL-1β, CD86, TNF-α, IL-6, IL-8, CRP, MCP-1/CCL2, CCL3, CCL4, CCL5, CCR2, CXCL-10, Gata3, IL-20 family members, IL-33, LIF, IFN-gamma, OSM, CNTF, CSF1, OPN, CD11c, GM-CSF, IL-11, IL-12, IL-17, IL-18, and IL-23.

In certain embodiments, pro-inflammatory mediators include inflammatory receptors. Accordingly, in certain embodiments, the anti-TREM2 antibodies of the present disclosure may modulate expression of one or more inflammatory receptors. Examples of inflammatory receptors whose expression may be reduced by the anti-TREM2 antibodies of the present disclosure include, without limitation, CD86.

As used herein, a pro-inflammatory mediator may have modulated expression if its expression in one or more cells of a subject treated with an anti-TREM2 antibody of the present disclosure is modulated (e.g., increased or decreased) as compared to the expression of the same pro-inflammatory mediator expressed in one or more cells of a corresponding subject that is not treated with the anti-TREM2 antibody. In some embodiments, the anti-TREM2 antibody of the present disclosure may modulate pro-inflammatory mediator expression in one or more cells of a subject by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, at least 115%, at least 120%, at least 125%, at least 130%, at least 135%, at least 140%, at least 145%, at least 150%, at least 160%, at least 170%, at least 180%, at least 190%, or at least 200% for example, as compared to pro-inflammatory mediator expression in one or more cells of a corresponding subject that is not treated with the anti-TREM2 antibody. In other embodiments, the anti-TREM2 antibody may modulate pro-inflammatory mediator expression in one or more cells of a subject by at least 1.5 fold, at least 1.6 fold, at least 1.7 fold, at least 1.8 fold, at least 1.9 fold, at least 2.0 fold, at least 2.1 fold, at least 2.15 fold, at least 2.2 fold, at least 2.25 fold, at least 2.3 fold, at least 2.35 fold, at least 2.4 fold, at least 2.45 fold, at least 2.5 fold, at least 2.55 fold, at least 3.0 fold, at least 3.5 fold, at least 4.0 fold, at least 4.5 fold, at least 5.0 fold, at least 5.5 fold, at least 6.0 fold, at least 6.5 fold, at least 7.0 fold, at least 7.5 fold, at least 8.0 fold, at least 8.5 fold, at least 9.0 fold, at least 9.5 fold, or at least 10 fold, for example, as compared to pro-inflammatory mediator expression in one or more cells of a corresponding subject that is not treated with the anti-TREM2 antibody.

In some embodiments, anti-TREM2 antibodies of the present disclosure may be useful for preventing, lowering the risk of, or treating conditions and/or diseases associated with abnormal levels of one or more pro-inflammatory mediators, including dementia, frontotemporal dementia, Alzheimer's disease, vascular dementia, mixed dementia, Creutzfeldt-Jakob disease, normal pressure hydrocephalus, amyotrophic lateral sclerosis, Huntington's disease, tauopathy disease, Nasu-Hakola disease, stroke, acute trauma, chronic trauma, cognitive deficit, memory loss, lupus, acute and chronic colitis, rheumatoid arthritis, wound healing, Crohn's disease, inflammatory bowel disease, ulcerative colitis, obesity, malaria, essential tremor, central nervous system lupus, Behcet's disease, Parkinson's disease, dementia with Lewy bodies, multiple system atrophy, Shy-Drager syndrome, progressive supranuclear palsy, cortical basal ganglionic degeneration, acute disseminated encephalomyelitis, granulomartous disorders, sarcoidosis, diseases of aging, seizures, spinal cord injury, traumatic brain injury, age related macular degeneration, glaucoma, retinitis pigmentosa, retinal degeneration, respiratory tract infection, sepsis, eye infection, systemic infection, lupus, arthritis, multiple sclerosis, low bone density, osteoporosis, osteogenesis, osteopetrotic disease, Paget's disease of bone, cancer, bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, acute lymphoblastic leukemia (ALL), acute myeloid leukemia (AML), chronic lymphocytic leukemia (CLL), chronic myeloid leukemia (CML), multiple myeloma, polycythemia vera, essential thrombocytosis, primary or idiopathic myelofibrosis, primary or idiopathic myelosclerosis, myeloid-derived tumors, tumors that express TREM2, thyroid cancer, infections, CNS herpes, parasitic infections, Trypanosome infection, Cruzi infection, *Pseudomonas aeruginosa* infection, *Leishmania donovani* infection, group B *Streptococcus* infection, *Campylobacter jejuni* infection, *Neisseria meningiditis* infection, type I HIV, and *Haemophilus influenza*, comprising administering to an individual in need thereof a therapeutically effective amount of an agent that does not inhibit interaction between TREM2 and one or more TREM2 ligands, and/or enhance one or more activities of at least one TREM2 ligand. Other aspects of the present disclosure relate to an agent that does not inhibit interaction between TREM2 and one or more TREM2 ligands, and/or enhance one or more activities of at least one TREM2 ligand, for use in preventing, reducing risk, or treating a disease, disorder, or injury selected from dementia, frontotemporal dementia, Alzheimer's disease, vascular dementia, mixed dementia, Creutzfeldt-Jakob disease, normal pressure hydrocephalus, amyotrophic lateral sclerosis, Huntington's disease, tauopathy disease, Nasu-Hakola disease, stroke, acute trauma, chronic trauma, cognitive deficit, memory loss, lupus, acute and chronic colitis, rheumatoid arthritis, wound healing, Crohn's disease, inflammatory bowel disease, ulcerative colitis, obesity, malaria, essential tremor, central nervous system lupus, Behcet's disease, Parkinson's disease, dementia with Lewy bodies, multiple system atrophy, Shy-Drager syndrome, progressive supranuclear palsy, cortical basal ganglionic degeneration, acute disseminated encephalomyelitis, granulomartous disorders, sarcoidosis, diseases of aging, seizures, spinal cord injury, traumatic brain injury, age related macular degeneration, glaucoma, retinitis pigmentosa, retinal degeneration, respiratory tract infection, sepsis, eye infection, systemic infection, lupus, arthritis, multiple sclerosis, low bone density, osteoporosis, osteogenesis, osteopetrotic disease, Paget's disease of bone, cancer, bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, acute lymphoblastic leukemia (ALL), acute myeloid leukemia (AML), chronic lymphocytic leukemia (CLL), chronic myeloid leukemia (CML), multiple myeloma, polycythemia vera, essential thrombocytosis, primary or idiopathic myelofibrosis, primary or idiopathic myelosclerosis, myeloid-derived tumors, tumors that express TREM2, thyroid cancer, infections, CNS herpes, parasitic infections, Trypanosome infection, Cruzi infection, *Pseudomonas aeruginosa* infection, *Leishmania donovani* infection, group B *Streptococcus* infection, *Campylobacter jejuni* infection, *Neisseria meningiditis* infection, type I HIV, and *Haemophilus influenza*.

Syk Phosphorylation

In some embodiments, the anti-TREM2 antibodies of the present disclosure may induce spleen tyrosine kinase (Syk) phosphorylation after binding to a TREM2 protein expressed in a cell.

Spleen tyrosine kinase (Syk) is an intracellular signaling molecule that functions downstream of TREM2 by phosphorylating several substrates, thereby facilitating the formation of a signaling complex leading to cellular activation and inflammatory processes.

In some embodiments, anti-TREM2 antibodies of the present disclosure may be beneficial for preventing, lowering the risk of, or treating conditions and/or diseases associated with decreased levels of Syk phosphorylation, including dementia, frontotemporal dementia, Alzheimer's disease, vascular dementia, mixed dementia, Creutzfeldt-Jakob disease, normal pressure hydrocephalus, amyotrophic lateral sclerosis, Huntington's disease, tauopathy disease, Nasu-Hakola disease, stroke, acute trauma, chronic trauma, cognitive deficit, memory loss, lupus, acute and chronic colitis, rheumatoid arthritis, wound healing, Crohn's disease, inflammatory bowel disease, ulcerative colitis, obesity, malaria, essential tremor, central nervous system lupus, Behcet's disease, Parkinson's disease, dementia with Lewy bodies, multiple system atrophy, Shy-Drager syndrome, progressive supranuclear palsy, cortical basal ganglionic degeneration, acute disseminated encephalomyelitis, granulomartous disorders, sarcoidosis, diseases of aging, seizures, spinal cord injury, traumatic brain injury, age related macular degeneration, glaucoma, retinitis pigmentosa, retinal degeneration, respiratory tract infection, sepsis, eye infection, systemic infection, lupus, arthritis, multiple sclerosis, low bone density, osteoporosis, osteogenesis, osteopetrotic disease, Paget's disease of bone, cancer, bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, acute lymphoblastic leukemia (ALL), acute myeloid leukemia (AML), chronic lymphocytic leukemia (CLL), chronic myeloid leukemia (CML), multiple myeloma, polycythemia vera, essential thrombocytosis, primary or idiopathic myelofibrosis, primary or idiopathic myelosclerosis, myeloid-derived tumors, tumors that express TREM2, thyroid cancer, infections, CNS herpes, parasitic infections, Trypanosome infection, Cruzi infection, *Pseudomonas aeruginosa* infection, *Leishmania donovani* infection, group B *Streptococcus* infection, *Campylobacter jejuni* infection, *Neisseria meningiditis* infection, type I HIV, and *Haemophilus influenza*, comprising administering to an individual in need thereof a therapeutically effective amount of an agent that does not inhibit interaction between TREM2 and one or more TREM2 ligands, and/or enhance one or more activities of at least one TREM2 ligand. Other aspects of the present disclosure relate to an agent that does not inhibit interaction between TREM2 and one or more TREM2 ligands, and/or enhance one or more activities of at least one TREM2 ligand, for use in preventing, reducing risk, or treating a disease, disorder, or injury selected from dementia, frontotemporal dementia, Alzheimer's disease, vascular dementia, mixed dementia, Creutzfeldt-Jakob disease, normal pressure hydrocephalus, amyotrophic lateral sclerosis, Huntington's disease, tauopathy disease, Nasu-Hakola disease, stroke, acute trauma, chronic trauma, cognitive deficit, memory loss, lupus, acute and chronic colitis, rheumatoid arthritis, wound healing, Crohn's disease, inflammatory bowel disease, ulcerative colitis, obesity, malaria, essential tremor, central nervous system lupus, Behcet's disease, Parkinson's disease, dementia with Lewy bodies, multiple system atrophy, Shy-Drager syndrome, progressive supranuclear palsy, cortical basal ganglionic degeneration, acute disseminated encephalomyelitis, granulomartous disorders, sarcoidosis, diseases of aging, seizures, spinal cord injury, traumatic brain injury, age related macular degeneration, glaucoma, retinitis pigmentosa, retinal degeneration, respiratory tract infection, sepsis, eye infection, systemic infection, lupus, arthritis, multiple sclerosis, low bone density, osteoporosis, osteogenesis, osteopetrotic disease, Paget's disease of bone, cancer, bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, acute lymphoblastic leukemia (ALL), acute myeloid leukemia (AML), chronic lymphocytic leukemia (CLL), chronic myeloid leukemia (CML), multiple myeloma, polycythemia vera, essential thrombocytosis, primary or idiopathic myelofibrosis, primary or idiopathic myelosclerosis, myeloid-derived tumors, tumors that express TREM2, thyroid cancer, infections, CNS herpes, parasitic infections, Trypanosome infection, Cruzi infection, *Pseudomonas aeruginosa* infection, *Leishmania donovani* infection, group B *Streptococcus* infection, *Campylobacter jejuni* infection, *Neisseria meningiditis* infection, type I HIV, and *Haemophilus influenza*.

DAP12 Binding and Phosphorylation

In some embodiments, the anti-TREM2 antibodies of the present disclosure may induce binding of TREM2 to DAP12. In other embodiments, the anti-TREM2 antibodies of the present disclosure may induce DAP12 phosphorylation after binding to a TREM2 protein expressed in a cell. In other embodiments, TREM2-mediated DAP12 phosphorylation is induced by one or more SRC family tyrosine kinases. Examples of Src family tyrosine kinases include, without limitation, Src, Syk, Yes, Fyn, Fgr, Lck, Hck, Blk, Lyn, and Frk.

DAP12 is variously referred to as TYRO protein tyrosine kinase-binding protein, TYROBP, KARAP, and PLOSL. DAP12 is a transmembrane signaling protein that contains an immunoreceptor tyrosine-based activation motif (ITAM) in its cytoplasmic domain. In certain embodiments, the anti-TREM2 antibody may induce DAP12 phosphorylation in its ITAM motif. Any method known in the art for determining protein phosphorylation, such as DAP12 phosphorylation, may be used.

In some embodiments, DAP12 is phosphorylated by SRC family kinases, resulting in the recruitment and activation of the Syk kinase, ZAP70 kinase, or both, to a DAP12/TREM2 complex. Thus, in certain embodiments, the anti-TREM2 antibodies of the present disclosure may recruit Syk, ZAP70, or both to a DAP12/TREM2 complex. Without wishing to be bound by theory, it is believed that anti-TREM2 a antibodies of the present disclosure are useful for preventing, lowering the risk of, or treating conditions and/or diseases associated with decreased levels of DAP12 activity, DAP12 phosphorylation, or recruitment of Syk, ZAP70, or both to a DAP12/TREM2 complex, including dementia, frontotemporal dementia, Alzheimer's disease, vascular dementia, mixed dementia, Creutzfeldt-Jakob disease, normal pressure hydrocephalus, amyotrophic lateral sclerosis, Huntington's disease, tauopathy disease, Nasu-Hakola disease, stroke, acute trauma, chronic trauma, cognitive deficit, memory loss, lupus, acute and chronic colitis, rheumatoid arthritis, wound healing, Crohn's disease, inflammatory bowel disease, ulcerative colitis, obesity, malaria, essential tremor, central nervous system lupus, Behcet's disease, Parkinson's disease, dementia with Lewy bodies, multiple system atrophy, Shy-Drager syndrome, progressive supranuclear palsy, cortical basal ganglionic degeneration, acute disseminated encephalomyelitis, granulomartous disorders, sarcoidosis, diseases of aging, seizures, spinal cord injury, traumatic brain injury, age related macular degeneration, glaucoma, retinitis pigmentosa, retinal degeneration, respiratory tract infection, sepsis, eye infection, systemic infection, lupus, arthritis, multiple sclerosis, low bone density, osteoporosis, osteogenesis, osteopetrotic disease, Paget's disease of bone, cancer, bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, acute lymphoblastic leukemia (ALL), acute myeloid leukemia (AML), chronic lymphocytic leukemia (CLL), chronic myeloid leukemia (CML), multiple myeloma, polycythemia vera, essential thrombocytosis, primary or idiopathic myelofibrosis, primary or idiopathic myelosclerosis, myeloid-derived tumors, tumors that express TREM2, thyroid cancer, infections, CNS herpes, parasitic infections, Trypanosome infection, Cruzi infection, *Pseudomonas aeruginosa* infection, *Leishmania donovani* infection, group B *Streptococcus* infection, *Campylobacter jejuni* infection, *Neisseria meningiditis* infection, type I HIV, and *Haemophilus influenza*, comprising administering to an individual in need thereof a therapeutically effective amount of an agent that does not inhibit interaction between TREM2 and one or more TREM2 ligands, and/or enhance one or more activities of one or more TREM2 ligands, Other aspects of the present disclosure relate to an agent does not inhibit interaction between TREM2 and one or more TREM2 ligands, and/or enhance one or more activities of one or more TREM2 ligands, use in preventing, reducing risk, or treating a disease, disorder, or injury selected from dementia, frontotemporal dementia, Alzheimer's disease, vascular dementia, mixed dementia, Creutzfeldt-Jakob disease, normal pressure hydrocephalus, amyotrophic lateral sclerosis, Huntington's disease, tauopathy disease, Nasu-Hakola disease, stroke, acute trauma, chronic trauma, cognitive deficit, memory loss, lupus, acute and chronic colitis, rheumatoid arthritis, wound healing, Crohn's disease, inflammatory bowel disease, ulcerative colitis, obesity, malaria, essential tremor, central nervous system lupus, Behcet's disease, Parkinson's disease, dementia with Lewy bodies, multiple system atrophy, Shy-Drager syndrome, progressive supranuclear palsy, cortical basal ganglionic degeneration, acute disseminated encephalomyelitis, granulomartous disorders, sarcoidosis, diseases of aging, seizures, spinal cord injury, traumatic brain injury, age related macular degeneration, glaucoma, retinitis pigmentosa, retinal degeneration, respiratory tract infection, sepsis, eye infection, systemic infection, lupus, arthritis, multiple sclerosis, low bone density, osteoporosis, osteogenesis, osteopetrotic disease, Paget's disease of bone, cancer, bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, acute lymphoblastic leukemia (ALL), acute myeloid leukemia (AML), chronic lymphocytic leukemia (CLL), chronic myeloid leukemia (CML), multiple myeloma, polycythemia vera, essential thrombocytosis, primary or idiopathic myelofibrosis, primary or idiopathic myelosclerosis, myeloid-derived tumors, tumors that express TREM2, thyroid cancer, infections, CNS herpes, parasitic infections, Trypanosome infection, Cruzi infection, *Pseudomonas aeruginosa* infection, *Leishmania donovani* infection, group B *Streptococcus* infection, *Campylobacter jejuni* infection, *Neisseria meningiditis* infection, type I HIV, and *Haemophilus influenza*.

Proliferation, Survival and Functionality of TREM2-Expressing Cells

In some embodiments, the anti-TREM2 antibodies of the present disclosure may increase the proliferation, survival, and/or function of dendritic cells, macrophages, monocytes, osteoclasts, Langerhans cells of skin, Kupffer cells, and microglial cells (microglia) after binding to TREM2 protein expressed in a cell. In some embodiments, the anti-TREM2 antibodies of the present disclosure do not inhibit the growth (e.g., proliferation and/or survival) of one or more innate immune cells.

Microglial cells are a type of glial cell that are the resident macrophages of the brain and spinal cord, and thus act as the first and main form of active immune defense in the central nervous system (CNS). Microglial cells constitute 20% of the total glial cell population within the brain. Microglial cells are constantly scavenging the CNS for plaques, damaged neurons and infectious agents. The brain and spinal cord are considered "immune privileged" organs in that they are separated from the rest of the body by a series of endothelial cells known as the blood-brain barrier, which prevents most infections from reaching the vulnerable nervous tissue. In the case where infectious agents are directly introduced to the brain or cross the blood-brain barrier, microglial cells must react quickly to decrease inflammation and destroy the infectious agents before they damage the sensitive neural tissue. Due to the unavailability of antibodies from the rest of the body (few antibodies are small enough to cross the blood brain barrier), microglia must be able to recognize foreign bodies, swallow them, and act as antigen-presenting cells activating T-cells. Since this process must be done quickly to prevent potentially fatal damage, microglial cells are extremely sensitive to even small pathological changes in the CNS. They achieve this sensitivity in part by having unique potassium channels that respond to even small changes in extracellular potassium.

As used herein, macrophages of the present disclosure include, without limitation, M1 macrophages, activated M1 macrophages, and M2 macrophages. As used herein, microglial cells of the present disclosure include, without limitation, M1 microglial cells, activated M1 microglial cells, and M2 microglial cells. In some embodiments, anti-TREM2 antibodies of the present disclosure may be beneficial for, lowering the risk of, or treating conditions and/or diseases associated with decreased proliferation or survival, of immune cells, including dementia, frontotemporal dementia, Alzheimer's disease, vascular dementia, mixed dementia, Creutzfeldt-Jakob disease, normal pressure hydrocephalus, amyotrophic lateral sclerosis, Huntington's disease, tauopathy disease, Nasu-Hakola disease, stroke, acute trauma, chronic trauma, cognitive deficit, memory loss, lupus, acute and chronic colitis, rheumatoid arthritis, wound healing, Crohn's disease, inflammatory bowel disease, ulcerative colitis, obesity, malaria, essential tremor, central nervous system lupus, Behcet's disease, Parkinson's disease, dementia with Lewy bodies, multiple system atrophy, Shy-Drager syndrome, progressive supranuclear palsy, cortical basal ganglionic degeneration, acute disseminated encephalomyelitis, granulomartous disorders, sarcoidosis, diseases of aging, seizures, spinal cord injury, traumatic brain injury, age related macular degeneration, glaucoma, retinitis pigmentosa, retinal degeneration, respiratory tract infection, sepsis, eye infection, systemic infection, lupus, arthritis, multiple sclerosis, low bone density, osteoporosis, osteogenesis, osteopetrotic disease, Paget's disease of bone, cancer, bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, acute lymphoblastic leukemia (ALL), acute myeloid leukemia (AML), chronic lymphocytic leukemia (CLL), chronic myeloid leukemia (CML), multiple myeloma, polycythemia vera, essential thrombocytosis, primary or idiopathic myelofibrosis, primary or idiopathic myelosclerosis, myeloid-derived tumors, tumors that express TREM2, thyroid cancer, infections, CNS herpes, parasitic infections, Trypanosome infection, Cruzi infection, *Pseudomonas aeruginosa* infection, *Leishmania donovani* infection, group B *Streptococcus* infection, *Campylobacter jejuni* infection, *Neisseria meningiditis* infection, type I HIV, and *Haemophilus influenza*, comprising administering to an individual in need thereof a therapeutically effective amount of an agent that does not inhibit interaction between TREM2 and one or more TREM2 ligands, and/or enhance one or more activities of one or more TREM2 ligands. Other aspects of the present disclosure relate to an agent that does not inhibit interaction between TREM2 and one or more TREM2 ligands, and/or enhance one or more activities of one or more TREM2 ligands for use in preventing, reducing risk, or treating a disease, disorder, or injury selected from dementia, frontotemporal dementia, Alzheimer's disease, vascular dementia, mixed dementia, Creutzfeldt-Jakob disease, normal pressure hydrocephalus, amyotrophic lateral sclerosis, Huntington's disease, tauopathy disease, Nasu-Hakola disease, stroke, acute trauma, chronic trauma, cognitive deficit, memory loss, lupus, acute and chronic colitis, rheumatoid arthritis, wound healing, Crohn's disease, inflammatory bowel disease, ulcerative colitis, obesity, malaria, essential tremor, central nervous system lupus, Behcet's disease, Parkinson's disease, dementia with Lewy bodies, multiple system atrophy, Shy-Drager syndrome, progressive supranuclear palsy, cortical basal ganglionic degeneration, acute disseminated encephalomyelitis, granulomartous disorders, sarcoidosis, diseases of aging, seizures, spinal cord injury, traumatic brain injury, age related macular degeneration, glaucoma, retinitis pigmentosa, retinal degeneration, respiratory tract infection, sepsis, eye infection, systemic infection, lupus, arthritis, multiple sclerosis, low bone density, osteoporosis, osteogenesis, osteopetrotic disease, Paget's disease of bone, cancer, bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, acute lymphoblastic leukemia (ALL), acute myeloid leukemia (AML), chronic lymphocytic leukemia (CLL), chronic myeloid leukemia (CML), multiple myeloma, polycythemia vera, essential thrombocytosis, primary or idiopathic myelofibrosis, primary or idiopathic myelosclerosis, myeloid-derived tumors, tumors that express TREM2, thyroid cancer, infections, CNS herpes, parasitic infections, Trypanosome infection, Cruzi infection, *Pseudomonas aeruginosa* infection, *Leishmania donovani* infection, group B *Streptococcus* infection, *Campylobacter jejuni* infection, *Neisseria meningiditis* infection, type I HIV, and *Haemophilus influenza*.

In some embodiments, anti-TREM2 antibodies of the present disclosure may increase the expression of CD83 and/or CD86 on dendritic cells, monocytes, and/or macrophages.

As used herein, the rate of proliferation, survival, and/or function of macrophages, dendritic cells, monocytes, and/or microglia may include increased expression if the rate of proliferation, survival, and/or function of dendritic cells, macrophages, monocytes, osteoclasts, Langerhans cells of skin, Kupffer cells, and/or microglia in a subject treated with an anti-TREM2 antibody of the present disclosure is greater than the rate of proliferation, survival, and/or function of dendritic cells, macrophages, monocytes, osteoclasts, Langerhans cells of skin, Kupffer cells, and/or microglia in a corresponding subject that is not treated with the anti-TREM2 antibody. In some embodiments, an anti-TREM2 antibody of the present disclosure may increase the rate of proliferation, survival, and/or function of dendritic cells, macrophages, monocytes, osteoclasts, Langerhans cells of skin, Kupffer cells, and/or microglia in a subject by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, at least 115%, at least 120%, at least 125%, at least 130%, at least 135%, at least 140%, at least 145%, at least 150%, at least 160%, at least 170%, at least 180%, at least 190%, or at least 200% for example, as compared to the rate of proliferation, survival, and/or function of dendritic cells, macrophages, monocytes, osteoclasts, Langerhans cells of skin, Kupffer cells, and/or microglia in a corresponding subject that is not treated with the anti-TREM2 antibody. In other embodiments, an anti-TREM2 antibody of the present disclosure may increase the rate of proliferation, survival, and/or function of dendritic cells, macrophages, monocytes, osteoclasts, Langerhans cells of skin, Kupffer cells, and/or microglia in a subject by at least 1.5 fold, at least 1.6 fold, at least 1.7 fold, at least 1.8 fold, at least 1.9 fold, at least 2.0 fold, at least 2.1 fold, at least 2.15 fold, at least 2.2 fold, at least 2.25 fold, at least 2.3 fold, at least 2.35 fold, at least 2.4 fold, at least 2.45 fold, at least 2.5 fold, at least 2.55 fold, at least 3.0 fold, at least 3.5 fold, at least 4.0 fold, at least 4.5 fold, at least 5.0 fold, at least 5.5 fold, at least 6.0 fold, at least 6.5 fold, at least 7.0 fold, at least 7.5 fold, at least 8.0 fold, at least 8.5 fold, at least 9.0 fold, at least 9.5 fold, or at least 10 fold, for example, as compared to the rate of proliferation, survival, and/or function of dendritic cells, macrophages, monocytes, osteoclasts, Langerhans cells of skin, Kupffer cells, and/or microglia in a corresponding subject that is not treated with the anti-TREM2 antibody.

In some embodiments, anti-TREM2 antibodies of the present disclosure may be beneficial for preventing, lowering the risk of, or treating conditions and/or diseases associated with a reduction in function of dendritic cells, macrophages, monocytes, osteoclasts, Langerhans cells of skin, Kupffer cells, and/or microglia including dementia, frontotemporal dementia, Alzheimer's disease, vascular dementia, mixed dementia, Creutzfeldt-Jakob disease, normal pressure hydrocephalus, amyotrophic lateral sclerosis, Huntington's disease, tauopathy disease, Nasu-Hakola disease, stroke, acute trauma, chronic trauma, cognitive deficit, memory loss, lupus, acute and chronic colitis, rheumatoid arthritis, wound healing, Crohn's disease, inflammatory bowel disease, ulcerative colitis, obesity, malaria, essential tremor, central nervous system lupus, Behcet's disease, Parkinson's disease, dementia with Lewy bodies, multiple system atrophy, Shy-Drager syndrome, progressive supranuclear palsy, cortical basal ganglionic degeneration, acute disseminated encephalomyelitis, granulomartous disorders, sarcoidosis, diseases of aging, seizures, spinal cord injury, traumatic brain injury, age related macular degeneration, glaucoma, retinitis pigmentosa, retinal degeneration, respiratory tract infection, sepsis, eye infection, systemic infection, lupus, arthritis, multiple sclerosis, low bone density, osteoporosis, osteogenesis, osteopetrotic disease, Paget's disease of bone, cancer, bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, acute lymphoblastic leukemia (ALL), acute myeloid leukemia (AML), chronic lymphocytic leukemia (CLL), chronic myeloid leukemia (CML), multiple myeloma, polycythemia vera, essential thrombocytosis, primary or idiopathic myelofibrosis, primary or idiopathic myelosclerosis, myeloid-derived tumors, tumors that express TREM2, thyroid cancer, infections, CNS herpes, parasitic infections, Trypanosome infection, Cruzi infection, *Pseudomonas aeruginosa* infection, *Leishmania donovani* infection, group B *Streptococcus* infection, *Campylobacter jejuni* infection, *Neisseria meningiditis* infection, type I HIV, and *Haemophilus influenza*, comprising administering to an individual in need thereof a therapeutically effective amount of an agent that does not inhibit interaction between TREM2 and one or more TREM2 ligands, and/or enhance one or more activities of at least one TREM2 ligand. Other aspects of the present disclosure relate to an agent that does not inhibit interaction between TREM2 and one or more TREM2 ligands, and/or enhance one or more activities of at least one TREM2 ligand for use in preventing, reducing risk, or treating a disease, disorder, or injury selected from dementia, frontotemporal dementia, Alzheimer's disease, vascular dementia, mixed dementia, Creutzfeldt-Jakob disease, normal pressure hydrocephalus, amyotrophic lateral sclerosis, Huntington's disease, tauopathy disease, Nasu-Hakola disease, stroke, acute trauma, chronic trauma, cognitive deficit, memory loss, lupus, acute and chronic colitis, rheumatoid arthritis, wound healing, Crohn's disease, inflammatory bowel disease, ulcerative colitis, obesity, malaria, essential tremor, central nervous system lupus, Behcet's disease, Parkinson's disease, dementia with Lewy bodies, multiple system atrophy, Shy-Drager syndrome, progressive supranuclear palsy, cortical basal ganglionic degeneration, acute disseminated encephalomyelitis, granulomartous disorders, sarcoidosis, diseases of aging, seizures, spinal cord injury, traumatic brain injury, age related macular degeneration, glaucoma, retinitis pigmentosa, retinal degeneration, respiratory tract infection, sepsis, eye infection, systemic infection, lupus, arthritis, multiple sclerosis, low bone density, osteoporosis, osteogenesis, osteopetrotic disease, Paget's disease of bone, cancer, bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, acute lymphoblastic leukemia (ALL), acute myeloid leukemia (AML), chronic lymphocytic leukemia (CLL), chronic myeloid leukemia (CML), multiple myeloma, polycythemia vera, essential thrombocytosis, primary or idiopathic myelofibrosis, primary or idiopathic myelosclerosis, myeloid-derived tumors, tumors that express TREM2, thyroid cancer, infections, CNS herpes, parasitic infections, Trypanosome infection, Cruzi infection, *Pseudomonas aeruginosa* infection, *Leishmania donovani* infection, group B *Streptococcus* infection, *Campylobacter jejuni* infection, *Neisseria meningiditis* infection, type I HIV, and *Haemophilus influenza*.

TREM2-Dependent Gene Expression

In some embodiments, anti-TREM2 antibodies of the present disclosure may increase the activity and/or expression of TREM2-dependent genes, such as one or more transcription factors of the nuclear factor of activated T-cells (NFAT) family of transcription factors.

In some embodiments, anti-TREM2 antibodies of the present disclosure may be beneficial for preventing, lowering the risk of, or treating conditions and/or diseases associated with decreased levels of TREM2-dependent genes, including dementia, frontotemporal dementia, Alzheimer's disease, vascular dementia, mixed dementia, Creutzfeldt-Jakob disease, normal pressure hydrocephalus, amyotrophic lateral sclerosis, Huntington's disease, tauopathy disease, Nasu-Hakola disease, stroke, acute trauma, chronic trauma, cognitive deficit, memory loss, lupus, acute and chronic colitis, rheumatoid arthritis, wound healing, Crohn's disease, inflammatory bowel disease, ulcerative colitis, obesity, malaria, essential tremor, central nervous system lupus, Behcet's disease, Parkinson's disease, dementia with Lewy bodies, multiple system atrophy, Shy-Drager syndrome, progressive supranuclear palsy, cortical basal ganglionic degeneration, acute disseminated encephalomyelitis, granulomartous disorders, sarcoidosis, diseases of aging, seizures, spinal cord injury, traumatic brain injury, age related macular degeneration, glaucoma, retinitis pigmentosa, retinal degeneration, respiratory tract infection, sepsis, eye infection, systemic infection, lupus, arthritis, multiple sclerosis, low bone density, osteoporosis, osteogenesis, osteopetrotic disease, Paget's disease of bone, cancer, bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, acute lymphoblastic leukemia (ALL), acute myeloid leukemia (AML), chronic lymphocytic leukemia (CLL), chronic myeloid leukemia (CML), multiple myeloma, polycythemia vera, essential thrombocytosis, primary or idiopathic myelofibrosis, primary or idiopathic myelosclerosis, myeloid-derived tumors, tumors that express TREM2, thyroid cancer, infections, CNS herpes, parasitic infections, Trypanosome infection, Cruzi infection, *Pseudomonas aeruginosa* infection, *Leishmania donovani* infection, group B *Streptococcus* infection, *Campylobacter jejuni* infection, *Neisseria meningiditis* infection, type I HIV, and *Haemophilus influenza*, comprising administering to an individual in need thereof a therapeutically effective amount of an agent that does not inhibit interaction between TREM2 and one or more TREM2 ligands, and/or enhance one or more activities of at least one TREM2 ligand. Other aspects of the present disclosure relate to an agent that does not inhibit interaction between TREM2 and one or more CD33 ligands for use in preventing, reducing risk, or treating a disease, disorder, or injury selected from dementia, frontotemporal dementia, Alzheimer's disease, vascular dementia, mixed dementia, Creutzfeldt-Jakob disease, normal pressure hydrocephalus, amyotrophic lateral sclerosis, Huntington's disease, tauopathy disease, Nasu-Hakola disease, stroke, acute trauma, chronic trauma, cognitive deficit, memory loss, lupus, acute and chronic colitis, rheumatoid arthritis, wound healing, Crohn's disease, inflammatory bowel disease, ulcerative colitis, obesity, malaria, essential tremor, central nervous system lupus, Behcet's disease, Parkinson's disease, dementia with Lewy bodies, multiple system atrophy, Shy-Drager syndrome, progressive supranuclear palsy, cortical basal ganglionic degeneration, acute disseminated encephalomyelitis, granulomartous disorders, sarcoidosis, diseases of aging, seizures, spinal cord injury, traumatic brain injury, age related macular degeneration, glaucoma, retinitis pigmentosa, retinal degeneration, respiratory tract infection, sepsis, eye infection, systemic infection, lupus, arthritis, multiple sclerosis, low bone density, osteoporosis, osteogenesis, osteopetrotic disease, Paget's disease of bone, cancer, bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, acute lymphoblastic leukemia (ALL), acute myeloid leukemia (AML), chronic lymphocytic leukemia (CLL), chronic myeloid leukemia (CML), multiple myeloma, polycythemia vera, essential thrombocytosis, primary or idiopathic myelofibrosis, primary or idiopathic myelosclerosis, myeloid-derived tumors, tumors that express TREM2, thyroid cancer, infections, CNS herpes, parasitic infections, Trypanosome infection, Cruzi infection, *Pseudomonas aeruginosa* infection, *Leishmania donovani* infection, group B *Streptococcus* infection, *Campylobacter jejuni* infection, *Neisseria meningiditis* infection, type I HIV, and *Haemophilus influenza*.

Antibody Preparation

Anti-TREM2 antibodies of the present disclosure can encompass polyclonal antibodies, monoclonal antibodies, humanized and chimeric antibodies, human antibodies, antibody fragments (e.g., Fab, Fab'-SH, Fv, scFv, and F(ab')$_2$), bispecific and polyspecific antibodies, multivalent antibodies, library derived antibodies, antibodies having modified effector functions, fusion proteins containing an antibody portion, and any other modified configuration of the immunoglobulin molecule that includes an antigen recognition site, such as an epitope having amino acid residues of a TREM2 protein of the present disclosure, including glycosylation variants of antibodies, amino acid sequence variants of antibodies, and covalently modified antibodies. The anti-TREM2 antibodies may be human, murine, rat, or of any other origin (including chimeric or humanized antibodies).

(1) Polyclonal Antibodies

Polyclonal antibodies, such as anti-TREM2 polyclonal antibodies, are generally raised in animals by multiple subcutaneous (sc) or intraperitoneal (ip) injections of the relevant antigen and an adjuvant. It may be useful to conjugate the relevant antigen (e.g., a purified or recombinant TREM2 protein of the present disclosure) to a protein that is immunogenic in the species to be immunized, e.g., keyhole limpet hemocyanin (KLH), serum albumin, bovine thyroglobulin, or soybean trypsin inhibitor, using a bifunctional or derivatizing agent, e.g., maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are independently lower alkyl groups. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation.

The animals are immunized against the desired antigen, immunogenic conjugates, or derivatives by combining, e.g., 100 μg (for rabbits) or 5 μg (for mice) of the protein or conjugate with 3 volumes of Freund's complete adjuvant and injecting the solution intradermally at multiple sites. One month later, the animals are boosted with ⅕ to ⅒ the original amount of peptide or conjugate in Freund's complete adjuvant by subcutaneous injection at multiple sites. Seven to fourteen days later, the animals are bled and the serum is assayed for antibody titer. Animals are boosted until the titer plateaus. Conjugates also can be made in recombinant-cell culture as protein fusions. Also, aggregating agents such as alum are suitable to enhance the immune response.

(2) Monoclonal Antibodies

Monoclonal antibodies, such as anti-TREM2 monoclonal antibodies, are obtained from a population of substantially homogeneous antibodies, i.e., the individual antibodies comprising the population are identical except for possible naturally occurring mutations and/or post-translational modifications (e.g., isomerizations, amidations) that may be present in minor amounts. Thus, the modifier "monoclonal" indicates the character of the antibody as not being a mixture of discrete antibodies.

For example, the anti-TREM2 monoclonal antibodies may be made using the hybridoma method first described by Kohler et al., *Nature*, 256:495 (1975), or may be made by recombinant DNA methods (U.S. Pat. No. 4,816,567).

In the hybridoma method, a mouse or other appropriate host animal, such as a hamster, is immunized as hereinabove described to elicit lymphocytes that produce or are capable of producing antibodies that will specifically bind to the protein used for immunization (e.g., a purified or recombinant TREM2 protein of the present disclosure). Alternatively, lymphocytes may be immunized in vitro. Lymphocytes then are fused with myeloma cells using a suitable fusing agent, such as polyethylene glycol, to form a hybridoma cell (Goding, *Monoclonal Antibodies: Principles and Practice*, pp. 59-103 (Academic Press, 1986)).

The immunizing agent will typically include the antigenic protein (e.g., a purified or recombinant TREM2 protein of the present disclosure) or a fusion variant thereof. Generally peripheral blood lymphocytes ("PBLs") are used if cells of human origin are desired, while spleen or lymph node cells are used if non-human mammalian sources are desired. The lymphoctyes are then fused with an immortalized cell line using a suitable fusing agent, such as polyethylene glycol, to form a hybridoma cell. Goding, *Monoclonal Antibodies: Principles and Practice*, Academic Press (1986), pp. 59-103.

Immortalized cell lines are usually transformed mammalian cells, particularly myeloma cells of rodent, bovine or human origin. Usually, rat or mouse myeloma cell lines are employed. The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which are substances that prevent the growth of HGPRT-deficient-cells.

Preferred immortalized myeloma cells are those that fuse efficiently, support stable high-level production of antibody by the selected antibody-producing cells, and are sensitive to a medium such as HAT medium. Among these, preferred are murine myeloma lines, such as those derived from MOPC-21 and MPC-11 mouse tumors (available from the Salk Institute Cell Distribution Center, San Diego, Calif. USA), as well as SP-2 cells and derivatives thereof (e.g., X63-Ag8-653) (available from the American Type Culture Collection, Manassas, Va. USA). Human myeloma and mouse-human heteromyeloma cell lines have also been described for the production of human monoclonal antibodies (Kozbor, *J. Immunol.*, 133:3001 (1984); Brodeur et al., *Monoclonal Antibody Production Techniques and Applications*, pp. 51-63 (Marcel Dekker, Inc., New York, 1987)).

Culture medium in which hybridoma cells are growing is assayed for production of monoclonal antibodies directed against the antigen (e.g., a TREM2 protein of the present disclosure). Preferably, the binding specificity of monoclonal antibodies produced by hybridoma cells is determined by immunoprecipitation or by an in vitro binding assay, such as radioimmunoassay (RIA) or enzyme-linked immunosorbent assay (ELISA).

The culture medium in which the hybridoma cells are cultured can be assayed for the presence of monoclonal antibodies directed against the desired antigen (e.g., a TREM2 protein of the present disclosure). Preferably, the binding affinity and specificity of the monoclonal antibody can be determined by immunoprecipitation or by an in vitro binding assay, such as radioimmunoassay (RIA) or enzyme-linked assay (ELISA). Such techniques and assays are known in the in art. For example, binding affinity may be determined by the Scatchard analysis of Munson et al., Anal. Biochem., 107:220 (1980).

After hybridoma cells are identified that produce antibodies of the desired specificity, affinity, and/or activity, the clones may be subcloned by limiting dilution procedures and grown by standard methods (Goding, supra). Suitable culture media for this purpose include, for example, D-MEM or RPMI-1640 medium. In addition, the hybridoma cells may be grown in vivo as tumors in a mammal.

The monoclonal antibodies secreted by the subclones are suitably separated from the culture medium, ascites fluid, or serum by conventional immunoglobulin purification procedures such as, for example, protein A-Sepharose chromatography, hydroxylapatite chromatography, gel electrophoresis, dialysis, affinity chromatography, and other methods as described above.

Anti-TREM2 monoclonal antibodies may also be made by recombinant DNA methods, such as those disclosed in U.S. Pat. No. 4,816,567, and as described above. DNA encoding the monoclonal antibodies is readily isolated and sequenced using conventional procedures (e.g., by using oligonucleotide probes that specifically bind to genes encoding the heavy and light chains of murine antibodies). The hybridoma cells serve as a preferred source of such DNA. Once isolated, the DNA may be placed into expression vectors, which are then transfected into host-cells such as $E.$ $coli$ cells, simian COS cells, Chinese hamster ovary (CHO) cells, or myeloma cells that do not otherwise produce immunoglobulin protein, in order to synthesize monoclonal antibodies in such recombinant host-cells. Review articles on recombinant expression in bacteria of DNA encoding the antibody include Skerra et al., Curr. Opin. Immunol., 5:256-262 (1993) and Plückthun, Immunol. Rev. 130:151-188 (1992).

In certain embodiments, anti-TREM2 antibodies can be isolated from antibody phage libraries generated using the techniques described in McCafferty et al., Nature, 348:552-554 (1990). Clackson et al., Nature, 352:624-628 (1991) and Marks et al., J. Mol. Biol., 222:581-597 (1991) described the isolation of murine and human antibodies, respectively, from phage libraries. Subsequent publications describe the production of high affinity (nanomolar ("nM") range) human antibodies by chain shuffling (Marks et al., Bio/Technology, 10:779-783 (1992)), as well as combinatorial infection and in vivo recombination as a strategy for constructing very large phage libraries (Waterhouse et al., Nucl. Acids Res., 21:2265-2266 (1993)). Thus, these techniques are viable alternatives to traditional monoclonal antibody hybridoma techniques for isolation of monoclonal antibodies of desired specificity (e.g., those that bind a TREM2 protein of the present disclosure).

The DNA encoding antibodies or fragments thereof may also be modified, for example, by substituting the coding sequence for human heavy- and light-chain constant domains in place of the homologous murine sequences (U.S. Pat. No. 4,816,567; Morrison, et al., Proc. Natl Acad. Sci. USA, 81:6851 (1984)), or by covalently joining to the immunoglobulin coding sequence all or part of the coding sequence for a non-immunoglobulin polypeptide. Typically such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

The monoclonal antibodies described herein (e.g., anti-TREM2 antibodies of the present disclosure or fragments thereof) may by monovalent, the preparation of which is well known in the art. For example, one method involves recombinant expression of immunoglobulin light chain and a modified heavy chain. The heavy chain is truncated generally at any point in the Fc region so as to prevent heavy chain crosslinking. Alternatively, the relevant cysteine residues may be substituted with another amino acid residue or are deleted so as to prevent crosslinking. In vitro methods are also suitable for preparing monovalent antibodies. Digestion of antibodies to produce fragments thereof, particularly Fab fragments, can be accomplished using routine techniques known in the art.

Chimeric or hybrid anti-TREM2 antibodies also may be prepared in vitro using known methods in synthetic protein chemistry, including those involving crosslinking agents. For example, immunotoxins may be constructed using a disulfide-exchange reaction or by forming a thioether bond. Examples of suitable reagents for this purpose include iminothiolate and methyl-4-mercaptobutyrimidate.

(3) Humanized Antibodies

Anti-TREM2 antibodies of the present disclosure or antibody fragments thereof may further include humanized or human antibodies. Humanized forms of non-human (e.g., murine) antibodies are chimeric immunoglobulins, immunoglobulin chains or fragments thereof (such as Fab, Fab'-SH, Fv, scFv, F(ab')$_2$ or other antigen-binding subsequences of antibodies) which contain minimal sequence derived from non-human immunoglobulin. Humanized antibodies include human immunoglobulins (recipient antibody) in which residues from a complementarity determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally will also comprise at least a portion of an immunoglobulin constant region (Fc), typically that of a human immunoglobulin. Jones et al., Nature 321: 522-525 (1986); Riechmann et al., Nature 332: 323-329 (1988) and Presta, Curr. Opin. Struct. Biol. 2: 593-596 (1992).

Methods for humanizing non-human anti-TREM2 antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers, Jones et al., Nature 321:522-525 (1986); Riechmann et al., Nature 332: 323-327 (1988); Verhoeyen et al., Science 239:1534-1536 (1988), or through substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody. Sims et al., J. Immunol., 151:2296 (1993); Chothia et al., J. Mol. Biol., 196:901 (1987). Another method uses a particular framework derived from the consensus sequence of all human antibodies of a particular subgroup of light or heavy chains. The same framework may be used for several different humanized antibodies. Carter et al., Proc. Nat'l Acad. Sci. USA 89:4285 (1992); Presta et al., J. Immunol. 151:2623 (1993).

Furthermore, it is important that antibodies be humanized with retention of high affinity for the antigen and other favorable biological properties. To achieve this goal, according to a preferred method, humanized antibodies are prepared by a process of analyzing the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen or antigens (e.g., TREM2 proteins of the present disclosure), is achieved. In general, the CDR residues are directly and most substantially involved in influencing antigen binding.

Various forms of the humanized anti-TREM2 antibody are contemplated. For example, the humanized anti-TREM2 antibody may be an antibody fragment, such as an Fab, which is optionally conjugated with one or more TREM2 ligand, such as HSP60. Alternatively, the humanized anti-TREM2 antibody may be an intact antibody, such as an intact IgG1 antibody.

(4) Antibody Fragments

In certain embodiments there are advantages to using anti-TREM2 antibody fragments, rather than whole anti-TREM2 antibodies. In some embodiments, smaller fragment sizes allow for rapid clearance and better brain penetration.

Various techniques have been developed for the production of antibody fragments. Traditionally, these fragments were derived via proteolytic digestion of intact antibodies (see, e.g., Morimoto et al., J. Biochem. Biophys. Method. 24:107-117 (1992); and Brennan et al., Science 229:81 (1985)). However, these fragments can now be produced directly by recombinant host-cells, for example, using nucleic acids encoding anti-TREM2 antibodies of the present disclosure. Fab, Fv and scFv antibody fragments can all be expressed in and secreted from E. coli, thus allowing the straightforward production of large amounts of these fragments. Anti-TREM2 antibody fragments can also be isolated from the antibody phage libraries as discussed above. Alternatively, Fab'-SH fragments can be directly recovered from E. coli and chemically coupled to form $F(ab')_2$ fragments (Carter et al., Bio/Technology 10:163-167 (1992)). According to another approach, $F(ab')_2$ fragments can be isolated directly from recombinant host-cell culture. Production of Fab and $F(ab')_2$ antibody fragments with increased in vivo half-lives are described in U.S. Pat. No. 5,869,046. In other embodiments, the antibody of choice is a single chain Fv fragment (scFv). See WO 93/16185; U.S. Pat. Nos. 5,571, 894 and 5,587,458. The anti-TREM2 antibody fragment may also be a "linear antibody," e.g., as described in U.S. Pat. No. 5,641,870. Such linear antibody fragments may be monospecific or bispecific.

(5) Bispecific and Polyspecific Antibodies

Bispecific antibodies (BsAbs) are antibodies that have binding specificities for at least two different epitopes, including those on the same or another protein (e.g., one or more TREM2 proteins of the present disclosure). Alternatively, one part of a BsAb can be armed to bind to the target TREM2 antigen, and another can be combined with an arm that binds to a second protein. Such antibodies can be derived from full-length antibodies or antibody fragments (e.g., $F(ab')_2$ bispecific antibodies).

Methods for making bispecific antibodies are known in the art. Traditional production of full-length bispecific antibodies is based on the coexpression of two immunoglobulin heavy-chain/light chain pairs, where the two chains have different specificities. Millstein et al., Nature, 305:537-539 (1983). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829 and in Traunecker et al., EMBO J., 10:3655-3659 (1991).

According to a different approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, $C_H2$, and $C_H3$ regions. It is preferred to have the first heavy-chain constant region ($C_H1$) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only half of the bispecific molecules provides for an easy way of separation. This approach is disclosed in WO 94/04690. For further details of generating bispecific antibodies, see, for example, Suresh et al., *Methods in Enzymology* 121: 210 (1986); and Garber, *Nature Reviews Drug Discovery* 13, 799-801 (2014).

According to another approach described in WO 96/27011 or U.S. Pat. No. 5,731,168, the interface between a pair of antibody molecules can be engineered to maximize the percentage of heterodimers which are recovered from recombinant-cell culture. The preferred interface comprises at least a part of the $C_H3$ region of an antibody constant domain. In this method, one or more small amino acid side chains from the interface of the first antibody molecule are replaced with larger side chains (e.g., tyrosine or tryptophan). Compensatory "cavities" of identical or similar size to the large side chains(s) are created on the interface of the second antibody molecule by replacing large amino acid side chains with smaller ones (e.g., alanine or threonine). This provides a mechanism for increasing the yield of the heterodimer over other unwanted end-products such as homodimers.

Techniques for generating bispecific antibodies from antibody fragments have been described in the literature. For example, bispecific antibodies can be prepared using chemical linkage. Brennan et al., *Science* 229:81 (1985) describe a procedure wherein intact antibodies are proteolytically cleaved to generate F(ab')₂ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-TNB derivative to form the bispecific antibody. The bispecific antibodies produced can be used as agents for the selective immobilization of enzymes.

Fab' fragments may be directly recovered from *E. coli* and chemically coupled to form bispecific antibodies. Shalaby et al., *J. Exp. Med* 175: 217-225 (1992) describes the production of fully humanized bispecific antibody F(ab')₂ molecules. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T-cells, as well as trigger the lytic activity of human cytotoxic lymphocytes against human breast tumor targets.

Various techniques for making and isolating bivalent antibody fragments directly from recombinant-cell culture have also been described. For example, bivalent heterodimers have been produced using leucine zippers. Kostelny et al., *J. Immunol.*, 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. The "diabody" technology described by Hollinger et al., *Proc. Nat'l Acad. Sci. USA*, 90: 6444-6448 (1993) has provided an alternative mechanism for making bispecific/bivalent antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific/bivalent antibody fragments by the use of single-chain Fv (sFv) dimers has also been reported. See Gruber et al., *J. Immunol.*, 152:5368 (1994).

Another method to generate bispecific antibodies is designated controlled Fab-arm exchange (cFAE), which is an easy-to-use method to generate bispecific IgG1 (bsIgG1). The protocol involves the following: (i) separate expression of two parental IgG1s containing single matching point mutations in the CH3 domain; (ii) mixing of parental IgG1s under permissive redox conditions in vitro to enable recombination of half-molecules; (iii) removal of the reductant to allow reoxidation of interchain disulfide bonds; and (iv) analysis of exchange efficiency and final product using chromatography-based or mass spectrometry (MS)-based methods. The protocol generates bsAbs with regular IgG architecture, characteristics and quality attributes both at bench scale (micrograms to milligrams) and at a minibioreactor scale (milligrams to grams) that is designed to model large-scale manufacturing (kilograms). Starting from good-quality purified proteins, exchange efficiencies of ≥95% can be obtained within 2-3 days (including quality control). See Labrijn et al., *Natur Protocols* 9, 2450-2463 (2014); and Garber, *Nature Reviews Drug Discovery* 13, 799-801 (2014).

Antibodies with more than two valencies are also contemplated. For example, trispecific antibodies can be prepared. Tutt et al., *J. Immunol.* 147:60 (1991).

Exemplary bispecific antibodies may bind to two different epitopes on a given molecule (e.g., a TREM2 protein of the present disclosure). In some embodiments a bispecific antibody binds to a first antigen, such as a TREM2 or DAP12 protein of the present disclosure, and a second antigen facilitating transport across the blood-brain barrier. Numerous antigens are known in the art that facilitate transport across the blood-brain barrier (see, e.g., Gabathuler R., Approaches to transport therapeutic drugs across the blood-brain barrier to treat brain diseases, Neurobiol. Dis. 37 (2010) 48-57). Such second antigens include, without limitation, transferrin receptor (TR), insulin receptor (HIR), Insulin-like growth factor receptor (IGFR), low-density lipoprotein receptor related proteins 1 and 2 (LPR-1 and 2), diphtheria toxin receptor, including CRM197 (a non-toxic mutant of diphtheria toxin), llama single domain antibodies such as TMEM 30(A) (Flippase), protein transduction domains such as TAT, Syn-B, or penetratin, poly-arginine or generally positively charged peptides, Angiopep peptides such as ANG1005 (see, e.g., Gabathuler, 2010), and other cell surface proteins that are enriched on blood-brain barrier endothelial cells (see, e.g., Daneman et al., PLoS One. 2010 Oct. 29; 5(10):e13741). In some embodiments, second antigens for an anti-TREM2 antibody may include, without limitation, a DAP12 antigen of the present disclosure. In other embodiments, bispecific antibodies that bind to both TREM2 and DAP12 may facilitate and enhance one or more TREM2 activities. In other embodiments, second antigens for an anti-TREM2 antibody may include, without limitation, A beta peptide, antigen or an alpha synuclein protein antigen or, Tau protein antigen or, TDP-43 protein antigen or, prion protein antigen or, huntingtin protein antigen, or RAN, translation Products antigen, including the DiPeptide Repeats, (DPRs peptides) composed of glycine-alanine (GA), glycine-proline (GP), glycine-arginine (GR), proline-alanine (PA), or proline-arginine (PR).

(6) Multivalent Antibodies

A multivalent antibody may be internalized (and/or catabolized) faster than a bivalent antibody by a cell expressing an antigen to which the antibodies bind. The anti-TREM2 antibodies of the present disclosure or antibody fragments thereof can be multivalent antibodies (which are other than of the IgM class) with three or more antigen binding sites (e.g., tetravalent antibodies), which can be readily produced by recombinant expression of nucleic acid encoding the polypeptide chains of the antibody. The multivalent antibody can comprise a dimerization domain and three or more antigen binding sites. The preferred dimerization domain comprises an Fc region or a hinge region. In this scenario, the antibody will comprise an Fc region and three or more antigen binding sites amino-terminal to the Fc region. The preferred multivalent antibody herein contains three to about eight, but preferably four, antigen binding sites. The multivalent antibody contains at least one polypeptide chain (and preferably two polypeptide chains), wherein the polypeptide chain or chains comprise two or more variable domains. For instance, the polypeptide chain or chains may comprise VD1-(X1)n-VD2-(X2)n-Fc, wherein VD1 is a first variable domain, VD2 is a second variable domain, Fc is one polypeptide chain of an Fc region, X1 and X2 represent an amino acid or polypeptide, and n is 0 or 1. Similarly, the polypeptide chain or chains may comprise $V_H$-$C_H$1-flexible linker-$V_H$-$C_H$1-Fc region chain; or $V_H$-$C_H$1-$V_H$-$C_H$1-Fc region chain. The multivalent antibody herein preferably further comprises at least two (and preferably four) light chain variable domain polypeptides. The multivalent antibody herein may, for instance, comprise from about two to about eight light chain variable domain polypeptides. The light chain variable domain polypeptides contemplated here comprise a light chain variable domain and, optionally, further comprise a CL domain. The Multivalent antibodies may recognize the TREM2 antigen as well as without limitation additional antigens A beta peptide, antigen or an alpha synuclein protein antigen or, Tau protein antigen or, TDP-43 protein antigen or, prion protein antigen or, huntingtin protein antigen, or RAN, translation Products antigen, including the DiPeptide Repeats, (DPRs peptides) composed of glycine-alanine (GA), glycine-proline (GP), glycine-arginine (GR), proline-alanine (PA), or proline-arginine (PR), Insulin receptor, insulin like growth factor receptor. Transferrin receptor or any other antigen that facilitate antibody transfer across the blood brain barrier.

(7) Effector Function Engineering

It may also be desirable to modify an anti-TREM2 antibody of the present disclosure to modify effector function and/or to increase serum half-life of the antibody. For example, the Fc receptor binding site on the constant region may be modified or mutated to remove or reduce binding affinity to certain Fc receptors, such as FcγRI, FcγRII, and/or FcγRIII to reduce Antibody-dependent cell-mediated cytotoxicity. In some embodiments, the effector function is impaired by removing N-glycosylation of the Fc region (e.g., in the CH 2 domain of IgG) of the antibody. In some embodiments, the effector function is impaired by modifying regions such as 233-236, 297, and/or 327-331 of human IgG as described in PCT WO 99/58572 and Armour et al., *Molecular Immunology* 40: 585-593 (2003); Reddy et al., *J. Immunology* 164:1925-1933 (2000). In other embodiments, it may also be desirable to modify an anti-TREM2 antibody of the present disclosure to modify effector function to increase finding selectivity toward the ITIM-containing FcgRIIb (CD32b) to increase clustering of TREM2 antibodies on adjacent cells without activating humoral responses including Antibody-dependent cell-mediated cytotoxicity and antibody-dependent cellular phagocytosis.

To increase the serum half-life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., $IgG_1$, $IgG_2$, $IgG_3$, or $IgG_4$) that is responsible for increasing the in vivo serum half-life of the IgG molecule.

(8) Other Amino Acid Sequence Modifications

Amino acid sequence modifications of anti-TREM2 antibodies of the present disclosure, or antibody fragments thereof, are also contemplated. For example, it may be desirable to improve the binding affinity and/or other biological properties of the antibodies or antibody fragments. Amino acid sequence variants of the antibodies or antibody fragments are prepared by introducing appropriate nucleotide changes into the nucleic acid encoding the antibodies or antibody fragments, or by peptide synthesis. Such modifications include, for example, deletions from, and/or insertions into and/or substitutions of, residues within the amino acid sequences of the antibody. Any combination of deletion, insertion, and substitution is made to arrive at the final construct, provided that the final construct possesses the desired characteristics (i.e., the ability to bind or physically interact with a TREM2 protein of the present disclosure). The amino acid changes also may alter post-translational processes of the antibody, such as changing the number or position of glycosylation sites.

A useful method for identification of certain residues or regions of the anti-TREM2 antibody that are preferred locations for mutagenesis is called "alanine scanning mutagenesis" as described by Cunningham and Wells in *Science*, 244:1081-1085 (1989). Here, a residue or group of target residues are identified (e.g., charged residues such as arg, asp, his, lys, and glu) and replaced by a neutral or negatively charged amino acid (most preferably alanine or polyalanine) to affect the interaction of the amino acids with the target antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, alanine scanning or random mutagenesis is conducted at the target codon or region and the expressed antibody variants are screened for the desired activity.

Amino acid sequence insertions include amino-("N") and/or carboxy-("C") terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to a cytotoxic polypeptide. Other insertional variants of the antibody molecule include the fusion to the N- or C-terminus of the antibody to an enzyme or a polypeptide which increases the serum half-life of the antibody.

Another type of variant is an amino acid substitution variant. These variants have at least one amino acid residue in the antibody molecule replaced by a different residue. The sites of greatest interest for substitutional mutagenesis include the hypervariable regions, but FR alterations are also contemplated. Conservative substitutions are shown in the Table C below under the heading of "preferred substitutions". If such substitutions result in a change in biological activity, then more substantial changes, denominated "exemplary substitutions" in Table B, or as further described below in reference to amino acid classes, may be introduced and the products screened.

TABLE B

Amino Acid Substitutions

| Original Residue | Exemplary Substitutions | Preferred Substitutions |
| --- | --- | --- |
| Ala (A) | val; leu; ile | val |
| Arg (R) | lys; gln; asn | lys |
| Asn (N) | gln; his; asp, lys; arg | gln |
| Asp (D) | glu; asn | glu |
| Cys (C) | ser; ala | ser |
| Gln (Q) | asn; glu | asn |
| Glu (E) | asp; gln | asp |
| Gly (G) | ala | ala |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | tyr |
| Pro (P) | ala | ala |
| Ser (S) | thr | thr |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common sidechain properties:

(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic: trp, tyr, phe.

Non-conservative substitutions entail exchanging a member of one of these classes for another class.

Any cysteine residue not involved in maintaining the proper conformation of the antibody also may be substituted, generally with serine, to improve the oxidative stability of the molecule and prevent aberrant crosslinking. Conversely, cysteine bond(s) may be added to the antibody to improve its stability (particularly where the antibody is an antibody fragment, such as an Fv fragment).

A particularly preferred type of substitutional variant involves substituting one or more hypervariable region residues of a parent antibody (e.g. a humanized or human anti-TREM2 antibody). Generally, the resulting variant(s) selected for further development will have improved biological properties relative to the parent antibody from which they are generated. A convenient way for generating such substitutional variants involves affinity maturation using phage display. Briefly, several hypervariable region sites (e.g., 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g., binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and the antigen (e.g., a TREM2 protein of the present disclosure). Such contact residues and neighboring residues are candidates for substitution according to the techniques elaborated herein. Once such variants are generated, the panel of variants is subjected to screening as described herein and antibodies with superior properties in one or more relevant assays may be selected for further development. Affinity maturation may also be performed by employing a yeast presentation technology such as that disclosed in, for example, WO2009/036379A2; WO2010105256; WO2012009568; and Xu et al., Protein Eng. Des. Sel., 26(10): 663-70 (2013).

Another type of amino acid variant of the antibody alters the original glycosylation pattern of the antibody. By altering is meant deleting one or more carbohydrate moieties found in the antibody, and/or adding one or more glycosylation sites that are not present in the antibody.

Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Nucleic acid molecules encoding amino acid sequence variants of the anti-IgE antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibodies (e.g., anti-TREM2 antibodies of the present disclosure) or antibody fragments.

(9) Other Antibody Modifications

Anti-TREM2 antibodies of the present disclosure, or antibody fragments thereof, can be further modified to contain additional non-proteinaceous moieties that are known in the art and readily available, or to contain different types of drug conjugates that are known in the art and readily available. Preferably, the moieties suitable for derivatization of the antibody are water-soluble polymers. Non-limiting examples of water-soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, polypropylene glycol homopolymers, polypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer is attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc. Such techniques and other suitable formulations are disclosed in *Remington: The Science and Practice of Pharmacy*, 20th Ed., Alfonso Gennaro, Ed., Philadelphia College of Pharmacy and Science (2000).

Drug conjugation involves coupling of a biological active cytotoxic (anticancer) payload or drug to an antibody that specifically targets a certain tumor marker (e.g. a protein that, ideally, is only to be found in or on tumor cells). Antibodies track these proteins down in the body and attach themselves to the surface of cancer cells. The biochemical reaction between the antibody and the target protein (antigen) triggers a signal in the tumor cell, which then absorbs or internalizes the antibody together with the cytotoxin. After the ADC is internalized, the cytotoxic drug is released and kills the cancer. Due to this targeting, ideally the drug has lower side effects and gives a wider therapeutic window than other chemotherapeutic agents. Technics to conjugate antibodies are disclosed are known in the art (see, e.g., Jane de Lartigue, OncLive Jul. 5, 2012; ADC Review on antibody-drug conjugates; and Ducry et al., (2010). *Bioconjugate Chemistry* 21 (1): 5-13).

Binding Assays and Other Assays

Anti-TREM2 antibodies of the present disclosure may be tested for antigen binding activity, e.g., by known methods such as ELISA, Western blot, etc.

In some embodiments, competition assays may be used to identify an antibody that competes with any of the antibodies listed in Tables 2A-2C, 3A-3C, 4A-4D, 5A-5D, 6, and 7, or selected from AL2p-h50, AL2p-2, AL2p-3, AL2p-4, AL2p-5, AL2p-6, AL2p-7, AL2p-8, AL2p-9, AL2p-10, AL2p-11, AL2p-12, AL2p-13, AL2p-14, AL2p-15, AL2p-16, AL2p-17, AL2p-18, AL2p-19, AL2p-20, AL2p-21, AL2p-22, AL2p-23, AL2p-24, AL2p-25, AL2p-26, AL2p-27, AL2p-28, AL2p-29, AL2p-30, AL2p-31, AL2p-32, AL2p-33, AL2p-h77, AL2p-35, AL2p-36, AL2p-37, AL2p-38, AL2p-39, AL2p-40, AL2p-41, AL2p-42, AL2p-43, AL2p-44, AL2p-45, AL2p-46, AL2p-47, AL2p-48, AL2p-49, AL2p-50, AL2p-51, AL2p-52, AL2p-53, AL2p-54, AL2p-55, AL2p-56, AL2p-57, AL2p-58, AL2p-59, AL2p-60, AL2p-61, AL2p-62, AL2p-h19, AL2p-h21, AL2p-h22, AL2p-h23, AL2p-h24, AL2p-h25, AL2p-h26, AL2p-h27, AL2p-h28, AL2p-h29, AL2p-h30, AL2p-h31, AL2p-h32, AL2p-h33, AL2p-h34, AL2p-h35, AL2p-h36, AL2p-h42, AL2p-h43, AL2p-h44, AL2p-h47, AL2p-h59, AL2p-h76, and AL2p-h90 for binding to TREM2. In certain embodiments, such a competing antibody binds to the same epitope (e.g., a linear or a conformational epitope) that is bound by any of the antibodies listed in Tables 2A-2C, 3A-3C, 4A-4D, 5A-5D, 6, and 7, or selected from AL2p-h50, AL2p-2, AL2p-3, AL2p-4, AL2p-5, AL2p-6, AL2p-7, AL2p-8, AL2p-9, AL2p-10, AL2p-11, AL2p-12, AL2p-13, AL2p-14, AL2p-15, AL2p-16, AL2p-17, AL2p-18, AL2p-19, AL2p-20, AL2p-21, AL2p-22, AL2p-23, AL2p-24, AL2p-25, AL2p-26, AL2p-27, AL2p-28, AL2p-29, AL2p-30, AL2p-31, AL2p-32, AL2p-33, AL2p-h77, AL2p-35, AL2p-36, AL2p-37, AL2p-38, AL2p-39, AL2p-40, AL2p-41, AL2p-42, AL2p-43, AL2p-44, AL2p-45, AL2p-46, AL2p-47, AL2p-48, AL2p-49, AL2p-50, AL2p-51, AL2p-52, AL2p-53, AL2p-54, AL2p-55, AL2p-56, AL2p-57, AL2p-58, AL2p-59, AL2p-60, AL2p-61, AL2p-62, AL2p-h19, AL2p-h21, AL2p-h22, AL2p-h23, AL2p-h24, AL2p-h25, AL2p-h26, AL2p-h27, AL2p-h28, AL2p-h29, AL2p-h30, AL2p-h31, AL2p-h32, AL2p-h33, AL2p-h34, AL2p-h35, AL2p-h36, AL2p-h42, AL2p-h43, AL2p-h44, AL2p-h47, AL2p-h59, AL2p-h76, and AL2p-h90. Detailed exemplary methods for mapping an epitope to which an antibody binds are provided in Morris (1996) "Epitope Mapping Protocols," in *Methods in Molecular Biology* vol. 66 (Humana Press, Totowa, N.J.).

In an exemplary competition assay, immobilized TREM2 or cells expressing TREM2 on cell surface are incubated in a solution comprising a first labeled antibody that binds to TREM2 (e.g., human or non-human primate) and a second unlabeled antibody that is being tested for its ability to compete with the first antibody for binding to TREM2. The second antibody may be present in a hybridoma supernatant. As a control, immobilized TREM2 or cells expressing TREM2 is incubated in a solution comprising the first labeled antibody but not the second unlabeled antibody. After incubation under conditions permissive for binding of the first antibody to TREM2, excess unbound antibody is removed, and the amount of label associated with immobilized TREM2 or cells expressing TREM2 is measured. If the amount of label associated with immobilized TREM2 or cells expressing TREM2 is substantially reduced in the test sample relative to the control sample, then that indicates that the second antibody is competing with the first antibody for binding to TREM2. See Harlow and Lane (1988) *Antibodies: A Laboratory Manual* ch. 14 (Cold Spring Harbor Laboratory, Cold Spring Harbor, N.Y.).

Nucleic Acids, Vectors, and Host Cells

Anti-TREM2 antibodies of the present disclosure may be produced using recombinant methods and compositions, e.g., as described in U.S. Pat. No. 4,816,567. In some embodiments, isolated nucleic acids having a nucleotide sequence encoding any of the anti-TREM2 antibodies of the present disclosure are provided. Such nucleic acids may encode an amino acid sequence containing the VL and/or an amino acid sequence containing the VH of the anti-TREM2 antibody (e.g., the light and/or heavy chains of the antibody). In some embodiments, one or more vectors (e.g., expression vectors) containing such nucleic acids are provided. In some embodiments, a host cell containing such nucleic acid is also provided. In some embodiments, the host cell contains (e.g., has been transduced with): (1) a vector containing a nucleic acid that encodes an amino acid sequence containing the VL of the antibody and an amino acid sequence containing the VH of the antibody, or (2) a first vector containing a nucleic acid that encodes an amino acid sequence containing the VL of the antibody and a second vector containing a nucleic acid that encodes an amino acid sequence containing the VH of the antibody. In some embodiments, the host cell is eukaryotic, e.g., a Chinese Hamster Ovary (CHO) cell or lymphoid cell (e.g., Y0, NS0, Sp20 cell). Host cells of the present disclosure also include, without limitation, isolated cells, in vitro cultured cells, and ex vivo cultured cells.

Methods of making an anti-TREM2 antibody of the present disclosure are provided. In some embodiments, the method includes culturing a host cell of the present disclosure containing a nucleic acid encoding the anti-TREM2 antibody, under conditions suitable for expression of the antibody. In some embodiments, the antibody is subsequently recovered from the host cell (or host cell culture medium).

For recombinant production of an anti-TREM2 antibody of the present disclosure, a nucleic acid encoding the anti-TREM2 antibody is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable vectors containing a nucleic acid sequence encoding any of the anti-TREM2 antibodies of the present disclosure, or fragments thereof polypeptides (including antibodies) described herein include, without limitation, cloning vectors and expression vectors. Suitable cloning vectors can be constructed according to standard techniques, or may be selected from a large number of cloning vectors available in the art. While the cloning vector selected may vary according to the host cell intended to be used, useful cloning vectors generally have the ability to self-replicate, may possess a single target for a particular restriction endonuclease, and/or may carry genes for a marker that can be used in selecting clones containing the vector. Suitable examples include plasmids and bacterial viruses, e.g., pUC18, pUC19, Bluescript (e.g., pBS SK+) and its derivatives, mp18, mp19, pBR322, pMB9, ColE1, pCR1, RP4, phage DNAs, and shuttle vectors such as pSA3 and pAT28. These and many other cloning vectors are available from commercial vendors such as BioRad, Strategene, and Invitrogen.

Expression vectors generally are replicable polynucleotide constructs that contain a nucleic acid of the present disclosure. The expression vector may replicable in the host cells either as episomes or as an integral part of the chromosomal DNA. Suitable expression vectors include but are not limited to plasmids, viral vectors, including adenoviruses, adeno-associated viruses, retroviruses, cosmids, and expression vector(s) disclosed in PCT Publication No. WO 87/04462. Vector components may generally include, but are not limited to, one or more of the following: a signal sequence; an origin of replication; one or more marker genes; suitable transcriptional controlling elements (such as promoters, enhancers and terminator). For expression (i.e., translation), one or more translational controlling elements are also usually required, such as ribosome binding sites, translation initiation sites, and stop codons.

The vectors containing the nucleic acids of interest can be introduced into the host cell by any of a number of appropriate means, including electroporation, transfection employing calcium chloride, rubidium chloride, calcium phosphate, DEAE-dextran, or other substances; microprojectile bombardment; lipofection; and infection (e.g., where the vector is an infectious agent such as vaccinia virus). The choice of introducing vectors or polynucleotides will often depend on features of the host cell. In some embodiments, the vector contains a nucleic acid containing one or more amino acid sequences encoding an anti-TREM2 antibody of the present disclosure.

Suitable host cells for cloning or expression of antibody-encoding vectors include prokaryotic or eukaryotic cells. For example, anti-TREM2 antibodies of the present disclosure may be produced in bacteria, in particular when glycosylation and Fc effector function are not needed. For expression of antibody fragments and polypeptides in bacteria (e.g., U.S. Pat. Nos. 5,648,237, 5,789,199, and 5,840,523; and Charlton, *Methods in Molecular Biology*, Vol. 248 (B. K. C. Lo, ed., Humana Press, Totowa, N.J., 2003), pp. 245-254, describing expression of antibody fragments in *E. coli*). After expression, the antibody may be isolated from the bacterial cell paste in a soluble fraction and can be further purified.

In addition to prokaryotes, eukaryotic microorganisms, such as filamentous fungi or yeast, are also suitable cloning or expression hosts for antibody-encoding vectors, including fungi and yeast strains whose glycosylation pathways have been "humanized," resulting in the production of an antibody with a partially or fully human glycosylation pattern (e.g., Gerngross, *Nat. Biotech*. 22:1409-1414 (2004); and Li et al., *Nat. Biotech*. 24:210-215 (2006)).

Suitable host cells for the expression of glycosylated antibody can also be derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells. Plant cell cultures can also be utilized as hosts (e.g., U.S. Pat. Nos. 5,959,177, 6,040,498, 6,420,548, 7,125,978, and 6,417,429, describing PLANTIBODIES™ technology for producing antibodies in transgenic plants.).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., *J. Gen Virol*. 36:59 (1977)); baby hamster kidney cells (BHK); mouse sertoli cells (TM4 cells as described, e.g., in Mather, *Biol. Reprod*. 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., *Annals N.Y. Acad Sci*. 383:44-68 (1982); MRC 5 cells; and FS4 cells. Other useful mammalian host cell lines include Chinese hamster ovary (CHO) cells, including DHFR-CHO cells (Urlaub et al., *Proc. Natl. Acad. Sci. USA* 77:4216 (1980)); and myeloma cell lines such as Y0, NS0 and Sp2/0. For a review of certain mammalian host cell lines suitable for antibody production, see, e.g., Yazaki and Wu, *Methods in Molecular Biology*, Vol. 248 (B. K. C. Lo, ed., Humana Press, Totowa, N.J.), pp. 255-268 (2003).

Pharmaceutical Compositions

Anti-TREM2 antibodies of the present disclosure can be incorporated into a variety of formulations for therapeutic administration by combining the antibodies with appropriate pharmaceutically acceptable carriers or diluents, and may be formulated into preparations in solid, semi-solid, liquid or gaseous forms. Examples of such formulations include, without limitation, tablets, capsules, powders, granules, ointments, solutions, suppositories, injections, inhalants, gels, microspheres, and aerosols. Pharmaceutical compositions can include, depending on the formulation desired, pharmaceutically-acceptable, non-toxic carriers of diluents, which are vehicles commonly used to formulate pharmaceutical compositions for animal or human administration. The diluent is selected so as not to affect the biological activity of the combination. Examples of such diluents include, without limitation, distilled water, buffered water, physiological saline, PBS, Ringer's solution, dextrose solution, and Hank's solution. A pharmaceutical composition or formulation of the present disclosure can further include other carriers, adjuvants, or non-toxic, nontherapeutic, non-immunogenic stabilizers, excipients and the like. The compositions can also include additional substances to approximate physiological conditions, such as pH adjusting and buffering agents, toxicity adjusting agents, wetting agents and detergents.

A pharmaceutical composition of the present disclosure can also include any of a variety of stabilizing agents, such as an antioxidant for example. When the pharmaceutical composition includes a polypeptide, the polypeptide can be complexed with various well-known compounds that enhance the in vivo stability of the polypeptide, or otherwise enhance its pharmacological properties (e.g., increase the half-life of the polypeptide, reduce its toxicity, and enhance solubility or uptake). Examples of such modifications or complexing agents include, without limitation, sulfate, gluconate, citrate and phosphate. The polypeptides of a composition can also be complexed with molecules that enhance their in vivo attributes. Such molecules include, without limitation, carbohydrates, polyamines, amino acids, other peptides, ions (e.g., sodium, potassium, calcium, magnesium, manganese), and lipids.

Further examples of formulations that are suitable for various types of administration can be found in Remington's *Pharmaceutical Sciences*, Mace Publishing Company, Philadelphia, Pa., 17th ed. (1985). For a brief review of methods for drug delivery, see, Langer, Science 249:1527-1533 (1990).

For oral administration, the active ingredient can be administered in solid dosage forms, such as capsules, tablets, and powders, or in liquid dosage forms, such as elixirs, syrups, and suspensions. The active component(s) can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate. Examples of additional inactive ingredients that may be added to provide desirable color, taste, stability, buffering capacity, dispersion or other known desirable features are red iron oxide, silica gel, sodium lauryl sulfate, titanium dioxide, and edible white ink. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

Formulations suitable for parenteral administration include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

The components used to formulate the pharmaceutical compositions are preferably of high purity and are substantially free of potentially harmful contaminants (e.g., at least National Food (NF) grade, generally at least analytical grade, and more typically at least pharmaceutical grade). Moreover, compositions intended for in vivo use are usually sterile. To the extent that a given compound must be synthesized prior to use, the resulting product is typically substantially free of any potentially toxic agents, particularly any endotoxins, which may be present during the synthesis or purification process. Compositions for parental administration are also sterile, substantially isotonic and made under GMP conditions.

Formulations may be optimized for retention and stabilization in the brain or central nervous system. When the agent is administered into the cranial compartment, it is desirable for the agent to be retained in the compartment, and not to diffuse or otherwise cross the blood brain barrier. Stabilization techniques include cross-linking, multimerizing, or linking to groups such as polyethylene glycol, polyacrylamide, neutral protein carriers, etc. in order to achieve an increase in molecular weight.

Other strategies for increasing retention include the entrapment of the antibody, such as an anti-TREM2 antibody of the present disclosure, in a biodegradable or bioerodible implant. The rate of release of the therapeutically active agent is controlled by the rate of transport through the polymeric matrix, and the biodegradation of the implant. The transport of drug through the polymer barrier will also be affected by compound solubility, polymer hydrophilicity, extent of polymer cross-linking, expansion of the polymer upon water absorption so as to make the polymer barrier more permeable to the drug, geometry of the implant, and the like. The implants are of dimensions commensurate with the size and shape of the region selected as the site of implantation. Implants may be particles, sheets, patches, plaques, fibers, microcapsules and the like and may be of any size or shape compatible with the selected site of insertion.

The implants may be monolithic, i.e. having the active agent homogenously distributed through the polymeric matrix, or encapsulated, where a reservoir of active agent is encapsulated by the polymeric matrix. The selection of the polymeric composition to be employed will vary with the site of administration, the desired period of treatment, patient tolerance, the nature of the disease to be treated and the like. Characteristics of the polymers will include biodegradability at the site of implantation, compatibility with the agent of interest, ease of encapsulation, a half-life in the physiological environment.

Biodegradable polymeric compositions which may be employed may be organic esters or ethers, which when degraded result in physiologically acceptable degradation products, including the monomers. Anhydrides, amides, orthoesters or the like, by themselves or in combination with other monomers, may find use. The polymers will be condensation polymers. The polymers may be cross-linked or non-cross-linked. Of particular interest are polymers of hydroxyaliphatic carboxylic acids, either homo- or copolymers, and polysaccharides. Included among the polyesters of interest are polymers of D-lactic acid, L-lactic acid, racemic lactic acid, glycolic acid, polycaprolactone, and combinations thereof. By employing the L-lactate or D-lactate, a slowly biodegrading polymer is achieved, while degradation is substantially enhanced with the racemate. Copolymers of glycolic and lactic acid are of particular interest, where the rate of biodegradation is controlled by the ratio of glycolic to lactic acid. The most rapidly degraded copolymer has roughly equal amounts of glycolic and lactic acid, where either homopolymer is more resistant to degradation. The ratio of glycolic acid to lactic acid will also affect the brittleness of in the implant, where a more flexible implant is desirable for larger geometries. Among the polysaccharides of interest are calcium alginate, and functionalized celluloses, particularly carboxymethylcellulose esters characterized by being water insoluble, a molecular weight of about 5 kD to 500 kD, etc. Biodegradable hydrogels may also be employed in the implants of the subject invention. Hydrogels are typically a copolymer material, characterized by the ability to imbibe a liquid. Exemplary biodegradable hydrogels which may be employed are described in Heller in: Hydrogels in Medicine and Pharmacy, N. A. Peppes ed., Vol. III, CRC Press, Boca Raton, Fla., 1987, pp 137-149.

Pharmaceutical Dosages

Pharmaceutical compositions of the present disclosure containing an anti-TREM2 antibody of the present disclosure may be administered to an individual in need of treatment with the anti-TREM2 antibody, preferably a human, in accord with known methods, such as intravenous administration as a bolus or by continuous infusion over a period of time, by intramuscular, intraperitoneal, intracerobrospinal, intracranial, intraspinal, subcutaneous, intra-articular, intrasynovial, intrathecal, oral, topical, or inhalation routes.

Dosages and desired drug concentration of pharmaceutical compositions of the present disclosure may vary depending on the particular use envisioned. The determination of the appropriate dosage or route of administration is well within the skill of an ordinary artisan. Animal experiments provide reliable guidance for the determination of effective doses for human therapy. Interspecies scaling of effective doses can be performed following the principles described in Mordenti, J. and Chappell, W. "The Use of Interspecies Scaling in Toxicokinetics," In *Toxicokinetics and New Drug Development*, Yacobi et al., Eds, Pergamon Press, New York 1989, pp. 42-46.

For in vivo administration of any of the anti-TREM2 antibodies of the present disclosure, normal dosage amounts may vary from about 10 ng/kg up to about 100 mg/kg of an individual's body weight or more per day, preferably about 1 mg/kg/day to 10 mg/kg/day, depending upon the route of administration. For repeated administrations over several days or longer, depending on the severity of the disease, disorder, or condition to be treated, the treatment is sustained until a desired suppression of symptoms is achieved.

An exemplary dosing regimen may include administering an initial dose of an anti-TREM2 antibody, of about 2 mg/kg, followed by a weekly maintenance dose of about 1 mg/kg every other week. Other dosage regimens may be useful, depending on the pattern of pharmacokinetic decay that the physician wishes to achieve. For example, dosing an individual from one to twenty-one times a week is contemplated herein. In certain embodiments, dosing ranging from about 3 µg/kg to about 2 mg/kg (such as about 3 µg/kg, about 10 µg/kg, about 30 µg/kg, about 100 µg/kg, about 300 µg/kg, about 1 mg/kg, and about 2/mg/kg) may be used. In certain embodiments, dosing frequency is three times per day, twice per day, once per day, once every other day, once weekly, once every two weeks, once every four weeks, once every five weeks, once every six weeks, once every seven weeks, once every eight weeks, once every nine weeks, once every ten weeks, or once monthly, once every two months, once every three months, or longer. Progress of the therapy is easily monitored by conventional techniques and assays. The dosing regimen, including the anti-TREM2 antibody administered, can vary over time independently of the dose used.

Dosages for a particular anti-TREM2 antibody may be determined empirically in individuals who have been given one or more administrations of the anti-TREM2 antibody. Individuals are given incremental doses of an anti-TREM2 antibody. To assess efficacy of an anti-TREM2 antibody, a clinical symptom of any of the diseases, disorders, or conditions of the present disclosure (e.g., dementia, frontotemporal dementia, Alzheimer's disease, Nasu-Hakola disease, and multiple sclerosis) can be monitored.

Administration of an anti-TREM2 antibody of the present disclosure can be continuous or intermittent, depending, for example, on the recipient's physiological condition, whether the purpose of the administration is therapeutic or prophylactic, and other factors known to skilled practitioners. The administration of an anti-TREM2 antibody may be essentially continuous over a preselected period of time or may be in a series of spaced doses.

Guidance regarding particular dosages and methods of delivery is provided in the literature; see, for example, U.S. Pat. Nos. 4,657,760; 5,206,344; or 5,225,212. It is within the scope of the present disclosure that different formulations will be effective for different treatments and different disorders, and that administration intended to treat a specific organ or tissue may necessitate delivery in a manner different from that to another organ or tissue. Moreover, dosages may be administered by one or more separate administrations, or by continuous infusion. For repeated administrations over several days or longer, depending on the condition, the treatment is sustained until a desired suppression of disease symptoms occurs. However, other dosage regimens may be useful. The progress of this therapy is easily monitored by conventional techniques and assays.

Therapeutic Uses

As disclosed herein, anti-TREM2 antibodies of the present disclosure may be used for preventing, reducing risk, or treating dementia, frontotemporal dementia, Alzheimer's disease, vascular dementia, mixed dementia, Creutzfeldt-Jakob disease, normal pressure hydrocephalus, amyotrophic lateral sclerosis, Huntington's disease, tauopathy disease, Nasu-Hakola disease, stroke, acute trauma, chronic trauma, cognitive deficit, memory loss, lupus, acute and chronic colitis, rheumatoid arthritis, wound healing, Crohn's disease, inflammatory bowel disease, ulcerative colitis, obesity, malaria, essential tremor, central nervous system lupus, Behcet's disease, Parkinson's disease, dementia with Lewy bodies, multiple system atrophy, Shy-Drager syndrome, progressive supranuclear palsy, cortical basal ganglionic degeneration, acute disseminated encephalomyelitis, granulomartous disorders, sarcoidosis, diseases of aging, seizures, spinal cord injury, traumatic brain injury, age related macular degeneration, glaucoma, retinitis pigmentosa, retinal degeneration, respiratory tract infection, sepsis, eye infection, systemic infection, lupus, arthritis, multiple sclerosis, low bone density, osteoporosis, osteogenesis, osteopetrotic disease, Paget's disease of bone, cancer, bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, acute lymphoblastic leukemia (ALL), acute myeloid leukemia (AML), chronic lymphocytic leukemia (CLL), chronic myeloid leukemia (CML), multiple myeloma, polycythemia vera, essential thrombocytosis, primary or idiopathic myelofibrosis, primary or idiopathic myelosclerosis, myeloid-derived tumors, tumors that express TREM2, thyroid cancer, infections, CNS herpes, parasitic infections, Trypanosome infection, Cruzi infection, *Pseudomonas aeruginosa* infection, *Leishmania donovani* infection, group B *Streptococcus* infection, *Campylobacter jejuni* infection, *Neisseria meningiditis* infection, type I HIV, and/or *Haemophilus influenza*. In some embodiments, the anti-TREM2 antibodies are agonist antibodies.

In some embodiments, the present disclosure provides methods of preventing, reducing risk, or treating an individual having dementia, frontotemporal dementia, Alzheimer's disease, vascular dementia, mixed dementia, Creutzfeldt-Jakob disease, normal pressure hydrocephalus, amyotrophic lateral sclerosis, Huntington's disease, tauopathy disease, Nasu-Hakola disease, stroke, acute trauma, chronic trauma, cognitive deficit, memory loss, lupus, acute and chronic colitis, rheumatoid arthritis, wound healing, Crohn's disease, inflammatory bowel disease, ulcerative colitis, obesity, malaria, essential tremor, central nervous system lupus, Behcet's disease, Parkinson's disease, dementia with Lewy bodies, multiple system atrophy, Shy-Drager syndrome, progressive supranuclear palsy, cortical basal ganglionic degeneration, acute disseminated encephalomyelitis, granulomartous disorders, sarcoidosis, diseases of aging, seizures, spinal cord injury, traumatic brain injury, age related macular degeneration, glaucoma, retinitis pigmentosa, retinal degeneration, respiratory tract infection, sepsis, eye infection, systemic infection, lupus, arthritis, multiple sclerosis, low bone density, osteoporosis, osteogenesis, osteopetrotic disease, Paget's disease of bone, cancer, bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, acute lymphoblastic leukemia (ALL), acute myeloid leukemia (AML), chronic lymphocytic leukemia (CLL), chronic myeloid leukemia (CML), multiple myeloma, polycythemia vera, essential thrombocytosis, primary or idiopathic myelofibrosis, primary or idiopathic myelosclerosis, myeloid-derived tumors, tumors that express TREM2, thyroid cancer, infections, CNS herpes, parasitic infections, Trypanosome infection, Cruzi infection, *Pseudomonas aeruginosa* infection, *Leishmania donovani* infection, group B *Streptococcus* infection, *Campylobacter jejuni* infection, *Neisseria meningiditis* infection, type I HIV, and *Haemophilus influenza*, by administering to the individual a therapeutically effective amount of an anti-TREM2 antibody of the present disclosure. In some embodiments, the method further includes administering to the individual at least one antibody that specifically binds to an inhibitory checkpoint molecule, and/or another standard or investigational anti-cancer therapy. In some embodiments, the antibody that specifically binds to an inhibitory checkpoint molecule is administered in combination with the isolated antibody. In some embodiments, the at least one antibody that specifically binds to an inhibitory checkpoint molecule is selected from an anti-PD-L1 antibody, an anti-CTLA-4 antibody, an anti-PD-L2 antibody, an anti-PD-1 antibody, an anti-B7-H3 antibody, an anti-B7-H4 antibody, and anti-HVEM antibody, an anti-B- and T-lymphocyte attenuator (BTLA) antibody, an anti-Killer inhibitory receptor (KIR) antibody, an anti-GAL9 antibody, an anti-TIM3 antibody, an anti-A2AR antibody, an anti-LAG-3 antibody, an anti-phosphatidylserine antibody, an anti-CD27 antibody, and any combination thereof. In some embodiments, the standard or investigational anti-cancer therapy is one or more therapies selected from radiotherapy, cytotoxic chemotherapy, targeted therapy, hormonal therapy, imatinib (Gleevec®), trastuzumab (Herceptin®), bevacizumab (Avastin®), Ofatumumab (Arzerra®), Rituximab (Rituxan®, MabThera®, Zytux®), cryotherapy, ablation, radiofrequency ablation, adoptive cell transfer (ACT), chimeric antigen receptor T cell transfer (CAR-T), vaccine therapy, and cytokine therapy. In some embodiments, the method further includes administering to the individual at least one antibody that specifically binds to an inhibitory cytokine. In some embodiments, the at least one antibody that specifically binds to an inhibitory cytokine is administered in combination with the isolated antibody. In some embodiments, the at least one antibody that specifically binds to an inhibitory cytokine is selected from an anti-CCL2 antibody, an anti-CSF-1 antibody, an anti-IL-2 antibody, and any combination thereof. In some embodiments, the method further includes administering to the individual at least one agonistic antibody that specifically binds to a stimulatory checkpoint protein. In some embodiments, the at least one agonistic antibody that specifically binds to a stimulatory checkpoint protein is administered in combination with the isolated antibody. In some embodiments, the at least one agonistic antibody that specifically binds to a stimulatory checkpoint protein is selected from an agonist anti-CD40 antibody, an agonist anti-OX40 antibody, an agonist anti-ICOS antibody, an agonist anti-CD28 antibody, an agonist anti-CD137/4-1BB antibody, an agonist anti-CD27 antibody, an agonist anti-glucocorticoid-induced TNFR-related protein GITR antibody, and any combination thereof. In some embodiments, the method further includes administering to the individual at least one stimulatory cytokine. In some embodiments, the at least one stimulatory cytokine is administered in combination with the isolated antibody. In some embodiments, the at least one stimulatory cytokine is selected from TNF-α, IL-10, IL-6, IL-8, CRP, TGF-beta members of the chemokine protein families, IL20 family member, IL-33, LIF, OSM, CNTF, TGF-beta, IL-11, IL-12, IL-17, IL-8, IL-23, IFN-α, IFN-β, IL-2, IL-18, GM-CSF, G-CSF, and any combination thereof.

In some embodiments, the present disclosure provides methods of preventing, reducing risk, or treating an individual having Alzheimer's disease by administering to the individual a therapeutically effective amount of an anti-TREM2 antibody of the present disclosure. In some embodiments, the anti-TREM2 antibody increases expression of one or more inflammatory mediators, such as IL-1β, TNF-α, YM-1, CD86, CCL2, CCL3, CCL5, CCR2, CXCL10, Gata3, Rorc, and any combination thereof. In some embodiments, the anti-TREM2 antibody decreases expression of one or more inflammatory mediators, such as FLT1, OPN, CSF-1, CD11c, AXL, and any combination thereof. In some embodiments, the anti-TREM2 antibody decreases levels of Abeta peptide in the individual (e.g., in the brain of the individual). In some embodiments, the anti-TREM2 antibody increases the number of CD11b$^+$ microglial cells in the brain of the individual. In some embodiments, the anti-TREM2 antibody increases memory in the individual. In some embodiments, the anti-TREM2 antibody reduces cognitive deficit in the individual. In some embodiments, the anti-TREM2 antibody increases motor coordination in the individual.

In some embodiments, the present disclosure provides methods of increasing memory, reducing cognitive deficit, or both in an individual in need thereof, by administering to the individual a therapeutically effective amount of an anti-TREM2 antibody of the present disclosure.

In some embodiments, the present disclosure provides methods of increasing motor coordination in an individual in need thereof, by administering to the individual a therapeutically effective amount of an anti-TREM2 antibody of the present disclosure.

In some embodiments, the present disclosure provides methods of reducing Abeta peptide levels in an individual in need thereof, by administering to the individual a therapeutically effective amount of an anti-TREM2 antibody of the present disclosure.

In some embodiments, the present disclosure provides methods of increasing the number of CD11 b microglial cells in an individual in need thereof, by administering to the individual a therapeutically effective amount of an anti-TREM2 antibody of the present disclosure.

In some embodiments, the present disclosure provides methods of increasing levels of one or more of FLT1, OPNCSF1, CD11c, and AXL in an individual in need thereof, by administering to the individual a therapeutically effective amount of an anti-TREM2 antibody of the present disclosure.

In some embodiments, an anti-TREM2 antibody of the present disclosure may increases expression of one or more inflammatory mediators, such as IL-1β, TNF-α, YM-1, CD86, CCL2, CCL3, CCL5, CCR2, CXCL10, Gata3, Rorc, and any combination thereof in one or more cells of an individual by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, at least 115%, at least 120%, at least 125%, at least 130%, at least 135%, at least 140%, at least 145%, at least 150%, at least 160%, at least 170%, at least 180%, at least 190%, or at least 200% for example, as compared to expression of one or more inflammatory mediators, such as IL-1β, TNF-α, YM-1, CD86, CCL2, CCL3, CCL5, CCR2, CXCL10, Gata3, Rorc, and any combination thereof in one or more cells of a corresponding individual that is not treated with the anti-TREM2 antibody. In other embodiments, an anti-TREM2 antibody of the present disclosure increases expression of one or more inflammatory mediators, such as IL-1β, TNF-α, YM-1, CD86, CCL2, CCL3, CCL5, CCR2, CXCL10, Gata3, Rorc, and any combination thereof in one or more cells of an individual by at least 1.5 fold, at least 1.6 fold, at least 1.7 fold, at least 1.8 fold, at least 1.9 fold, at least 2.0 fold, at least 2.1 fold, at least 2.15 fold, at least 2.2 fold, at least 2.25 fold, at least 2.3 fold, at least 2.35 fold, at least 2.4 fold, at least 2.45 fold, at least 2.5 fold, at least 2.55 fold, at least 3.0 fold, at least 3.5 fold, at least 4.0 fold, at least 4.5 fold, at least 5.0 fold, at least 5.5 fold, at least 6.0 fold, at least 6.5 fold, at least 7.0 fold, at least 7.5 fold, at least 8.0 fold, at least 8.5 fold, at least 9.0 fold, at least 9.5 fold, or at least 10 fold, for example, as compared to expression of one or more inflammatory mediators, such as IL-1β, TNF-α, YM-1, CD86, CCL2, CCL3, CCL5, CCR2, CXCL10, Gata3, Rorc, and any combination thereof in one or more cells of a corresponding individual that is not treated with the anti-TREM2 antibody.

In some embodiments, an anti-TREM2 antibody of the present disclosure may decrease expression of one or more inflammatory mediators, such as FLT1, OPN, CSF-1, CD11c, AXL, and any combination thereof in one or more cells of an individual by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, at least 115%, at least 120%, at least 125%, at least 130%, at least 135%, at least 140%, at least 145%, at least 150%, at least 160%, at least 170%, at least 180%, at least 190%, or at least 200% for example, as compared to expression of one or more inflammatory mediators, such as FLT1, OPN, CSF-1, CD11c, AXL, and any combination thereof in one or more cells of a corresponding individual that is not treated with the anti-TREM2 antibody. In other embodiments, an anti-TREM2 antibody of the present disclosure decreases expression of one or more inflammatory mediators, such as FLT1, OPN, CSF-1, CD11c, AXL, and any combination thereof in one or more cells of an individual by at least 1.5 fold, at least 1.6 fold, at least 1.7 fold, at least 1.8 fold, at least 1.9 fold, at least 2.0 fold, at least 2.1 fold, at least 2.15 fold, at least 2.2 fold, at least 2.25 fold, at least 2.3 fold, at least 2.35 fold, at least 2.4 fold, at least 2.45 fold, at least 2.5 fold, at least 2.55 fold, at least 3.0 fold, at least 3.5 fold, at least 4.0 fold, at least 4.5 fold, at least 5.0 fold, at least 5.5 fold, at least 6.0 fold, at least 6.5 fold, at least 7.0 fold, at least 7.5 fold, at least 8.0 fold, at least 8.5 fold, at least 9.0 fold, at least 9.5 fold, or at least 10 fold, for example, as compared to expression of one or more inflammatory mediators, such as FLT1, OPN, CSF-1, CD11c, AXL, and any combination thereof in one or more cells of a corresponding individual that is not treated with the anti-TREM2 antibody.

In some embodiments, an anti-TREM2 antibody of the present disclosure may modulate expression of one or more Stage 2 microglia type associated with neurodegenerative diseases (DAM) markers, such as Trem2, Cst7, Ctsl, Lpl, Cd9, Axl, Csf1, Ccl6, Itgax, Clec7a, Lilrb4, Timp2, and any combination thereof in one or more cells of an individual by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, at least 115%, at least 120%, at least 125%, at least 130%, at least 135%, at least 140%, at least 145%, at least 150%, at least 160%, at least 170%, at least 180%, at least 190%, or at least 200% for example, as compared to expression of one or more DAM markers, such as Trem2, Cst7, Ctsl, Lpl, Cd9, Axl, Csf1, Ccl6, Itgax, Clec7a, Lilrb4, Timp2, and any combination thereof in one or more cells of a corresponding individual that is not treated with the anti-TREM2 antibody. See Keren-Shaul et al. Cell 169:1276-1290 (2017), which is incorporated by reference in its entirety. In other embodiments, an anti-TREM2 antibody of the present disclosure modulate expression of one or more DAM markers, such as Trem2, Cst7, Ctsl, Lpl, Cd9, Axl, Csf1, Ccl6, Itgax, Clec7a, Lilrb4, Timp2, and any combination thereof in one or more cells of an individual by at least 1.5 fold, at least 1.6 fold, at least 1.7 fold, at least 1.8 fold, at least 1.9 fold, at least 2.0 fold, at least 2.1 fold, at least 2.15 fold, at least 2.2 fold, at least 2.25 fold, at least 2.3 fold, at least 2.35 fold, at least 2.4 fold, at least 2.45 fold, at least 2.5 fold, at least 2.55 fold, at least 3.0 fold, at least 3.5 fold, at least 4.0 fold, at least 4.5 fold, at least 5.0 fold, at least 5.5 fold, at least 6.0 fold, at least 6.5 fold, at least 7.0 fold, at least 7.5 fold, at least 8.0 fold, at least 8.5 fold, at least 9.0 fold, at least 9.5 fold, or at least 10 fold, for example, as compared to expression of one or more DAM markers, such as Trem2, Cst7, Ctsl, Lpl, Cd9, Axl, Csf1, Ccl6, Itgax, Clec7a, Lilrb4, Timp2, and any combination thereof in one or more cells of a corresponding individual that is not treated with the anti-TREM2 antibody. In some embodiments, the DAM marker is Cst7. In some embodiments, the DAM marker is Ccl6. In some embodiments, the DAM marker is Itgax. In some embodiments, the modulation is increased expression.

Further provided herein are methods of determining whether an individual is a responder or is a non-responder to an anti-TREM2 antibody treatment which comprises the steps of: (a) measuring the levels of one or more Stage 2 microglia type associated with neurodegenerative diseases (DAM) markers, such as Trem2, Cst7, Ctsl, Lpl, Cd9, Axl, Csf1, Ccl6, Itgax, Clec7a, Lilrb4, Timp2, and any combination thereof in a sample from an individual obtained from said individual before the treatment, (b) measuring the level of one or more Stage 2 microglia type associated with neurodegenerative diseases (DAM) markers, such as Trem2, Cst7, Ctsl, Lpl, Cd9, Axl, Csf1, Ccl6, Itgax, Clec7a, Lilrb4, Timp2, and any combination thereof in a sample from an individual obtained from said at a time point after first treatment, and (c) comparing the levels measured at step ii) with the levels measured at step i) wherein a difference between said levels is indicative that said individual is a responder or non-responder. In some embodiments, the difference between said levels is an increase and is indicative that said individual is a responder. In some embodiments, the difference between said levels is a decrease or no change and is indicative that said individual is a non-responder. In some embodiments, the DAM marker is Cst7. In some embodiments, the DAM marker is Ccl6. In some embodiments, the DAM marker is Itgax.

In some embodiments, an anti-TREM2 antibody of the present disclosure may decrease levels of Abeta peptide in one or more cells of an individual by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, at least 115%, at least 120%, at least 125%, at least 130%, at least 135%, at least 140%, at least 145%, at least 150%, at least 160%, at least 170%, at least 180%, at least 190%, or at least 200% for example, as compared to levels of Abeta peptide in one or more cells of a corresponding individual that is not treated with the anti-TREM2 antibody. In other embodiments, an anti-TREM2 antibody of the present disclosure decreases levels of Abeta peptide in one or more cells of an individual by at least 1.5 fold, at least 1.6 fold, at least 1.7 fold, at least 1.8 fold, at least 1.9 fold, at least 2.0 fold, at least 2.1 fold, at least 2.15 fold, at least 2.2 fold, at least 2.25 fold, at least 2.3 fold, at least 2.35 fold, at least 2.4 fold, at least 2.45 fold, at least 2.5 fold, at least 2.55 fold, at least 3.0 fold, at least 3.5 fold, at least 4.0 fold, at least 4.5 fold, at least 5.0 fold, at least 5.5 fold, at least 6.0 fold, at least 6.5 fold, at least 7.0 fold, at least 7.5 fold, at least 8.0 fold, at least 8.5 fold, at least 9.0 fold, at least 9.5 fold, or at least 10 fold, for example, as compared to levels of Abeta peptide in one or more cells of a corresponding individual that is not treated with the anti-TREM2 antibody.

In some embodiments, an anti-TREM2 antibody of the present disclosure may increase memory of an individual by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, at least 115%, at least 120%, at least 125%, at least 130%, at least 135%, at least 140%, at least 145%, at least 150%, at least 160%, at least 170%, at least 180%, at least 190%, or at least 200% for example, as compared to the memory of a corresponding individual that is not treated with the anti-TREM2 antibody. In other embodiments, an anti-TREM2 antibody of the present disclosure increases memory of an individual by at least 1.5 fold, at least 1.6 fold, at least 1.7 fold, at least 1.8 fold, at least 1.9 fold, at least 2.0 fold, at least 2.1 fold, at least 2.15 fold, at least 2.2 fold, at least 2.25 fold, at least 2.3 fold, at least 2.35 fold, at least 2.4 fold, at least 2.45 fold, at least 2.5 fold, at least 2.55 fold, at least 3.0 fold, at least 3.5 fold, at least 4.0 fold, at least 4.5 fold, at least 5.0 fold, at least 5.5 fold, at least 6.0 fold, at least 6.5 fold, at least 7.0 fold, at least 7.5 fold, at least 8.0 fold, at least 8.5 fold, at least 9.0 fold, at least 9.5 fold, or at least 10 fold, for example, as compared to the memory of a corresponding individual that is not treated with the anti-TREM2 antibody.

In some embodiments, an anti-TREM2 antibody of the present disclosure may reduce cognitive deficit in an individual by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, at least 115%, at least 120%, at least 125%, at least 130%, at least 135%, at least 140%, at least 145%, at least 150%, at least 160%, at least 170%, at least 180%, at least 190%, or at least 200% for example, as compared to cognitive deficit in a corresponding individual that is not treated with the anti-TREM2 antibody. In other embodiments, an anti-TREM2 antibody of the present disclosure reduces cognitive deficit an individual by at least 1.5 fold, at least 1.6 fold, at least 1.7 fold, at least 1.8 fold, at least 1.9 fold, at least 2.0 fold, at least 2.1 fold, at least 2.15 fold, at least 2.2 fold, at least 2.25 fold, at least 2.3 fold, at least 2.35 fold, at least 2.4 fold, at least 2.45 fold, at least 2.5 fold, at least 2.55 fold, at least 3.0 fold, at least 3.5 fold, at least 4.0 fold, at least 4.5 fold, at least 5.0 fold, at least 5.5 fold, at least 6.0 fold, at least 6.5 fold, at least 7.0 fold, at least 7.5 fold, at least 8.0 fold, at least 8.5 fold, at least 9.0 fold, at least 9.5 fold, or at least 10 fold, for example, as compared to cognitive deficit in a corresponding individual that is not treated with the anti-TREM2 antibody.

In some embodiments, an anti-TREM2 antibody of the present disclosure may increase motor coordination in an individual by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, at least 115%, at least 120%, at least 125%, at least 130%, at least 135%, at least 140%, at least 145%, at least 150%, at least 160%, at least 170%, at least 180%, at least 190%, or at least 200% for example, as compared to motor coordination in a corresponding individual that is not treated with the anti-TREM2 antibody. In other embodiments, an anti-TREM2 antibody of the present disclosure increases motor coordination an individual by at least 1.5 fold, at least 1.6 fold, at least 1.7 fold, at least 1.8 fold, at least 1.9 fold, at least 2.0 fold, at least 2.1 fold, at least 2.15 fold, at least 2.2 fold, at least 2.25 fold, at least 2.3 fold, at least 2.35 fold, at least 2.4 fold, at least 2.45 fold, at least 2.5 fold, at least 2.55 fold, at least 3.0 fold, at least 3.5 fold, at least 4.0 fold, at least 4.5 fold, at least 5.0 fold, at least 5.5 fold, at least 6.0 fold, at least 6.5 fold, at least 7.0 fold, at least 7.5 fold, at least 8.0 fold, at least 8.5 fold, at least 9.0 fold, at least 9.5 fold, or at least 10 fold, for example, as compared to motor coordination in a corresponding individual that is not treated with the anti-TREM2 antibody.

Other aspects of the present disclosure relate to methods of enhancing one or more TREM2 activities induced by binding of one or more TREM2 ligands to a TREM2 protein in an individual in need thereof, by administering to the individual a therapeutically effective amount of an anti-TREM2 antibody of the present disclosure. Other aspects of the present disclosure relate to methods of inducing one or more TREM2 activities in an individual in need thereof, by administering to the individual a therapeutically effective amount of an anti-TREM2 antibody of the present disclosure. Any suitable method for measuring TREM2 activity, such as the in vitro cell-based assays or in vivo models of the present disclosure may be used. Exemplary TREM2 activities include, without limitation, TREM2 binding to DAP12; TREM2 phosphorylation; DAP12 phosphorylation; activation of one or more tyrosine kinases, optionally where the one or more tyrosine kinases comprise a Syk kinase, ZAP70 kinase, or both; activation of phosphatidylinositol 3-kinase (PI3K); activation of protein kinase B (Akt); recruitment of phospholipase C-gamma (PLC-gamma) to a cellular plasma membrane, activation of PLC-gamma, or both; recruitment of TEC-family kinase dVav to a cellular plasma membrane; activation of nuclear factor-rB (NF-rB); inhibition of MAPK signaling; phosphorylation of linker for activation of T cells (LAT), linker for activation of B cells (LAB), or both; activation of IL-2-induced tyrosine kinase (Itk); transient activation followed by inhibition of one or more pro-inflammatory mediators selected from IFN-α4, IFN-b, IL-1β, TNF-α, IL-10, IL-6, IL-8, CRP, TGF-beta members of the chemokine protein families, IL-20 family members, IL-33, LIF, IFN-gamma, OSM, CNTF, TGF-beta, GM-CSF, IL-11, IL-12, IL-17, IL-18, IL-23, CXCL10, VEGF, CCL4, and MCP-1, optionally where the transient activation followed by inhibition occur in one or more cells selected from macrophages, M1 macrophages, activated M1 macrophages, M2 macrophages, dendritic cells, monocytes, osteoclasts, Langerhans cells of skin, Kupffer cells, and microglial cells; phosphorylation of extracellular signal-regulated kinase (ERK); increased expression of C-C chemokine receptor 7 (CCR7) in one or more cells selected from macrophages, M1 macrophages, activated M1 macrophages, M2 macrophages, dendritic cells, monocytes, osteoclasts, Langerhans cells of skin, Kupffer cells, microglia, M1 microglia, activated M1 microglia, and M2 microglia, and any combination thereof; induction of microglial cell chemotaxis toward CCL19 and CCL21 expressing cells; normalization of disrupted TREM2/DAP12-dependent gene expression; recruitment of Syk, ZAP70, or both to a DAP12/TREM2 complex; increasing activity of one or more TREM2-dependent genes, optionally where the one or more TREM2-dependent genes comprise nuclear factor of activated T-cells (NFAT) transcription factors; increased maturation of dendritic cells, monocytes, microglia, M1 microglia, activated M1 microglia, and M2 microglia, macrophages, M1 macrophages, activated M1 macrophages, M2 macrophages, or any combination thereof; increased ability of dendritic cells, monocytes, microglia, M1 microglia, activated M1 microglia, and M2 microglia, macrophages, M1 macrophages, activated M1 macrophages, M2 macrophages, or any combination thereof to induce T-cell proliferation; enhanced ability, normalized ability, or both of bone marrow-derived dendritic cells to induce antigen-specific T-cell proliferation; induction of osteoclast production, increased rate of osteoclastogenesis, or both; increased survival of dendritic cells, macrophages, M1 macrophages, activated M1 macrophages, M2 macrophages, monocytes, osteoclasts, Langerhans cells of skin, Kupffer cells, microglia, M1 microglia, activated M1 microglia, and M2 microglia, or any combination thereof; increasing the function of dendritic cells, macrophages, M1 macrophages, activated M1 macrophages, M2 macrophages, microglia, M1 microglia, activated M1 microglia, and M2 microglia, or any combination thereof; modulating phagocytosis by dendritic cells, macrophages, M1 macrophages, activated M1 macrophages, M2 macrophages, monocytes, microglia, M1 microglia, activated M1 microglia, and M2 microglia, or any combination thereof; induction of one or more types of clearance selected from apoptotic neuron clearance, nerve tissue debris clearance, non-nerve tissue debris clearance, bacteria or other foreign body clearance, disease-causing agent clearance, tumor cell clearance, or any combination thereof, optionally where the disease-causing agent is selected from amyloid beta or fragments thereof, Tau, IAPP, alpha-synuclein, TDP-43, FUS protein, prion protein, PrPSc, huntingtin, calcitonin, superoxide dismutase, ataxin, Lewy body, atrial natriuretic factor, islet amyloid polypeptide, insulin, apolipoprotein AI, serum amyloid A, medin, prolactin, transthyretin, lysozyme, beta 2 microglobulin, gelsolin, keratoepithelin, cystatin, immunoglobulin light chain AL, S-IBM protein, and Repeat-associated non-ATG (RAN) translation products including DiPeptide Repeats, (DPRs peptides) composed of glycine-alanine (GA), glycine-proline (GP), glycine-arginine (GR), proline-alanine (PA), or proline-arginine (PR), antisense GGCCCC (G2C4) repeat-expansion RNA; induction of phagocytosis of one or more of apoptotic neurons, nerve tissue debris, non-nerve tissue debris, bacteria, other foreign bodies, disease-causing agents, tumor cells, or any combination thereof, optionally where the disease-causing agent is selected from amyloid beta or fragments thereof, Tau, IAPP, alpha-synuclein, TDP-43, FUS protein, prion protein, PrPSc, huntingtin, calcitonin, superoxide dismutase, ataxin, Lewy body, atrial natriuretic factor, islet amyloid polypeptide, insulin, apolipoprotein AI, serum amyloid A, medin, prolactin, transthyretin, lysozyme, beta 2 microglobulin, gelsolin, keratoepithelin, cystatin, immunoglobulin light chain AL, S-IBM protein, and Repeat-associated non-ATG (RAN) translation products including DiPeptide Repeats, (DPRs peptides) composed of glycine-alanine (GA), glycine-proline (GP), glycine-arginine (GR), proline-alanine (PA), or proline-arginine (PR), antisense GGCCCC (G2C4) repeat-expansion RNA; increased expression of one or more stimulatory molecules selected from CD83, CD86 MHC class II, CD40, and any combination thereof, optionally where the CD40 is expressed on dendritic cells, monocytes, macrophages, or any combination thereof, and optionally where the dendritic cells comprise bone marrow-derived dendritic cells; reduced secretion of one or more inflammatory mediators, optionally where the one or more inflammatory mediators are selected from CD86, IFN-a4, IFN-b, IL-1β, TNF-α, IL-10, IL-6, IL-8, CRP, TGF-beta members of the chemokine protein families, IL-20 family members, IL-33, LIF, IFN-gamma, OSM, CNTF, TGF-beta, GM-CSF, IL-11, IL-12, IL-17, IL-18, IL-23, CXCL10, VEGF, CCL4, and MCP-1, and any combination thereof; increased memory; and reduced cognitive deficit.

As disclosed herein, anti-TREM2 antibodies of the present disclosure may be used for decreasing cellular levels of TREM2 on one or more cells, including without limitation, dendritic cells, bone marrow-derived dendritic cells, monocytes, microglia, macrophages, neutrophils, NK cells, osteoclasts, Langerhans cells of skin, and Kupffer cells and/or cell lines. In some embodiments, the present disclosure provides methods of decreasing cellular levels of TREM2 on one or more cells in an individual in need thereof, by administering to the individual a therapeutically effective amount of an anti-TREM2 antibody of the present disclosure. In some embodiments, the one or more cells are selected from dendritic cells, bone marrow-derived dendritic cells, monocytes, microglia, macrophages, neutrophils, NK cells, osteoclasts, Langerhans cells of skin, and Kupffer cells, and any combination thereof. Cellular levels of TREM2 may refer to, without limitation, cell surface levels of TREM2, intracellular levels of TREM2, and total levels of TREM2. In some embodiments, a decrease in cellular levels of TREM2 comprises decrease in cell surface levels of TREM2. As used herein, cell surface levels of TREM2 may be measured by any in vitro cell-based assays or suitable in vivo model described herein or known in the art. In some embodiments, a decrease in cellular levels of TREM2 comprises a decrease in intracellular levels of TREM2. As used herein, intracellular levels of TREM2 may be measured by any in vitro cell-based assays or suitable in vivo model described herein or known in the art. In some embodiments, a decrease in cellular levels of TREM2 comprises a decrease in total levels of TREM2. As used herein, total levels of TREM2 may be measured by any in vitro cell-based assays or suitable in vivo model described herein or known in the art. In some embodiments, the anti-TREM2 antibodies induce TREM2 degradation, TREM2 cleavage, TREM2 internalization, TREM2 shedding, and/or downregulation of TREM2 expression. In some embodiments, cellular levels of TREM2 are measured on primary cells (e.g., dendritic cells, bone marrow-derived dendritic cells, monocytes, microglia, and macrophages) or on cell lines utilizing an in vitro cell assay.

As disclosed herein, anti-TREM2 antibodies of the present disclosure may also be used for increasing memory and/or reducing cognitive deficit. In some embodiments, the present disclosure provides methods of increasing memory and/or reducing cognitive deficit in an individual in need thereof, by administering to the individual a therapeutically effective amount of an anti-TREM2 antibody of the present disclosure.

In certain embodiments, the individual has a heterozygous TREM2 variant allele having an glutamic acid to stop codon substitution in the nucleic acid sequence encoding amino acid residue 14 of the human TREM2 protein (SEQ ID NO: 1). In certain embodiments, the individual has a heterozygous TREM2 variant allele having a glutamine to stop codon substitution in the nucleic acid sequence encoding amino acid residue 33 of the human TREM2 protein (SEQ ID NO: 1). In certain embodiments, the individual has a heterozygous TREM2 variant allele having a tryptophan to stop codon substitution in the nucleic acid sequence encoding amino acid residue 44 of the human TREM2 protein (SEQ ID NO: 1). In certain embodiments, the individual has a heterozygous TREM2 variant allele having an arginine to histidine amino acid substitution at amino acid residue 47 of the human TREM2 protein (SEQ ID NO: 1). In certain embodiments, the individual has a heterozygous TREM2 variant allele having a tryptophan to stop codon substitution in the nucleic acid sequence encoding amino acid residue 78 of the human TREM2 protein (SEQ ID NO: 1). In certain embodiments, the individual has a heterozygous TREM2 variant allele having a valine to glycine amino acid substitution at an amino acid corresponding to amino acid residue 126 of the human TREM2 protein (SEQ ID NO: 1). In certain embodiments, the individual has a heterozygous TREM2 variant allele having an aspartic acid to glycine amino acid substitution at an amino acid corresponding to amino acid residue 134 of the human TREM2 protein (SEQ ID NO: 1). In certain embodiments, the individual has a heterozygous TREM2 variant allele having a lysine to asparagine amino acid substitution at an amino acid corresponding to amino acid residue 186 of the human TREM2 protein (SEQ ID NO: 1).

In some embodiments, the individual has a heterozygous TREM2 variant allele having a guanine nucleotide deletion at a nucleotide corresponding to nucleotide residue G313 of the nucleic acid sequence encoding SEQ ID NO: 1; a guanine nucleotide deletion at a nucleotide corresponding to nucleotide residue G267 of the nucleic acid sequence encoding SEQ ID NO: 1; a threonine to methionine amino acid substitution at an amino acid corresponding to amino acid residue Thr66 of SEQ ID NO: 1; and/or a serine to cysteine amino acid substitution at an amino acid corresponding to amino acid residue Ser 16 of SEQ ID NO: 1.

As disclosed herein, anti-TREM2 antibodies of the present disclosure may also be used for inducing and/or promoting innate immune cell survival. In some embodiments, the present disclosure provides methods of inducing or promoting innate immune cell survival in an individual in need thereof, by administering to the individual a therapeutically effective amount of an anti-TREM2 antibody of the present disclosure.

As disclosed herein, anti-TREM2 antibodies of the present disclosure may also be used for inducing and/or promoting wound healing, such as after injury. In some embodiments, the wound healing may be colonic wound repair following injury. In some embodiments, the present disclosure provides methods of inducing or promoting wound healing an individual in need thereof, by administering to the individual a therapeutically effective amount of an anti-TREM2 antibody of the present disclosure.

In some embodiments, the methods of the present disclosure may involve the coadministration of anti-TREM2 antibodies, or bispecific antibodies with TLR antagonists or with agents neutralizing TLR agonist (e.g., neutralizing cytokine or interleukin antibodies).

In some embodiments, the methods of the present disclosure may involve the administration of chimeric constructs, including an anti-TREM2 antibody of the present disclosure in conjunction with a TREM2 ligand, such as HSP60.

In some embodiments, the anti-TREM2 antibodies of the present disclosure do not inhibit the growth of one or more innate immune cells. In some embodiments, the anti-TREM2 antibodies of the present disclosure bind to one or more primary immune cells with a $K_D$ of less than 50 nM, less than 45 nM, less than 40 nM, less than 35 nM, less than 30 nM, less than 25 nM, less than 20 nM, less than 15 nM, less than 10 nM, less than 9 nM, less than 8 nM, less than 7 nM, less than 6 nM, less than 5 nM, less than 4 nM, less than 3 nM, less than 2 nM, or less than 1 nM. In some embodiments, an anti-TREM2 antibody of the present disclosure accumulates in the brain, or the cerebrospinal fluid (CSF), or both to an extent that is 1% or more, 2% or more, 3% or more, 4% or more, 5% or more, 6% or more, 7% or more, 8% or more, 9% or more, 10% or more of the concentration of the antibody in the blood.

In some embodiments, a subject or individual is a mammal. Mammals include, without limitation, domesticated animals (e.g., cows, sheep, cats, dogs, and horses), primates (e.g., humans and non-human primates such as monkeys), rabbits, and rodents (e.g., mice and rats). In some embodiments, the subject or individual is a human.

Dementia

Dementia is a non-specific syndrome (i.e., a set of signs and symptoms) that presents as a serious loss of global cognitive ability in a previously unimpaired person, beyond what might be expected from normal ageing. Dementia may be static as the result of a unique global brain injury. Alternatively, dementia may be progressive, resulting in long-term decline due to damage or disease in the body. While dementia is much more common in the geriatric population, it can also occur before the age of 65. Cognitive areas affected by dementia include, without limitation, memory, attention span, language, and problem solving. Generally, symptoms must be present for at least six months to before an individual is diagnosed with dementia.

Exemplary forms of dementia include, without limitation, frontotemporal dementia, Alzheimer's disease, vascular dementia, semantic dementia, and dementia with Lewy bodies.

In some embodiments, administering an anti-TREM2 antibody of the present disclosure can prevent, reduce the risk, and/or treat dementia. In some embodiments, administering an anti-TREM2 antibody may induce one or more TREM2 activities in an individual having dementia (e.g., DAP12 phosphorylation, PI3K activation, increased expression of one or more anti-inflammatory mediators, or reduced expression of one or more pro-inflammatory mediators).

Frontotemporal Dementia

Frontotemporal dementia (FTD) is a condition resulting from the progressive deterioration of the frontal lobe of the brain. Over time, the degeneration may advance to the temporal lobe. Second only to Alzheimer's disease (AD) in prevalence, FTD accounts for 20% of pre-senile dementia cases. The clinical features of FTD include memory deficits, behavioral abnormalities, personality changes, and language impairments (Cruts, M. & Van Broeckhoven, C., Trends Genet. 24:186-194 (2008); Neary, D., et al., Neurology 51:1546-1554 (1998); Ratnavalli, E., Brayne, C., Dawson, K. & Hodges, J. R., Neurology 58:1615-1621 (2002)).

A substantial portion of FTD cases are inherited in an autosomal dominant fashion, but even in one family, symptoms can span a spectrum from FTD with behavioral disturbances, to Primary Progressive Aphasia, to Cortico-Basal Ganglionic Degeneration. FTD, like most neurodegenerative diseases, can be characterized by the pathological presence of specific protein aggregates in the diseased brain. Historically, the first descriptions of FTD recognized the presence of intraneuronal accumulations of hyperphosphorylated Tau protein in neurofibrillary tangles or Pick bodies. A causal role for the microtubule associated protein Tau was supported by the identification of mutations in the gene encoding the Tau protein in several families (Hutton, M., et al., *Nature* 393:702-705 (1998). However, the majority of FTD brains show no accumulation of hyperphosphorylated Tau but do exhibit immunoreactivity to ubiquitin (Ub) and TAR DNA binding protein (TDP43) (Neumann, M., et al., Arch. Neurol. 64:1388-1394 (2007)). A majority of those FTD cases with Ub inclusions (FTD-U) were shown to carry mutations in the progranulin gene.

In some embodiments, administering an anti-TREM2 antibody of the present disclosure can prevent, reduce the risk, and/or treat FTD. In some embodiments, administering an anti-TREM2 antibody may induce one or more TREM2 activities in an individual having FTD (e.g., DAP12 phosphorylation, PI3K activation, increased expression of one or more anti-inflammatory mediators, or reduced expression of one or more pro-inflammatory mediators).

Alzheimer's Disease

Alzheimer's disease (AD) is the most common form of dementia. There is no cure for the disease, which worsens as it progresses, and eventually leads to death. Most often, AD is diagnosed in people over 65 years of age. However, the less-prevalent early-onset Alzheimer's can occur much earlier.

Common symptoms of Alzheimer's disease include, behavioral symptoms, such as difficulty in remembering recent events; cognitive symptoms, confusion, irritability and aggression, mood swings, trouble with language, and long-term memory loss. As the disease progresses bodily functions are lost, ultimately leading to death. Alzheimer's disease develops for an unknown and variable amount of time before becoming fully apparent, and it can progress undiagnosed for years.

In some embodiments, administering an anti-TREM2 antibody of the present disclosure can prevent, reduce the risk, and/or treat Alzheimer's disease. In some embodiments, administering an anti-TREM2 antibody may induce one or more TREM2 activities in an individual having Alzheimer's disease (e.g., DAP12 phosphorylation, PI3K activation, increased expression of one or more anti-inflammatory mediators, or reduced expression of one or more pro-inflammatory mediators).

Nasu-Hakola Disease

Nasu-Hakola disease (NHD), which may alternatively be referred to as polycystic lipomembranous osteodysplasia with sclerosing leukoencephalopathy (PLOSL), is a rare inherited leukodystrophy characterized by progressive pre-senile dementia associated with recurrent bone fractures due to polycystic osseous lesions of the lower and upper extremities. NHD disease course is generally divided into four stages: latent, osseous, early neurologic, and late neurologic. After a normal development during childhood (latent stage), NHD starts manifesting during adolescence or young adulthood (typical age of onset 20-30 years) with pain in the hands, wrists, ankles, and feet. Patients then start suffering from recurrent bone fractures due to polycystic osseous and osteoporotic lesions in the limb bones (osseous stage). During the third or fourth decade of life (early neurologic stage), patients present with pronounced personality changes (e.g., euphoria, lack of concentration, loss of judgment, and social inhibitions) characteristic of a frontal lobe syndrome. Patients also typically suffer from progressive memory disturbances. Epileptic seizures are also frequently observed. Finally (late neurologic stage), patients progress to a profound dementia, are unable to speak and move, and usually die by the age of 50.

In some embodiments, administering an anti-TREM2 antibody of the present disclosure can prevent, reduce the risk, and/or treat Nasu-Hakola disease (NHD). In some embodiments, administering an anti-TREM2 antibody may induce one or more TREM2 activities in an individual having NHD (e.g., DAP12 phosphorylation, PI3K activation, increased expression of one or more anti-inflammatory mediators, or reduced expression of one or more pro-inflammatory mediators).

Parkinson's Disease

Parkinson's disease, which may be referred to as idiopathic or primary parkinsonism, hypokinetic rigid syndrome (HRS), or paralysis agitans, is a neurodegenerative brain disorder that affects motor system control. The progressive death of dopamine-producing cells in the brain leads to the major symptoms of Parkinson's. Most often, Parkinson's disease is diagnosed in people over 50 years of age. Parkinson's disease is idiopathic (having no known cause) in most people. However, genetic factors also play a role in the disease.

Symptoms of Parkinson's disease include, without limitation, tremors of the hands, arms, legs, jaw, and face, muscle rigidity in the limbs and trunk, slowness of movement (bradykinesia), postural instability, difficulty walking, neuropsychiatric problems, changes in speech or behavior, depression, anxiety, pain, psychosis, dementia, hallucinations, and sleep problems.

In some embodiments, administering an anti-TREM2 antibody of the present disclosure can prevent, reduce the risk, and/or treat Parkinson's disease. In some embodiments, administering an anti-TREM2 antibody may induce one or more TREM2 activities in an individual having Parkinson's disease (e.g., DAP12 phosphorylation, PI3K activation, increased expression of one or more anti-inflammatory mediators, or reduced expression of one or more pro-inflammatory mediators).

Amyotrophic Lateral Sclerosis

As used herein, amyotrophic lateral sclerosis (ALS) or, motor neuron disease or, Lou Gehrig's disease are used interchangeably and refer to a debilitating disease with varied etiology characterized by rapidly progressive weakness, muscle atrophy and fasciculations, muscle spasticity, difficulty speaking (dysarthria), difficulty swallowing (dysphagia), and difficulty breathing (dyspnea).

It has been shown that progranulin play a role in ALS (Schymick, J C et al., (2007) J Neurol Neurosurg Psychiatry; 78:754-6) and protects again the damage caused by ALS causing proteins such as TDP-43 (Laird, A S et al., (2010). PLoS ONE 5: e13368). It was also demonstrated that pro-NGF induces p75 mediated death of oligodendrocytes and corticospinal neurons following spinal cord injury (Beatty et al., Neuron (2002), 36, pp. 375-386; Giehl et al, Proc. Natl. Acad. Sci USA (2004), 101, pp 6226-30).

In some embodiments, administering an anti-TREM2 antibody of the present disclosure can prevent, reduce the risk, and/or treat ALS. In some embodiments, administering an anti-TREM2 antibody may induce one or more TREM2 activities in an individual having ALS (e.g., DAP12 phosphorylation, PI3K activation, increased expression of one or more anti-inflammatory mediators, or reduced expression of one or more pro-inflammatory mediators).

Huntington's Disease

Huntington's disease (HD) is an inherited neurodegenerative disease caused by an autosomal dominant mutation in the Huntingtin gene (HTT). Expansion of a cytokine-adenine-guanine (CAG) triplet repeat within the Huntingtin gene results in production of a mutant form of the Huntingtin protein (Htt) encoded by the gene. This mutant Huntingtin protein (mHtt) is toxic and contributes to neuronal death. Symptoms of Huntington's disease most commonly appear between the ages of 35 and 44, although they can appear at any age.

Symptoms of Huntington's disease, include, without limitation, motor control problems, jerky, random movements (chorea), abnormal eye movements, impaired balance, seizures, difficulty chewing, difficulty swallowing, cognitive problems, altered speech, memory deficits, thinking difficulties, insomnia, fatigue, dementia, changes in personality, depression, anxiety, and compulsive behavior.

In some embodiments, administering an anti-TREM2 antibody of the present disclosure can prevent, reduce the risk, and/or treat Huntington's disease (HD). In some embodiments, administering an anti-TREM2 antibody may induce one or more TREM2 activities in an individual having HD (e.g., DAP12 phosphorylation, PI3K activation, increased expression of one or more anti-inflammatory mediators, or reduced expression of one or more pro-inflammatory mediators).

Tauopathy Disease

Tauopathy diseases, or Tauopathies, are a class of neurodegenerative disease caused by aggregation of the microtubule-associated protein tau within the brain. Alzheimer's disease (AD) is the most well-known tauopathy disease, and involves an accumulation of tau protein within neurons in the form of insoluble neurofibrillary tangles (NFTs). Other tauopathy diseases and disorders include progressive supranuclear palsy, dementia pugilistica (chromic traumatic encephalopathy), Frontotemporal dementia and parkinsonism linked to chromosome 17, Lytico-Bodig disease (Parkinson-dementia complex of Guam), Tangle-predominant dementia, Ganglioglioma and gangliocytoma, Meningioangiomatosis, Subacute sclerosing panencephalitis, lead encephalopathy, tuberous sclerosis, Hallervorden-Spatz disease, lipofuscinosis, Pick's disease, corticobasal degeneration, Argyrophilic grain disease (AGD), Huntington's disease, frontotemporal dementia, and frontotemporal lobar degeneration.

In some embodiments, administering an anti-TREM2 antibody of the present disclosure can prevent, reduce the risk, and/or treat tauopathy disease. In some embodiments, administering an anti-TREM2 antibody may induce one or more TREM2 activities in an individual having tauopathy disease (e.g., DAP12 phosphorylation, PI3K activation, increased expression of one or more anti-inflammatory mediators, or reduced expression of one or more pro-inflammatory mediators).

Multiple Sclerosis

Multiple sclerosis (MS) can also be referred to as disseminated sclerosis or encephalomyelitis disseminata. MS is an inflammatory disease in which the fatty myelin sheaths around the axons of the brain and spinal cord are damaged, leading to demyelination and scarring as well as a broad spectrum of signs and symptoms. MS affects the ability of nerve cells in the brain and spinal cord to communicate with each other effectively. Nerve cells communicate by sending electrical signals called action potentials down long fibers called axons, which are contained within an insulating substance called myelin. In MS, the body's own immune system attacks and damages the myelin. When myelin is lost, the axons can no longer effectively conduct signals. MS onset usually occurs in young adults, and is more common in women.

Symptoms of MS include, without limitation, changes in sensation, such as loss of sensitivity or tingling; pricking or numbness, such as hypoesthesia and paresthesia; muscle weakness; clonus; muscle spasms; difficulty in moving; difficulties with coordination and balance, such as ataxia; problems in speech, such as dysarthria, or in swallowing, such as dysphagia; visual problems, such as nystagmus, optic neuritis including phosphenes, and diplopia; fatigue; acute or chronic pain; and bladder and bowel difficulties; cognitive impairment of varying degrees; emotional symptoms of depression or unstable mood; Uhthoffs phenomenon, which is an exacerbation of extant symptoms due to an exposure to higher than usual ambient temperatures; and Lhermitte's sign, which is an electrical sensation that runs down the back when bending the neck.

In some embodiments, administering an anti-TREM2 antibody of the present disclosure can prevent, reduce the risk, and/or treat multiple sclerosis. In some embodiments, administering an anti-TREM2 antibody may induce one or more TREM2 activities in an individual having multiple sclerosis (e.g., DAP12 phosphorylation, PI3K activation, increased expression of one or more anti-inflammatory mediators, and reduced expression of one or more pro-inflammatory mediators).

Cancer

Yet further aspects of the present disclosure provide methods for preventing, reducing risk, or treating an individual having cancer, comprising administering to the individual a therapeutically effective amount of an isolated anti-TREM2 antibody of the present disclosure. Any of the isolated antibodies of the present disclosure may be used in these methods.

As described above, the tumor microenvironment is known to contain a heterogeneous immune infiltrate, which includes T lymphocytes, macrophages and cells of myeloid/granulocytic lineage. In particular, the presence of M2-macrophages in tumors is associated with poor prognosis. Therapies that reduce the number of these cells in the tumor, such as CSF-1R blocking agents, are showing beneficial effects in preclinical models and early stage clinical studies. It has been shown that TREM2 synergizes with CSF-1 to promote survival of macrophages in vitro, and that this effect is particularly prominent in M2-type macrophages, compared to other types of phagocytic cells. A seminal preclinical study has also shown synergies between drugs that target tumor-associated macrophages (e.g., CSF-1/CSF-1R blocking antibodies) and checkpoint blocking antibodies that target T cells, indicating that manipulating both cell types shows efficacy in tumor models where individual therapies are poorly effective (Zhu Y; Cancer Res. 2014 Sep. 15; 74(18):5057-69). Therefore, without wishing to be bound by theory, it is thought that blocking TREM2 signaling in tumor associated macrophages may inhibit suppression of the immune response in the tumor microenvironment, resulting in a therapeutic anti-tumor immune response.

Due to the synergies between TREM2 and CSF-1, and between targeting tumor-associated macrophages and targeting T cells, in some embodiments, the methods for preventing, reducing risk, or treating an individual having cancer further include administering to the individual at least one antibody that specifically binds to an inhibitory checkpoint molecule. Examples of antibodies that specifically bind to an inhibitory checkpoint molecule include, without limitation, an anti-PD-L1 antibody, an anti-CTLA-4 antibody, an anti-PD-L2 antibody, an anti-PD-1 antibody, an anti-B7-H3 antibody, an anti-B7-H4 antibody, and anti-HVEM antibody, an anti-BTLA antibody, an anti-GAL9 antibody, an anti-TIM3 antibody, an anti-A2AR antibody, an anti-LAG-3 antibody, an anti-phosphatidylserine antibody, and any combination thereof. In some embodiments, the at least one antibody that specifically binds to an inhibitory checkpoint molecule is administered in combination with an anti-TREM2 antibody of the present disclosure.

In some embodiments, a cancer to be prevented or treated by the methods of the present disclosure includes, but is not limited to, squamous cell cancer (e.g., epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer and gastrointestinal stromal cancer, pancreatic cancer, glioblastoma, cervical cancer, ovarian cancer, liver cancer, bladder cancer, cancer of the urinary tract, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, melanoma, superficial spreading melanoma, lentigo maligna melanoma, acral lentiginous melanomas, nodular melanomas, multiple myeloma and B-cell lymphoma; chronic lymphocytic leukemia (CLL); acute lymphoblastic leukemia (ALL); hairy cell leukemia; chronic myeloblastic leukemia; and post-transplant lymphoproliferative disorder (PTLD), as well as abnormal vascular proliferation associated with phakomatoses, edema (such as that associated with brain tumors), Meigs' syndrome, brain, as well as head and neck cancer, and associated metastases. In some embodiments, the cancer is colorectal cancer. In some embodiments, the cancer is selected from non-small cell lung cancer, glioblastoma, neuroblastoma, renal cell carcinoma, bladder cancer, ovarian cancer, melanoma, breast carcinoma, gastric cancer, and hepatocellular carcinoma. In some embodiments, the cancer is triple-negative breast carcinoma. In some embodiments, the cancer may be an early stage cancer or a late stage cancer. In some embodiments, the cancer may be a primary tumor. In some embodiments, the cancer may be a metastatic tumor at a second site derived from any of the above types of cancer.

In some embodiments, anti-TREM2 antibodies of the present disclosure may be used for preventing, reducing risk, or treating cancer, including, without limitation, bladder cancer breast cancer, colon and rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, and thyroid cancer.

In some embodiments, the present disclosure provides methods of preventing, reducing risk, or treating an individual having cancer, by administering to the individual a therapeutically effective amount of an anti-TREM2 antibody of the present disclosure.

In some embodiments, the method further includes administering to the individual at least one antibody that specifically binds to an inhibitory checkpoint molecule, and/or another standard or investigational anti-cancer therapy. In some embodiments, the at least one antibody that specifically binds to an inhibitory checkpoint molecule is administered in combination with the isolated antibody. In some embodiments, the at least one antibody that specifically binds to an inhibitory checkpoint molecule is selected from an anti-PD-L1 antibody, an anti-CTLA-4 antibody, an anti-PD-L2 antibody, an anti-PD-1 antibody, an anti-B7-H3 antibody, an anti-B7-H4 antibody, and anti-HVEM antibody, an anti-B- and T-lymphocyte attenuator (BTLA) antibody, an anti-Killer inhibitory receptor (KIR) antibody, an anti-GAL9 antibody, an anti-TIM3 antibody, an anti-A2AR antibody, an anti-LAG-3 antibody, an anti-phosphatidylserine antibody, an anti-CD27 antibody, and any combination thereof. In some embodiments, the standard or investigational anti-cancer therapy is one or more therapies selected from radiotherapy, cytotoxic chemotherapy, targeted therapy, imatinib (Gleevec®), trastuzumab (Herceptin®), adoptive cell transfer (ACT), chimeric antigen receptor T cell transfer (CAR-T), vaccine therapy, hormonal therapy, bevacizumab (Avastin®), Ofatumumab (Arzerra®), Rituximab (Rituxan®, MabThera®, Zytux®), cryotherapy, ablation, radiofrequency ablation, and cytokine therapy.

In some embodiments, the method further includes administering to the individual at least one antibody that specifically binds to an inhibitory cytokine. In some embodiments, the at least one antibody that specifically binds to an inhibitory cytokine is administered in combination with the isolated antibody. In some embodiments, the at least one antibody that specifically binds to an inhibitory cytokine is selected from an anti-CCL2 antibody, an anti-CSF-1 antibody, an anti-IL-2 antibody, and any combination thereof.

In some embodiments, the method further includes administering to the individual at least one agonistic antibody that specifically binds to a stimulatory checkpoint protein. In some embodiments, the at least one agonistic antibody that specifically binds to a stimulatory checkpoint protein is administered in combination with the isolated antibody. In some embodiments, the at least one agonistic antibody that specifically binds to a stimulatory checkpoint protein is selected from an agonist anti-CD40 antibody, an agonist anti-OX40 antibody, an agonist anti-ICOS antibody, an agonist anti-CD28 antibody, an agonist anti-CD137/4-1BB antibody, an agonist anti-CD27 antibody, an agonist anti-glucocorticoid-induced TNFR-related protein GITR antibody, and any combination thereof.

In some embodiments, the method further includes administering to the individual at least one stimulatory cytokine. In some embodiments, the at least one stimulatory cytokine is administered in combination with the isolated antibody. In some embodiments, the at least one stimulatory cytokine is selected from TNF-α, IL-1☐, IL-1β, IL-10, IL-6, IL-8, CRP, TGF-beta members of the chemokine protein families, IL-20 family members, IL-33, LIF, IFN-gamma, OSM, CNTF, TGF-beta, IL-11, IL-12, IL-17, IL-8, CRP, IFN-α, IFN-β, IL-2, IL-18, IL-23, CXCL10, CCL4, MCP-1, VEGF, GM-CSF, G-CSF, and any combination thereof.

Kits/Articles of Manufacture

The present disclosure also provides kits containing an isolated antibody of the present disclosure (e.g., an anti-TREM2 antibody described herein), or a functional fragment thereof. Kits of the present disclosure may include one or more containers comprising a purified antibody of the present disclosure. In some embodiments, the kits further include instructions for use in accordance with the methods of this disclosure. In some embodiments, these instructions comprise a description of administration of the isolated antibody of the present disclosure (e.g., an anti-TREM2 antibody described herein) to prevent, reduce risk, or treat an individual having a disease, disorder, or injury selected from dementia, frontotemporal dementia, Alzheimer's disease, Nasu-Hakola disease, multiple sclerosis, and cancer, according to any methods of this disclosure.

In some embodiments, the instructions comprise a description of how to detect TREM2, for example in an individual, in a tissue sample, or in a cell. The kit may further comprise a description of selecting an individual suitable for treatment based on identifying whether that individual has the disease and the stage of the disease.

In some embodiments, the kits may further include another antibody of the present disclosure (e.g., at least one antibody that specifically binds to an inhibitory checkpoint molecule, at least one antibody that specifically binds to an inhibitory cytokine, and/or at least one agonistic antibody that specifically binds to a stimulatory checkpoint protein) and/or at least one stimulatory cytokine. In some embodiments, the kits may further include instructions for using the antibody and/or stimulatory cytokine in combination with an isolated antibody of the present disclosure (e.g., an anti-TREM2 antibody described herein), instructions for using the isolated antibody of the present disclosure in combination with an antibody and/or stimulatory cytokine, or instructions for using an isolated antibody of the present disclosure and an antibody and/or stimulatory cytokine, according to any methods of this disclosure.

The instructions generally include information as to dosage, dosing schedule, and route of administration for the intended treatment. The containers may be unit doses, bulk packages (e.g., multi-dose packages) or sub-unit doses. Instructions supplied in the kits of the present disclosure are typically written instructions on a label or package insert (e.g., a paper sheet included in the kit), but machine-readable instructions (e.g., instructions carried on a magnetic or optical storage disk) are also acceptable.

The label or package insert indicates that the composition is used for treating, e.g., a disease of the present disclosure. Instructions may be provided for practicing any of the methods described herein.

The kits of this disclosure are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (e.g., the container may be an intravenous solution bag or a vial having a stopper pierceable by a hypodermic injection needle). At least one active agent in the composition is an isolated antibody of the present disclosure (e.g., an anti-TREM2 antibody described herein). The container may further comprise a second pharmaceutically active agent.

Kits may optionally provide additional components such as buffers and interpretive information. Normally, the kit comprises a container and a label or package insert(s) on or associated with the container.

Diagnostic Uses

The isolated antibodies of the present disclosure (e.g., an anti-TREM2 antibody described herein) also have diagnostic utility. This disclosure therefore provides for methods of using the antibodies of this disclosure, or functional fragments thereof, for diagnostic purposes, such as the detection of TREM2 in an individual or in tissue samples derived from an individual.

In some embodiments, the individual is a human. In some embodiments, the individual is a human patient suffering from, or at risk for developing, cancer. In some embodiments, the diagnostic methods involve detecting TREM2 in a biological sample, such as a biopsy specimen, a tissue, or a cell. An isolated antibody of the present disclosure (e.g., an anti-TREM2 antibody described herein) is contacted with the biological sample and antigen-bound antibody is detected. For example, a tumor sample (e.g., a biopsy specimen) may be stained with an anti-TREM2 antibody described herein in order to detect and/or quantify tumor-associated macrophages (e.g., M2-type macrophages). The detection method may involve quantification of the antigen-bound antibody. Antibody detection in biological samples may occur with any method known in the art, including immunofluorescence microscopy, immunocytochemistry, immunohistochemistry, ELISA, FACS analysis, immunoprecipitation, or micro-positron emission tomography. In certain embodiments, the antibody is radiolabeled, for example with $^{18}$F and subsequently detected utilizing micro-positron emission tomography analysis. Antibody-binding may also be quantified in a patient by non-invasive techniques such as positron emission tomography (PET), X-ray computed tomography, single-photon emission computed tomography (SPECT), computed tomography (CT), and computed axial tomography (CAT).

In other embodiments, an isolated antibody of the present disclosure (e.g., an anti-TREM2 antibody described herein) may be used to detect and/or quantify, for example, microglia in a brain specimen taken from a preclinical disease model (e.g., a non-human disease model). As such, an isolated antibody of the present disclosure (e.g., an anti-TREM2 antibody described herein) may be useful in evaluating therapeutic response after treatment in a model for a nervous system disease or injury such as dementia, frontotemporal dementia, Alzheimer's disease, Nasu-Hakola disease, or multiple sclerosis, as compared to a control.

Antibodies with Modified Constant Regions

Other aspects of the present disclosure relate to antibodies having modified constant regions (i.e., Fc regions). In some embodiments the modified Fc regions include two or more amino acid substitutions that increase antibody clustering without activating complement as compared to a corresponding antibody having an Fc region that does not include the two or more amino acid substitutions. Accordingly, in some embodiments, the antibody is an antibody comprising an Fc region, where the antibody comprises an amino acid substitution at position E430G and one or more amino acid substitutions in the Fc region at a residue position selected from: L234F, L235A, L235E, S267E, K322A, L328F, A330S, P331S, and any combination thereof, where the numbering of the residues is according to EU or Kabat numbering. In some embodiments, the Fc region comprises an amino acid substitution at positions E430G, L243A, L235A, and P331S, where the numbering of the residue position is according to EU numbering. In some embodiments, the Fc region comprises an amino acid substitution at positions E430G and P331S, where the numbering of the residue position is according to EU numbering. In some embodiments, the Fc region comprises an amino acid substitution at positions E430G and K322A, where the numbering of the residue position is according to EU numbering. In some embodiments, the Fc region comprises an amino acid substitution at positions E430G, A330S, and P331S, where the numbering of the residue position is according to EU numbering. In some embodiments, the Fc region comprises an amino acid substitution at positions E430G, K322A, A330S, and P331S, where the numbering of the residue position is according to EU numbering. In some embodiments, the Fc region comprises an amino acid substitution at positions E430G, K322A, and A330S, where the numbering of the residue position is according to EU numbering. In some embodiments, the Fc region comprises an amino acid substitution at positions E430G, K322A, and P331S, where the numbering of the residue position is according to EU numbering.

In some embodiments, the Fc region increases clustering without activating complement as compared to a corresponding antibody comprising an Fc region that does not comprise the amino acid substitutions. In some embodiments, the antibody induces one or more activities of a target specifically bound by the antibody. In some embodiments, the antibody binds to TREM2.

The present disclosure will be more fully understood by reference to the following Examples. They should not, however, be construed as limiting the scope of the present disclosure. All citations throughout the disclosure are hereby expressly incorporated by reference.

EXAMPLES

Example 1: Humanized AL2p Antibodies Retain Affinity and Function

The mouse anti-TREM2 antibody AL2p is also known as 9F5 and 9F5a in WO 2017/062672 (PCT/US2016/055828).

Methods

Humanized versions of the mouse anti-TREM2 antibody AL2p were generated by combining 21 human IgG1 versions of VH with 6 human IgG1 versions of VK, each containing from 0 to 11 framework residue mutations. These variants were tested by ForteBio for affinity to the TREM2 antigen and 94 variants were chosen for further in vitro analysis.

The affinity of the TREM2 antibodies was determined by measuring their $K_D$, as well as on- and off-rates by ForteBio OctetRed as previously described by Estep et al., Mabs 2013: 5(2):270-278. Briefly, IgG's were loaded on-line onto AHQ sensors. Sensors were equilibrated off-line in assay buffer for 30 minutes and then monitored on-line for 60 seconds for baseline establishment. For avid binding measurement, sensors with loaded IgGs were exposed to 100 nM antigen (human TREM2 Fc fusion using the entire TREM2 ECD; only one Fc arm was fused to TREM2) for 3 minutes, afterwards they were transferred to assay buffer for 3 minutes for off-rate measurement. Monovalent binding measurements were obtained by loading human TREM2 Fc fusion antigens to AHQ sensor and followed by exposure to ~100 nM TREM2 antibody Fab. Kinetics data were fit using a 1:1 binding model in the data analysis software provided by ForteBio. Assay was run at room temperature (25° C.).

To examine cell binding of anti-TREM2 antibodies, recombinant, human TREM2-expressing BW5147.G.1.4 cells (ATCC® TIB48™) were established by stably expressing either mouse TREM2 or human TREM2 together with Dap12 using viral infection. Cells were harvested by scraping, washed in PBS, counted and plated on 96-well U bottom plates at $1 \times 10^5$ cells/well. The plates were spun at 1,400 rpm for 3 minutes and primary anti-TREM2 or control antibodies were added in FACS buffer (PBS+2% FBS) and incubated on ice for one hour. Cells were subsequently centrifuged as before and washed thrice with FACS buffer. Cells were then incubated with anti-human PE conjugated secondary antibody (BD Biosciences) in FACS buffer for 30 minutes on ice. Cells were again washed thrice with FACS buffer and analyzed on a BD FACS Canto. Binding was measured as mean fluorescence intensity in the APC channel.

The ability of plate-bound full-length anti-TREM2 antibodies to activate human TREM2-dependent genes was evaluated using a luciferase reporter gene under the control of an NFAT (nuclear factor of activated T-cells) promoter. The cell line BW5147.G.1.4, derived from mouse thymus lymphoma T lymphocytes, was infected with a human TREM2/DAP12 fusion protein, and with Cignal Lenti NFAT-Luciferase virus (Qiagen). To test antibodies in solution, they were added to the culture plates together with the cells and incubated for 4 to 6 hours at 37° C. Luciferase activity was measured by adding OneGlo Reagent (Promega) to each well and incubating for 3 minutes at room temperature on a plate shaker. Luciferase signal was measured using a BioTek plate reader.

Results

Humanized versions of anti-TREM2 antibody AL2p were generated by combining 21 human IgG1 versions of VH with 6 human IgG1 versions of VK, each containing from 0 to 11 framework residue mutations. The heavy chain and light chain variable region sequences of 26 humanized anti-TREM2 antibodies are depicted in Tables 6 and 7.

Clones were tested for affinity to human TREM2 by ForteBio Octet Red (Table 1). Most humanized AL2p variants retained a similar affinity as the human mouse AL2p chimeric parental antibody (which has a mouse antibody variable region and a human Fc region). In addition, humanized variants retained ability to bind to human TREM2 expressed on BW cells, with some even showing an improved affinity over the parental antibody (Table 1). Furthermore, humanized variants retained the ability to induce TREM2 signaling in a heterologous NFAT:luciferase signaling assay (Table 1). Two variants (AL2p-h50 and AL2p-h77) were chosen to move into affinity maturation as they both retained affinity and function of the parental antibody, while containing few changes from human germline indicating low immunogenicity.

TABLE 1

Characterization of humanized versions of anti-TREM2 antibody AL2p

| Antibody | Fab $K_D$ human TREM2-Fc (M) Monovalent | Cell binding human TREM2/DAP12 BWZ (FOB) | Soluble luciferase activation at 10 µg/ml Fold over control |
|---|---|---|---|
| AL2p | 1.02E-07 | 79 | 3.55 |
| AL2p-h19 | 1.93E-07 | 87 | 4.97 |
| AL2p-h21 | 1.37E-07 | 76 | 6.28 |
| AL2p-h22 | 3.25E-07 | 61 | 5.00 |
| AL2p-h23 | 3.34E-07 | 76 | 5.38 |
| AL2p-h24 | 1.15E-06 | 69 | 4.36 |
| AL2p-h25 | 1.53E-07 | 90 | 7.45 |
| AL2p-h26 | 9.53E-08 | 78 | 7.25 |
| AL2p-h27 | 1.20E-07 | 78 | 7.23 |
| AL2p-h28 | N.B. | 79 | 5.59 |
| AL2p-h29 | N.B. | 82 | 5.80 |
| AL2p-h30 | 1.81E-07 | 88 | 6.01 |
| AL2p-h31 | 1.16E-07 | 83 | 5.04 |
| AL2p-h32 | 1.44E-07 | 81 | 5.60 |
| AL2p-h33 | 2.25E-07 | 74 | 6.21 |
| AL2p-h34 | 1.42E-07 | 84 | 6.92 |
| AL2p-h35 | 1.27E-07 | 69 | 6.81 |
| AL2p-h36 | N.B. | 85 | 4.13 |
| AL2p-h42 | 1.41E-07 | 79 | 9.29 |
| AL2p-h43 | 1.34E-07 | 91 | 8.65 |
| AL2p-h44 | 1.80E-07 | 80 | 7.29 |
| AL2p-h47 | 1.61E-07 | 93 | 9.28 |
| AL2p-h50 | 1.80E-07 | 78 | 6.36 |
| AL2p-h59 | 1.30E-07 | 69 | 7.06 |
| AL2p-h76 | 8.30E-08 | 86 | 6.52 |
| AL2p-h77 | 9.39E-08 | 83 | 7.14 |
| AL2p-h90 | 6.12E-08 | 126 | 4.35 |

In Table 1, "N.B." refers to no binding; and "FOB" refers to fold over background.

Example 2: Affinity Matured AL2p Antibodies Show Highly Improved Affinity

Methods

Affinity maturation of humanized AL2p variants AL2p-h50 and AL2p-h77 was performed. Briefly, key amino acid residues in the heavy or light chain were selectively mutagenized and mutants that improved binding were selected through additional rounds of screening. This process simultaneously improves specificity, species cross-reactivity, and developability profiles, allowing precise tuning of properties critical for the desired mechanism of action, potency in biological assays, and pre-clinical modeling. Delivery characterizations included Forte Bio and MSD affinity measurements, cell binding and several developability assays. After the first round of affinity maturation, antibodies with elevated affinity also displayed elevated polyspecific reactivity (PSR), which is used to determine unspecific binding of the antibody. Thus, a second round of affinity maturation was performed to improve affinity without elevating PSR.

The affinity of the affinity matured anti-TREM2 antibodies was determined by measuring their $K_D$, as well as on- and off-rates by ForteBio OctetRed as previously described by Estep et al., Mabs 2013: 5(2):270-278. Briefly, IgGs were loaded on-line onto AHQ sensors. Sensors were equilibrated off-line in assay buffer for 30 minutes and then monitored on-line for 60 seconds for baseline establishment. For avid binding measurement, sensors with loaded IgGs were exposed to 100 nM antigen (human or cynomolgus monkey TREM2 Fc fusion using the entire TREM2 ECD; only one Fc arm was fused to TREM2) for 3 minutes, afterwards they were transferred to assay buffer for 3 minutes for off-rate measurement. Monovalent binding measurements were obtained by loading human TREM2 Fc fusion antigens to AHQ sensor and followed by exposure to ~100 nM TREM2 antibody Fab. Kinetics data were fit using a 1:1 binding model in the data analysis software provided by ForteBio. Assay was run at room temperature (25° C.).

To examine cell binding of affinity matured anti-TREM2 antibodies, both primary human monocyte derived dendritic cells and recombinant, human TREM2 expressing cells were utilized. For the latter, BW5147.G.1.4 (ATCC® TIB48™) and HEK293T cells stably expressing human TREM2 together with Dap12 using viral infection were established. For primary human monocyte derived dendritic cells, human monocytes were isolated from whole blood using RosetteSep Human monocyte enrichment cocktail (Stemcell technologies) and Ficoll centrifugation per manufacturer protocols. After lysing red blood cells with ACK lysing buffer, monocytes were resuspended in complete media (RPMI, 10% FBS, Pen/Strep, L-glutamine, HEPES, non-essential amino acid, Sodium pyruvate) with 100 ng/ml human GM-CSF (hu-GMCSF) and human IL-4 (hu-IL-4) to differentiate dendritic cells for 6 days.

Cells were harvested by trypsinization (Hek293T) or scraping (BW and dendritic cells), washed in PBS, counted and plated on 96-well U bottom plates at $1 \times 10^5$ cells/well. The plates were spun at 1,400 rpm for 3 minutes and primary TREM2 or control antibodies were added in FACS buffer (PBS+2% FBS) and incubated on ice for one hour. Cells were subsequently centrifuged as before and washed thrice with FACS buffer. Cells were then incubated with anti-human PE conjugated secondary antibody (BD Biosciences) in FACS buffer for 30 minutes on ice. Cells were again washed thrice with FACS buffer and analyzed on a BD FACS Canto or an Intellicyt Flow Cytometer. Binding was measured as mean fluorescence intensity in the APC channel.

Results

Two rounds of affinity maturation were performed on AL2p variants AL2p-h50 and AL2p-h77. In total, 57 affinity matured clones were selected from the AL2p-h50 lineage and 4 clones from the AL2p-h77 lineage. The heavy chain variable region HVR sequences of the antibodies are depicted in Tables 2A to 2C. The light chain variable region HVR sequences of the antibodies are depicted in Tables 3A to 3C. The heavy chain framework regions of the antibodies are depicted in Tables 4A to 4D. The light chain framework regions of the antibodies are depicted in Tables 5A to 5D. The heavy chain variable region sequences of the antibodies are depicted in Table 6A. The heavy chain sequences of AL2p variant antibodies are depicted in Table 6B. The light chain variable region sequences of the antibodies are depicted in Table 7A. The light chain sequences of AL2p variant antibodies are depicted in Table 7B.

TABLE 2A

Heavy chain HVR H1 sequences of anti-TREM2 antibodies

| Ab | HVR H1 | SEQ ID NO: |
|---|---|---|
| AL2p-h50, AL2p-2, AL2p-3, AL2p-4, AL2p-5, AL2p-6, AL2p-33, AL2p-h77, and AL2p-36 | YAFSSSWMN | 124 |
| AL2p-29, AL2p-30, AL2p-31, AL2p-37, AL2p-58, AL2p-60, AL2p-61, and AL2p-62 | YAFSSQWMN | 132 |
| AL2p-10, AL2p-11, AL2p-45, AL2p-46, AL2p-47, AL2p-48, and AL2p-49 | YAFSSDWMN | 136 |
| AL2p-7 and AL2p-8 | YAFSLSWMN | 157 |
| AL2p-9 | YAFSRSWMN | 158 |
| AL2p-12, AL2p-13, AL2p-14, AL2p-15, AL2p-16, AL2p-17, AL2p-18, AL2p-19, AL2p-20, AL2p-21, AL2p-22, AL2p-23, AL2p-24, AL2p-25, AL2p-26, AL2p-27, AL2p-28, AL2p-38, AL2p-39, AL2p-40, AL2p-41, AL2p-42, AL2p-43, AL2p-44, AL2p-50, AL2p-51, AL2p-52, AL2p-53, AL2p-54, AL2p-55, AL2p-56, AL2p-57, and AL2p-59 | YAFSSHWMN | 159 |
| AL2p-32 | YAFSSEWMN | 160 |
| AL2p-35 | YAFWSSWMN | 161 |
| Formula I | YAFX$_1$X$_2$X$_3$WMN<br>X$_1$ is S or W<br>X$_2$ is S, L, or R<br>X$_3$ is S, D, H, Q, or E | 121 |

TABLE 2B

Heavy chain HVR H2 sequences of anti-TREM2 antibodies

| Ab | HVR H2 | SEQ ID NO: |
|---|---|---|
| AL2p-h50, AL2p-5, AL2p-6, AL2p-9, AL2p-10, AL2p-14, AL2p-15, AL2p-29, AL2p-32, AL2p-33, AL2p-h77, and AL2p-35 | RIYPGDGDTNYAQKFQG | 125 |
| AL2p-31 and AL2p-60 | RIYPGGGDTNYARKFQG | 133 |
| AL2p-37 and AL2p-58 | RIYPGGGDTNYAGKFQG | 135 |
| AL2p-47, AL2p-48, AL2p-49 | RIYPGEGDTNYARKFHG | 137 |
| AL2p-45, AL2p-46, and AL2p-61 | RIYPGEGDTNYARKFQG | 141 |
| AL2p-62 | RIYPGEGDTNYAGKFQG | 143 |
| AL2p-2 and AL2p-24 | RIYPGGGDTNYAQKFQG | 162 |
| AL2p-3 | RIYPGEGDTNYAQKFQG | 163 |
| AL2p-4 and AL2p-27 | RIYPGQGDTNYAQKFQG | 164 |
| AL2p-7 and AL2p-16 | RIYPGDGDTNYAQKFRG | 165 |
| AL2p-8, AL2p-11, AL2p-19, AL2p-20, and AL2p-36 | RIYPGDGDTNYARKFQG | 166 |
| AL2p-12 | RIYPGDGDTNYAHKFQG | 167 |
| AL2p-13 | RIYPGDGDTNYAQKFKG | 168 |
| AL2p-17 | RIYPGDGDTNYAQKRQG | 169 |
| AL2p-18 | RIYPGDGDTNYAQKWQG | 170 |
| AL2p-21 and AL2p-30 | RIYPGDGDTNYAWKFQG | 171 |
| AL2p-22 | RIYPGDGDTNYAYKFQG | 172 |
| AL2p-23 | RIYPGDGQTNYAQKRQG | 173 |
| AL2p-25, AL2p-38, AL2p-39, and AL2p-40 | RIYPGGGDTNYAQKFRG | 174 |
| AL2p-26 | RIYPGGGDTNYAQKRQG | 175 |
| AL2p-28 | RIYPGVGDTNYAQKFQG | 176 |
| AL2p-41 and AL2p-42 | RIYPGEGDTNYAQKFRG | 177 |
| AL2p-43 and AL2p-44 | RIYPGGGDTNYARKFRG | 178 |
| AL2p-50, AL2p-51, AL2p-52, AL2p-53, AL2p-54, AL2p-55, AL2p-56, and AL2p-57 | RIYPGEGDTNYAQKFHG | 179 |
| AL2p-59 | RIYPGEGQTNYAQKRQG | 180 |
| Formula II | RIYPGX$_1$GX$_2$TNYAX$_3$KX$_4$X$_5$G<br>X$_1$ is D, G, E, Q, or V<br>X$_2$ is D or Q<br>X$_3$ is Q, R, H, W, Y, or G<br>X$_4$ is F, R, or W<br>X$_5$ is Q, R, K, or H | 122 |

TABLE 2C

Heavy chain HVR H3 sequences of anti-TREM2 antibodies

| Ab | HVR H3 | SEQ ID NO: |
|---|---|---|
| AL2p-h50, AL2p-2, AL2p-3, AL2p-4, AL2p-5, AL2p-6, AL2p-7, AL2p-10, AL2p-11, AL2p-12, AL2p-13, AL2p-14, AL2p-15, AL2p-17, AL2p-19, AL2p-20, AL2p-21, AL2p-22, AL2p-23, AL2p-24, AL2p-25, AL2p-26, AL2p-27, AL2p-28, AL2p-29, AL2p-30, AL2p-31, AL2p-32, AL2p-33, AL2p-h77, AL2p-37, AL2p-50, AL2p-51, | ARLLRNQPGESYAMDY | 126 |

TABLE 2C-continued

Heavy chain HVR H3 sequences of anti-TREM2 antibodies

| Ab | HVR H3 | SEQ ID NO: |
|---|---|---|
| AL2p-52, AL2p-53, AL2p-58, AL2p-59, AL2p-60, AL2p-61, and AL2p-62 | | |
| AL2p-45, AL2p-46, AL2p-47, AL2p-48, AL2p-49, AL2p-54, AL2p-55, AL2p-56, and AL2p-57 | ARLLRNKPGESYAMDY | 138 |
| AL2p-8 and AL2p-18 | ARLLRNQPGSSYAMDY | 181 |
| AL2p-9, AL2p-16, AL2p-36, AL2p-38, AL2p-39, AL2p-40, AL2p-41, AL2p-42, AL2p-43, and AL2p-44 | ARLLRNQPGASYAMDY | 182 |
| AL2p-35 | ARLLRNQPGESYAHDY | 183 |
| Formula III | ARLLRN$X_1$PG$X_2$SYA$X_3$DY<br>$X_1$ is Q or K<br>$X_2$ is E, S, or A<br>$X_3$ is M or H | 123 |

TABLE 3A

Light chain HVR L1 sequences of anti-TREM2 antibodies

| Ab | HVR L1 | SEQ ID NO: |
|---|---|---|
| AL2p-h50, AL2p-2, AL2p-3, AL2p-4, AL2p-10, AL2p-12, AL2p-31, AL2p-32, AL2p-h77, AL2p-35, AL2p-36, and AL2p-37 | RSSQSLVHSNGYTYLH | 130 |
| AL2p-45, AL2p-47, AL2p-50, AL2p-52, AL2p-55, and AL2p-56 | RTSQSLVHSNAYTYLH | 139 |
| AL2p-61 and AL2p-62 | RSSQSLVHSNQYTYLH | 142 |
| AL2p-5, AL2p-58, and AL2p-60 | RSSQSLVHSNRYTYLH | 144 |
| AL2p-6 | RSSQSLVHSNWYTYLH | 184 |
| AL2p-7, AL2p-8, AL2p-13, and AL2p-26 | RSSQSLIHSNGYTYLH | 185 |
| AL2p-9, AL2p-16, AL2p-18, AL2p-20, AL2p-23, AL2p-25, AL2p-28, and AL2p-33 | RTSQSLVHSNGYTYLH | 186 |
| AL2p-11, AL2p-14, AL2p-17, AL2p-19, AL2p-22, AL2p-24, AL2p-27, and AL2p-29 | RSSRSLVHSNGYTYLH | 187 |
| AL2p-15, AL2p-21, and AL2p-30 | RSSSSLVHSNGYTYLH | 188 |
| AL2p-38 and AL2p-43 | RSSRSLVHSNRYTYLH | 189 |
| AL2p-39 and AL2p-41 | RSSRSLVHSNQYTYLH | 190 |
| AL2p-40, AL2p-42, and AL2p-44 | RTSRSLVHSNRYTYLH | 191 |
| AL2p-46, AL2p-48, AL2p-49, AL2p-51, AL2p-53, AL2p-54, AL2p-57, and AL2p-59 | RTSQSLVHSNQYTYLH | 192 |
| Formula IV | R$X_1$S$X_2$SL$X_3$HSN$X_4$YTYLH<br>$X_1$ is S or T<br>$X_2$ is Q, R, or S<br>$X_3$ is V or I<br>$X_4$ is G, R, W, Q, or A | 127 |

TABLE 3B

Light chain HVR L2 sequences of anti-TREM2 antibodies

| Ab | HVR L2 | SEQ ID NO: |
|---|---|---|
| AL2p-h50, AL2p-2, AL2p-3, AL2p-4, AL2p-5, AL2p-6, AL2p-14, AL2p-24, AL2p-29, AL2p-h77, AL2p-35, AL2p-36, AL2p-37, AL2p-58, and AL2p-62 | KVSNRFS | 131 |
| AL2p-7, AL2p-8, AL2p-10, AL2p-12, AL2p-13, AL2p-22, AL2p-26, AL2p-31, AL2p-32, AL2p-38, AL2p-39, AL2p-40, AL2p-41, AL2p-42, AL2p-43, AL2p-44, AL2p-60, and AL2p-61 | KVSNRRS | 134 |
| AL2p-9, AL2p-11, AL2p-16, AL2p-17, AL2p-18, AL2p-19, AL2p-20, AL2p-23, AL2p-25, AL2p-27, AL2p-28, AL2p-33, AL2p-45, AL2p-46, AL2p-47, AL2p-48, AL2p-49, AL2p-50, AL2p-51, AL2p-52, AL2p-53, AL2p-54, AL2p-55, AL2p-56, AL2p-57, and AL2p-59 | KVSNRVS | 140 |
| AL2p-15, AL2p-21, and AL2p-30 | KVSNRKS | 193 |
| Formula V | KVSNR$X_1$S<br>$X_1$ is F, R, V, or K | 128 |

TABLE 3C

Light chain HVR L3 sequences of anti-TREM2 antibodies

| Ab | HVR L3 | SEQ ID NO: |
|---|---|---|
| AL2p-h50, AL2p-2, AL2p-3, AL2p-4, AL2p-5, AL2p-6, AL2p-7, AL2p-8, AL2p-9, AL2p-10, AL2p-11, AL2p-12, AL2p-13, AL2p-14, AL2p-15, AL2p-16, AL2p-17, AL2p-18, AL2p-19, AL2p-20, AL2p-21, AL2p-22, AL2p-23, AL2p-24, AL2p-25, AL2p-26, AL2p-27, AL2p-28, AL2p-29, AL2p-30, AL2p-31, AL2p-32, AL2p-33, AL2p-h77, AL2p-35, AL2p-36, | SQSTRVPYT | 129 |

TABLE 3C-continued

Light chain HVR L3 sequences of anti-TREM2 antibodies

| Ab | HVR L3 | SEQ ID NO: |
|---|---|---|
| AL2p-37, AL2p-38, AL2p-39, AL2p-40, AL2p-41, AL2p-42, AL2p-43, AL2p-44, AL2p-45, AL2p-46, AL2p-47, AL2p-48, AL2p-49, AL2p-50, AL2p-51, AL2p-52, AL2p-53, AL2p-54, AL2p-55, AL2p-56, AL2p-57, AL2p-58, AL2p-59, AL2p-60, AL2p-61, and AL2p-62 | | |

TABLE 4A

Heavy chain framework 1 sequences of anti-TREM2 antibodies

| Ab | VH FR1 | SEQ ID NO: |
|---|---|---|
| AL2p-h50, AL2p-2, AL2p-3, AL2p-4, AL2p-5, AL2p-6, AL2p-7, AL2p-8, AL2p-9, AL2p-10, AL2p-11, AL2p-12, AL2p-13, AL2p-14, AL2p-15, AL2p-16, AL2p-17, AL2p-18, AL2p-19, AL2p-20, AL2p-21, AL2p-22, AL2p-23, AL2p-24, AL2p-25, AL2p-26, AL2p-27, AL2p-28, AL2p-29, AL2p-30, AL2p-31, AL2p-32, AL2p-38, AL2p-39, AL2p-40, AL2p-41, AL2p-42, AL2p-43, AL2p-44, AL2p-45, AL2p-46, AL2p-47, AL2p-48, AL2p-50, AL2p-51, AL2p-54, AL2p-59, AL2p-60, and AL2p-61 | QVQLVQSGAEVKKPGSSVKVSCKASG | 9 |
| AL2p-33, AL2p-49, AL2p-52, AL2p-53, AL2p-55, AL2p-56, and AL2p-57 | EVQLVQSGAEVKKPGSSVKVSCKASG | 10 |
| AL2p-h77, AL2p-35, AL2p-36, AL2p-37, AL2p-58, and AL2p-62 | QVQLVQSGAEVKKPGASVKVSCKASG | 11 |

TABLE 4B

Heavy chain framework 2 sequences of anti-TREM2 antibodies

| Ab | VH FR2 | SEQ ID NO: |
|---|---|---|
| AL2p-h50, AL2p-2, AL2p-3, AL2p-4, AL2p-5, AL2p-6, AL2p-7, AL2p-8, AL2p-9, AL2p-10, AL2p-11, AL2p-12, AL2p-13, AL2p-14, AL2p-15, AL2p-16, AL2p-17, AL2p-18, AL2p-19, AL2p-20, AL2p-21, | WVRQAPGQGLEWMG | 12 |

TABLE 4B-continued

Heavy chain framework 2 sequences of anti-TREM2 antibodies

| Ab | VH FR2 | SEQ ID NO: |
|---|---|---|
| AL2p-22, AL2p-23, AL2p-24, AL2p-25, AL2p-26, AL2p-27, AL2p-28, AL2p-29, AL2p-30, AL2p-31, AL2p-32, AL2p-33, AL2p-38, AL2p-39, AL2p-40, AL2p-41, AL2p-42, AL2p-43, AL2p-44, AL2p-45, AL2p-46, AL2p-47, AL2p-48, AL2p-49, AL2p-50, AL2p-51, AL2p-52, AL2p-53, AL2p-54, AL2p-55, AL2p-56, AL2p-57, AL2p-59, AL2p-60, and AL2p-61 | | |
| AL2p-h77, AL2p-35, AL2p-36, AL2p-37, AL2p-58, and AL2p-62 | WVRQAPGQRLEWIG | 13 |

TABLE 4C

Heavy chain framework 3 sequences of anti-TREM2 antibodies

| Ab | VH FR3 | SEQ ID NO: |
|---|---|---|
| AL2p-h50, AL2p-2, AL2p-3, AL2p-4, AL2p-5, AL2p-6, AL2p-7, AL2p-8, AL2p-9, AL2p-10, AL2p-11, AL2p-12, AL2p-13, AL2p-14, AL2p-15, AL2p-16, AL2p-17, AL2p-18, AL2p-19, AL2p-20, AL2p-21, AL2p-22, AL2p-23, AL2p-24, AL2p-25, AL2p-26, AL2p-27, AL2p-28, AL2p-29, AL2p-30, AL2p-31, AL2p-32, AL2p-33, AL2p-38, AL2p-39, AL2p-40, AL2p-41, AL2p-42, AL2p-43, AL2p-44, AL2p-45, AL2p-46, AL2p-47, AL2p-48, AL2p-49, AL2p-50, AL2p-51, AL2p-52, AL2p-53, AL2p-54, AL2p-55, AL2p-56, AL2p-57, AL2p-59, AL2p-60, and AL2p-61 | RVTITADESTSTAYMELSSLRSEDTAVYYC | 14 |
| AL2p-h77, AL2p-35, AL2p-36, AL2p-37, AL2p-58, and AL2p-62 | RVTITADTSASTAYMELSSLRSEDTAVYYC | 15 |

TABLE 4D

Heavy chain framework 4 sequences of anti-TREM2 antibodies

| Ab | VH FR4 | SEQ ID NO: |
|---|---|---|
| AL2p-h50, AL2p-2, AL2p-3, AL2p-4, AL2p-5, AL2p-6, AL2p-7, AL2p-8, AL2p-9, AL2p-10, AL2p-11, AL2p-12, AL2p-13, AL2p-14, AL2p-15, AL2p-16, AL2p-17, AL2p-18, AL2p-19, AL2p-20, AL2p-21, AL2p-22, AL2p-23, AL2p-24, AL2p-25, AL2p-26, AL2p-27, AL2p-28, AL2p-29, AL2p-30, | WGQGTLVTVSS | 16 |

TABLE 4D-continued

Heavy chain framework 4 sequences of anti-TREM2 antibodies

| Ab | VH FR4 | SEQ ID NO: |
|---|---|---|
| AL2p-31, AL2p-32, AL2p-33, AL2p-h77, AL2p-35, AL2p-36, AL2p-37, AL2p-38, AL2p-39, AL2p-40, AL2p-41, AL2p-42, AL2p-43, AL2p-44, AL2p-45, AL2p-46, AL2p-47, AL2p-48, AL2p-49, AL2p-50, AL2p-51, AL2p-52, AL2p-53, AL2p-54, AL2p-55, AL2p-56, AL2p-57, AL2p-58, AL2p-59, AL2p-60, AL2p-61, and AL2p-62 | | |

TABLE 5A

Light chain framework 1 sequences of anti-TREM2 antibodies

| Ab | VL FR1 | SEQ ID NO: |
|---|---|---|
| AL2p-h50, AL2p-2, AL2p-3, AL2p-4, AL2p-5, AL2p-6, AL2p-11, AL2p-17, AL2p-19, AL2p-45, AL2p-46, AL2p-47, AL2p-48, AL2p-49, AL2p-50, AL2p-51, AL2p-52, AL2p-53, AL2p-54, AL2p-55, AL2p-56, and AL2p-57 | DVVMTQTPLSLSVTPGQPASISC | 17 |
| AL2p-7, AL2p-8, AL2p-9, AL2p-10, AL2p-12, AL2p-13, AL2p-14, AL2p-15, AL2p-16, AL2p-18, AL2p-20, AL2p-21, AL2p-22, AL2p-23, AL2p-24, AL2p-25, AL2p-26, AL2p-27, AL2p-28, AL2p-29, AL2p-30, AL2p-31, AL2p-32, AL2p-38, AL2p-39, AL2p-40, AL2p-41, AL2p-42, AL2p-43, AL2p-44, AL2p-59, AL2p-60, and AL2p-61 | GVVMTQTPLSLSVTPGQPASISC | 18 |
| AL2p-33 | GVVMAQTPLSLSVTPGQPASISC | 19 |
| AL2p-h77, AL2p-35, AL2p-36, AL2p-37, AL2p-58, and AL2p-62 | DVVMTQSPDSLAVSLGERATINC | 20 |

TABLE 5B

Light chain framework 2 sequences of anti-TREM2 antibodies

| Ab | VL FR2 | SEQ ID NO: |
|---|---|---|
| AL2p-h50, AL2p-2, AL2p-3, AL2p-4, AL2p-5, AL2p-6, | WYLQKPGQSPQLLIY | 21 |
| AL2p-7, AL2p-8, AL2p-9, AL2p-10, AL2p-11, AL2p-12, AL2p-13, AL2p-14, AL2p-15, AL2p-16, AL2p-17, AL2p-18, AL2p-19, AL2p-20, AL2p-21, AL2p-22, AL2p-23, AL2p-24, AL2p-25, AL2p-26, AL2p-27, AL2p-28, AL2p-29, AL2p-30, AL2p-31, AL2p-32, AL2p-33, AL2p-38, AL2p-39, AL2p-40, AL2p-41, AL2p-42, AL2p-43, AL2p-44, AL2p-45, AL2p-46, AL2p-47, AL2p-48, AL2p-49, AL2p-50, AL2p-51, AL2p-52, AL2p-53, AL2p-54, AL2p-55, AL2p-56, AL2p-57, AL2p-59, AL2p-60, and AL2p-61 | | |
| AL2p-h77, AL2p-35, AL2p-36, AL2p-37, AL2p-58, and AL2p-62 | WYQQKPGQSPKLLIY | 22 |

TABLE 5C

Light chain framework 3 sequences of anti-TREM2 antibodies

| Ab | VL FR3 | SEQ ID NO: |
|---|---|---|
| AL2p-h50, AL2p-2, AL2p-3, AL2p-4, AL2p-5, AL2p-6, AL2p-7, AL2p-8, AL2p-9, AL2p-10, AL2p-11, AL2p-12, AL2p-13, AL2p-14, AL2p-15, AL2p-16, AL2p-17, AL2p-18, AL2p-19, AL2p-20, AL2p-21, AL2p-22, AL2p-23, AL2p-24, AL2p-25, AL2p-26, AL2p-27, AL2p-28, AL2p-29, AL2p-30, AL2p-31, AL2p-32, AL2p-33, AL2p-38, AL2p-39, AL2p-40, AL2p-41, AL2p-42, AL2p-43, AL2p-44, AL2p-45, AL2p-46, AL2p-47, AL2p-48, AL2p-49, AL2p-50, AL2p-51, AL2p-52, AL2p-53, AL2p-54, AL2p-55, AL2p-56, AL2p-57, AL2p-58, AL2p-59, AL2p-60, and AL2p-61 | GVPDRFSGSGSGTDFTLKI SRVEAEDVGVYYC | 23 |
| AL2p-h77, AL2p-35, AL2p-36, AL2p-37, and AL2p-62 | GVPDRFSGSGSGTDFTLTI SSLQAEDVAVYYC | 24 |

TABLE 5D

Light chain framework 4 sequences of anti-TREM2 antibodies

| Ab | VL FR4 | SEQ ID NO: |
|---|---|---|
| AL2p-h50, AL2p-2, AL2p-3, AL2p-4, AL2p-5, AL2p-6, AL2p-7, AL2p-8, AL2p-9, AL2p-10, AL2p-11, AL2p-12, AL2p-13, AL2p-14, AL2p-15, AL2p-16, AL2p-17, AL2p-18, AL2p-19, AL2p-20, AL2p-21, AL2p-22, AL2p-23, AL2p-24, AL2p-25, AL2p-26, AL2p-27, AL2p-28, AL2p-29, AL2p-30, AL2p-31, AL2p-32, AL2p-33, AL2p-38, AL2p-39, AL2p-40, AL2p-41, AL2p-42, AL2p-43, AL2p-44, AL2p-45, AL2p-46, AL2p-47, AL2p-48, AL2p-49, AL2p-50, AL2p-51, AL2p-52, AL2p-53, AL2p-54, AL2p-55, AL2p-56, AL2p-57, AL2p-58, AL2p-59, AL2p-60, and AL2p-61 | FGQGTKLEIK | 25 |
| AL2p-h77, AL2p-35, AL2p-36, AL2p-37, and AL2p-62 | FGGGTKVEIK | 26 |

TABLE 6A

Heavy chain variable region sequences of anti-TREM2 antibodies

| Ab | HCVR | SEQ ID NO: |
|---|---|---|
| AL2p-h50, AL2p-5, and AL2p-6 | QVQLVQSGAEVKKPGSSVKVSCKASGYAFSSSWM NWVRQAPGQGLEWMGRIYPGDGDTNYAQKFQGR VTITADESTSTAYMELSSLRSEDTAVYYCARLLRN QPGESYAMDYWGQGTLVTVSS | 27 |
| AL2p-2 | QVQLVQSGAEVKKPGSSVKVSCKASGYAFSSSWM NWVRQAPGQGLEWMGRIYPGGGDTNYAQKFQGR VTITADESTSTAYMELSSLRSEDTAVYYCARLLRN QPGESYAMDYWGQGTLVTVSS | 28 |
| AL2p-3 | QVQLVQSGAEVKKPGSSVKVSCKASGYAFSSSWM NWVRQAPGQGLEWMGRIYPGEGDTNYAQKFQGR VTITADESTSTAYMELSSLRSEDTAVYYCARLLRN QPGESYAMDYWGQGTLVTVSS | 29 |
| AL2p-4 | QVQLVQSGAEVKKPGSSVKVSCKASGYAFSSSWM NWVRQAPGQGLEWMGRIYPGQGDTNYAQKFQGR VTITADESTSTAYMELSSLRSEDTAVYYCARLLRN QPGESYAMDYWGQGTLVTVSS | 30 |
| AL2p-7 | QVQLVQSGAEVKKPGSSVKVSCKASGYAFSLSWM NWVRQAPGQGLEWMGRIYPGDGDTNYAQKFRGR VTITADESTSTAYMELSSLRSEDTAVYYCARLLRN QPGESYAMDYWGQGTLVTVSS | 31 |
| AL2p-8 | QVQLVQSGAEVKKPGSSVKVSCKASGYAFSLSWM NWVRQAPGQGLEWMGRIYPGDGDTNYARKFQGR VTITADESTSTAYMELSSLRSEDTAVYYCARLLRN QPGSSYAMDYWGQGTLVTVSS | 32 |
| AL2p-9 | QVQLVQSGAEVKKPGSSVKVSCKASGYAFSRSWM NWVRQAPGQGLEWMGRIYPGDGDTNYAQKFQGR VTITADESTSTAYMELSSLRSEDTAVYYCARLLRN QPGASYAMDYWGQGTLVTVSS | 33 |
| AL2p-10 | QVQLVQSGAEVKKPGSSVKVSCKASGYAFSSDW MNWVRQAPGQGLEWMGRIYPGDGDTNYAQKFQ GRVTITADESTSTAYMELSSLRSEDTAVYYCARLL RNQPGESYAMDYWGQGTLVTVSS | |

TABLE 6A-continued

Heavy chain variable region sequences of anti-TREM2 antibodies

| Ab | HCVR | SEQ ID NO: |
|---|---|---|
| AL2p-11 | QVQLVQSGAEVKKPGSSVKVSCKASGYAFSSDW MNWVRQAPGQGLEWMGRIYPGDGDTNYARKFQ GRVTITADESTSTAYMELSSLRSEDTAVYYCARLL RNQPGESYAMDYWGQGTLVTVSS | 35 |
| AL2p-12 | QVQLVQSGAEVKKPGSSVKVSCKASGYAFSSHW MNWVRQAPGQGLEWMGRIYPGDGDTNYAHKFQ GRVTITADESTSTAYMELSSLRSEDTAVYYCARLL RNQPGESYAMDYWGQGTLVTVSS | 36 |
| AL2p-13 | QVQLVQSGAEVKKPGSSVKVSCKASGYAFSSHW MNWVRQAPGQGLEWMGRIYPGDGDTNYAQKFK GRVTITADESTSTAYMELSSLRSEDTAVYYCARLL RNQPGESYAMDYWGQGTLVTVSS | 37 |
| AL2p-14 and AL2p-15 | QVQLVQSGAEVKKPGSSVKVSCKASGYAFSSHW MNWVRQAPGQGLEWMGRIYPGDGDTNYAQKFQ GRVTITADESTSTAYMELSSLRSEDTAVYYCARLL RNQPGESYAMDYWGQGTLVTVSS | 38 |
| AL2p-16 | QVQLVQSGAEVKKPGSSVKVSCKASGYAFSSHW MNWVRQAPGQGLEWMGRIYPGDGDTNYAQKFR GRVTITADESTSTAYMELSSLRSEDTAVYYCARLL RNQPGASYAMDYWGQGTLVTVSS | 39 |
| AL2p-17 | QVQLVQSGAEVKKPGSSVKVSCKASGYAFSSHW MNWVRQAPGQGLEWMGRIYPGDGDTNYAQKRQ GRVTITADESTSTAYMELSSLRSEDTAVYYCARLL RNQPGESYAMDYWGQGTLVTVSS | 40 |
| AL2p-18 | QVQLVQSGAEVKKPGSSVKVSCKASGYAFSSHW MNWVRQAPGQGLEWMGRIYPGDGDTNYAQKWQ GRVTITADESTSTAYMELSSLRSEDTAVYYCARLL RNQPGSSYAMDYWGQGTLVTVSS | 41 |
| AL2p-19 and AL2p-20 | QVQLVQSGAEVKKPGSSVKVSCKASGYAFSSHW MNWVRQAPGQGLEWMGRIYPGDGDTNYARKFQ GRVTITADESTSTAYMELSSLRSEDTAVYYCARLL RNQPGESYAMDYWGQGTLVTVSS | 42 |
| AL2p-21 | QVQLVQSGAEVKKPGSSVKVSCKASGYAFSSHW MNWVRQAPGQGLEWMGRIYPGDGDTNYAWKFQ GRVTITADESTSTAYMELSSLRSEDTAVYYCARLL RNQPGESYAMDYWGQGTLVTVSS | 43 |
| AL2p-22 | QVQLVQSGAEVKKPGSSVKVSCKASGYAFSSHW MNWVRQAPGQGLEWMGRIYPGDGDTNYAYKFQ GRVTITADESTSTAYMELSSLRSEDTAVYYCARLL RNQPGESYAMDYWGQGTLVTVSS | 44 |
| AL2p-23 | QVQLVQSGAEVKKPGSSVKVSCKASGYAFSSHW MNWVRQAPGQGLEWMGRIYPGDGQTNYAQKRQ GRVTITADESTSTAYMELSSLRSEDTAVYYCARLL RNQPGESYAMDYWGQGTLVTVSS | 45 |
| AL2p-24 | QVQLVQSGAEVKKPGSSVKVSCKASGYAFSSHW MNWVRQAPGQGLEWMGRIYPGGGDTNYAQKFQ GRVTITADESTSTAYMELSSLRSEDTAVYYCARLL RNQPGESYAMDYWGQGTLVTVSS | 46 |
| AL2p-25 | QVQLVQSGAEVKKPGSSVKVSCKASGYAFSSHW MNWVRQAPGQGLEWMGRIYPGGGDTNYAQKFR GRVTITADESTSTAYMELSSLRSEDTAVYYCARLL RNQPGESYAMDYWGQGTLVTVSS | 47 |
| AL2p-26 | QVQLVQSGAEVKKPGSSVKVSCKASGYAFSSHW MNWVRQAPGQGLEWMGRIYPGGGDTNYAQKRQ GRVTITADESTSTAYMELSSLRSEDTAVYYCARLL RNQPGESYAMDYWGQGTLVTVSS | 48 |

34

TABLE 6A-continued

Heavy chain variable region sequences of anti-TREM2 antibodies

| Ab | HCVR | SEQ ID NO: |
|---|---|---|
| AL2p-27 | QVQLVQSGAEVKKPGSSVKVSCKASGYAFSSHWMNWVRQAPGQGLEWMGRIYPGQGDTNYAQKFQGRVTITADESTSTAYMELSSLRSEDTAVYYCARLLRNQPGESYAMDYWGQGTLVTVSS | 49 |
| AL2p-28 | QVQLVQSGAEVKKPGSSVKVSCKASGYAFSSHWMNWVRQAPGQGLEWMGRIYPGVGDTNYAQKFQGRVTITADESTSTAYMELSSLRSEDTAVYYCARLLRNQPGESYAMDYWGQGTLVTVSS | 50 |
| AL2p-29 | QVQLVQSGAEVKKPGSSVKVSCKASGYAFSSQWMNWVRQAPGQGLEWMGRIYPGDGDTNYAQKFQGRVTITADESTSTAYMELSSLRSEDTAVYYCARLLRNQPGESYAMDYWGQGTLVTVSS | 51 |
| AL2p-30 | QVQLVQSGAEVKKPGSSVKVSCKASGYAFSSQWMNWVRQAPGQGLEWMGRIYPGDGDTNYAWKFQGRVTITADESTSTAYMELSSLRSEDTAVYYCARLLRNQPGESYAMDYWGQGTLVTVSS | 52 |
| AL2p-31, AL2p-60, and AL2p-h31 | QVQLVQSGAEVKKPGSSVKVSCKASGYAFSSQWMNWVRQAPGQGLEWMGRIYPGGGDTNYARKFQGRVTITADESTSTAYMELSSLRSEDTAVYYCARLLRNQPGESYAMDYWGQGTLVTVSS | 53 |
| AL2p-32 | QVQLVQSGAEVKKPGSSVKVSCKASGYAFSSEWMNWVRQAPGQGLEWMGRIYPGDGDTNYAQKFQGRVTITADESTSTAYMELSSLRSEDTAVYYCARLLRNQPGESYAMDYWGQGTLVTVSS | 54 |
| AL2p-33 | EVQLVQSGAEVKKPGSSVKVSCKASGYAFSSSWMNWVRQAPGQGLEWMGRIYPGDGDTNYAQKFQGRVTITADESTSTAYMELSSLRSEDTAVYYCARLLRNQPGESYAMDYWGQGTLVTVSS | 55 |
| AL2p-h77, AL2p-h26, and AL2p-h90 | QVQLVQSGAEVKKPGASVKVSCKASGYAFSSSWMNWVRQAPGQRLEWIGRIYPGDGDTNYAQKFQGRVTITADTSASTAYMELSSLRSEDTAVYYCARLLRNQPGESYAMDYWGQGTLVTVSS | 56 |
| AL2p-35 | QVQLVQSGAEVKKPGASVKVSCKASGYAFWSSWMNWVRQAPGQRLEWIGRIYPGDGDTNYAQKFQGRVTITADTSASTAYMELSSLRSEDTAVYYCARLLRNQPGESYAHDYWGQGTLVTVSS | 57 |
| AL2p-36 | QVQLVQSGAEVKKPGASVKVSCKASGYAFSSSWMNWVRQAPGQRLEWIGRIYPGDGDTNYARKFQGRVTITADTSASTAYMELSSLRSEDTAVYYCARLLRNQPGASYAMDYWGQGTLVTVSS | 58 |
| AL2p-37 and AL2p-58 | QVQLVQSGAEVKKPGASVKVSCKASGYAFSSQWMNWVRQAPGQRLEWIGRIYPGGGDTNYAGKFQGRVTITADTSASTAYMELSSLRSEDTAVYYCARLLRNQPGESYAMDYWGQGTLVTVSS | 59 |
| AL2p-38, AL2p-39, and AL2p-40 | QVQLVQSGAEVKKPGSSVKVSCKASGYAFSSHWMNWVRQAPGQGLEWMGRIYPGGGDTNYAQKFRGRVTITADESTSTAYMELSSLRSEDTAVYYCARLLRNQPGASYAMDYWGQGTLVTVSS | 60 |
| AL2p-41 and AL2p-42 | QVQLVQSGAEVKKPGSSVKVSCKASGYAFSSHWMNWVRQAPGQGLEWMGRIYPGEGDTNYAQKFRGRVTITADESTSTAYMELSSLRSEDTAVYYCARLLRNQPGASYAMDYWGQGTLVTVSS | 61 |
| AL2p-43 and AL2p-44 | QVQLVQSGAEVKKPGSSVKVSCKASGYAFSSHWMNWVRQAPGQGLEWMGRIYPGEGDTNYARKFRGRVTITADESTSTAYMELSSLRSEDTAVYYCARLLRNQPGASYAMDYWGQGTLVTVSS | 62 |
| AL2p-45 and AL2p-46 | QVQLVQSGAEVKKPGSSVKVSCKASGYAFSSDWMNWVRQAPGQGLEWMGRIYPGEGDTNYARKFQGRVTITADESTSTAYMELSSLRSEDTAVYYCARLLRNKPGESYAMDYWGQGTLVTVSS | 63 |
| AL2p-47 and AL2p-48 | QVQLVQSGAEVKKPGSSVKVSCKASGYAFSSDWMNWVRQAPGQGLEWMGRIYPGEGDTNYARKFHGRVTITADESTSTAYMELSSLRSEDTAVYYCARLLRNKPGESYAMDYWGQGTLVTVSS | 64 |
| AL2p-49 | EVQLVQSGAEVKKPGSSVKVSCKASGYAFSSDWMNWVRQAPGQGLEWMGRIYPGEGDTNYARKFHGRVTITADESTSTAYMELSSLRSEDTAVYYCARLLRNKPGESYAMDYWGQGTLVTVSS | 65 |
| AL2p-50 and AL2p-51 | QVQLVQSGAEVKKPGSSVKVSCKASGYAFSSHWMNWVRQAPGQGLEWMGRIYPGEGDTNYAQKFHGRVTITADESTSTAYMELSSLRSEDTAVYYCARLLRNQPGESYAMDYWGQGTLVTVSS | 66 |
| AL2p-52 and AL2p-53 | EVQLVQSGAEVKKPGSSVKVSCKASGYAFSSHWMNWVRQAPGQGLEWMGRIYPGEGDTNYAQKFHGRVTITADESTSTAYMELSSLRSEDTAVYYCARLLRNQPGESYAMDYWGQGTLVTVSS | 67 |
| AL2p-54 | QVQLVQSGAEVKKPGSSVKVSCKASGYAFSSHWMNWVRQAPGQGLEWMGRIYPGEGDTNYAQKFHGRVTITADESTSTAYMELSSLRSEDTAVYYCARLLRNKPGESYAMDYWGQGTLVTVSS | 68 |
| AL2p-55, AL2p-56, and AL2p-57 | EVQLVQSGAEVKKPGSSVKVSCKASGYAFSSHWMNWVRQAPGQGLEWMGRIYPGEGDTNYAQKFHGRVTITADESTSTAYMELSSLRSEDTAVYYCARLLRNKPGESYAMDYWGQGTLVTVSS | 69 |
| AL2p-61 | QVQLVQSGAEVKKPGSSVKVSCKASGYAFSSQWMNWVRQAPGQGLEWMGRIYPGEGDTNYARKFQGRVTITADESTSTAYMELSSLRSEDTAVYYCARLLRNQPGESYAMDYWGQGTLVTVSS | 70 |
| AL2p-62 | QVQLVQSGAEVKKPGASVKVSCKASGYAFSSQWMNWVRQAPGQRLEWIGRIYPGEGDTNYAGKFQGRVTITADTSASTAYMELSSLRSEDTAVYYCARLLRNQPGESYAMDYWGQGTLVTVSS | 71 |
| AL2p-h19 and AL2p-h35 | QVQLVQSGAEVKKPGSSVKVSCKASGYAFSSSWMNWVRQAPGQGLEWMGRIYPGDGDTNYAQKFQGRATITADTSTSTAYMELSSLRSEDTAVYYCARLLRNQPGESYAMDYWGQGTLVTVSS | 72 |
| AL2p-h21 | QVQLVQSGAEVKKPGASVKVSCKASGYAFSSSWMNWVRQAPGQGLEWMGRIYPGDGDTNYAQKFQGRVTMTRDTSTSTVYMELSSLRSEDTAVYYCARLLRNQPGESYAMDYWGQGTLVTVSS | 73 |
| AL2p-h22 | QVQLVQSGAEVKKPGASVKVSCKASGYAFSSSWMNWVRQAPGQGLEWIGRIYPGDGDTNYAQKFQGRVTMTADTSTSTVYMELSSLRSEDTAVYYCARLLRNQPGESYAMDYWGQGTLVTVSS | 74 |
| AL2p-h23 | QVQLVQSGAEVKKPGASLKISCKASGYAFSSSWMNWVRQAPGQGLEWIGRIYPGDGDTNYAQKFQGRATLTADTSTSTAYMELSSLRSEDTAVYYCARLLRNQPGESYAMDYWGQGALVTVSS | 75 |
| AL2p-h24 | QVQLVQSGAEVVKPGASLKISCKASGYAFSSSWMNWVRQAPGQGLEWIGRIYPGDGDTNYNQKFQGRATLTADTSTSTAYMELSSLRSEDTAVYFCARLLRNQPGESYAMDYWGQGALVTVSS | 76 |
| AL2p-h25 | QVQLVQSGAEVKKPGASLKISCKASGYAFSSSWMNWVRQAPGQGLEWIGRIYPGDGDTNYNGEFRVRATLTADTSTSTAYMELSSLRSEDTAVYYCARLLRNQPGESYAMDYWGQGALVTVSS | 77 |

TABLE 6A-continued

Heavy chain variable region sequences of anti-TREM2 antibodies

| Ab | HCVR | SEQ ID NO: |
|---|---|---|
| AL2p-h27 | QVQLVQSGAEVKKPGASVKVSCKASGYAFSSSWMNWVRQAPGQGLEWIGRIYPGDGDTNYNGEFRVRATLTADTSTSTAYMELSSLRSEDTAVYFCARLLRNQPGESYAMDYWGQGTLVTVSS | 78 |
| AL2p-h28 | QVQLVQSGAEVKKPGASVKVSCKASGYAFSSSWMNWVRQAPGQGLEWIGRIYPGDGDTNYAQKFQGRATLTADTSTSTAYMELSSLRSEDTAVYFCARLLRNQPGESYAMDYWGQGTLVTVSS | 79 |
| AL2p-h29 | QVQLVQSGAEVKKPGASVKVSCKASGYAFSSSWMNWVRQAPGQGLEWIGRIYPGDGDTNYAQKFQGRATMTADTSTSTAYMELSSLRSEDTAVYYCARLLRNQPGESYAMDYWGQGTLVTVSS | 80 |
| AL2p-h30 | QVQLVQSGAEVKKPGASVKVSCKASGYAFSSSWMNWVRQAPGQGLEWMGRIYPGDGDTNYAQKFQGRVTMTADTSTSTAYMELSSLRSEDTAVYYCARLLRNQPGESYAMDYWGQGTLVTVSS | 81 |
| AL2p-h32 | QVQLVQSGAEVKKPGSSVKVSCKASGYAFSSSWMNWVRQAPGQGLEWIGRIYPGDGDTNYNGEFRVRATLTADTSTSTAYMELSSLRSEDTAVYFCARLLRNQPGESYAMDYWGQGTLVTVSS | 82 |
| AL2p-h33 | QVQLVQSGAEVKKPGSSVKVSCKASGYAFSSSWMNWVRQAPGQGLEWIGRIYPGDGDTNYAQKFQGRATLTADTSTSTAYMELSSLRSEDTAVYFCARLLRNQPGESYAMDYWGQGTLVTVSS | 83 |
| AL2p-h34 | QVQLVQSGAEVKKPGSSVKVSCKASGYAFSSSWMNWVRQAPGQGLEWIGRIYPGDGDTNYAQKFQGRATITADTSTSTAYMELSSLRSEDTAVYFCARLLRNQPGESYAMDYWGQGTLVTVSS | 84 |
| AL2p-h36 | EVQLLESGGGLVQPGGSLRLSCAASGYAFSSSWMNWVRQAPGKGLEWIGRIYPGDGDTNYAQKFQGRATISADTSKNTAYLQMNSLRAEDTAVYYCARLLRNQPGESYAMDYWGQGTLVTVSS | 85 |
| AL2p-h42 and AL2p-h59 | QVQLVQSGAEVKKPGASVKVSCKASGYAFSSSWMNWVRQAPGQRLEWMGRIYPGDGDTNYAQKFQGRVTITRDTSASTAYMELSSLRSEDTAVYYCARLLRNQPGESYAMDYWGQGTLVTVSS | 86 |
| AL2p-h43 | QVQLVQSGAEVKKPGASLKVSCKASGYAFSSSWMNWVRQAPGQRLEWIGRIYPGDGDTNYNGEFRVRATLTADTSASTAYMELSSLRSEDTAVYFCARLLRNQPGESYAMDYWGQGTLVTVSS | 87 |
| AL2p-h44 | QVQLVQSGAEVKKPGASLKVSCKASGYAFSSSWMNWVRQAPGQRLEWIGRIYPGDGDTNYAQKFQGRATLTADTSASTAYMELSSLRSEDTAVYYCARLLRNQPGESYAMDYWGQGTLVTVSS | 88 |
| AL2p-h47 | QVQLVQSGAEVKKPGASVKVSCKASGYAFSSSWMNWVRQAPGQGLEWMGRIYPGDGDTNYNGEFRVRVTMTRDTSTSTVYMELSSLRSEDTAVYFCARLLRNQPGESYAMDYWGQGTLVTVSS | 89 |
| AL2p-h76 | QVQLVQSGAEVKKPGASVKVSCKASGYAFSSSWMNWVRQAPGQRLEWIGRIYPGDGDTNYAQKFQGRATITADTSASTAYMELSSLRSEDTAVYFCARLLRNQPGESYAMDYWGQGTLVTVSS | 90 |
| AL2p-59 | QVQLVQSGAEVKKPGSSVKVSCKASGYAFSSHWMNWVRQAPGQGLEWMGRIYPGEGQTNYAQKRQGRVTITADESTSTAYMELSSLRSEDTAVYYCARLLRNQPGESYAMDYWGQGTLVTVSS | 91 |

TABLE 6B

Heavy chain sequences of anti-TREM2 antibodies

| Ab | HC | SEQ ID NO: |
|---|---|---|
| AL2p-58 huIgG1 | QVQLVQSGAEVKKPGASVKVSCKASGYAFSSQWMNWVRQAPGQRLEWIGRIYPGGGDTNYAGKFQGRVTITADTSASTAYMELSSLRSEDTAVYYCARLLRNQPGESYAMDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK | 198 |
| AL2p-58 huIgG1 | QVQLVQSGAEVKKPGASVKVSCKASGYAFSSQWMNWVRQAPGQRLEWIGRIYPGGGDTNYAGKFQGRVTITADTSASTAYMELSSLRSEDTAVYCARLLRNQPGESYAMDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPG | 199 |
| AL2p-58 huIgG1 PSEG | QVQLVQSGAEVKKPGASVKVSCKASGYAFSSQWMNWVRQAPGQRLEWIGRIYPGGGDTNYAGKFQGRVTITADTSASTAYMELSSLRSEDTAVYYCARLLRNQPGESYAMDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPASIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHGALHNHYTQKSLSLSPGK | 200 |
| AL2p-58 huIgG1 PSEG | QVQLVQSGAEVKKPGASVKVSCKASGYAFSSQWMNWVRQAPGQRLEWIGRIYPGGGDTNYAGKFQGRVTITADTSASTAYMELSSLRSEDTAVYYCARLLRNQPGESYAMDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPASIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHGALHNHYTQKSLSLSPG | 201 |
| AL2p-47 huIgG1 | QVQLVQSGAEVKKPGSSVKVSCKASGYAFSSDWMNWVRQAPGQGLEWMGRIYPEGDTNYARKFHGRVTITADESTSTAYMELSSLRSEDTAVYYCARLLRNKPGESYAMDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK | 202 |

TABLE 6B-continued

Heavy chain sequences of anti-TREM2 antibodies

| Ab | HC | SEQ ID NO: |
|---|---|---|
| AL2p-47 huIgG1 | QVQLVQSGAEVKKPGSSVKVSCKASGYAFSSDWMNWVRQAPGQGLEWMGRIYPGEGDTNYARKFHGRVTITADESTSTAYMELSSLRSEDTAVYYCARLLRNKPGESYAMDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPG | 203 |
| AL2p-47 huIgG1 PSEG | QVQLVQSGAEVKKPGSSVKVSCKASGYAFSSDWMNWVRQAPGQGLEWMGRIYPGEGDTNYARKFHGRVTITADESTSTAYMELSSLRSEDTAVYYCARLLRNKPGESYAMDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPASIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHGALHNHYTQKSLSLSPGK | 204 |
| AL2p-47 huIgG1 PSEG | QVQLVQSGAEVKKPGSSVKVSCKASGYAFSSDWMNWVRQAPGQGLEWMGRIYPGEGDTNYARKFHGRVTITADESTSTAYMELSSLRSEDTAVYYCARLLRNKPGESYAMDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPASIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHGALHNHYTQKSLSLSPG | 205 |
| AL2p-61 huIgG1 | QVQLVQSGAEVKKPGSSVKVSCKASGYAFSSQWMNWVRQAPGQGLEWMGRIYPGEGDTNYARKFQGRVTITADESTSTAYMELSSLRSEDTAVYYCARLLRNQPGESYAMDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK | 206 |
| AL2p-61 huIgG1 | QVQLVQSGAEVKKPGSSVKVSCKASGYAFSSQWMNWVRQAPGQGLEWMGRIYPGEGDTNYARKFQGRVTITADESTSTAYMELSSLRSEDTAVYYCARLLRNQPGESYAMDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPG | 207 |
| AL2p-40 huIgG1 | QVQLVQSGAEVKKPGSSVKVSCKASGYAFSSHWMNWVRQAPGQGLEWMGRIYPGGGDTNYAQKFRGRVTITADESTSTAYMELSSLRSEDTAVYYCARLLRNQPGASYAMDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK | 208 |
| AL2p-40 huIgG1 | QVQLVQSGAEVKKPGSSVKVSCKASGYAFSSHWMNWVRQAPGQGLEWMGRIYPGGGDTNYAQKFRGRVTITADESTSTAYMELSSLRSEDTAVYYCARLLRNQPGASYAMDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPG | 209 |
| AL2p-44 huIgG1 | QVQLVQSGAEVKKPGSSVKVSCKASGYAFSSHWMNWVRQAPGQGLEWMGRIYPGGGDTNYARKFRGRVTITADESTSTAYMELSSLRSEDTAVYYCARLLRNQPGASYAMDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK | 210 |
| AL2p-44 huIgG1 | QVQLVQSGAEVKKPGSSVKVSCKASGYAFSSHWMNWVRQAPGQGLEWMGRIYPGGGDTNYARKFRGRVTITADESTSTAYMELSSLRSEDTAVYYCARLLRNQPGASYAMDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPG | 211 |
| AL2p-41 huIgG1 | QVQLVQSGAEVKKPGSSVKVSCKASGYAFSSHWMNWVRQAPGQGLEWMGRIYPGEGDTNYAQKFRGRVTITADESTSTAYMELSSLRSEDTAVYYCARLLRNQPGASYAMDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKA | 212 |

TABLE 6B-continued

Heavy chain sequences of anti-TREM2 antibodies

| Ab | HC | SEQ ID NO: |
|---|---|---|
|  | KGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK |  |
| AL2p-41 huIgG1 | QVQLVQSGAEVKKPGSSVKVSCKASGYAFSSHWMNWVRQAPGQGLEWMGRIYPGEGDTNYAQKFRGRVTITADESTSTAYMELSSLRSEDTAVYYCARLLRNQPGASYAMDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPG | 213 |

TABLE 7A

Light chain variable region sequences of anti-TREM2 antibodies

| Ab | LCVR | SEQ ID NO: |
|---|---|---|
| AL2p-h50, AL2p-2, AL2p-3, AL2p-4, AL2p-h42, AL2p-h43, AL2p-h44, and AL2p-h47 | DVVMTQTPLSLSVTPGQPASISCRSSQSLVHSNGYTYLHWYLQKPGQSPQLLIYKVSNRFSGVPDRFSGSGSGTDFTLKISRVEAEDVGVYYCSQSTRVPYTFGQGTKLEIK | 92 |
| AL2p-5 | DVVMTQTPLSLSVTPGQPASISCRSSQSLVHSNRYTYLHWYLQKPGQSPQLLIYKVSNRFSGVPDRFSGSGSGTDFTLKISRVEAEDVGVYYCSQSTRVPYTFGQGTKLEIK | 93 |
| AL2p-6 | DVVMTQTPLSLSVTPGQPASISCRSSQSLVHSNWYTYLHWYLQKPGQSPQLLIYKVSNRFSGVPDRFSGSGSGTDFTLKISRVEAEDVGVYYCSQSTRVPYTFGQGTKLEIK | 94 |
| AL2p-7, AL2p-8, AL2p-13, and AL2p-26 | GVVMTQTPLSLSVTPGQPASISCRSSQSLIHSNGYTYLHWYLQKPGQSPQLLIYKVSNRRSGVPDRFSGSGSGTDFTLKISRVEAEDVGVYYCSQSTRVPYTFGQGTKLEIK | 95 |
| AL2p-9, AL2p-16, AL2p-18, AL2p-20, AL2p-23, AL2p-25, and AL2p-28 | GVVMTQTPLSLSVTPGQPASISCRTSQSLVHSNGYTYLHWYLQKPGQSPQLLIYKVSNRVSGVPDRFSGSGSGTDFTLKISRVEAEDVGVYYCSQSTRVPYTFGQGTKLEIK | 96 |
| AL2p-10, AL2p-12, AL2p-31, and AL2p-32 | GVVMTQTPLSLSVTPGQPASISCRSSQSLVHSNGYTYLHWYLQKPGQSPQLLIYKVSNRRSGVPDRFSGSGSGTDFTLKISRVEAEDVGVYYCSQSTRVPYTFGQGTKLEIK | 97 |
| AL2p-11, AL2p-17, and AL2p-19 | DVVMTQTPLSLSVTPGQPASISCRSSRSLVHSNGYTYLHWYLQKPGQSPQLLIYKVSNRVSGVPDRFSGSGSGTDFTLKISRVEAEDVGVYYCSQSTRVPYTFGQGTKLEIK | 98 |
| AL2p-14, AL2p-24, and AL2p-29 | GVVMTQTPLSLSVTPGQPASISCRSSRSLVHSNGYTYLHWYLQKPGQSPQLLIYKVSNRFSGVPDRFSGSGSGTDFTLKISRVEAEDVGVYYCSQSTRVPYTFGQGTKLEIK | 99 |
| AL2p-15, AL2p-21, and AL2p-30 | GVVMTQTPLSLSVTPGQPASISCRSSSSLVHSNGYTYLHWYLQKPGQSPQLLIYKVSNRKSGVPDRFSGSGSGTDFTLKISRVEAEDVGVYYCSQSTRVPYTFGQGTKLEIK | 100 |
| AL2p-22 | GVVMTQTPLSLSVTPGQPASISCRSSRSLVHSNGYTYLHWYLQKPGQSPQLLIYKVSNRRSGVPDRFSGSGSGTDFTLKISRVEAEDVGVYYCSQSTRVPYTFGQGTKLEIK | 101 |
| AL2p-27 | GVVMTQTPLSLSVTPGQPASISCRSSRSLVHSNGYTYLHWYLQKPGQSPQLLIYKVSNRVSGVPDRFSGSGSGTDFTLKISRVEAEDVGVYYCSQSTRVPYTFGQGTKLEIK | 102 |
| AL2p-33 | GVVMAQTPLSLSVTPGQPASISCRTSQSLVHSNGYTYLHWYLQKPGQSPQLLIYKVSNRVSGVPDRFSGSGSGTDFTLKISRVEAEDVGVYYCSQSTRVPYTFGQGTKLEIK | 103 |
| AL2p-h77, AL2p-35, AL2p-36, AL2p-37, and AL2p-h76 | DVVMTQSPDSLAVSLGERATINCRSSQSLVHSNGYTYLHWYQQKPGQSPKLLIYKVSNRFSGVPDRFSGSGSGTDFTLTISSLQAEDVAVYYCSQSTRVPYTFGGGTKVEIK | 104 |
| AL2p-38 and AL2p-43 | GVVMTQTPLSLSVTPGQPASISCRSSRSLVHSNRYTYLHWYLQKPGQSPQLLIYKVSNRRSGVPDRFSGSGSGTDFTLKISRVEAEDVGVYYCSQSTRVPYTFGQGTKLEIK | 105 |
| AL2p-39 and AL2p-41 | GVVMTQTPLSLSVTPGQPASISCRSSRSLVHSNQYTYLHWYLQKPGQSPQLLIYKVSNRRSGVPDRFSGSGSGTDFTLKISRVEAEDVGVYYCSQSTRVPYTFGQGTKLEIK | 106 |
| AL2p-40, AL2p-42, and AL2p-44 | GVVMTQTPLSLSVTPGQPASISCRTSRSLVHSNRYTYLHWYLQKPGQSPQLLIYKVSNRRSGVPDRFSGSGSGTDFTLKISRVEAEDVGVYYCSQSTRVPYTFGQGTKLEIK | 107 |
| AL2p-45, AL2p-47, AL2p-50, AL2p-52, AL2p-55, and AL2p-56 | DVVMTQTPLSLSVTPGQPASISCRTSQSLVHSNAYTYLHWYLQKPGQSPQLLIYKVSNRVSGVPDRFSGSGSGTDFTLKISRVEAEDVGVYYCSQSTRVPYTFGQGTKLEIK | 108 |
| AL2p-46, AL2p-48, AL2p-49, AL2p-51, AL2p-53, AL2p-54, and AL2p-57 | DVVMTQTPLSLSVTPGQPASISCRTSQSLVHSNQYTYLHWYLQKPGQSPQLLIYKVSNRVSGVPDRFSGSGSGTDFTLKISRVEAEDVGVYYCSQSTRVPYTFGQGTKLEIK | 109 |

TABLE 7A-continued

Light chain variable region sequences of anti-TREM2 antibodies

| Ab | LCVR | SEQ ID NO: |
|---|---|---|
| AL2p-61 | GVVMTQTPLSLSVTPGQPASISCRSSQSLVHSNQYTYLHWYLQKPGQSPQLLIYKVSNRRSGVPDRFSGSGSGTDFTLKISRVEAEDVGVYYCSQSTRVPYTFGQGTKLEIK | 110 |
| AL2p-62 | DVVMTQSPDSLAVSLGERATINCRSSQSLVHSNQYTYLHWYQQKPGQSPKLLIYKVSNRFSGVPDRFSGSGSGTDFTLTISSLQAEDVAVYYCSQSTRVPYTFGGGTKVEIK | 111 |
| AL2p-58 | DVVMTQSPDSLAVSLGERATINCRSSQSLVHSNRYTYLHWYQQKPGQSPKLLIYKVSNRFSGVPDRFSGSGSGTDFTLKISRVEAEDVGVYYCSQSTRVPYTFGQGTKLEIK | 112 |
| AL2p-60 | GVVMTQTPLSLSVTPGQPASISCRSSQSLVHSNRYTYLHWYLQKPGQSPQLLIYKVSNRRSGVPDRFSGSGSGTDFTLKISRVEAEDVGVYYCSQSTRVPYTFGQGTKLEIK | 113 |
| AL2p-h19 | DIVMTQTPLSLSVTPGQPASISCRSSQSLVHSNGYTYLHWYLQKPGQSPQLLIYKVSNRFSGVPDRFSGSGSGTDFTLKISRVEAEDVGVYYCSQSTRVPYTFGQGTKLEIK | 114 |
| AL2p-h21, AL2p-h22, AL2p-h23, AL2p-h24, AL2p-h25, AL2p-h26, AL2p-h27, AL2p-h28, AL2p-h29, AL2p-h30, AL2p-h31, AL2p-h32, AL2p-h33, AL2p-h34, AL2p-h35, AL2p-h36 | DVVMTQTPLSLSVTPGQPASISCRSSQSLVHSNGYTYLHWYLQKPGQSPQLLIYKVSNRFSGVPDRFSGSGSGTDFTLKISRVEAEDLGVYFCSQSTRVPYTFGQGTKLEIK | 115 |
| AL2p-h59 | DIVMTQSPLSLPVTPGEPASISCRSSQSLVHSNGYTYLHWYLQKPGQSPQLLIYKVSNRFSGVPDRFSGSGSGTDFTLKISRVEAEDVGVYYCSQSTRVPYTFGGGTKVEIK | 116 |
| AL2p-h90 | DVQMTQSPSSLSASVGDRVTITCRSSQSLVHSNGYTYLHWYQQKPGKSPKLLIYKVSNRFSGVPSRFSGSGSGTDFTLTISSLQPEDFATYYCSQSTRVPYTFGGGTKVEIK | 117 |
| AL2p-59 | GVVMTQTPLSLSVTPGQPASISCRTSQSLVHSNQYTYLHWYLQKPGQSPQLLIYKVSNRVSGVPDRFSGSGSGTDFTLKISRVEAEDVGVYYCSQSTRVPYTFGQGTKLEIK | 118 |

TABLE 7B

Light chain sequences of anti-TREM2 antibodies

| Ab | LC | SEQ ID NO: |
|---|---|---|
| AL2p-58 huIgG1, and AL2p-58 huIgG1 PSEG | DVVMTQSPDSLAVSLGERATINCRSSQSLVHSNRYTYLHWYQQKPGQSPKLLIYKVSNRFSGVPDRFSGSGSGTDFTLKISRVEAEDVGVYYCSQSTRVPYTFGQGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 214 |
| AL2p-47 huIgG1, and AL2p-47 huIgG1 PSEG | DVVMTQTPLSLSVTPGQPASISCRTSQSLVHSNAYTYLHWYLQKPGQSPQLLIYKVSNRVSGVPDRFSGSGSGTDFTLKISRVEAEDVGVYYCSQSTRVPYTFGQGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 215 |
| AL2p-61 huIgG1 | GVVMTQTPLSLSVTPGQPASISCRSSQSLVHSNQYTYLHWYLQKPGQSPQLLIYKVSNRRSGVPDRFSGSGSGTDFTLKISRVEAEDVGVYYCSQSTRVPYTFGQGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 216 |
| AL2p-41 huIgG1 | GVVMTQTPLSLSVTPGQPASISCRSSRSLVHSNQYTYLHWYLQKPGQSPQLLIYKVSNRRSGVPDRFSGSGSGTDFTLKISRVEAEDVGVYYCSQSTRVPYTFGQGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 217 |
| AL2p-40 huIgG1, and AL2p-44 huIgG1 | GVVMTQTPLSLSVTPGQPASISCRTSRSLVHSNRYTYLHWYLQKPGQSPQLLIYKVSNRRSGVPDRFSGSGSGTDFTLKISRVEAEDVGVYYCSQSTRVPYTFGQGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 218 |

Clones were tested for affinity using OctetRed and a strong increase in monovalent affinity was observed (Table 8). In addition, clones were tested for binding to cynomolgus monkey TREM2 and all clones were able to bind monovalently (Table 8). Clones were tested for binding to human TREM2-expressing BW cells and improved affinity was observed in this setting as well (Table 8). In addition, antibodies showed increased binding to primary human dendritic cells that express human TREM2 endogenously (Table 8).

The parental AL2p antibody contains two residues that are subject to de-amidation, a DG in VH-CDR2 and a NG in VL-CDR1. When testing affinity matured AL2p variant antibodies, five clones with amino acid substitutions at these positions were produced: AL2p-2 (DG to GG), AL2p-3 (DG to EG), AL2p-4 (DG to QG), AL2p-5 (NG to NR), AL2p-6 (NG to NW). These variants were confirmed to retain that same affinity as the parental AL2p-h50 antibody (Table 8). Additionally, variants AL2p-38 to AL2p-57 already included amino acid substitutions at these positions, which are DG to GG or EG in VH-CDR2 together with NG to NR or NQ or NA in VL-CDR1. These clones show improved affinity and function compared to the parental clone, suggesting that the combination of amino acid substitutions at these positions does not affect function.

TABLE 8

Summary of binding experiments of AL2p variant antibodies

| Antibody | ForteBio Fab $K_D$ huTREM2-Fc (M) monovalent | ForteBio IgG $K_D$ huTREM2-Fc (M) avid | ForteBio Fab $K_D$ cyno TREM2-Fc (M) monovalent | cell binding huT2 BW $K_D$ (nM) | MFI binding to huDCs |
|---|---|---|---|---|---|
| AL2p-h50 | 1.12E−07 | 1.19E−09 | 7.70E−06 | 3.7 | 26 |
| AL2p-h77 | 1.02E−07 | 1.17E−09 | 1.84E−07 | 3.9 | 162 |
| AL2p-2 | 6.33E−08 | 8.37E−10 | 1.40E−06 | 2.2 | |
| AL2p-3 | 1.00E−07 | 1.19E−09 | 4.58E−06 | 2.3 | |
| AL2p-4 | 1.32E−07 | 8.17E−10 | P.F. | 2.1 | |
| AL2p-5 | 9.92E−08 | 1.00E−09 | 4.63E−06 | 2.0 | |
| AL2p-6 | 2.59E−07 | 1.06E−09 | 1.15E−06 | 4.2 | |
| AL2p-7 | 8.38E−09 | 4.27E−10 | 8.95E−09 | 1.6 | |
| AL2p-8 | 4.01E−09 | 3.00E−10 | 3.10E−09 | 1.2 | 310 |
| AL2p-9 | 6.44E−09 | 3.49E−10 | 5.63E−09 | 1.1 | 322 |
| AL2p-10 | 1.85E−08 | 8.35E−10 | 2.77E−08 | 3.1 | |
| AL2p-11 | 9.83E−09 | 5.36E−10 | 1.02E−08 | 2.4 | |
| AL2p-12 | 5.86E−09 | 5.14E−10 | 5.25E−09 | 1.8 | |
| AL2p-13 | 4.80E−09 | 3.40E−10 | 4.93E−09 | 1.5 | |
| AL2p-14 | 4.74E−09 | 3.15E−10 | 4.66E−09 | 2.1 | |
| AL2p-15 | 8.85E−09 | 5.38E−10 | 8.76E−09 | 2.2 | 262 |
| AL2p-16 | 1.83E−08 | 2.22E−10 | 1.36E−09 | 1.2 | 327 |
| AL2p-17 | 4.83E−09 | 2.55E−10 | 4.62E−09 | 1.4 | |
| AL2p-18 | 3.17E−09 | 2.29E−10 | 2.73E−09 | 1.3 | |
| AL2p-19 | 4.02E−09 | 3.03E−10 | 4.01E−09 | 1.4 | |
| AL2p-20 | 4.73E−09 | 3.50E−10 | 4.72E−09 | 1.2 | |
| AL2p-21 | 4.15E−09 | 3.99E−10 | 3.84E−09 | 1.5 | |
| AL2p-22 | 1.58E−09 | 2.19E−10 | 1.28E−09 | 1.5 | |
| AL2p-23 | 4.35E−09 | 3.34E−10 | 4.16E−09 | 1.2 | |
| AL2p-24 | 2.10E−09 | 2.33E−10 | 1.63E−09 | 1.7 | |
| AL2p-25 | 2.34E−09 | 2.20E−10 | 1.76E−09 | 1.7 | |
| AL2p-26 | 3.15E−09 | 2.01E−10 | 2.69E−09 | 1.1 | 296 |
| AL2p-27 | 1.99E−09 | 2.74E−10 | 1.82E−09 | 1.5 | |
| AL2p-28 | 7.60E−09 | 4.17E−10 | 7.91E−09 | 2.2 | |
| AL2p-29 | 6.38E−09 | 4.03E−10 | 6.47E−09 | 1.3 | |
| AL2p-30 | 6.50E−09 | 3.77E−10 | 5.66E−09 | 1.2 | |
| AL2p-31 | 4.03E−09 | 3.17E−10 | 3.44E−09 | 1.0 | 288 |
| AL2p-32 | 3.60E−08 | 1.12E−09 | 3.48E−08 | 2.8 | |
| AL2p-33 | 1.03E−08 | 8.89E−10 | 8.84E−10 | 4.5 | |
| AL2p-35 | 2.84E−08 | 1.85E−09 | 2.46E−08 | 3.6 | 130 |
| AL2p-36 | 1.21E−08 | 4.95E−10 | 7.38E−09 | 1.7 | 240 |
| AL2p-37 | 2.38E−08 | 7.79E−10 | 1.61E−08 | 2.9 | 194 |
| AL2p-38 | 6.23E−10 | | 3.70E−10 | 4.79 | 499 |
| AL2p-39 | 6.31E−10 | | 3.46E−10 | 1.53 | 590 |
| AL2p-40 | 6.02E−10 | | 3.70E−10 | 2.27 | 547 |
| AL2p-41 | 7.24E−10 | | 3.52E−10 | 1.31 | 534 |
| AL2p-42 | 8.29E−10 | | 3.12E−10 | 1.91 | 662 |
| AL2p-43 | 4.93E−10 | | 3.60E−10 | 5.01 | 1035 |
| AL2p-44 | 4.10E−10 | | 2.71E−10 | 4.18 | 1467 |
| AL2p-45 | 1.78E−08 | | 2.09E−08 | 1.54 | 318 |
| AL2p-46 | 1.30E−08 | | 1.61E−08 | 1.33 | 187 |
| AL2p-47 | 1.48E−08 | | 1.63E−08 | 1.09 | 372 |
| AL2p-48 | 1.12E−08 | | 1.49E−08 | 1.40 | 408 |
| AL2p-49 | 1.16E−08 | | 1.41E−08 | 1.15 | 413 |
| AL2p-50 | 2.39E−08 | | 3.61E−08 | 1.80 | 235 |
| AL2p-51 | 2.12E−08 | | 2.72E−08 | 1.92 | 195 |
| AL2p-52 | 2.70E−08 | | 2.80E−08 | 2.42 | 224 |
| AL2p-53 | 2.11E−08 | | 3.13E−08 | 1.72 | 159 |
| AL2p-54 | 1.39E−08 | | 1.68E−08 | 2.30 | 235 |
| AL2p-55 | 1.85E−08 | | 2.26E−08 | 2.05 | 141 |
| AL2p-56 | 1.87E−08 | | 1.88E−08 | 2.01 | 155 |
| AL2p-57 | 1.78E−08 | | 1.76E−08 | 1.83 | 152 |
| AL2p-59 | 3.85E−09 | | 3.95E−09 | | |
| AL2p-61 | 3.73E−06 | | 3.84E−09 | | |
| AL2p-62 | 2.11E−08 | | 1.94E−08 | | |
| AL2p-58 | 1.33E−08 | | 1.24E−08 | 0.51 | |

In Table 8, experiments for clones AL2p-2 to AL2p-37 were performed separately from experiments characterizing AL2p-38 to AL2p-57. Binding to human dendritic cells (DC's) was performed on different donors for these two sets of antibodies and because there is a large donor to donor variability in TREM2 expression, MFI values cannot be directly compared across donors. P.F.=poor fit; MFI=mean fluorescence intensity.

Example 3: Affinity Matured AL2p Antibodies Show Highly Improved Function

Methods

The ability of plate-bound, full-length anti-TREM2 antibodies to activate human TREM2-dependent genes was evaluated using a luciferase reporter gene under the control of an NFAT (nuclear factor of activated T-cells) promoter. The cell line BW5147.G.1.4, derived from mouse thymus lymphoma T lymphocytes, was infected with a human TREM2/DAP12 fusion protein, and with Cignal Lenti NFAT-Luciferase virus (Qiagen). To test the antibodies, plate bound, anti-TREM2 and isotype control antibodies were dissolved in PBS, plated on tissue culture plates at a concentration of 10 µg/ml and incubated overnight at 4° C. to allow the antibodies to absorb to the plate. After washing of the plates, cells were plated on the plate-bound antibodies and incubated for 4 to 6 hours at 37° C. To test antibodies in solution, they were added to the culture plates together with the cells and incubated for 4 to 6 hours at 37° C. Luciferase activity was measured by adding OneGlo Reagent (Promega) to each well and incubating for 3 minutes at room temperature on a plate shaker. Luciferase signal was measured using a BioTek plate reader.

The ability of soluble, full-length anti-TREM2 antibodies to change the activity of natural ligands of human TREM2 was evaluated using a luciferase reporter gene assay as well. Cells were incubated for 4 to 6 hours, together with soluble anti-TREM2 and isotype control antibodies, on plates that were pre-coated with phosphatidylserine (lipid was dissolved and titrated in methanol, added to the plates and methanol was allowed to evaporate overnight). Cells were lysed and luciferase activity was measured by adding One-Glo Reagent (Promega) to each well and incubating for 3 minutes at room temperature on a plate shaker. Luciferase signal was measured using a BioTek plate reader.

To assess viability of human dendritic cells and macrophages human monocytes were isolated from whole blood using RosetteSep Human monocyte enrichment cocktail (Stemcell technologies) and Ficoll centrifugation per manufacturer protocols. After lysing red blood cells with ACK lysing buffer, monocytes were resuspended in complete media (RPMI, 10% FBS, Pen/Strep, L-glutamine, HEPES, non-essential amino acid, Sodium pyruvate) with 100 ng/ml human GM-CSF (hu-GMCSF) and human IL-4 (hu-IL-4) to differentiate dendritic cells for 6 days. Macrophages were differentiated for 5-6 days in complete media (RPMI, 10% FBS, Pen/Strep, L-glutamine, HEPES, non-essential amino acid, Sodium pyruvate) with 100 ng/ml human hu-MCSF.

Anti-TREM2 antibodies or control antibody were added into a 96 well plate and left at 4° C. overnight. The next day, the plate was washed twice with PBS. Cells were plated at 25000 cells/well and cultured for 2 days. Cells were then quantified using the CellTiter-Glo Luminescent cell viability kit (Promega) per manufacturer's protocol and luminescence was determined as a measure of cell viability.

Results

To test whether increased affinity correlates with enhanced function, affinity matured anti-TREM2 antibodies were tested first for their ability to trigger TREM2 signaling when added either soluble or plate bound to BW cells expressing human TREM2/Dap12 and the NFAT:luciferase reporter. The parental AL2p antibody can cluster and activate TREM2 signaling when added in a soluble solution to the cells or when bound to the plate. In line with their increase in affinity, AL2p affinity matured variant antibodies displayed enhanced ability to cluster and activate TREM2, both in the plate bound and soluble format (Table 9A). Particularly in the plate bound format, affinity matured antibodies strongly enhanced NFAT:luciferase signaling compared to the parental humanized clones (Table 9A).

Figure 3A:
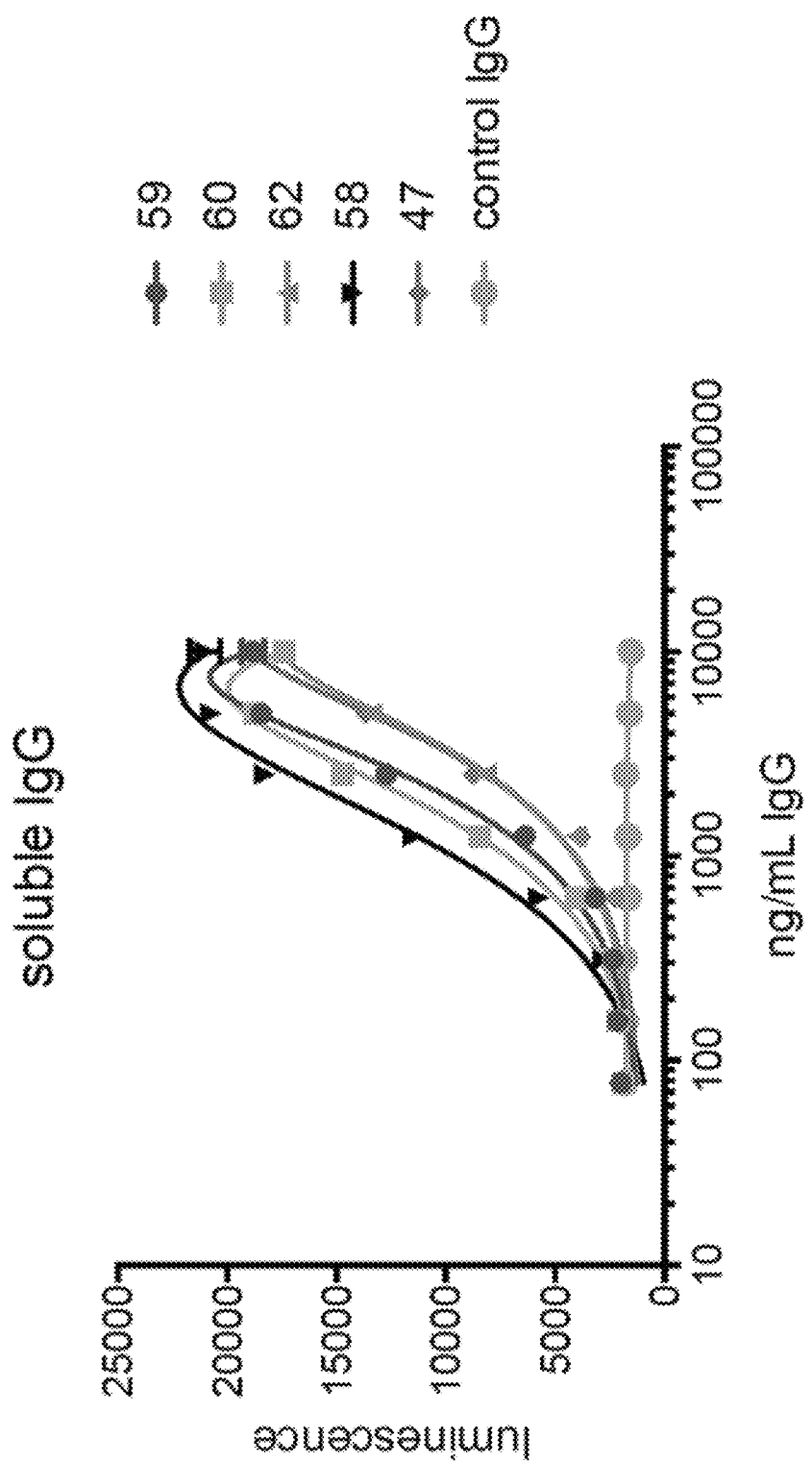
FIG. 3A shows increased activity of soluble anti-TREM2 antibodies.
Figure 3B:
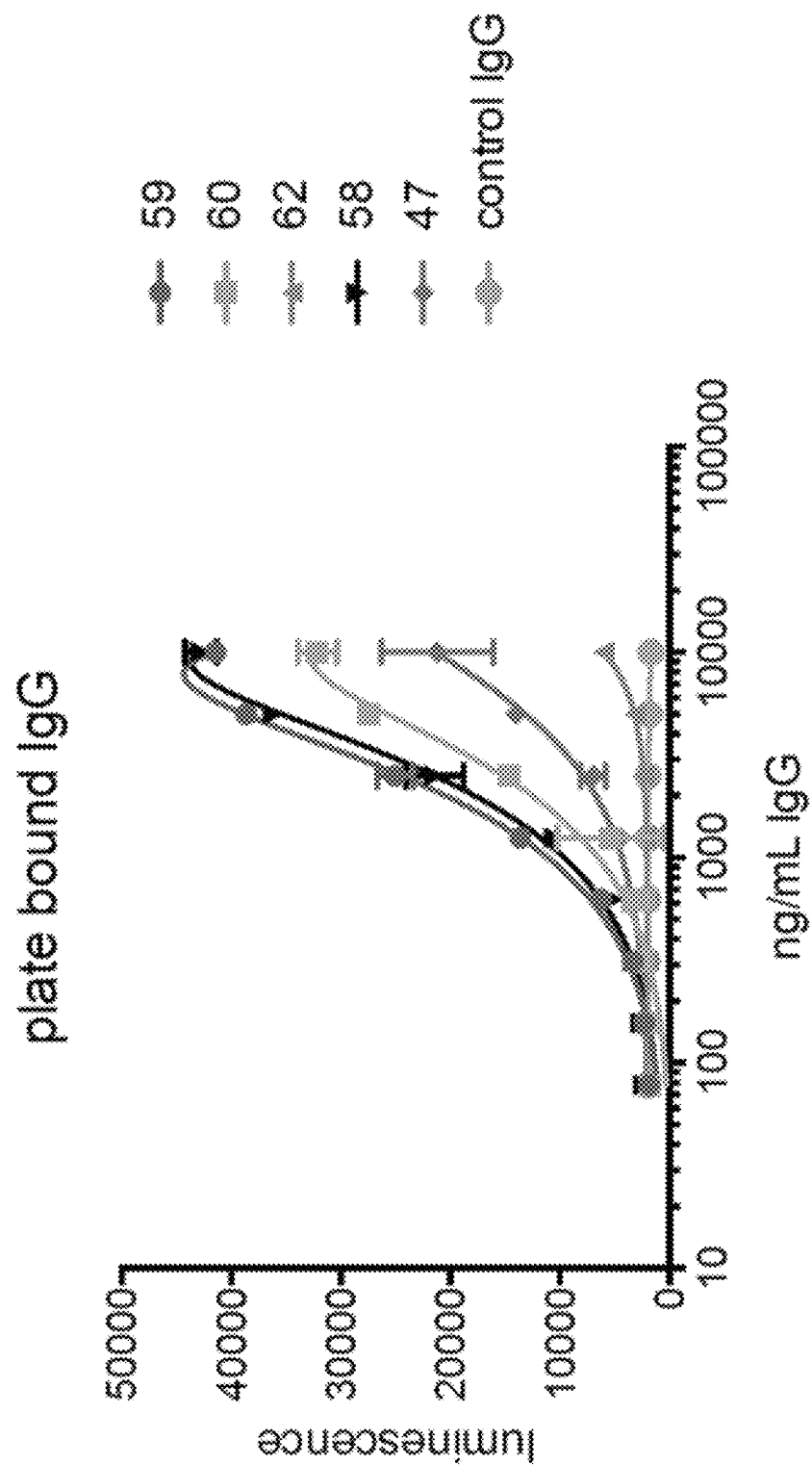
FIG. 3B shows increased activity of plate bound anti-TREM2 antibodies.

FIG. 3A and FIG. 3B show the results of functional analysis of AL2p affinity matured antibodies AL2p-58, AL2p-59, AL2p-60, AL2p-62, AL2p-47, and isotype control IgG antibody. As in Table 10A, antibodies were tested for their ability to induce TREM2 signaling in BW cells expressing NFAT:luciferase, added either soluble or plate bound. Antibody AL2p-58 is an affinity matured antibody derived from the AL2p-62 clone, but that includes light chain framework regions from two different germlines (i.e., parental humanized anti-TREM2 antibody clones). In particular, the AL2p-58 antibody has the light chain framework regions 1 and 2 (FR1 and FR2) from the AL2p-h77 germline and has the light chain framework regions 3 and 4 (FR3 and FR4) from the AL2p-h50 germline. In contrast, all four light chain framework regions of antibody AL2p-62 are from the AL2p-h77 germline. The results show that antibody AL2p-58 has surprisingly good TREM2 signaling-inducing activity, particularly as compared to the AL2p-62 antibody, despite both antibodies sharing the same variable CDR's, except for CDR-H2 and CDR-L1 (FIG. 3A and FIG. 3B). However, the differences with the CDR-H2 and CDR-L1 sequences of AL2p-58 and AL2p-62 are due to different hotfixes, which were not shown to positively or negatively affect antibody affinity or function (Table 9A). The results also indicate that while AL2p-58 has the sane heavy chain variable region sequence as AL2p-37, AL2p-58 shows an unexpectedly high improvement in functional properties compared to AL2-p37.

The results in Table 10A also indicate that AL2p-47 shows surprisingly better functional properties, as well as higher affinity to cell-expressed TREM2, as compared to antibodies AL2p-45, AL2p-55, and AL2p-56, which all share the same light chain variable domain and very similar heavy chain variable domain sequences. In particular, the only difference in sequence between AL2p-47 and AL2p-45 is in the HVR-H2, where AL2p-47 has an H at the $16^{th}$ position and AL2p-45 has a Q (Table 2B). The differences in sequence between AL2-47 and AL2p-55 and AL2p-56 are a single amino acid difference in HVR-H1 (Table 2A), a single amino acid difference in heavy chain FR1 (Table 4A), and a single amino acid difference in HVR-H2, where AL2p-47 has an R at the $13^{th}$ position and both AL2p-55 and AL2p-56 have a Q (Table 2B). Based on these results, it appears that the combination of the R at the $13^{th}$ position of the HVR-H2 sequence and the H at the $16^{th}$ position o HVR-H2 sequence of antibody AL2p-47 shows a surprising effect compared to the R at the $13^{th}$ position alone (as is the case for AL2-p45) or the H at the $16^{th}$ position alone (as is the case for AL2p-55 and AL2p-56), especially given that AL2p-47 has similar affinity to human TREM2 protein as do AL2p-45, AL2p-55, and AL2p-56.

Figure 3C:
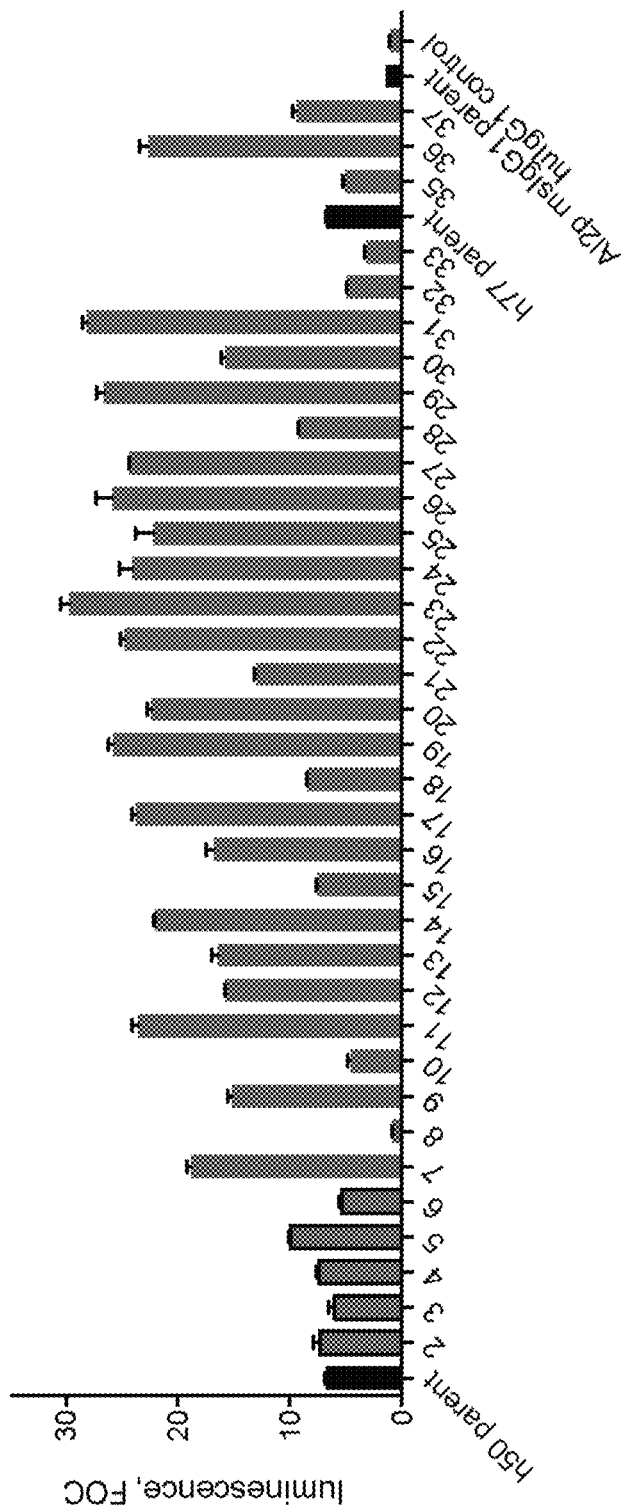
FIG. 3C shows reporter activity of affinity matured anti-TREM2 antibodies plate bound at 5 µg/ml (grey bars) compared to parental humanized antibody Alp2-h50 (h50), parental humanized antibody AL2p-77 (h77), and parental murine antibody AL2p (AL2p msIgG1 parent) clones (black bars). Clones in grey bars with black outlines represent AL2p-h50 antibody variant containing different amino acid substitutions.

FIG. 3C shows the ability of plate bound affinity matured antibody variants to induce TREM2 signaling as measured by the NFAT:luciferase reporter assay. The results indicate a dramatic (up to 4-fold) increase in efficacy of affinity matured antibodies as compared to the corresponding parental humanized AL2p antibody (h50 or h77) or the parental murine IgG1 antibody (AL2p).

TREM2 was shown to affect survival of primary murine macrophages and microglia in vitro, with TREM2 knock-out cells showing reduced viability (Wang et al., Cell 2015, 160(6):1061-1071). To verify functionality of AL2p variant antibodies in primary cells, human monocyte derived macrophages or dendritic cells were stimulated with plate bound AL2p variant antibodies and the viability of cells was measured 2 days later. It was found that plate bound AL2p parental antibody increases viability in a dose dependent fashion. Compared to the parental clone, affinity matured AL2p variant antibodies increase viability even further (Tables 9A and 10A).

Clones AL2p-23, AL2p-31 and AL2p-37 were produced in CHO cells containing the following variants: DG to EG and NG to NQ. These clones retain the affinity of the parental clones (Table 9B).

TABLE 9A

Functional analysis affinity matured antibodies

| Antibody | Luciferase activation soluble 10 nM IgG, FOC | Luciferase activation plate bound 33 nM IgG, FOC | Survival huDCs plate bound IgG, AUC |
|---|---|---|---|
| AL2p-h50 | 1.26 | 6.83 | 337353 |
| AL2p-h77 | 1.47 | 6.77 | 380527 |
| AL2p-2 | 1.70 | 7.36 | 461171 |
| AL2p-3 | 1.29 | 6.03 | 363252 |
| AL2p-4 | 1.45 | 7.42 | 495712 |
| AL2p-5 | 1.27 | 9.99 | 709979 |
| AL2p-6 | 1.20 | 5.39 | 546995 |
| AL2p-7 | 2.35 | 18.87 | n.d. |
| AL2p-8 | 2.78 | n.d. | 1088000 |
| AL2p-9 | 2.62 | 15.21 | 976481 |
| AL2p-10 | 1.60 | 4.63 | n.d. |
| AL2p-11 | 1.71 | 23.64 | n.d. |
| AL2p-12 | 1.96 | 15.80 | n.d. |
| AL2p-13 | 2.17 | 16.53 | n.d. |
| AL2p-14 | 1.79 | 22.07 | n.d. |
| AL2p-15 | 1.80 | 7.54 | 487849 |
| AL2p-16 | 2.60 | 16.87 | 880480 |
| AL2p-17 | 2.13 | 23.83 | n.d. |
| AL2p-18 | 2.06 | 8.46 | n.d. |
| AL2p-19 | 2.06 | 25.85 | n.d. |
| AL2p-20 | 2.12 | 22.45 | n.d. |
| AL2p-21 | 1.83 | 13.05 | n.d. |
| AL2p-22 | 1.75 | 24.86 | n.d. |
| AL2p-23 | 2.53 | 29.75 | 1108000 |
| AL2p-24 | 2.12 | 24.13 | n.d. |
| AL2p-25 | 2.35 | 22.28 | n.d. |
| AL2p-26 | 2.59 | 25.91 | 1113000 |
| AL2p-27 | 2.06 | 24.39 | n.d. |
| AL2p-28 | 2.14 | 9.27 | n.d. |
| AL2p-29 | 2.17 | 26.64 | 1113000 |
| AL2p-30 | 2.31 | 15.78 | n.d. |
| AL2p-31 | 2.83 | 28.25 | 1209000 |
| AL2p-32 | 1.47 | 4.90 | n.d. |
| AL2p-33 | 1.72 | 3.21 | n.d. |
| AL2p-35 | 2.05 | 5.15 | 453094 |
| AL2p-36 | 2.64 | 22.70 | 1143000 |
| AL2p-37 | 2.16 | 9.42 | 679678 |

Table 9A shows a functional analysis of a set of AL2p affinity matured antibodies, as compared to the parental antibodies AL2p-h50 and AL2p-h77. In the Table, n.d.=not determined; AUC=area under curve; FOC=fold over control, where the control is an isotype control antibody. Clones AL2p-2 to AL2p-6 are variants of parental antibody AL2p-h50 that include hotfixes to eliminate a de-amidation site.

TABLE 9B

Testing HVR variants for anti-TREM2 antibodies

| Antibody | VH-HVR2 variants | VL-HVR1 variants | cell binding huT2 BW $K_D$ (M) | luciferase activation, soluble IgG, $EC_{50}$ (M) |
|---|---|---|---|---|
| AL2p-h50 | none | none | 3.7E−01 | 6.31E−08 |
| AL2p-h77 | none | none | 3.90E−01 | 2.01E−08 |
| AL2p-2 | DG to GG | none | 2.2E−01 | 2.30E−08 |
| AL2p-3 | DG to EG | none | 2.3E−09 | 5.00E−08 |
| AL2p-4 | DG to QG | none | 2.1E−09 | 6.62E−08 |
| AL2p-5 | none | NG to NR | 2.0E−09 | 3.81E−08 |
| AL2p-6 | none | NG to NW | 4.2E−09 | 3.86E−08 |
| AL2p-59 | DG to EG | NG to NQ | 1.24E−09 | 1.12E−08 |
| AL2p-60 | GG to EG | NG to NQ | 1.12E−09 | 1.03E−08 |
| AL2p-62 | DG to EG | NG to NQ | 2.63E−09 | 2.51E−08 |
| AL2p-31 | DG to GG | none | 1.23E−09 | 6.92E−09** |

In Table 9B, values marked with ** were obtained in a different experiment than the other values of the same column.

TABLE 10A

Functional analysis of AL2p affinity matured antibodies that include amino acid substitutions at positions susceptible to de-amidation

| Antibody | BW Luc assay plate bound 7.3 nM IgG, FOC | BW Luc assay soluble 7.3 nM IgG, FOC | DC viability (AUC) | Mac viability (AUC) |
|---|---|---|---|---|
| AL2p-31 | 7.49 | 4.48 | 860213 | 83712 |
| AL2p-38 | 4.47 | 4.98 | 785505 | 39036 |
| AL2p-39 | 8.12 | 3.81 | 850801 | 66855 |
| AL2p-40 | 8.49 | 9.92 | 824725 | 63235 |
| AL2p-41 | 7.61 | 2.92 | 859989 | 80670 |
| AL2p-42 | 6.52 | 5.95 | 780879 | 57916 |
| AL2p-43 | 5.41 | 8.84 | n.d. | n.d. |
| AL2p-44 | 7.17 | 11.50 | 750071 | 74651 |
| AL2p-45 | 2.29 | 2.38 | 543378 | 3676 |
| AL2p-46 | 1.64 | 2.98 | 596898 | 6044 |
| AL2p-47 | 3.54 | 3.48 | 771393 | 22055 |
| AL2p-48 | 3.25 | 3.65 | 769717 | 23589 |
| AL2p-49 | 3.12 | 3.28 | 753554 | 15109 |
| AL2p-50 | 1.19 | 2.07 | 286306 | −10420 |
| AL2p-51 | 1.22 | 2.30 | 259485 | −11153 |
| AL2p-52 | 1.30 | 1.75 | 283169 | −13548 |
| AL2p-53 | 1.45 | 2.32 | 234316 | −10245 |
| AL2p-54 | 1.53 | 2.17 | 569761 | −7639 |
| AL2p-55 | 1.49 | 2.08 | 630883 | −5284 |
| AL2p-56 | 1.51 | 2.02 | 643293 | −7621 |
| AL2p-57 | 1.41 | 2.03 | 505964 | −3564 |

Table 10A shows a functional analysis of AL2p affinity matured antibodies from the second round of affinity maturation. Antibodies were tested for their ability to induce TREM2 signaling in BW cells expressing NFAT:luciferase, added either soluble or plate bound, as well as their ability to increase viability of macrophages or dendritic cells in a plate bound format. In Table 10A, n.d.=not determined; AUC=area under curve. DC=primary human dendritic cells; Mac=primary human macrophages; FOC=fold over control.

TABLE 10B

Functional analysis of AL2p affinity matured antibody variants

| Antibody | luciferase activation, soluble IgG, $EC_{50}$ (nM) | luciferase activation, plate bound IgG, $EC_{50}$ (nM) |
|---|---|---|
| AL2p | 19.3 | n.d. |
| AL2p-31 | 1.14 | 10.1 |
| AL2p-47 | 104 | 206 |
| AL2p-58 | 14 | 36 |

Figure 4A:
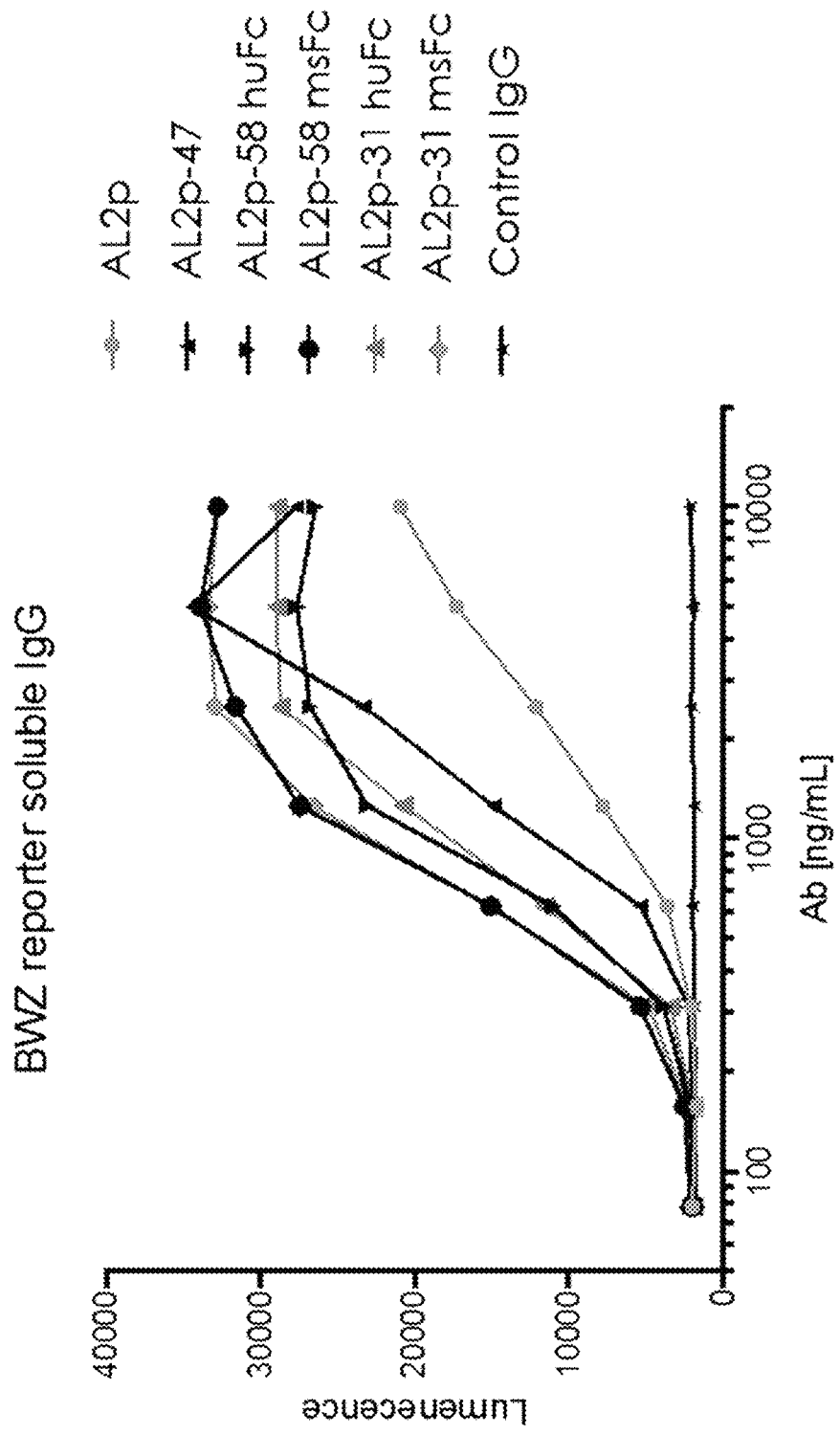
FIG. 4A shows increased activity of soluble anti-TREM2 antibodies.
Figure 4B:
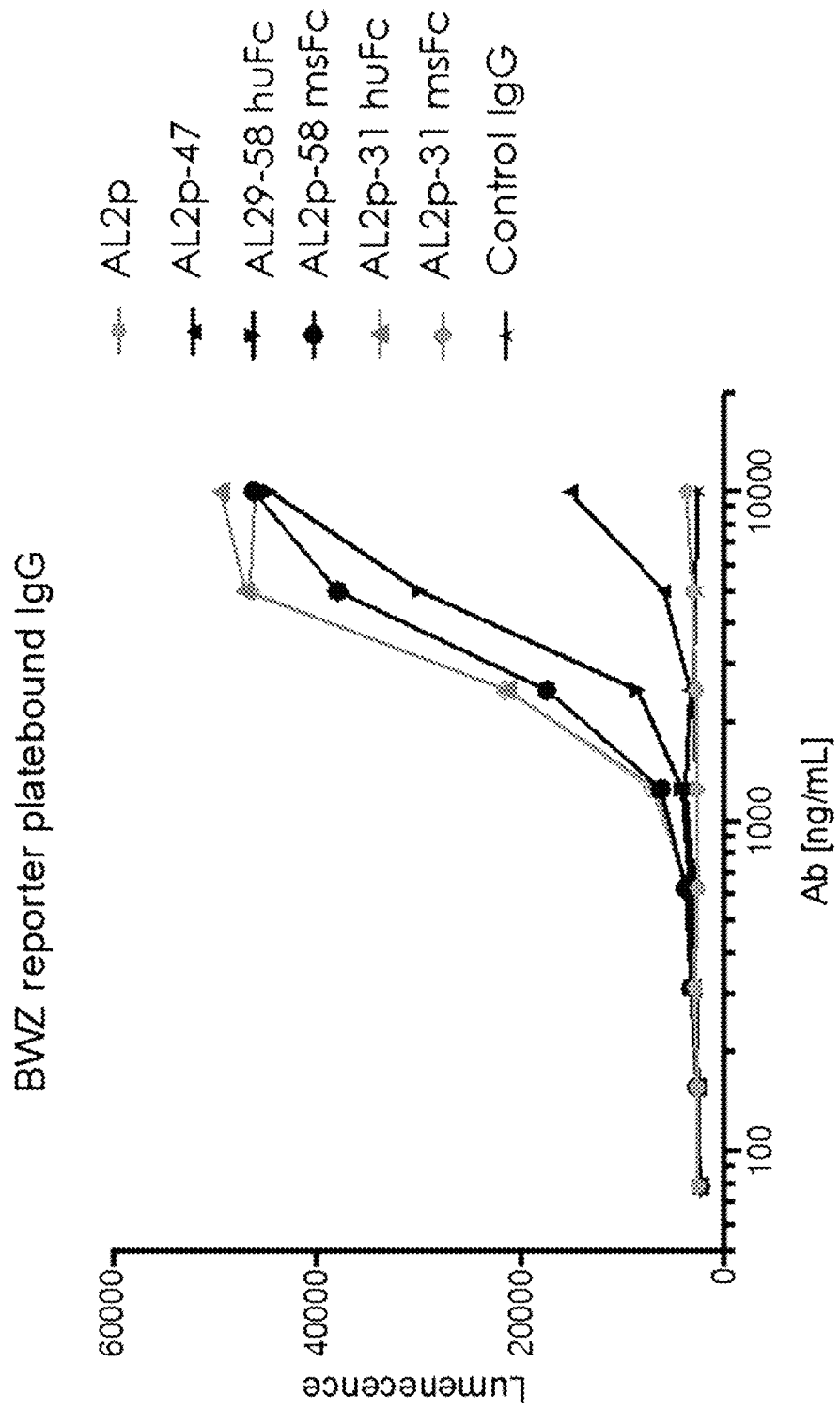
FIG. 4B shows increased activity of plate bound anti-TREM2 antibodies.

Table 10B and FIG. 4A and FIG. 4B show the results of functional analysis of parental mouse antibody AL2p, affinity matured antibodies AL2p-31, AL2p-47, AL2p-58, and a control antibody. For antibodies AL2p-31 and AL2p-58, the antibodies were generated using both a human IgG constant region (huFC) or a mouse IgG constant region (msFc). Antibodies were tested for their ability to induce TREM2 signaling in BW cells expressing NFAT:luciferase, added either soluble or plate bound, as well as their ability to increase viability of macrophages or dendritic cells in a plate bound format. In Table 10B, n.d.=not determined. The results indicate that the affinity matured antibodies had better TREM2 signaling-inducing activity and lower $EC_{50}$ than the parental mouse antibody AL2p (Table 10B and FIG. 4A and FIG. 4B).

Table 10C shows a comparison of antibody characteristics between affinity matured antibodies AL2p-31, AL2p-47, and AL2p-58, and the parental mouse antibody AL2p.

TABLE 10C

Comparison of affinity matured antibodies to parental murine antibody

| Characteristic | AL2p | AL2p-47 | AL2p-31 | AL2p-58 |
|---|---|---|---|---|
| Germline | Murine | VH1-69; CK2D-29 | VH1-69; CK2D-29 | VH1-69; VK4-1/VK2D-29 |
| Fab $K_D$ (nM) to recombinant hTREM2 | $1.12 \times 10^{-7}$ | $1.27 \times 10^{-8}$ | $3.73 \times 10^{-9}$ | $1.33 \times 10^{-8}$ |
| Fab $k_{on}$ (M) to recombinant hTREM2 | $1.94 \times 10^{5}$ | $2.67 \times 10^{5}$ | $3.35 \times 10^{5}$ | $3.26 \times 10^{5}$ |
| Fab $k_{off}$ (M) to recombinant hTREM2 | $3.4 \times 10^{-3}$ | $3.40 \times 10^{-3}$ | $1.26 \times 10^{-3}$ | $4.33 \times 10^{-3}$ |
| Binding to hTREM2 expressing cell line $K_D$ (nM) | 3.04 | 1.22 | 0.56 | 0.51 |
| Reporter assay plate bound IgG ($EC_{50}$, nM) | Low | 206.3 | 10.1 | 36.1 |

TABLE 10C-continued

Comparison of affinity matured antibodies to parental murine antibody

| Characteristic | AL2p | AL2p-47 | AL2p-31 | AL2p-58 |
|---|---|---|---|---|
| Reporter assay soluble IgG (EC$_{50}$, nM) | 19 | 104.7 | 11.4 | 14.0 |
| Dendritic cell viability | −(1) | +(2) | ++(3) | ++(3) |

Example 4: PK/PD Analysis of Affinity Matured AL2p Antibodies

Methods

Human TREM2 transgenic (Tg) mice as well as wild-type (WT) littermate controls that only express murine TREM2 were used in a PK/PD study to test both the half-life of different AL2p affinity matured variant antibodies in the presence or absence of target engagement, as well as the effect of AL2p antibody on soluble TREM2 in the plasma of TREM2 Tg mice.

Human TREM2 Tg mice were injected intraperitoneally on day 0 with 15 mg/kg of HEK or CHO produced AL2p variants AL2p-31-HF as WT and PSEG huIgG1, AL2p-23-HF, AL2p-37-HF, AL2p-58-HF, AL2p-40, AL2p-41, AL2p-47, all in a huIgG1 backbone, as well as control huIgG1 (n=2-3 mice/group). Human TREM2 Tg mice were injected intraperitoneally on day 0 with 15 mg/kg of HEK or CHO produced AL2p variants AL2p-60 as PSEG huIgG1, AL2p-47 as huIgG1, AL2p-58 as huIgG1, as well as control huIgG1 (n=2-3 mice/group). Blood was collected by tail vein puncture at the following time points: 4h after injection, days 1, 3, 6, 10 and 14. For plasma isolation, the blood was collected in heparinized tubes and centrifuged at 10,000×g for 10 min at 4° C. Plasma supernatant was collected at stored at −80° C.

Levels of human IgG1 antibodies in the plasma were determined using a custom (MesoScale Discovery) MSD assay. Briefly, 96-well multi-array plates (MesoScale Discovery) were coated overnight at 4° C. with 50 μl of 1 μg/ml of goat anti-human Fab fragment specific for IgG (Jackson Immuno Research) at 500 rpm on a plate shaker. Plates were washed three times in 150 μl wash buffer (PBS+0.05% Tween) and blocked in binding buffer (PBS+1% BSA) for 1 hr at RT at 500 rpm on a plate shaker. Plasma was diluted in binding buffer at 1:200 and 1:10,000 and added to the blocked plates and incubated for 1 h at 37° C. Control huIgG1 was used as a standard. Plates were subsequently washed three times in 150 μl wash buffer and incubated with a goat anti-human sulfo-tag conjugated secondary antibody (MesoScale Discovery) at 1 μg/ml in binding buffer for 1 hr at RT. Plates were subsequently washed three times in 150 μl wash buffer and 15 μl 1× Read Buffer was added to each well and the plates were imaged in a Sector Imager (MesoScale Discovery). Data were analyzed using GraphPad Prism.

For the human specific TREM2 ELISA, capture antibody T2KO8F11 was plated at 2 μg/ml in PBS overnight at 4 C (100 μL per well in high bind Elisa plates). The plates were washed thrice with a plate washer and 300 μL PBS+0.05% Triton per well. As a standard 156-10,000 pg/ml human TREM2-Fc (R&D Systems) was added to the plates, as well as diluted plasma samples in binding buffer (PBS+1% BSA). Plates containing samples and standard were incubated at RT for 1 hour. The plates were washed thrice with a plate washer and 300 μL PBS+0.05% Triton per well. Biotinylated goat anti-human TREM2 polyclonal antibody (R&D Systems) was added at 1:2,000 dilution in binding buffer and incubated for 1 hour at RT. The plates were washed thrice with a plate washer and 300 μL PBS+0.05% Triton per well. Streptavidin-HRP (1:200 in binding buffer, R&D Systems) was added to the plates and incubated for 20-30 minutes at RT. The plates were washed thrice with a plate washer and 300 μL PBS+0.05% Triton per well. 100 μL TMB substrate solution was added and incubated until color developed. The reaction was stopped by adding 50 μL of 2N sulfuric acid and the plate was read in a Synergy H1 plate reader at 450 and 630 nm. Data were analyzed using GraphPad Prism.

Results

The half-life of AL2p variant antibodies was measured in human TREM2 Tg mice (Table 11). After injection of AL2p variant antibody, levels of sTREM2 significantly decreased down to 65% of control levels and remained low for at least 6 days (Table 11). It is unclear what causes this decrease. It could either be caused by AL2p blocking shedding of sTREM2 or by AL2p causing internalization of TREM2 after inducing clustering. And these data suggest that sTREM2 levels in plasma or CSF can be used as indicators for peripheral or brain target engagement in vivo in patients.

TABLE 11

Parameters measured in vivo in human TREM2 Tg mice for control huIgG1 and AL2p affinity matured variant antibodies

| Antibody | Estimated half-life (days) | Plasma sTREM2 as % of baseline on day 6 |
|---|---|---|
| Control huIgG1 | 14.6 | 99.97 |
| AL2p-60 huIgG1 PSEG | 1.5 | 51.75 |
| AL2p-47 huIgG1 | 2.8 | 73.37 |
| AL2p-58 huIgG1 | 4.6 | 43.70 |

Example 5: Production and Testing of Fc Mutant Variants of TREM-2 Agonistic Antibodies Materials and Methods Production of Fc Mutant Antibodies Fc mutant antibodies were produced recombinantly via transient transfection of HEK cells, and purification via Protein-A affinity capture and size exclusion chromatography (SEC) polishing.

BWZ Reporter Assay

In addition to the BWZ reporter assays described in Examples 2 and 3, reporter cell assays for Fc-mutants were also carried out in co-culture with various FcgR-expressing cell lines such as THP-1 or Raji. In this case, the assay was modified to include $10^5$ each of the reporter cell line as well as the FcgR-expressing line, in the same final volume of media (100 μL per well). The two cell types were counted on a Vi-CELL XR (Beckman Coulter) and mixed in reporter cell media (DMEM+10% FBS) immediately prior to aliquoting into 96 well plates and addition of antibody. The assay was then carried out in the same manner as described previously (6 hour incubation with antibody at 37° C., followed by detection of luciferase with the ONE-GLO reagent (Promega) and a BioTek plate reader).

Complement (C3b) Deposition Assay

The ability of anti-TREM2 antibodies to drive complement deposition was measured on a stable HEK cell line overexpressing human TREM2 and DAP12, as well as on primary cells (monocyte-derived DCs). TREM2-expressing cells were diluted to $10^{-5}$ cells per 70 µL in media (DMEM+10% FBS for HEK, RPMI for DCs) and 70 µL of cells aliquoted per well in round-bottom 96 well plates (Falcon #351177). To these cells was added 10 uL of 10× antibody diluted in the same media. Cells+antibody were incubated at 37° C. for 30 min, then 20 µL of pooled complement human serum (Innovative Research, IPLA-CSER) was added per well as a complement source and the plates incubated for a further 2 hours at 37° C. Afterwards, the cells were washed 2× with FACS buffer (PBS+2% FBS+1 mM EDTA), and 100 µL of 1:50 diluted anti-C3b-APC antibody (Biolegend 846106) was added per well and incubated on ice for 30 minutes. The cells were then washed 2× with FACS buffer and resuspended in 50 µL/well of FACS buffer+0.25 µL/well of propidium iodide (Fischer Scientific, BD 556463 prior to analysis on an iQue flow cytometer (IntelliCyt).

Production of Fc-Gamma-Receptor Detection Reagents

Human and mouse FcgR detection reagents were designed by fusing the extracellular domain of each FcgR with the C-terminal addition of an AVI/His tag to facilitate site-specific biotinylation and purification (Boesch et al, 2014). AVI-His FcgRs were produced by transient transfection of HEK cells via and purified via immobilized metal affinity chromatography (IMAC) capture followed by size exclusion chromatography (SEC) for polishing. Purified FcgRs were biotinylated according to the conditions of the BirA biotin-protein ligase bulk reaction kit (Avidity). Tetrameric FcgR reagents were prepared immediately prior to use by mixing 1 ug/mL of FcgR with a ¼$^{th}$ molar ratio of streptavidin-APC (eBioscience 17-4317-82) in FACS buffer and incubating for 10 min with rotation.

Fc-Gamma-Receptor Binding Assay

The ability of antigen-bound antibody to engage Fc receptors was measured on the stable TREM2/DAP12 expressing HEK cell line. Briefly, TREM2-expressing cells were diluted to 100 k cells per 90 µL in media (DMEM+10% FBS for HEK) and 90 uL of cells aliquoted per well in round-bottom 96 well plates (Falcon). To these cells was added 10 µL of 10× antibody diluted in the same media. Cells+antibody were incubated at 37° C. for 1h to opsonize target cells, then the cells were washed 2× in FACS buffer, and 100 uL of the tetrameric FcgR detection reagent of FACS buffer were added per well. Opsonized cells were incubated with FcgR tetramers for 1h at 4° C., and the cells were washed 2× with FACS buffer and resuspended in FACS buffer prior to analysis on an iQue flow cytometer (IntelliCyt).

Results

In the following example the sequence FC1 (human IgG1 Glm 17,1) was used as the parental human IgG1 Fc and sequence FC10 was used as the parental human IgG2 Fc for all further modifications.

Self-clustering Fc mutants that induce strong complement responses also may drive an agonistic response by inducing clustering (e.g., by inducing antibody multimerization), which can activate receptors; however, such mutants may also target the complement system towards the very target cells from which the beneficial activity is being elicited. Therefore, combinations of Fc mutants were tested for ability to retain the beneficial effects of clustering (e.g., hexamer-forming mutants) while reducing complement dependent cytotoxicity (CDC), for example by reducing the monomeric affinity to C1q.

Combinations of E430G with Fc mutants (e.g., K322A, A330S and P331S), which can reduce complement activation; as well as with other Fc mutants (e.g., combinations of L234A, L234F, L235A, L235E, and A330L) that reduce binding to activating Fc-gamma-receptors (Armour et al, 2003; Idusogie et al, 2001) were tested in the context of anti-TREM2 antibody binding.

BWZ Reporter Assay

Figure 1B:
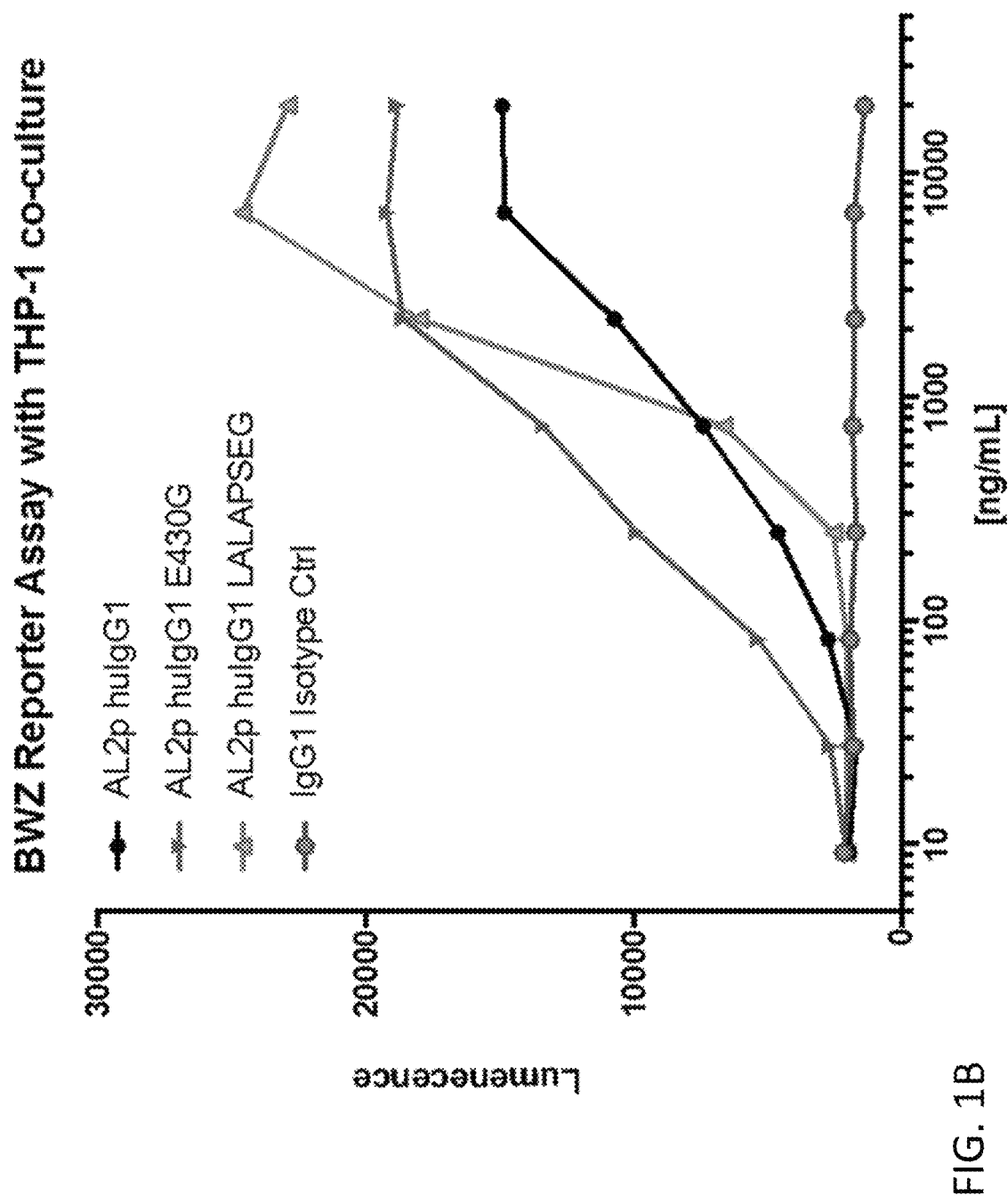
FIG. 1B shows increased agonistic activity of Fc variant anti-TREM2 antibodies. Luciferase activity after 6 hr co-culture of Fc variant antibodies with BWZ reporter cells and THP-1 cells in 1:1 ratio.

Using the reporter-cell assay agonistic ability of the resulting antibodies was evaluated as well as their ability to drive complement activation through CDC and C3b-deposition assays. E430G Fc variants of an anti-TREM2 antibody strongly enhance agonistic activity, even in the presence of compensatory mutations to remove C1q binding, such as P331S (FIG. 1A). To further probe these results, the ability of anti-TREM2 antibodies to activate TREM2 in the presence of cell types bearing Fc gamma receptors was tested. Fc-gamma-receptor dependent clustering may be an important mechanism for the activity of these antibodies in vivo, and as such should be retained if possible. In a co-culture system with THP-1 cells (ATCC® TIB-202™), a monocytic leukemia cell line expressing several Fc gamma receptors, enhanced TREM2 signaling activity was seen from the humanized IgG1 variant (FIG. 1B). Adding in the E430G mutation further enhanced the activity, showing a possible additive or synergistic effect of these two mechanisms. However, adding in compensatory mutations to fully remove Fc-receptor binding, such as LALAPS (L234A, L235A, P331S), also removed much of the benefit of using E430G in this system.

Complement (C3b) Deposition Assay

Figure 2A:
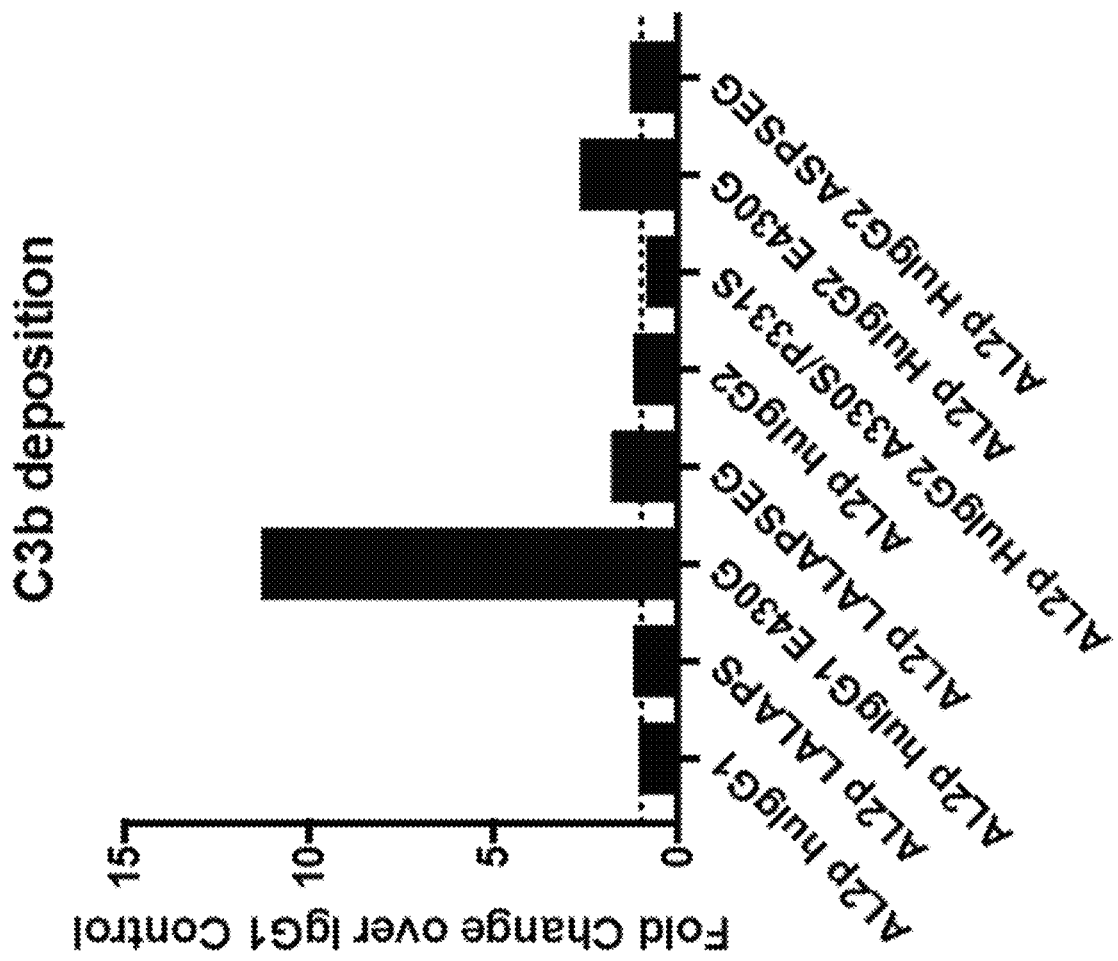
FIG. 2A shows C3b deposition induced by Fc variant anti-TREM2 antibodies. Fold change of C3b deposition on HEK expressing TREM2 cell line by AL2p Fc variants over human IgG1 isotype control antibody at 10 µg/mL.
Figure 2B:
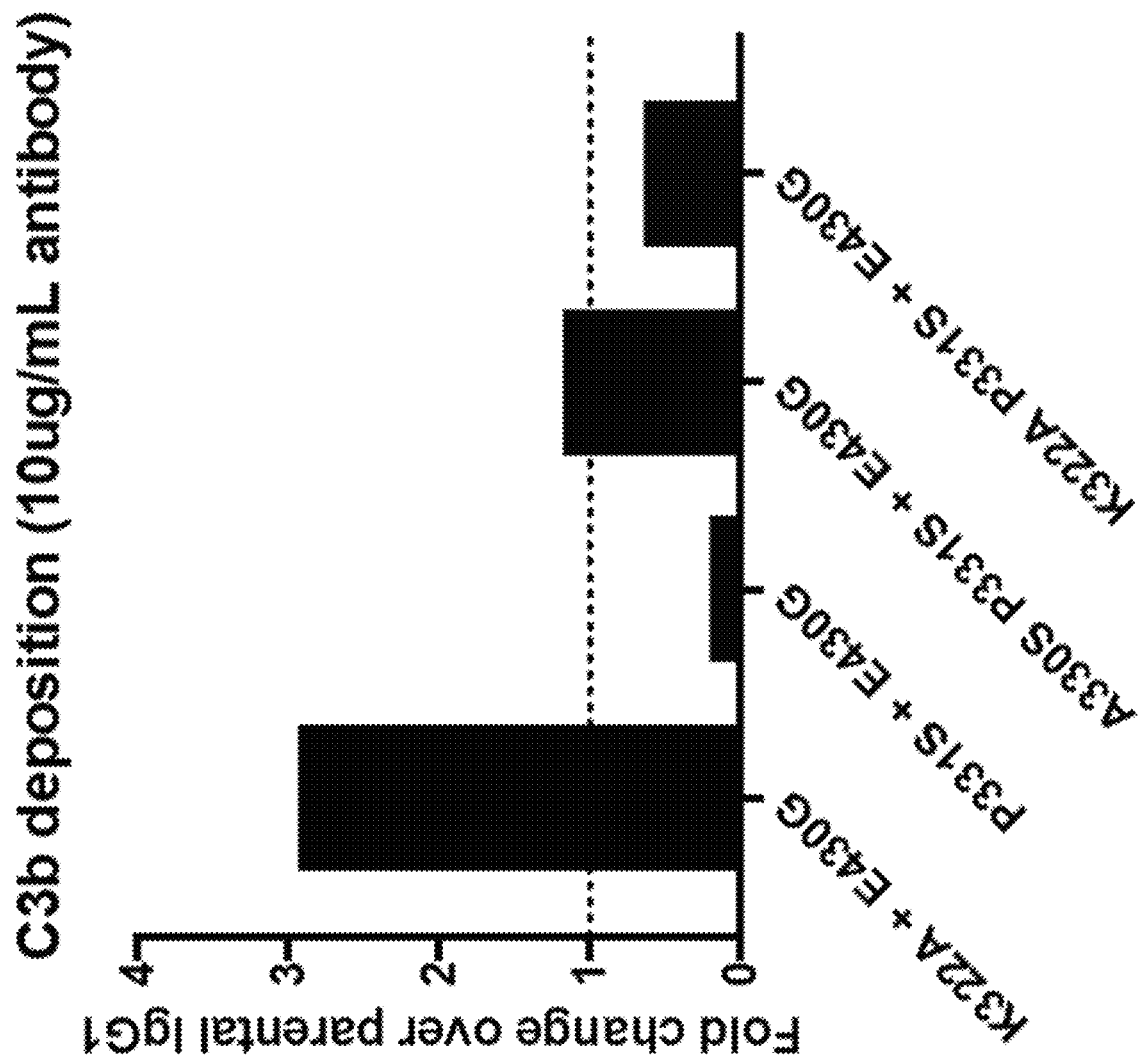
FIG. 2B shows C3b deposition induced by Fc variant anti-TREM2 antibodies. Fold change of C3b deposition by AL2p affinity matured variants with the listed Fc mutations over their parental IgG1 Fc variant.

E430G mutant can cause a strong increase in C3b deposition and CDC, over the parental IgG1. This increase could be ameliorated following the addition of compensatory mutations such as LALAPS (FIG. 2A). Various Fc mutant combinations of K322A, A330S and P331S together with E430G were tested for their ability to retain agonistic functionality (including through FcgR-based mechanisms) while reducing complement activation. Inclusion of P331S alone with E430G (PSEG) was sufficient to reduce complement activation below the level of that induced by the parental IgG1 in one affinity-matured AL2p variant (FIG. 2B), while K322A and A330S had limited effect even in combination with P331S.

Fc-Gamma-Receptor Binding Assay

Fc mutant variants of AL2p leads are also tested for their ability to engage Fc-gamma-receptors. In this assay TREM-2 expressing cells are opsonized with anti-TREM2 antibodies and then a tetramerized FcgR/streptavidin-APC probe is used to evaluate their ability to engage FcgRs. Both mouse and human FcgRs are tested.

Example 6: Improved Binding of Affinity Matured TREM2 Antibodies to BW Cells Expressing Human TREM2

Materials and Methods

Binding assay: FACS-based cell binding was performed as described in Example 2.

Results

Side-by side comparison in binding was performed of the chimeric parental AL2p antibody as huIgG1 and various humanized and affinity matured variants thereof on either huIgG1 or huIgG1 PSEG Fc. AL2p-58 and AL2p-61 show a 2 to 3.6 fold increase in apparent affinity, while there is not great affinity improvement by AL2p-37 and AL2p-47 on cell expressed TREM2, despite both antibodies showing increased affinity to recombinant TREM2 (Table 12).

TABLE 12

Cell-based binding assay of high affinity binding of 9F5 affinity matured variants

| Antibody ID | Fc isotype | Kd (nM) | Bmax (MFI) |
|---|---|---|---|
| AL2p | huIgG1 | 1.32 | 199026 |
| AL2p-58 | huIgG1 | 0.63 | 196455 |
| AL2p-58 | huIgG1 PSEG | 0.36 | 140225 |
| AL2p-37 | huIgG1 | 1.17 | 216292 |
| AL2p-47 | huIgG1 | 1.20 | 226371 |
| AL2p-61 | huIgG1 | 0.42 | 210636 |

Example 7: Improved Soluble and Plate Bound TREM2 Signaling Activation Upon Affinity Maturation of AL2p Materials and Methods Luciferase assay—The ability of plate-bound or soluble, full-length anti-TREM2 antibodies to activate human TREM2-dependent genes was evaluated using a luciferase reporter assay as described in Example 3.

Results

The ability of AL2p variant antibodies to activate TREM2-mediated signaling was tested in a heterologous NFAT:luciferase system. BW cells express human TREM2/DAP12 chimera, as well as a NFAT:luciferase reporter gene that is activated upon TREM2 clustering either by natural ligands or TREM2 antibodies. Compared to AL2p, which had little stimulatory activity when plate bound, all affinity matured AL2p offspring, except for AL2p-37, showed dramatic improvement in plate bound signal activation, up to 10-fold over AL2p for AL2p-58 huIgG1 PSEG (Table 13). A similar improvement was observed for signaling activation by soluble IgG, where all affinity matured antibodies tested activated signaling with a reduced EC50 and increased signaling levels compared to AL2p.

TABLE 13

Activation of TREM2 signaling in NFAT: luciferase expressing BW cells

| Antibody ID | Fc isotype | Plate bound IgG, fold over unstimulated control (25 nM IgG) | Soluble IgG, EC50 (nM) | Soluble IgG, fold over control IgG (17 nM IgG) |
|---|---|---|---|---|
| AL2p | huIgG1 | 1.29 | 14.59 | 4.51 |
| AL2p-58 | huIgG1 | 9.88 | 4.83 | 9.97 |
| AL2p-58 | huIgG1 PSEG | 12.91 | 2.99 | 12.11 |
| AL2p-37 | huIgG1 | 1.56 | 9.41 | 7.63 |
| AL2p-47 | huIgG1 | 3.94 | 6.50 | 8.77 |
| AL2p-61 | huIgG1 | 8.97 | 5.24 | 10.75 |

Example 8: AL2p Variants Block Production of sTREM2 by Primary Human Dendritic Cells In Vitro Materials and Methods Generation of human dendritic cells and treatment with TREM2 antibodies-Human monocytes were isolated from whole blood using RosetteSep Human monocyte enrichment cocktail (Stemcell technologies) and Ficoll centrifugation per manufacturer protocols. After lysing red blood cells with ACK lysing buffer, monocytes were resuspended in complete media (RPMI, 10% FBS, Pen/Strep, L-glutamine, HEPES, non-essential amino acid, Sodium pyruvate) with 100 ng/ml human GM-CSF (hu-GMCSF) and human IL-4 (hu-IL-4) to differentiate dendritic cells for 6 days.

All suspended dendritic cells were harvested and tested for CD11c expression by FACS staining Briefly, cells were washed in FACS buffer (PBS+2% FBS) and incubated with 1:5 dilution of anti-human CD11c-FITC or isotype control-FITC (BD Biosciences) for 1 hr on ice. Cells were washed with 2 ml FACS buffer, pelleted by centrifugation and 250 ul FACS buffer was added and cells were analyzed with a BD FACS Canto. For both donors tested, >90% of cells were CD11c positive and thus differentiated to human dendritic cells.

Harvested DC's were washed with PBS to remove cytokines, counted and plated at 100,000 cells/well in complete RPMI media in 96 well plates at 50 ul. Cells were incubated at 37 C for one hour to let them settle and to block the plate with serum albumin. Thereafter, 50 ul of 2× antibody titrations in RPMI were added to the plates. Cells were incubated for 48h.

Cell supernatant was harvested to measure sTREM2. PBS+3 mM EDTA was added to the plates. Plates were incubated at 37 C for 5-10 minutes, until cells would go into suspension upon pipetting. Cells were transferred to 96 well U-bottom plates, pelleted by centrifugation and resuspended in 45 ul FACS buffer and analyzed on iQE. Relative cell numbers were measured by counting the number of cells in a fixed volume of FACS buffer. Data were analyzed using Microsoft Excel and GraphPad Prism.

TREM2 MSD assay-A human TREM2-specific MSD assay was developed. The capture anti-TREM2 antibody T2KO811 was plated at 1 μg/ml in PBS overnight at 4 C (25 μL per well in single spot MSD plates, Meso Scale Discovery). The plates were washed thrice with a plate washer and 150 μL PBS+0.05% Triton per well. As a standard 100-0.02 ng/ml human TREM2-Fc (R&D Systems) was added to the plates, as well as cell supernatant diluted in binding buffer (PBS+1% BSA), all at 50 ul per well. Plates containing samples and standard were incubated at RT for 1 hour. The plates were washed thrice with a plate washer and 150 μL PBS+0.05% Triton per well. Biotinylated goat anti-human TREM2 polyclonal antibody (R&D Systems) was added at 1:2,000 dilution in binding buffer and incubated for 1 hour at RT. The plates were washed thrice with a plate washer and 150 μL PBS+0.05% Triton per well. 25 μl sulfo-tag conjugated Streptavidin (0.2 μg/ml in binding buffer, MesoScale Discovery) was added to the plates and incubated for 20 min at RT. The plates were washed thrice with a plate washer and 150 μL PBS+0.05% Triton per well. 150 μl of 1× Read Buffer (MesoScale Discovery) was added to each well and plates were read on a Sector Imager (MesoScale Discovery). Data were analyzed in Excel and Graph Pad Prism. It was tested whether AL2p lineage antibodies interfere with the assay, by spiking the MSD assay with different concentrations of AL2p variant antibodies. This had no effect on signal levels measured, suggesting that there is no assay interference by AL2p variant antibodies.

Results

TREM2 is produced as a cell surface receptor that can be cleaved to release the extracellular domain. A rare TREM2 mutation in humans (H157Y) causes increased production of sTREM2 and increases the risk of development of late onset Alzheimer's disease (Thornton et al, EMBO Mol Med 2017, 9(10): 1366-78).

Figure 5A:
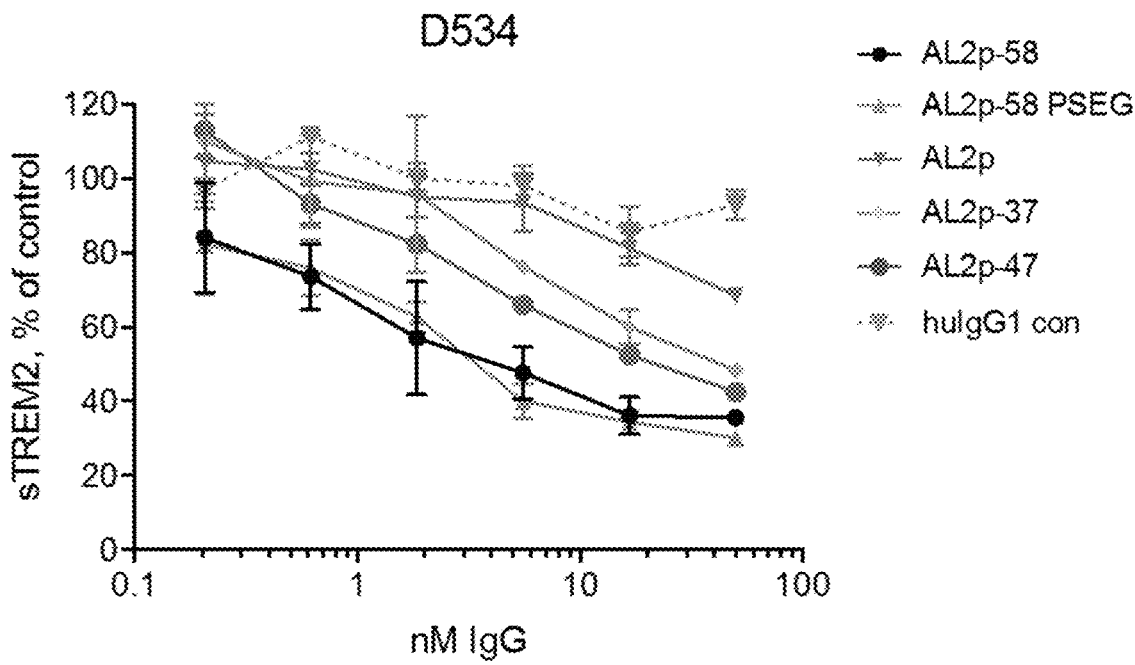
FIG. 5A shows sTREM2 secreted over 48 h by primary human dendritic cells from donor 534 upon incubation with anti-TREM2 or control antibodies.
Figure 5B:
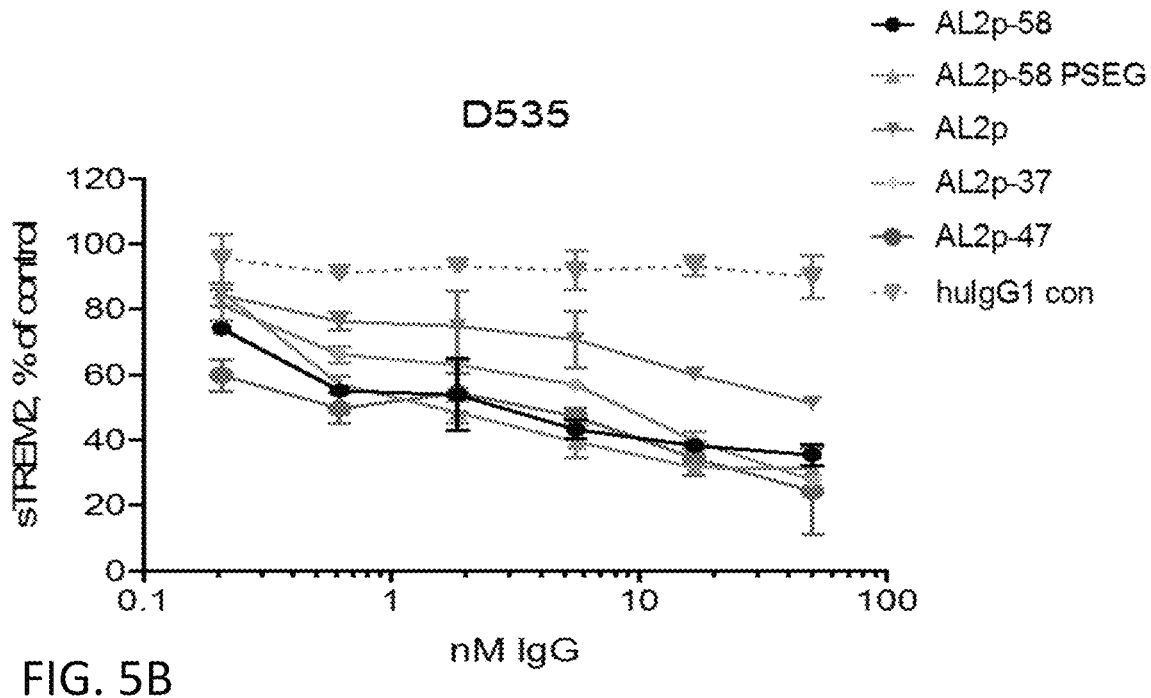
FIG. 5B shows sTREM2 secreted over 48 h by primary human dendritic cells from donor 535 upon incubation with anti-TREM2 or control antibodies.

To test whether TREM2 antibodies block shedding of the receptor, sTREM2 secreted into the media by primary human dendritic cells over the course of 48h was measured by ELISA. Dendritic cells derived from monocytes of two human blood donors were tested, donor 534 and 535. The average concentration of sTREM2 for donor 534 was 97.0 ng/ml and for donor 535 72.5 ng/ml. Upon addition of TREM2 antibodies sTREM2 secretion decreased with increasing antibody concentrations (FIG. 5A and FIG. 5B). The weakest effect was observed by the parental AL2p antibody as a huIgG1 chimera, although it did significantly reduce sTREM2 level at higher antibody concentrations in both donors. The humanized, affinity matured variant AL20-58 either as huIgG1 WT or PSEG showed the strongest decrease at the lowest antibody concentration. Results were similar across the two donors.

Figure 6A:
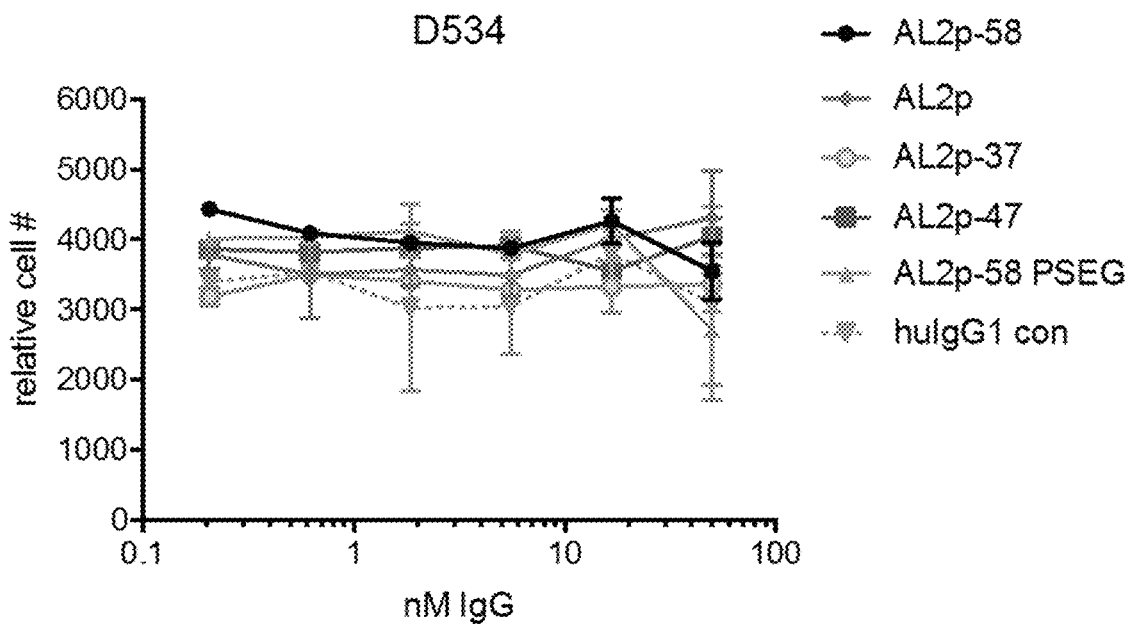
FIG. 6A shows that there is no change in cell numbers upon incubation of primary human dendritic cells of donor 534 with anti-TREM2 or control antibodies.
Figure 6B:
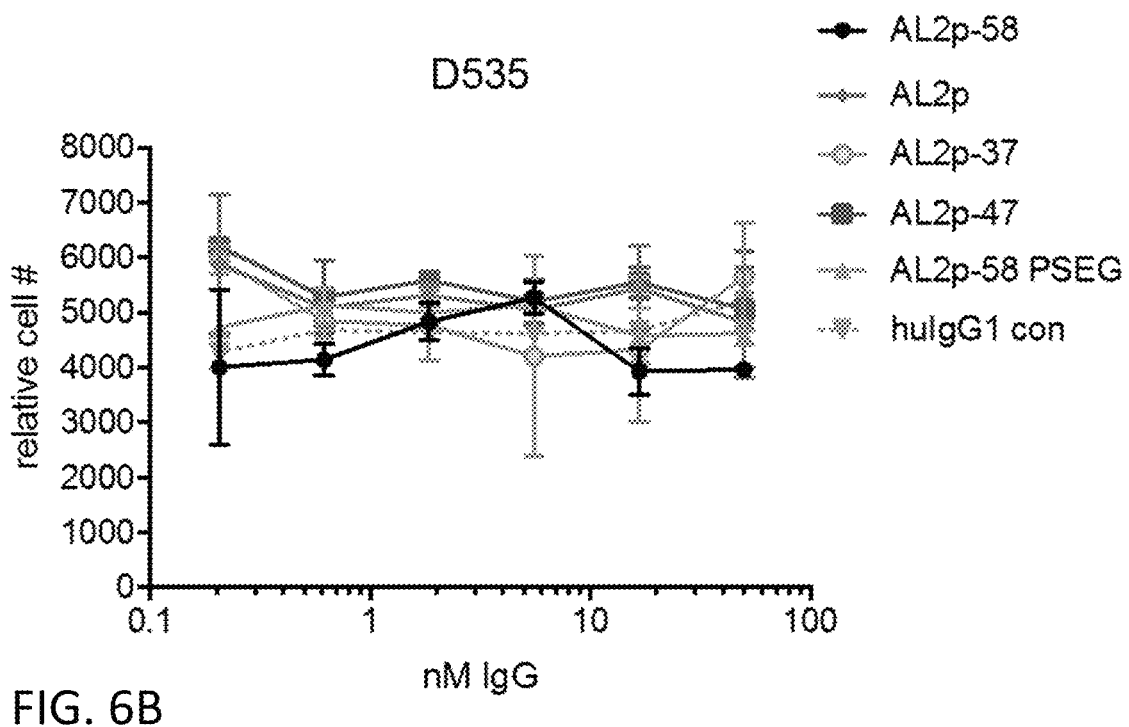
FIG. 6B shows that there is no change in cell numbers upon incubation of primary human dendritic cells of donor 535 with anti-TREM2 or control antibodies.

To test whether the reduction in sTREM2 was due to cell death and therefore reduction in cell numbers, cell density after antibody incubation was measured using iQE FACS analysis. There was no change in cell numbers upon treatment of dendritic cells with TREM2 antibodies in neither of the two donors (FIG. 6A and FIG. 6B).

Example 9: TREM2 Agonistic Antibodies Increase Viability of Primary Human Macrophages and Dendritic Cells Methods Human monocytes from three different donors were isolated from whole blood using RosetteSep Human monocyte enrichment cocktail (Stemcell technologies) and Ficoll centrifugation per manufacturer protocols. After lysing red blood cells with ACK lysing buffer, monocytes were resuspended in complete media (RPMI, 10% FBS, Pen/Strep, L-glutamine, HEPES, non-essential amino acid, Sodium pyruvate). For dendritic cell differentiation, 100 ng/ml human GM-CSF (hu-GMCSF) and human IL-4 (hu-IL-4) were added to the monocyte culture for six days. For macrophage differentiation, 100 ng/ml human M-CSF (huM-CSF) was used instead.

For plate bound antibodies, one day before, 10 μg/ml anti-TREM2 or control antibodies were added into a 96 well plate and left at 4° C. overnight. The next day, the plate was washed twice with PBS. Cells were plated at 25000 cells/well without additional cytokines for human DCs and macrophages, and cultured for 2 days. For soluble antibody conditions, antibodies were added to the media when the cells are plated. Cell viability was quantified using the CellTiter-Glo Luminescent cell viability kit (Promega) per manufacturer's protocol and luminescence was measured using a Biotek Synergy H1 plate reader. Data were analyzed using Microsoft Excel and GraphPad Prism.

Results

Both the parental AL2p antibody and its affinity matured offspring were tested for their ability to promote survival of primary human dendritic cells and macrophages. Cells were added to plates containing a titration of plate bound antibodies, incubated for 48 hours and viability was evaluated by measuring ATP content of the cells using CellTiterGlo (Promega).

Compared to the isotype control antibody, stimulating cells with TREM2 antibodies increased viability of both primary human macrophages and dendritic cells in a dose dependent manner (FIG. 8A and FIG. 8B). Compared to the parental AL2p antibody, all affinity matured variants showed up to a several hundred-fold increase in efficacy, as evidenced by reduced half-maximal activity (see EC50 values in Table 14 (EC50 values (nM) for different TREM2 antibodies in promoting viability of primary human macrophages or dendritic cells from three different donors (D558-560). P.F. denotes poor curve fit. All antibodies were tested as huIgG1, with AL1p-58 also being tested as huIgG1 PSEG). The parental AL2p antibody does show a dose dependent increase in viability, however, affinity matured versions of the antibody, especially AL2p-58 (both as huIgG1 and huIgG1 PSEG), AL2p-47 and AL2p-60, show several hundred-fold lower EC50, suggesting a much higher potency. AL2p-37 still showed a reduced EC50 compared to the parental IgG, but it is of lower potency than the other antibodies.

In addition, the ability of antibody AL2p-58 to increase viability in soluble format was evaluated in a similar assay, but the antibody was added to the media when the cells were plated. Compared to isotype control antibody, AL2p-58 was able to increase viability of both primary human macrophages and dendritic cells (FIG. 8C-8F). These results suggest that antibody AL2p-58 will be functionally active in vivo.

TABLE 14

|  | Macrophages | | | Dendritic cells | | |
| --- | --- | --- | --- | --- | --- | --- |
| Antibody | D558 | D559 | D560 | D558 | D559 | D560 |
| AL2p | 12.267 | 146.067 | 128.667 | 95.733 | 41.180 | 55.120 |
| AL2p-58 | 0.005 | 0.359 | 0.469 | 0.288 | 0.341 | 0.271 |
| AL2p-58 PSEG | 0.001 | 0.322 | 0.426 | 0.206 | 0.276 | 0.206 |
| AL2p-47 | 0.013 | 1.557 | 1.247 | 1.017 | 1.131 | 0.672 |
| AL2p-60 | P.F. | 0.194 | 0.154 | 0.152 | 0.244 | 0.178 |
| AL2p-37 | 1.235 | 18.313 | 31.827 | 4.187 | 6.155 | 4.472 |

Example 10: AL2p Variants Reduce Levels of Plasma sTREM2 Levels In Vivo

Methods

In vivo procedures-Human TREM2 BAC Tg mice were group-housed in polycarbonate cages and acclimated for at least 5 days prior to commencing studies. Animals were maintained in a 12 hr light/dark cycle with room temperature maintained at 22±2° C. and approximately 50% humidity, and received food and water ad libitum. For Experiments I-III animals were injected I.P. or I.V. with AL2p-47 huIgG1, AL2p-47 huIgG1 ASPSEG, AL2p-58 huIgG1, AL2p-58 huIgG1 PSEG, AL2p-61 huIgG1 PSEG or control huIgG1 on day 0 and blood for plasma was collected in heparinized tubes 2-4 days prior to study initiation and on Days 0 (4 hrs after injections), 1, 3, 6, 10 and 14. For Experiment IV, either AL2p msIgG1, T-21-9 msIgG1 or control msIgG1 were injected at 20 mg/kg I. P. on day 0 and plasma was collected on days 0 (4h after injection), 2, 5, 8 and 14. Plasma was isolated by spinning blood samples for 5 minutes at 5,000 rpm then collecting the supernatant. A total of four in vivo experiments were performed: experiment I: n=3 animals/group; experiment II: n=10 animals/group; experiment III: n=4 animals/group; experiment IV: n=4 animals/group.

Human TREM2 MSD assay-Plasma sTREM2 was measured by MSD as outlined in Example 8.

Results

Figure 7A:
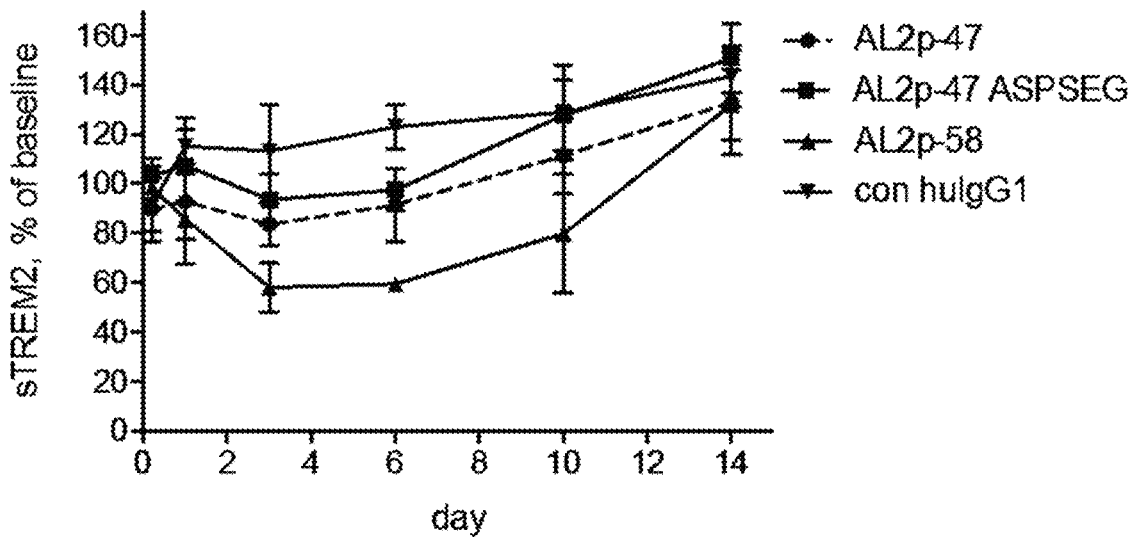
FIG. 7A shows plasma sTREM2 as % of baseline levels upon single injection of 15 mg/kg TREM2 antibodies AL2p-47 huIgG1, AL2p-47 huIgG1 ASPSEG, AL2p-58 huIgG1 or control huIgG1.
Figure 7B:
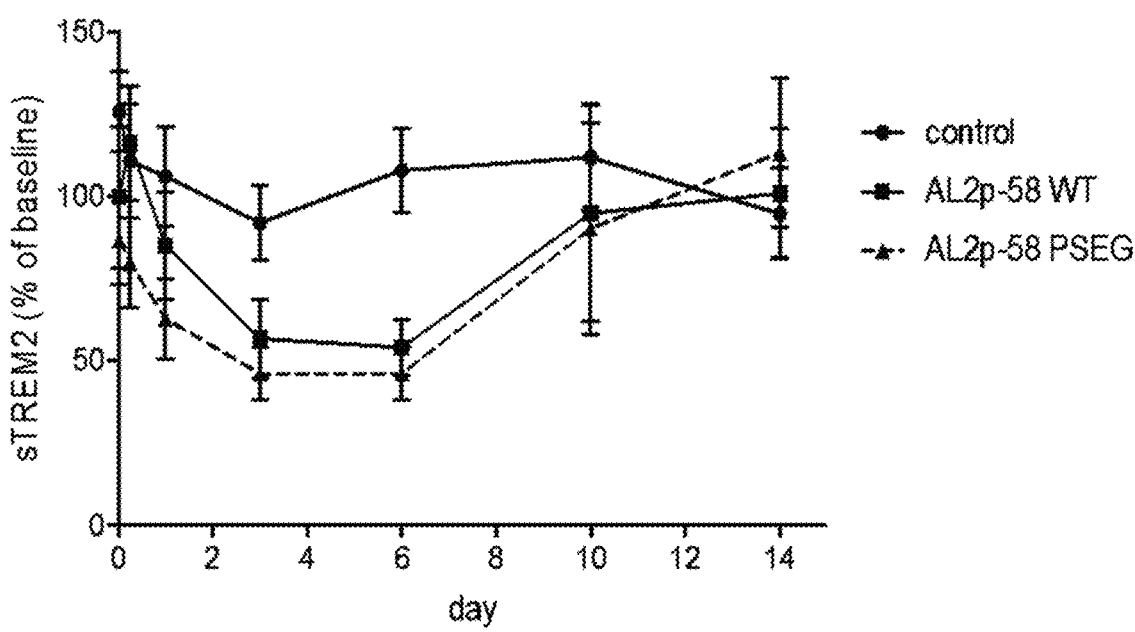
FIG. 7B shows plasma sTREM2 as % of baseline levels upon single injection of 15 mg/kg TREM2 antibodies AL2p-58 huIgG1, AL2p-58 huIgG1 PSEG or control huIgG1.
Figure 7C:
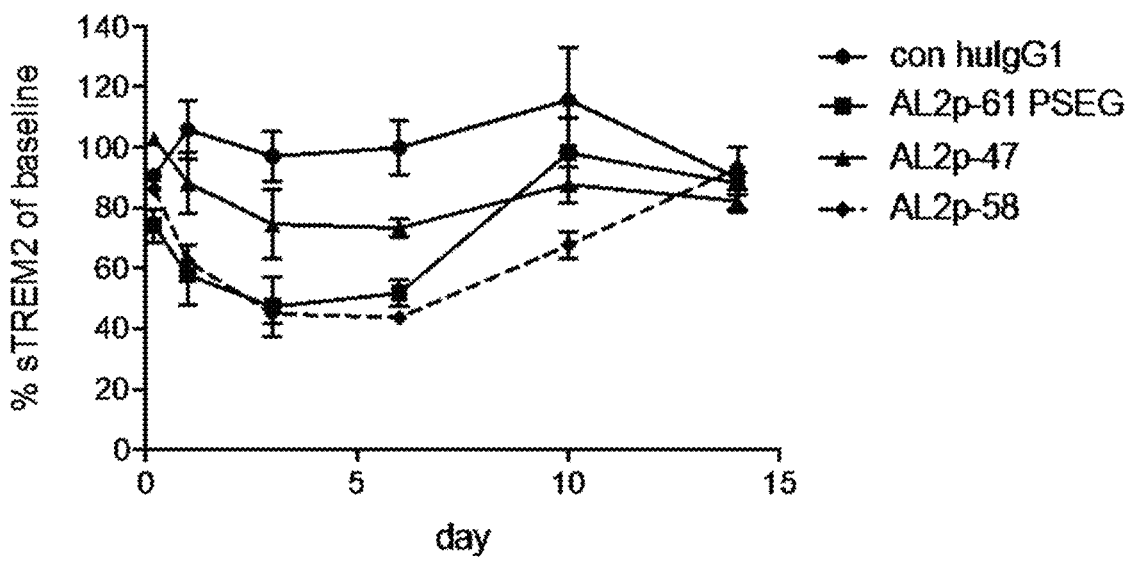
FIG. 7C shows plasma sTREM2 as % of baseline levels upon single injection of 15 mg/kg TREM2 antibodies AL2p-61 huIgG1 PSEG, AL2p-47 huIgG1, AL2p-58 huIgG1 or control huIgG1.
Figure 7D:
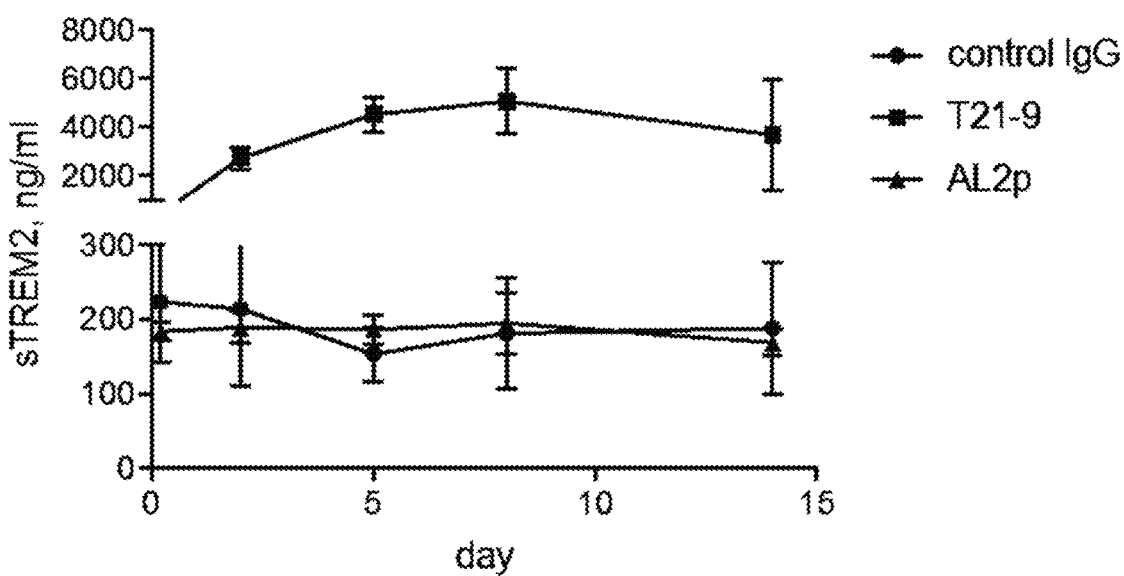
FIG. 7D shows plasma sTREM2 in ng/ml upon single injection of 20 mg/kg TREM2 antibodies AL2p msIgG1, T21-9 msIgG1 or control msIgG1.

Affinity matured variants of AL2p were tested for their ability to reduce sTREM2 levels, based on in vitro experiments shown in Example 8 that suggest AL2p antibodies block TREM2 shedding either directly by blocking binding of the ADAM sheddase or indirectly by inducing TREM2 signal activation and endocytosis. Human TREM2 expressing BAC Tg mice were injected with 15 mg/kg IgG on day 0 and sTREM2 levels were monitored over the course of 14 days and normalized to pre-treatment baseline. Table 15 outlines the % reduction in plasma sTREM2 observed after treatment with the different AL2p variants and FIG. 7A-C show graphs depicting reduction in sTREM2 after treatment of human BAC Tg mice with affinity matured versions of AL2p. In contrast, parental AL2p had no significant effect on plasma sTREM2 levels (FIG. 7D), while another TREM2 antibody that binds the Ig domain of the protein (T21-9) causes a several fold elevation of plasma sTREM2, likely because it stabilizes the protein. All variants induced reduction of sTREM2 for several days after treatment. AL2p-58 huIgG1 PSEG induced the strongest and longest lasting downregulation of sTREM2. These data suggest that sTREM2 in both plasma and CSF can be used as a marker for target engagement in vivo in human patients.

Mm Tris-HCl (pH 8.0), 150 mM NaCl, 1 mM EDTA, 1.5 mM $MgCl_2$, 10% glycerol, plus protease and phosphatase inhibitors), split after lysis and immunoprecipitated with rat anti-h/m TREM2 (RD, clone 237920) or isotype control. Precipitated proteins were fractionated by SDS-PAGE (non-reducing conditions), transferred to nitrocellulose membranes and probed with anti-phosphotyrosine antibody (Millipore, 4G10). To confirm that each cell lysate used for TREM2 immunoprecipitations contained equal amount of proteins, an equal amount of lysates were collected before immunoprecipitation and fractionated by SDS-PAGE (reducing conditions). Immunoblots were probed with antibodies directed against human TREM2 (R&D #AF1828).

Results

TREM2 ligand binding induces receptor clustering, which triggers phosphorylation of its adaptor protein Dap12 and an intracellular signaling cascade. To test if AL2p variant antibodies induce TREM2 signal activation in vivo, WT or human TREM2 expressing Bac-Tg mice were treated with thioglycollate to recruit macrophages to the peritoneum. After three days, mice were injected with anti-TREM2 or control huIgG1 antibodies and subsequently, peritoneal macrophages were harvested, lysed and phosphorylation of Dap12 associated with TREM2 was probed as a measure of TREM2 signaling activation.

Figure 9:
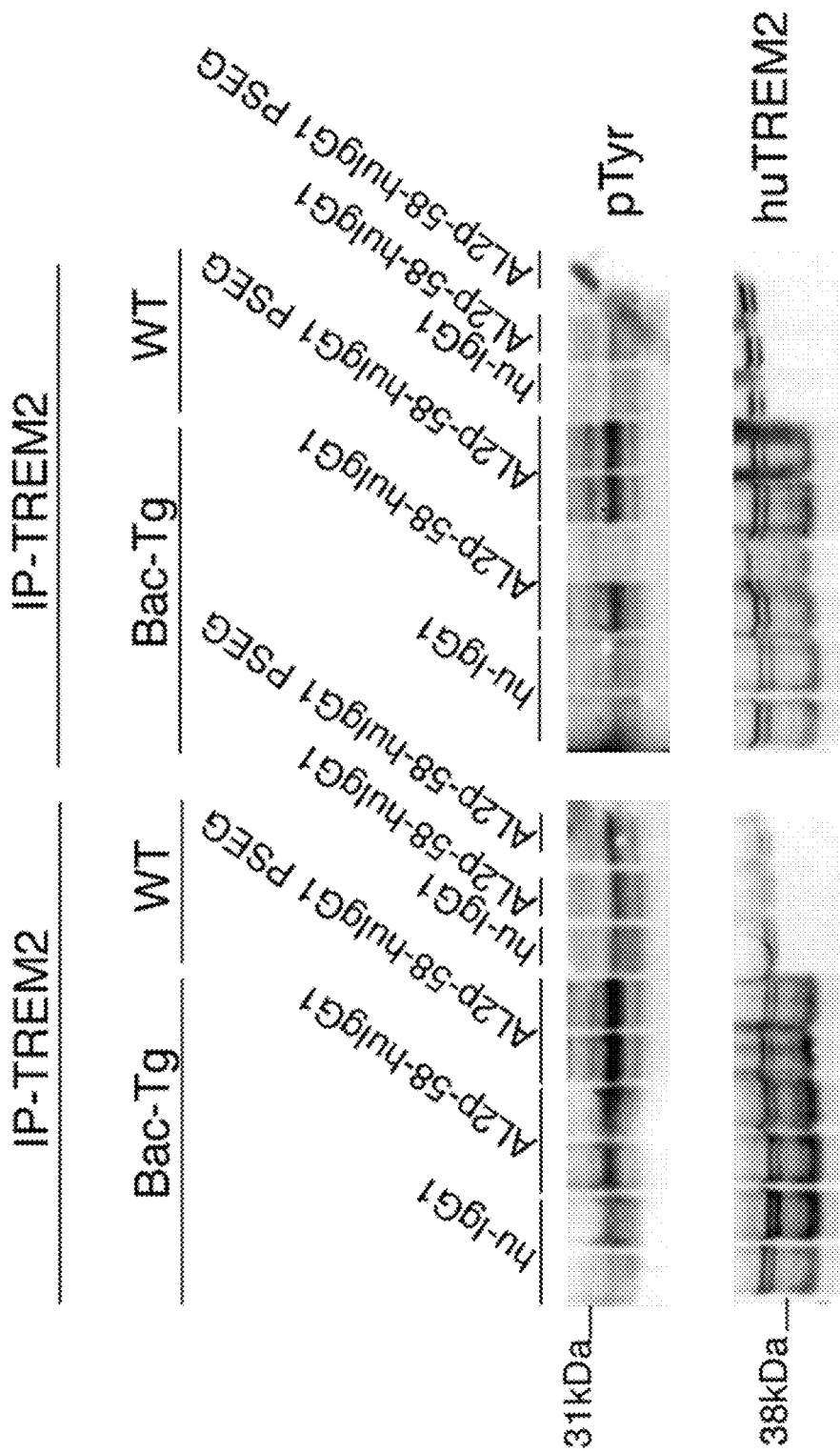
FIG. 9 shows Western blot analysis of Dap12 phosphorylation in peritoneal macrophages upon treatment of either WT or TREM2 Bac-Tg mice with AL2p-58 huIgG1, AL2p-58 huIgG1 PSEG or control huIgG1. Cell lysates were immunoprecipitated with anti-TREM2; upper set of bands show staining with a phosphotyrosine antibody and lower set show total human TREM2 levels.

Treatment of Bac-Tg mice with AL2p-58 huIgG1 or AL2p huIgG1 PSEG caused a strong increase in Dap12 phosphorylation compared to control huIgG1 (FIG. 9). In contrast, the TREM2 antibodies showed no effect on Dap12 in WT mice, since these antibodies are not murine cross-reactive. These results demonstrate that AL2p-58 antibodies can cluster and activate the TREM2 receptor in vivo.

Example 12: Unspecific Reactivity of AL2p Variants

Methods

A FACS-based assay to measure polyspecific reactivity (PSR) was performed as described in Xu et al., Protein Engineering, Design and Selection, 2013, 26 (10), 663-70.

Results

TABLE 15

Reduction in plasma sTREM2 after treatment with AL2p variant antibodies

| Antibody | huIgG1 | Expt. # | 4 h, day 0 | Day 1 | Day 3 | Day 6 | Day 10 | Day 14 |
|---|---|---|---|---|---|---|---|---|
| AL2p-47 | WT | I | 102.9 | 88.3 | 74.6* | 73.4** | 87.7** | 82.3 |
|  |  | III |  | 89.7 | 92.9 | 83.6* | 91.5** | 111.5 | 133.0 |
| AL2p-47 | ASPSEG | III | 103.1 | 107.5 | 93.5 | 97.5* | 127.7 | 150.8 |
| AL2p-58 | WT | I | 86.3 | 62.3**** | 45.0**** | 43.7**** | 67.7**** | 93.2 |
|  |  | II |  | 85.0* | 56.7**** | 54.0**** | 94.8 | 100.9 |
|  |  | III | 98.5 | 85.8* | 58.0**** | 59.4**** | 79.9**** | 131.9 |
| AL2p-58 | PSEG | II |  | 62.8**** | 46.2**** | 46.2**** | 90.2* | 113.2 |
| AL2p-61 | PSEG | I | 74.2 | 57.8**** | 47.4**** | 51.8**** | 98.2 | 88.2 |

Shown is % sTREM2 found in plasma of human TREM2 BAC Tg mice treated with different TREM2 antibody variants either as huIgG1 WT or huIgG1 PSEG or huIgG1 ASPSEG. Stars indicate values that are significantly lower compared to control huIgG1 injected mice (*p < 0.05, p < 0.01, *p < 001, ****p < 0.0001) using Two-way ANOVA and post hoc test for pairwise comparisons.

Example 11: AL2p Variants In Vivo

Methods 8 week old C57BL/6 (WT) or Bac-TG-hTREM2 mice were injected i.p. with 3 ml of 3% thioglycollate. After 3 days, when the peritoneal cavity was enriched with peritoneal macrophages ($CD11b^+F4/80^+$ expressing TREM2, mice were injected with huIgG1 or TREM2-specific antibodies AL2p-58 huIgG1 or AL2p-58 huIgG1 (40 mg/kg). Peritoneal cells were recovered after one hour and immediately lysed in lysis buffer (n-dodecyl-b-malthoside 1%, 50

While the parental humanized versions of AL2p (AL2p-h50, AL2p-h77) were PSR low, indicating that they do not unspecifically bind to non-TREM2 targets, upon increasing affinity to TREM2 by affinity maturation, AL2p antibody variants showed elevated PSR values (Table 16). PSR positively correlates with affinity and higher unspecific binding, which can result in faster elimination of circulating antibody from the body and thus a shorter half-life. The results in Table 16, when combined with those in Tables 9A-9C, 10A-10C, 11, 13 and 14 indicate that AL2p antibody variants with a high PSR have too short a half-life and AL2p antibody variants with low PSR do not exhibit sufficient functionality. However, AL2p antibody variants with medium PSR exhibit both low unspecific binding and better functionality than AL2p antibody variants with low PSR (Tables 9A-9C, 10A-10C, 13 and 14).

TABLE 16

Summary of PSR reactivity of AL2p variant antibodies

| Antibody | PSR value | PSR range |
|---|---|---|
| AL2p-h50 | 0.01 | Low |
| AL2p-h77 | 0.09 | Low |
| AL2p-2 | 0.10 | Low |
| AL2p-3 | 0.05 | Low |
| AL2p-4 | 0.10 | Low |
| AL2p-5 | 0.15 | Low |
| AL2p-6 | 0.10 | Low |
| AL2p-7 | 0.74 | High |
| AL2p-8 | 0.82 | High |
| AL2p-9 | 0.80 | High |
| AL2p-10 | 0.14 | Low |
| AL2p-11 | 0.68 | High |
| AL2p-12 | 0.57 | Medium |
| AL2p-13 | 0.71 | High |
| AL2p-14 | 0.80 | High |
| AL2p-15 | 0.34 | Medium |
| AL2p-16 | 0.84 | High |
| AL2p-17 | 0.77 | High |
| AL2p-18 | 0.72 | High |
| AL2p-19 | 0.84 | High |
| AL2p-20 | 0.74 | High |
| AL2p-21 | 0.75 | High |
| AL2p-22 | 0.88 | High |
| AL2p-23 | 0.70 | High |
| AL2p-24 | 0.85 | High |
| AL2p-25 | 0.80 | High |
| AL2p-26 | 0.80 | High |
| AL2p-27 | 0.87 | High |

TABLE 16-continued

Summary of PSR reactivity of AL2p variant antibodies

| Antibody | PSR value | PSR range |
|---|---|---|
| AL2p-28 | 0.52 | Medium |
| AL2p-29 | 0.72 | High |
| AL2p-30 | 0.70 | High |
| AL2p-31 | 0.85 | High |
| AL2p-32 | 0.10 | Low |
| AL2p-33 | 0.05 | Low |
| AL2p-35 | 0.10 | Low |
| AL2p-36 | 0.82 | High |
| AL2p-37 | 0.15 | Low |
| AL2p-38 | 0.73 | High |
| AL2p-39 | 0.66 | High |
| AL2p-40 | 0.69 | High |
| AL2p-41 | 0.77 | High |
| AL2p-42 | 0.76 | High |
| AL2p-43 | 0.70 | High |
| AL2p-44 | 0.67 | High |
| AL2p-45 | 0.33 | Medium |
| AL2p-46 | 0.44 | Medium |
| AL2p-47 | 0.48 | Medium |
| AL2p-48 | 0.55 | Medium |
| AL2p-49 | 0.54 | Medium |
| AL2p-50 | 0.16 | Low |
| AL2p-51 | 0.20 | Low |
| AL2p-52 | 0.14 | Low |
| AL2p-53 | 0.22 | Low |
| AL2p-54 | 0.38 | Medium |
| AL2p-55 | 0.37 | Medium |
| AL2p-56 | 0.37 | Medium |
| AL2p-57 | 0.42 | Medium |
| AL2p-59 | n.d. | |
| AL2p-61 | 0.74 | High |
| AL2p-62 | 0.19 | Low |
| AL2p-58 | 0.59 | Medium |

```
SEQUENCES
Human TREM2 protein
                                                      (SEQ ID NO: 1)
MEPLRLLILLFVTELSGAHNTTVFQGVAGQSLQVSCPYDSMKHWGRRKAWCRQLGEKGPCQ

RVVSTHNLWLLSFLRRWNGSTAITDDTLGGTLTITLRNLQPHDAGLYQCQSLHGSEADTLRK

VLVEVLADPLDHRDAGDLWFPGESESFEDAHVEHSISRSLLEGEIPFPPTSILLLLACIFLIKILA

ASALWAAAWHGQKPGTHPPSELDCGHDPGYQLQTLPGLRDT

Mouse TREM2 protein
                                                      (SEQ ID NO: 2)
MGPLHQFLLLLITALSQALNTTVLQGMAGQSLRVSCTYDALKHWGRRKAWCRQLGEEGPC

QRVVSTHGVWLLAFLKKRNGSTVIADDTLAGTVTITLKNLQAGDAGLYQCQSLRGREAEVL

QKVLVEVLEDPLDDQDAGDLWVPEESSSFEGAQVEHSTSRNQETSFPPTSILLLLACVLLSKF

LAASILWAVARGRQKPGTPVVRGLDCGQDAGHQLQILTGPGGT

Rat TREM2 protein
                                                      (SEQ ID NO: 3)
MEPLHVFVLLLVTELSQALNTTVLQGVAGQSLRVSCTYDALRHWGRRKAWCRQLAEEGPC

QRVVSTHGVWLLAFLRKQNGSTVITDDTLAGTVTITLRNLQAGDAGLYQCQSLRGREAEVL

QKVVVEVLEDPLDDQDAGDLWVPEESESFEGAQVEHSTSSQVSSCGSPLTYHLPPKEPIRKDL

LPTHFHSSPPGLCPPEQASYSQHPLGCGQGQAEAGDTCGQWARL

Rhesus monkey TREM2 protein
                                                      (SEQ ID NO: 4)
MPDPLFSAVQGKDKILHKALCICPWPGKGGMEPLRLLILLFATELSGAHNTTVFQGVEGQSL

QVSCPYDSMKHWGRRKAWCRQLGEKGPCQRVVSTHNLWLLSFLRRRNGSTAITDDTLGGT
```

-continued

LTITLRNLQPHDAGFYQCQSLHGSEADTLRKVLVEVLADPLDHRDAGDLWVPGESESFEDAH

VEHSISRSLLEGEIPFPPTSVLLLLACIFLIKILAASALWAAAWHGQKPGTHPPSEPDCGHDPGH

QLQTLPGLRDT

Cynomolgus monkey TREM2 protein
(SEQ ID NO: 5)
MEPLRLLILLFATELSGAHNTTVFQGVEGQSLQVSCPYDSMKHWGRRKAWCRQLGEKGPCQ

RVVSTHNLWLLSFLRRRNGSTAITDDTLGGTLTITLRNLQPHDAGFYQCQSLHGSEADTLRK

VLVEVLADPLDHRDAGDLWVPGESESFEDAHVEHSISRSLLEGEIPFPPTSVLLLLACIFLIKIL

AASALWAAAWHGQKPGTHPPSEPDCGHDPGHQLQTLPGLRDT

Equine TREM2 protein
(SEQ ID NO: 6)
MEPLPLLILLSVAELSRGHNTTVFQGTAGRSLKVSCPYNSLMHWGRRKAWCRQLGEDGPCQ

QVVSTHSLWLLSFLKRRNGSTVITDDALGGILTITLRNLQAHDAGFYQCQSLHGGEADTLRK

VLVEVLADPLDHQEPGDLWIPKESESFEDAQVEHSISRSLVEEEIPSLPTSILLLLACIFLSKLLA

ASAIWAAAWHGQKQETPPASEPDRGHDPGYQLHTLTGERDT

Pig TREM2 protein
(SEQ ID NO: 7)
METLGLLLLLWVAELSRAHNTSVFQGTAGQSLRVSCSYNSLKHWGRRKAWCRQLSEEGLC

QHVVSTHPTWLLSFLKRRNGSTAITDDALGGTLTITLRNLQAHDAGLYQCQSLHGSEADTLK

KVLVEVLADPLESQSKSFQDVQMEHSISRNLSEESLFPPTSTLFLLACVFLSKLLVASALWAA

AWHGHKQRTSPAGGLDCGRDPGDQDQTLTDELGESSDQDQTLTELRDT

Dog TREM2 protein
(SEQ ID NO: 8)
MEPLWLLILLAVTELSGAHNTTVFQGMAGRSLQVSCPYNSLKHWGRRKAWCRQVDKEGPC

QRVVSTHRSWLLSFLKRWNGSTAIVDDALGGTLTITLRNLQAHDAGLYQCQSLYGDEADTL

RKVLVEVLADPLDHLDPGDLWIPEESKGFEDAHVEPSVSRSLSEEEIPFPPTSILFLLACIFLSKF

LAASALWAAAWRGQKLGTPQASELDCSCDPGYQLQTLTEPRDM

Parental mouse AL2p heavy chain variable region
(SEQ ID NO: 119)
QVQLQQSGPELVKPGASLKISCKASGYAFSSSWMNWVKQRPGKGLEWIGRIYPGDGDTNYN

GEFRVRATLTADTSSTTAYMQLSSLTSEDSAVYFCARLLRNQPGESYAMDYWGQGASVTVS

S

Parental mouse AL2p light chain variable region
(SEQ ID NO: 120)
DVVMTQTPLSLPVSLGDQASISCRSSQSLVHSNGYTYLHWYLQKPGQSPKLLIYKVSNRFSG

VPDRFSGSGSGTDFTLKISRVEADDLGVYFCSQSTRVPYTFGGGTKLEIK

FC1 (wild-type human IgG1)
(SEQ ID NO: 146)
ASTKGPSVFPLAPSSKSTSGGTAALGCLVKDYFPEPVTVSWNSGALTSGVHTFPAVLQSSGLY

SLSSVVTVPSSSLGTQTYICNVNHKPSNTKVDKKVEPKSCDKTHTCPPCPAPELLGGPSVFLFP

PKPKDTLMISRTPEVTCVVVDVSHEDPEVKFNWYVDGVEVHNAKTKPREEQYNSTYRVVSV

LTVLHQDWLNGKEYKCKVSNKALPAPIEKTISKAKGQPREPQVYTLPPSRDELTKNQVSLTC

LVKGFYPSDIAVEWESNGQPENNYKTTPPVLDSDGSFFLYSKLTVDKSRWQQGNVFSCSVM

HEALHNHYTQKSLSLSPGK

FC2 (IgG1 E430G)
(SEQ ID NO: 147)
ASTKGPSVFPLAPSSKSTSGGTAALGCLVKDYFPEPVTVSWNSGALTSGVHTFPAVLQSSGLY

SLSSVVTVPSSSLGTQTYICNVNHKPSNTKVDKKVEPKSCDKTHTCPPCPAPELLGGPSVFLFP

PKPKDTLMISRTPEVTCVVVDVSHEDPEVKFNWYVDGVEVHNAKTKPREEQYNSTYRVVSV

LTVLHQDWLNGKEYKCKVSNKALPAPIEKTISKAKGQPREPQVYTLPPSRDELTKNQVSLTC

LVKGFYPSDIAVEWESNGQPENNYKTTPPVLDSDGSFFLYSKLTVDKSRWQQGNVFSCSVM

HGALHNHYTQKSLSLSPGK

FC3 (IgG1 L234A, L235A, P331S: LALAPS)
(SEQ ID NO: 148)
ASTKGPSVFPLAPSSKSTSGGTAALGCLVKDYFPEPVTVSWNSGALTSGVHTFPAVLQSSGLY

SLSSVVTVPSSSLGTQTYICNVNHKPSNTKVDKKVEPKSCDKTHTCPPCPAPEAAGGPSVFLF

PPKPKDTLMISRTPEVTCVVVDVSHEDPEVKFNWYVDGVEVHNAKTKPREEQYNSTYRVVS

VLTVLHQDWLNGKEYKCKVSNKALPASIEKTISKAKGQPREPQVYTLPPSRDELTKNQVSLT

CLVKGFYPSDIAVEWESNGQPENNYKTTPPVLDSDGSFFLYSKLTVDKSRWQQGNVFSCSV

MHEALHNHYTQKSLSLSPGK

FC4 (IgG1 L234A, L235A, P331S, E430G: LALAPSEG)
(SEQ ID NO: 149)
ASTKGPSVFPLAPSSKSTSGGTAALGCLVKDYFPEPVTVSWNSGALTSGVHTFPAVLQSSGLY

SLSSVVTVPSSSLGTQTYICNVNHKPSNTKVDKKVEPKSCDKTHTCPPCPAPEAAGGPSVFLF

PPKPKDTLMISRTPEVTCVVVDVSHEDPEVKFNWYVDGVEVHNAKTKPREEQYNSTYRVVS

VLTVLHQDWLNGKEYKCKVSNKALPASIEKTISKAKGQPREPQVYTLPPSRDELTKNQVSLT

CLVKGFYPSDIAVEWESNGQPENNYKTTPPVLDSDGSFFLYSKLTVDKSRWQQGNVFSCSV

MHGALHNHYTQKSLSLSPGK

FC5 (IgG1 K322A, E430G: KAEG)
(SEQ ID NO: 150)
ASTKGPSVFPLAPSSKSTSGGTAALGCLVKDYFPEPVTVSWNSGALTSGVHTFPAVLQSSGLY

SLSSVVTVPSSSLGTQTYICNVNHKPSNTKVDKKVEPKSCDKTHTCPPCPAPELLGGPSVFLFP

PKPKDTLMISRTPEVTCVVVDVSHEDPEVKFNWYVDGVEVHNAKTKPREEQYNSTYRVVSV

LTVLHQDWLNGKEYKCAVSNKALPAPIEKTISKAKGQPREPQVYTLPPSRDELTKNQVSLTC

LVKGFYPSDIAVEWESNGQPENNYKTTPPVLDSDGSFFLYSKLTVDKSRWQQGNVFSCSVM

HGALHNHYTQKSLSLSPGK

FC6 (IgG1 P331S, E430G: PSEG)
(SEQ ID NO: 151)
ASTKGPSVFPLAPSSKSTSGGTAALGCLVKDYFPEPVTVSWNSGALTSGVHTFPAVLQSSGLY

SLSSVVTVPSSSLGTQTYICNVNHKPSNTKVDKKVEPKSCDKTHTCPPCPAPELLGGPSVFLFP

PKPKDTLMISRTPEVTCVVVDVSHEDPEVKFNWYVDGVEVHNAKTKPREEQYNSTYRVVSV

LTVLHQDWLNGKEYKCAVSNKALPAPIEKTISKAKGQPREPQVYTLPPSRDELTKNQVSLTC

LVKGFYPSDIAVEWESNGQPENNYKTTPPVLDSDGSFFLYSKLTVDKSRWQQGNVFSCSVM

HGALHNHYTQKSLSLSPGK

FC7 (IgG1 A330S, P331S, E430G: ASPSEG)
(SEQ ID NO: 152)
ASTKGPSVFPLAPSSKSTSGGTAALGCLVKDYFPEPVTVSWNSGALTSGVHTFPAVLQSSGLY

SLSSVVTVPSSSLGTQTYICNVNHKPSNTKVDKKVEPKSCDKTHTCPPCPAPELLGGPSVFLFP

PKPKDTLMISRTPEVTCVVVDVSHEDPEVKFNWYVDGVEVHNAKTKPREEQYNSTYRVVSV

LTVLHQDWLNGKEYKCKVSNKALPSSIEKTISKAKGQPREPQVYTLPPSRDELTKNQVSLTCL

VKGFYPSDIAVEWESNGQPENNYKTTPPVLDSDGSFFLYSKLTVDKSRWQQGNVFSCSVMH

GALHNHYTQKSLSLSPGK

-continued

FC8 (IgG1 K322A, P331S, E430G: KAPSEG)
(SEQ ID NO: 153)
ASTKGPSVFPLAPSSKSTSGGTAALGCLVKDYFPEPVTVSWNSGALTSGVHTFPAVLQSSGLY

SLSSVVTVPSSSLGTQTYICNVNHKPSNTKVDKKVEPKSCDKTHTCPPCPAPELLGGPSVFLFP

PKPKDTLMISRTPEVTCVVVDVSHEDPEVKFNWYVDGVEVHNAKTKPREEQYNSTYRVVSV

LTVLHQDWLNGKEYKCAVSNKALPASIEKTISKAKGQPREPQVYTLPPSRDELTKNQVSLTC

LVKGFYPSDIAVEWESNGQPENNYKTTPPVLDSDGSFFLYSKLTVDKSRWQQGNVFSCSVM

HGALHNHYTQKSLSLSPGK

FC9 (wild-type human IgG2)
(SEQ ID NO: 154)
ASTKGPSVFPLAPCSRSTSESTAALGCLVKDYFPEPVTVSWNSGALTSGVHTFPAVLQSSGLY

SLSSVVTVPSSNFGTQTYTCNVDHKPSNTKVDKTVERKCCVECPPCPAPPVAGPSVFLFPPKP

KDTLMISRTPEVTCVVVDVSHEDPEVQFNWYVDGVEVHNAKTKPREEQFNSTFRVVSVLTV

VHQDWLNGKEYKCKVSNKGLPAPIEKTISKTKGQPREPQVYTLPPSREEMTKNQVSLTCLVK

GFYPSDIAVEWESNGQPENNYKTTPPMLDSDGSFFLYSKLTVDKSRWQQGNVFSCSVMHEA

LHNHYTQKSLSLSPGK

FC10 (IgG2 E430G)
(SEQ ID NO: 155)
ASTKGPSVFPLAPCSRSTSESTAALGCLVKDYFPEPVTVSWNSGALTSGVHTFPAVLQSSGLY

SLSSVVTVPSSNFGTQTYTCNVDHKPSNTKVDKTVERKCCVECPPCPAPPVAGPSVFLFPPKP

KDTLMISRTPEVTCVVVDVSHEDPEVQFNWYVDGVEVHNAKTKPREEQFNSTFRVVSVLTV

VHQDWLNGKEYKCKVSNKGLPAPIEKTISKTKGQPREPQVYTLPPSREEMTKNQVSLTCLVK

GFYPSDIAVEWESNGQPENNYKTTPPMLDSDGSFFLYSKLTVDKSRWQQGNVFSCSVMHGA

LHNHYTQKSLSLSPGK

FC11 (IgG2 A330S P331S E430G: ASPSEG)
(SEQ ID NO: 156)
ASTKGPSVFPLAPCSRSTSESTAALGCLVKDYFPEPVTVSWNSGALTSGVHTFPAVLQSSGLY

SLSSVVTVPSSNFGTQTYTCNVDHKPSNTKVDKTVERKCCVECPPCPAPPVAGPSVFLFPPKP

KDTLMISRTPEVTCVVVDVSHEDPEVQFNWYVDGVEVHNAKTKPREEQFNSTFRVVSVLTV

VHQDWLNGKEYKCKVSNKGLPSSIEKTISKTKGQPREPQVYTLPPSREEMTKNQVSLTCLVK

GFYPSDIAVEWESNGQPENNYKTTPPMLDSDGSFFLYSKLTVDKSRWQQGNVFSCSVMHGA

LHNHYTQKSLSLSPGK

What is claimed is:

1. An antibody that binds to a human TREM2 protein, wherein the antibody comprises a heavy chain variable region comprising an HVR-H1, HVR-H2, and HVR-H3 and a light chain variable region comprising an HVR-L1, HVR-L2, and HVR-L3, wherein
the HVR-H1 comprises the sequence of SEQ ID NO: 132, the HVR-H2 comprises the sequence of SEQ ID NO: 135, the HVR-H3 comprises the sequence of SEQ ID NO: 126, the HVR-L1 comprises the sequence of SEQ ID NO: 144, the HVR-L2 comprises the sequence of SEQ ID NO: 131, and the HVR-L3 comprises the sequence of SEQ ID NO: 129.

2. The antibody of claim 1, wherein the antibody binds to one or more human TREM2 proteins selected from the group consisting of wild-type human TREM2, a naturally occurring variant of human TREM2, and a disease variant of human TREM2.

3. The antibody of claim 1, wherein the antibody is an antibody fragment selected from an Fab, Fab', Fab'-SH, F(ab')2, Fv, scFv, or an antibody fragment comprising an antigen binding region.

4. The antibody of claim 1, wherein the antibody is a monoclonal antibody.

5. The antibody of claim 1, wherein the antibody is a humanized antibody.

6. The antibody of claim 1, wherein the antibody is of the IgG class, the IgM class, or the IgA class.

7. The antibody of claim 6, wherein the antibody is of the IgG class and has an IgG1, IgG2, IgG3, or IgG4 isotype.

8. The antibody of claim 7, wherein the antibody comprises one or more amino acid substitutions in the Fc region at a residue position selected from the group consisting of: C127S, L234A, L234F, L235A, L235E, S267E, K322A, L328F, A330S, P331S, E345R, E430G, S440Y, and any combination thereof, wherein the numbering of the residues is according to EU numbering.

9. The antibody of claim 7, wherein the antibody has an IgG1 or IgG2 isotype, and wherein:
the Fc region comprises an amino acid substitution at positions E430G, L234A, L235A, and P331S, wherein the numbering of the residue position is according to EU numbering;
the Fc region comprises an amino acid substitution at positions E430G and P331S, wherein the numbering of the residue position is according to EU numbering;
the Fc region comprises an amino acid substitution at positions E430G and K322A, wherein the numbering of the residue position is according to EU numbering;
the Fc region comprises an amino acid substitution at positions E430G, A330S, and P331S, wherein the numbering of the residue position is according to EU numbering;

the Fc region comprises an amino acid substitution at positions E430G, K322A, A330S, and P331S, wherein the numbering of the residue position is according to EU numbering;

the Fc region comprises an amino acid substitution at positions E430G, K322A, and A330S, wherein the numbering of the residue position is according to EU numbering;

the Fc region comprises an amino acid substitution at positions E430G, K322A, and P331S, wherein the numbering of the residue position is according to EU numbering;

the Fc region comprises an amino acid substitution at positions S267E and L328F, wherein the numbering of the residue position is according to EU numbering;

the Fc region comprises an amino acid substitution at position C127S, wherein the numbering of the residue position is according to EU numbering;

the Fc region comprises an amino acid substitution at positions E345R, E430G and S440Y, wherein the numbering of the residue position is according to EU numbering; or the Fc region comprises an amino acid sequence selected from the group consisting of SEQ ID NOs: 146-156.

10. The antibody of claim 9, wherein the antibody has an IgG1 isotype, and wherein the Fc region comprises an amino acid substitution at positions E430G and P331S, wherein the numbering of the residue position is according to EU numbering.

11. The antibody of claim 1, wherein the antibody is a bispecific antibody recognizing a first antigen and a second antigen, wherein the first antigen is human TREM2 or a naturally occurring variant thereof, and the second antigen is:

(a) an antigen facilitating transport across the blood-brain-barrier;

(b) an antigen facilitating transport across the blood-brain-barrier selected from the group consisting of transferrin receptor (TR), insulin receptor (HIR), insulin-like growth factor receptor (IGFR), low-density lipoprotein receptor related proteins 1 and 2 (LPR-1 and 2), diphtheria toxin receptor, CRM197, a llama single domain antibody, TMEM 30(A), a protein transduction domain, TAT, Syn-B, penetratin, a poly-arginine peptide, an angiopeptide, and ANG1005;

(c) a disease-causing agent selected from the group consisting of disease-causing peptides or proteins or, disease-causing nucleic acids, wherein the disease-causing nucleic acids are antisense GGCCCC (G2C4) repeat-expansion RNA, the disease-causing proteins are selected from the group consisting of amyloid beta, oligomeric amyloid beta, amyloid beta plaques, amyloid precursor protein or fragments thereof, Tau, IAPP, alpha-synuclein, TDP-43, FUS protein, C9orf72 (chromosome 9 open reading frame 72), c9RAN protein, prion protein, PrPSc, huntingtin, calcitonin, superoxide dismutase, ataxin, ataxin 1, ataxin 2, ataxin 3, ataxin 7, ataxin 8, ataxin 10, Lewy body, atrial natriuretic factor, islet amyloid polypeptide, insulin, apolipoprotein AI, serum amyloid A, medin, prolactin, transthyretin, lysozyme, beta 2 microglobulin, gelsolin, keratoepithelin, cystatin, immunoglobulin light chain AL, S-IBM protein, Repeat-associated non-ATG (RAN) translation products, DiPeptide repeat (DPR) peptides, glycine-alanine (GA) repeat peptides, glycine-proline (GP) repeat peptides, glycine-arginine (GR) repeat peptides, proline-alanine (PA) repeat peptides, ubiquitin, and proline-arginine (PR) repeat peptides;

(d) ligands and/or proteins expressed on immune cells, wherein the ligands and/or proteins selected from the group consisting of CD40, OX40, ICOS, CD28, CD137/4-1BB, CD27, GITR, PD-L1, CTLA-4, PD-L2, PD-1, B7-H3, B7-H4, HVEM, BTLA, KIR, GALS, TIM3, A2AR, LAG-3, and phosphatidylserine; and (e) a protein, lipid, polysaccharide, or glycolipid expressed on one or more tumor cells.

12. The antibody of claim 1, wherein the antibody binds specifically to both human TREM2 and cynomolgus monkey TREM2.

13. The antibody of claim 12, wherein the antibody has a dissociation constant ($K_D$) for cynomolgus monkey TREM2 that ranges from about 100 pM to about 50 nM, wherein the $K_D$ is determined at a temperature of approximately 25° C.

14. The antibody of claim 1, wherein the antibody binds to primary human immune cells with an affinity that is at least 10 times higher than that of an anti-TREM2 antibody comprising a heavy chain variable region comprising the amino acid sequence of SEQ ID NO: 27 and a light chain variable region comprising the amino acid sequence of SEQ ID NO: 92; or at least 10 times higher than an anti-TREM2 antibody comprising a heavy chain variable region comprising the amino acid sequence of SEQ ID NO: 56 and a light chain variable region comprising the amino acid sequence of SEQ ID NO: 104.

15. The antibody of claim 1, wherein the antibody clusters and activates TREM2 signaling in an amount that is greater than that of a human control IgG1 antibody.

16. The antibody of claim 1, wherein the antibody increases immune cell survival in vitro to an extent that is greater than a human control IgG1 antibody.

17. The antibody of claim 1, wherein the antibody has an in vivo half-life that is lower than a human control IgG1 antibody.

18. The antibody of claim 1, wherein the antibody decreases plasma levels of soluble TREM2 in vivo by at least 25% compared to a human control IgG1 antibody.

19. The antibody of claim 18, wherein the antibody decreases plasma levels of soluble TREM2 in vivo by blocking cleavage and/or by inducing internalization.

20. A pharmaceutical composition comprising the antibody of claim 1 and a pharmaceutically acceptable carrier.

21. An isolated nucleic acid comprising a nucleic acid sequence encoding the antibody of claim 1.

22. A vector comprising the nucleic acid of claim 21.

23. An isolated host cell comprising the vector of claim 22.

24. A method of producing an antibody that binds to TREM2, comprising culturing the cell of claim 23 so that the antibody is produced.

25. The method of claim 24, further comprising recovering the antibody produced by the cell.

26. An isolated antibody that binds to TREM2 produced by the method of claim 25.

27. An antibody that binds to a human TREM2 protein, wherein the antibody comprises a heavy chain variable region comprising the amino acid sequence of SEQ ID NO: 59 and a light chain variable region comprising the amino acid sequence of SEQ ID NO: 112.

28. The antibody of claim 27, wherein the antibody binds to one or more human TREM2 proteins selected from the group consisting of wild-type human TREM2, a naturally occurring variant of human TREM2, and a disease variant of human TREM2.

29. The antibody of claim 27, wherein the antibody is an antibody fragment selected from an Fab, Fab', Fab'-SH, F(ab')2, Fv or scFv, or an antibody fragment comprising an antigen binding region.

30. The antibody of claim 27, wherein the antibody is a monoclonal antibody.

31. The antibody of claim 27, wherein the antibody is of the IgG class, the IgM class, or the IgA class.

32. The antibody of claim 31, wherein the antibody is of the IgG class and has an IgG1, IgG2, IgG3, or IgG4 isotype.

33. The antibody of claim 32, wherein the antibody comprises one or more amino acid substitutions in the Fc region at a residue position selected from the group consisting of: C127S, L234A, L234F, L235A, L235E, S267E, K322A, L328F, A330S, P331S, E345R, E430G, S440Y, and any combination thereof, wherein the numbering of the residues is according to EU numbering.

34. The antibody of claim 32, wherein the antibody has an IgG1 or IgG2 isotype, and wherein:
the Fc region comprises an amino acid substitution at positions E430G, L234A, L235A, and P331S, wherein the numbering of the residue position is according to EU numbering;
the Fc region comprises an amino acid substitution at positions E430G and P331S, wherein the numbering of the residue position is according to EU numbering;
the Fc region comprises an amino acid substitution at positions E430G and K322A, wherein the numbering of the residue position is according to EU numbering;
the Fc region comprises an amino acid substitution at positions E430G, A330S, and P331S, wherein the numbering of the residue position is according to EU numbering;
the Fc region comprises an amino acid substitution at positions E430G, K322A, A330S, and P331S, wherein the numbering of the residue position is according to EU numbering;
the Fc region comprises an amino acid substitution at positions E430G, K322A, and A330S, wherein the numbering of the residue position is according to EU numbering;
the Fc region comprises an amino acid substitution at positions E430G, K322A, and P331S, wherein the numbering of the residue position is according to EU numbering;
the Fc region comprises an amino acid substitution at positions S267E and L328F, wherein the numbering of the residue position is according to EU numbering;
the Fc region comprises an amino acid substitution at position C127S, wherein the numbering of the residue position is according to EU numbering;
the Fc region comprises an amino acid substitution at positions E345R, E430G and S440Y, wherein the numbering of the residue position is according to EU numbering; or
the Fc region comprises an amino acid sequence selected from the group consisting of SEQ ID NOs: 146-156.

35. The antibody of claim 34, wherein the antibody has an IgG1 isotype, and wherein the Fc region comprises an amino acid substitution at positions E430G and P331S, wherein the numbering of the residue position is according to EU numbering.

36. A pharmaceutical composition comprising the antibody of claim 27 and a pharmaceutically acceptable carrier.

37. An isolated nucleic acid comprising a nucleic acid sequence encoding the antibody of claim 27.

38. A vector comprising the nucleic acid of claim 37.

39. An isolated host cell comprising the vector of claim 38.

40. A method of producing an antibody that binds to TREM2, comprising culturing the cell of claim 39 so that the antibody is produced.

41. The method of claim 40, further comprising recovering the antibody produced by the cell.

42. An isolated antibody that binds to TREM2 produced by the method of claim 41.

43. An antibody that binds to a human TREM2 protein, comprising a heavy chain and a light chain, wherein:
(a) the heavy chain comprises the amino acid sequence of SEQ ID NO: 198, and the light chain comprises the amino acid sequence of SEQ ID NO: 214;
(b) the heavy chain comprises the amino acid sequence of SEQ ID NO: 199, and the light chain comprises the amino acid sequence of SEQ ID NO: 214;
(c) the heavy chain comprises the amino acid sequence of SEQ ID NO: 200, and the light chain comprises the amino acid sequence of SEQ ID NO: 214; or
(d) the heavy chain comprises the amino acid sequence of SEQ ID NO: 201, and the light chain comprises the amino acid sequence of SEQ ID NO: 214.

44. A pharmaceutical composition comprising the antibody of claim 43 and a pharmaceutically acceptable carrier.

45. A monoclonal antibody that binds to a human TREM2 protein, wherein the antibody comprises a heavy chain and a light chain, and wherein the heavy chain comprises the amino acid sequence of SEQ ID NO: 200 and the light chain comprises the amino acid sequence of SEQ ID NO: 214.

46. A pharmaceutical composition comprising the antibody of claim 45 and a pharmaceutically acceptable carrier.

47. An isolated nucleic acid comprising a nucleic acid sequence encoding the antibody of claim 45.

48. A vector comprising the nucleic acid of claim 47.

49. An isolated host cell comprising the vector of claim 48.

50. A method of producing an antibody that binds to TREM2, comprising culturing the cell of claim 49 so that the antibody is produced.

51. The method of claim 50, further comprising recovering the antibody produced by the cell.

52. An isolated antibody that binds to TREM2 produced by the method of claim 51.

53. A monoclonal antibody that binds to a human TREM2 protein, wherein the antibody comprises a heavy chain and a light chain, and wherein the heavy chain comprises the amino acid sequence of SEQ ID NO: 201 and the light chain comprises the amino acid sequence of SEQ ID NO: 214.

54. A pharmaceutical composition comprising the antibody of claim 53 and a pharmaceutically acceptable carrier.

55. An isolated nucleic acid comprising a nucleic acid sequence encoding the antibody of claim 53.

56. A vector comprising the nucleic acid of claim 55.

57. An isolated host cell comprising the vector of claim 56.

58. A method of producing an antibody that binds to TREM2, comprising culturing the cell of claim 57 so that the antibody is produced.

59. The method of claim 58, further comprising recovering the antibody produced by the cell.

60. An isolated antibody that binds to TREM2 produced by the method of claim 59.

* * * * *